United States Patent
Heo et al.

(10) Patent No.: US 12,029,115 B2
(45) Date of Patent: Jul. 2, 2024

(54) ORGANIC LIGHT-EMITTING DEVICE

(71) Applicant: LG CHEM, LTD., Seoul (KR)

(72) Inventors: Dong Uk Heo, Daejeon (KR); Sung Kil Hong, Daejeon (KR); Jungoh Huh, Daejeon (KR); Miyeon Han, Daejeon (KR); Jae Tak Lee, Daejeon (KR); Junghoon Yang, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 833 days.

(21) Appl. No.: 17/251,344

(22) PCT Filed: Sep. 3, 2019

(86) PCT No.: PCT/KR2019/011317
§ 371 (c)(1),
(2) Date: Dec. 11, 2020

(87) PCT Pub. No.: WO2020/050585
PCT Pub. Date: Mar. 12, 2020

(65) Prior Publication Data
US 2021/0305516 A1    Sep. 30, 2021

(30) Foreign Application Priority Data
Sep. 3, 2018 (KR) .................. 10-2018-0104688

(51) Int. Cl.
*H01L 51/50* (2006.01)
*C07D 213/16* (2006.01)
(Continued)

(52) U.S. Cl.
CPC ......... *H10K 85/654* (2023.02); *C07D 213/16* (2013.01); *C07D 251/24* (2013.01);
(Continued)

(58) Field of Classification Search
None
See application file for complete search history.

(56) References Cited

U.S. PATENT DOCUMENTS

| 2004/0251816 A1 | 12/2004 | Leo et al. |
| 2017/0194387 A1 | 7/2017 | Oh et al. |

(Continued)

FOREIGN PATENT DOCUMENTS

| JP | 2006-120689 | 5/2006 |
| JP | 2012-049523 | 3/2012 |

(Continued)

*Primary Examiner* — Gregory D Clark
(74) *Attorney, Agent, or Firm* — Bryan Cave Leighton Paisner LLP

(57) ABSTRACT

Provided is an organic light emitting device including a first electrode; a second electrode opposite to the first electrode; and a first organic material layer and a second organic material layer provided between the first electrode and the second electrode, wherein the first organic material layer includes a compound of Chemical Formula 1:

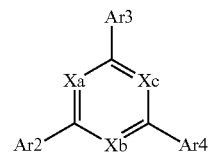

wherein:
at least one of Xa to Xc is N, and the rest are CR; and
Ar2 to Ar4 are each independently a substituted or unsubstituted aryl or heterocyclic group, and
(Continued)

| 8 |
| 7 |
| 6 |
| 5 |
| 5 |
| 5 |
| 4 |
| 3 |
| 2 |
| 1 | the second organic material layer includes a compound of

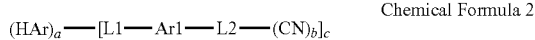

Chemical Formula 2 wherein:
HAr is a substituted or unsubstituted heterocyclic group including at least one or more Ns;
L1 and L2 are each independently a direct bond or a substituted or unsubstituted arylene or divalent heterocyclic group; and
Ar1 is a direct bond, —O—, or a substituted or unsubstituted arylene or divalent heterocyclic group.

20 Claims, 2 Drawing Sheets

(51) Int. Cl.
| | | |
|---|---|---|
| *C07D 251/24* | (2006.01) | |
| *C07D 405/04* | (2006.01) | |
| *C07D 405/10* | (2006.01) | |
| *C07D 487/04* | (2006.01) | |
| *C07D 495/04* | (2006.01) | |
| *C09K 11/06* | (2006.01) | |
| *H10K 85/60* | (2023.01) | |
| *H10K 50/11* | (2023.01) | |
| *H10K 50/13* | (2023.01) | |
| *H10K 50/18* | (2023.01) | |
| *H10K 101/10* | (2023.01) | |

(52) U.S. Cl.
CPC ......... *C07D 405/04* (2013.01); *C07D 405/10* (2013.01); *C07D 487/04* (2013.01); *C07D 495/04* (2013.01); *C09K 11/06* (2013.01); *H10K 85/615* (2023.02); *H10K 85/624* (2023.02); *H10K 85/657* (2023.02); *H10K 85/6572* (2023.02); *H10K 85/6574* (2023.02); *C09K 2211/1018* (2013.01); *H10K 50/11* (2023.02); *H10K 50/13* (2023.02); *H10K 50/18* (2023.02); *H10K 2101/10* (2023.02)

(56) References Cited

U.S. PATENT DOCUMENTS

| | | |
|---|---|---|
| 2017/0279055 A1 | 9/2017 | Jang et al. |
| 2018/0053900 A1 | 2/2018 | Eum et al. |
| 2018/0066180 A1 | 3/2018 | Huh et al. |
| 2018/0315930 A1 | 11/2018 | Han et al. |
| 2019/0067591 A1 | 2/2019 | Jang |
| 2019/0106391 A1 | 4/2019 | Wucherer-Plietker et al. |
| 2020/0287142 A1* | 9/2020 | Huh ............... H10K 85/615 |

FOREIGN PATENT DOCUMENTS

| | | | | |
|---|---|---|---|---|
| JP | 4956893 | | 6/2012 | |
| KR | 10-2016-0019764 | | 2/2016 | |
| KR | 10-2016-0126862 | | 11/2016 | |
| KR | 10-2017-0049440 | | 5/2017 | |
| KR | 10-2017-0073567 | | 6/2017 | |
| KR | 10-2017-0080923 | | 7/2017 | |
| KR | 10-2018-0042818 | * | 4/2018 | ............ H01L 51/52 |
| WO | 2003-012890 | | 2/2003 | |
| WO | 2016-105141 | | 6/2016 | |
| WO | 2017-157983 | | 9/2017 | |
| WO | 2019-151733 | | 8/2019 | |

* cited by examiner

【FIG. 1】
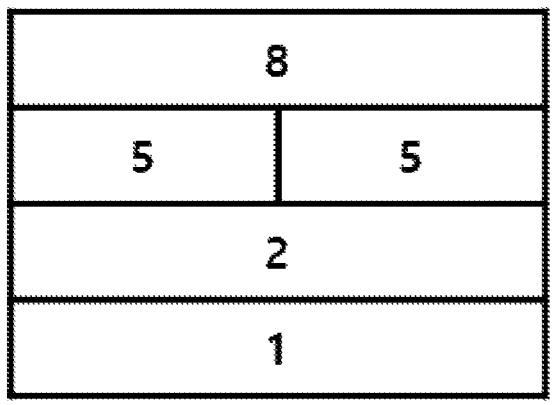
【FIG. 2】
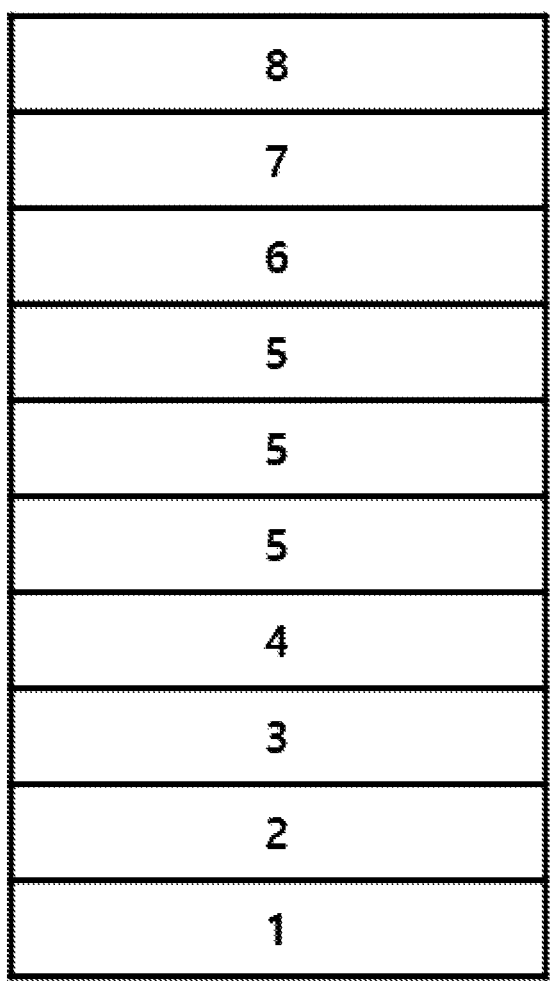

[FIG. 3]
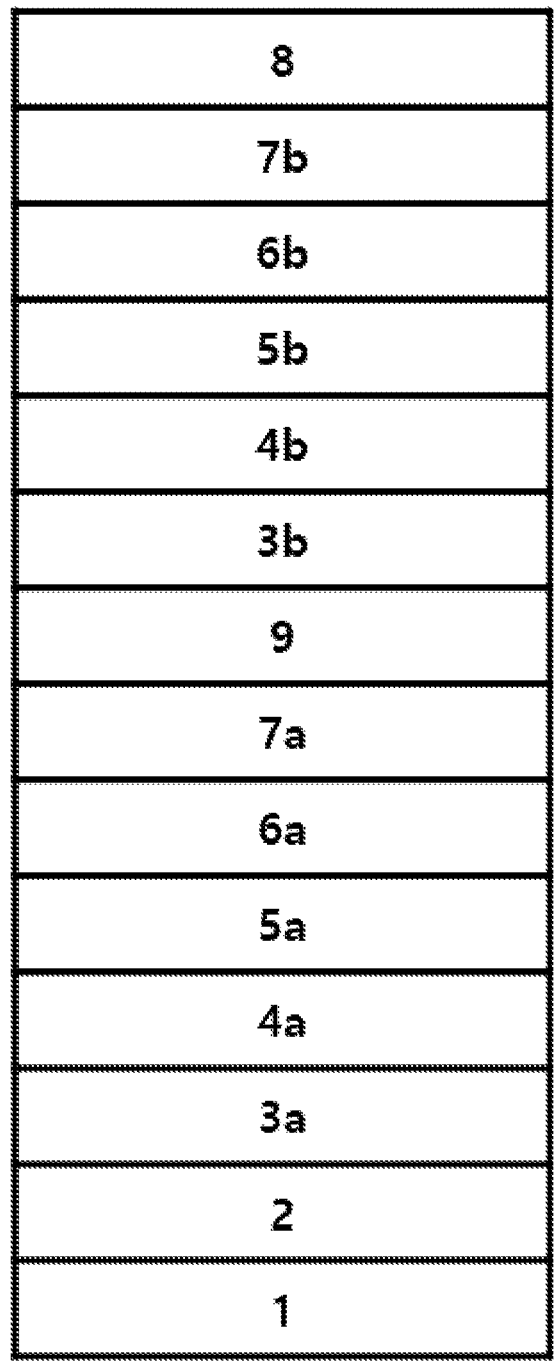

ORGANIC LIGHT-EMITTING DEVICE

CROSS-REFERENCE TO RELATED APPLICATIONS

This application is a National Stage Application of International Application No. PCT/KR2019/011317 filed on Sep. 3, 2019, which claims priority to and the benefits of Korean Patent Application No. 10-2018-0104688, filed with the Korean Intellectual Property Office on Sep. 3, 2018, the entire contents of which are incorporated herein by reference.

TECHNICAL FIELD

The present application relates to an organic light emitting device.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

In the art, aromatic diamine derivatives or aromatic fused ring diamine derivatives have been known as a hole transfer material used in an organic EL device. However, since an applied voltage is mostly high in this case, problems such as a decrease in the device lifetime or an increase in the power consumption have been caused. In view of these problems, a method of doping an electron accepting compound such as a Lewis acid or using the compound alone in a hole injection layer of an organic EL device has been proposed. However, it has been shown that the above-described method has a limit in injecting and transferring holes, and accordingly, there have been attempts to achieve effects of low voltage, high efficiency and long lifetime using a combination of materials between a hole transfer layer or a hole control layer, or materials of a hole transfer layer and a plurality of hole control layers. A general hole transfer layer has been aromatic group-substituted tertiary amine, and device properties found from the group of combinations of these materials have been diverse. Accordingly, development of new materials for enhancing device properties obtained by hole transfer and carrier control has been continuously required.

BRIEF DESCRIPTION

Technical Problem

The present application is directed to providing an organic light emitting device.

Technical Solution

One embodiment of the present application provides an organic light emitting device including a first electrode; a second electrode provided opposite to the first electrode; and a first organic material layer and a second organic material layer provided between the first electrode and the second electrode,
wherein the first organic material layer includes a compound of the following Chemical Formula 1,
the second organic material layer includes a compound of the following Chemical Formula 2, and
a dipole moment value of the second organic material layer is larger than a dipole moment value of the first organic material layer:

Chemical Formula 1

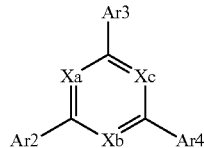

wherein in Chemical Formula 1:
at least one of Xa to Xc is N, and the rest are CR;
R is hydrogen, deuterium, a cyano group, a nitrile group, a substituted or unsubstituted silyl group, a substituted or unsubstituted alkyl group, a substituted or unsubstituted haloalkyl group, a substituted or unsubstituted cycloalkyl group, a substituted or unsubstituted alkenyl group, a substituted or unsubstituted aryl group, or a substituted or unsubstituted heterocyclic group; and
Ar2 to Ar4 are each independently a substituted or unsubstituted aryl group, or a substituted or unsubstituted heterocyclic group;

Chemical Formula 2

wherein in Chemical Formula 2:
HAr is a substituted or unsubstituted heterocyclic group including at least one or more Ns;
L1 and L2 are each independently a direct bond, a substituted or unsubstituted arylene group, or a substituted or unsubstituted divalent heterocyclic group;
Ar1 is a direct bond, or a substituted or unsubstituted arylene group;
a to c are each an integer of 1 to 3; and
when a to c are each 2 or greater, the structures in the two or more parentheses are the same as or different from each other.

Advantageous Effects

An organic light emitting device using a compound according to one embodiment of the present application in each of a hole blocking layer, an electron control layer or an electron transfer layer is capable of obtaining low driving voltage, high light emission efficiency or long lifetime. In addition, when the compound satisfies a relation of $P_{El} > P_{Eb}$, over-injection of an amount of electrons transferred to a light emitting layer can be controlled, and the organic light emitting device is capable of obtaining high efficiency and long lifetime.

DESCRIPTION OF THE DRAWINGS

FIG. 1 illustrates an example of an organic light emitting device in which a substrate (1), an anode (2), a light emitting layer (5) and a cathode (8) are consecutively laminated.

FIG. 2 illustrates an example of an organic light emitting device in which a substrate (1), an anode (2), a hole injection layer (3), a hole transfer layer (4), a light emitting layer (5), a hole blocking layer or an electron control layer (6), an electron injection or transfer layer (7) and a cathode (8) are consecutively laminated.

FIG. 3 illustrates an example of an organic light emitting device in which a substrate (1), an anode (2), a first hole injection layer (3a), a first hole transfer layer (4a), a first light emitting layer (5a), a first hole blocking layer (6a), a first electron injection or transfer layer (7a), a charge generating layer (9), a second hole injection layer (3b), a second hole transfer layer (4b), a second light emitting layer (5b), a second hole blocking layer (6b), a second electron injection and transfer layer (7b) and a cathode (8) are consecutively laminated.

REFERENCE NUMERALS

1: Substrate
2: Anode
3: Hole Injection Layer
3a: First Hole Injection Layer
3b: Second Hole Injection Layer
4: Hole Transfer Layer
4a: First Hole Transfer Layer
4b: Second Hole Transfer Layer
5: Light Emitting Layer
5a: First Light Emitting Layer
5b: Second Light Emitting Layer
6: Hole Blocking Layer or Electron Control Layer
6a: First Hole Blocking Layer
6b: Second Hole Blocking Layer
7: Electron Injection or Transfer Layer
7a: First Electron Injection or Transfer Layer
7b: Second Electron Injection or Transfer Layer
8: Cathode
9: Charge Generating Layer

DETAILED DESCRIPTION

Hereinafter, the present specification will be described in more detail.

In the present application, a description of a certain member being placed "on" another member includes not only a case of the one member in contact with the another member but a case of still another member being present between the two members.

In the present application, a description of a certain part "including" certain constituents means capable of further including other constituents, and does not exclude other constituents unless particularly stated on the contrary.

One embodiment of the present application provides an organic light emitting device including a first electrode; a second electrode provided opposite to the first electrode; and a first organic material layer and a second organic material layer provided between the first electrode and the second electrode, wherein the first organic material layer includes a compound of Chemical Formula 1, and the second organic material layer includes a compound of Chemical Formula 2.

According to one embodiment of the present application, the compound of Chemical Formula 1 has an advantage of controlling triplet energy by having a core structure as described above, and when each used as a compound of a host, properties of long lifetime and high efficiency can be obtained.

Examples of substituents in the present specification are described below, however, the substituents are not limited thereto.

The term "substitution" means a hydrogen atom bonding to a carbon atom of a compound is changed to another substituent. The position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of hydrogen, a halogen group, a nitrile group, a nitro group, a hydroxyl group, a substituted or unsubstituted alkyl group, a substituted or unsubstituted cycloalkyl group, a substituted or unsubstituted alkenyl group, a substituted or unsubstituted amine group, a substituted or unsubstituted aryl group, and a substituted or unsubstituted heterocyclic group, or being substituted with a substituent linking two or more substituents among the substituents illustrated above, or having no substituents. For example, "a substituent linking two or more substituents" can be a biphenyl group. In other words, a biphenyl group can be an aryl group, or interpreted as a substituent linking two phenyl groups.

In the present specification, examples of the halogen group can include fluorine, chlorine, bromine or iodine.

In the present specification, the number of carbon atoms of the ester group is not particularly limited, but is preferably from 1 to 50. Specifically, compounds having the following structures can be included, however, the ester group is not limited thereto:

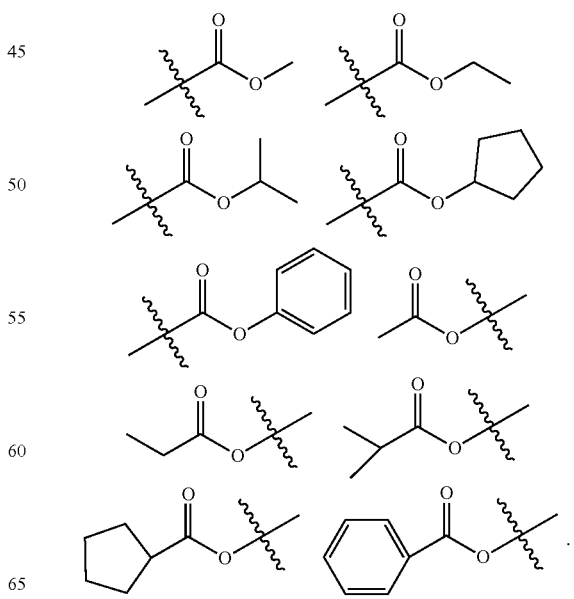

In the present specification, the number of carbon atoms of the carbonyl group is not particularly limited, but is preferably from 1 to 50. Specifically, compounds having structures as below can be included, however, the carbonyl group is not limited thereto:

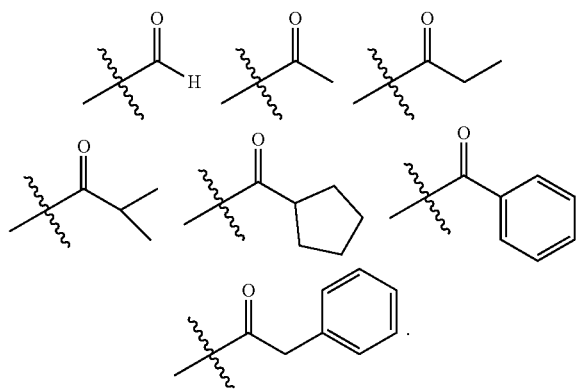

In the present specification, the alkyl group can be linear or branched, and although not particularly limited thereto, the number of carbon atoms is preferably from 1 to 60. Specific examples thereof can include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof can include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 20. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group can be linear or branched, and although not particularly limited thereto, the number of carbon atoms is preferably from 2 to 40. Specific examples thereof can include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, when the aryl group is a monocyclic aryl group, the number of carbon atoms is not particularly limited, but is preferably from 6 to 25. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 24. Specific examples of the polycyclic aryl group can include a naphthyl group, an anthracenyl group, a phenanthryl group, a pyrenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

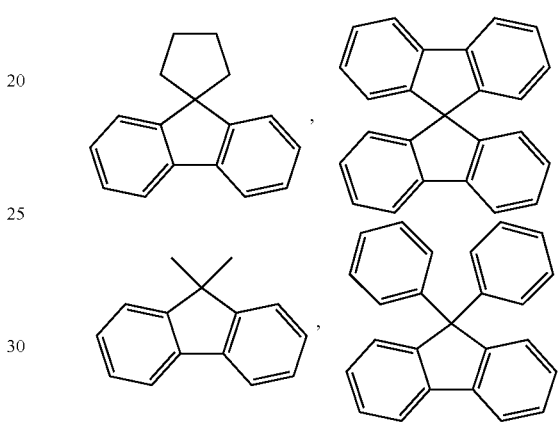

and the like can be included. However, the structure is not limited thereto.

In the present specification, the heterocyclic group is a group including one or more atoms that are not carbon, that is, heteroatoms, and specifically, the heteroatom can include one or more atoms selected from the group consisting of O, N, Se, S and the like. The number of carbon atoms of the heterocyclic group is not particularly limited, but is preferably from 2 to 60. Examples of the heterocyclic group can include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

Hereinafter, Chemical Formula 1 will be described in detail.

According to one embodiment of the present application, at least one of Xa to Xc is N, and the rest are CR.

According to one embodiment of the present application, Xa is N, and Xb and Xc are CR.

According to one embodiment of the present application, Xb is N, and Xa and Xc are CR.

According to one embodiment of the present application, Xc is N, and Xa and Xb are CR.

According to one embodiment of the present application, Xa and Xb are N, and Xc is CR.

According to one embodiment of the present application, Xa and Xc are N, and Xb is CR.

According to one embodiment of the present application, Xb and Xc are N, and Xa is CR.

According to one embodiment of the present application, Xa to Xc are N.

According to one embodiment of the present application, R is hydrogen, deuterium, a cyano group, a nitrile group, a substituted or unsubstituted silyl group, a substituted or unsubstituted alkyl group, a substituted or unsubstituted haloalkyl group, a substituted or unsubstituted cycloalkyl group, a substituted or unsubstituted alkenyl group, a substituted or unsubstituted aryl group, or a substituted or unsubstituted heterocyclic group.

According to one embodiment of the present application, R is hydrogen.

According to one embodiment of the present application, Ar2 to Ar4 are each independently a substituted or unsubstituted aryl group, or a substituted or unsubstituted heterocyclic group.

According to one embodiment of the present application, Ar2 to Ar4 are each independently a substituted or unsubstituted aryl group having 6 to 60 carbon atoms, or a substituted or unsubstituted heterocyclic group having 2 to 60 carbon atoms.

According to one embodiment of the present application, Ar2 to Ar4 are each independently a substituted or unsubstituted aryl group having 6 to 30 carbon atoms, or a substituted or unsubstituted heterocyclic group having 2 to 30 carbon atoms.

According to one embodiment of the present application, Ar2 to Ar4 are each independently an aryl group having 6 to 30 carbon atoms unsubstituted or substituted with one or more groups of an alkyl group, an aryl group and a heterocyclic group, or a group bonding two or more thereof.

According to one embodiment of the present application, Ar2 to Ar4 are each independently an aryl group having 6 to 30 carbon atoms unsubstituted or substituted with one or more groups of an alkyl group having 1 to 20 carbon atoms, an aryl group having 6 to 30 carbon atoms and a heterocyclic group having 2 to 30 carbon atoms, or a group bonding two or more thereof.

According to one embodiment of the present application, Ar2 to Ar4 are each independently an aryl group having 6 to 30 carbon atoms unsubstituted or substituted with any one of a dimethylfluorenyl group, a diphenylfluorenyl group, a spirobifluorenyl group, and a triphenylenyl group unsubstituted or substituted with a phenyl group substituted with a methyl group.

According to one embodiment of the present application, Ar2 to Ar4 are each independently a phenyl group unsubstituted or substituted with any one of a dimethylfluorenyl group, a diphenylfluorenyl group, a spirobifluorenyl group, and a triphenylenyl group unsubstituted or substituted with a phenyl group substituted with a methyl group; a biphenyl group unsubstituted or substituted with any one of a dimethylfluorenyl group, a diphenylfluorenyl group, a spirobifluorenyl group, and a triphenylenyl group unsubstituted or substituted with a phenyl group substituted with a methyl group; or a terphenyl group unsubstituted or substituted with any one of a dimethylfluorenyl group, a diphenylfluorenyl group, a spirobifluorenyl group, and a triphenylenyl group unsubstituted or substituted with a phenyl group substituted with a methyl group.

According to one embodiment of the present application, Ar2 to Ar4 are each independently a phenyl group unsubstituted or substituted with any one of the following substituents; a biphenyl group unsubstituted or substituted with any one of the following substituents; or a terphenyl group unsubstituted or substituted with any one of the following substituents:

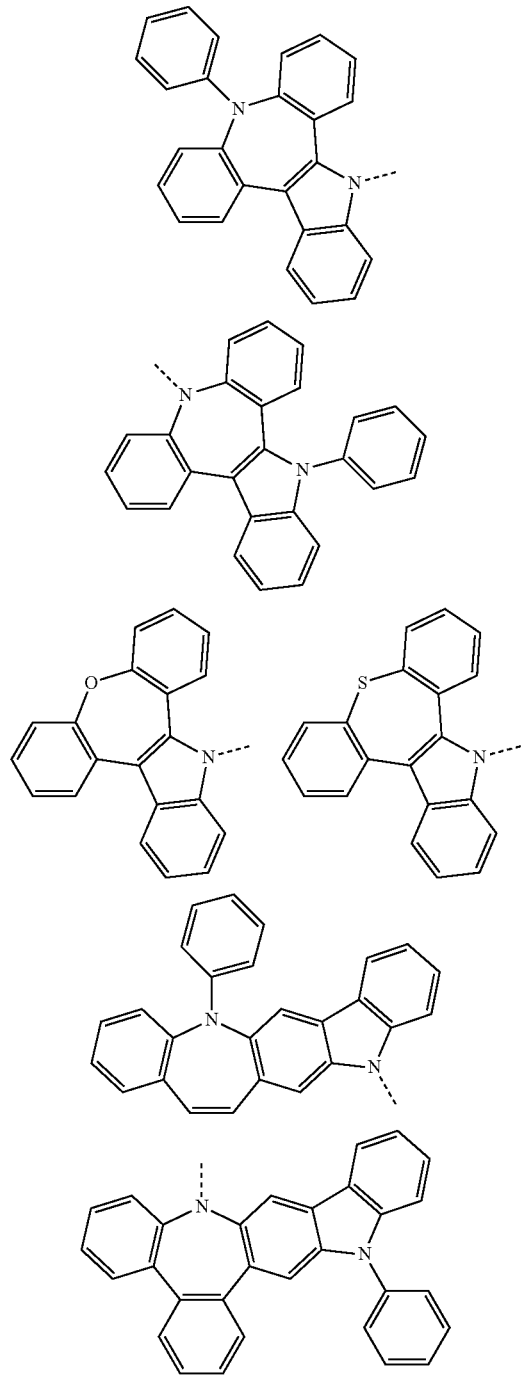

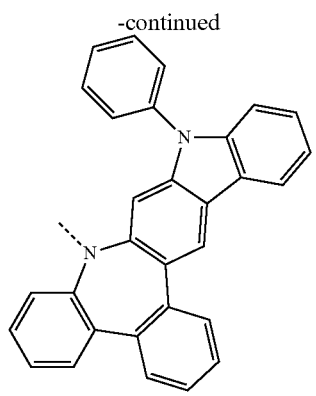

In the substituents, the dotted part means a bonding position.

According to one embodiment of the present application, at least one of Ar2 to Ar4 is a substituted or unsubstituted heterocyclic group, and the rest are a substituted or unsubstituted aryl group.

According to one embodiment of the present application, Ar2 to Ar4 are the same as or different from each other, and each independently is —L11-Ar11;
the L11s are the same as or different from each other, and each independently a direct bond, or a substituted or unsubstituted arylene group; and
the Ar11s are the same as or different from each other, and each independently a substituted or unsubstituted aryl group, or a substituted or unsubstituted heterocyclic group.

According to one embodiment of the present application, Ar2 and Ar3 are a substituted or unsubstituted aryl group, and Ar4 is —L11-Ar11.

According to one embodiment of the present application, Ar2 and Ar4 are a substituted or unsubstituted aryl group, and Ar3 is —L11-Ar11.

According to one embodiment of the present application, Ar3 and Ar4 are a substituted or unsubstituted aryl group, and Ar2 is —L11-Ar11.

According to one embodiment of the present application, Ar2 and Ar3 are a phenyl group, and Ar4 is —L11-Ar11.

According to one embodiment of the present application, Ar2 and Ar4 are a phenyl group, and Ar3 is —L11-Ar11.

According to one embodiment of the present application, Ar3 and Ar4 are a phenyl group, and Ar2 is —L11-Ar11.

According to one embodiment of the present application, L11s are the same as or different from each other, and each independently a direct bond, or a substituted or unsubstituted arylene group having 6 to 60 carbon atoms.

According to one embodiment of the present application, L11s are the same as or different from each other, and each independently a direct bond, or a substituted or unsubstituted arylene group having 6 to 30 carbon atoms.

According to one embodiment of the present application, L11s are the same as or different from each other, and each independently a direct bond, or a substituted or unsubstituted arylene group having 6 to 20 carbon atoms.

According to one embodiment of the present application, L11s are the same as or different from each other, and each independently a direct bond, a substituted or unsubstituted phenylene group, a substituted or unsubstituted biphenylene group, or a substituted or unsubstituted terphenylene group.

According to one embodiment of the present application, L11s are the same as or different from each other, and each independently a direct bond, a phenylene group, a biphenylene group, or a terphenylene group.

According to one embodiment of the present application, L11s are the same as or different from each other, and each independently a phenylene group, a biphenylene group, or a terphenylene group.

According to one embodiment of the present application, L11s are the same as or different from each other, and are any one of the following substituents:

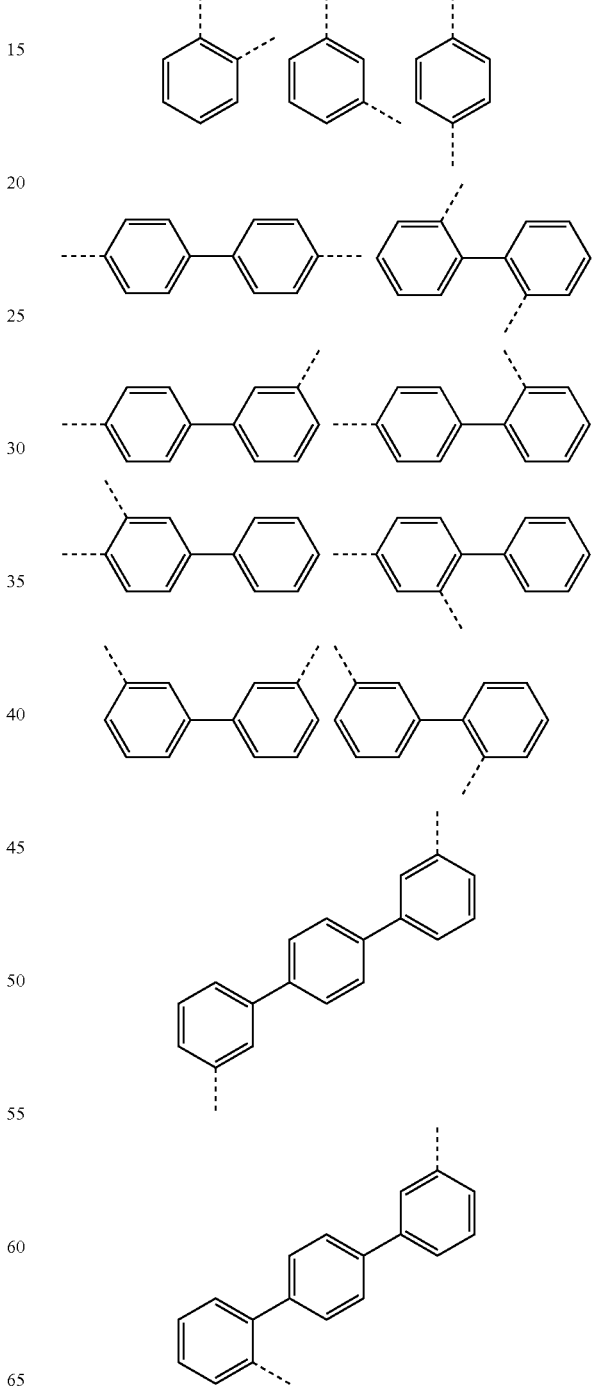

-continued

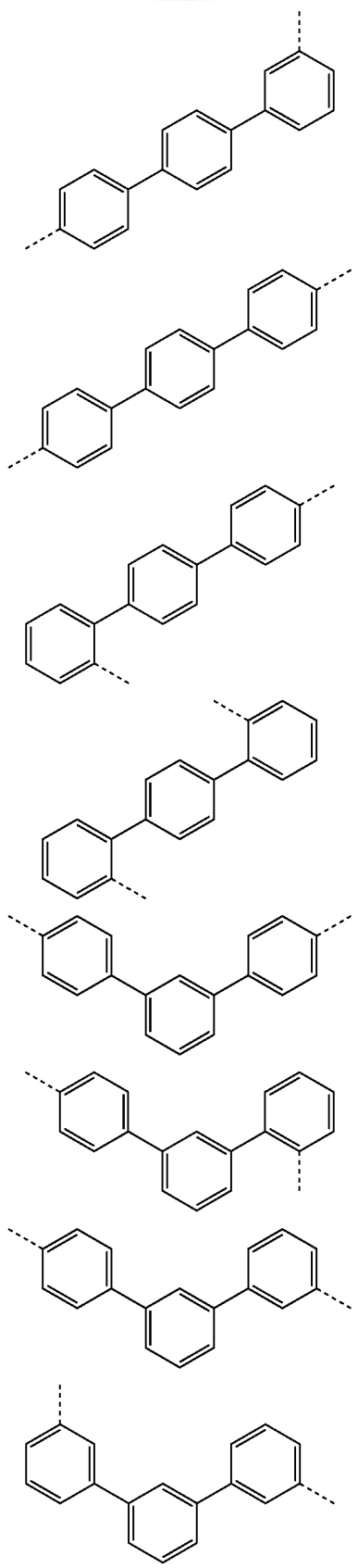

-continued

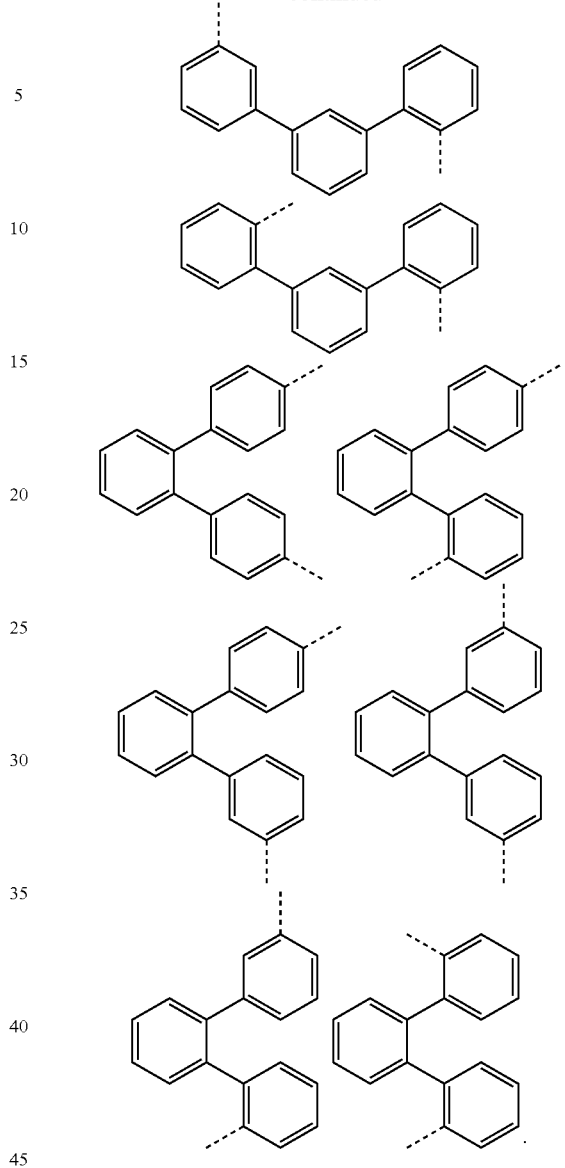

In the substituents, the dotted part means a bonding position.

According to one embodiment of the present application, Ar11s are the same as or different from each other, and each independently a substituted or unsubstituted aryl group having 6 to 60 carbon atoms, or a substituted or unsubstituted heterocyclic group having 2 to 60 carbon atoms.

According to one embodiment of the present application, Ar11s are the same as or different from each other, and each independently a substituted or unsubstituted aryl group having 6 to 30 carbon atoms, or a substituted or unsubstituted heterocyclic group having 2 to 30 carbon atoms.

According to one embodiment of the present application, Ar11s are the same as or different from each other, and each independently an aryl group unsubstituted or substituted with one or more groups of an alkyl group and an aryl group, or a group bonding two or more thereof, or a heterocyclic group unsubstituted or substituted with one or more groups of an alkyl group and an aryl group, or a group bonding two or more thereof.

According to one embodiment of the present application, Ar11s are the same as or different from each other, and each independently an aryl group having 6 to 30 carbon atoms unsubstituted or substituted with one or more groups of an alkyl group having 1 to 10 carbon atoms and an aryl group having 6 to 20 carbon atoms, or a group bonding two or more thereof, or a heterocyclic group having 2 to 30 carbon atoms unsubstituted or substituted with one or more groups of an alkyl group and an aryl group, or a group bonding two or more thereof.

According to one embodiment of the present application, Ar11s are the same as or different from each other, and each independently a phenyl group unsubstituted or substituted with one or more groups of an alkyl group having 1 to 10 carbon atoms and an aryl group having 6 to 20 carbon atoms, or a group bonding two or more thereof; a biphenyl group unsubstituted or substituted with one or more groups of an alkyl group having 1 to 10 carbon atoms and an aryl group having 6 to 20 carbon atoms, or a group bonding two or more thereof; a terphenyl group unsubstituted or substituted with one or more groups of an alkyl group having 1 to 10 carbon atoms and an aryl group having 6 to 20 carbon atoms, or a group bonding two or more thereof; a fluorenyl group unsubstituted or substituted with one or more groups of an alkyl group having 1 to 10 carbon atoms and an aryl group having 6 to 20 carbon atoms, or a group bonding two or more thereof; a spirobifluorenyl group unsubstituted or substituted with one or more groups of an alkyl group having 1 to 10 carbon atoms and an aryl group having 6 to 20 carbon atoms, or a group bonding two or more thereof; a triphenylenyl group unsubstituted or substituted with one or more groups of an alkyl group having 1 to 10 carbon atoms and an aryl group having 6 to 20 carbon atoms, or a group bonding two or more thereof; or any one of the following substituents.

According to one embodiment of the present application, Ar11s are the same as or different from each other, and each independently a dimethylfluorenyl group; a diphenylfluorenyl group; a spirobifluorenyl group; a triphenylenyl group unsubstituted or substituted with a phenyl group substituted with a methyl group; or any one of the following substituents:

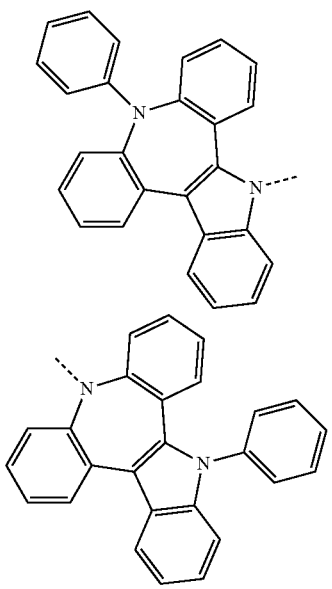

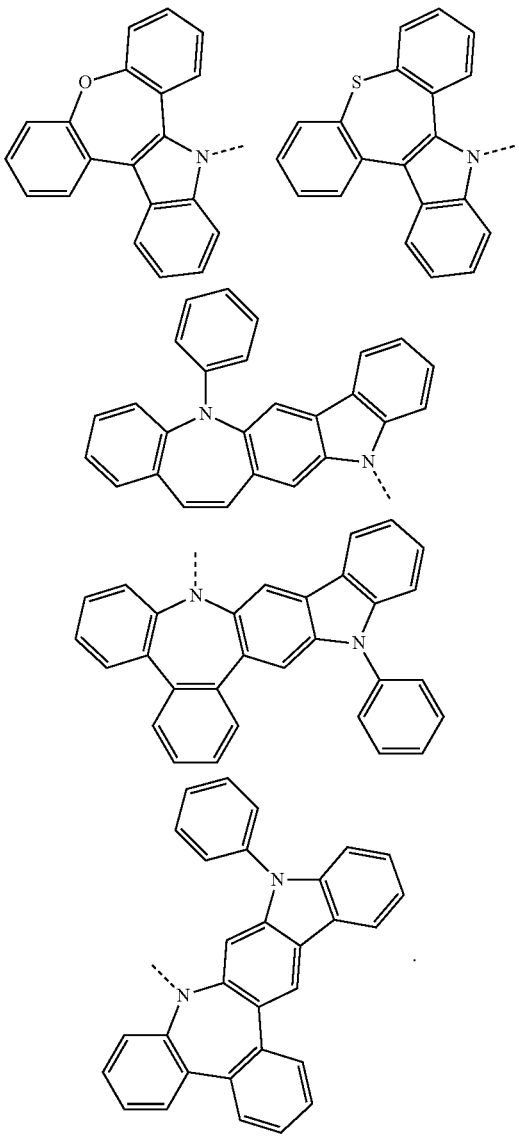

In the substituents, the dotted part means a bonding position.

According to one embodiment of the present application, Ar11 is any one of the following substituents:

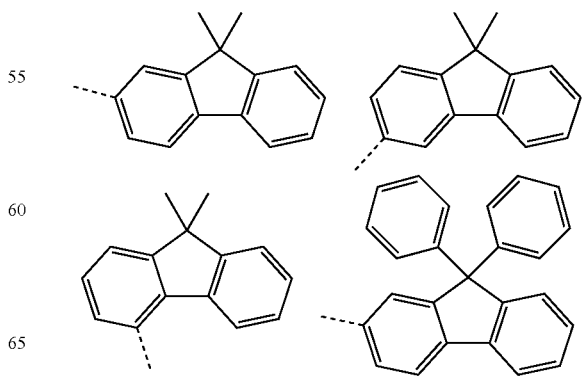

-continued

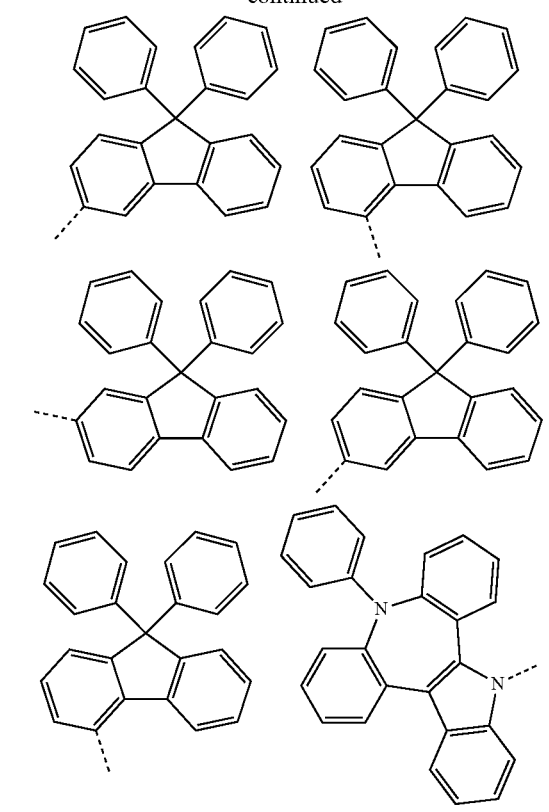

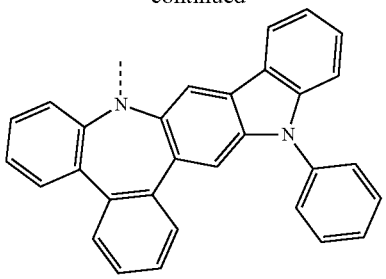

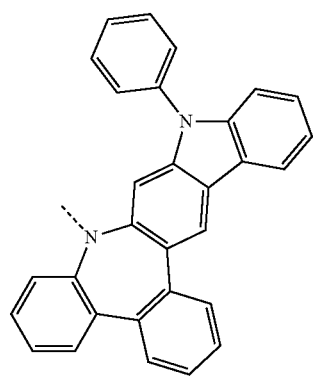

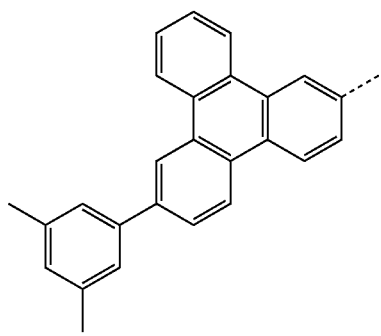

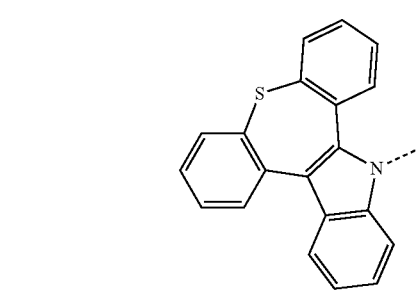

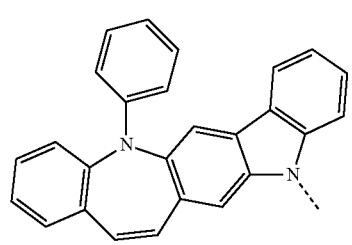

In the substituents, the dotted part means a bonding position.

According to one embodiment of the present application, Chemical Formula 1 is the following Chemical Formula 101:

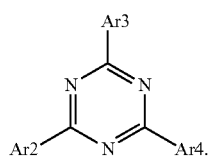

Chemical Formula 101

In Chemical Formula 101, Ar2 to Ar4 have the same definitions as in Chemical Formula 1.

According to one embodiment of the present application, Chemical Formula 1 is any one of the following Chemical Formulae 1-1 to 1-3:

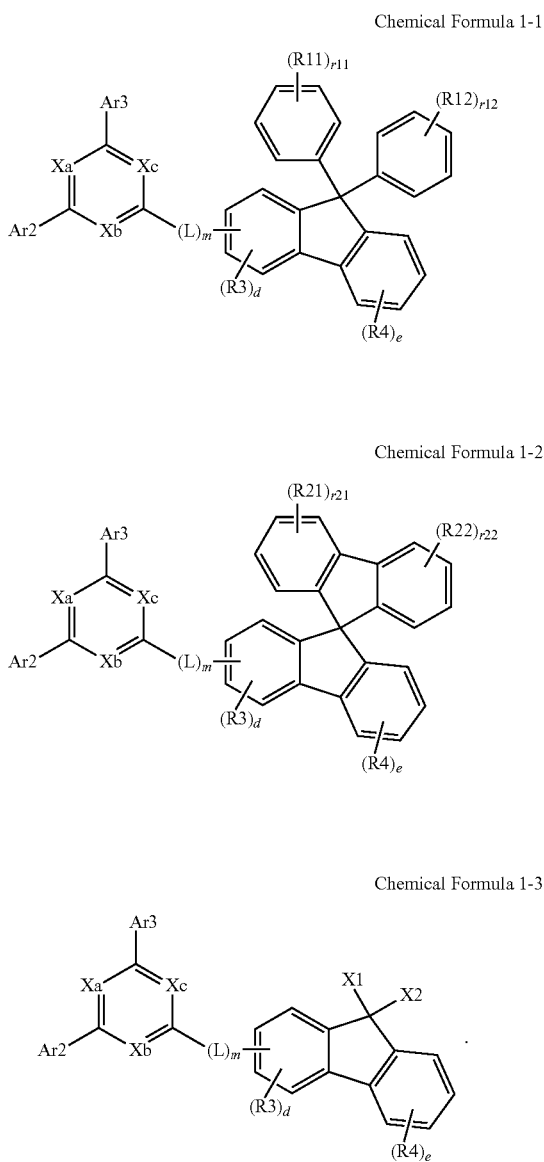

Chemical Formula 1-1

Chemical Formula 1-2

Chemical Formula 1-3

In Chemical Formulae 1-1 to 1-3:

Xa to Xc, Ar2 and Ar3 have the same definitions as in Chemical Formula 1;

L is substituted or unsubstituted phenylene, or substituted or unsubstituted biphenylylene, or substituted or unsubstituted terphenylene;

R3, R4, R11, R12, R21 and R22 are the same as or different from each other, and each independently hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted arylphosphine group, or a substituted or unsubstituted phosphine oxide group, or can bond to adjacent groups to form a substituted or unsubstituted ring;

X1 and X2 are the same as or different from each other, and each independently hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, or a substituted or unsubstituted phosphine oxide group, or can bond to adjacent groups to form a substituted or unsubstituted ring;

r11 and r12 are the same as or different from each other, and each independently an integer of 0 to 5;

r21 and r22 are the same as or different from each other, and each independently an integer of 0 to 4;

m is an integer of 1 to 3;

d is an integer of 1 to 3;

e is an integer of 1 to 4; and when r11, r12, r21, r22, m, d and e are each 2 or greater, the structures in the parentheses are the same as or different from each other.

According to one embodiment of the present application, R3, R4, R11, R12, R21 and R22 are each independently hydrogen, deuterium, a substituted or unsubstituted alkyl group, a substituted or unsubstituted cycloalkyl group, a substituted or unsubstituted aralkyl group, a substituted or unsubstituted alkylaryl group, a substituted or unsubstituted alkylamine group, or a substituted or unsubstituted aralkylamine group, or can bond to adjacent groups to form a substituted or unsubstituted ring.

According to one embodiment of the present specification, R3, R4, R11, R12, R21 and R22 are each independently hydrogen, deuterium, a halogen group, or an alkyl group.

According to one embodiment of the present specification, R3, R4, R11, R12, R21 and R22 are hydrogen.

According to one embodiment of the present specification, R3 and R4 are hydrogen.

According to one embodiment of the present specification, R4 is hydrogen.

According to one embodiment of the present specification, R3 is hydrogen.

According to one embodiment of the present specification, L is phenylene, biphenylylene, or terphenylene.

According to one embodiment of the present specification, L is any one of the following substituents:
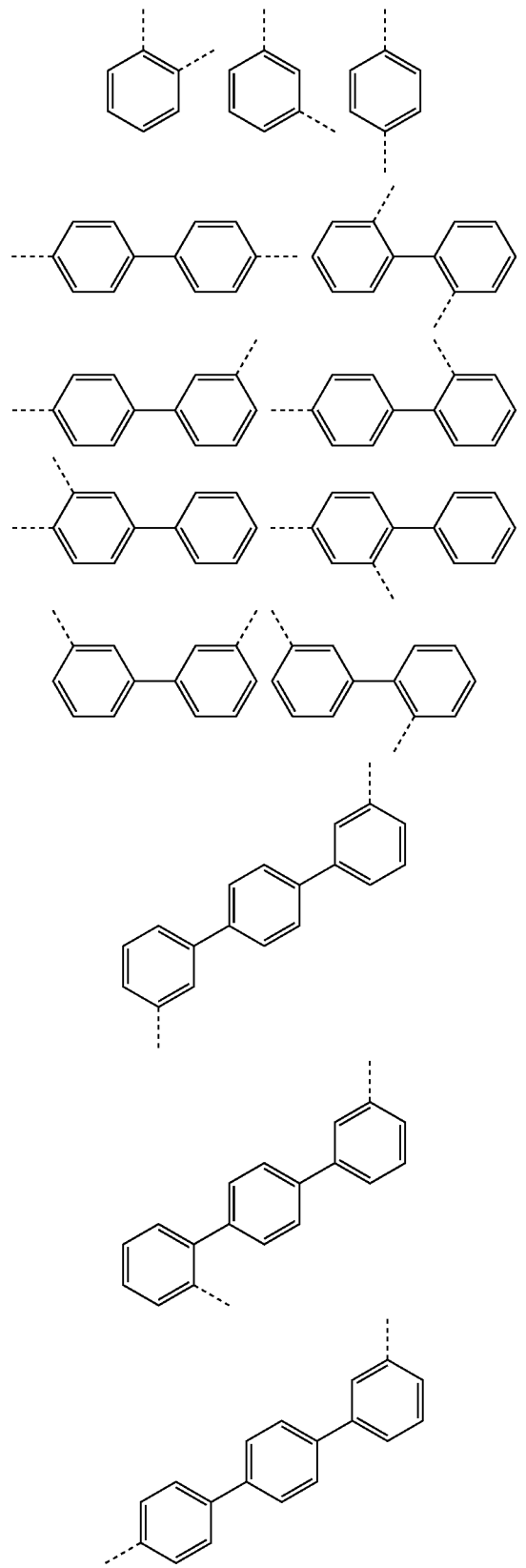
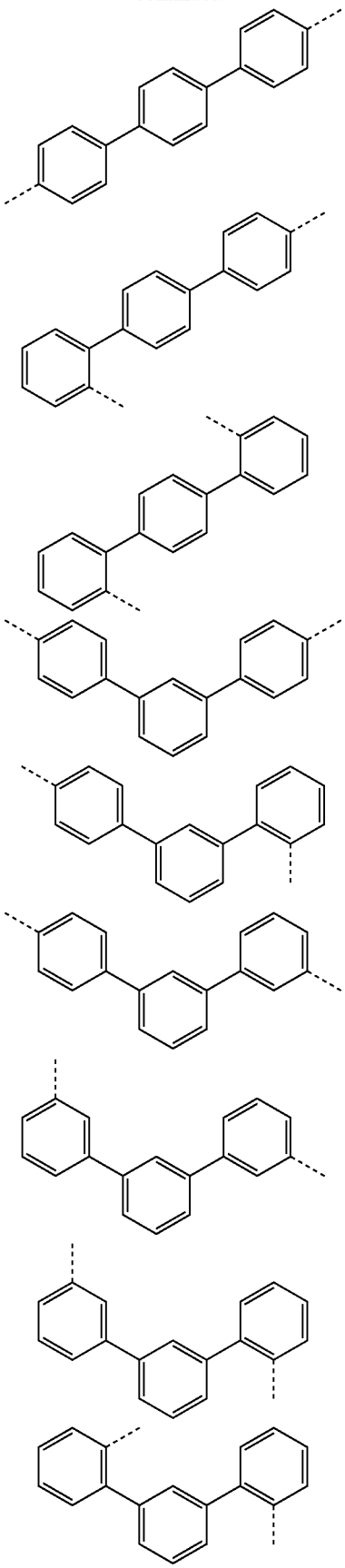

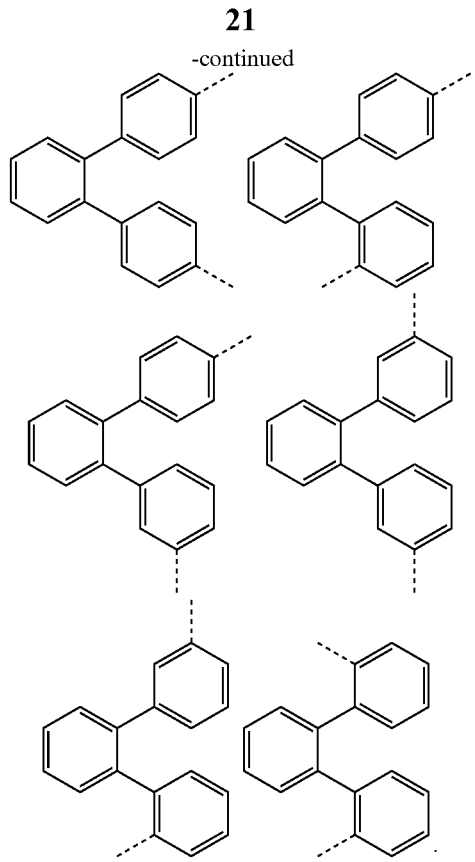

In the substituents, the dotted part means a bonding position.

According to one embodiment of the present application, X1 and X2 are a substituted or unsubstituted alkyl group.

According to one embodiment of the present application, X1 and X2 are a substituted or unsubstituted alkyl group having 1 to 20 carbon atoms.

According to one embodiment of the present application, X1 and X2 are a substituted or unsubstituted alkyl group having 1 to 10 carbon atoms.

According to one embodiment of the present application, X1 and X2 are a substituted or unsubstituted methyl group.

According to one embodiment of the present application, X1 and X2 are a methyl group.

According to one embodiment of the present application, Chemical Formula 1-1 is any one of the following Chemical Formulae 1-1-1 to 1-1-3.

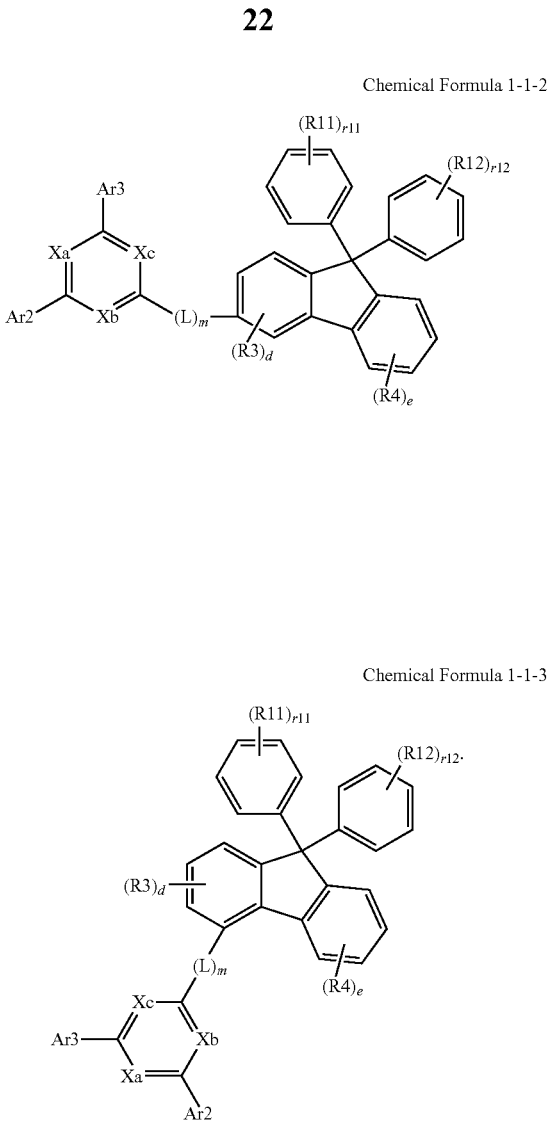

In Chemical Formulae 1-1-1 to 1-1-3:

Ar2, Ar3, Xa to Xc, L, R3, R4, R11, R12, r11, r12, m, d and e have the same definitions as in Chemical Formula 1-1.

According to one embodiment of the present application, Chemical Formula 1-2 is any one of the following Chemical Formulae 1-2-1 to 1-2-3:

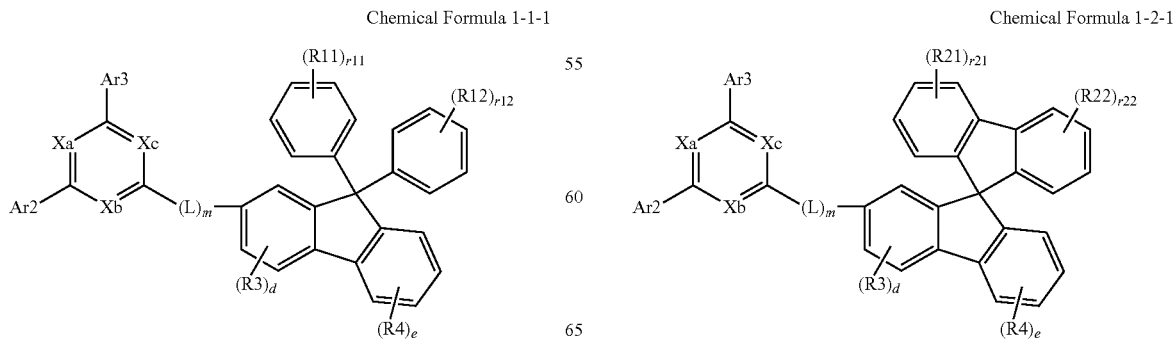

Chemical Formula 1-2-2

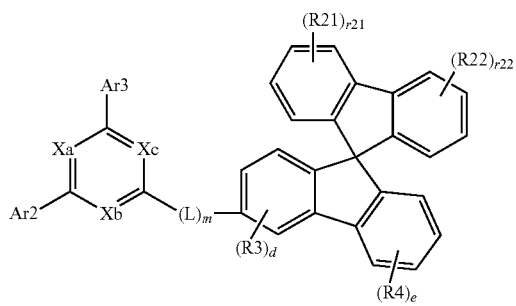

Chemical Formula 1-3-2

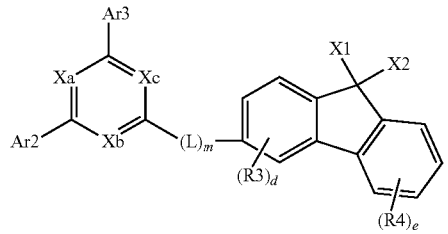

Chemical Formula 1-2-3

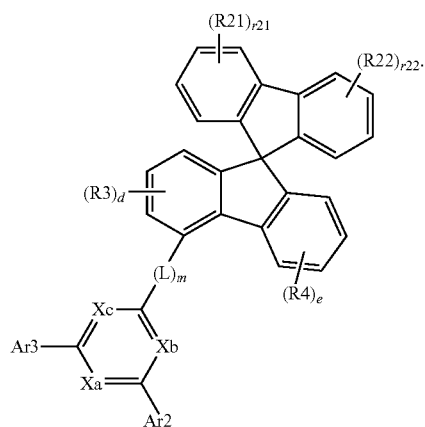

Chemical Formula 1-3-3

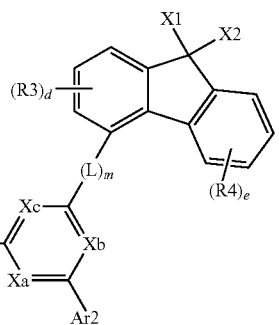

In Chemical Formulae 1-2-1 to 1-2-3:

Ar2, Ar3, Xa to Xc, L, R3, R4, R21, R22, r21, r22, m, d and e have the same definitions as in Chemical Formula 1-2.

According to one embodiment of the present application, Chemical Formula 1-3 is any one of the following Chemical Formulae 1-3-1 to 1-3-3:

In Chemical Formulae 1-3-1 to 1-3-3:

Ar2, Ar3, Xa to Xc, L, R3, R4, X1, X2, m, d and e have the same definitions as in Chemical Formula 1-3.

According to one embodiment of the present application, Chemical Formula 1 is any one of the following Chemical Formulae 1-4 to 1-6:

Chemical Formula 1-3-1

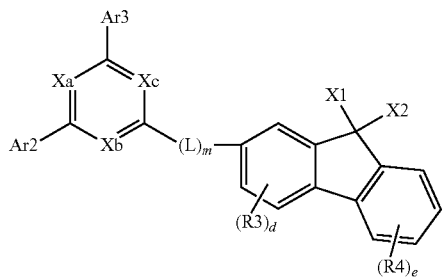

Chemical Formula 1-4

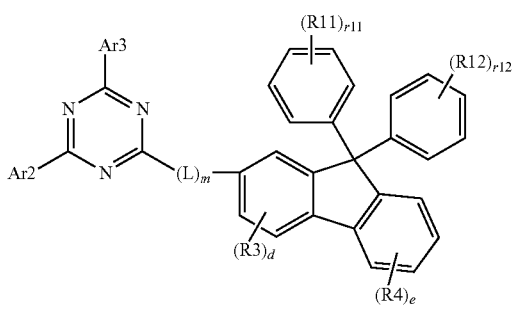

Chemical Formula 1-5

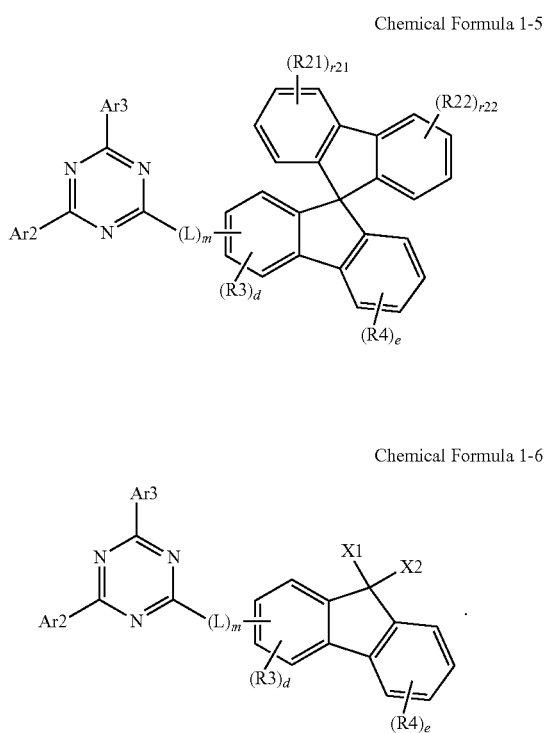

Chemical Formula 1-6

In Chemical Formulae 1-4 to 1-6:

Ar2, Ar3, L, R3, R4, R11, R12, R21, R22, X1, X2, r11, r12, r21, r22, m, d and e have the same definitions as described above.

Hereinafter, Chemical Formula 2 will be described in detail.

According to one embodiment of the present application, HAr is a substituted or unsubstituted heterocyclic group including at least one or more Ns.

According to one embodiment of the present application, HAr is a substituted or unsubstituted heterocyclic group having 2 to 60 carbon atoms including at least one or more Ns.

According to one embodiment of the present application, HAr is a substituted or unsubstituted heterocyclic group having 2 to 30 carbon atoms including at least one or more Ns.

According to one embodiment of the present application, HAr is a heterocyclic group including at least one or more Ns unsubstituted or substituted with an aryl group or a heterocyclic group.

According to one embodiment of the present application, HAr is a pyridyl group unsubstituted or substituted with an aryl group or a heterocyclic group; a pyrimidyl group unsubstituted or substituted with an aryl group or a heterocyclic group; a triazinyl group unsubstituted or substituted with an aryl group or a heterocyclic group; or a phenanthroline group unsubstituted or substituted with an aryl group or a heterocyclic group.

According to one embodiment of the present application, HAr is a pyridyl group unsubstituted or substituted with one or more of a phenyl group, a biphenyl group, a dimethylfluorenyl group, a diphenylfluorenyl group and a spiro[fluorene-9,9'-xanthene] group; a pyrimidyl group unsubstituted or substituted with one or more of a phenyl group, a biphenyl group, a dimethylfluorenyl group, a diphenylfluorenyl group and a spiro[fluorene-9,9'-xanthene] group; a triazinyl group unsubstituted or substituted with a phenyl group, a biphenyl group, a dimethylfluorenyl group, a diphenylfluorenyl group and a spiro[fluorene-9,9'-xanthene] group; or a phenanthroline group.

According to one embodiment of the present application, HAr is the following Chemical Formula 2-1:

Chemical Formula 2-1

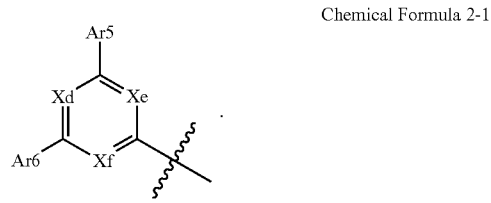

In Chemical Formula 2-1:

Ar5 and Ar6 are a substituted or unsubstituted aryl group; or a substituted or unsubstituted heterocyclic group, or bond to adjacent groups to form a ring; and at least one of Xd to Xf is N, and the rest are CH.

According to one embodiment of the present application, Ar5 and Ar6 are a substituted or unsubstituted aryl group having 6 to 60 carbon atoms, or a heterocyclic group having 2 to 60 carbon atoms, or bond to adjacent groups to form a ring having 2 to 30 carbon atoms.

According to one embodiment of the present application, Ar5 and Ar6 are a substituted or unsubstituted aryl group having 6 to 30 carbon atoms, or a heterocyclic group having 2 to 30 carbon atoms, or bond to adjacent groups to form a ring having 2 to 20 carbon atoms.

According to one embodiment of the present application, Ar5 and Ar6 are a substituted or unsubstituted aryl group having 6 to 20 carbon atoms, or a heterocyclic group having 2 to 20 carbon atoms, or bond to adjacent groups to form a ring having 2 to 15 carbon atoms.

According to one embodiment of the present application, Ar5 and Ar6 are a substituted or unsubstituted phenyl group, a substituted or unsubstituted biphenyl group, a substituted or unsubstituted fluorenyl group, or a substituted or unsubstituted spiro[fluorene-9,9'-xanthene] group, or bond to adjacent groups to foam a quinol group.

According to one embodiment of the present application, Ar5 and Ar6 are a phenyl group, a biphenyl group, a dimethylfluorenyl group, a diphenylfluorenyl group, or a spiro[fluorene-9,9'-xanthene] group.

According to one embodiment of the present application, Ar5 and Ar6 are a phenyl group, a biphenyl group, a diphenylfluorenyl group, or a spiro[fluorene-9,9'-xanthene] group.

According to one embodiment of the present application, Ar5 and Ar6 are any one of the following substituents:

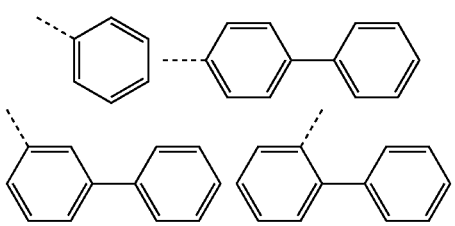

-continued

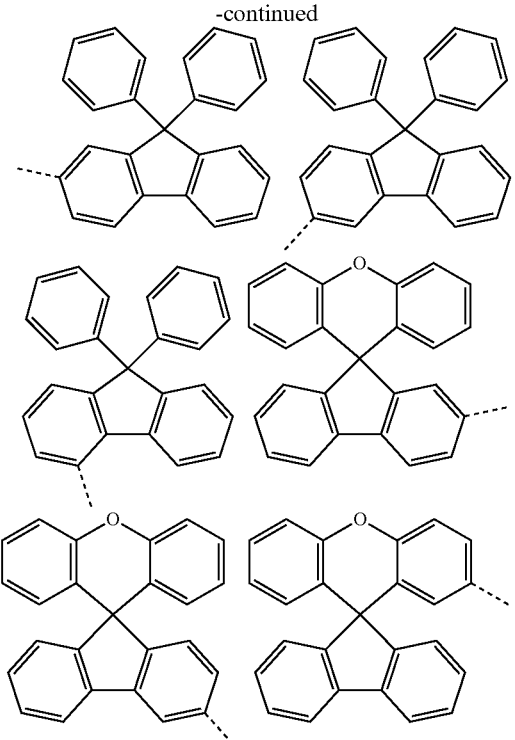

According to one embodiment of the present application, at least one of Ar2 to Ar4 is a substituted or unsubstituted heterocyclic group, and the rest are a substituted or unsubstituted aryl group.

In one embodiment of the present application, Xd is N, and the rest are CH.

In one embodiment of the present application, Xe is N, and the rest are CH.

In one embodiment of the present application, Xf is N, and the rest are CH.

In one embodiment of the present application, Xd and Xe are N, and the rest is CH.

In one embodiment of the present application, Xd and Xf are N, and the rest is CH.

In one embodiment of the present application, Xe and Xf are N, and the rest is CH.

In one embodiment of the present application, Xd to Xf are N.

According to one embodiment of the present application, L1 and L2 are each independently a direct bond, a substituted or unsubstituted arylene group, or a substituted or unsubstituted divalent heterocyclic group.

According to one embodiment of the present application, L1 and L2 are each independently a direct bond, a substituted or unsubstituted arylene group having 6 to 60 carbon atoms, or a substituted or unsubstituted divalent heterocyclic group having 2 to 60 carbon atoms.

According to one embodiment of the present application, L1 and L2 are each independently a direct bond, a substituted or unsubstituted arylene group having 6 to 30 carbon atoms, or a substituted or unsubstituted divalent heterocyclic group having 2 to 30 carbon atoms.

According to one embodiment of the present application, L1 and L2 are each independently a direct bond, a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, a substituted or unsubstituted divalent dibenzofuranyl group, a substituted or unsubstituted divalent dibenzothiophenyl group, or a substituted or unsubstituted divalent spiro[fluorene-9,9'-xanthene] group.

According to one embodiment of the present application, L1 and L2 are each independently a direct bond; a phenylene group, a biphenylene group, a naphthylene group, a terphenylene group, a dimethylfluorenylene group, a diphenylfluorenylene group, a divalent dibenzofuranyl group, a divalent dibenzothiophenyl group, or a divalent spiro[fluorene-9,9'-xanthene] group, and the substituent can be unsubstituted or substituted with one or more groups of a cyano group, an aryl group having 6 to 20 carbon atoms and a heterocyclic group having 2 to 20 carbon atoms, or a group bonding two or more thereof.

According to one embodiment of the present application, L1 and L2 are each independently a direct bond, a phenylene group, a biphenylene group, a naphthylene group, a terphenylene group, a dimethylfluorenylene group, a diphenylfluorenylene group, a divalent dibenzofuranyl group, a divalent dibenzothiophenyl group, or a divalent spiro[fluorene-9,9'-xanthene] group, and the substituent can be unsubstituted or substituted with one or more groups of a cyano group, a phenyl group, a biphenyl group, a phenanthrenyl group, a dimethylfluorenyl group, a dibenzofuranyl group, a dibenzothiophenyl group, a pyridyl group, a pyrimidyl group and a triazinyl group, or a group bonding two or more thereof.

According to one embodiment of the present application, L1 and L2 are each independently a direct bond, or any one of the following structural formulae:

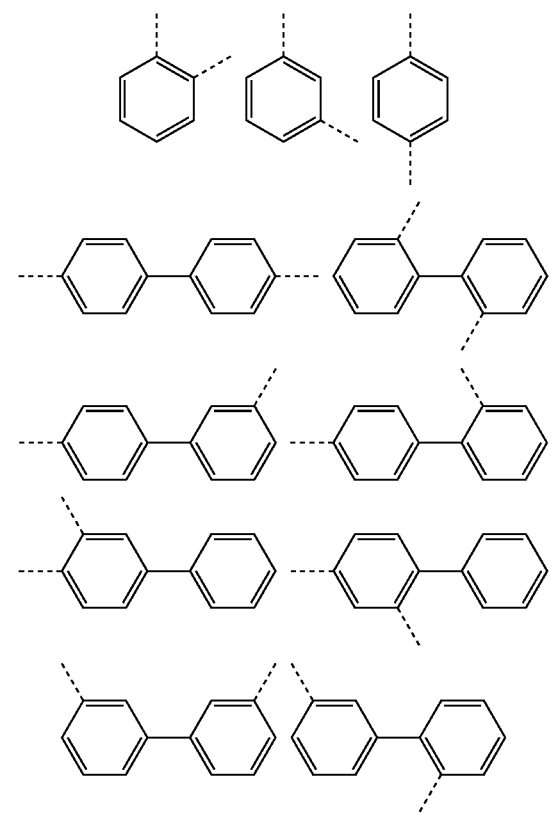

-continued
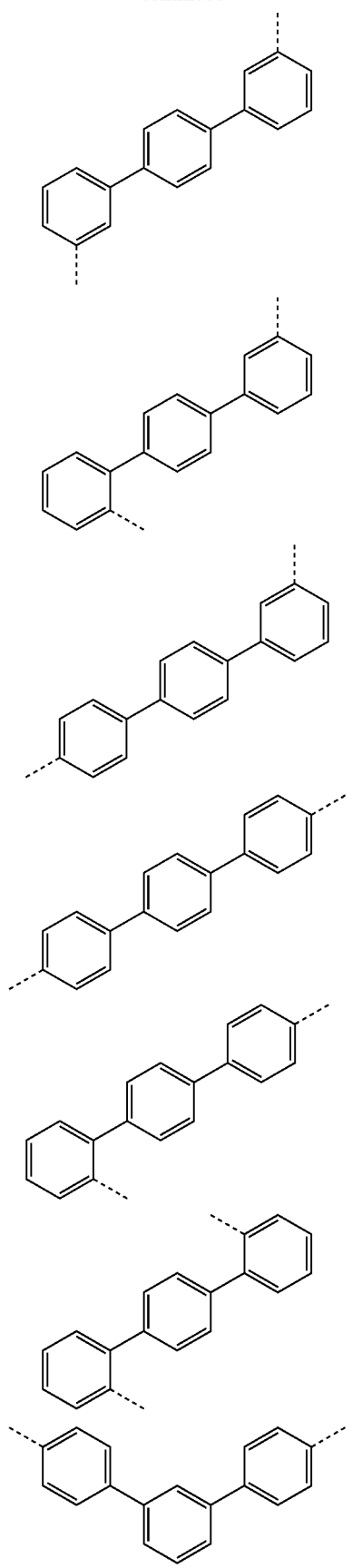
-continued
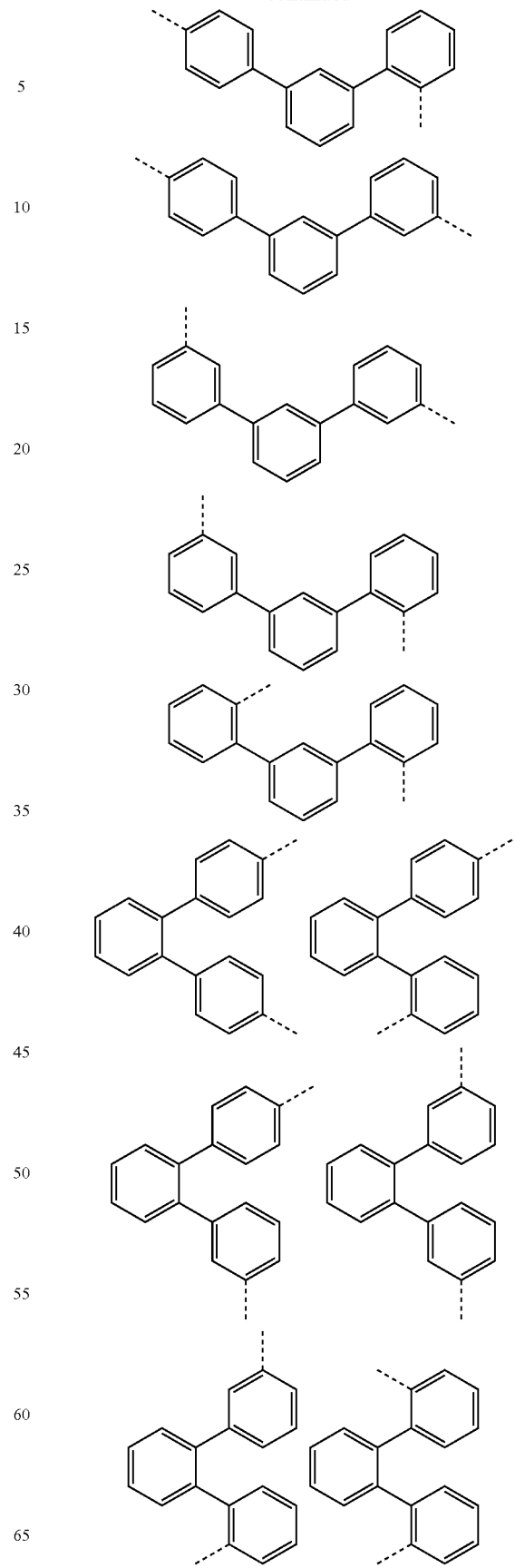

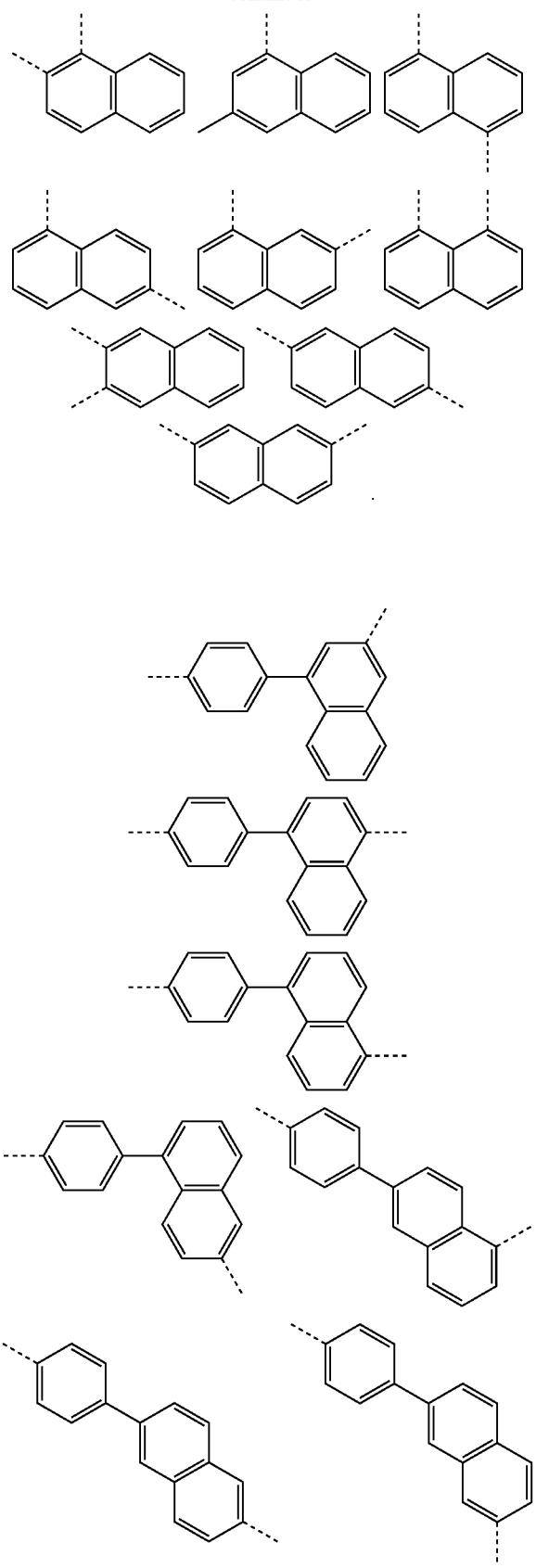
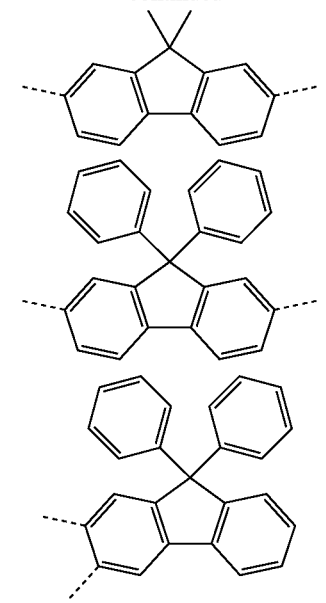
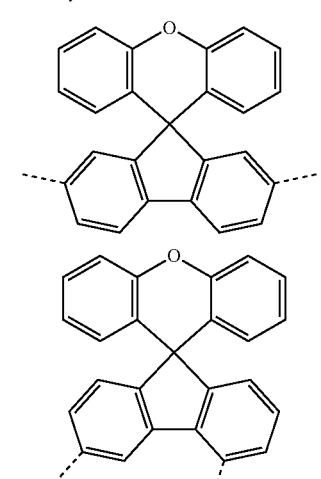
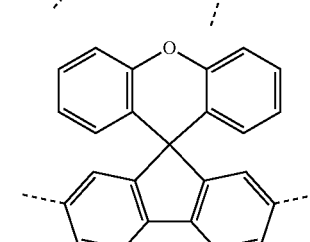
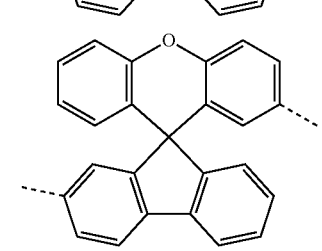
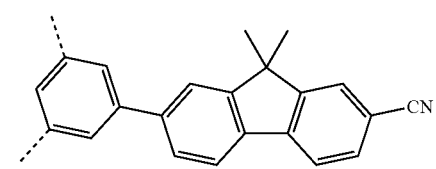

-continued

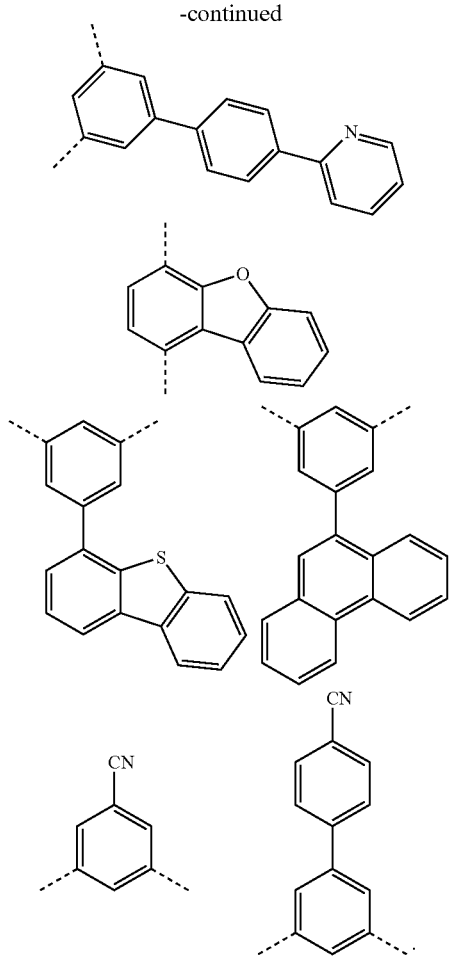

In the structural formulae, the dotted part means a bonding position.

In one embodiment of the present specification, Ar1 is a direct bond, —O—, a substituted or unsubstituted arylene group, or a substituted or unsubstituted divalent heterocyclic group.

In one embodiment of the present specification, Ar1 is a direct bond, —O—, a substituted or unsubstituted arylene group having 6 to 60 carbon atoms, or a substituted or unsubstituted divalent heterocyclic group having 2 to 60 carbon atoms.

In one embodiment of the present specification, Ar1 is a direct bond, —O—, a substituted or unsubstituted arylene group having 6 to 30 carbon atoms, or a substituted or unsubstituted divalent heterocyclic group having 2 to 30 carbon atoms.

In one embodiment of the present specification, Ar1 is a direct bond, —O—, a substituted or unsubstituted arylene group having 6 to 20 carbon atoms, or a substituted or unsubstituted divalent heterocyclic group having 2 to 20 carbon atoms.

According to one embodiment of the present application, Ar1 is a direct bond, —O—, a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, a substituted or unsubstituted divalent dibenzofuranyl group, a substituted or unsubstituted divalent dibenzothiophenyl group, or a substituted or unsubstituted divalent spiro[fluorene-9,9'-xanthene] group.

According to one embodiment of the present application, Ar1 is a direct bond; —O—, a phenylene group, a biphenylene group, a naphthylene group, a terphenylene group, a dimethylfluorenylene group; a diphenylfluorenylene group, a divalent dibenzofuranyl group, or a divalent dibenzothiophenyl group, and the substituent is unsubstituted or substituted with one or more groups of a cyano group, an aryl group having 6 to 20 carbon atoms and a heterocyclic group having 2 to 20 carbon atoms, or a group bonding two or more thereof.

According to one embodiment of the present application, Ar1 is a direct bond; —O—, a direct bond; a phenylene group, a biphenylene group, a naphthylene group, a terphenylene group, a dimethylfluorenylene group, a diphenylfluorenylene group, a divalent dibenzofuranyl group, a divalent dibenzothiophenyl group, or a divalent spiro[fluorene-9,9'-xanthene] group, and the substituent is unsubstituted or substituted with one or more groups of a cyano group, a phenyl group, a biphenyl group, a phenanthrenyl group, a dimethylfluorenyl group, a dibenzofuranyl group, a dibenzothiophenyl group, a pyridyl group, a pyrimidyl group and a triazinyl group, or a group bonding two or more thereof.

According to one embodiment of the present application, Ar1s are each independently a direct bond, or —O—, or any one of the following structural formulae:

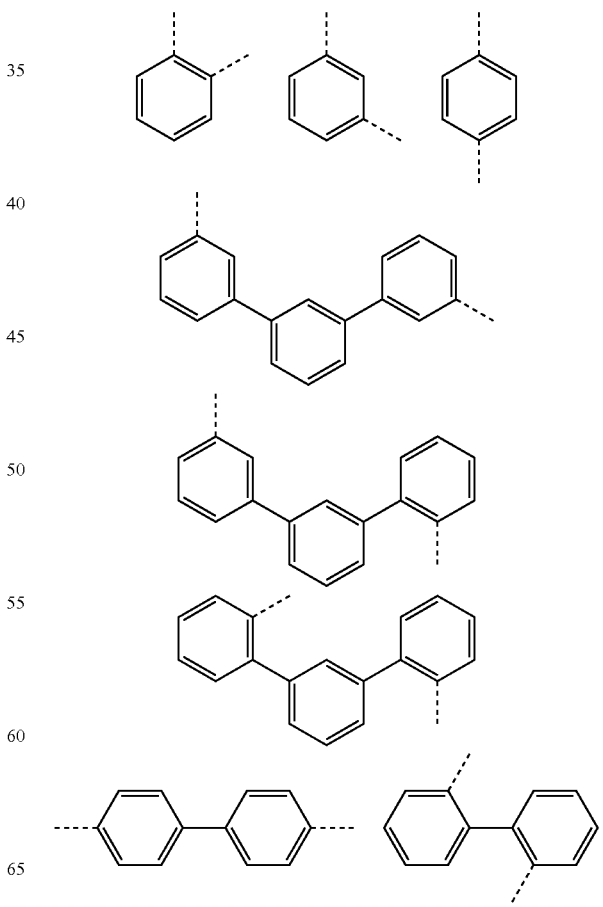

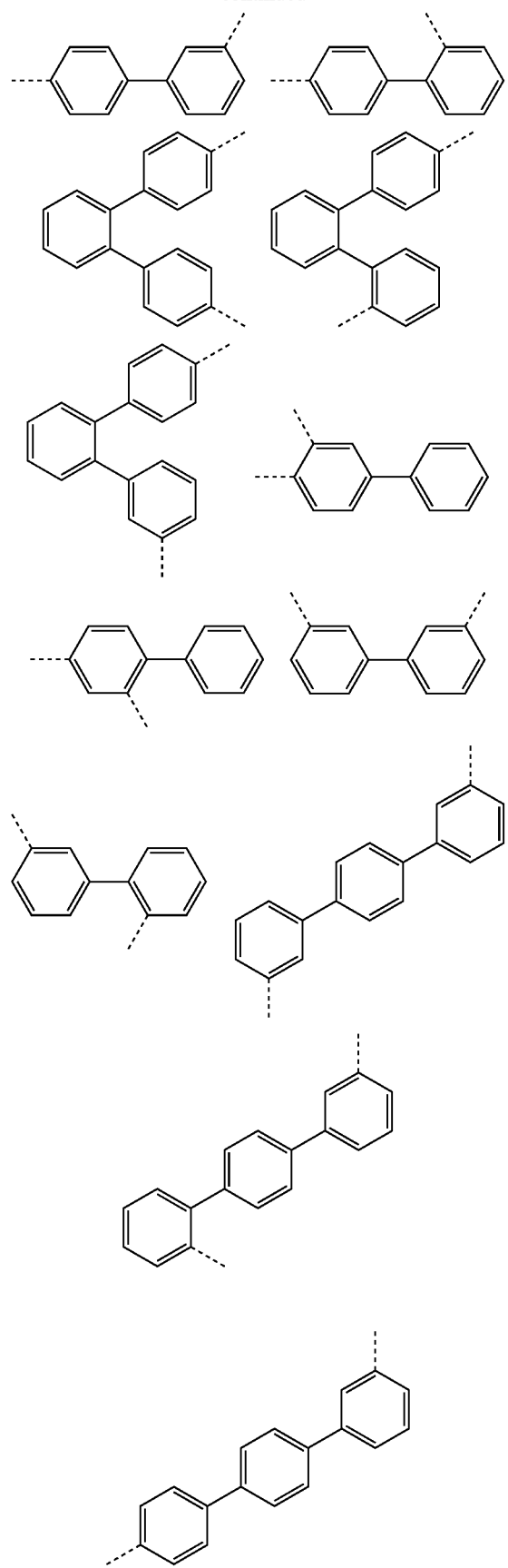
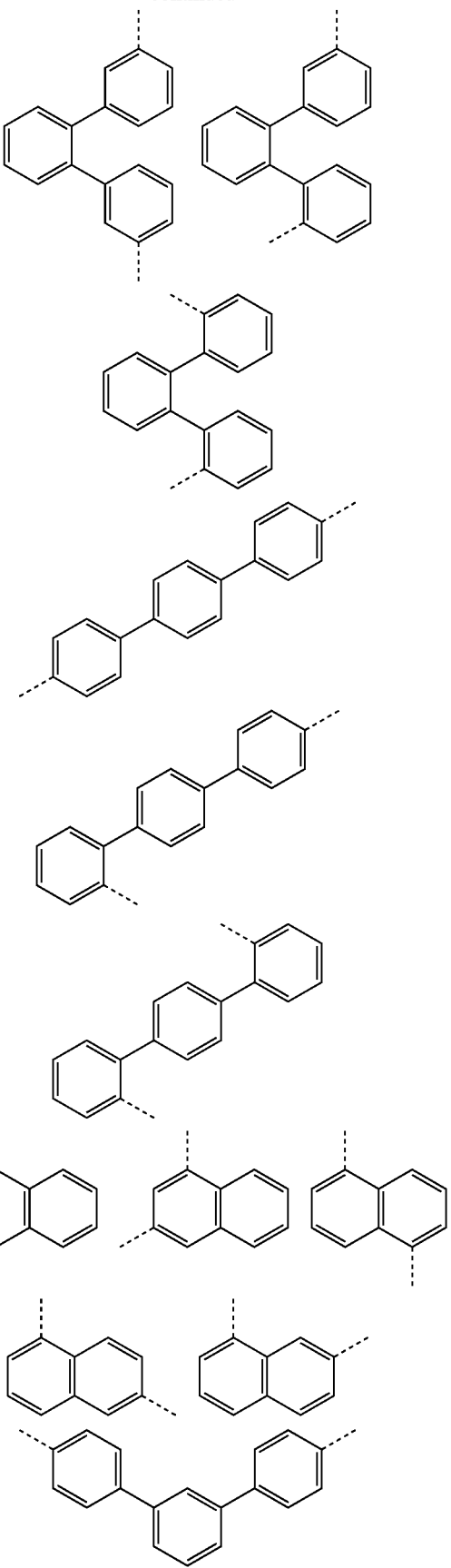

37
-continued
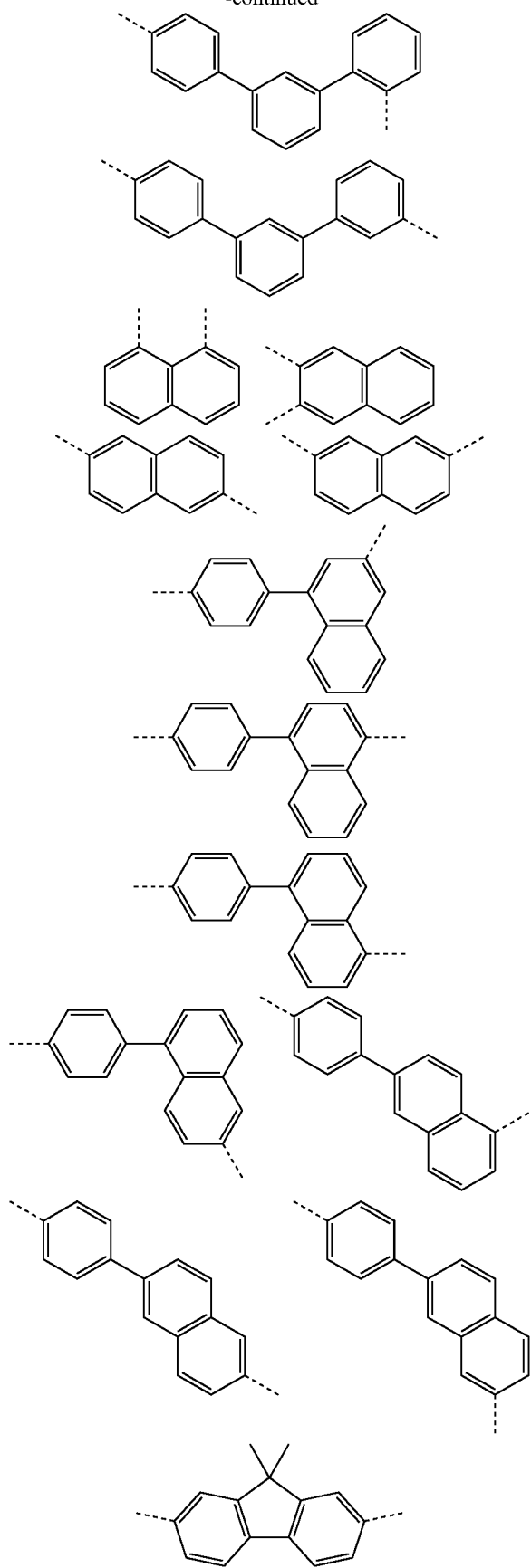
38
-continued
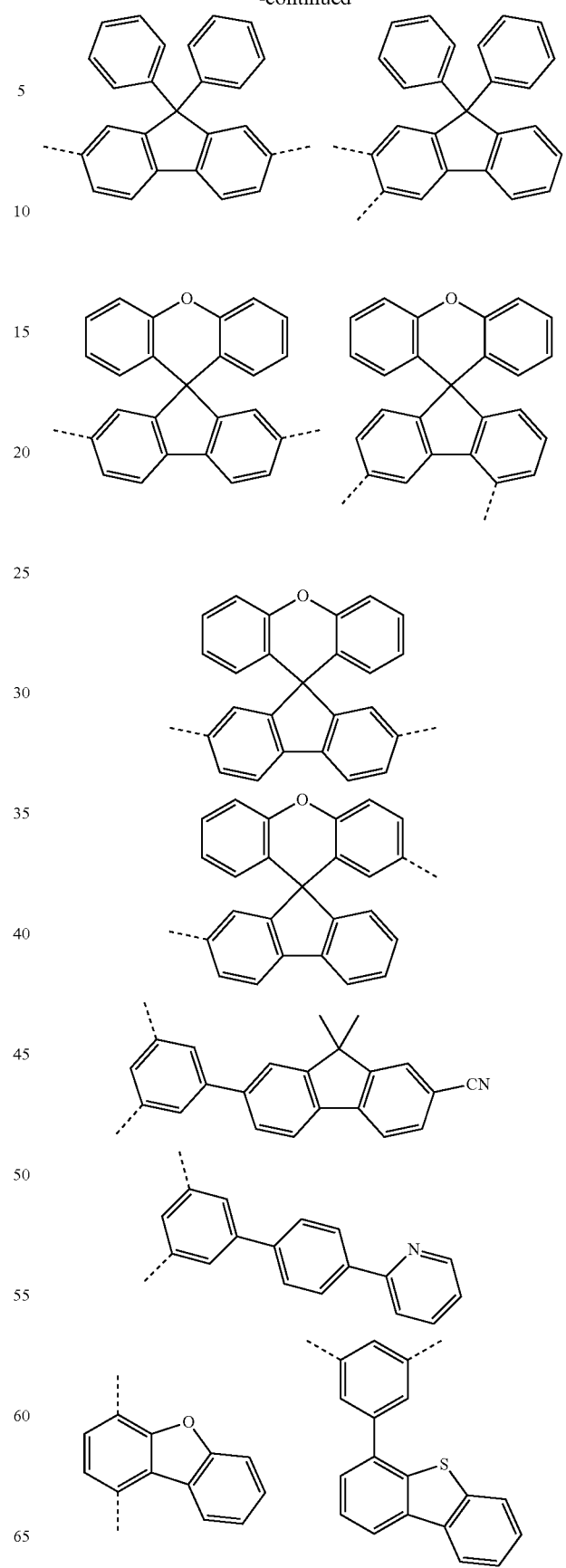

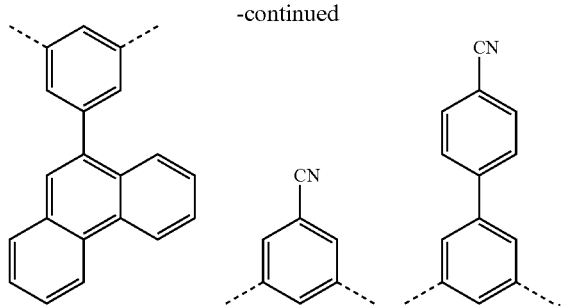
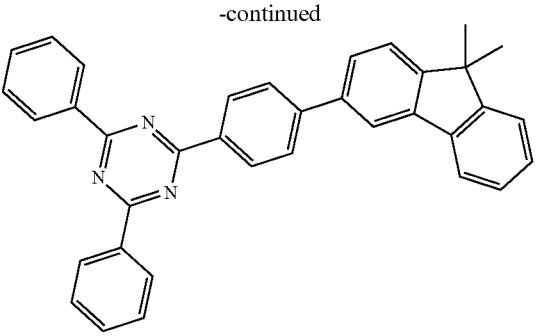

In the structural formulae, the dotted part means a bonding position.

In one embodiment of the present specification, a to c are each an integer of 1 to 3, and when a to c are each 2 or greater, the structures in the two or more parentheses are the same as or different from each other.

In one embodiment of the present specification, a is 1 or 2.

In one embodiment of the present specification, b is 1 or 2.

In one embodiment of the present specification, c is 1 or 2.

In addition, in one embodiment of the present application, the compound of Chemical Formula 1 can be selected from among the following compounds:

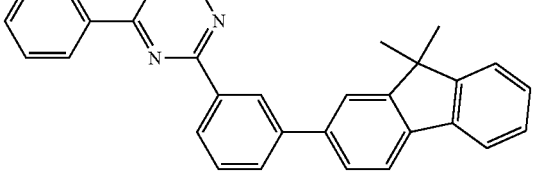

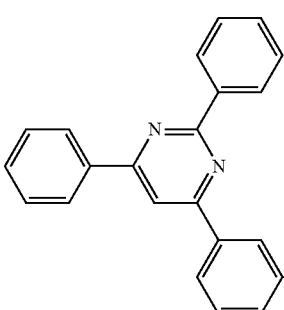

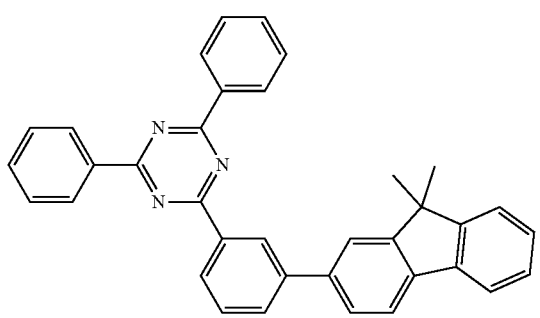

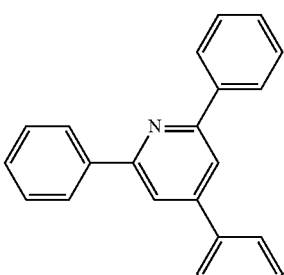

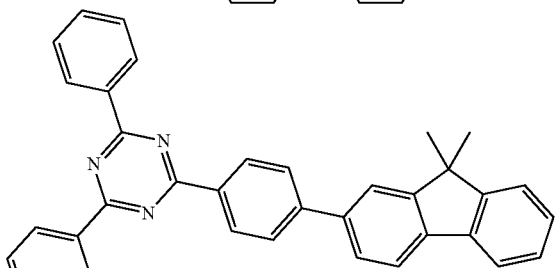

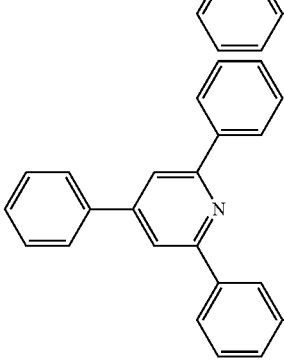

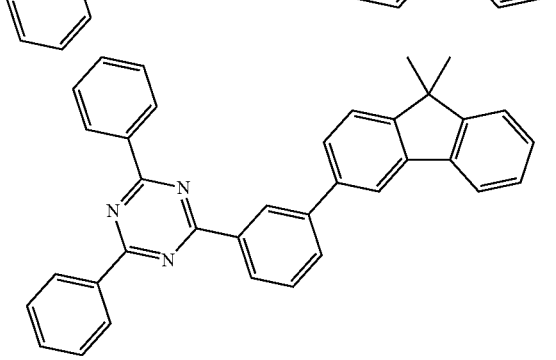

-continued
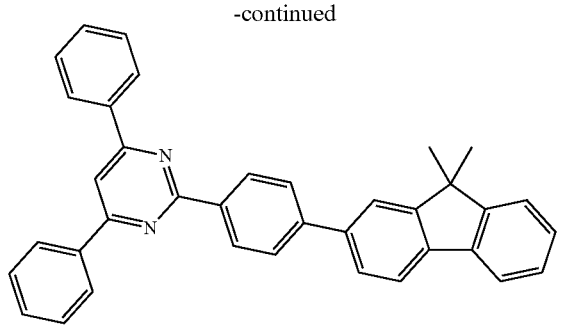
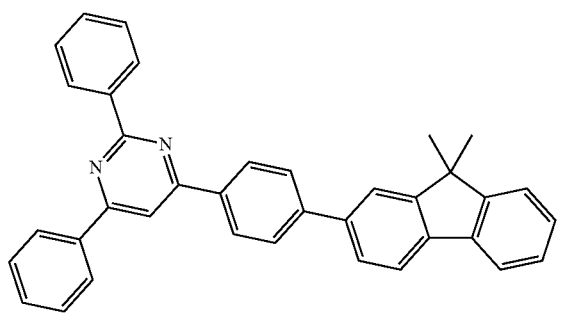
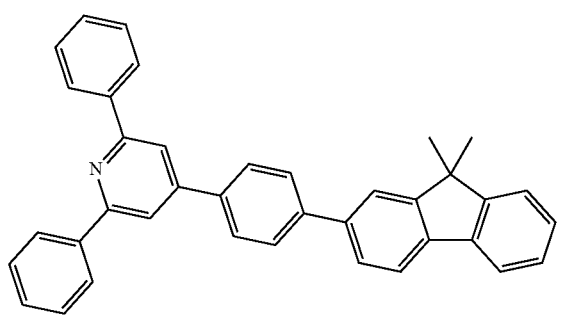
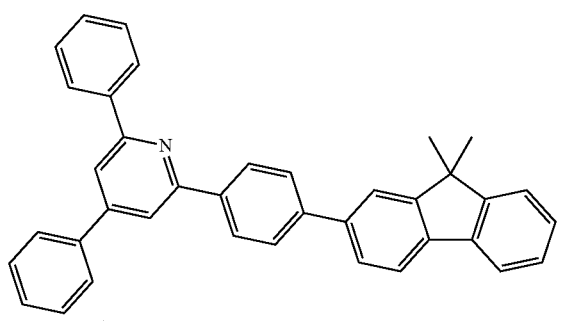
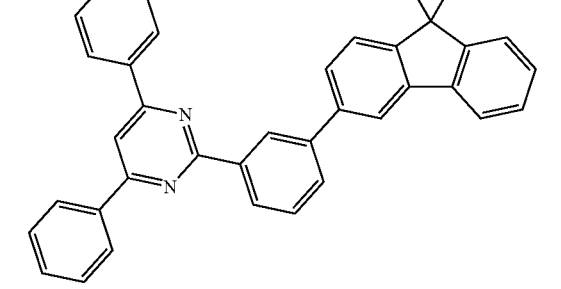
-continued
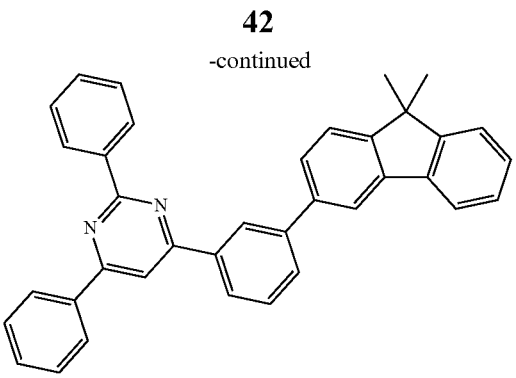
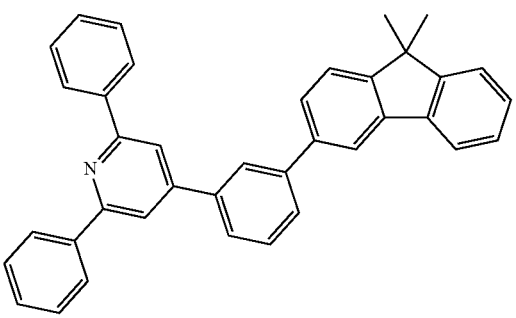
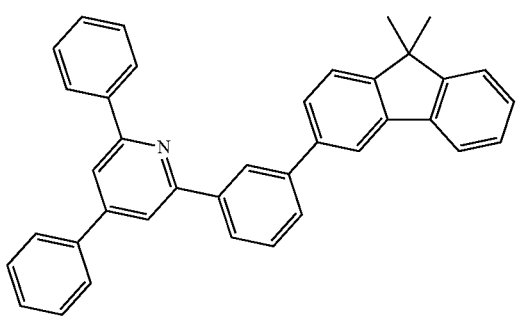
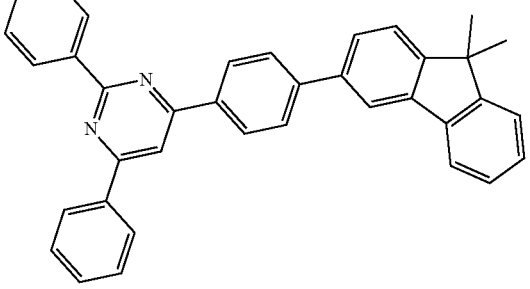

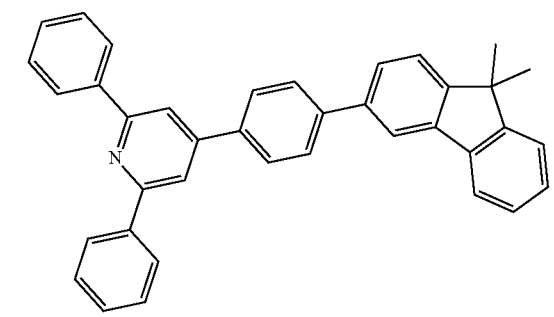
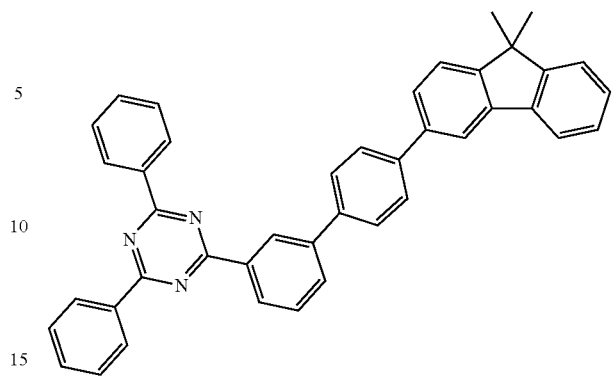
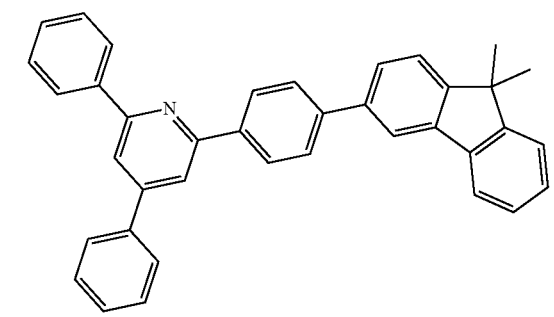
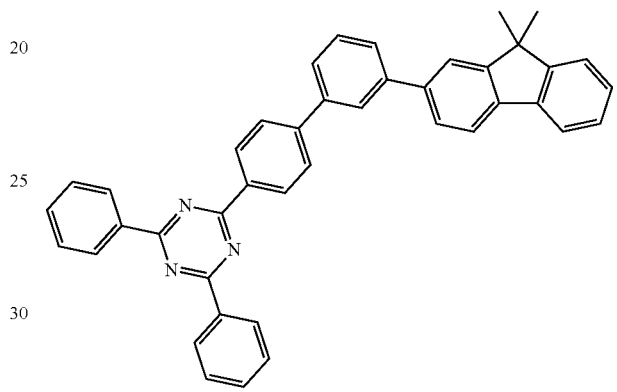
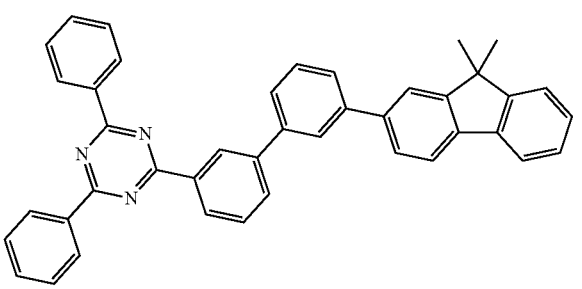
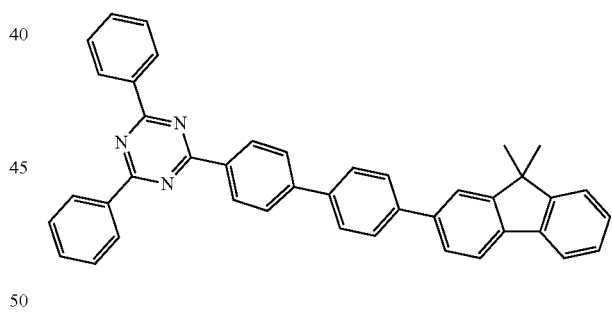
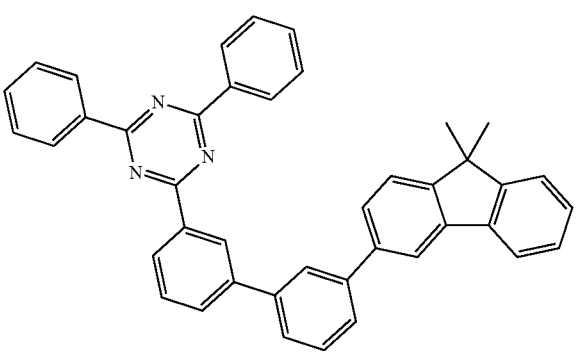
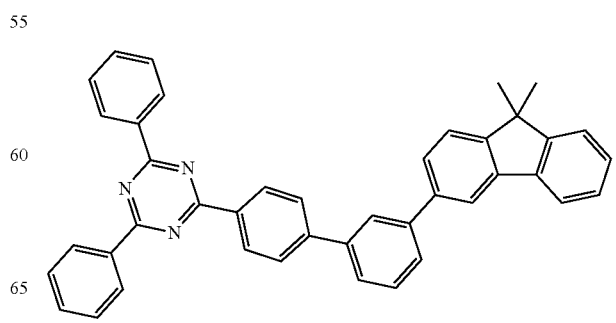

-continued
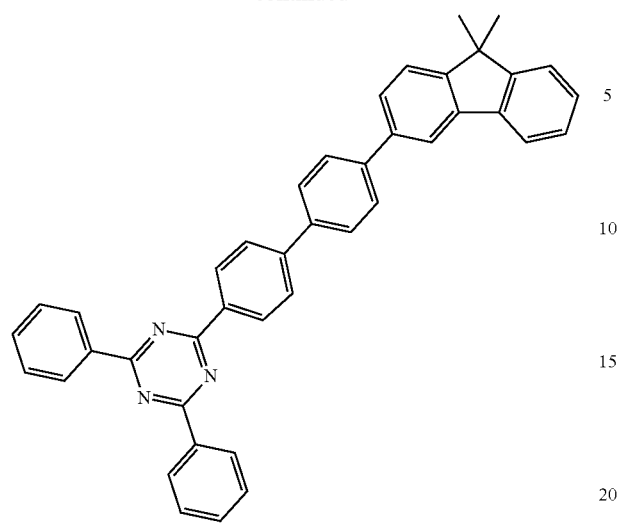
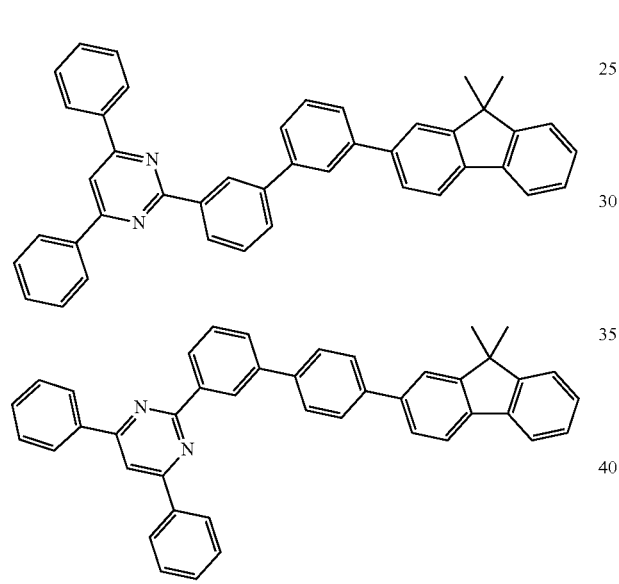
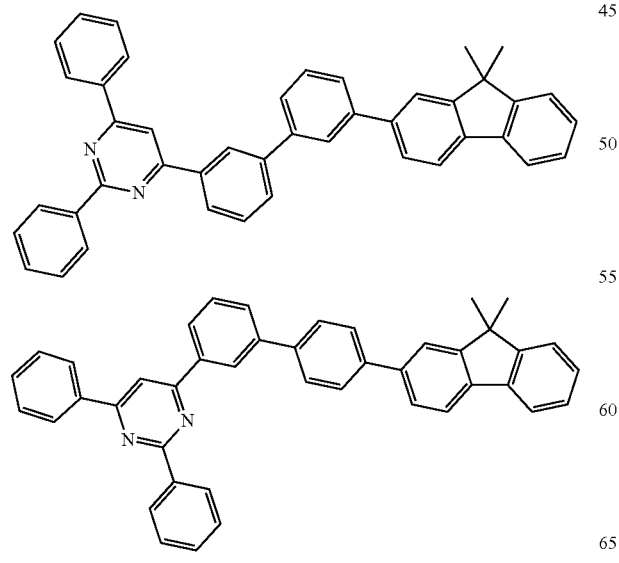
-continued
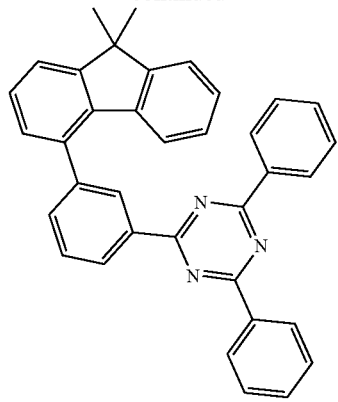
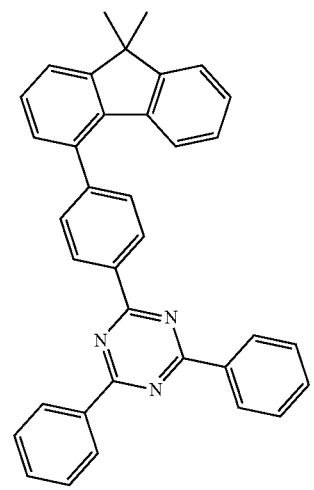
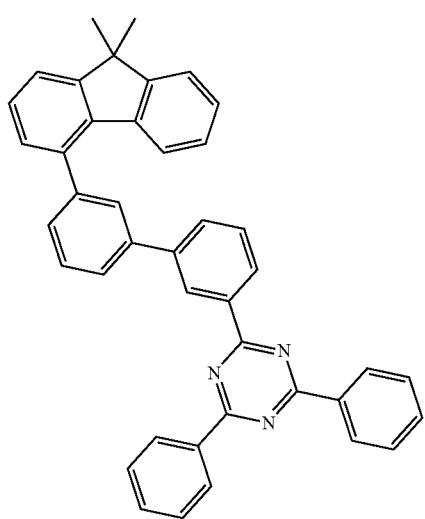

47
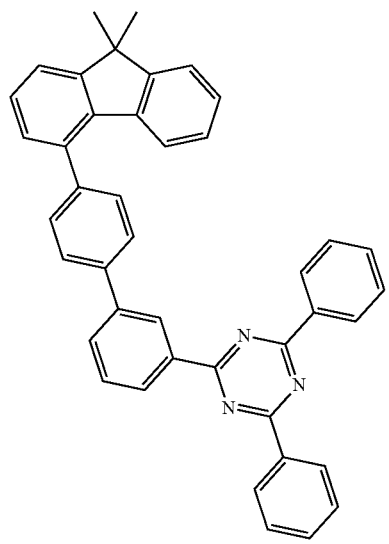
48
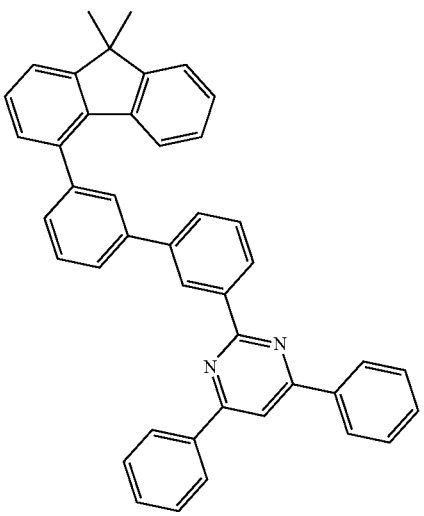
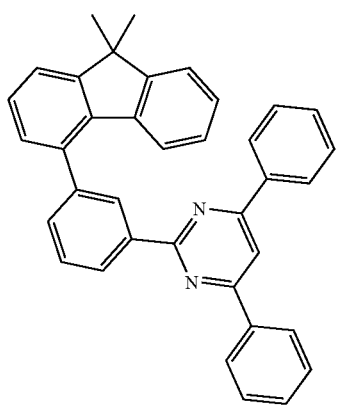
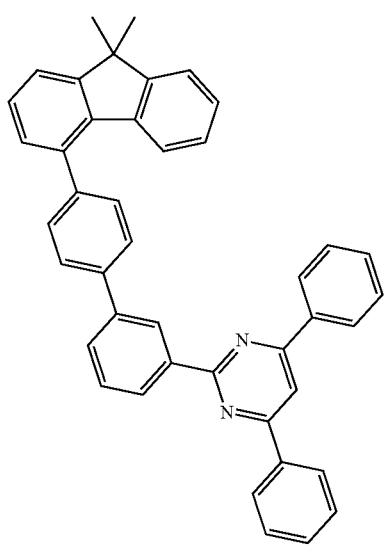
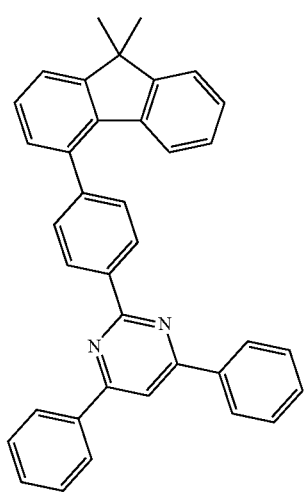
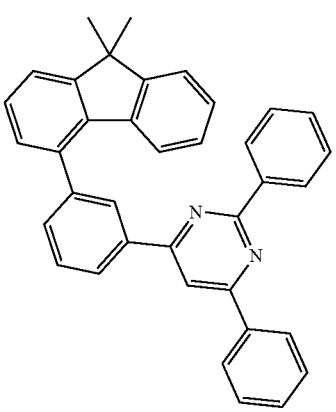

-continued
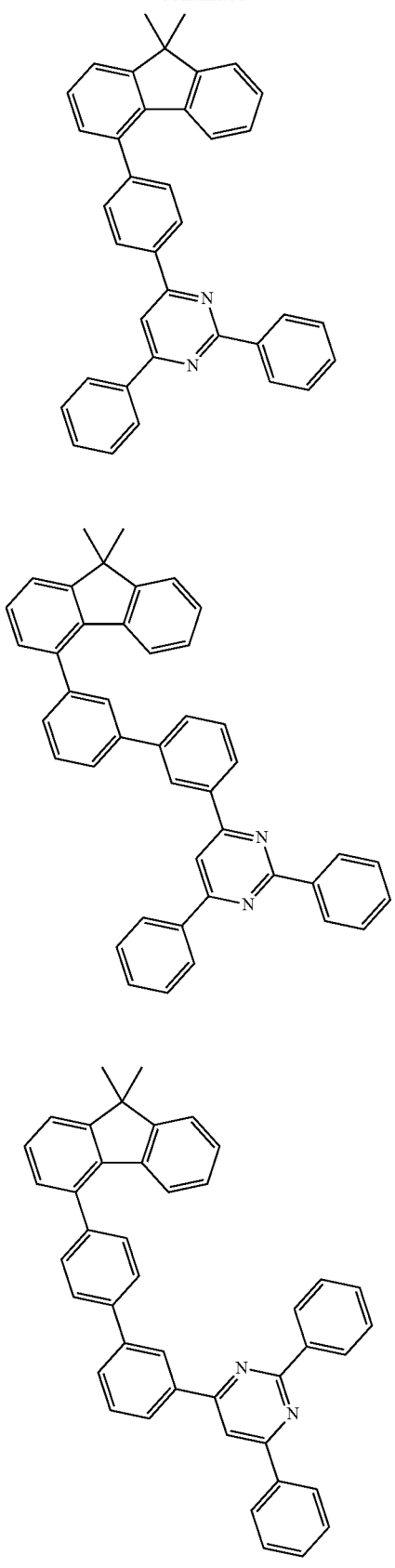
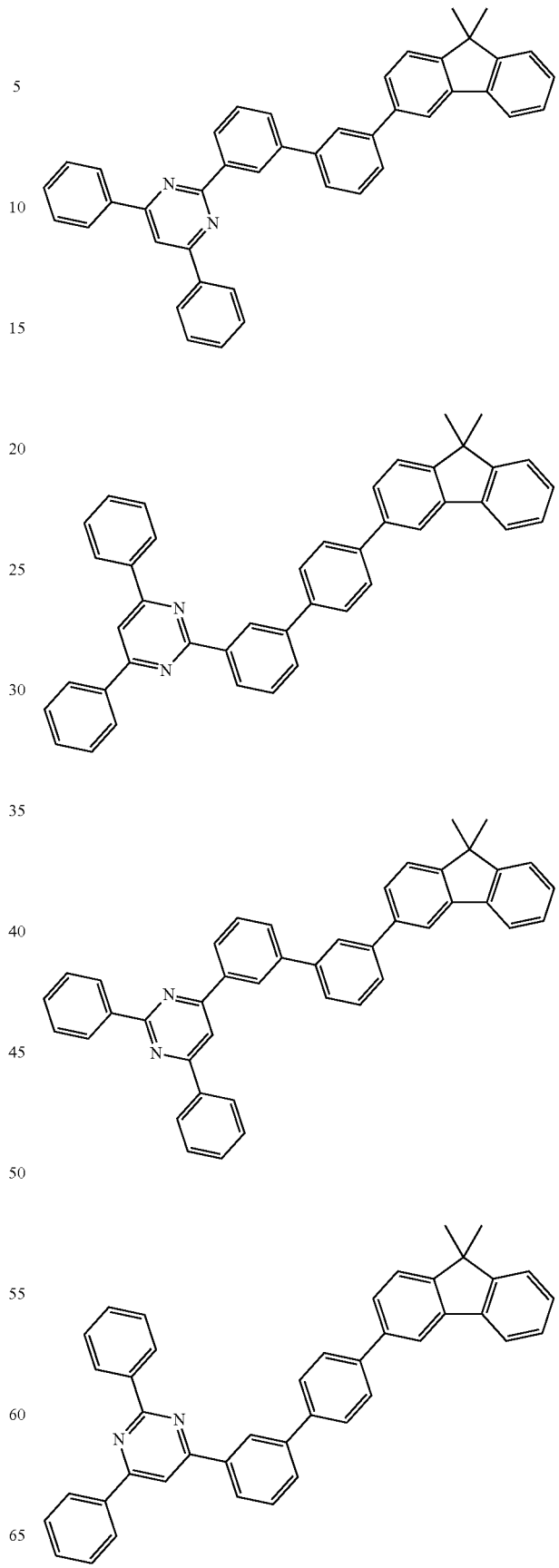

51
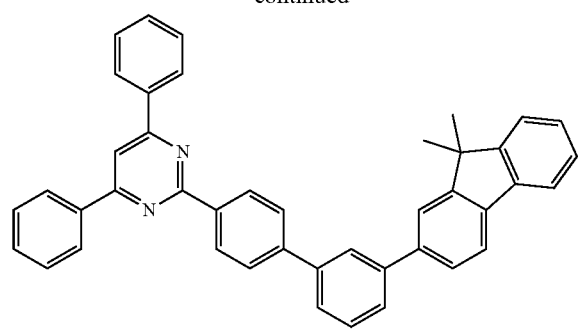
52
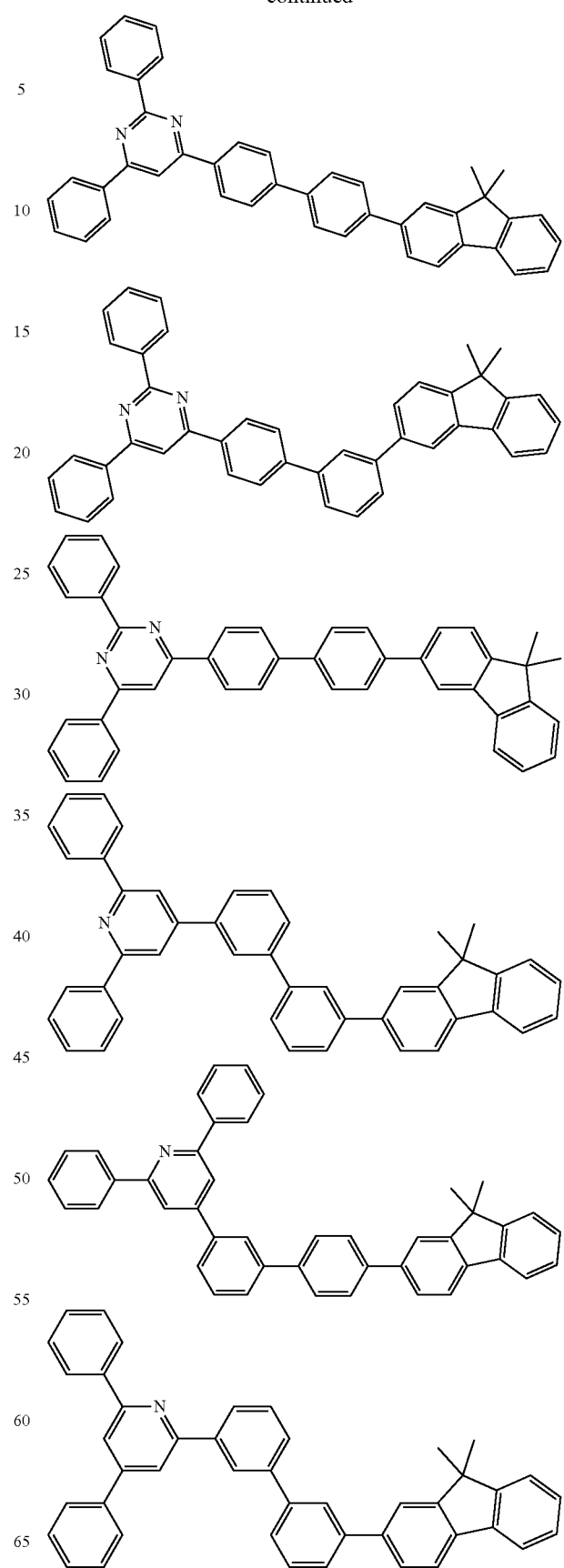

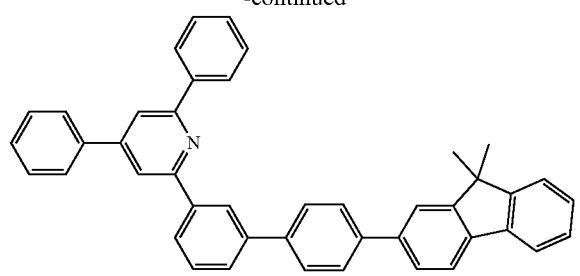
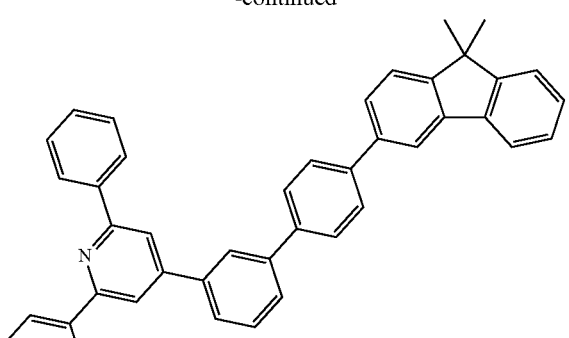
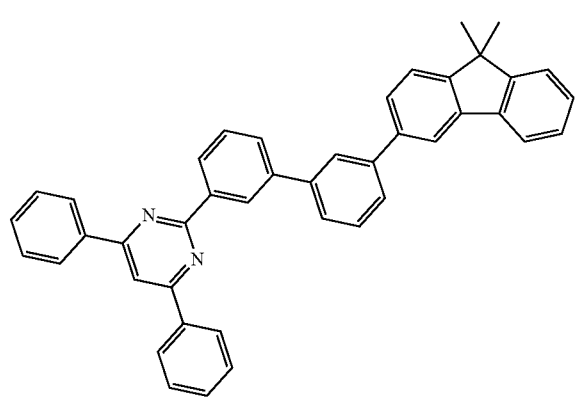
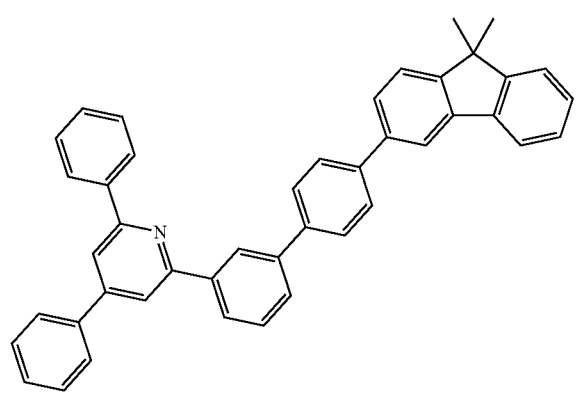
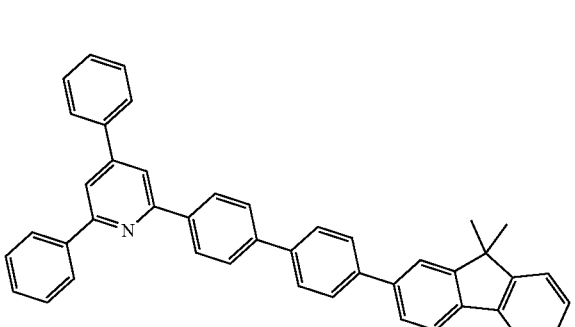
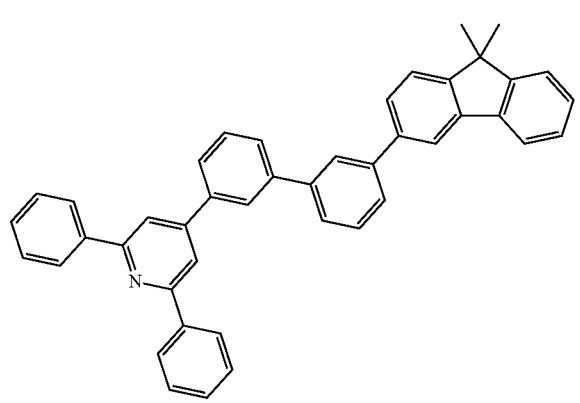
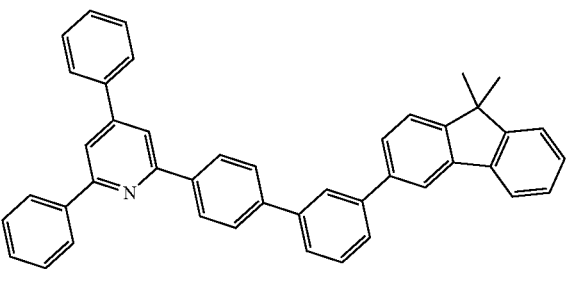
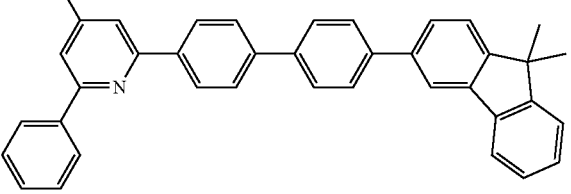

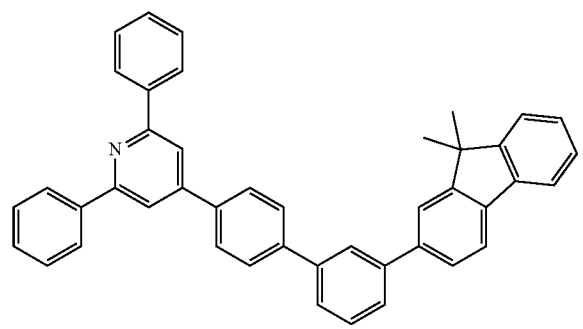
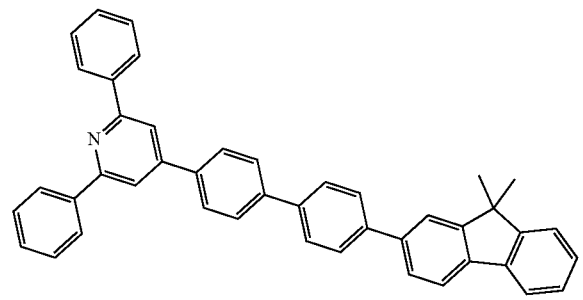
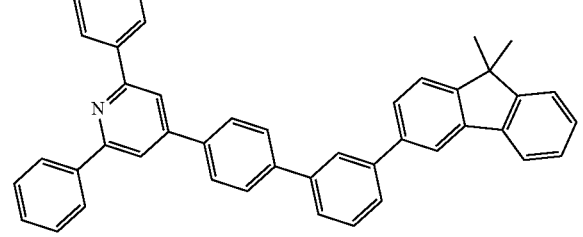
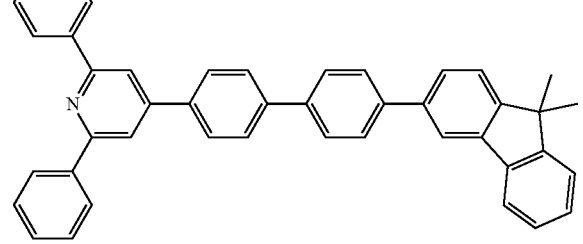
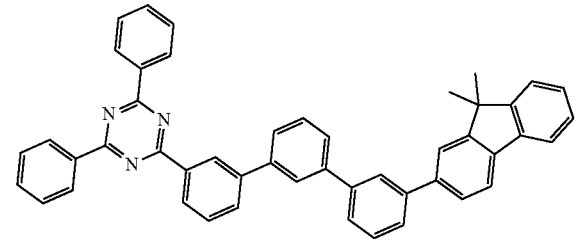
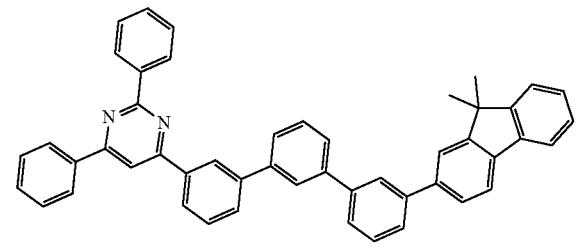
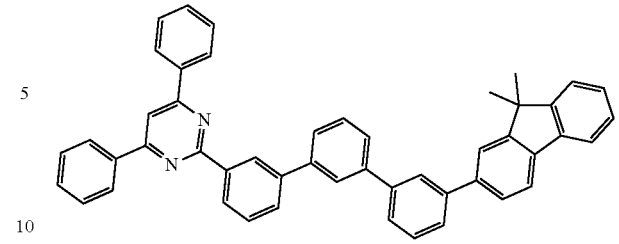
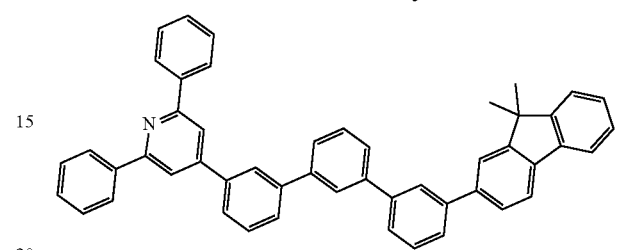
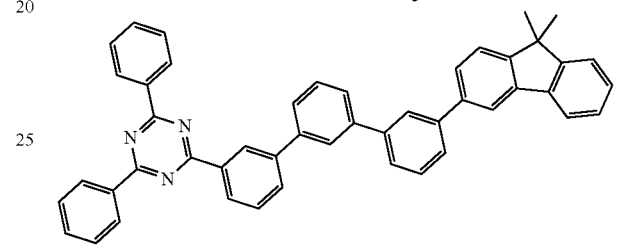
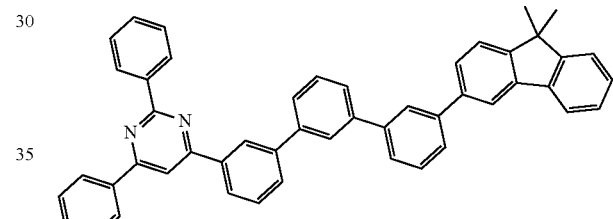
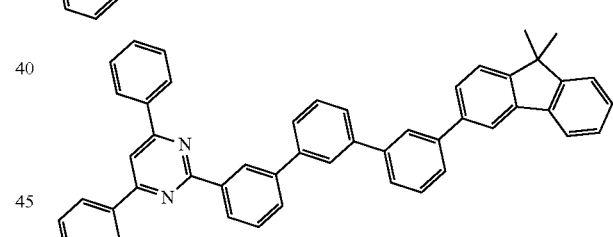
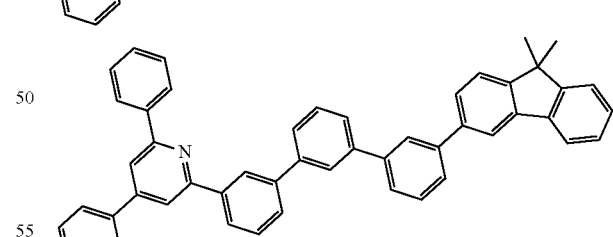

-continued
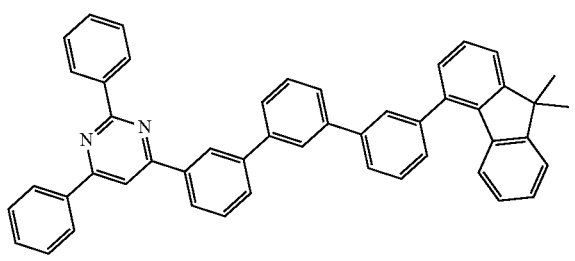
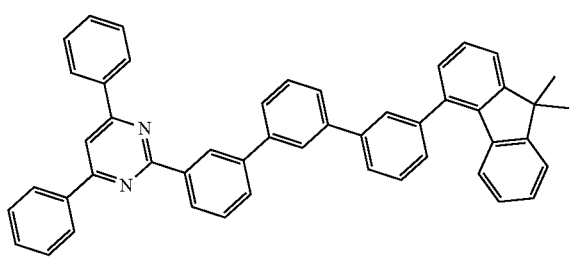
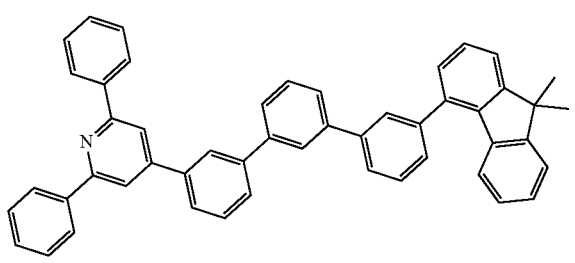
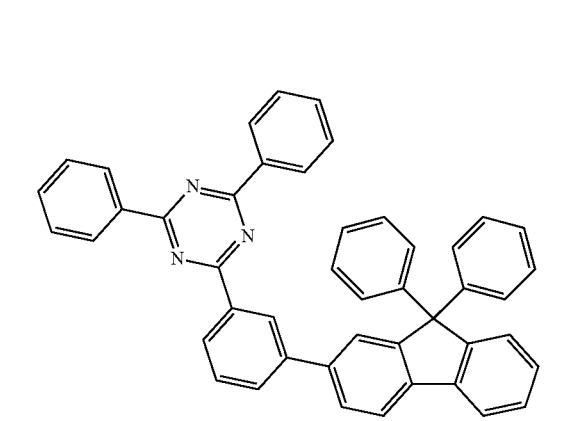
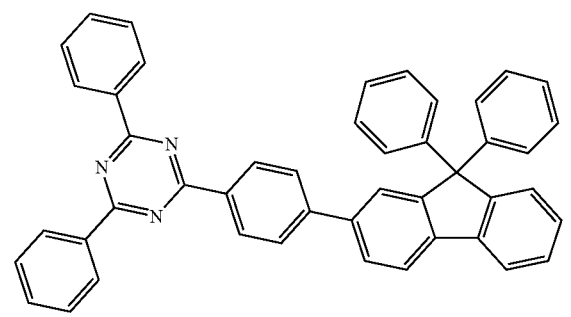
-continued
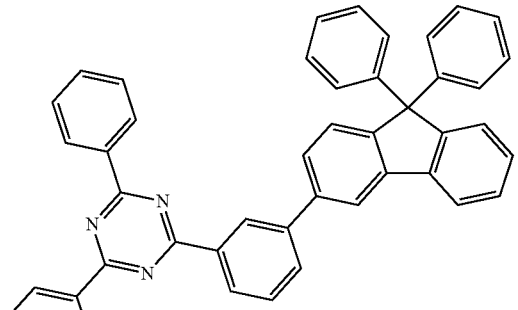
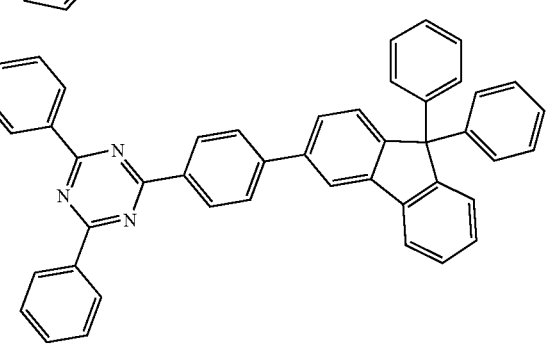
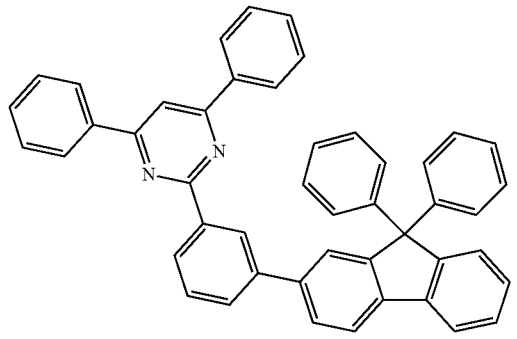
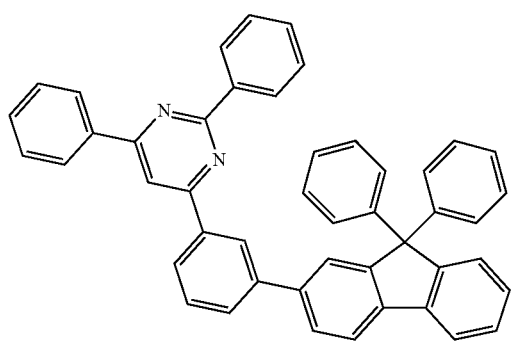
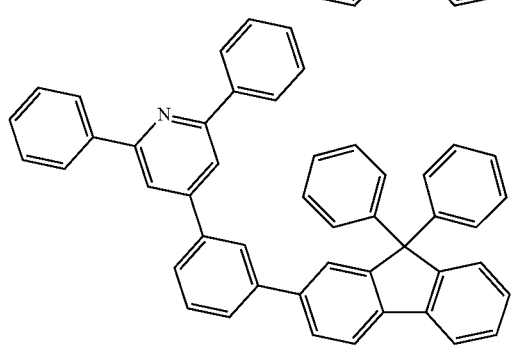

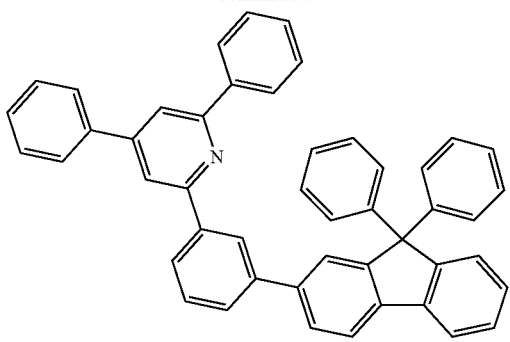
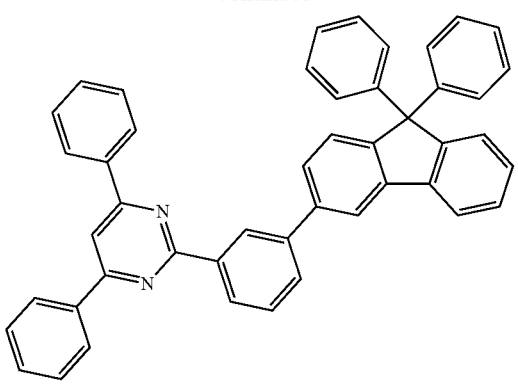

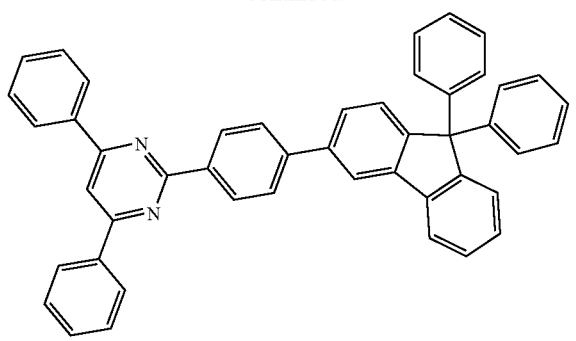
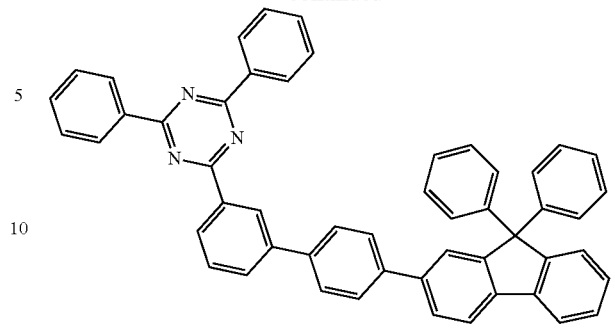
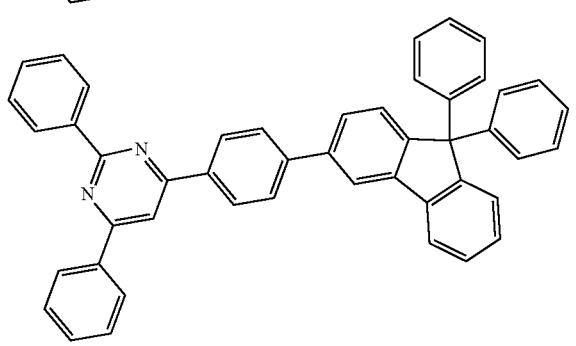
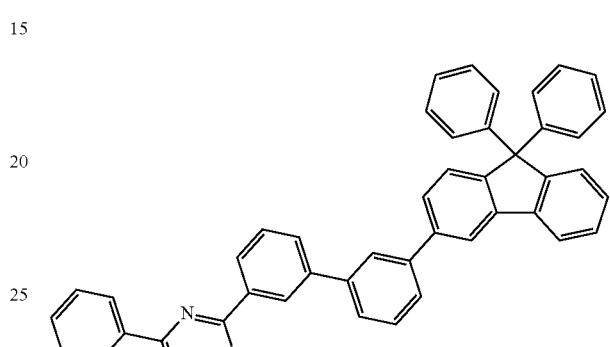
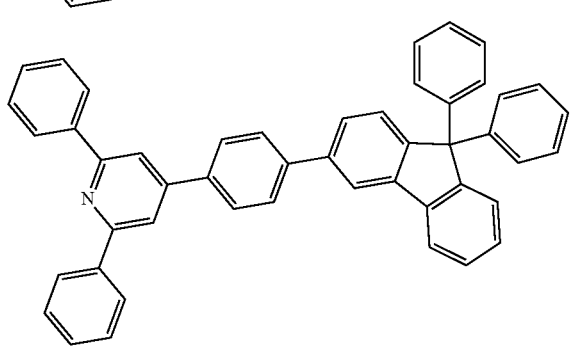
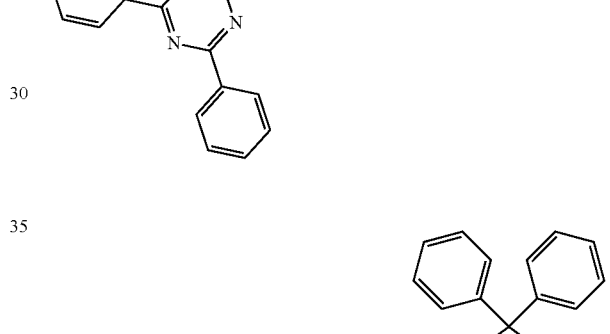
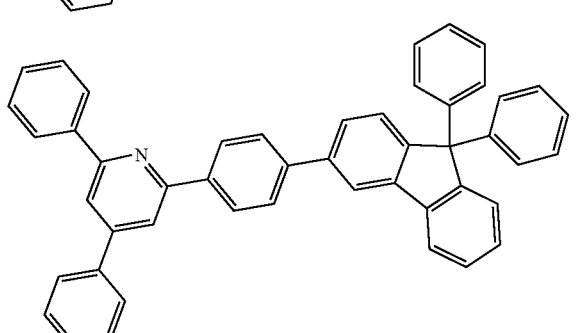
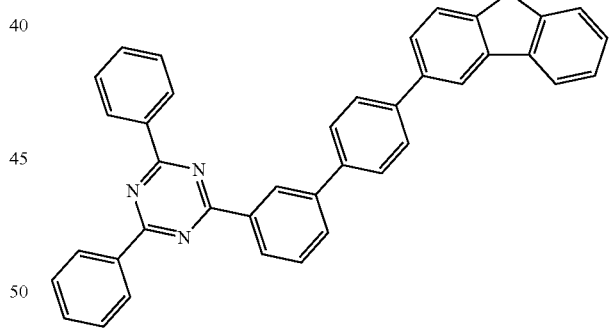
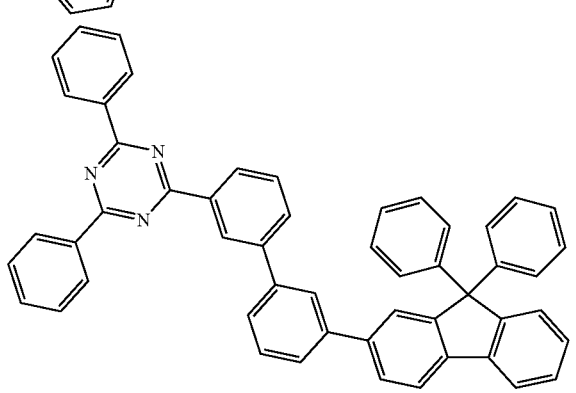
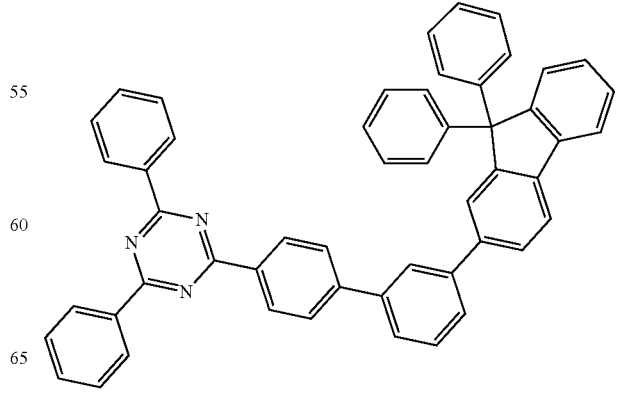

63
-continued
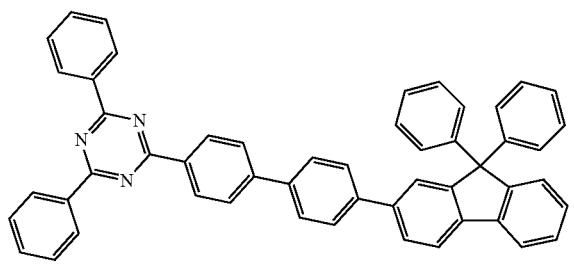
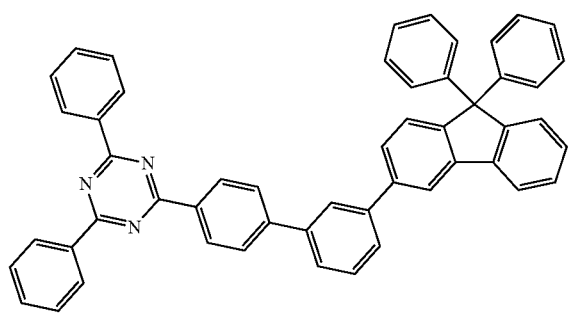
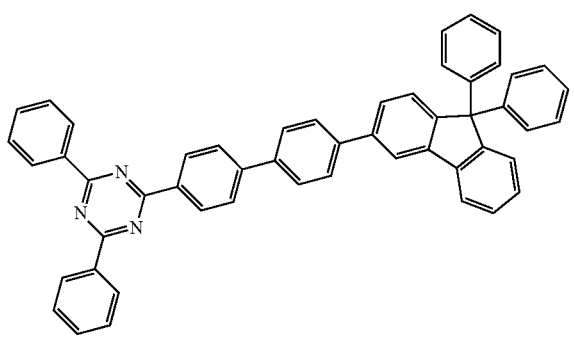
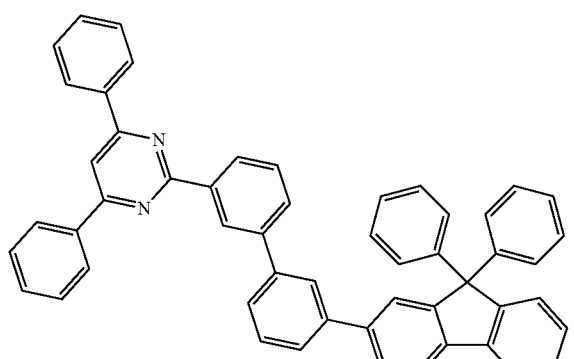
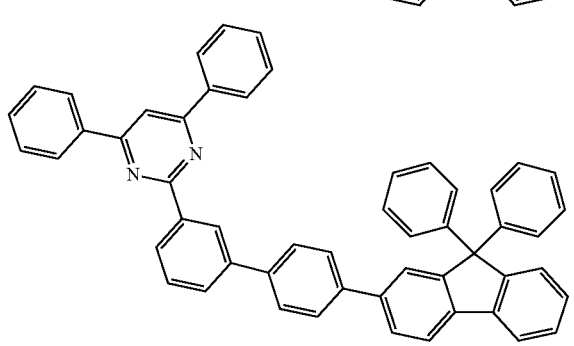
64
-continued
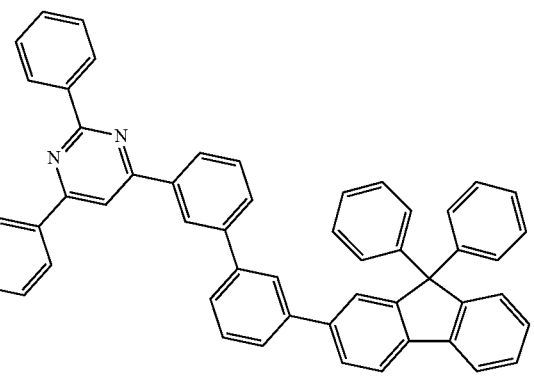
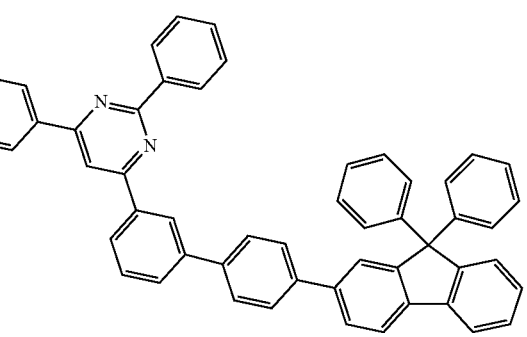
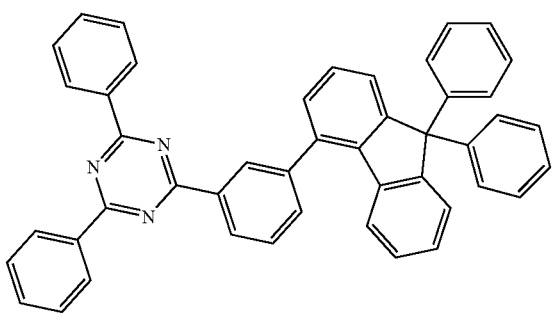
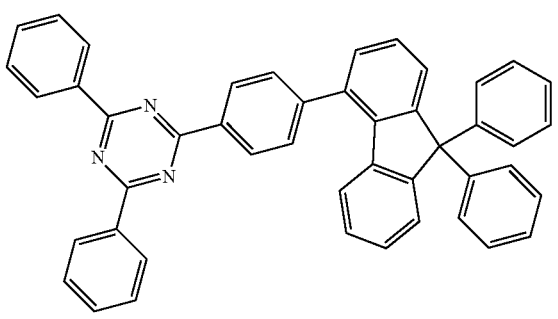
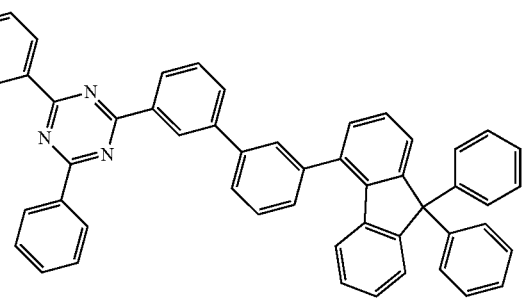

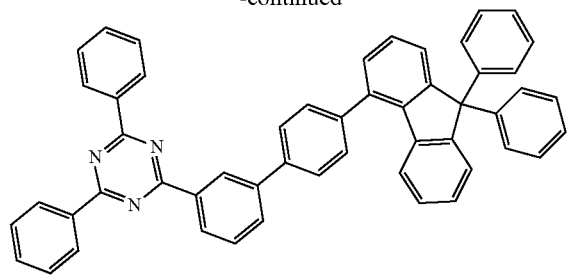
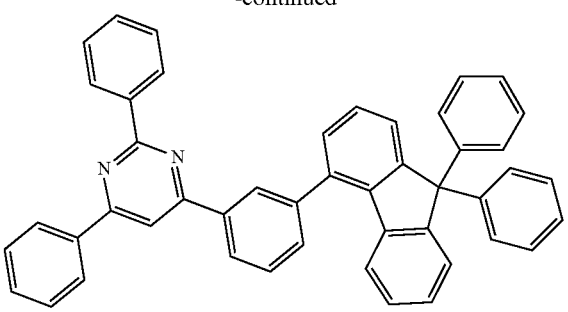
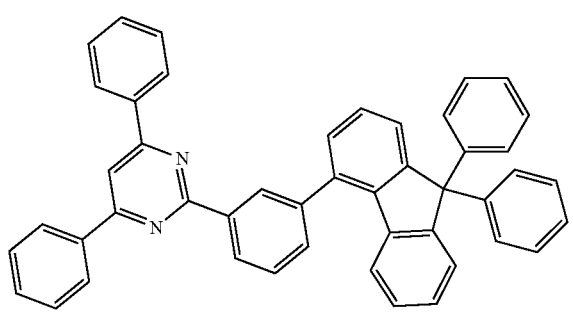
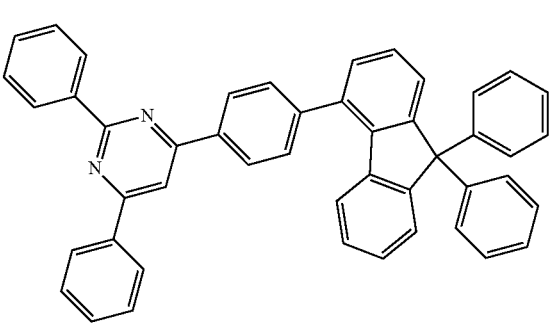
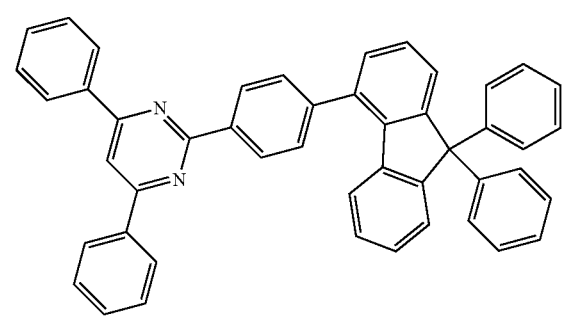
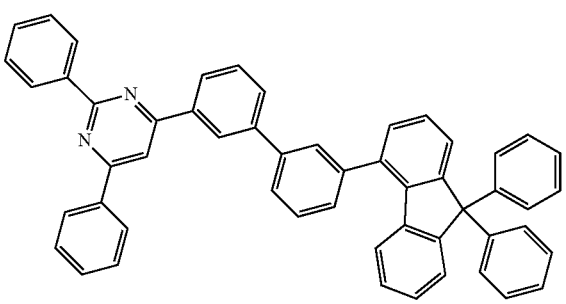
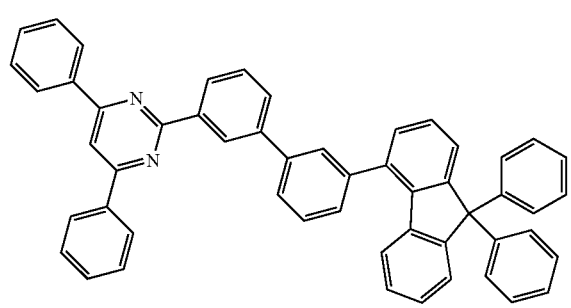
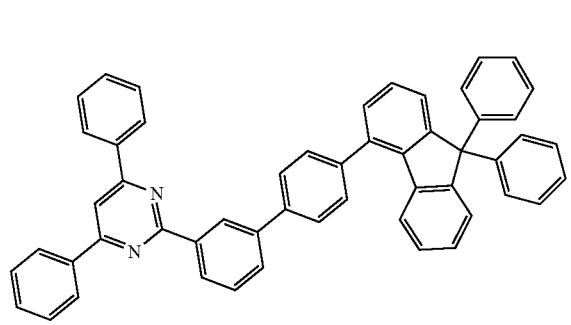
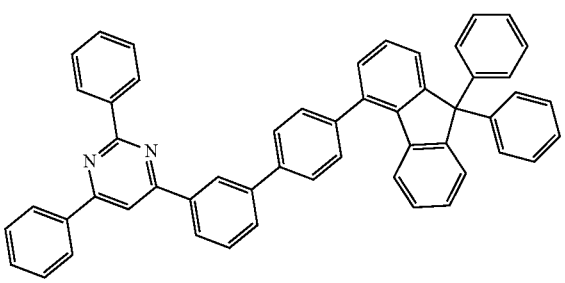

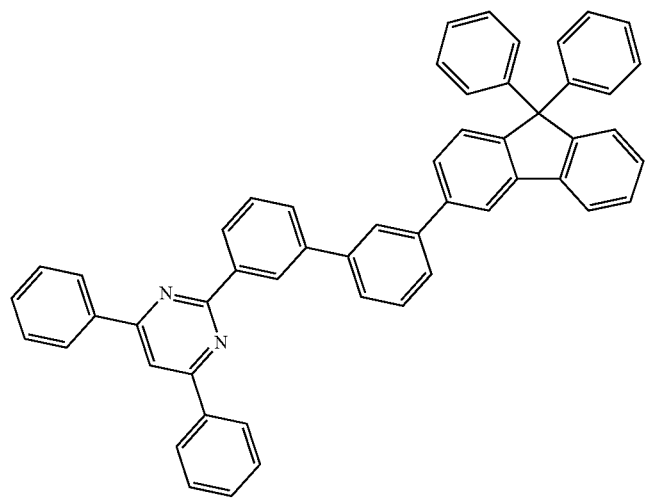
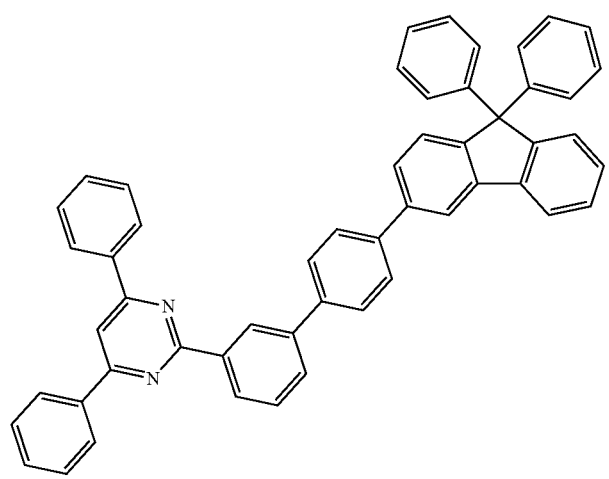
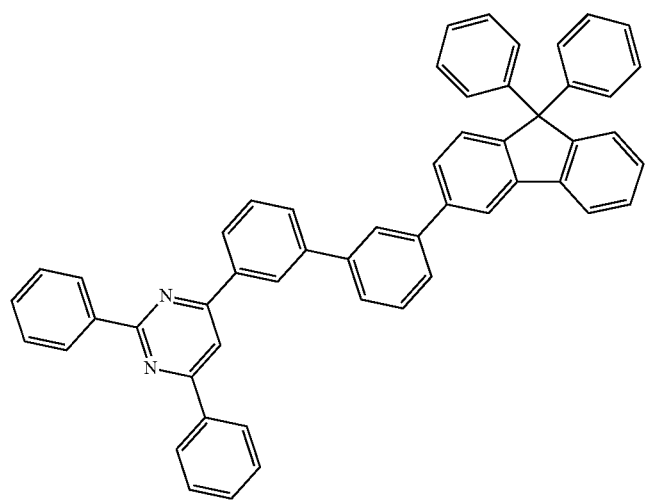

-continued
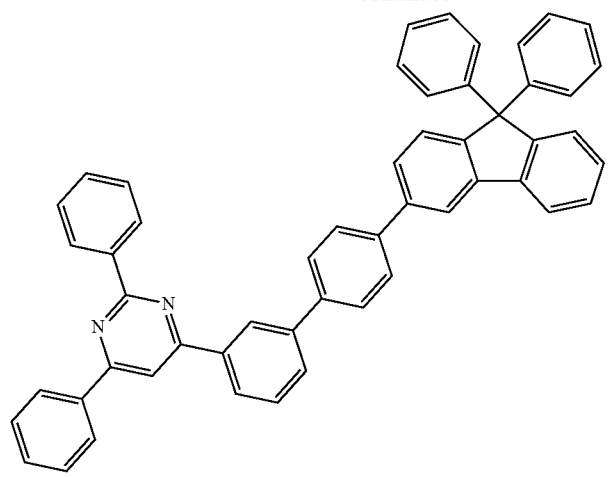
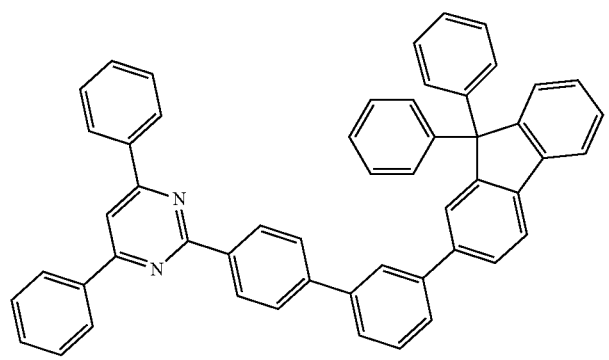
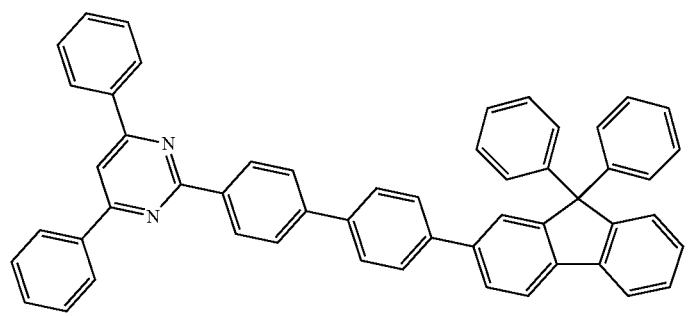
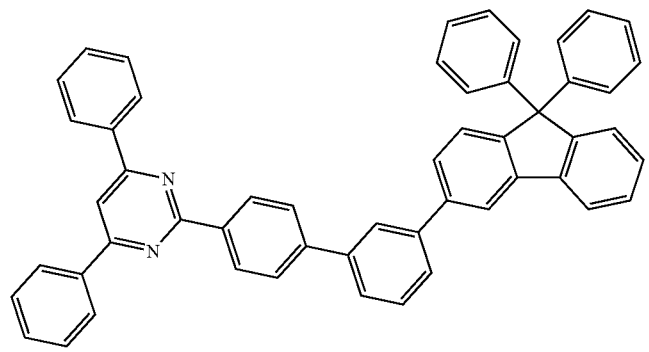

-continued
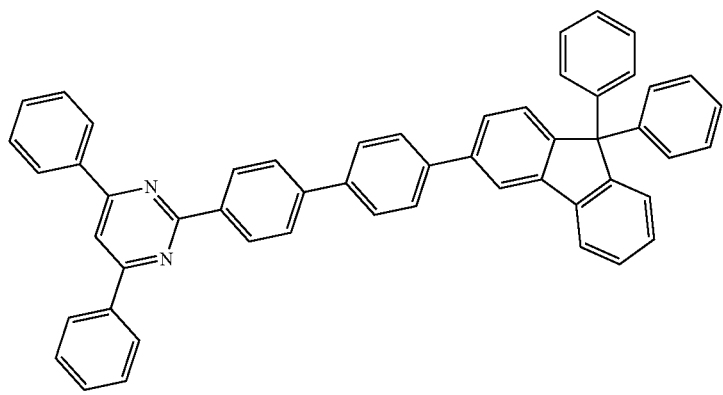
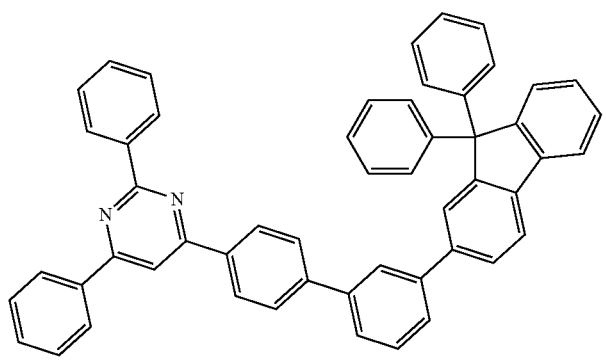
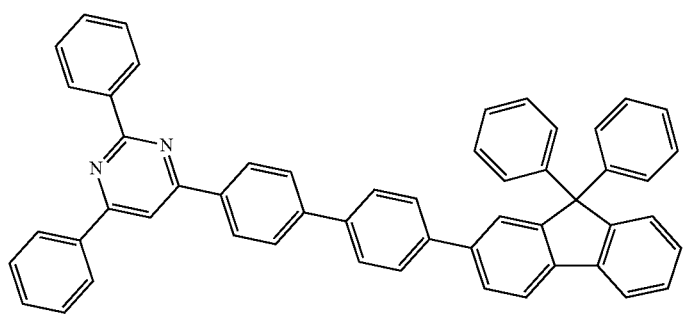
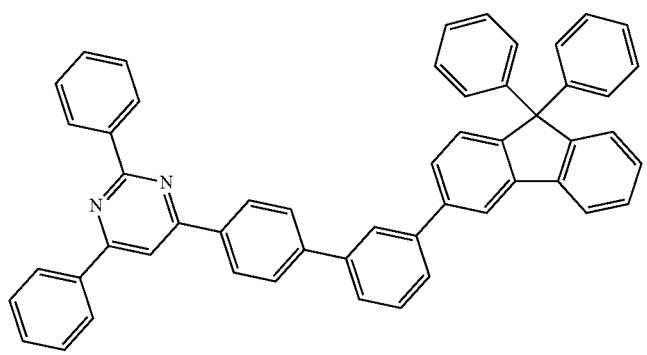

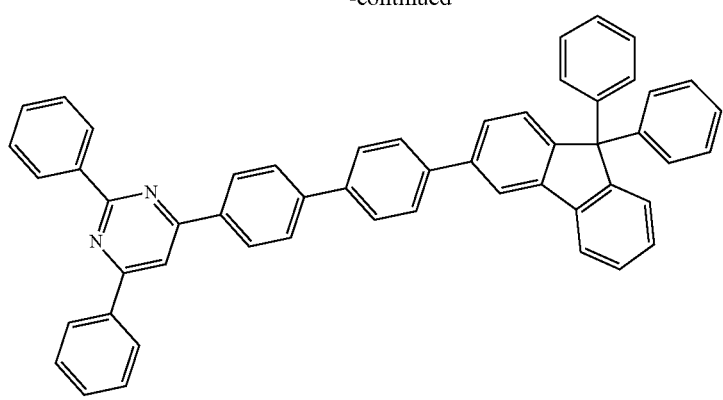
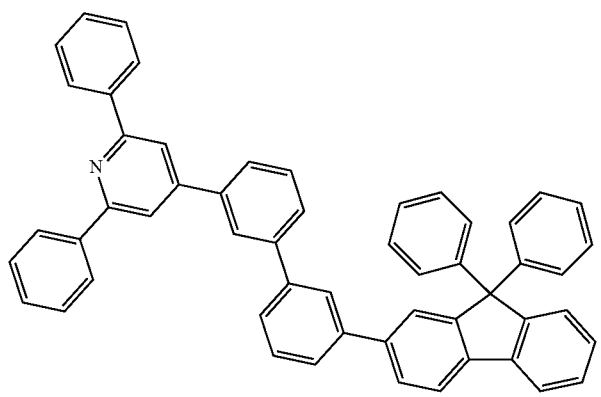
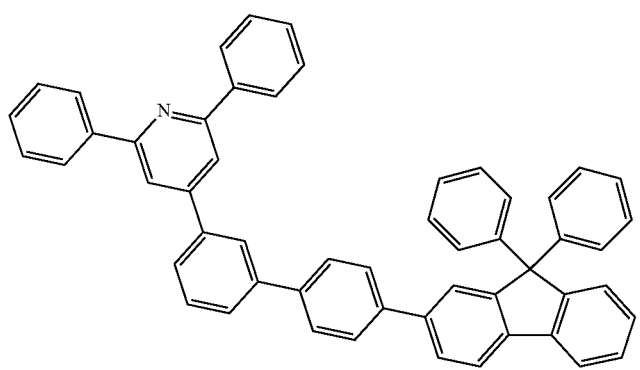
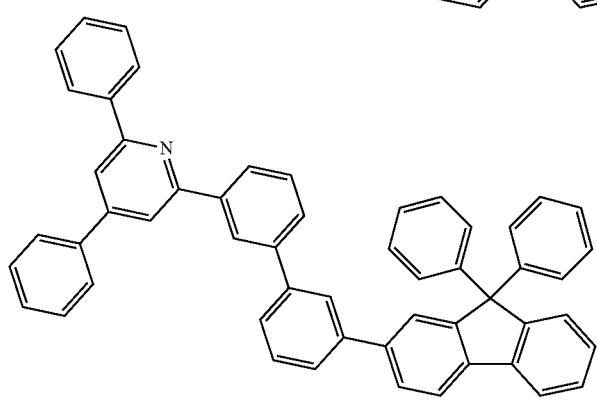

-continued
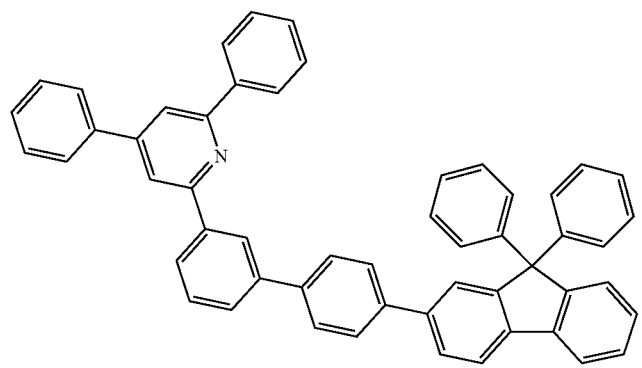
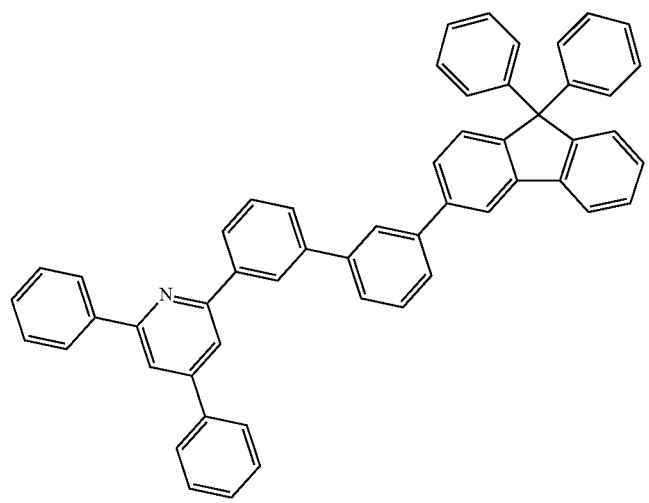
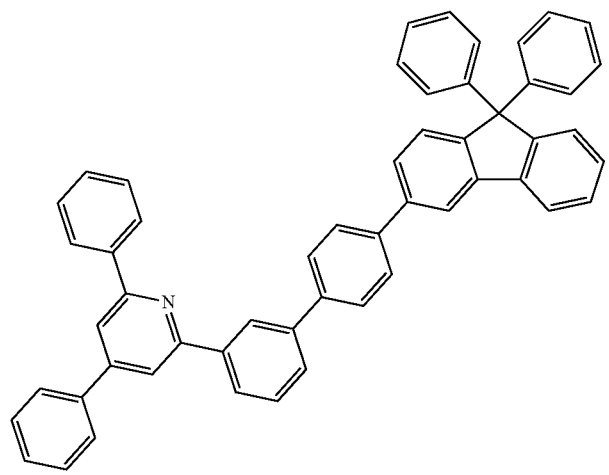

-continued
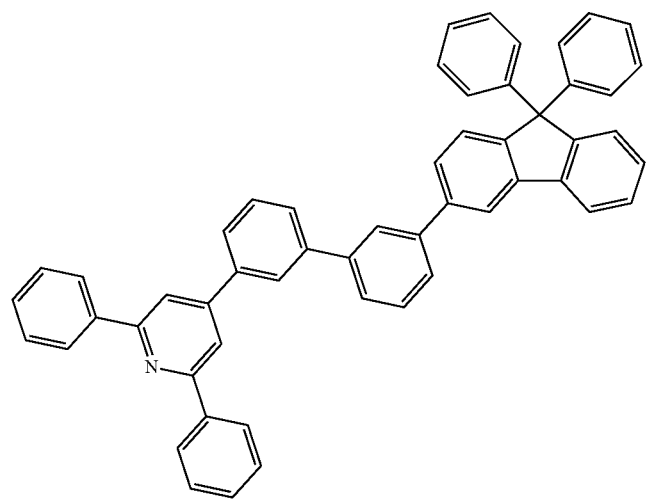
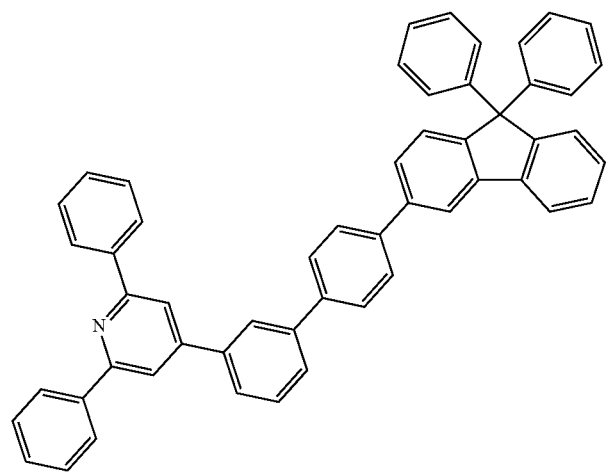
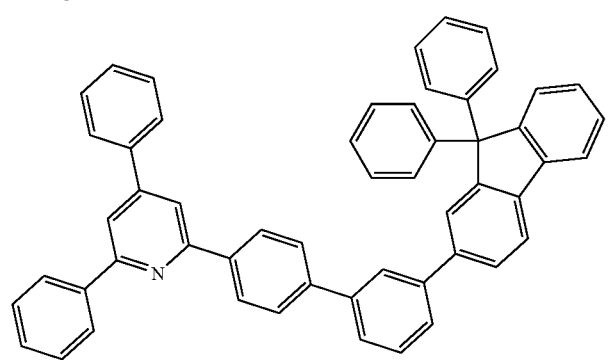
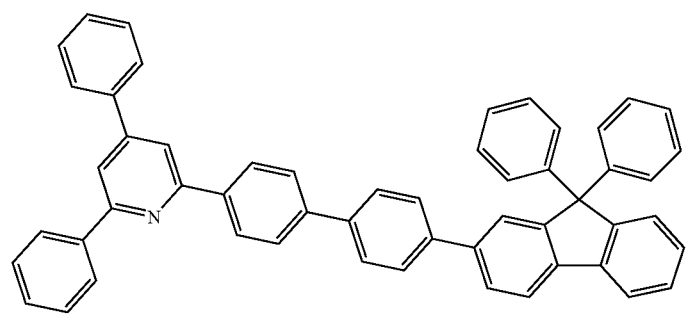

-continued
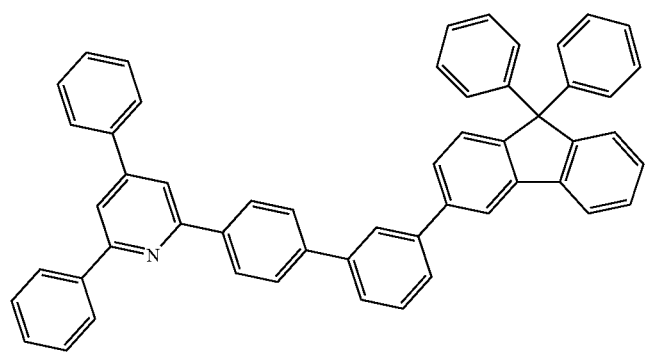
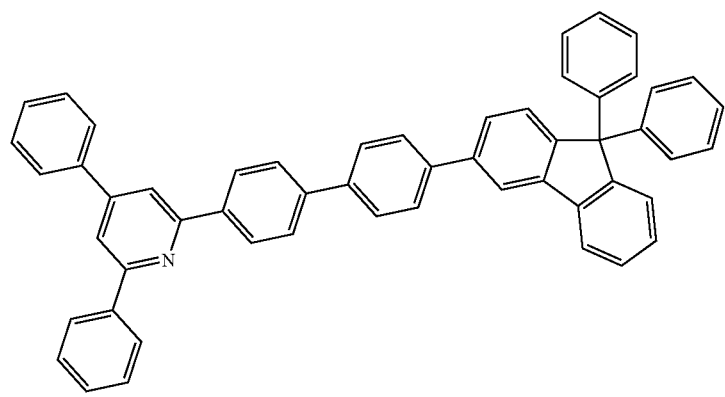
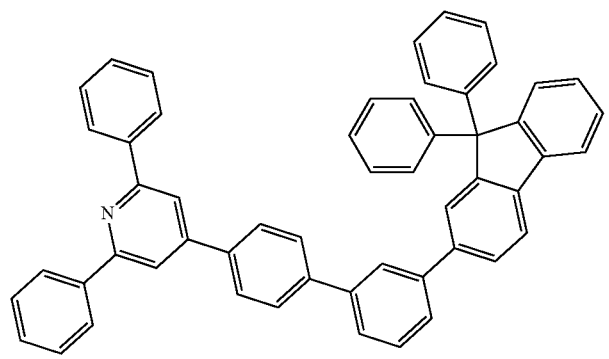
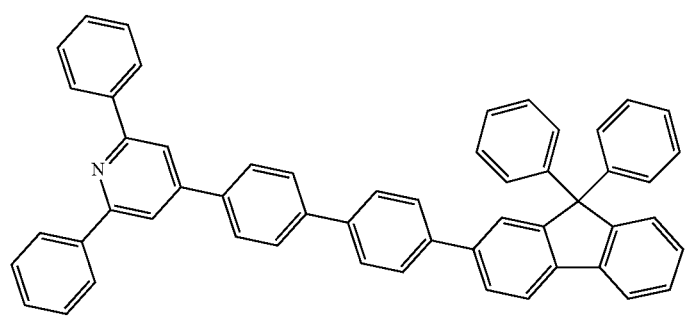

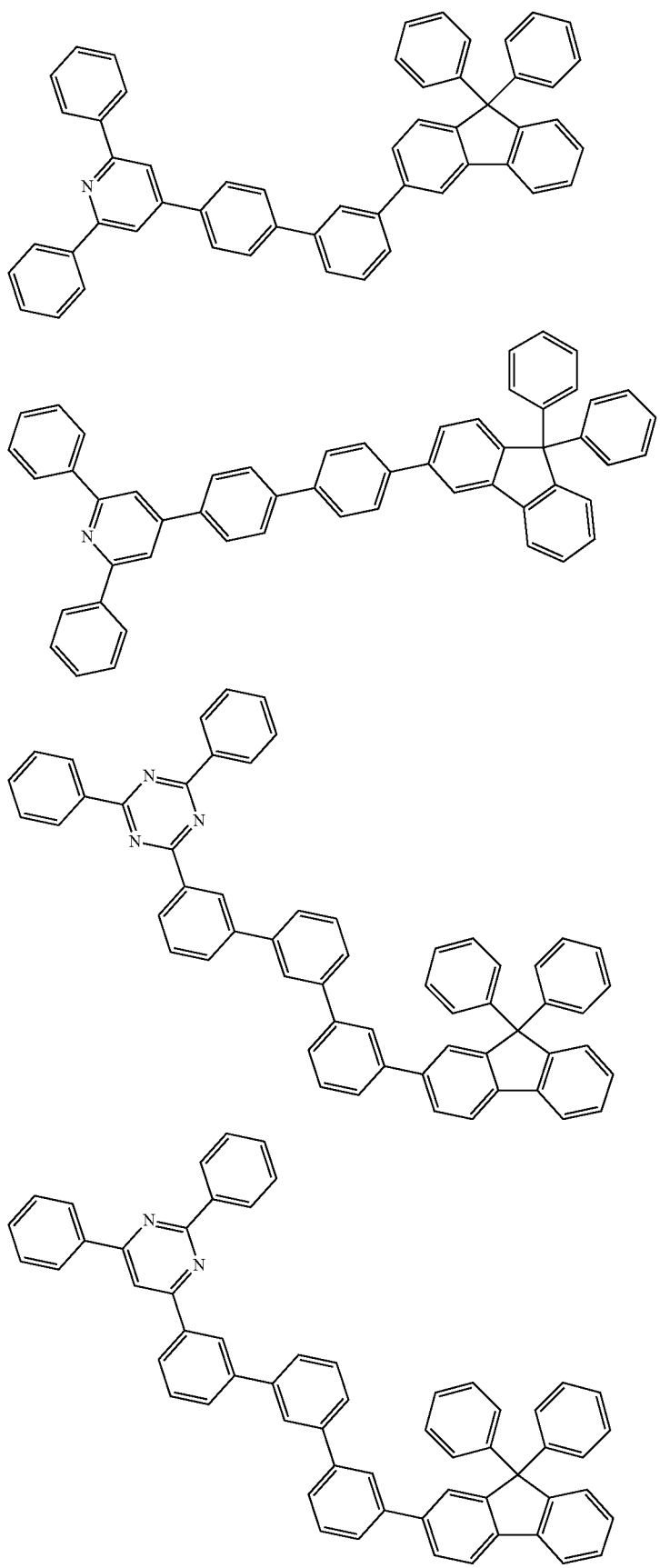

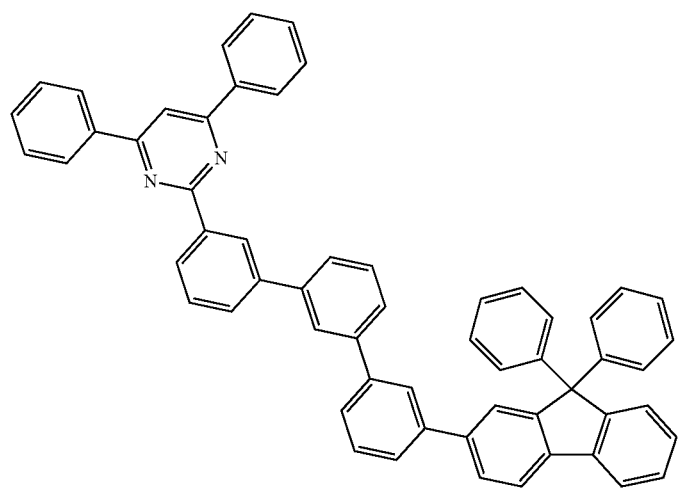
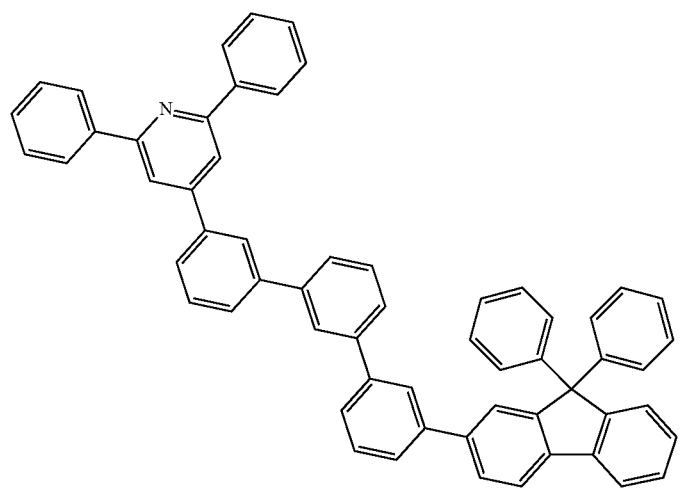
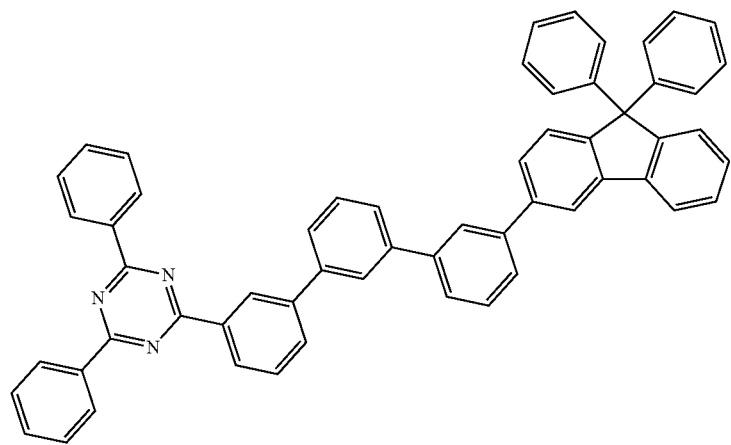

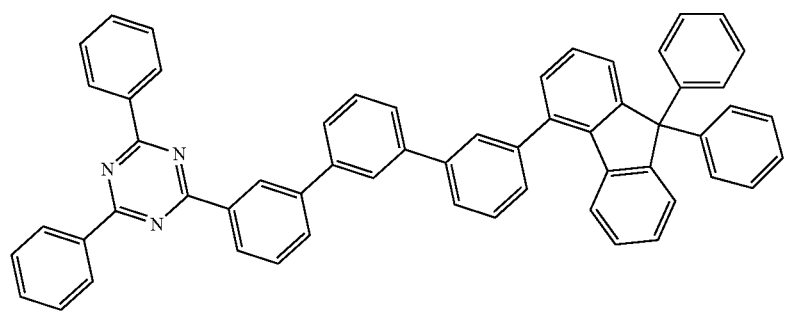

-continued
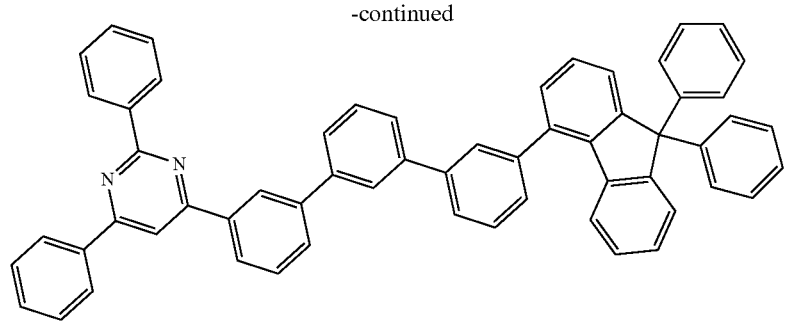
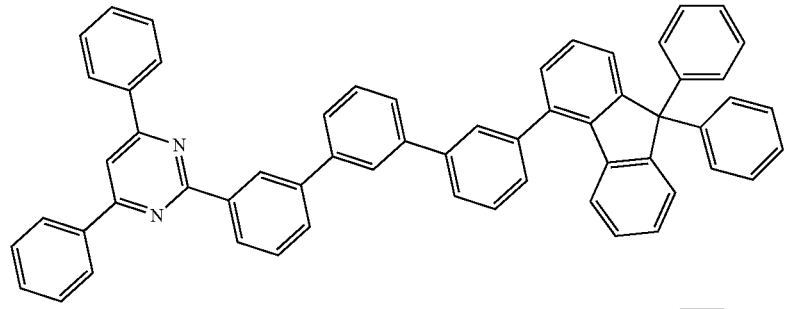
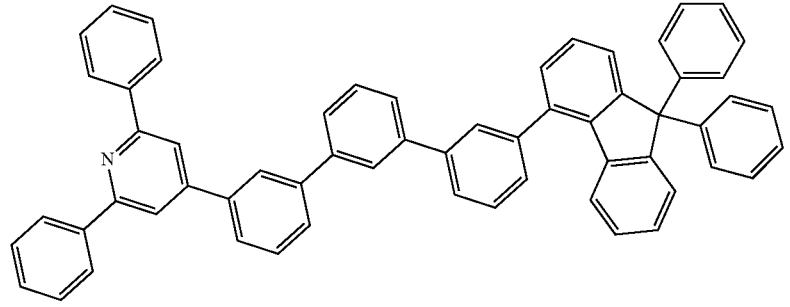
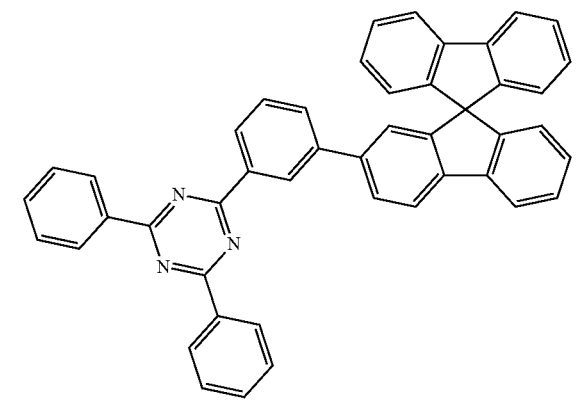
-continued
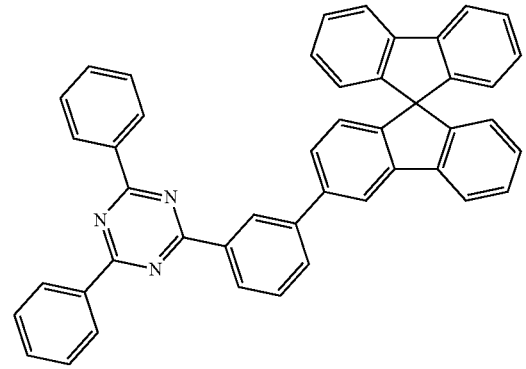
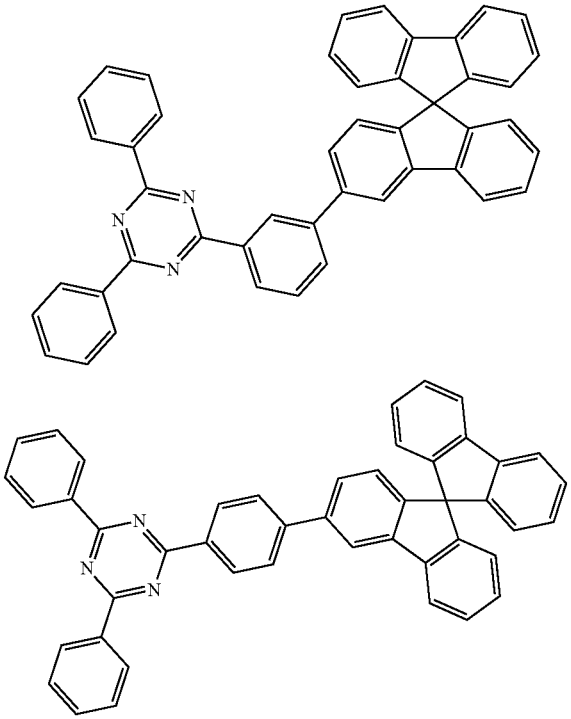

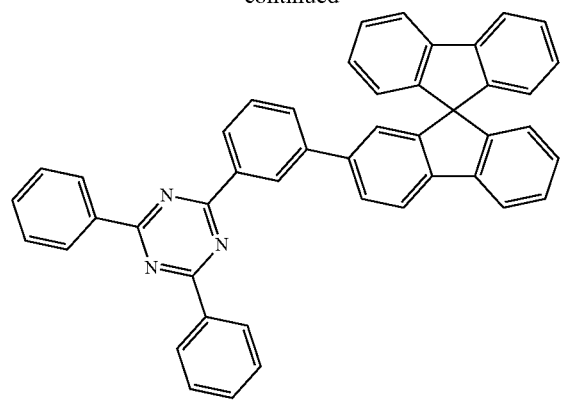
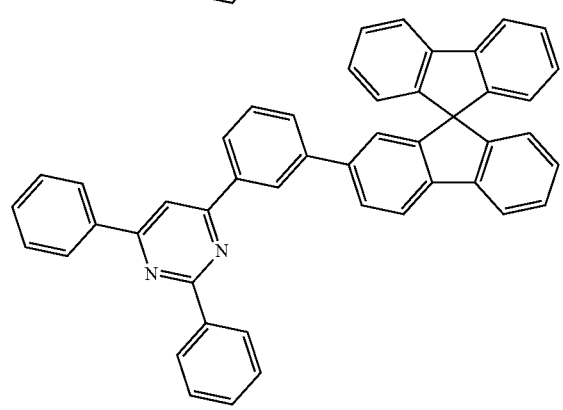
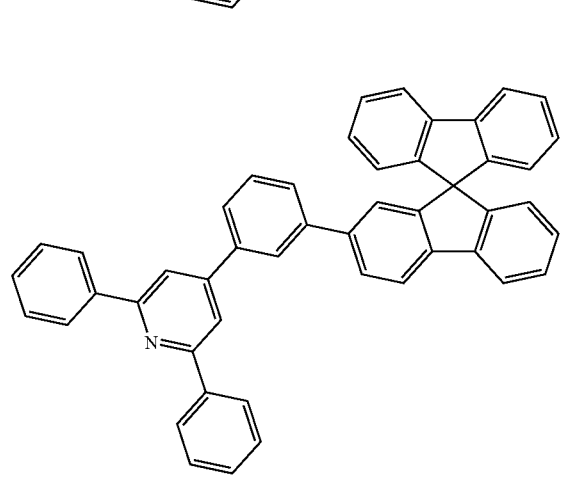
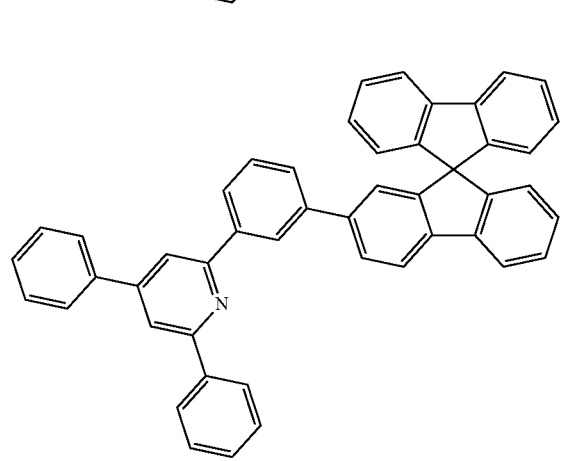
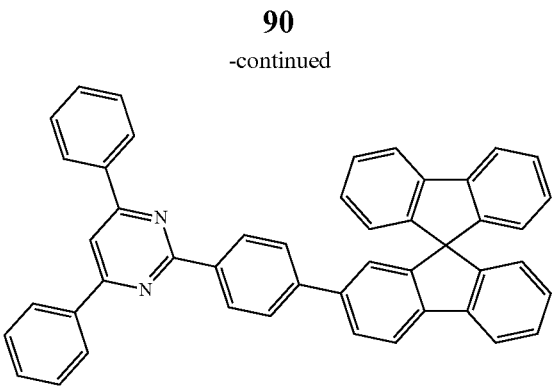
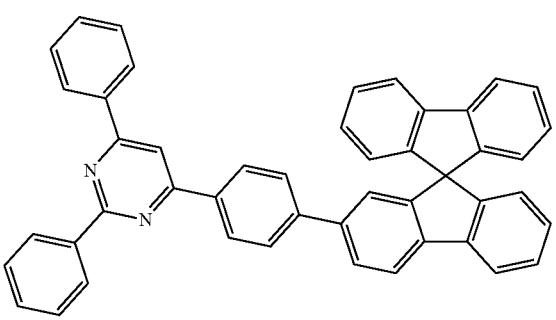
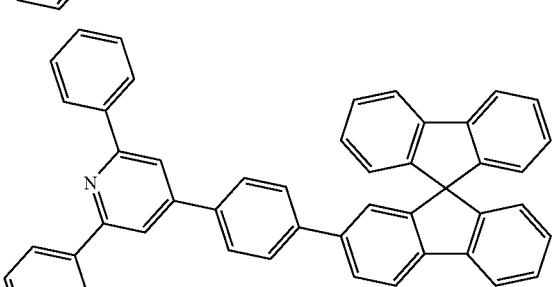
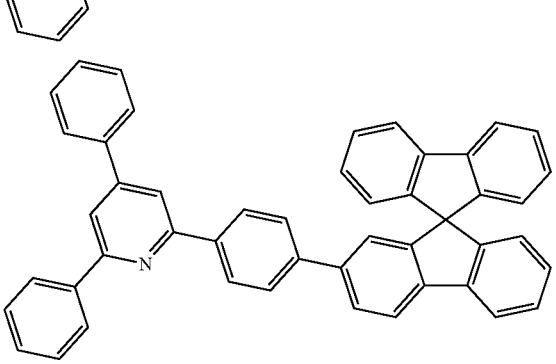
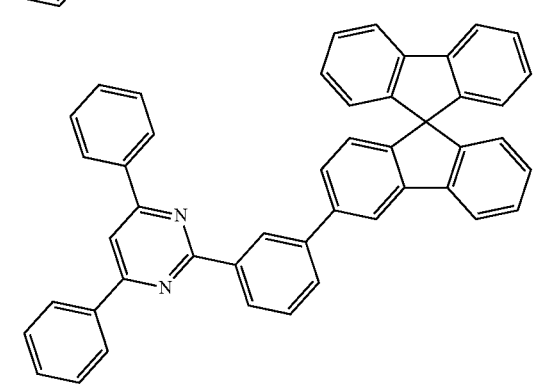

-continued
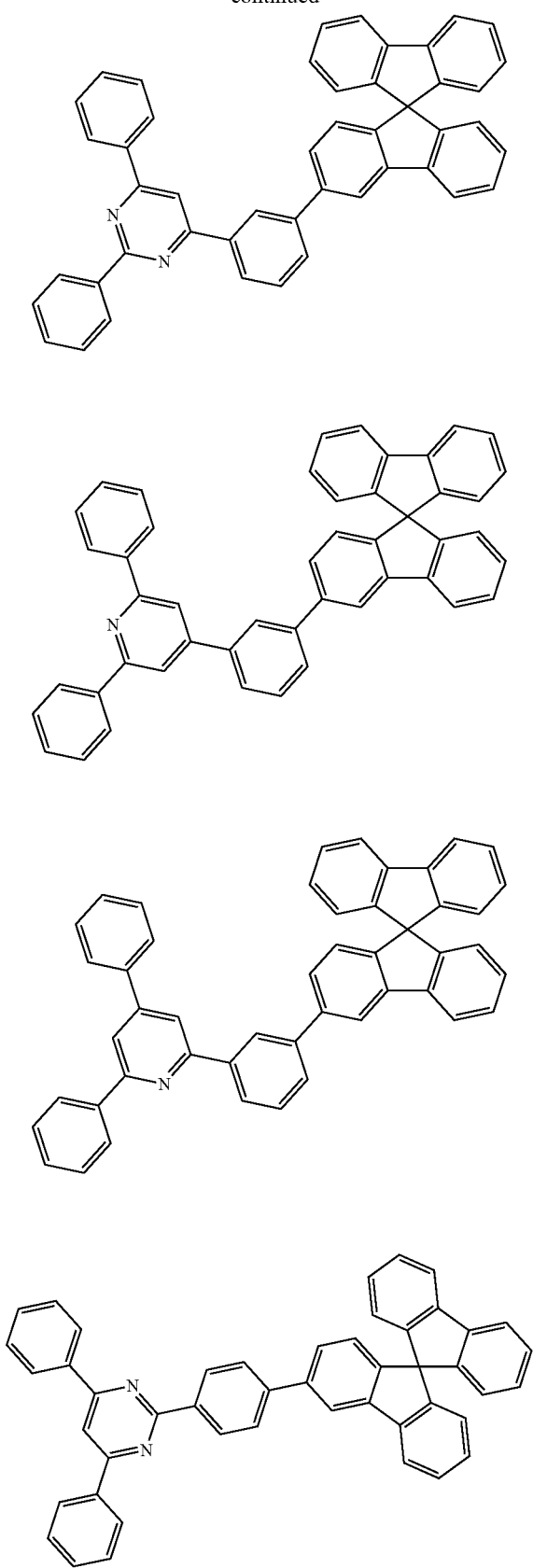
-continued
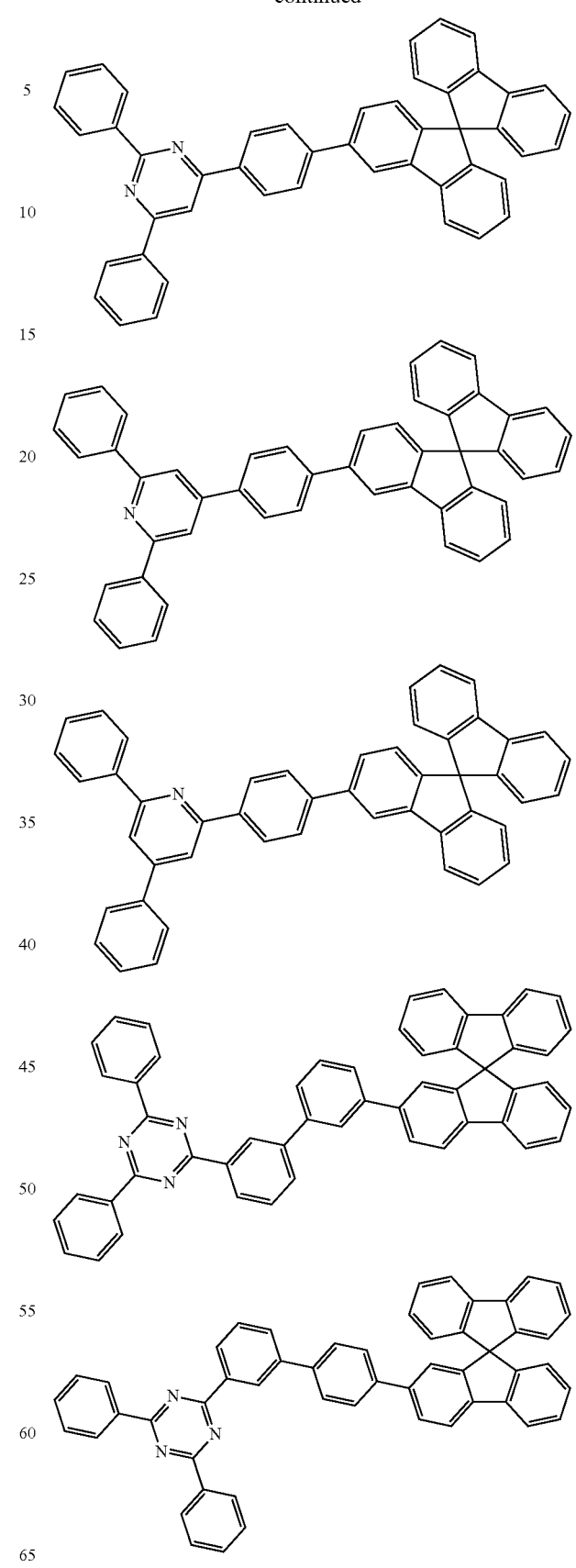

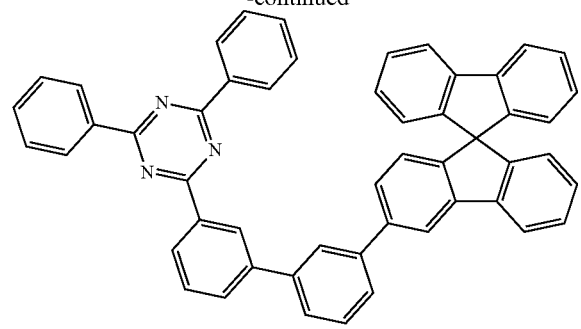
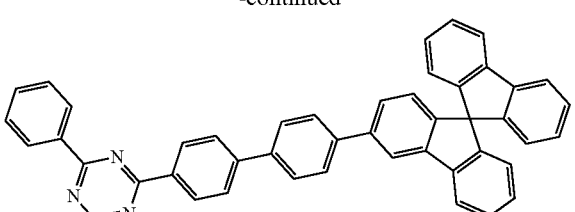

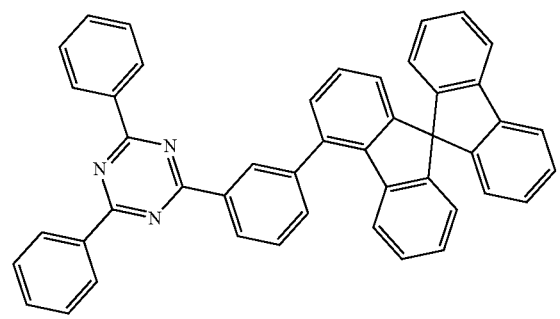
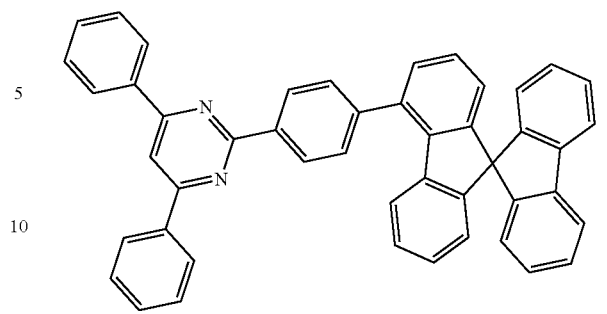
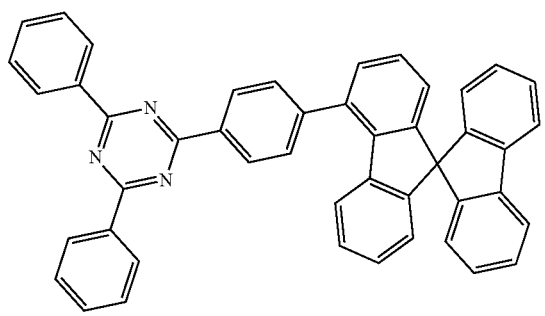
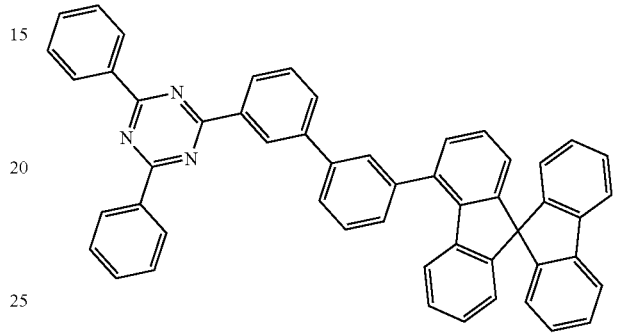
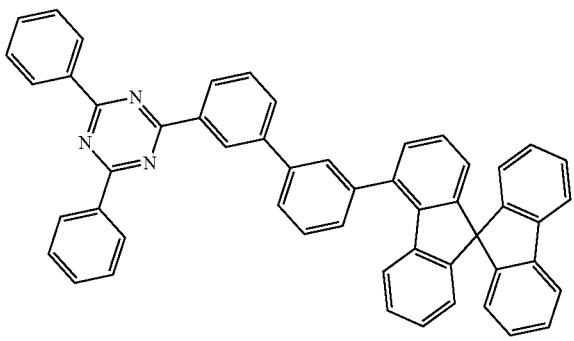
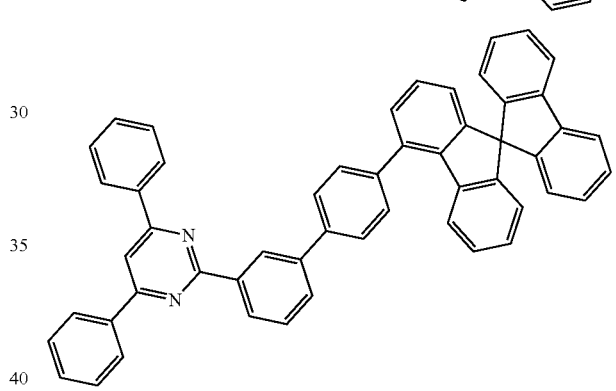
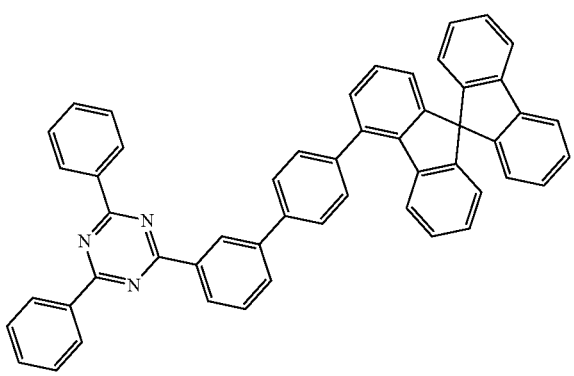
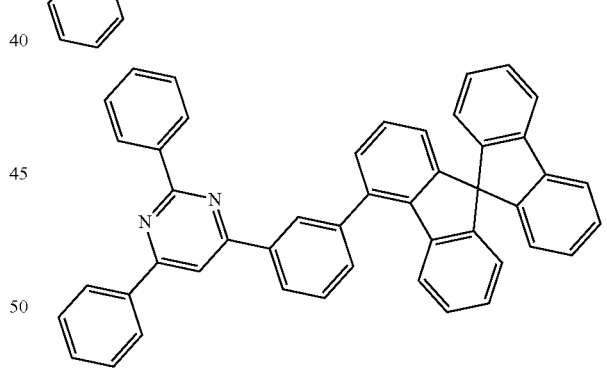
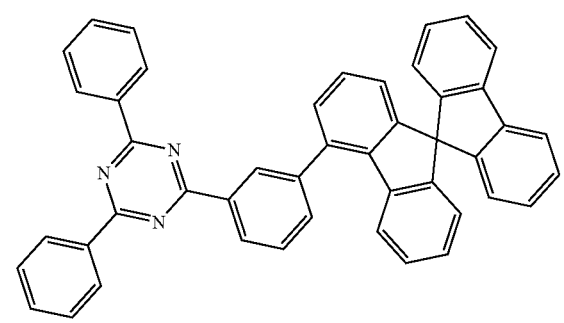
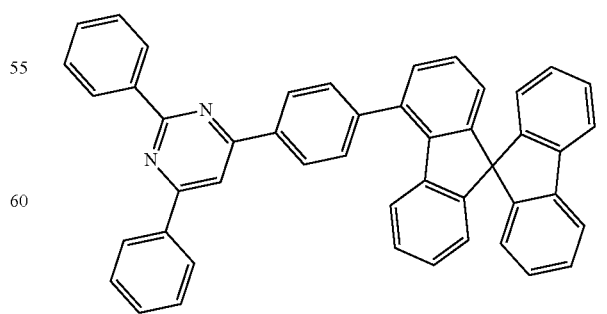

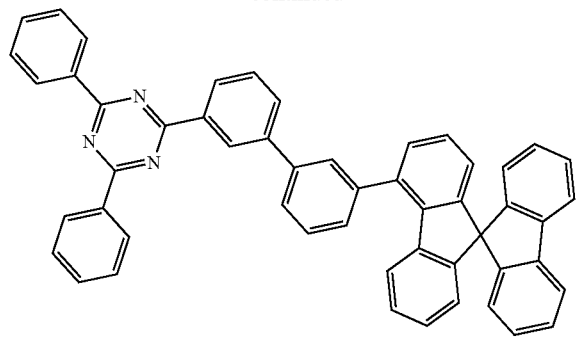
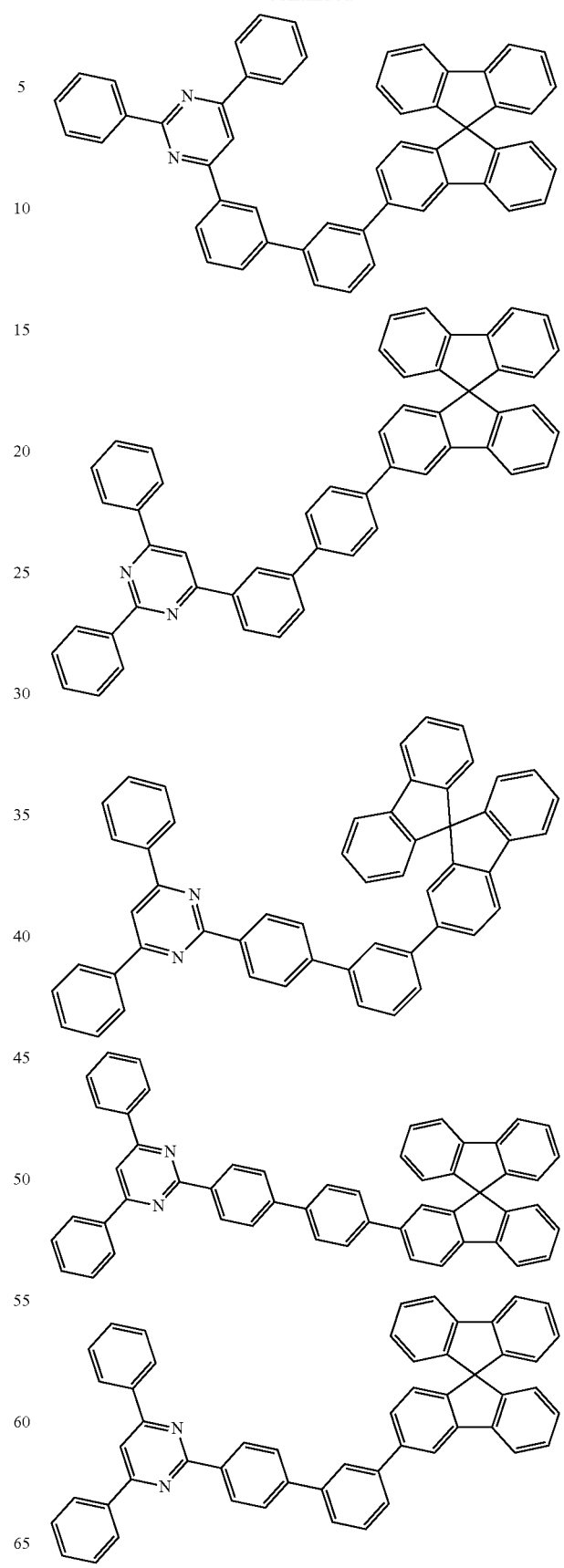

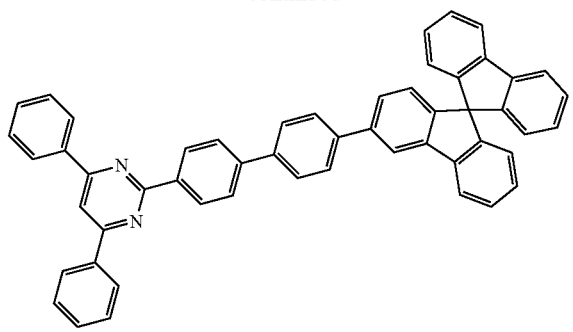
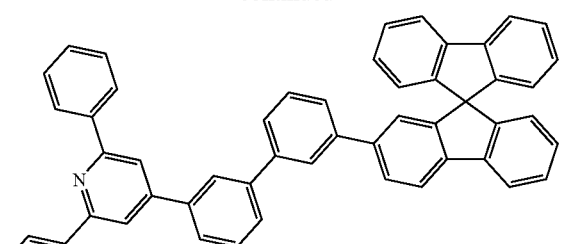
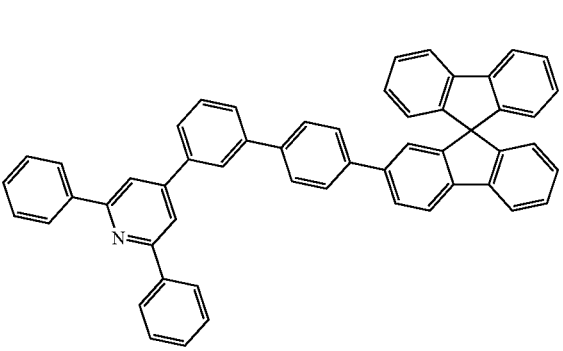
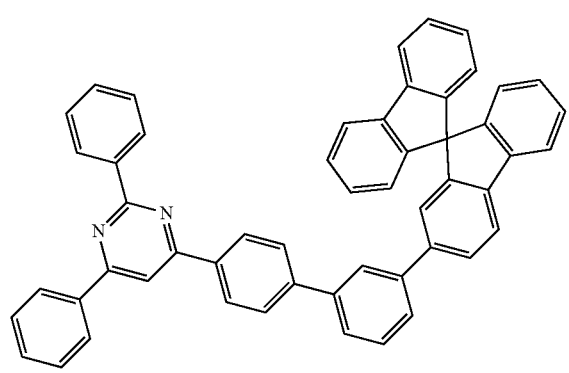
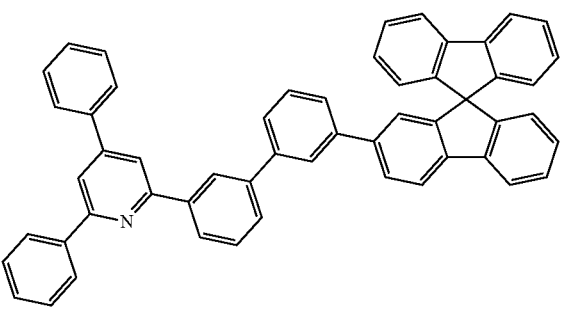
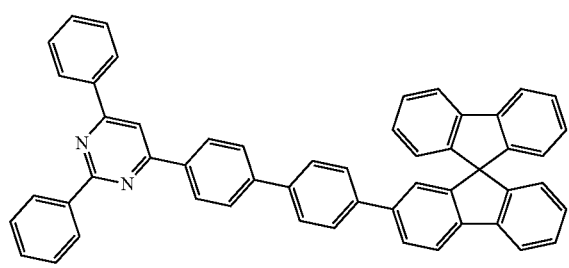
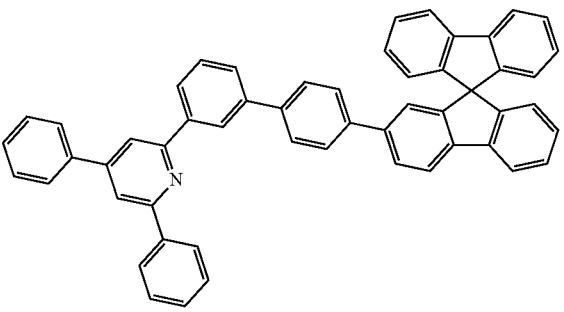
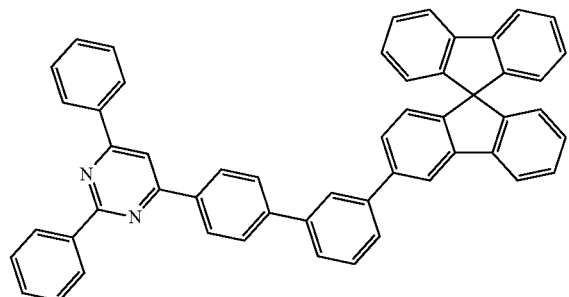
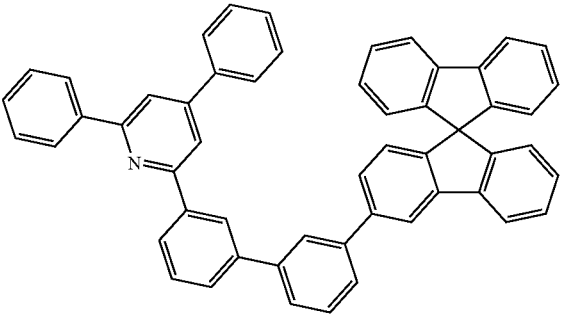

101
-continued
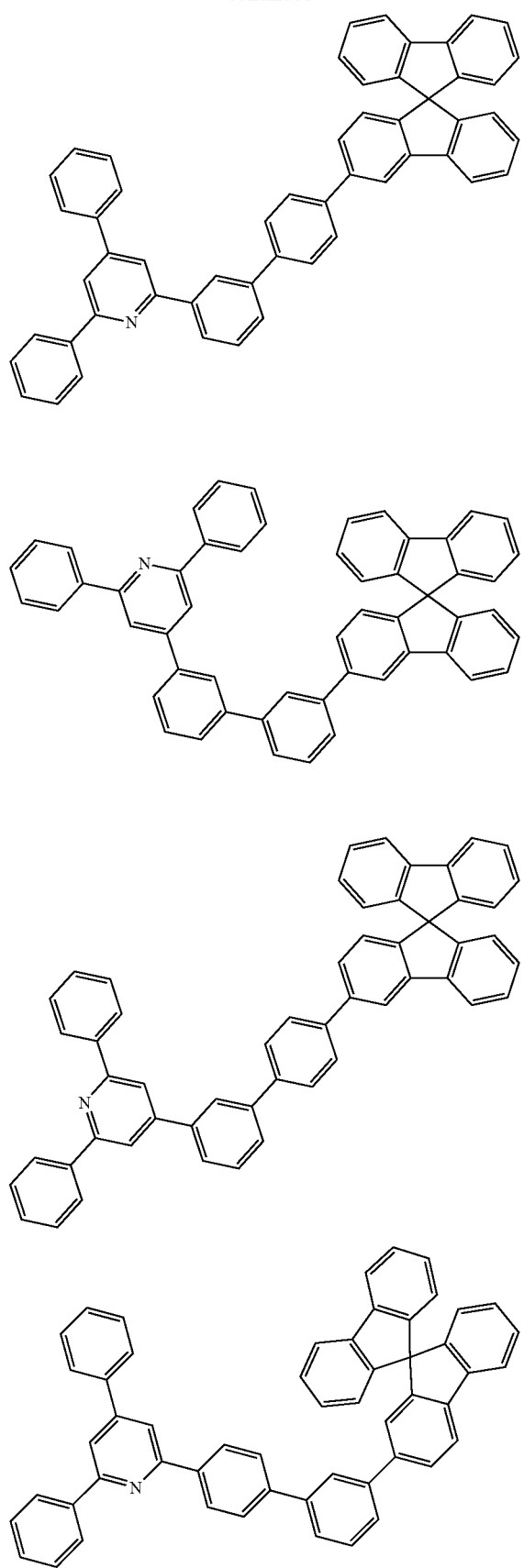
102
-continued
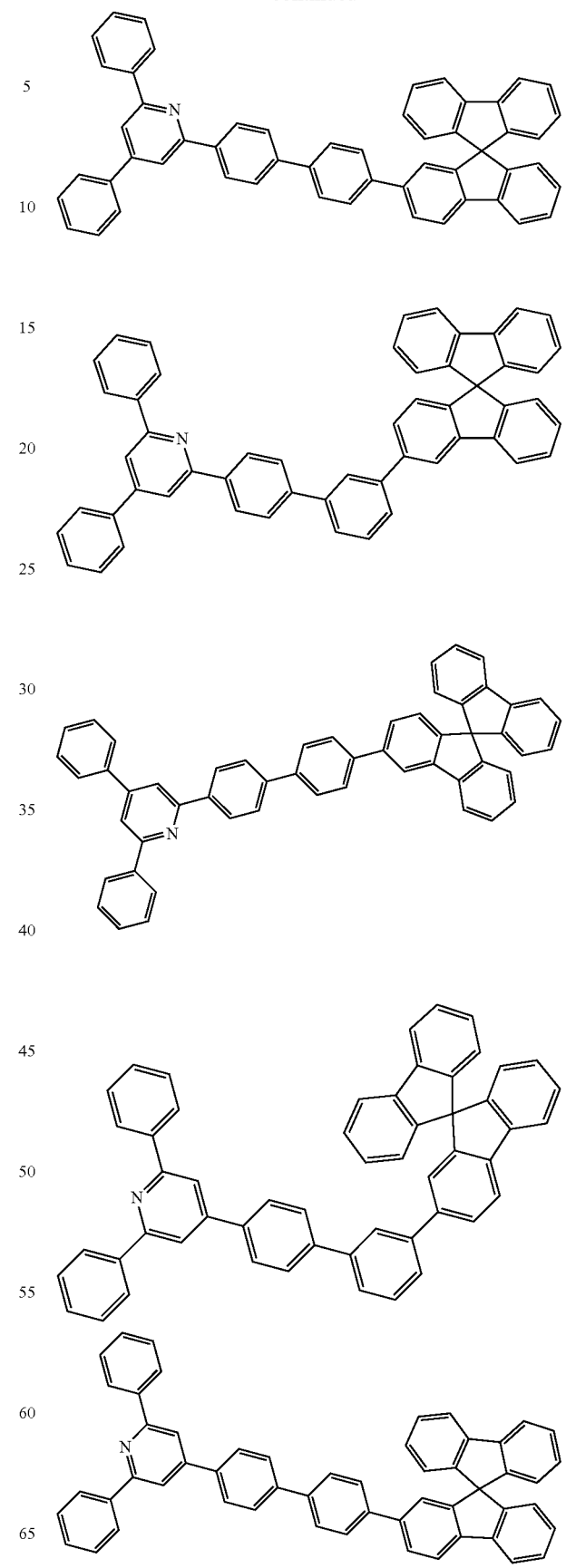

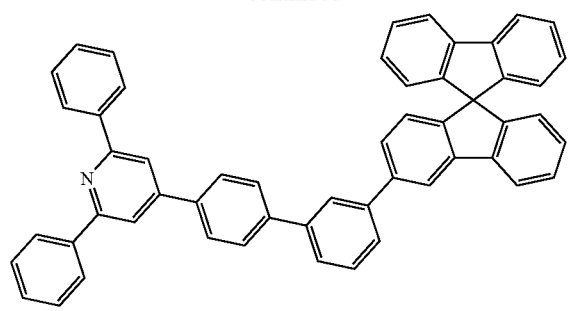
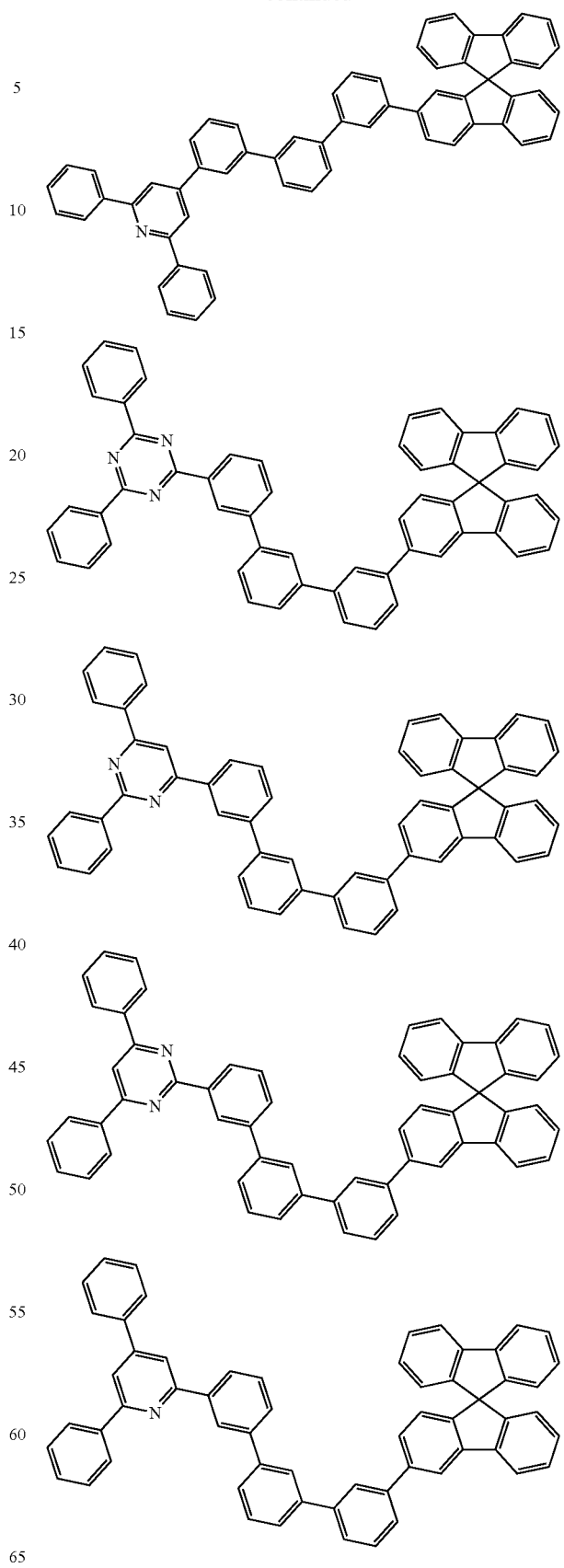

105
-continued
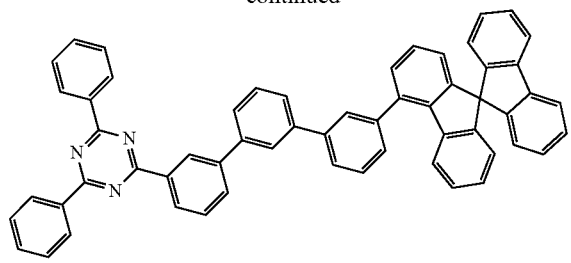
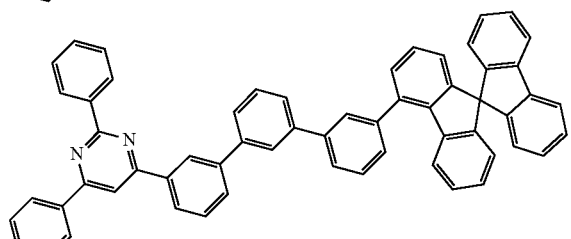
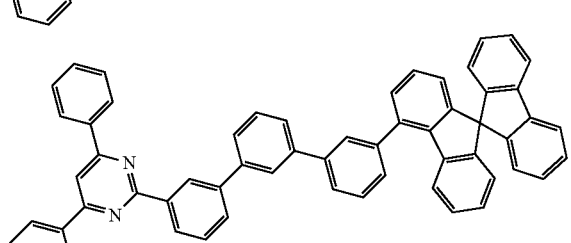
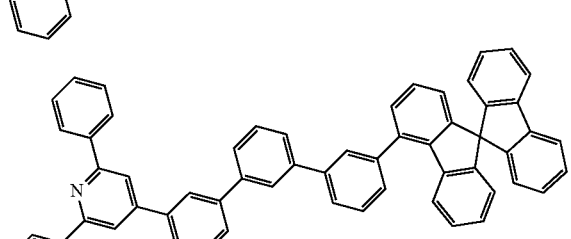
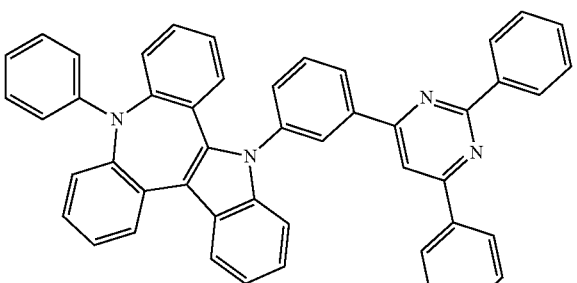
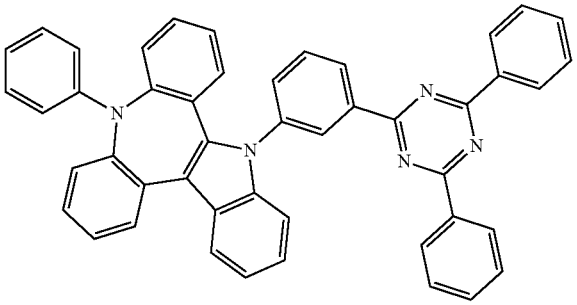
106
-continued
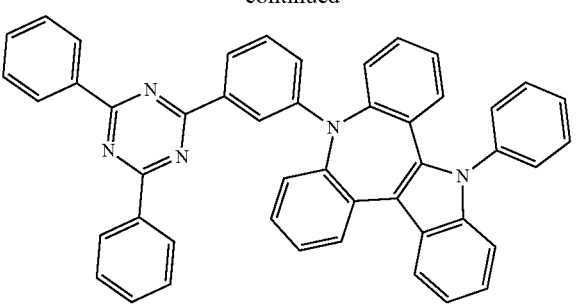
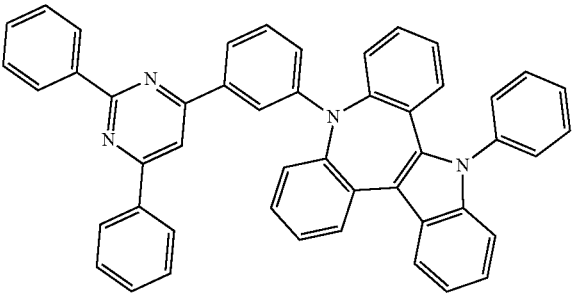
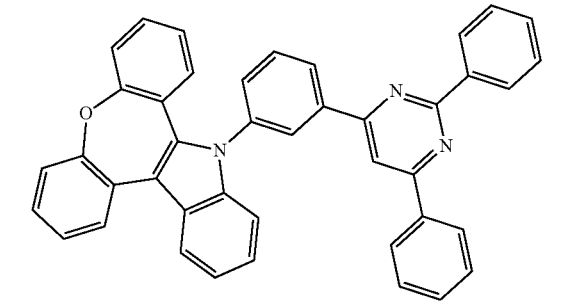
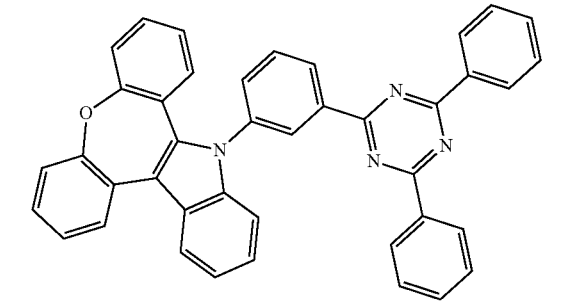
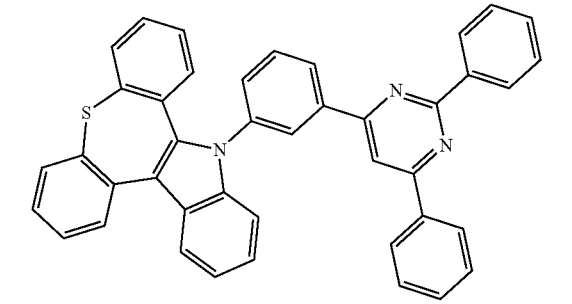

107
-continued
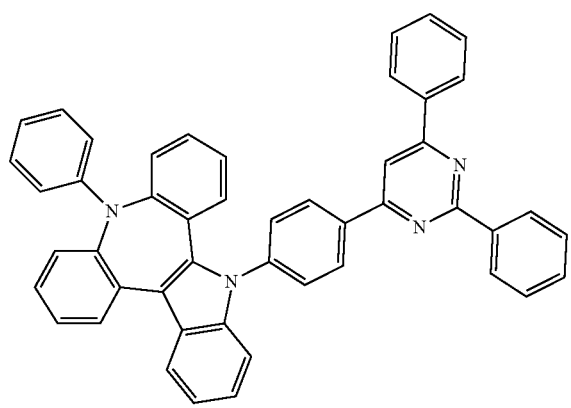
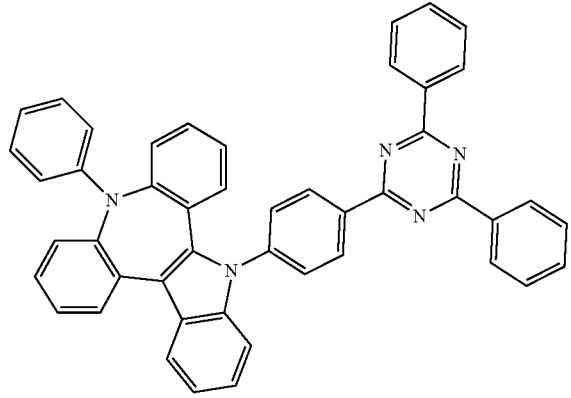
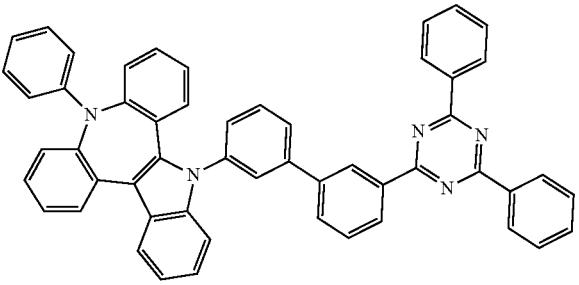
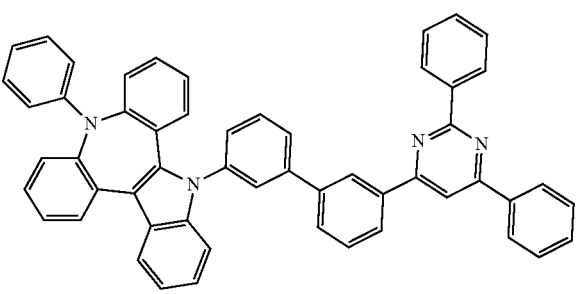
108
-continued
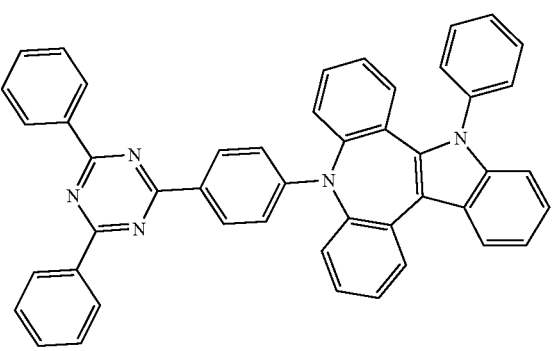
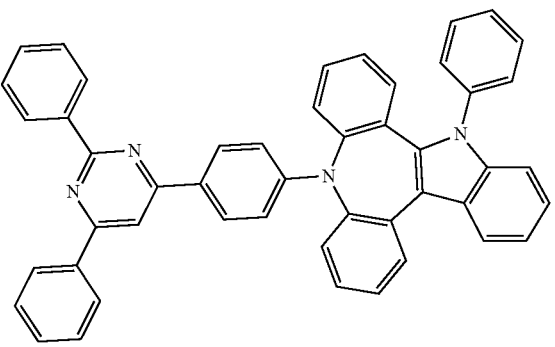
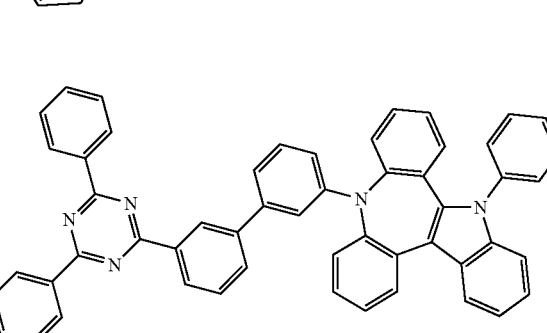
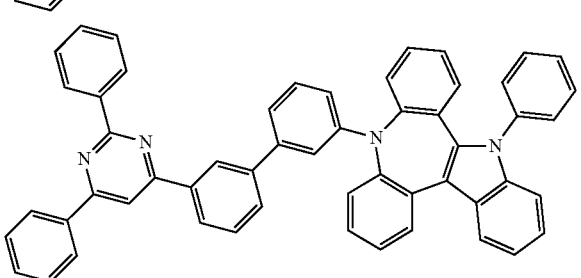
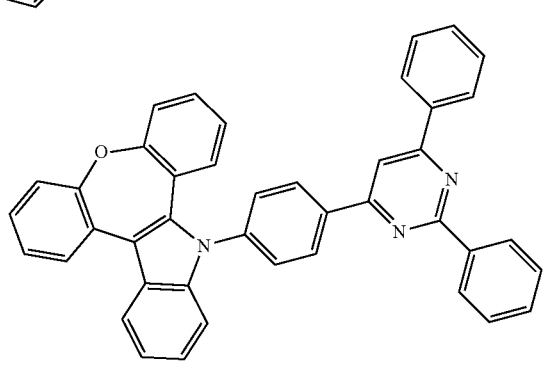

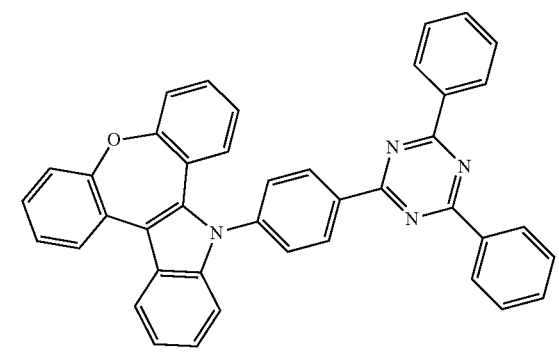
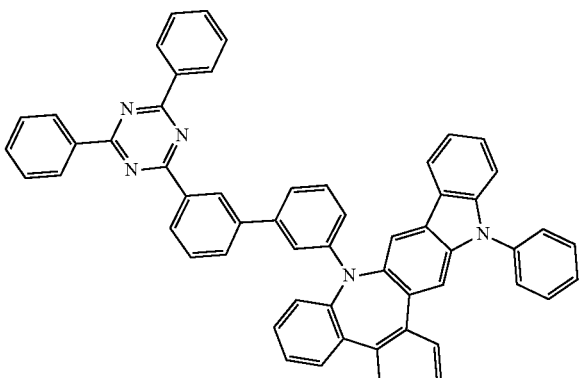

111
-continued
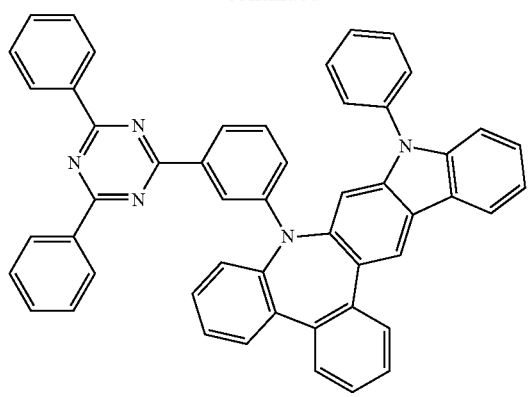
112
-continued
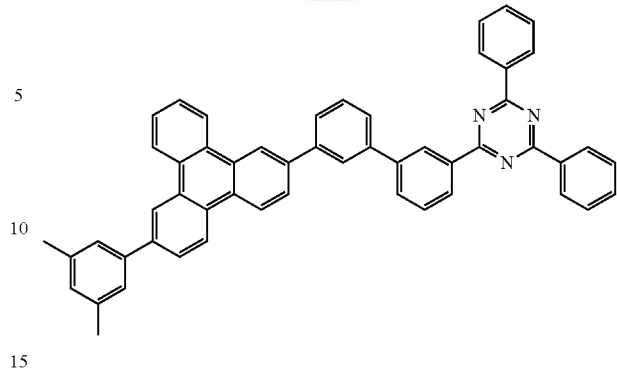
In addition, in one embodiment of the present application, the compound of Chemical Formula 2 is selected from among the following compounds:
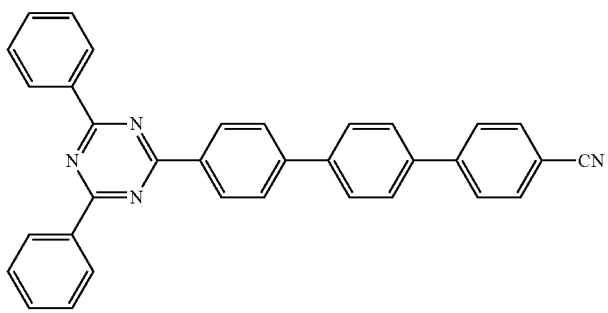
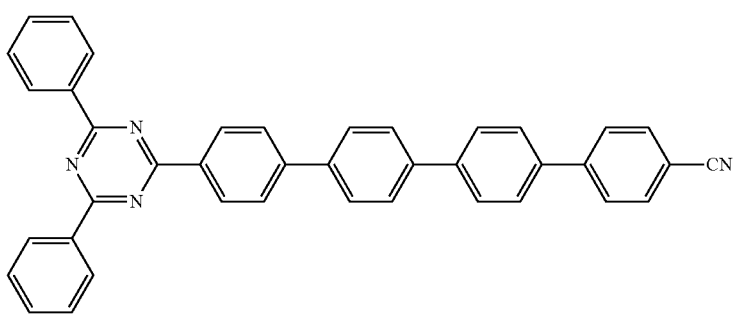
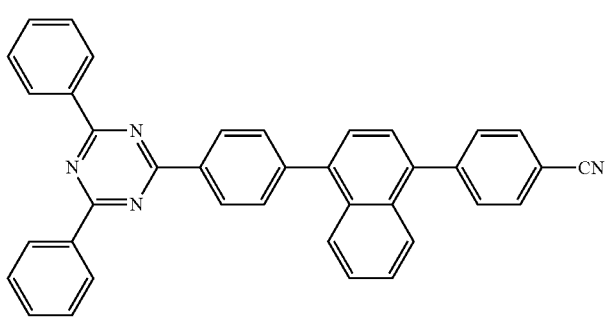

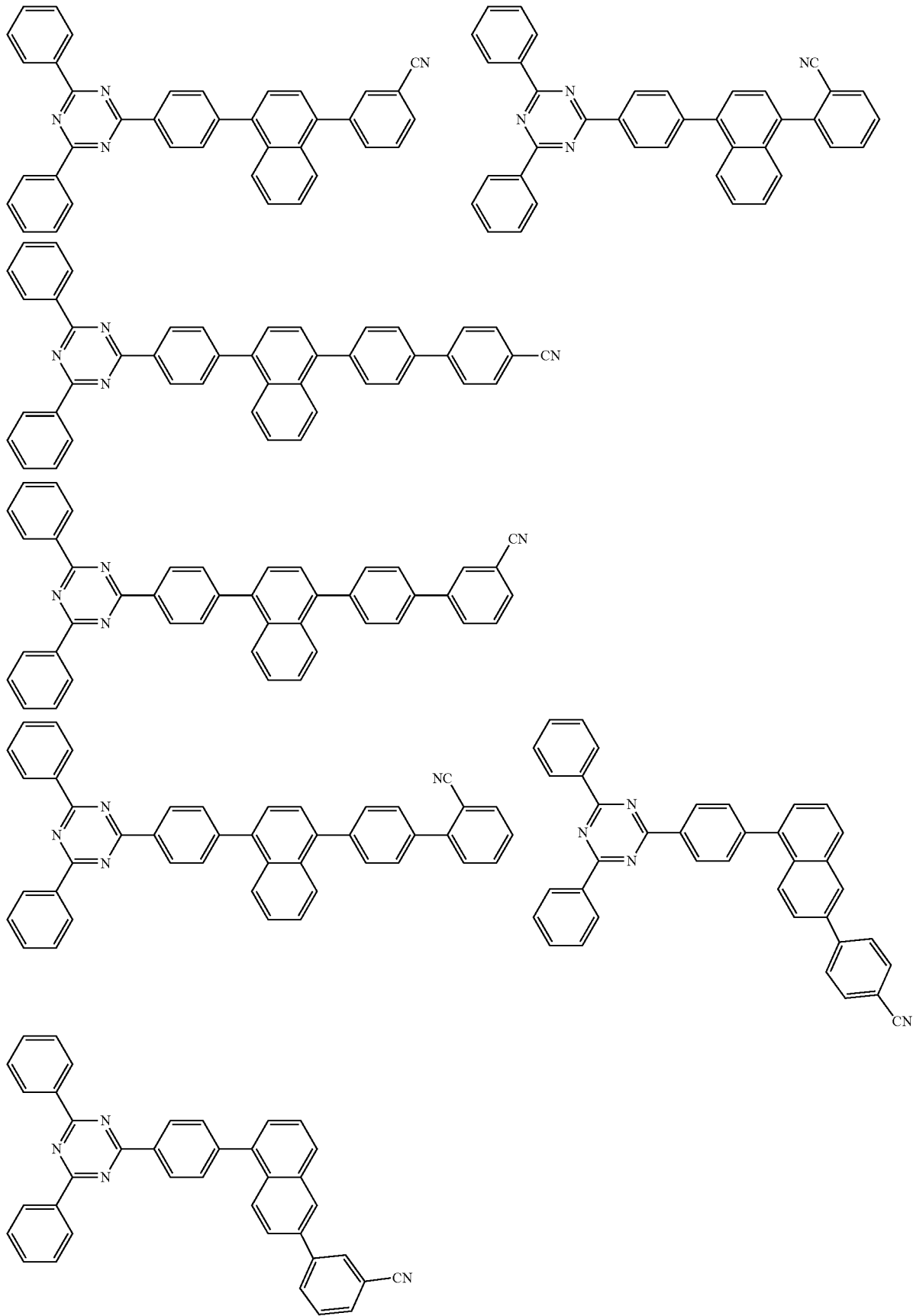

-continued
115
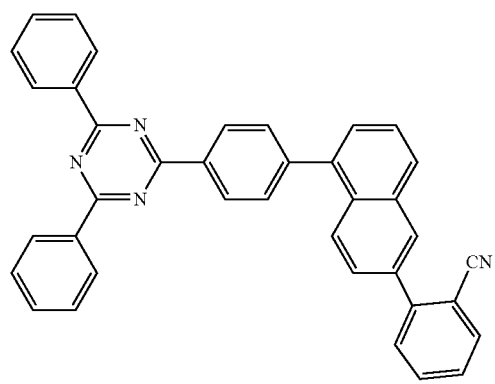
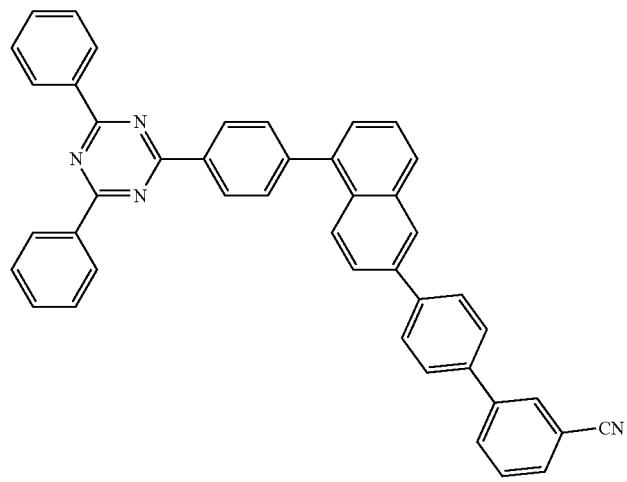
116
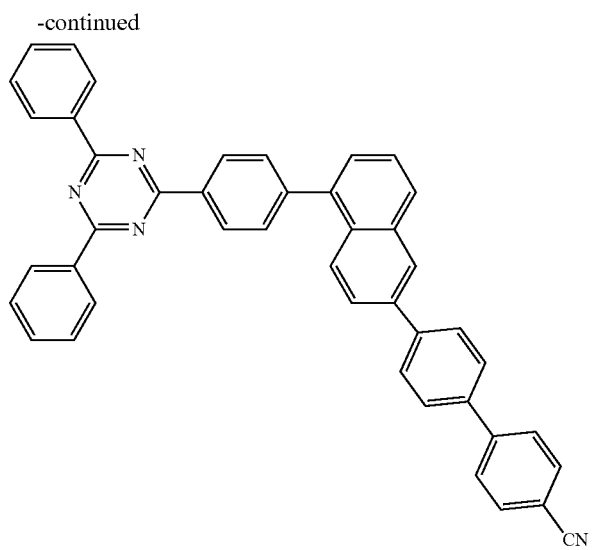
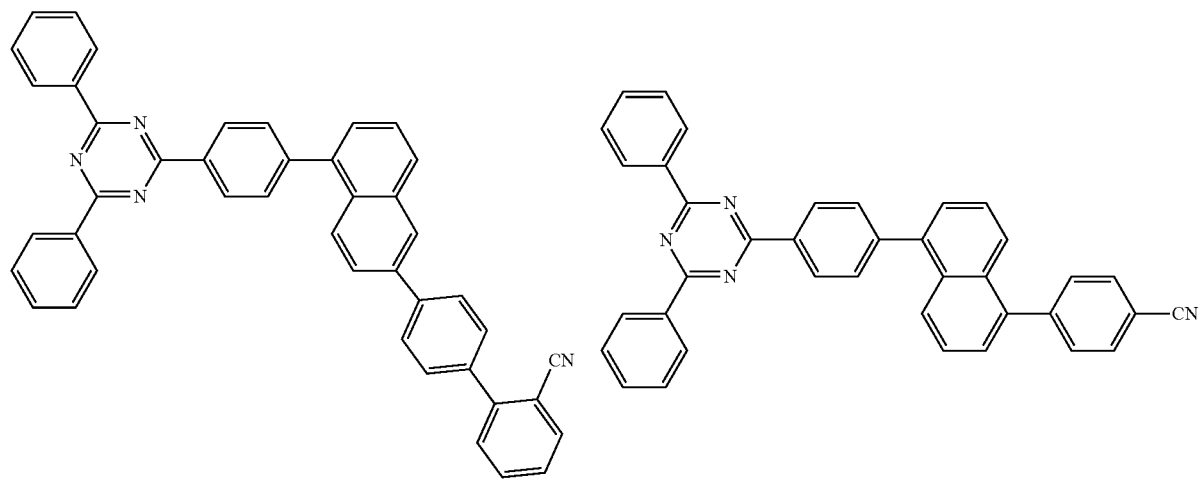

117 118
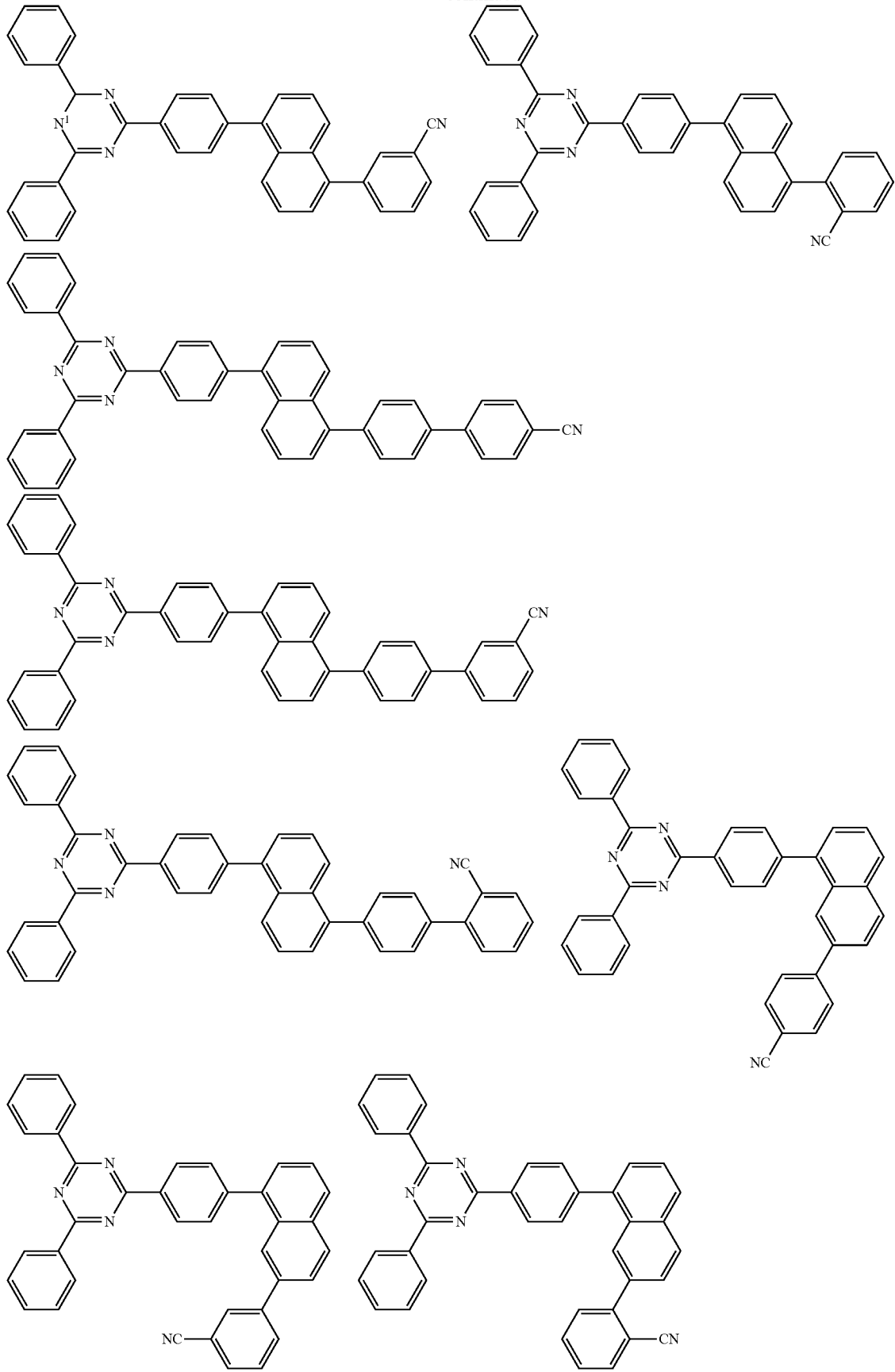
-continued

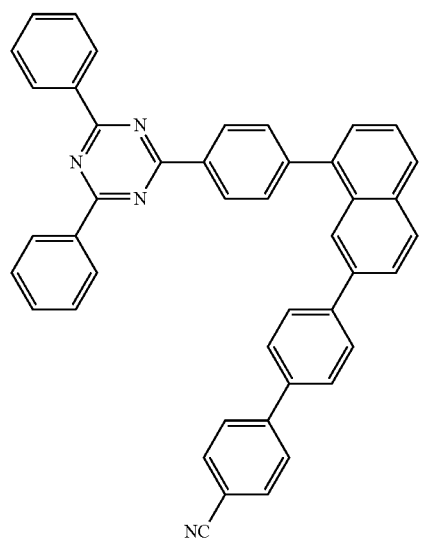
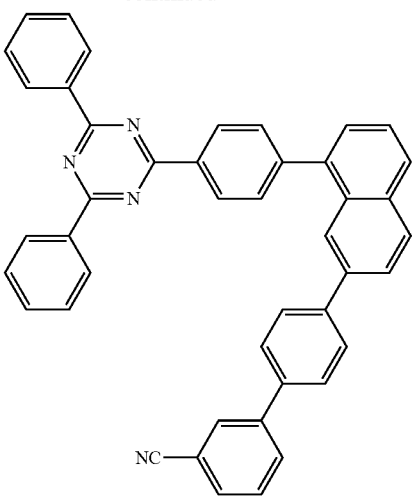
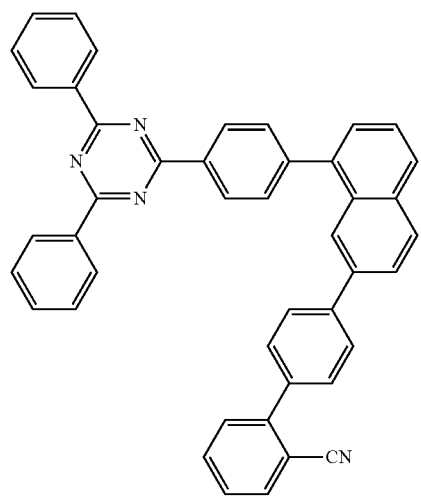
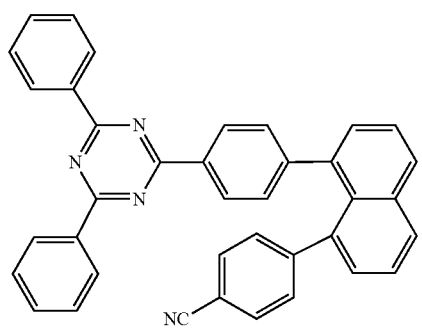
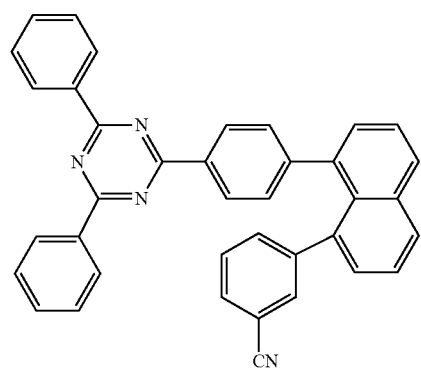
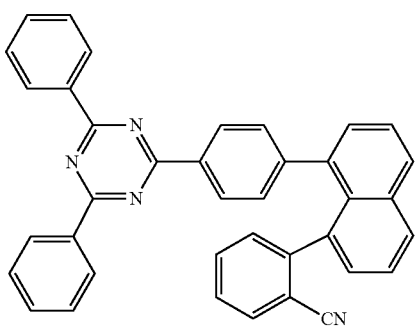

-continued
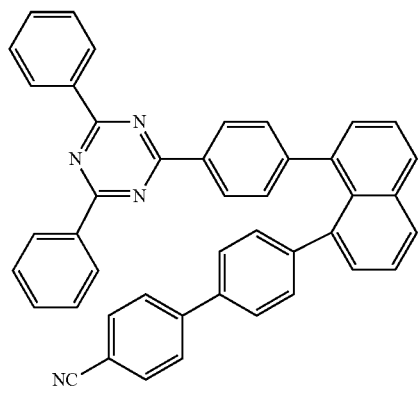
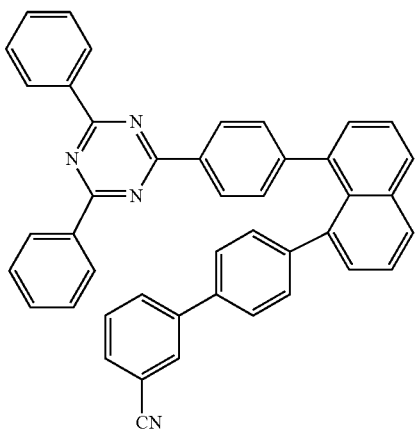
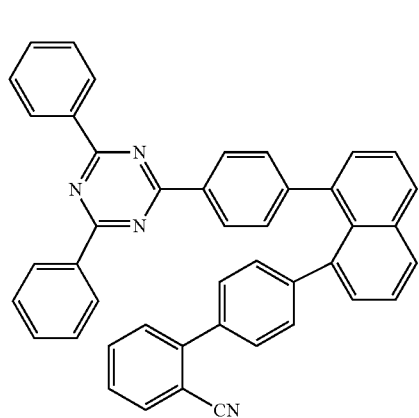
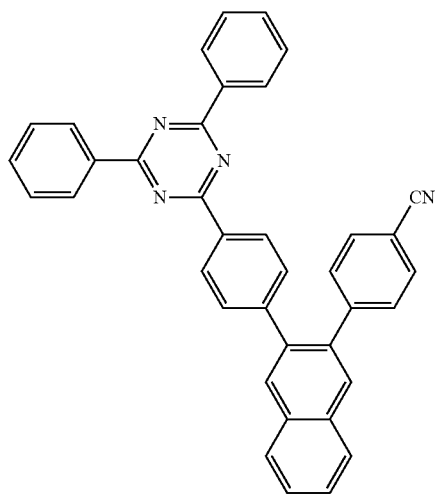
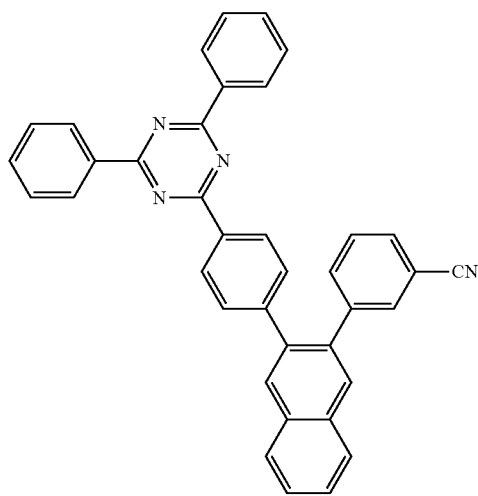
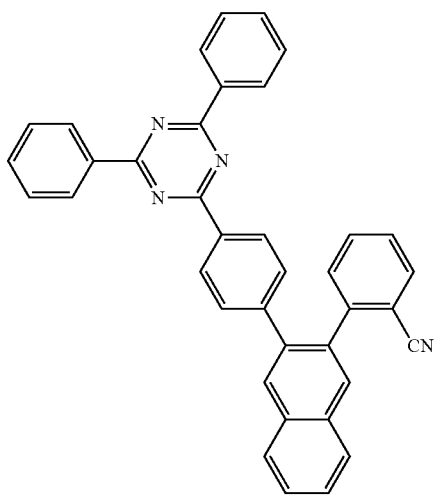

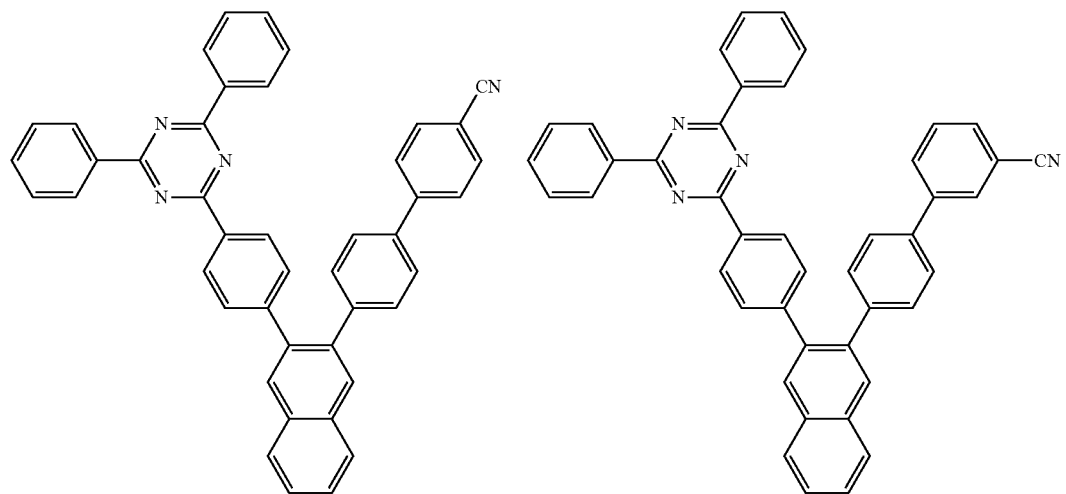
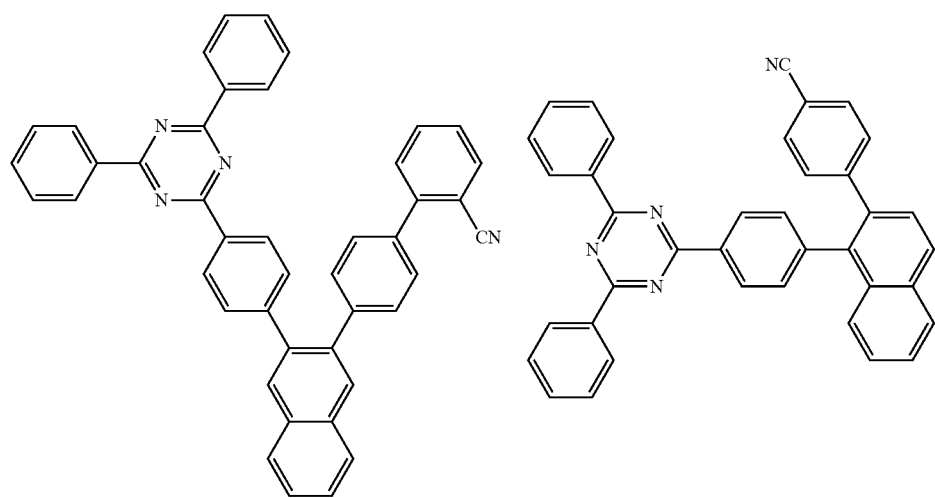
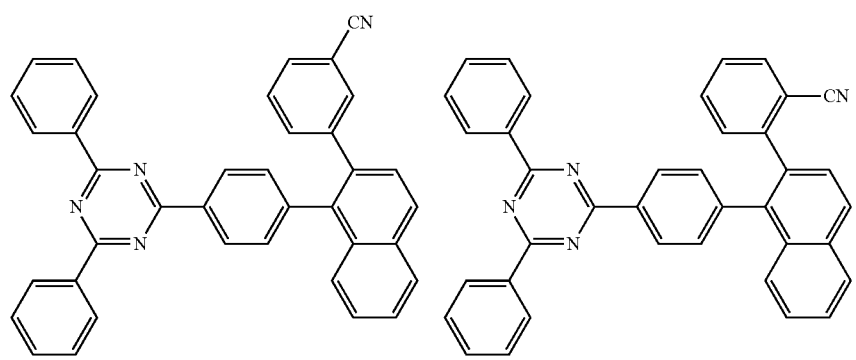

-continued
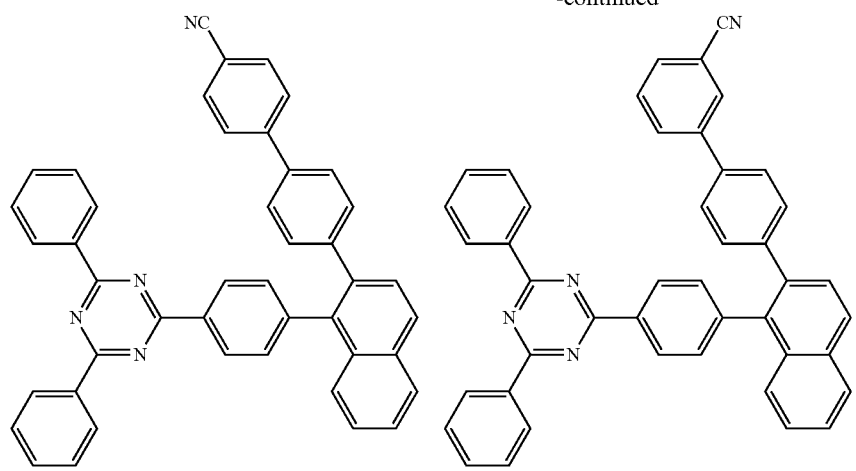
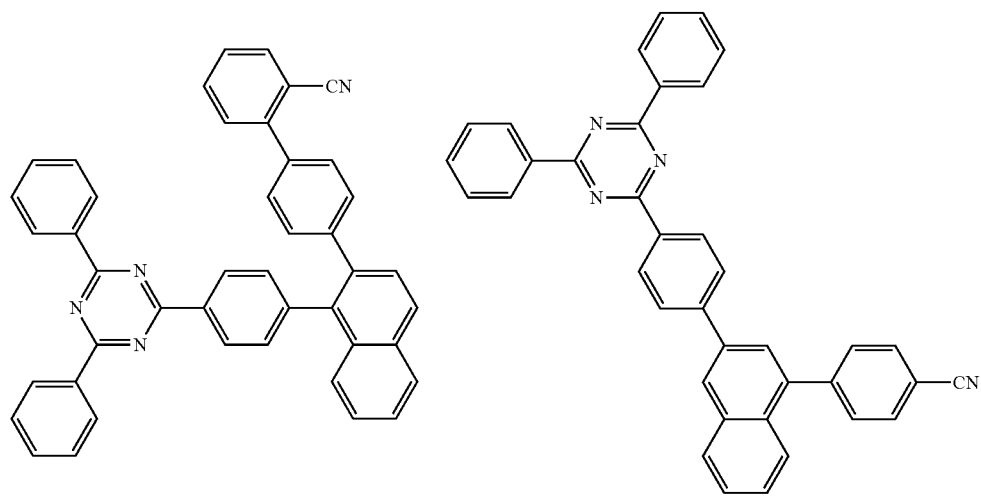
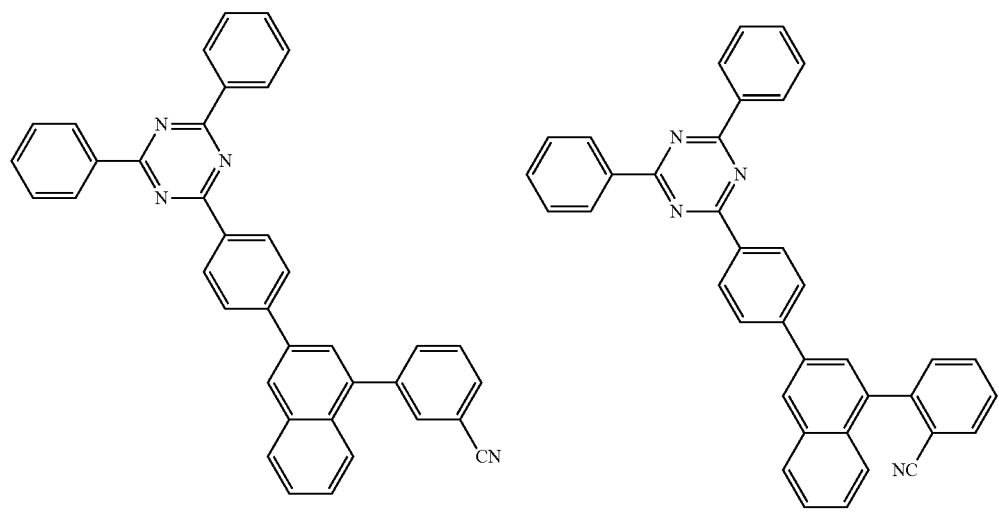

-continued
| 127 | 128 |
|---|---|
| 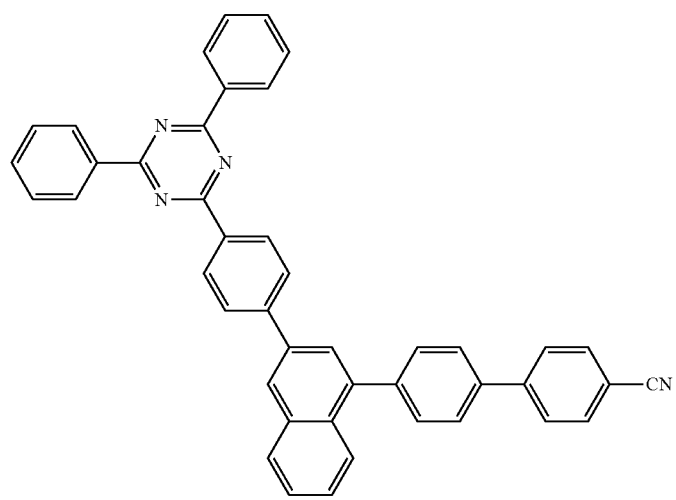 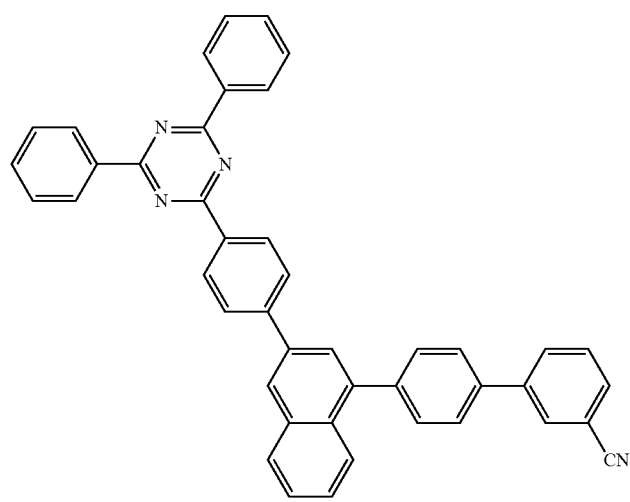 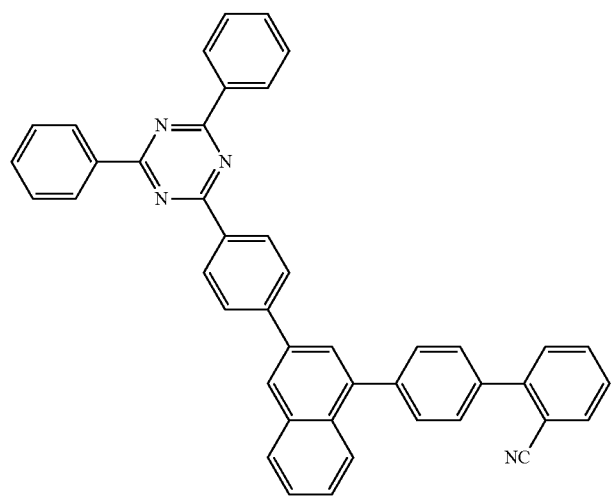 | 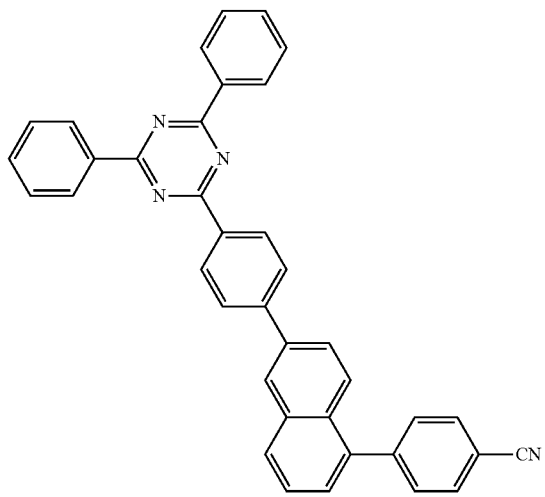 |

-continued
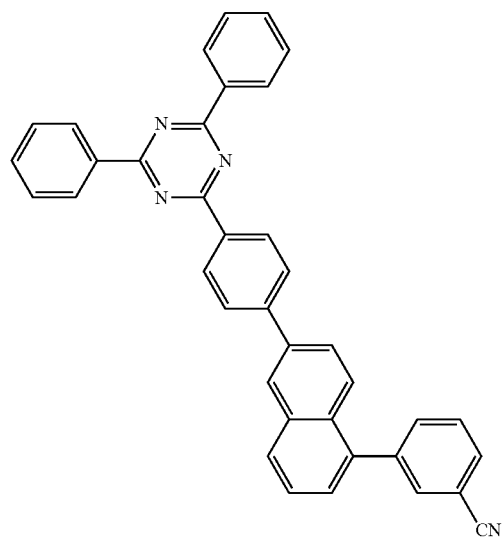
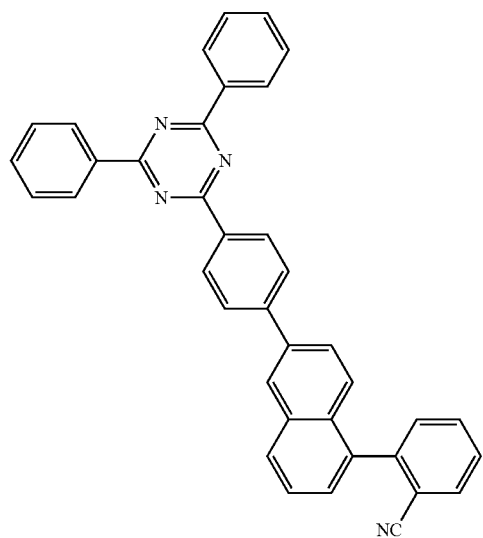
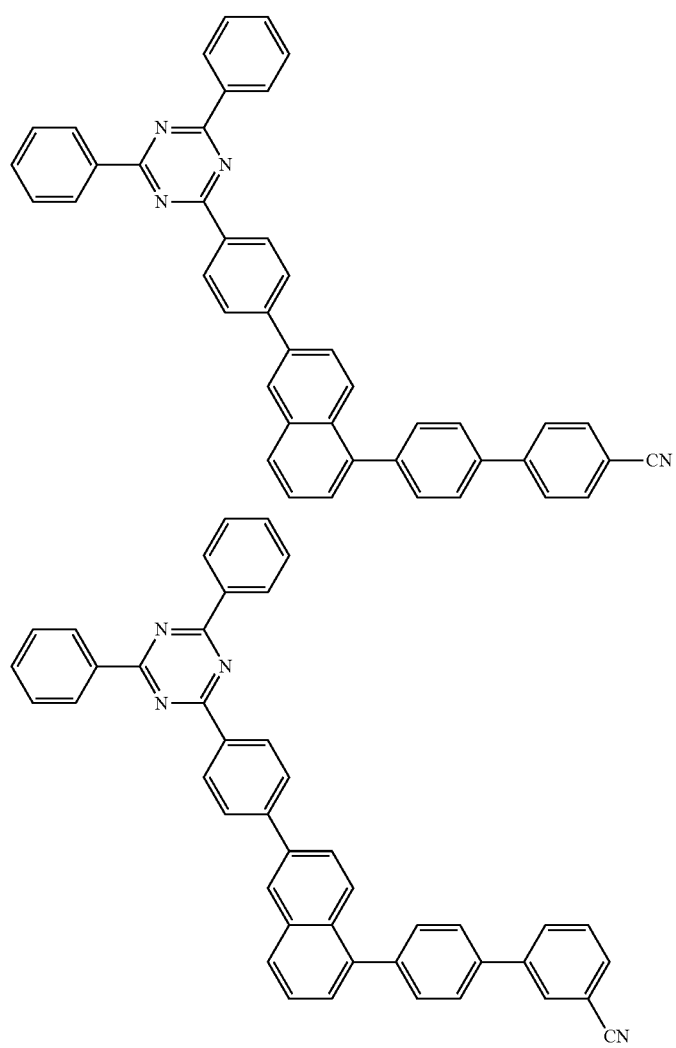

-continued
131
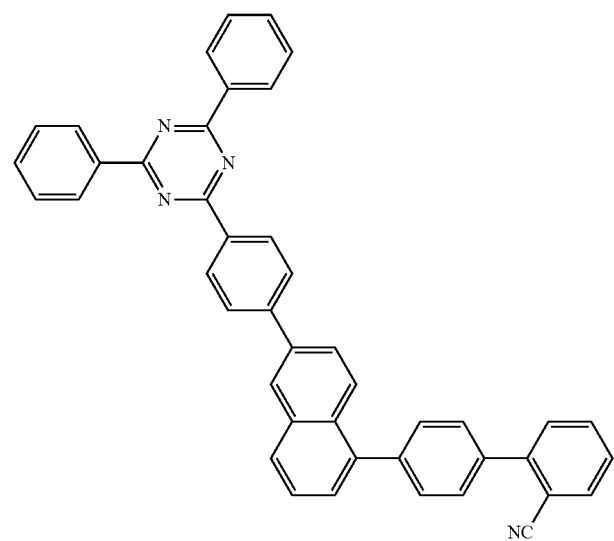
132
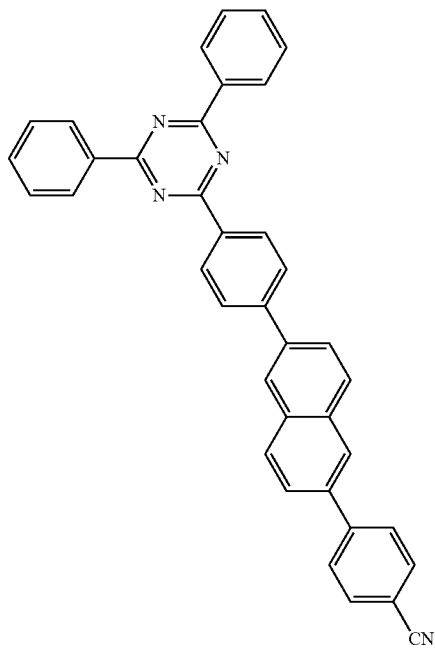
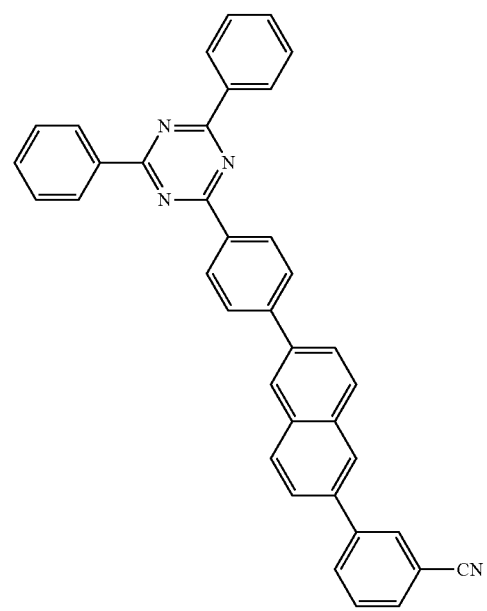
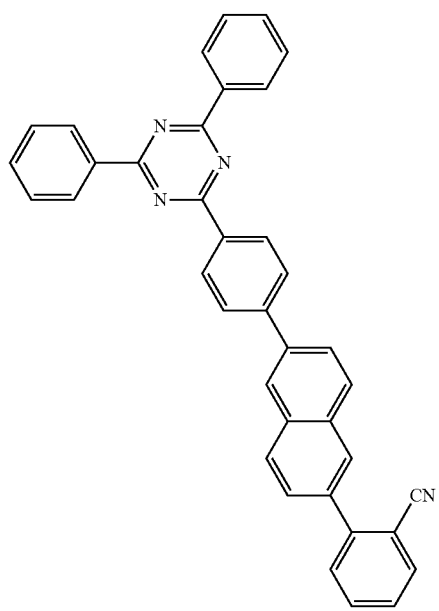

-continued
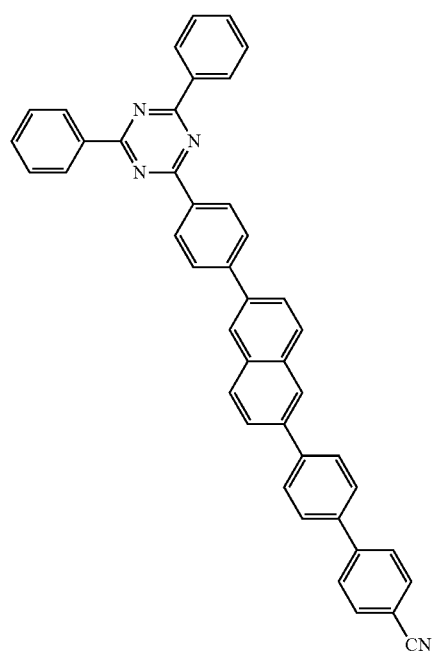
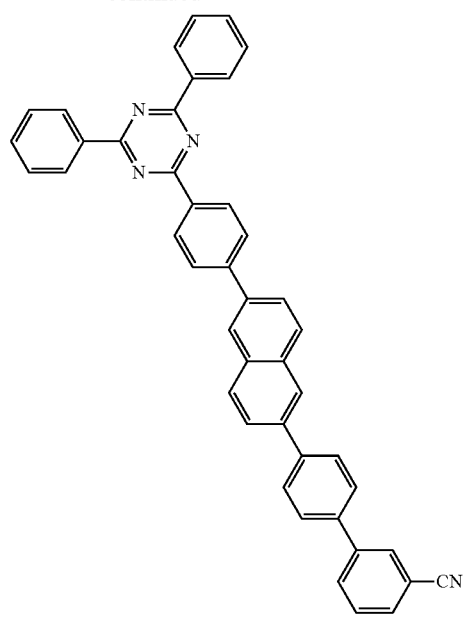
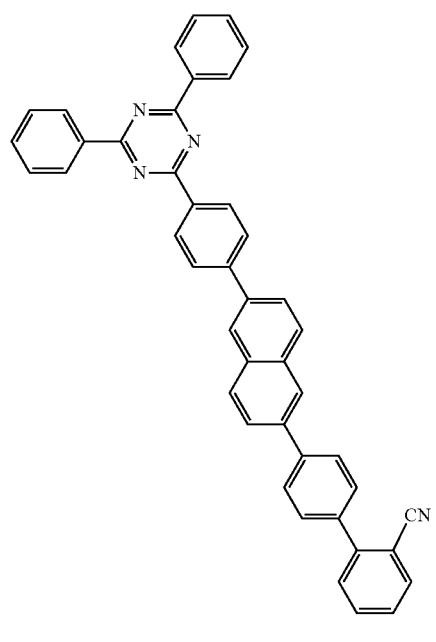
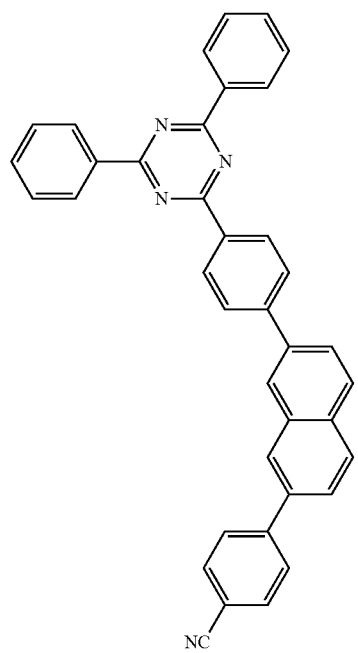
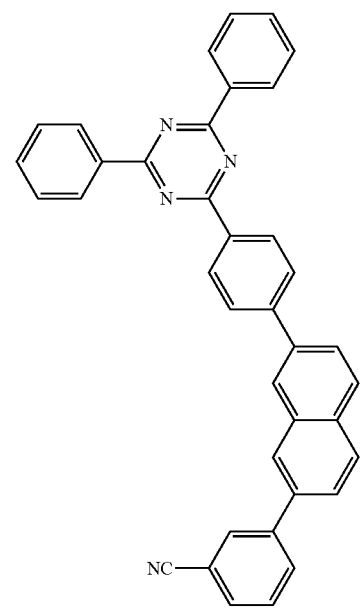

-continued
135
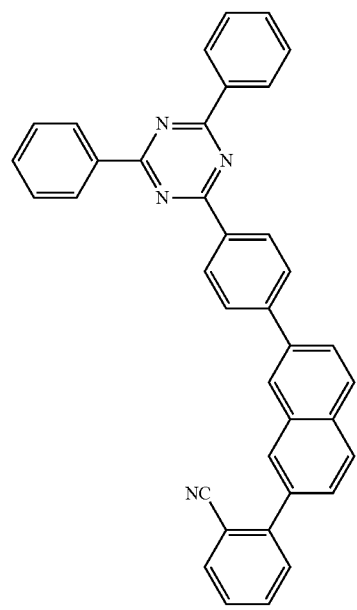
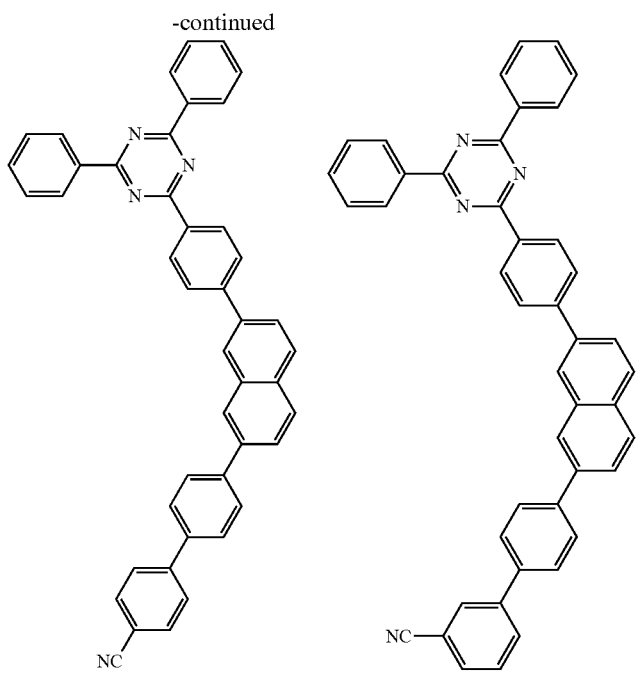
136
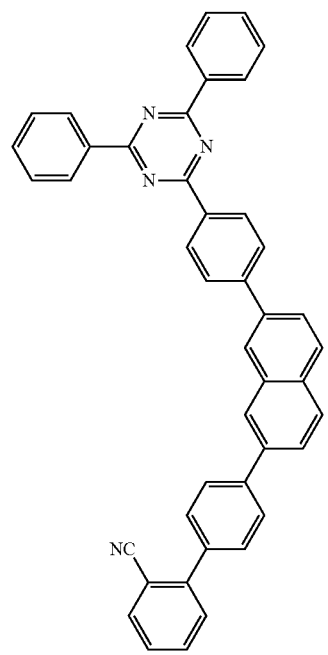
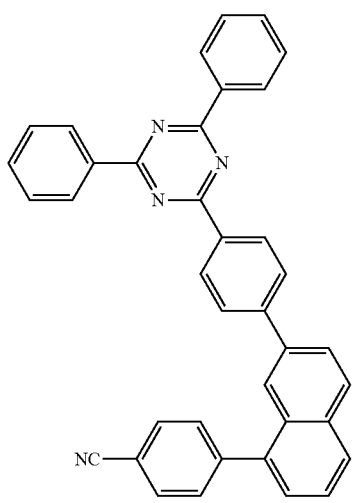
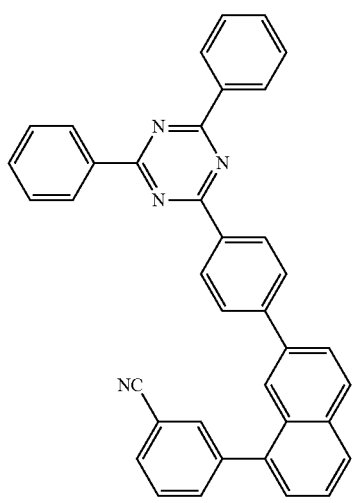

-continued
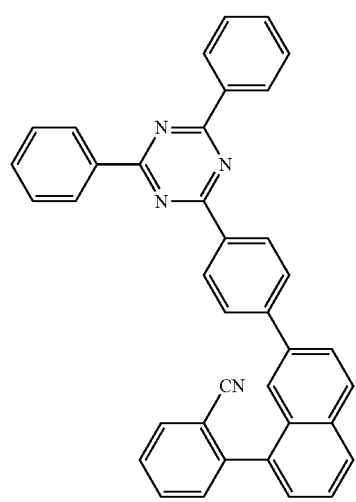
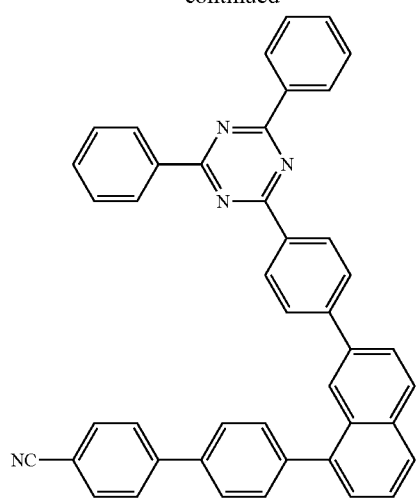
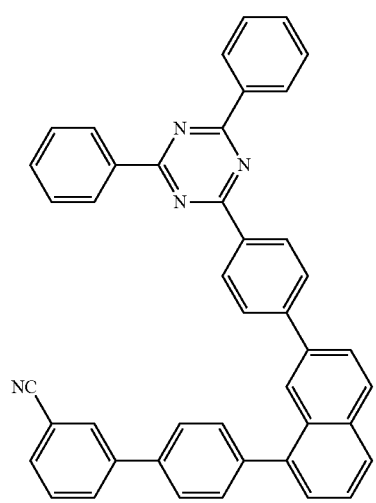
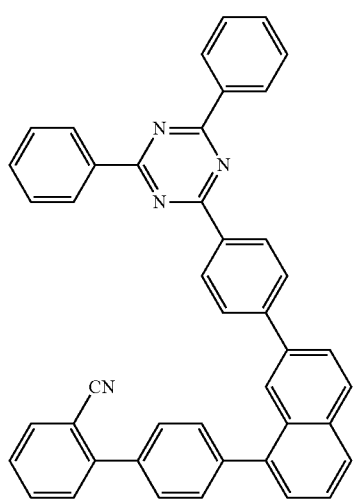
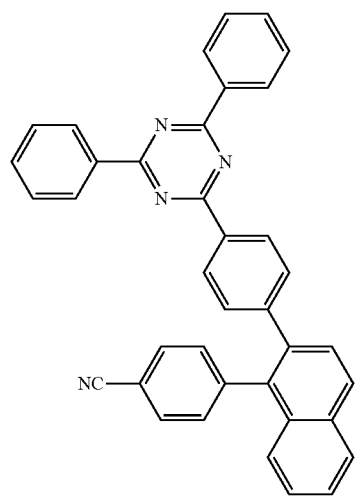
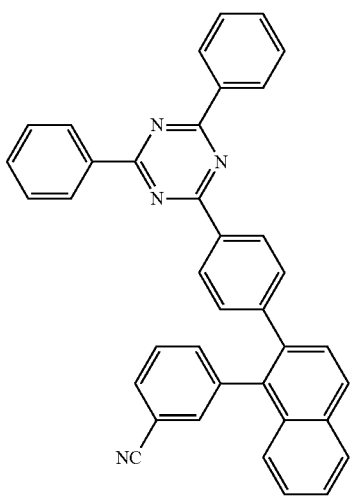
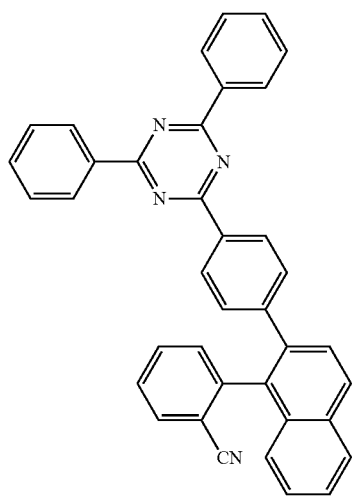

-continued
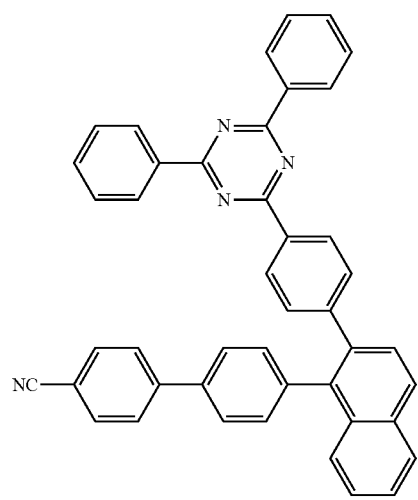
139
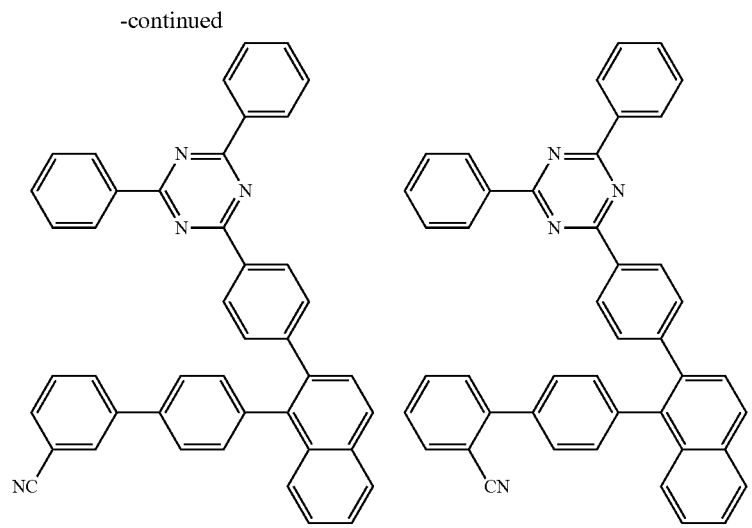
140
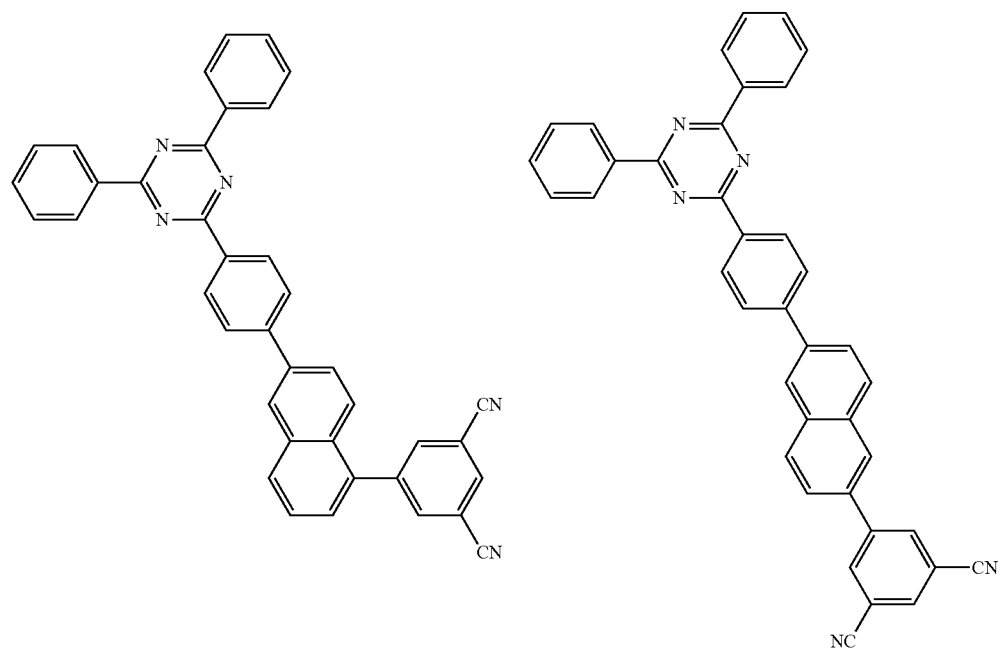

141
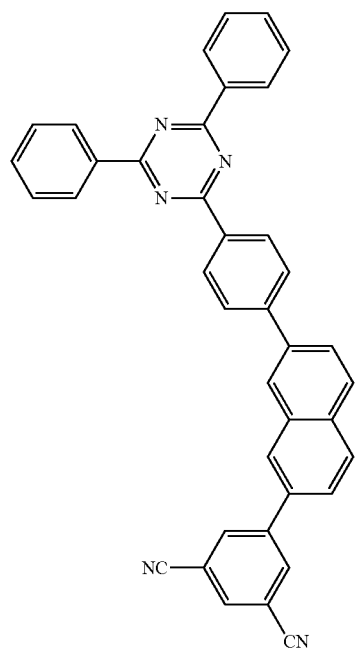
142
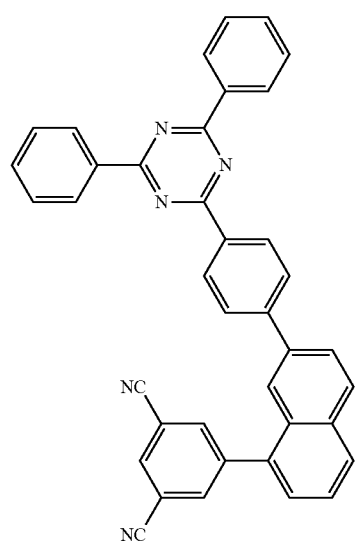
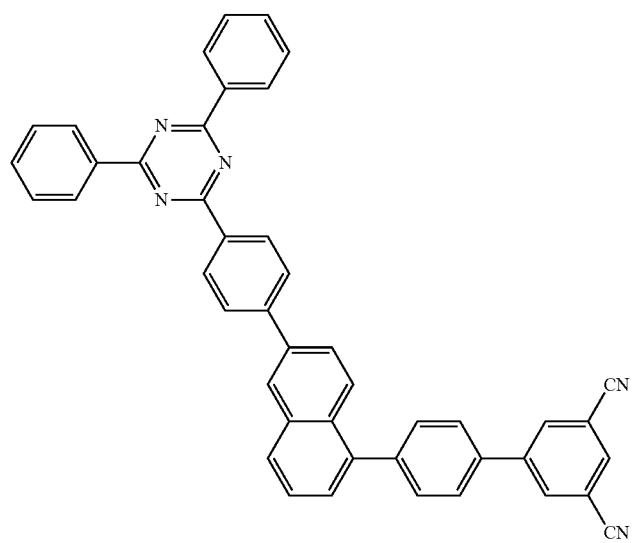
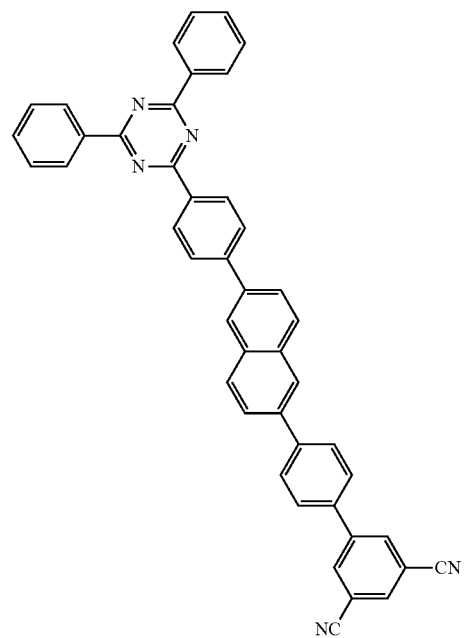

-continued
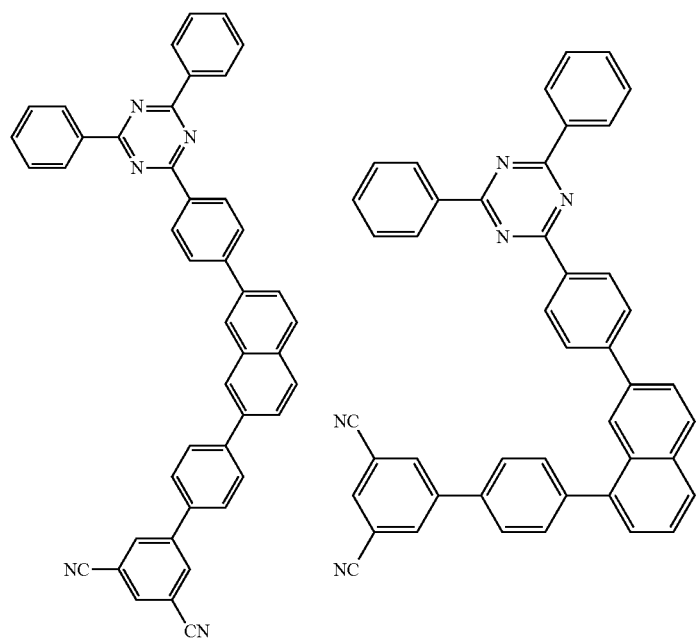
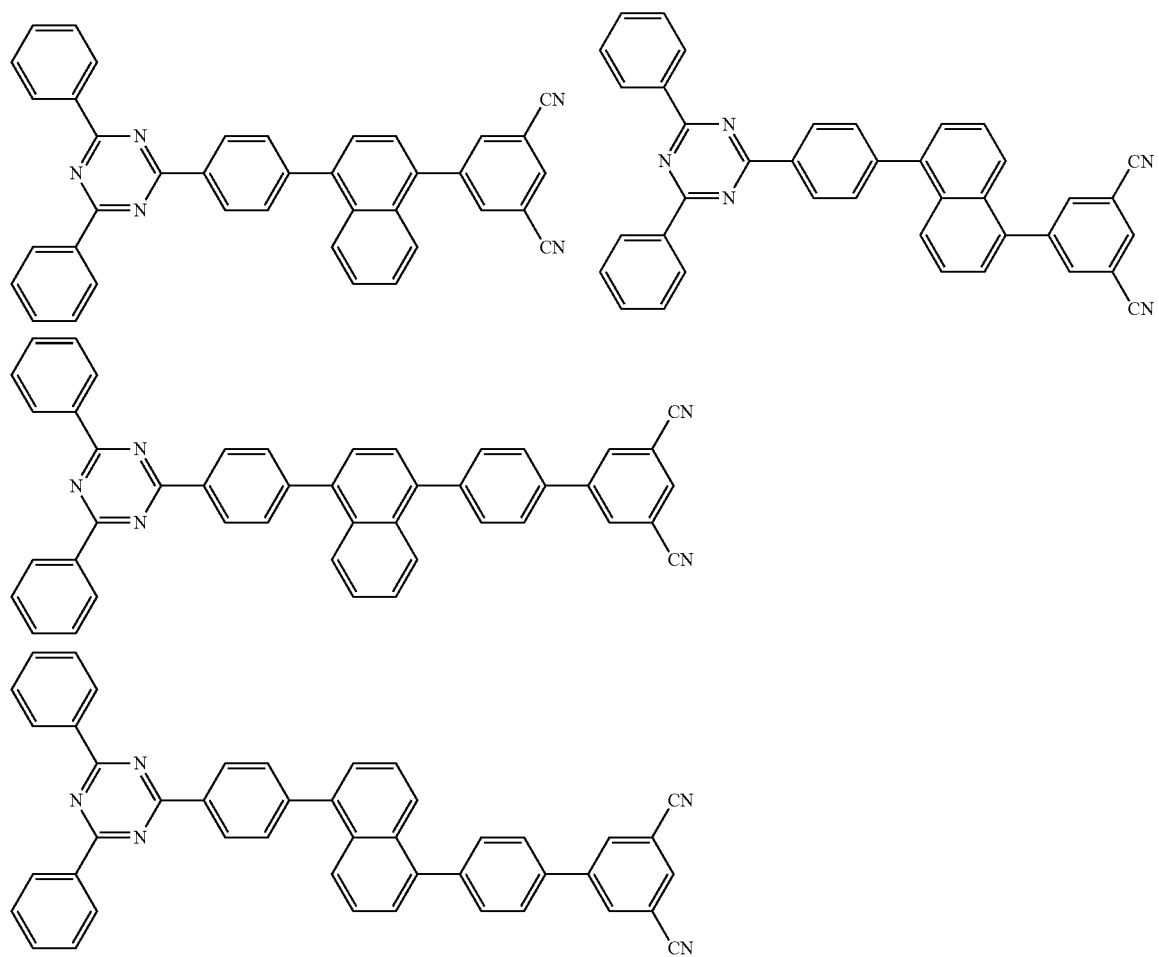

-continued
145
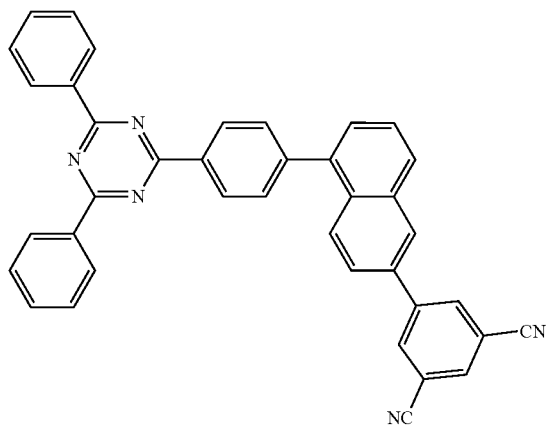
146
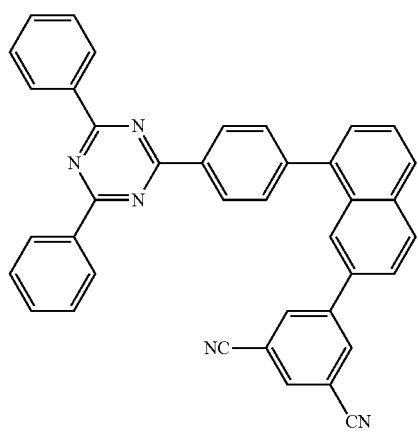
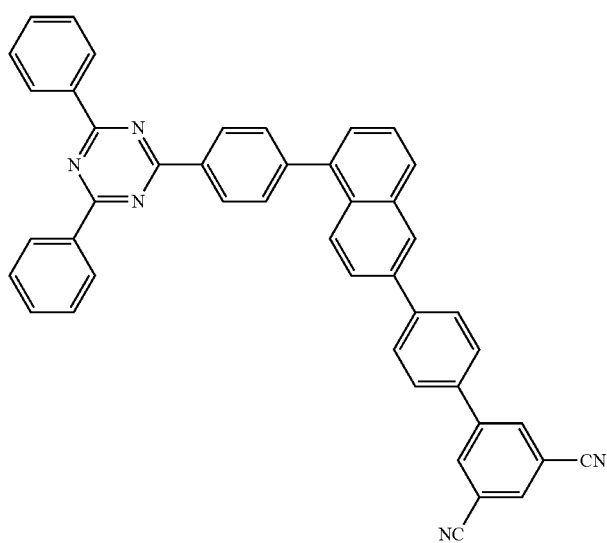
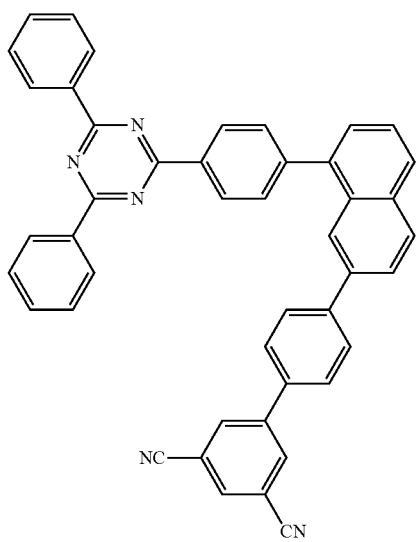
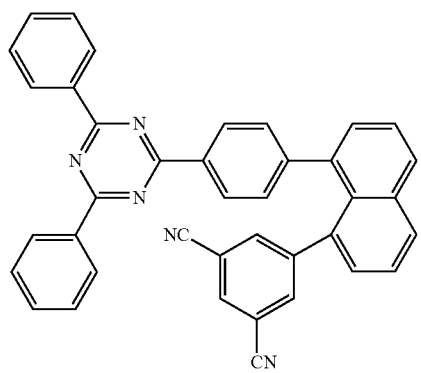
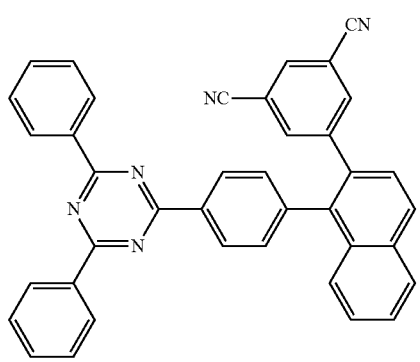

-continued
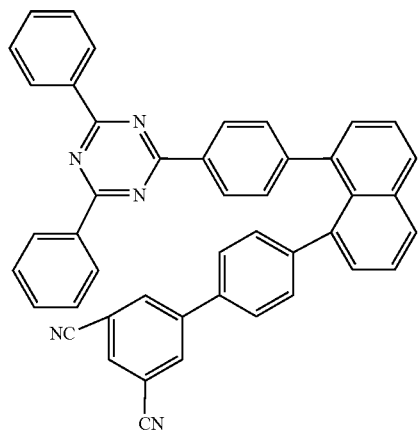
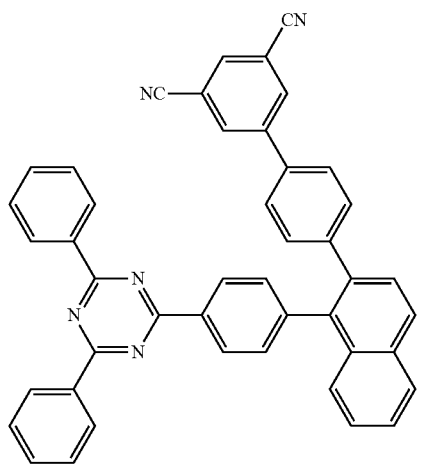
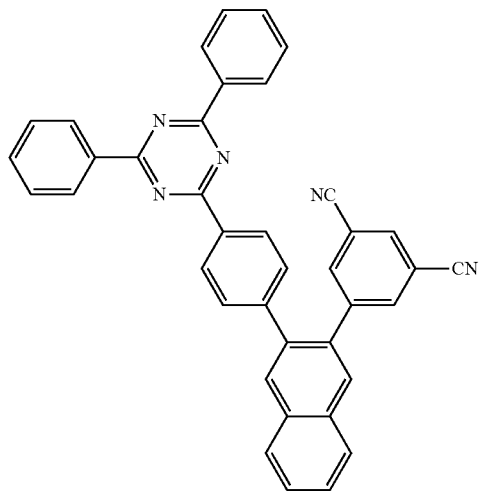
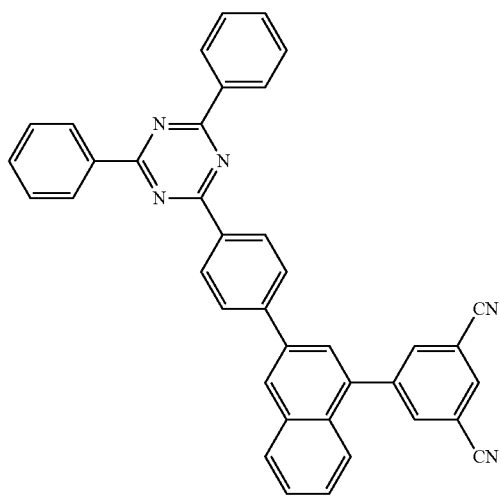
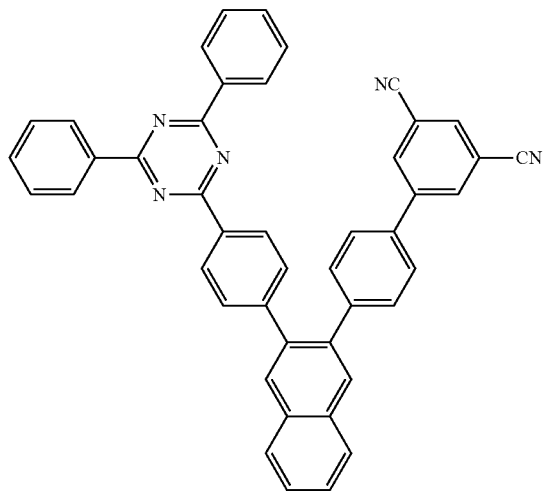
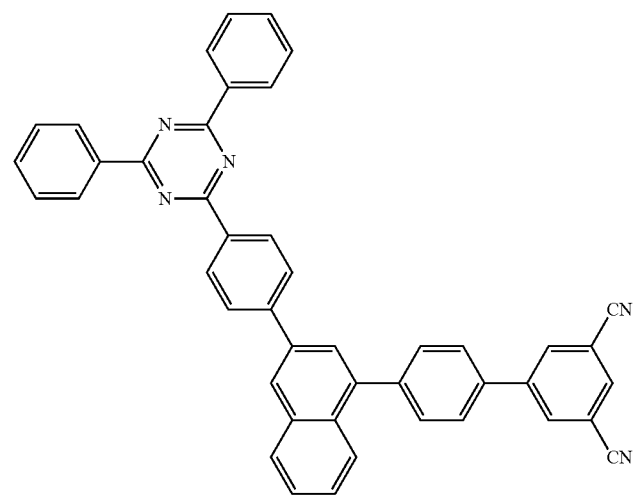

149
150
-continued
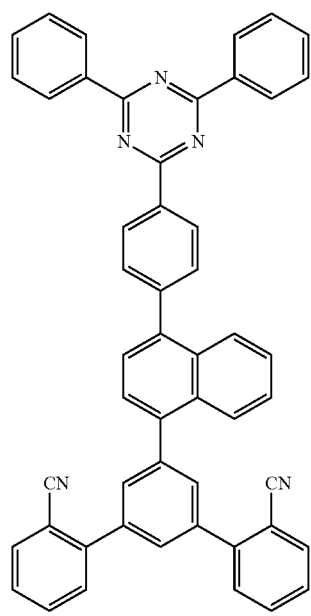
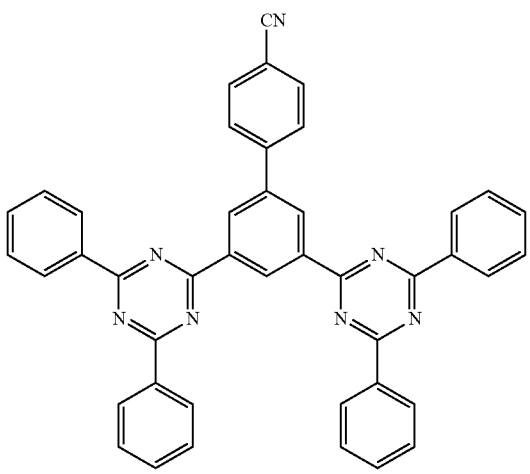
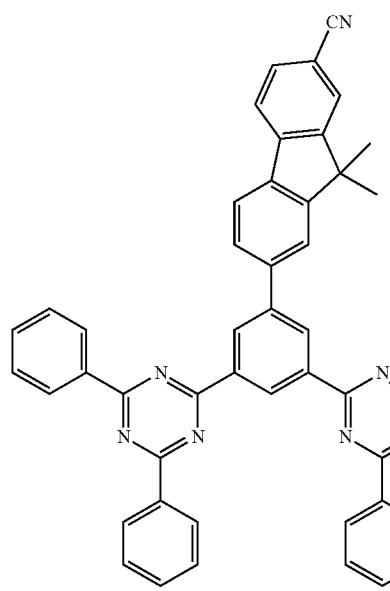
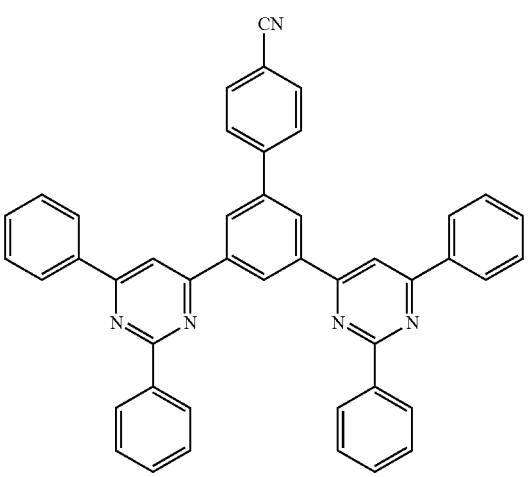
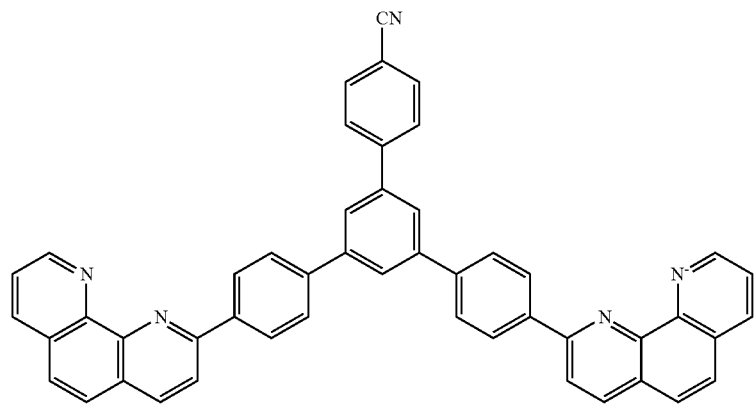

-continued
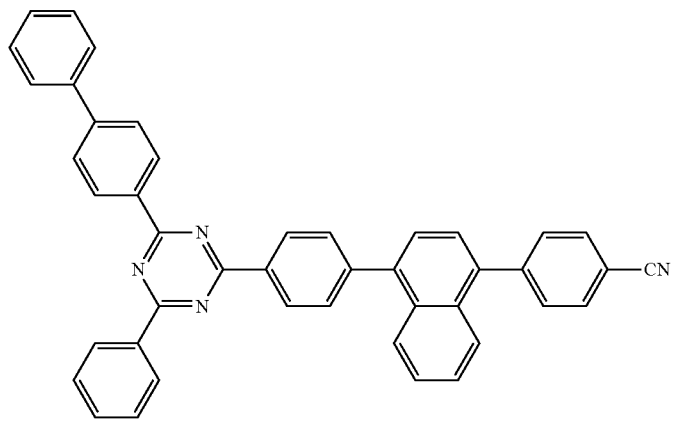
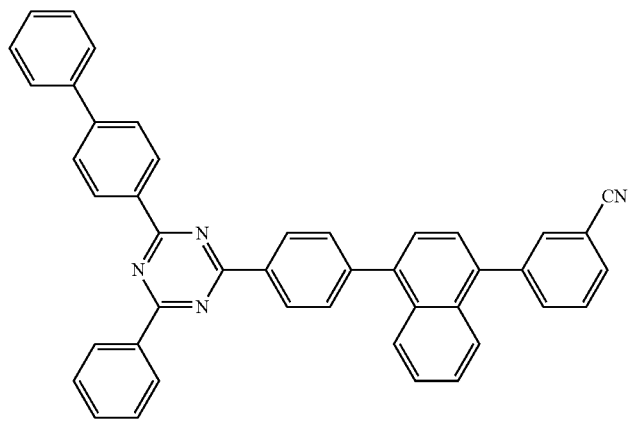
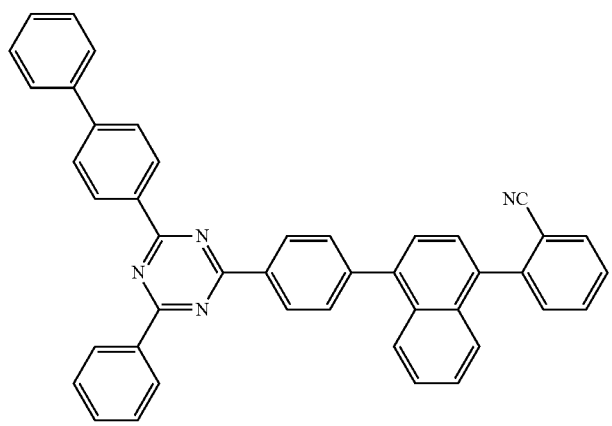
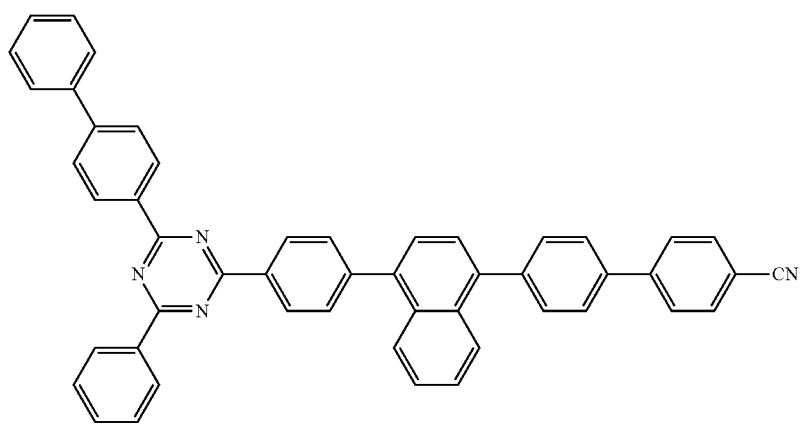

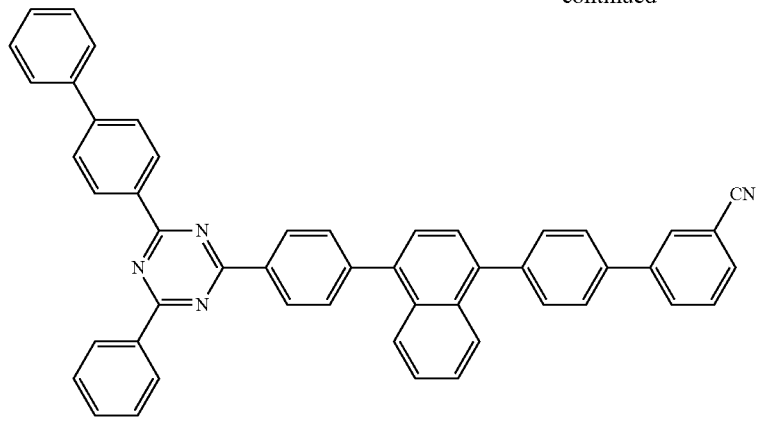
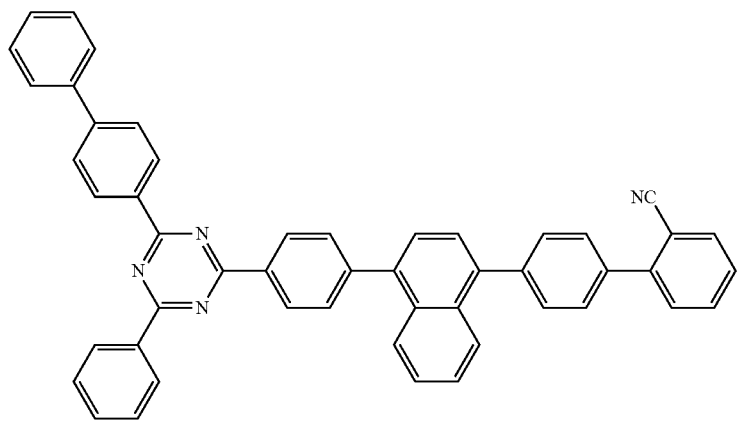
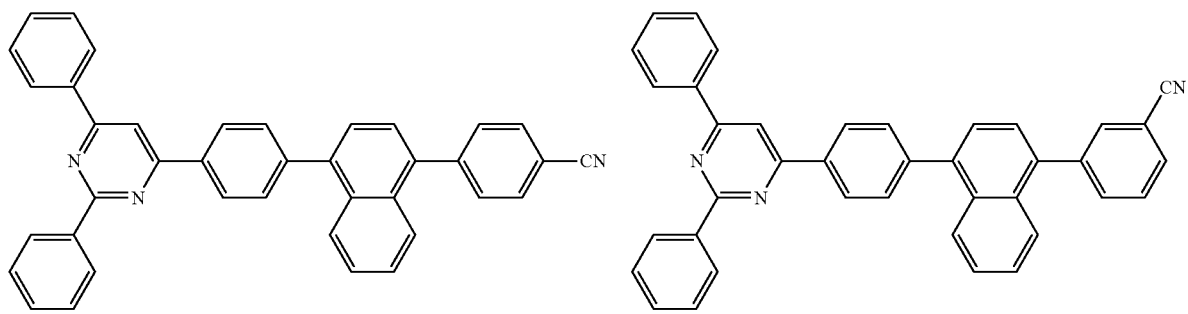
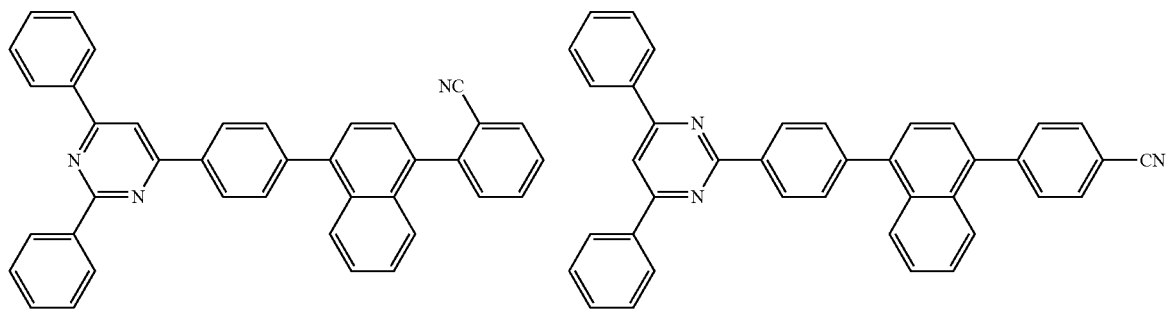

-continued
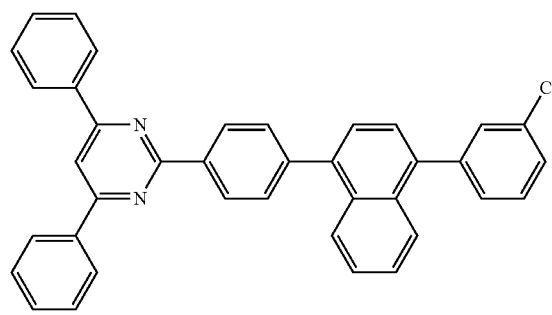
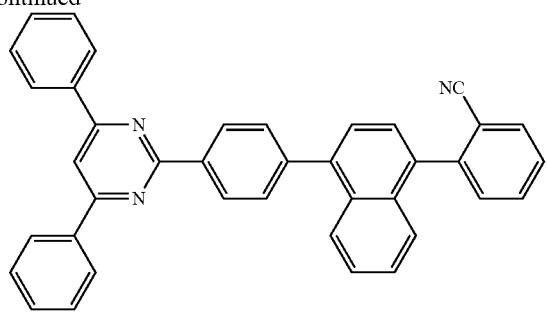
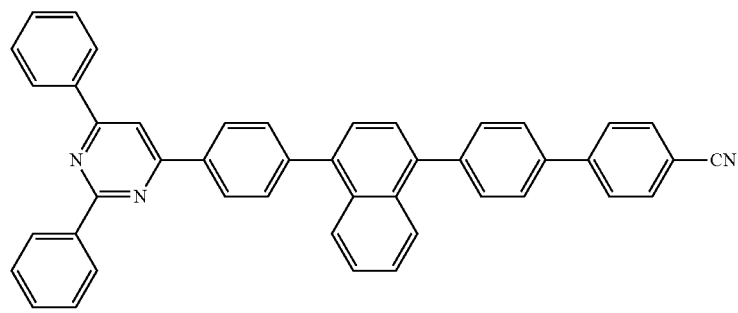
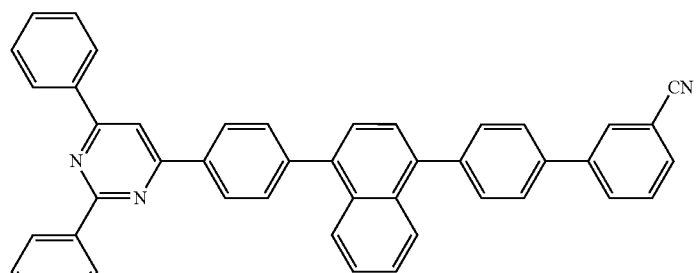
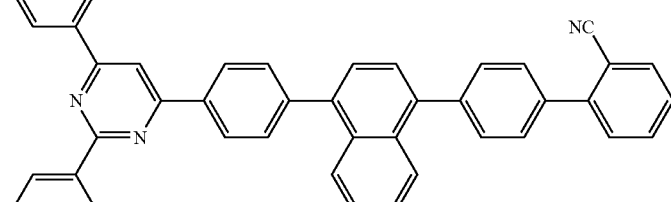
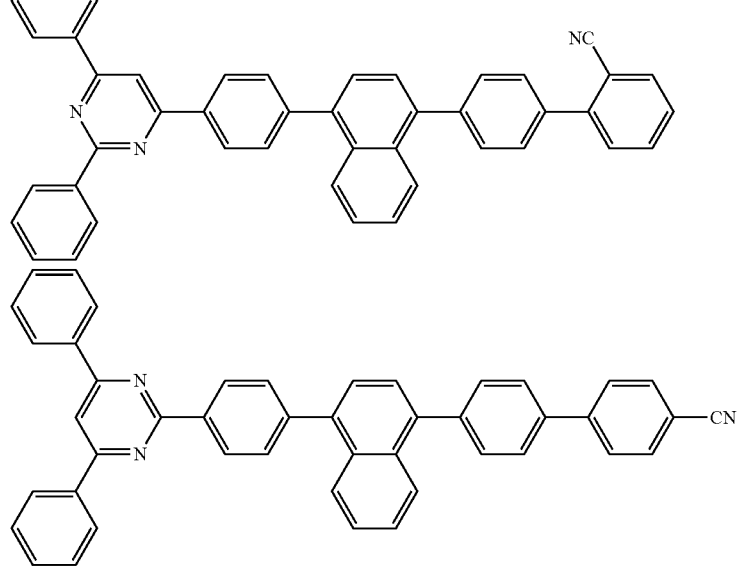

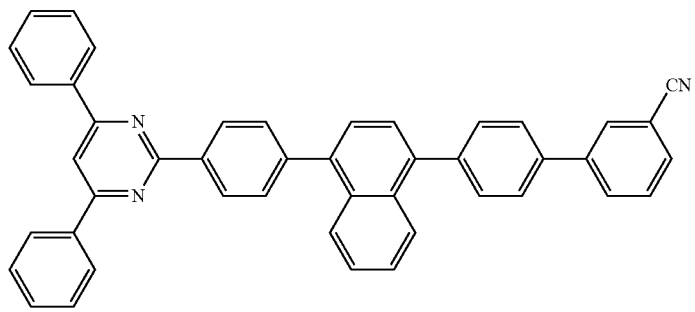
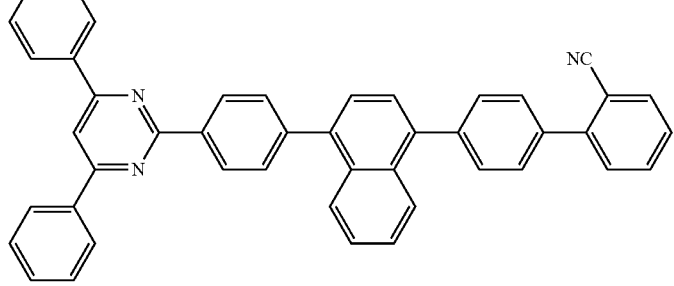
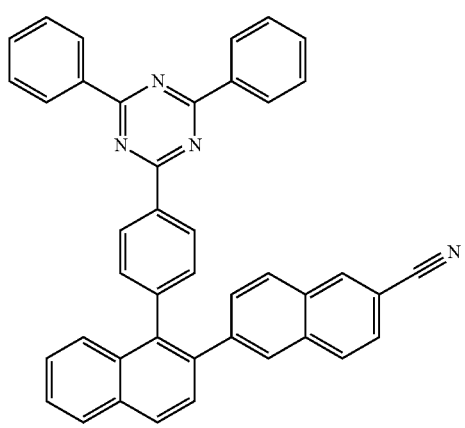
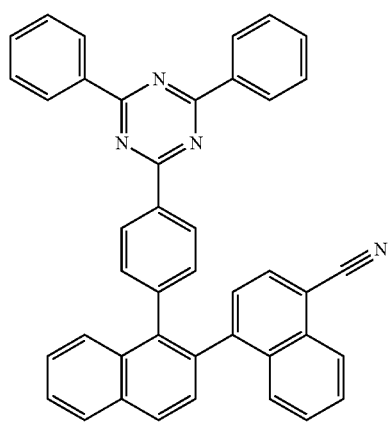
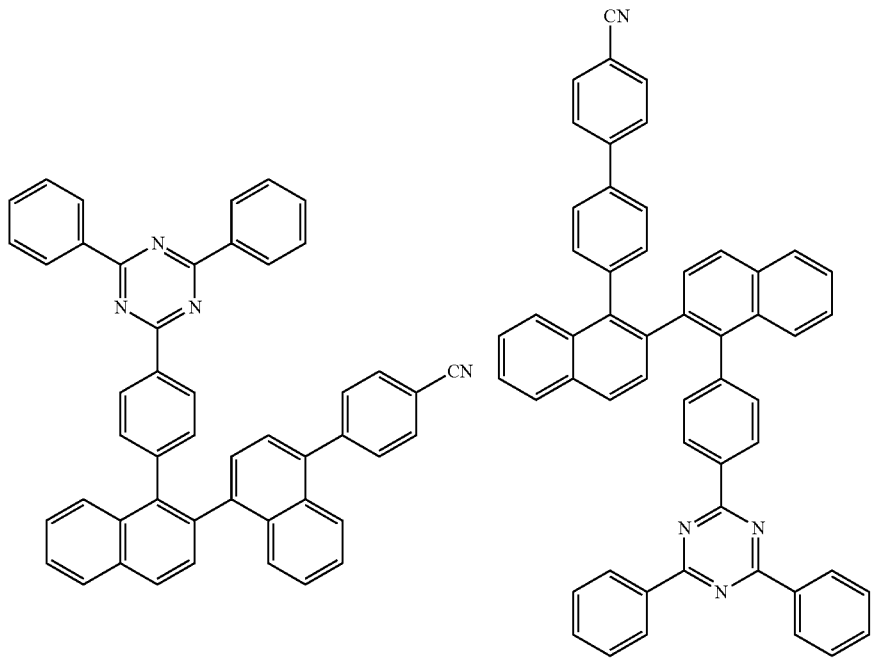

-continued
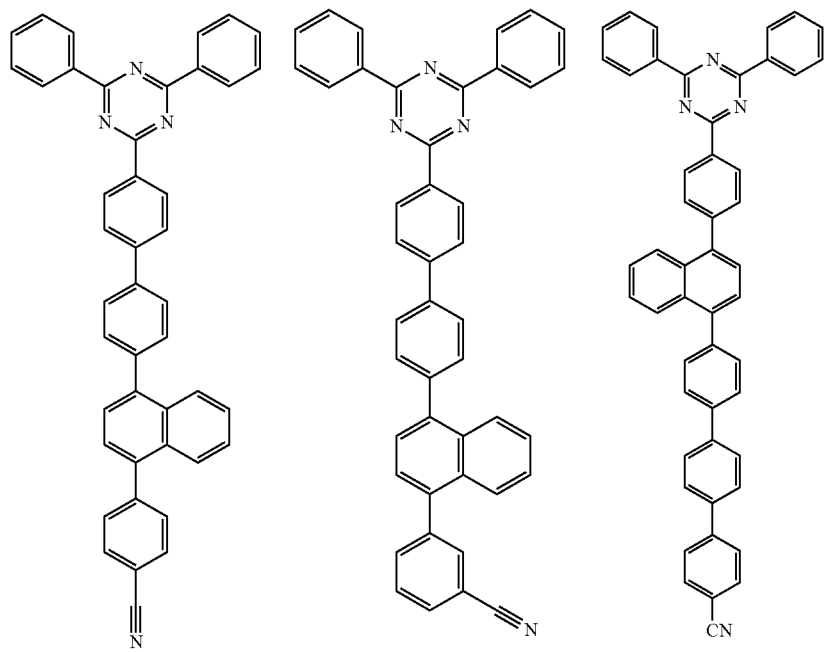
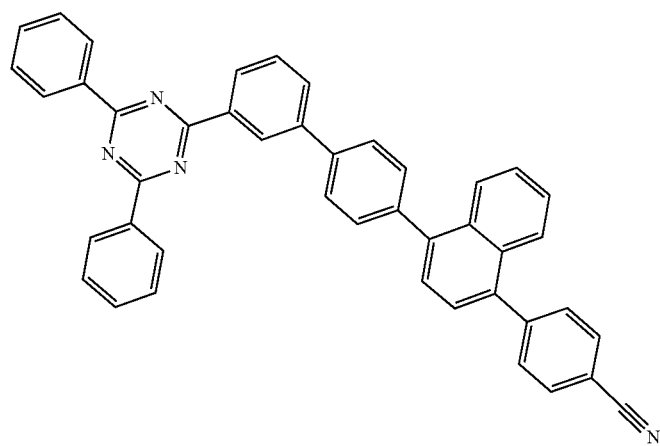

-continued
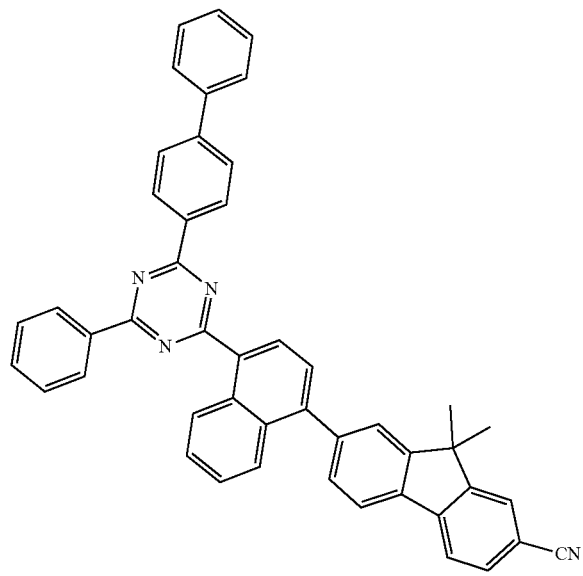
161
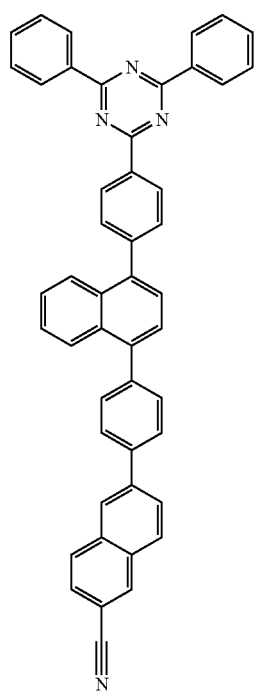
162
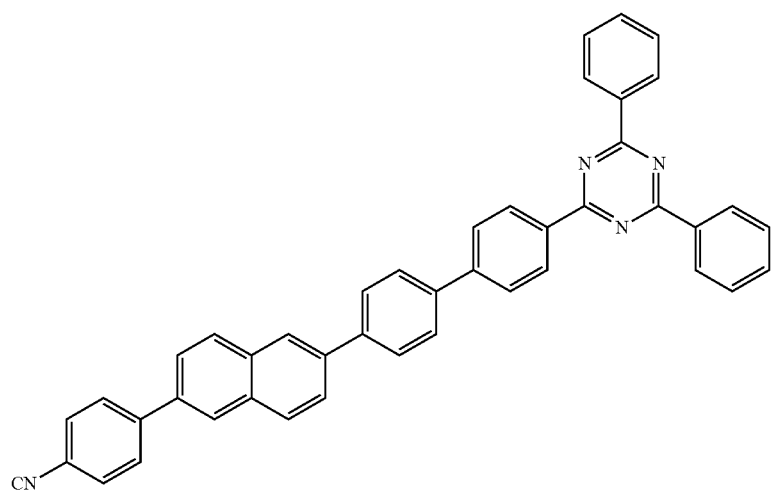

163
164
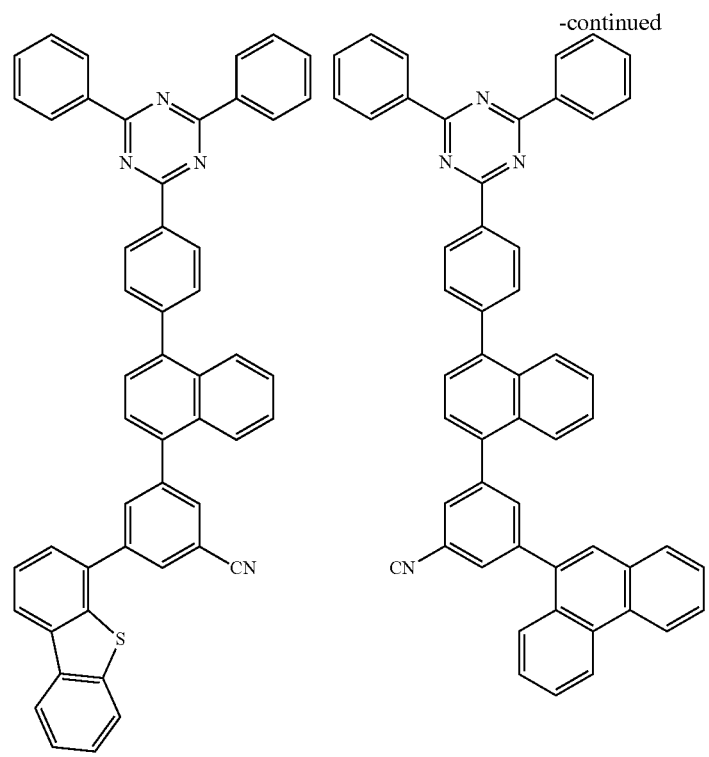
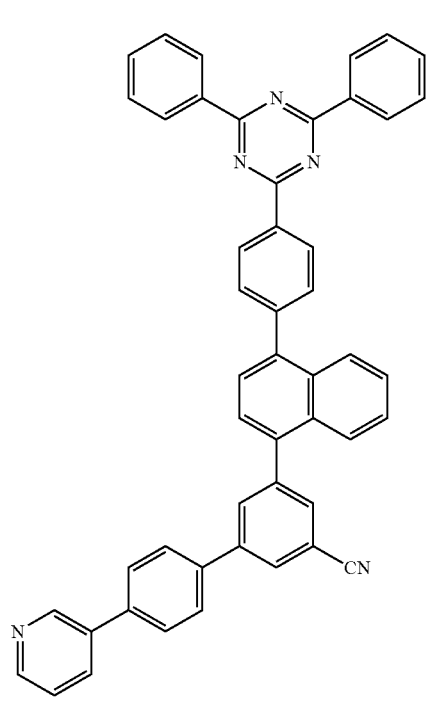
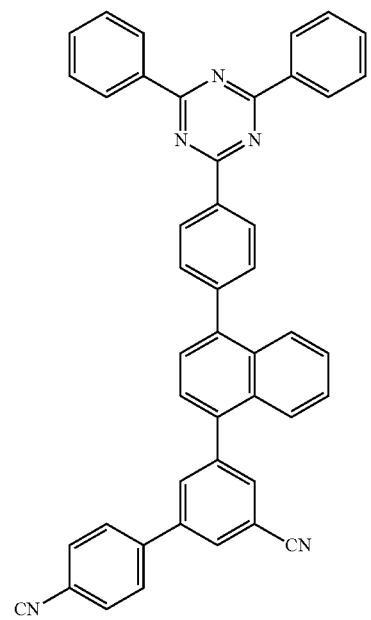
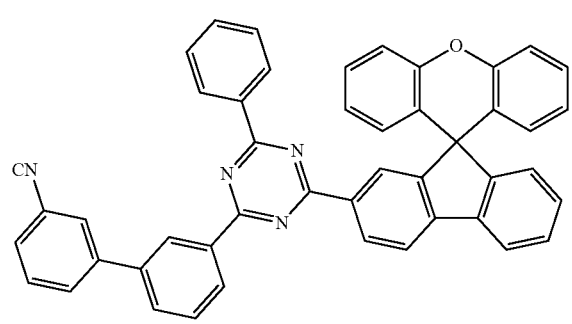

-continued
165
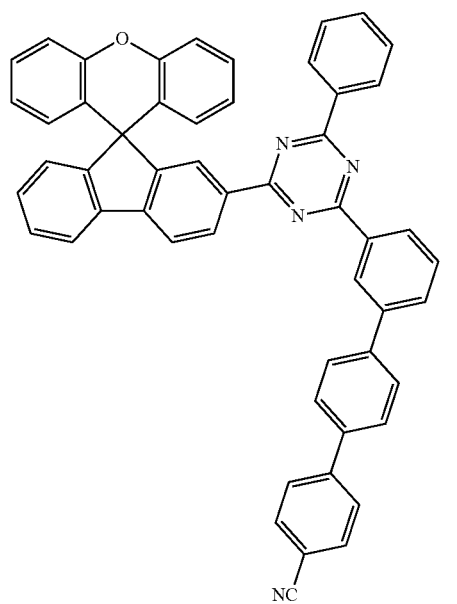
166
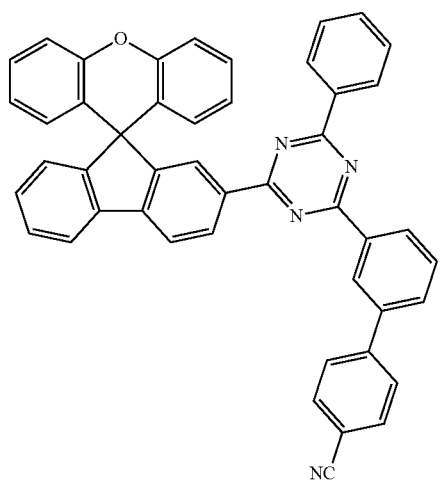
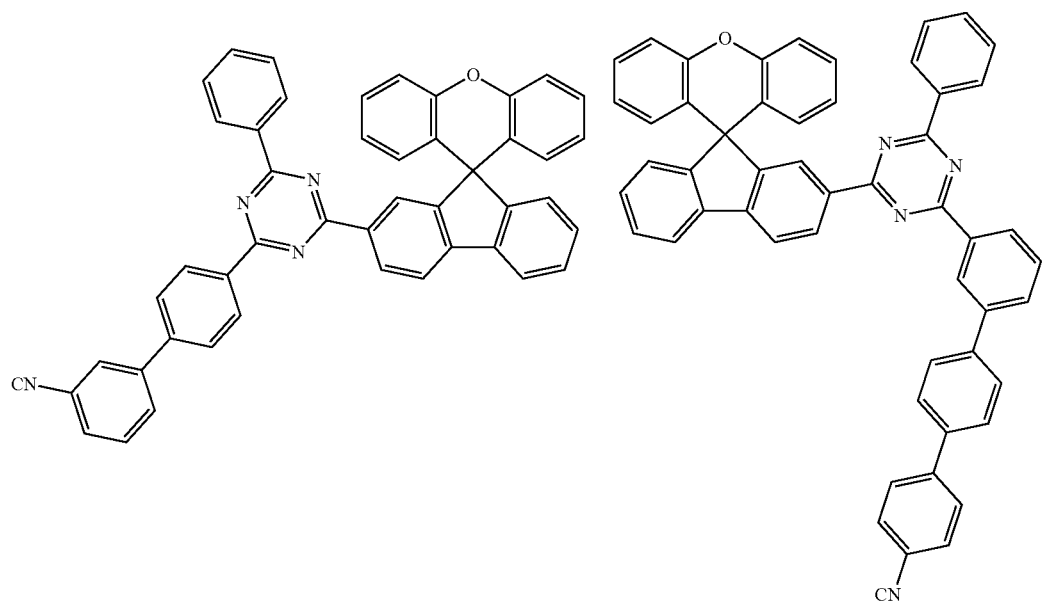

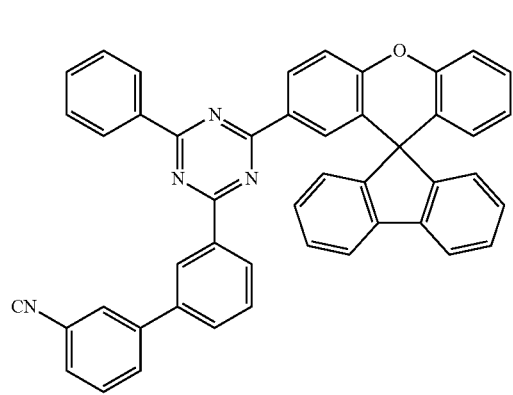
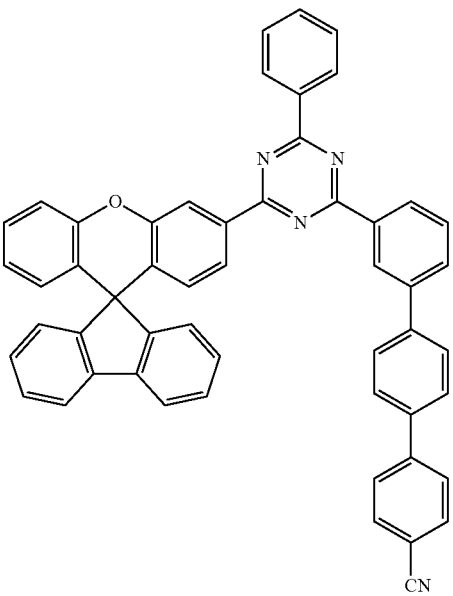
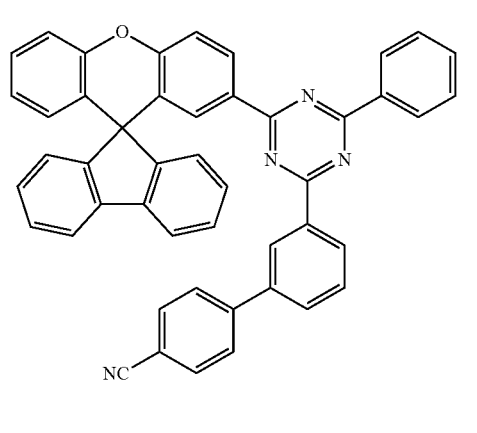
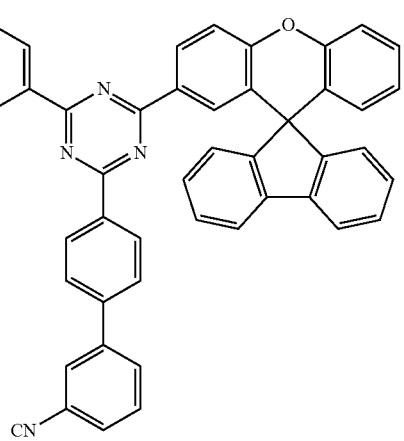
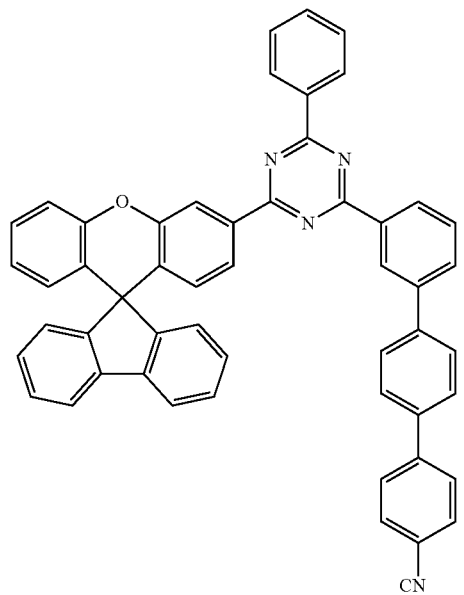
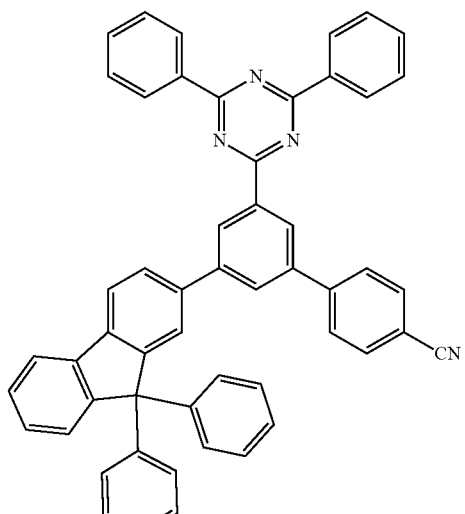

169
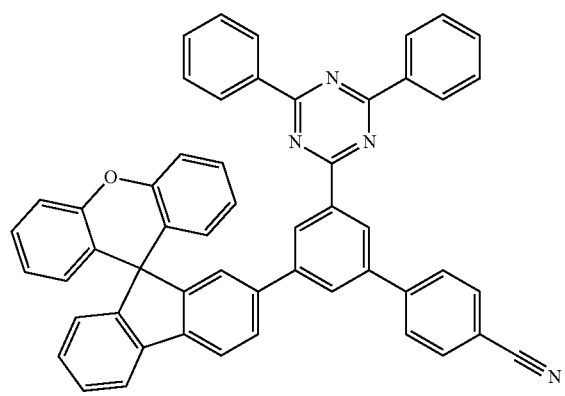
170
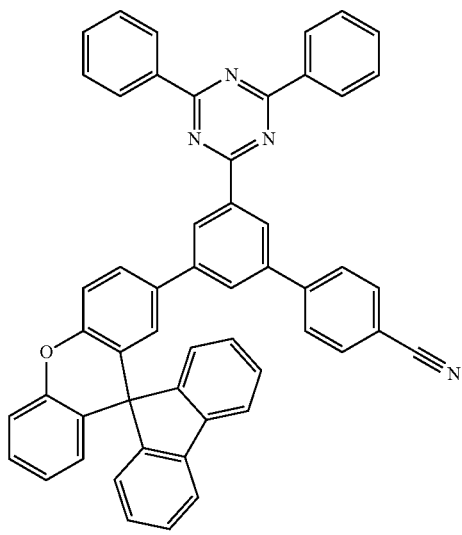
-continued
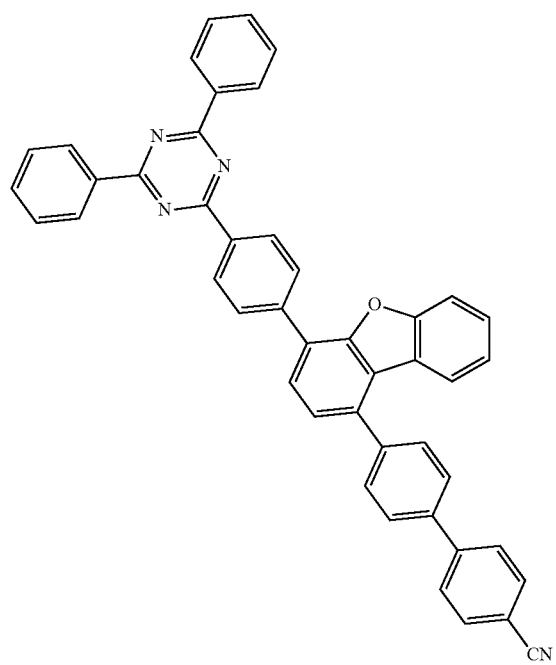
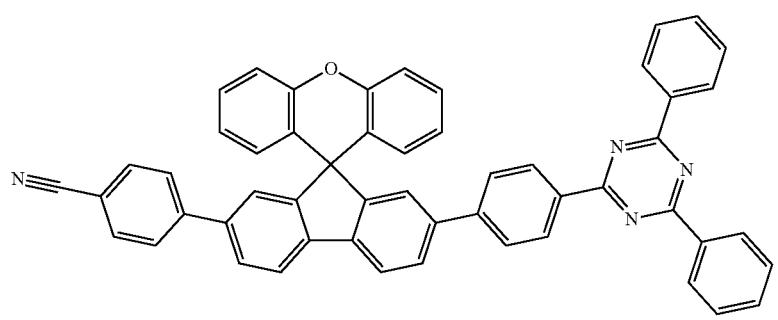

-continued
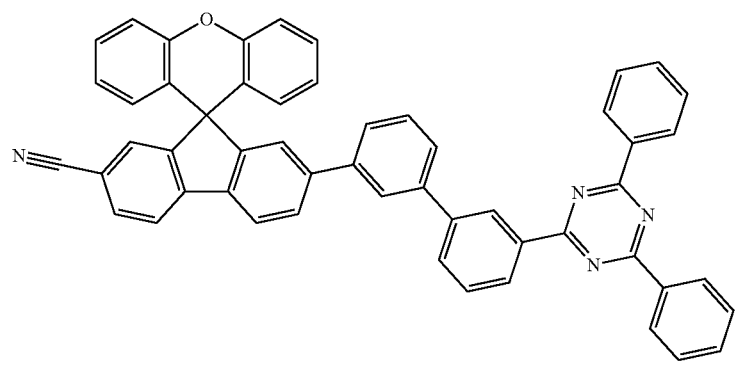
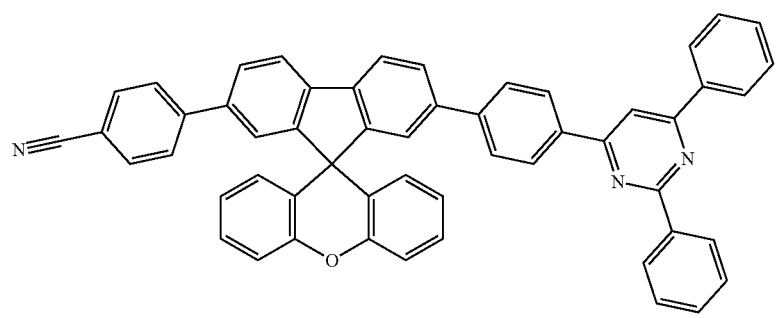
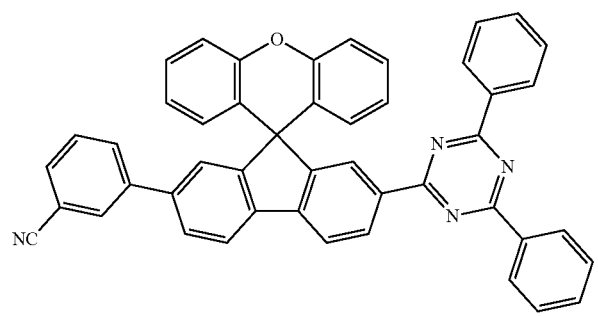
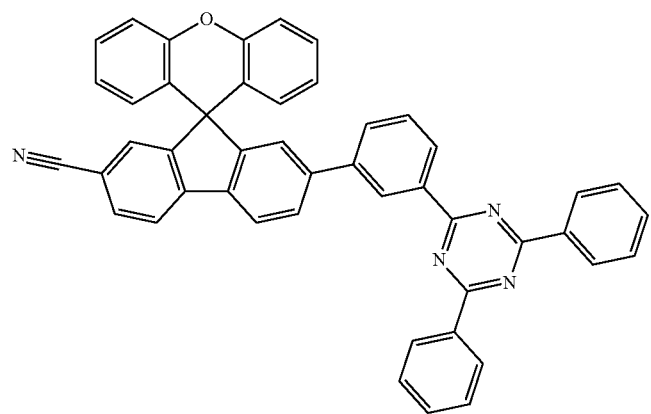

-continued
173
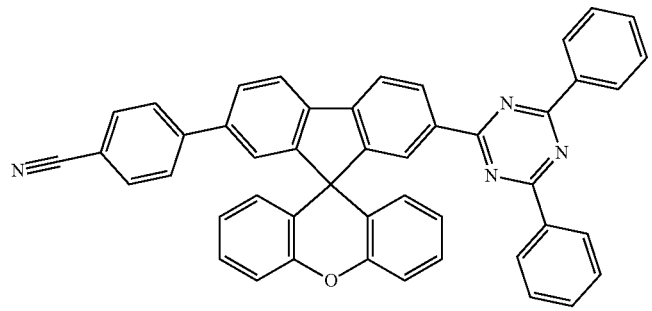
174
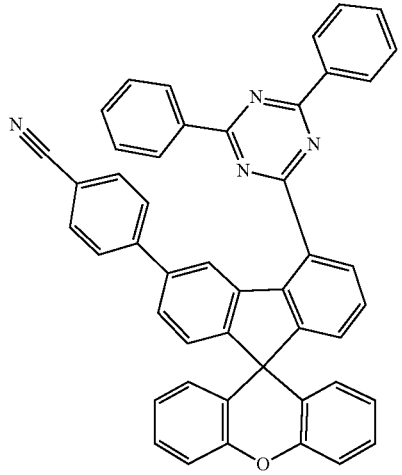
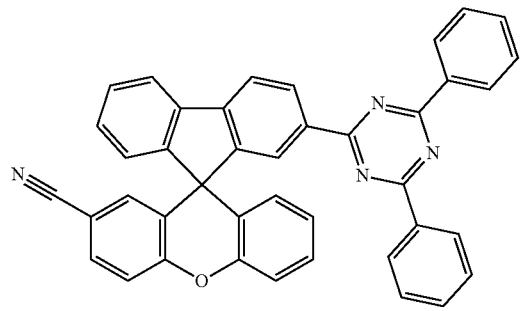
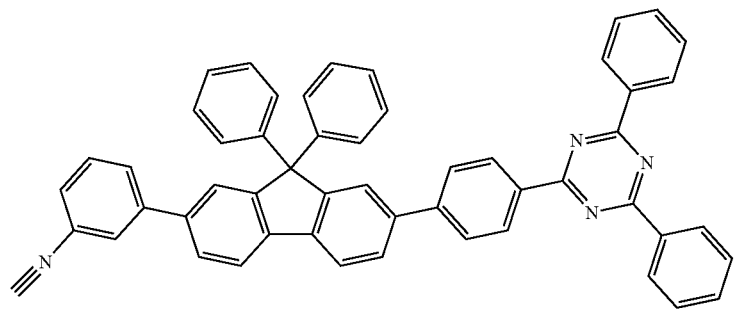
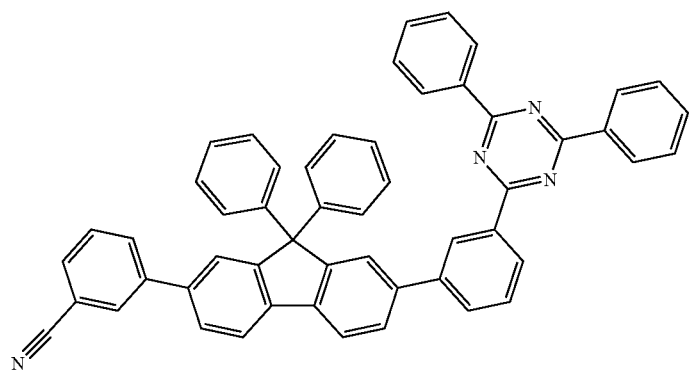

-continued
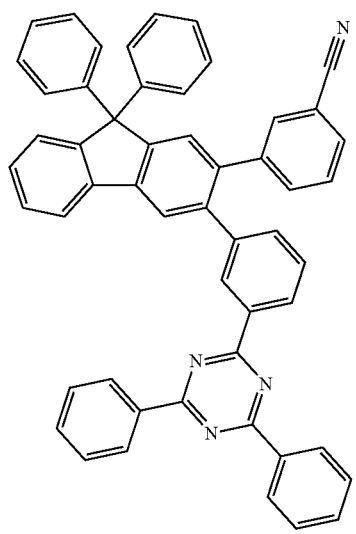
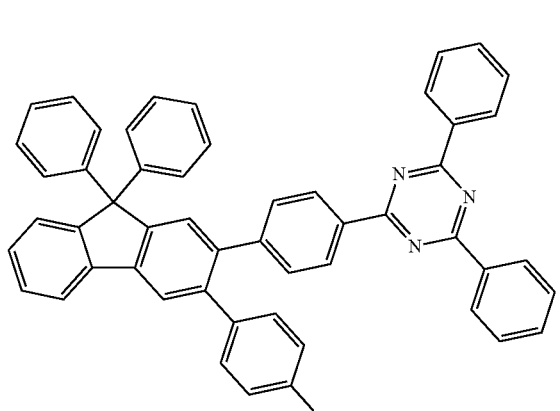
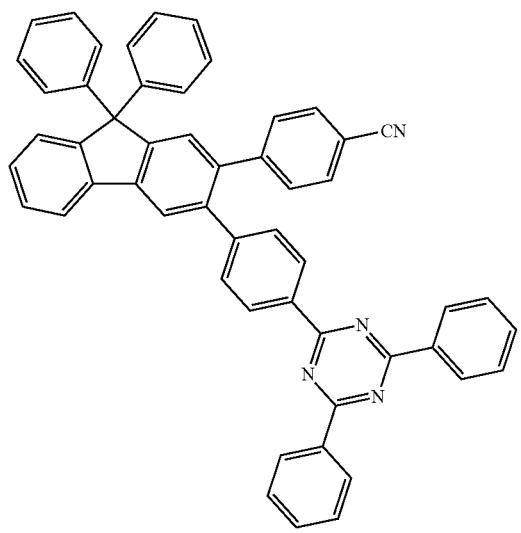
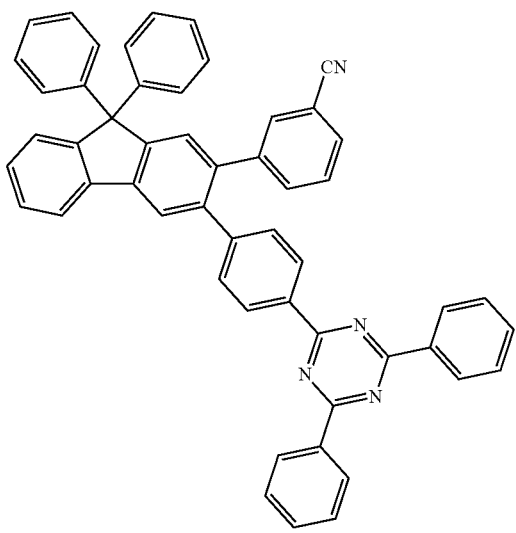
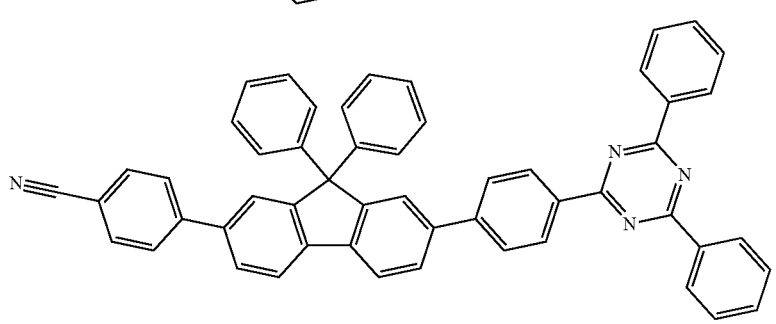
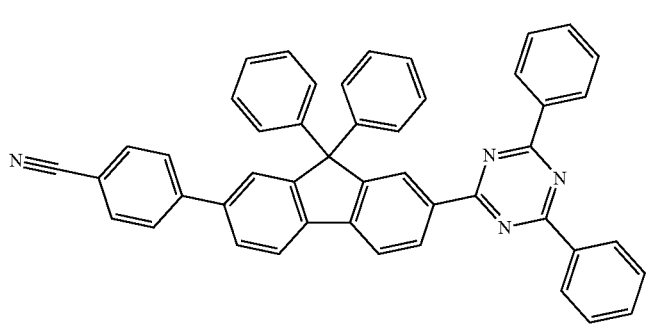

-continued
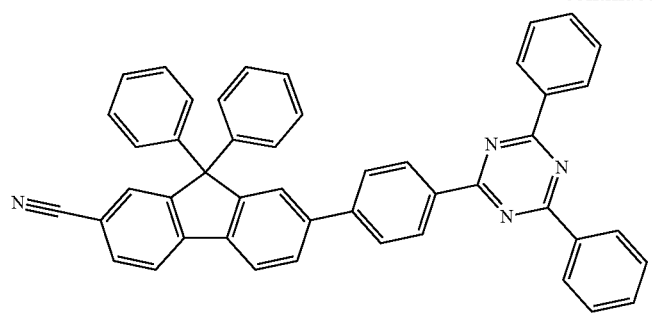
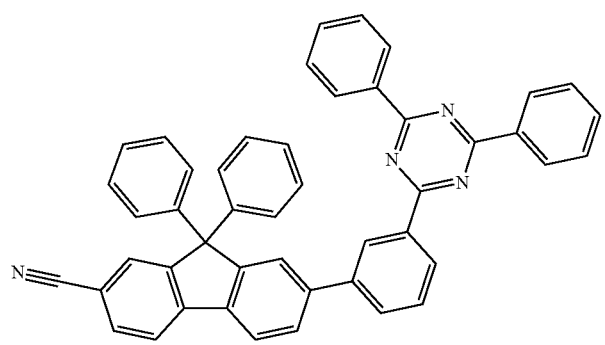
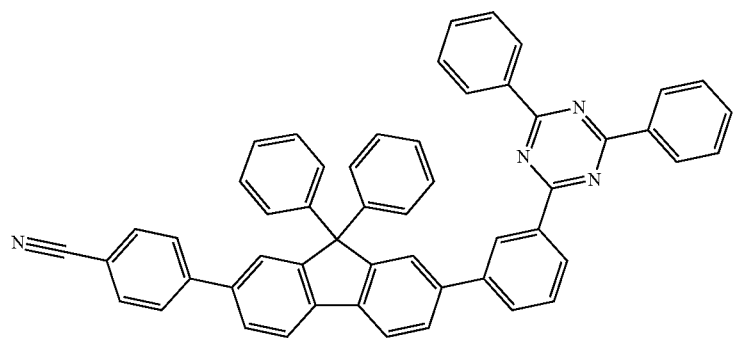
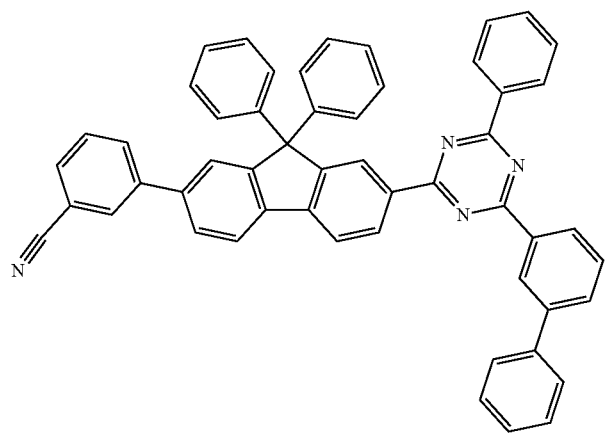

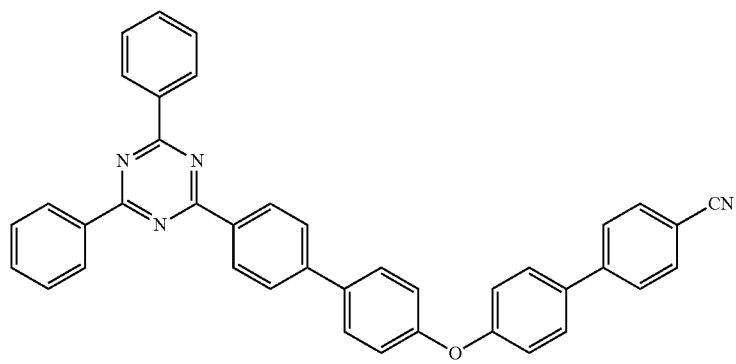
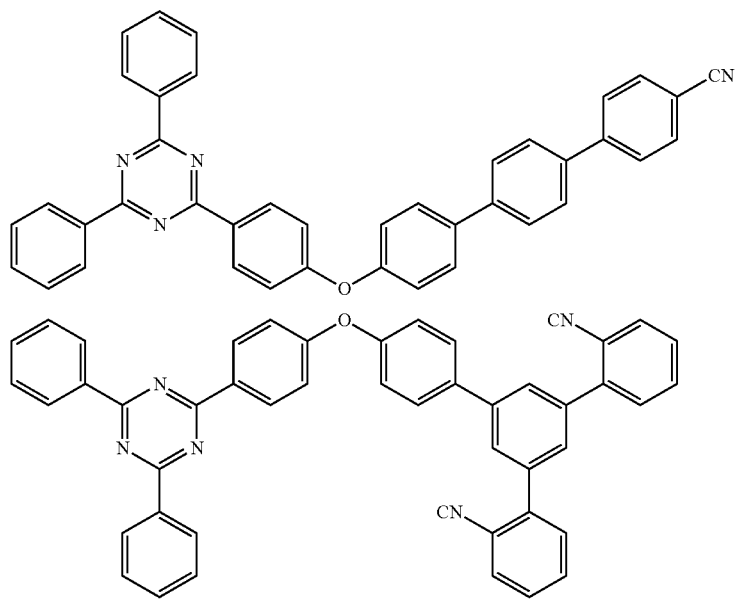
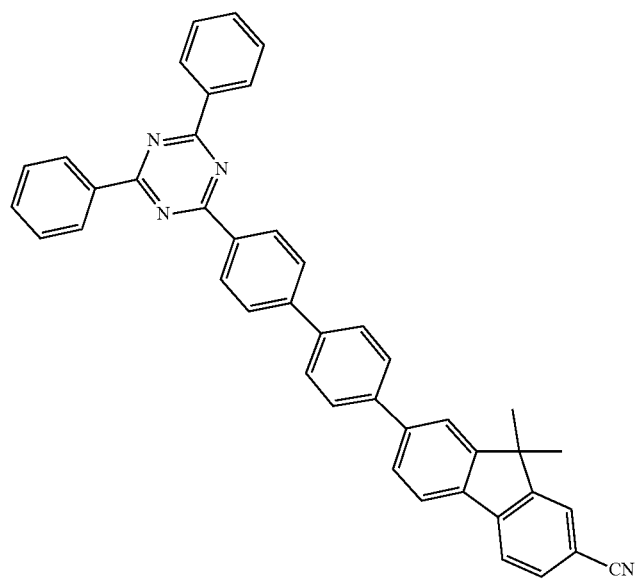

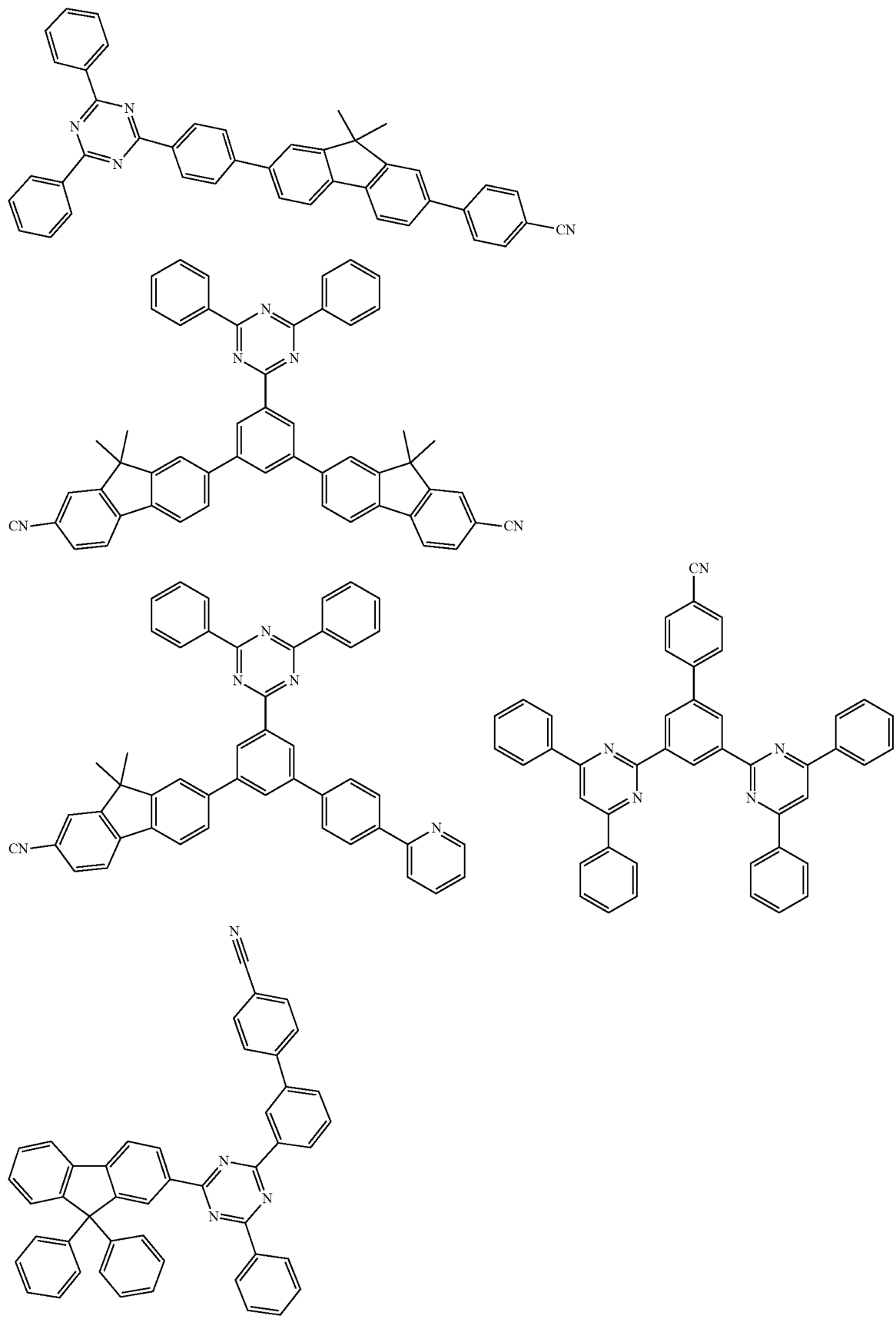

-continued
183
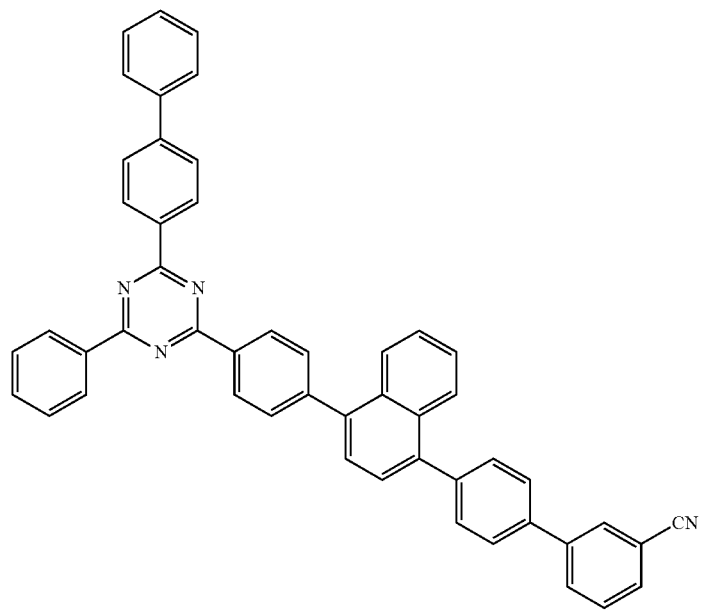
184
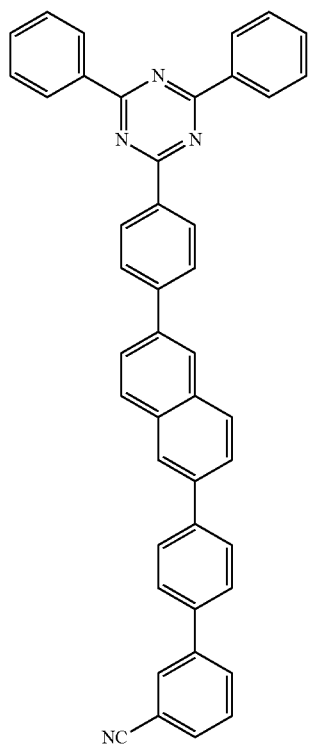
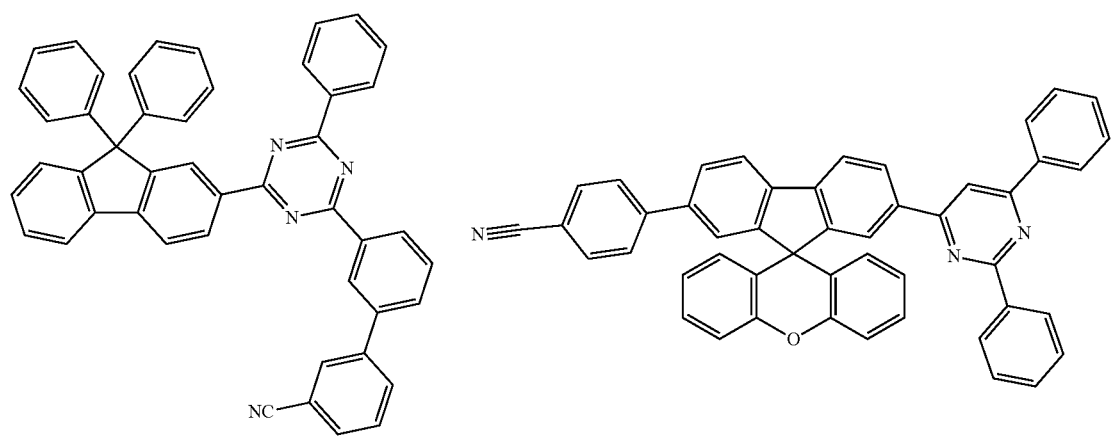
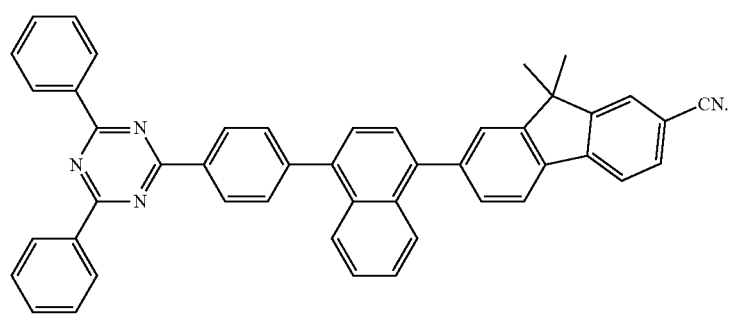

According to one embodiment of the present specification, the compound of Chemical Formula 1 and the compound of Chemical Formula 2 satisfy the following Equation 1:

$$|P_{EI}| > |P_{Eb}| \qquad \text{<Equation 1>}$$

In Equation 1, $|P_{Eb}|$ means an absolute value of a dipole moment of the compound of Chemical Formula 1, and $|P_{EI}|$ means an absolute value of a dipole moment of the compound of Chemical Formula 2.

According to one embodiment of the present specification, the dipole moment is a physical quantity representing a degree of polarity, and can be calculated by the following Mathematical Equation 1.

$$p(r) \int_V \rho(r_0)(r_0 - r) d^3 r_0 \qquad \text{<Mathematical Equation 1>}$$

$\rho(r_0)$: molecular density $V$: volume $r$: the point of observation $d^3 r_0$: an elementary volume In Mathematical Equation 1, a dipole moment value can be obtained by obtaining molecular density through calculation. For example, molecular density can be obtained through calculation according to the following equation after obtaining a charge and a dipole for each atom using a method of Hirshfeld Charge Analysis, and the calculation result is put into Mathematical Equation 1 to obtain a dipole moment.

Weight Function $$W_\alpha(r) = \rho_\alpha(r - R_\alpha) \left[ \sum_\beta \rho_\beta(r - R_\beta) \right]^{-1}$$

$\rho_\alpha(r - R_\alpha)$: spherically averaged ground-state atomic density $\sum_\beta \rho_\beta(r - R_\beta)$: promolecule density Deformation Density $$\rho_d(r)\rho(r) - \sum_\alpha \rho_\alpha(r - R_\alpha)$$

$\rho(r)$: molecular density $\rho_\alpha(r - R_\alpha)$: density of the free atom $\alpha$ located at coordinates $R_\alpha$ Atomic Charge $$q(\alpha) = -\int \rho_d(r) W_\alpha(r) d^3 r$$

$W_\alpha(r)$: weight function

According to one embodiment of the present specification, the structure of Chemical Formula 2 includes a cyano group capable of significantly increasing a dipole moment without significantly affecting the overall molecular shape, and the structure of Chemical Formula 1 does not include a cyano group.

Accordingly, Chemical Formula 2 including a cyano group has a dipole moment greatly increased, and the second organic material layer including the same and the first organic material layer including Chemical Formula 1 that does not include a cyano group satisfy Equation 1 resulting in a big difference in the dipole moment and the LUMO energy level. This functions as a barrier between the second organic material layer and the first organic material layer controlling the amount and the rate of electrons injected from a cathode to a light emitting layer, and as a result, an effect of improving a lifetime of an organic light emitting device is obtained.

The first organic material layer and the second organic material layer of the organic light emitting device of the present application can be formed in a single layer structure, but can be famed in a multilayer structure in which two or more organic material layers are laminated. For example, the first organic material layer of the present application can be formed in one to three layers. In addition, the organic light emitting device of the present application can have a structure including a hole injection layer, a light emitting layer, an electron transfer layer and the like as the organic material layer. However, the structure of the organic light emitting device is not limited thereto, and can include a larger or a smaller number of organic layers.

In one embodiment of the present application, the organic light emitting device further includes one, two or more layers selected from the group consisting of a hole injection layer, a hole transfer layer, an electron injection layer, an electron blocking layer and a hole blocking layer.

In one embodiment of the present application, the organic light emitting device includes a first electrode; a second electrode provided opposite to the first electrode; two or more light emitting layers provided between the first electrode and the second electrode; and two or more first and second organic material layers provided between the two or more light emitting layers and the first electrode, or between the two or more light emitting layers and the second electrode, wherein the two or more first and second organic material layers respectively include the compound of Chemical Formula 1 or the compound of Chemical Formula 2.

According to one embodiment of the present application, the first organic material layer includes a hole blocking layer or an electron control layer and the second organic material layer includes an electron transfer layer, and the hole blocking layer or the electron control layer includes the compound of Chemical Formula 1 and the electron control layer can include the compound of Chemical Formula 2.

In one embodiment of the present application, the first and the second organic material layers further include, in addition to the organic material layer including the compound, a hole injection layer or a hole transfer layer including a compound including an arylamino group, a carbazole group or a benzocarbazole group.

In another embodiment, the organic light emitting device can be an organic light emitting device having a structure in which an anode, one or more organic material layers and a cathode are consecutively laminated on a substrate (normal type).

In another embodiment, the organic light emitting device can be an organic light emitting device having a structure in a reverse direction in which a cathode, one or more organic material layers and an anode are consecutively laminated on a substrate (inverted type).

For example, a structure of the organic light emitting device according to one embodiment of the present application is illustrated in FIGS. 1 to 3.

FIG. 1 illustrates a structure of a general organic light emitting device in which a substrate (1), an anode (2), a light emitting layer (5) and a cathode (8) are consecutively laminated. When referring to FIG. 1, the organic light emitting device according to one embodiment of the present application can include two or more light emitting layers. In addition, the light emitting layers can each independently include a fluorescent dopant or a phosphorescent dopant. When there are two light emitting layers, one light emitting layer can include a fluorescent dopant, and the other one can include a phosphorescent dopant.

In addition, according to one embodiment of the present application, the two or more light emitting layers can be provided in a vertical direction from the first electrode to the second electrode direction, or can also be provided in a horizontal direction from the first electrode to the second electrode direction.

FIG. 2 illustrates a structure of the organic light emitting device in which a substrate (1), an anode (2), a hole injection layer (3), a hole transfer layer (4), a light emitting layer (5), a hole blocking layer or an electron control layer (6), an electron injection or transfer layer (7) and a cathode (8) are consecutively laminated. When referring to FIG. 2, the organic light emitting device according to one embodiment of the present application can include three or more light emitting layers. In addition, other layers can be further provided between each of the light emitting layers. When the light emitting layer is provided in three or more layers, the light emitting layers can each include a blue fluorescent light emitting layer. In addition, in the structure as in FIG. 2, the compound of Chemical Formula 1 can be included in the hole blocking layer or the electron control layer (6), and the compound of Chemical Formula 2 can be included in the electron injection or transfer layer (7).

According to one embodiment of the present application, the three or more light emitting layers can be provided consecutively in a direction from the first electrode to the second electrode direction.

In addition, according to one embodiment of the present application, the three or more light emitting layers can be provided in a vertical direction from the first electrode to the second electrode direction, or can also be provided in a horizontal direction from the first electrode to the second electrode direction. More specifically, the three or more light emitting layers can be provided in a horizontal direction from the first electrode to the second electrode direction.

According to one embodiment of the present application, the blue fluorescent light emitting layer includes a host and a dopant, and the host can be any one compound selected from among the following compounds:

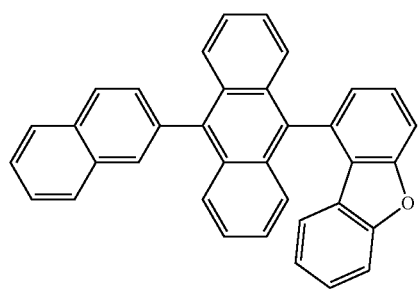

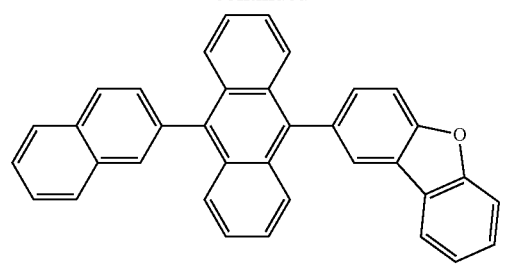

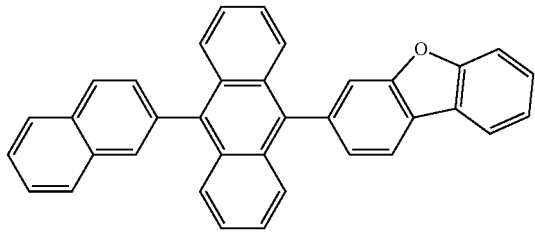

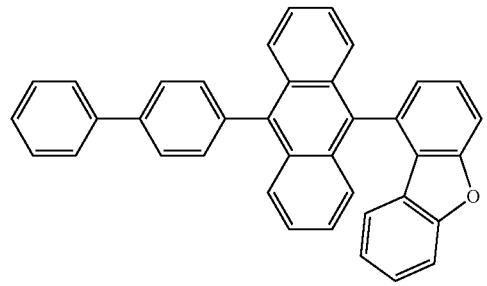

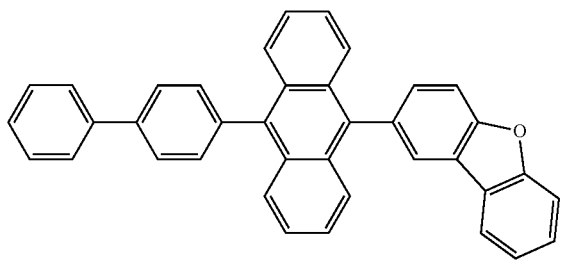

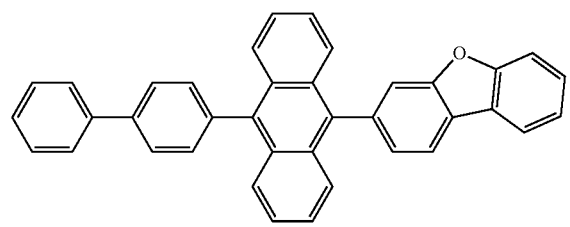

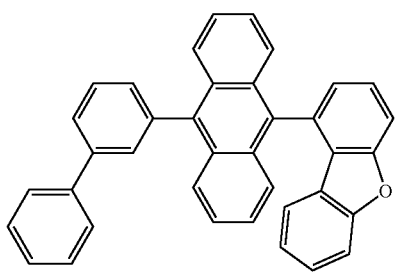

189
-continued
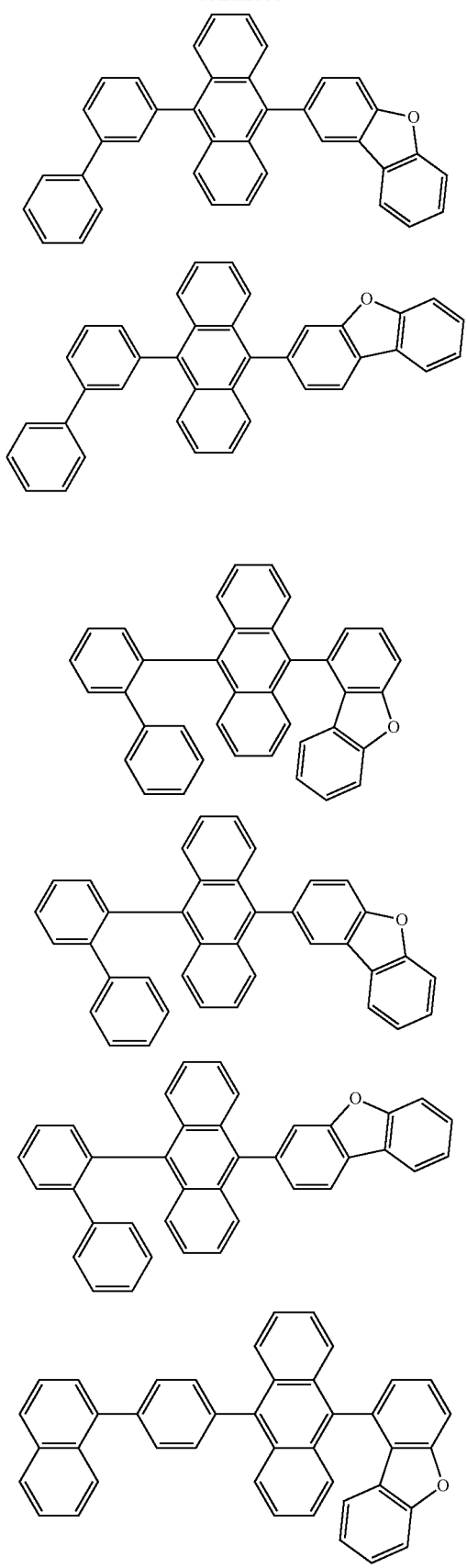
190
-continued
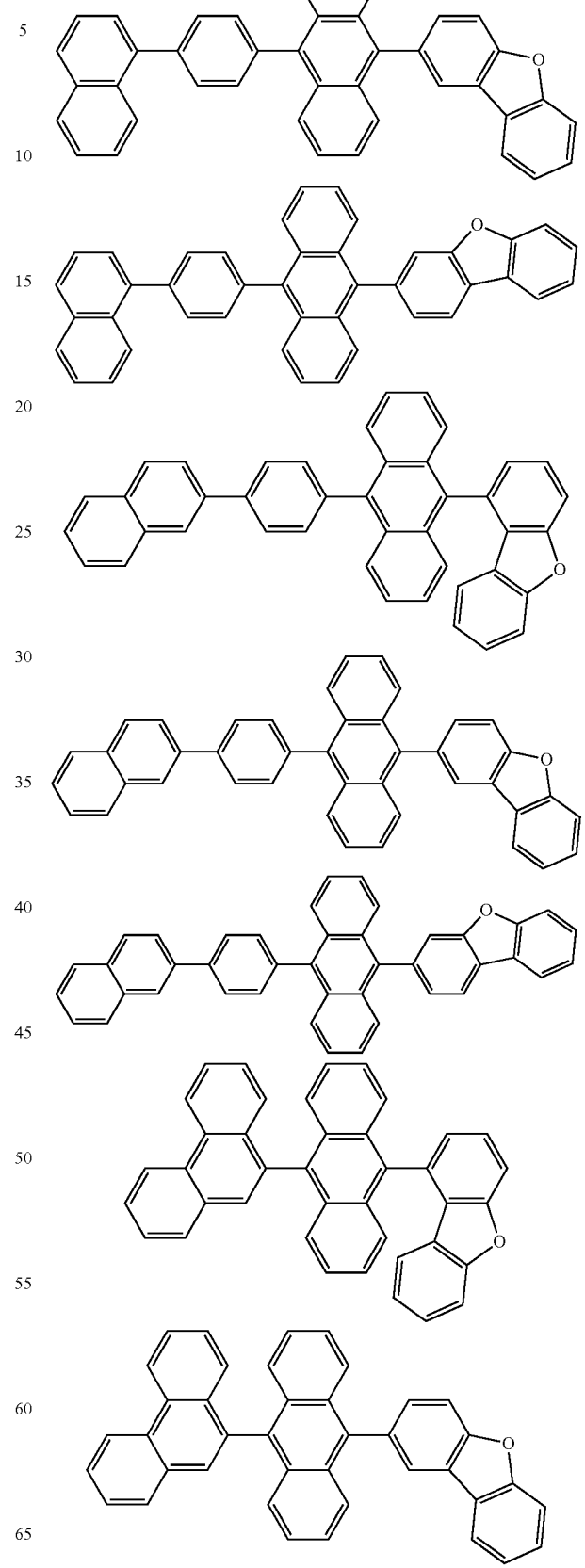

191
-continued
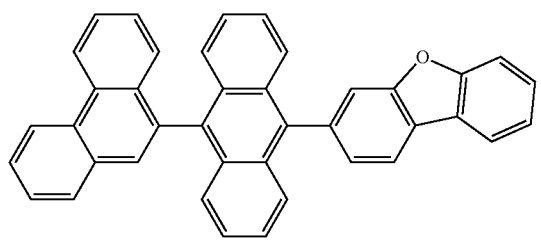
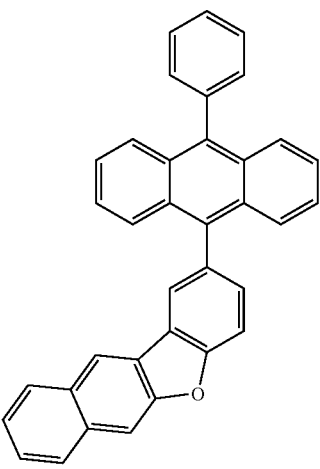
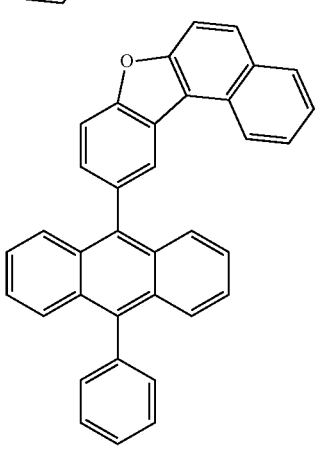
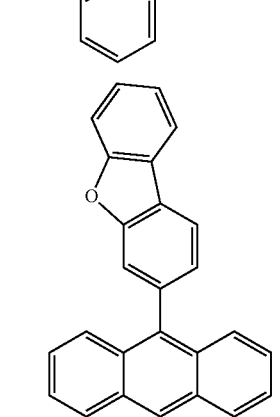
192
-continued
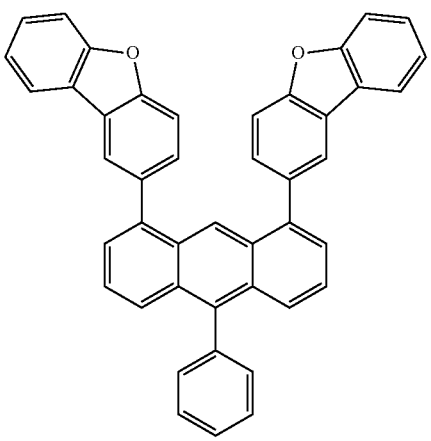
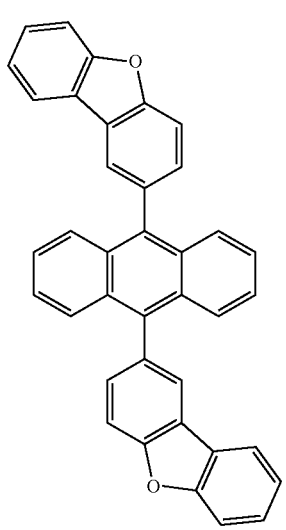
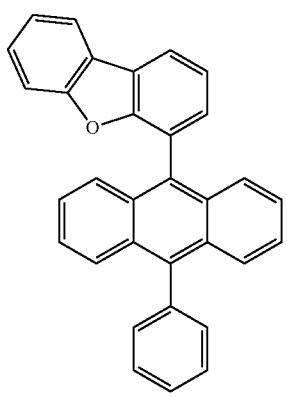

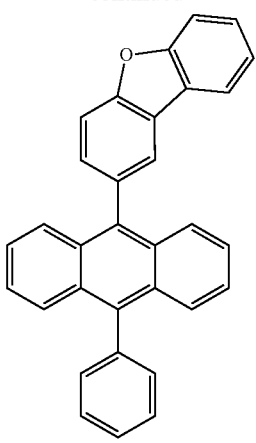

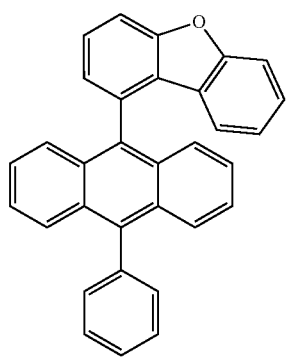

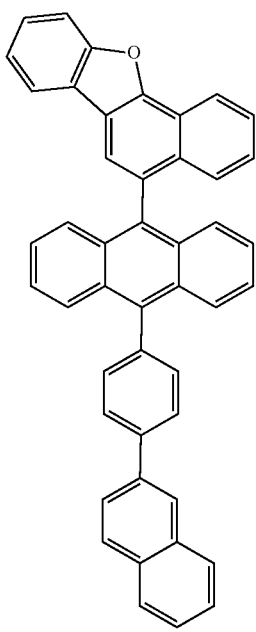

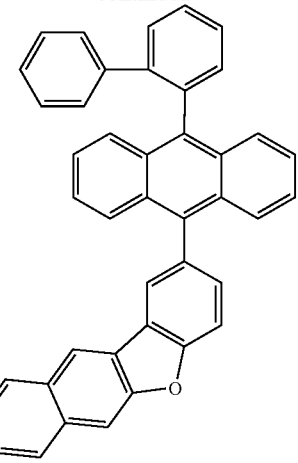

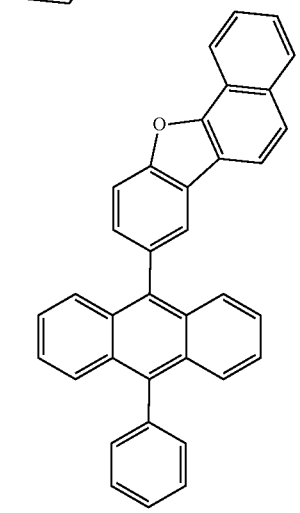

According to one embodiment of the present specification, the organic light emitting device can have a tandem structure in which two or more independent devices are connected in series. In one embodiment, the tandem structure can have a form of each of the organic light emitting devices being bonded by a charge generating layer. A tandem-structured device is capable of being driven at a lower current compared to a unit device based on the same brightness, which leads to an advantage of greatly enhancing lifetime properties of the device.

According to one embodiment of the present specification, the organic material layer includes a first stack including one or more light emitting layers; a second stack including one or more light emitting layers; and one or more charge generating layers provided between the first stack and the second stack.

According to another embodiment of the present specification, the organic material layer includes a first stack including one or more light emitting layers; a second stack including one or more light emitting layers; and a third stack including one or more light emitting layers, and includes one or more charge generating layers each of between the first stack and the second stack; and between the second stack and the third stack.

In the present specification, the charge generating layer means a layer generating holes and electrons when a voltage is applied. The charge generating layer can be an N-type charge generating layer or a P-type charge generating layer.

In the present specification, the N-type charge generating layer means a charge generating layer locating closer to an anode than the P-type charge generating layer, and the P-type charge generating layer means a charge generating layer locating closer to a cathode than the N-type charge generating layer.

The N-type charge generating layer and the P-type charge generating layer can be provided in contact with each other, and an NP junction is formed in this case. By the NP junction, holes are readily formed in the P-type charge generating layer, and electrons are readily formed in the N-type charge generating layer. The electrons are transferred to the anode direction through a LUMO level of the N-type charge generating layer, and the holes are transferred to the cathode direction through a HOMO level of the P-type organic material layer.

The first stack, the second stack and the third stack each include one or more light emitting layers, and in addition thereto, can further include one or more layers of a hole injection layer, a hole transfer layer, an electron blocking layer, an electron injection layer, an electron transfer layer, a hole blocking layer, a layer carrying out hole transfer and hole injection at the same time (hole injection and transfer layer), and a layer carrying out electron transfer and electron injection at the same time (electron injection and transfer layer).

The organic light emitting device including the first stack and the second stack is illustrated in FIG. 3.

FIG. 3 illustrates the organic light emitting device in which a substrate (1), an anode (2), a first hole injection layer (3a), a first hole transfer layer (4a), a first light emitting layer (5a), a first hole blocking layer (6a), a first electron injection or transfer layer (7a), a charge generating layer (9), a second hole injection layer (3b), a second hole transfer layer (4b), a second light emitting layer (5b), a second hole blocking layer (6b), a second electron injection and transfer layer (7b) and a cathode (8) are consecutively laminated. In such a structure, the compound of Chemical Formula 1 can be included in the first hole blocking layer (6a) or the second hole blocking layer (6b), and the compound of Chemical Formula 2 can be included in the first electron injection and transfer layer (7a) or the second electron injection and transfer layer (7b).

The N-type charge generating layer can include 2,3,5,6-tetrafluoro-7,7,8,8-tetracyanoquinodimethane (F4TCNQ), fluorine-substituted 3,4,9,10-perylene-tetracarboxylic dianhydride (PTCDA), cyano-substituted PTCDA, naphthalenetetracarboxylic dianhydride (NTCDA), fluorine-substituted NTCDA, cyano-substituted NTCDA, a hexaazatriphenylene derivative and the like, but is not limited thereto. In one embodiment, the N-type charge generating layer can include both a benzimidazophenanthridine-based derivative and Li metal.

The P-type charge generating layer can include both an arylamine-based derivative and a cyano group-including compound.

The organic light emitting device of the present application can be manufactured using materials and methods known in the art, except that one or more layers of the first or the second organic material layers include the compound of the present application, that is, the above-described compound.

When the organic light emitting device includes a plurality of the first or the second organic material layers, the organic material layers can be formed with materials the same as or different from each other.

The organic light emitting device of the present application can be manufactured using materials and methods known in the art, except that one or more layers of the first or the second organic material layers include the above-described compound, that is, the compound of any one of Chemical Formulae 1 and 2.

For example, the organic light emitting device of the present application can be manufactured by consecutively laminating a first electrode, first and second organic material layers and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the compounds of Chemical Formulae 1 and 2 can be formed into the organic material layer using a solution coating method as well as a vacuum deposition method when manufacturing the organic light emitting device. Herein, the solution coating method means spin coating, dip coating, doctor blading, ink jet printing, screen printing, a spray method, roll coating and the like, but is not limited thereto.

In addition to such methods, the organic light emitting device can also be manufactured by consecutively depositing a cathode material, an organic material layer and an anode material on a substrate (International Patent Application Laid-Open Publication No. 2003/012890). However, the manufacturing method is not limited thereto.

In one embodiment of the present application, the first electrode is an anode, and the second electrode is a cathode.

In another embodiment, the first electrode is a cathode, and the second electrode is an anode.

As the anode material, materials having large work function are normally preferred so that hole injection is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes and thereby has a hole injection effect in an anode and an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq 3); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, or the like, but are not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include, in addition to the compound of Chemical Formula 2, Al complexes of 8-hydroxyquinoline; complexes including Alq 3; organic radical compounds; hydroxyflavon-metal complexes, or the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film foaming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxy-benzo[h]quinolinato)zinc, bis(2-methyl-8-quinolinato)chloro-gallium, bis(2-methyl-8-quinolinato) (o-cresolato)gallium, bis(2-methyl-8-quinolinato) (1-naphtholato)aluminum, bis (2-methyl-8-quinolinato) (2-naphtholato)gallium and the like, but is not limited thereto.

The hole blocking layer is a layer blocking holes from reaching a cathode, and generally, can be formed under the same condition as the hole injection layer. Specifically, in addition to the compound of Chemical Formula 1, oxadiazole derivatives or triazole derivatives, phenanthroline derivatives, BCP, aluminum complexes and the like are included, however, the material is not limited thereto.

The organic light emitting device according to the present application can be a top-emission type, a bottom-emission type or a dual-emission type depending on the materials used.

EXAMPLES

Manufacture of the organic light emitting device including the compounds of Chemical Formulae 1 and 2 will be specifically described in the following examples. However, the following examples are for illustrative purposes only, and the scope of the present specification is not limited thereto.

Preparation Example 1: Preparation of Compound EC1

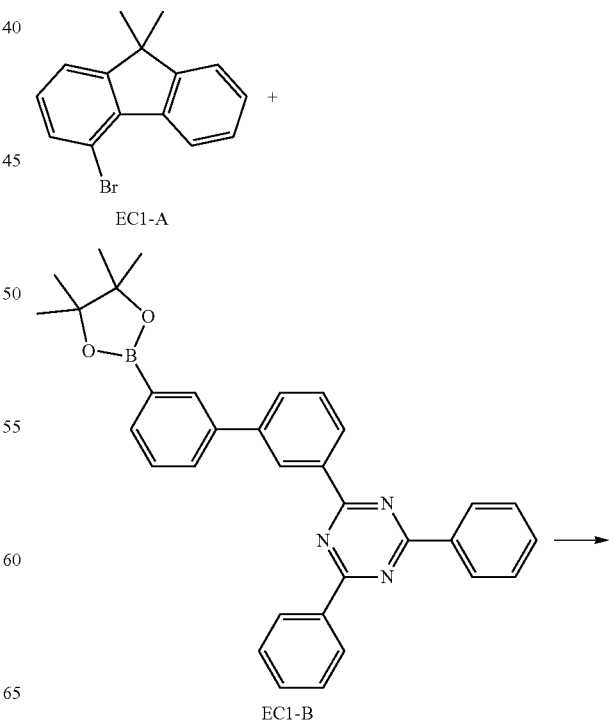

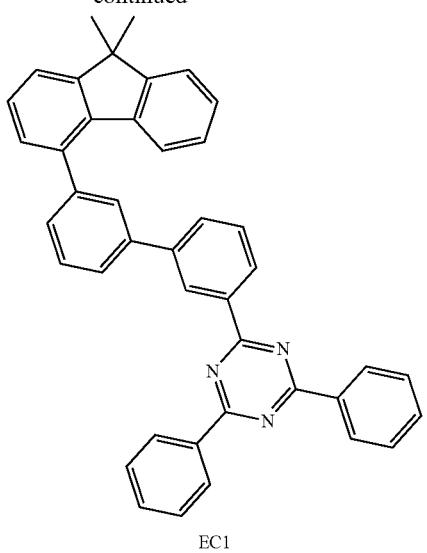

EC1

After completely dissolving Compound EC1-A (10 g, 36.6 mmol) and Compound EC1-B (18.7 g, 36.6 mmol) in tetrahydrofuran (200 mL), potassium carbonate (15.2 g, 109.8 mmol) dissolved in water (60 mL) was added thereto. Tetrakistriphenyl-phosphinopalladium (1.37 g, 0.110 mmol) was introduced thereto, and then the result was stirred for 8 hours while heating. After lowering the temperature to room temperature and terminating the reaction, the potassium carbonate solution was removed to filter white solids. The filtered white solids were washed twice each with tetrahydrofuran and ethyl acetate to prepare Compound EC1 (16.9 g, yield 80%).

MS [M+H]$^+$=578

Preparation Example 2: Preparation of Compound EC2

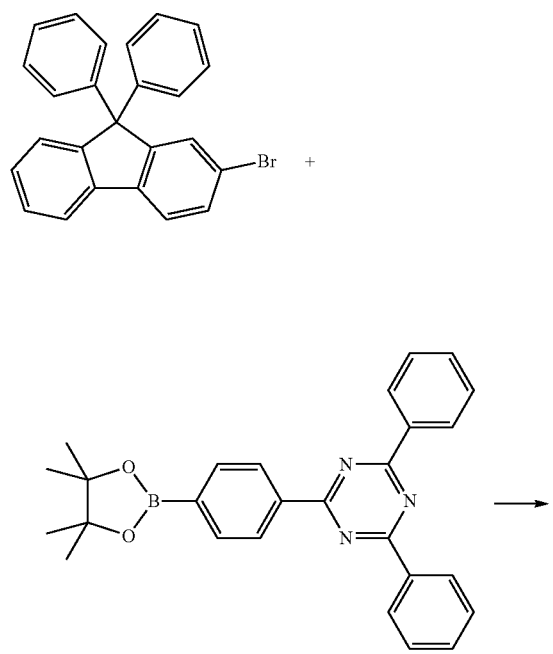

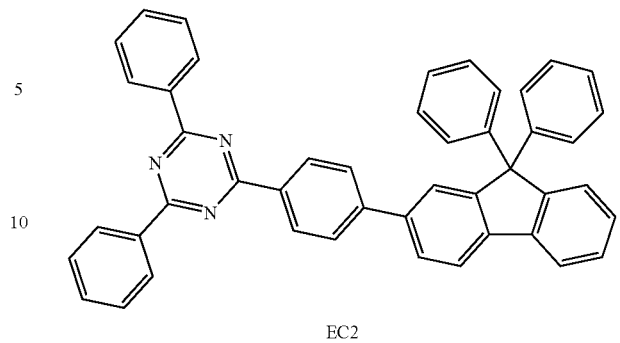

EC2

A compound of Chemical Formula EC2 was prepared in the same manner as in Preparation Example 1 except that the above-described compounds were used as each starting material.

MS [M+H]$^+$=626

Preparation Example 3: Preparation of Compound EC3

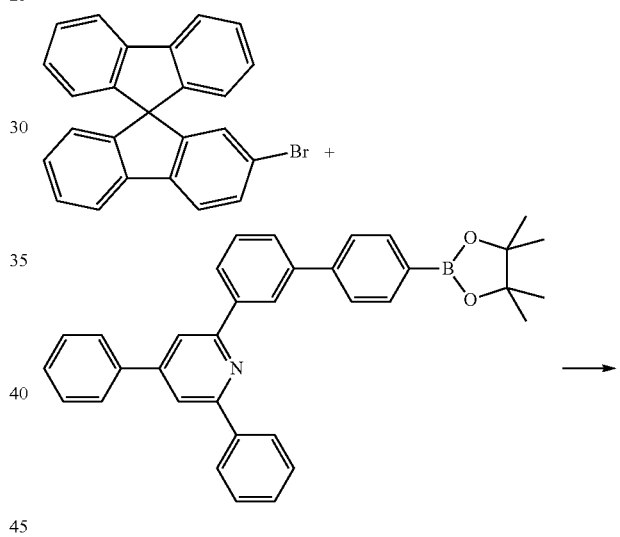

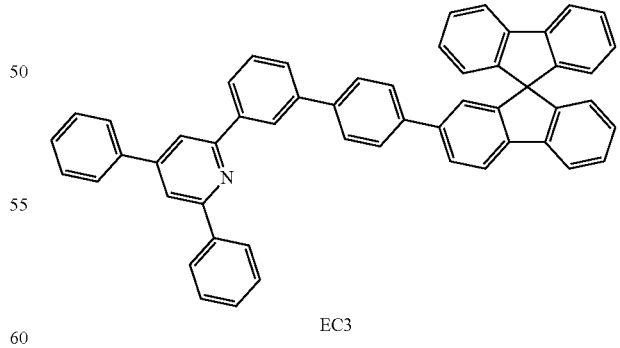

EC3

A compound of Chemical Formula EC3 was prepared in the same manner as in Preparation Example 1 except that the above-described compounds were used as each starting material.

MS [M+H]$^+$=698

Preparation Example 4: Preparation of Compound EC4

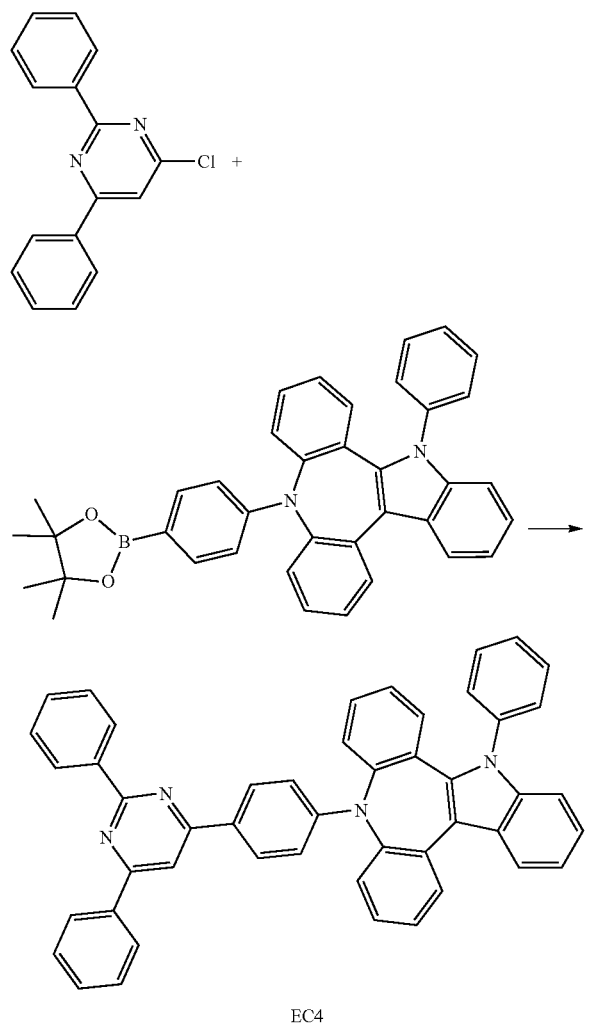

EC4

A compound of Chemical Formula EC4 was prepared in the same manner as in Preparation Example 1 except that the above-described compounds were used as each starting material.

MS [M+H]$^+$=665

Preparation Example 5: Preparation of Compound EC5

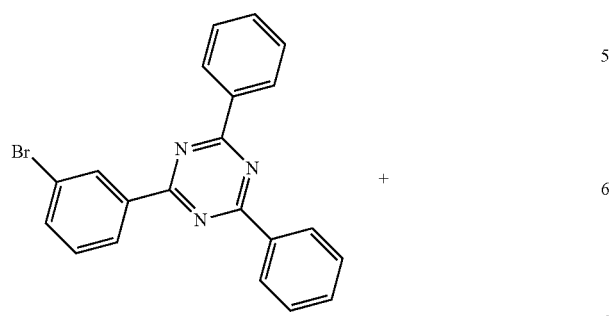

EC5

A compound of Chemical Formula EC5 was prepared in the same manner as in Preparation Example 1 except that the above-described compounds were used as each starting material.

MS [M+H]$^+$=689

Preparation Example 6: Preparation of Compound ET1

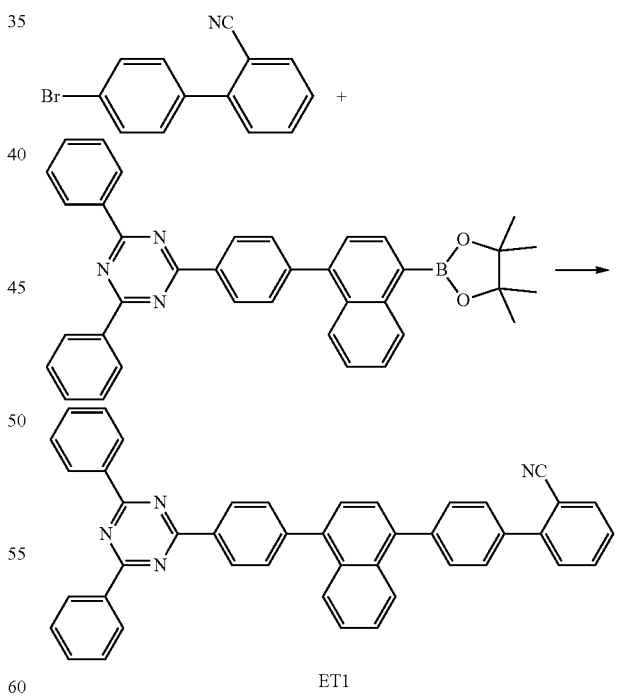

ET1

A compound of Chemical Formula ET1 was prepared in the same manner as in Preparation Example 1 except that the above-described compounds were used as each starting material.

MS [M+H]$^+$=613

Preparation Example 7: Preparation of Compound ET2

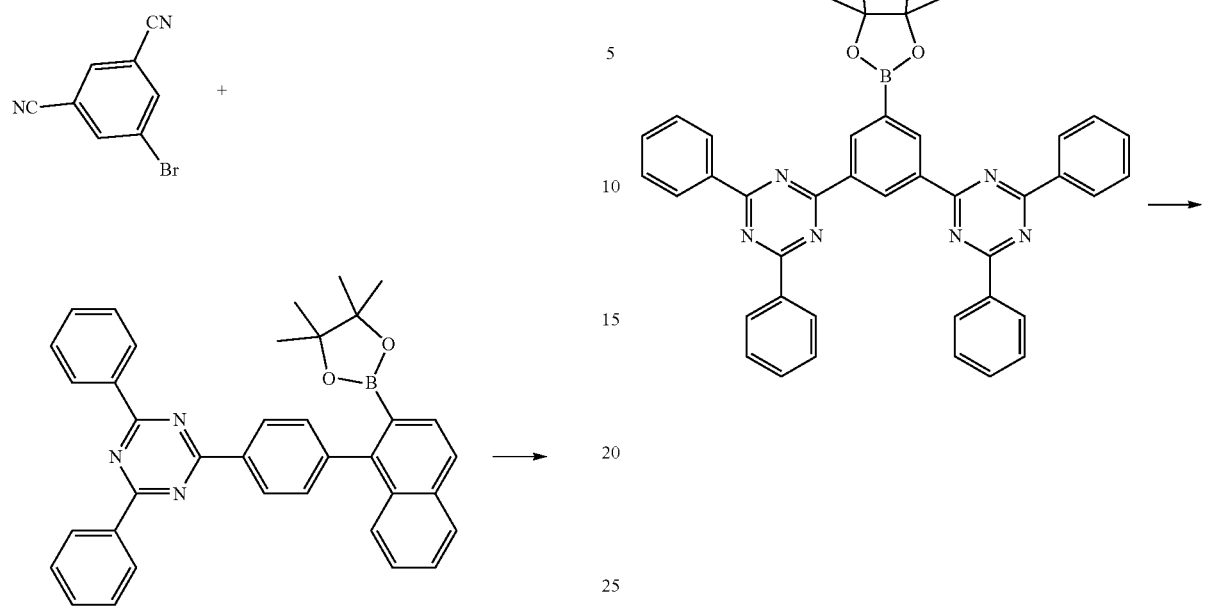

A compound of Chemical Formula ET2 was prepared in the same manner as in Preparation Example 1 except that the above-described compounds were used as each starting material.

MS [M+H]$^+$=562

Preparation Example 8: Preparation of Compound ET3

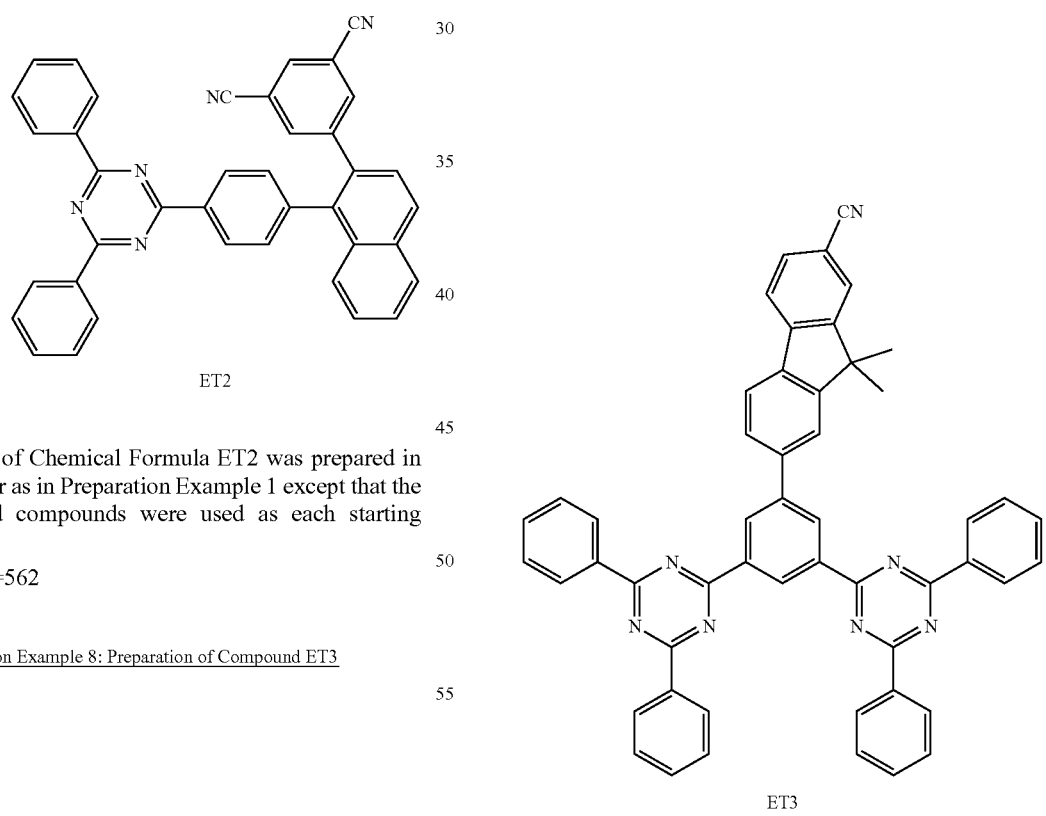

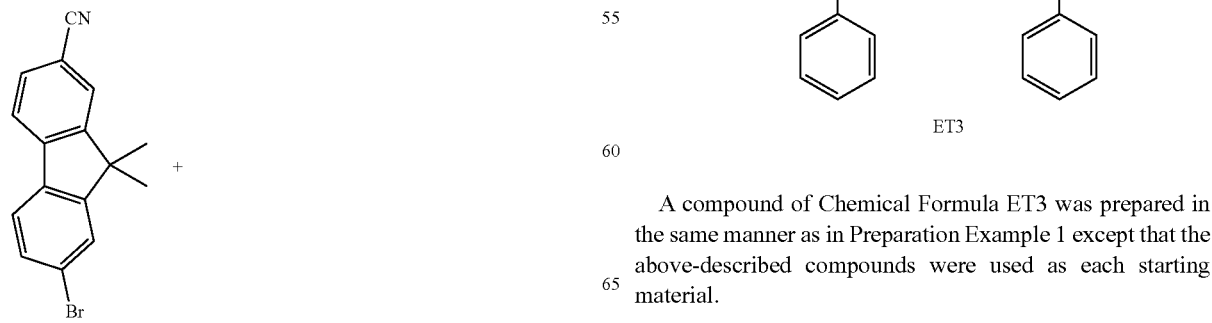

A compound of Chemical Formula ET3 was prepared in the same manner as in Preparation Example 1 except that the above-described compounds were used as each starting material.

MS [M+H]$^+$=758

Preparation Example 9: Preparation of Compound ET4

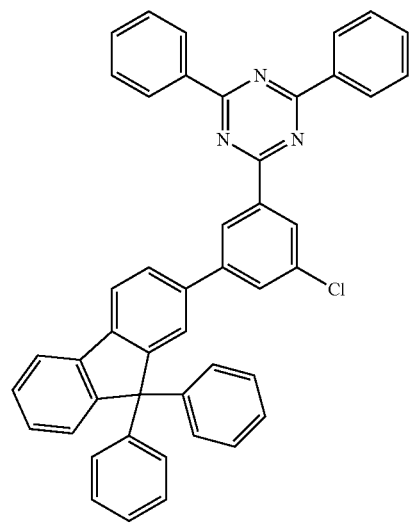

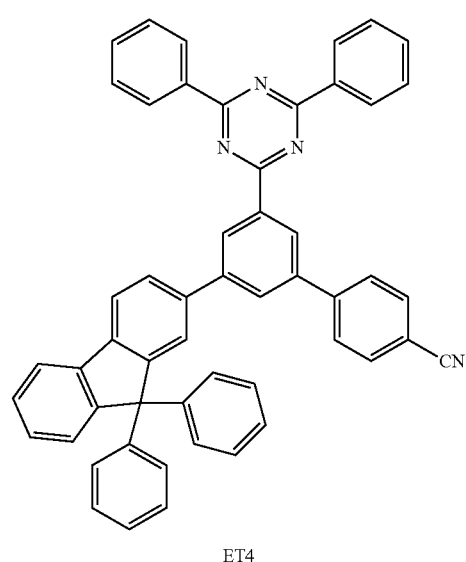

ET4

Preparation Example 10: Preparation of Compound ET5

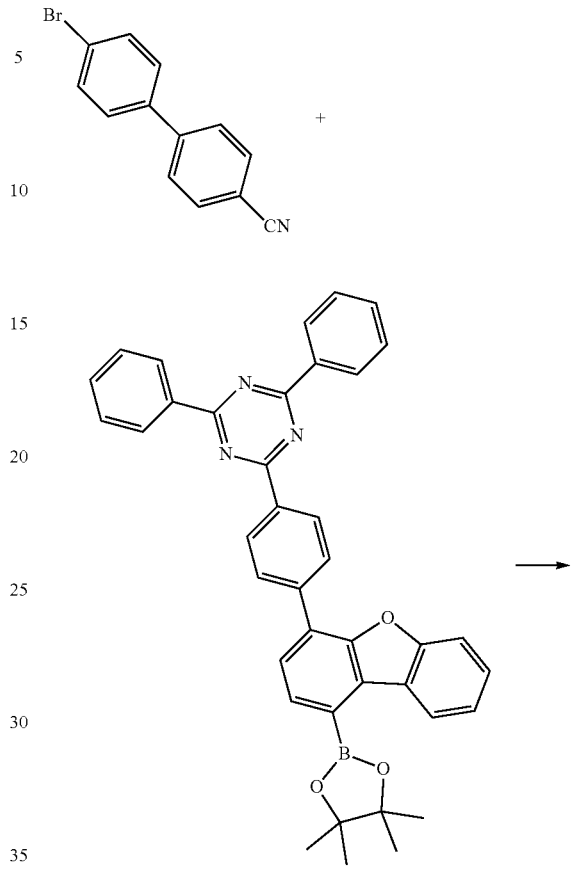

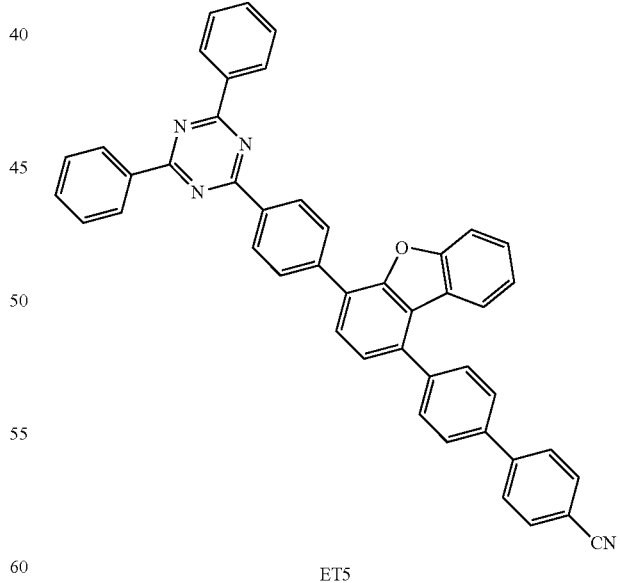

ET5

A compound of Chemical Formula ET4 was prepared in the same manner as in Preparation Example 1 except that the above-described compounds were used as each starting material.

MS [M+H]$^+$=727

A compound of Chemical Formula ET5 was prepared in the same manner as in Preparation Example 1 except that the above-described compounds were used as each starting material.

MS [M+H]$^+$=653

Preparation Example 11: Preparation of Compound ET6

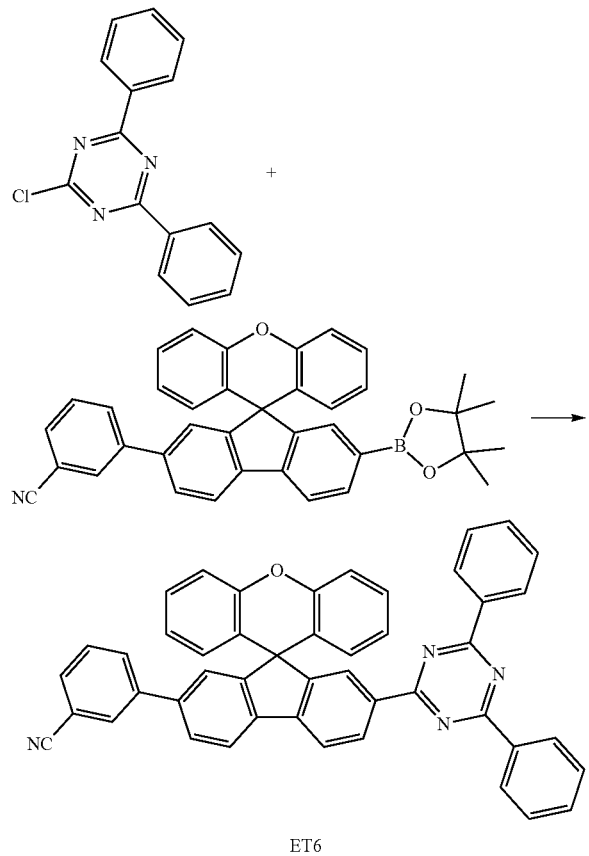

ET6

A compound of Chemical Formula ET6 was prepared in the same manner as in Preparation Example 1 except that the above-described compounds were used as each starting material.
MS [M+H]⁺=665

Preparartion Example 12: Preparation of Compound ET7

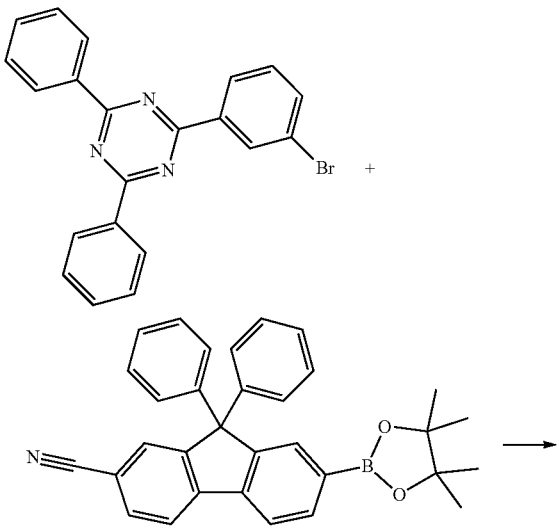

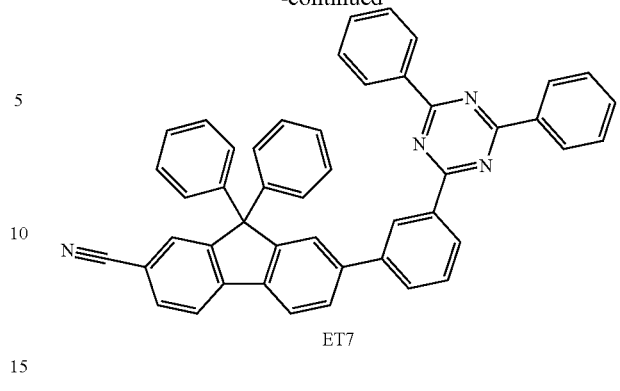

ET7

A compound of Chemical Formula ET7 was prepared in the same manner as in Preparation Example 1 except that the above-described compounds were used as each starting material.
MS [M+H]⁺=651

Preparation Example 13: Preparation of Compound ET8

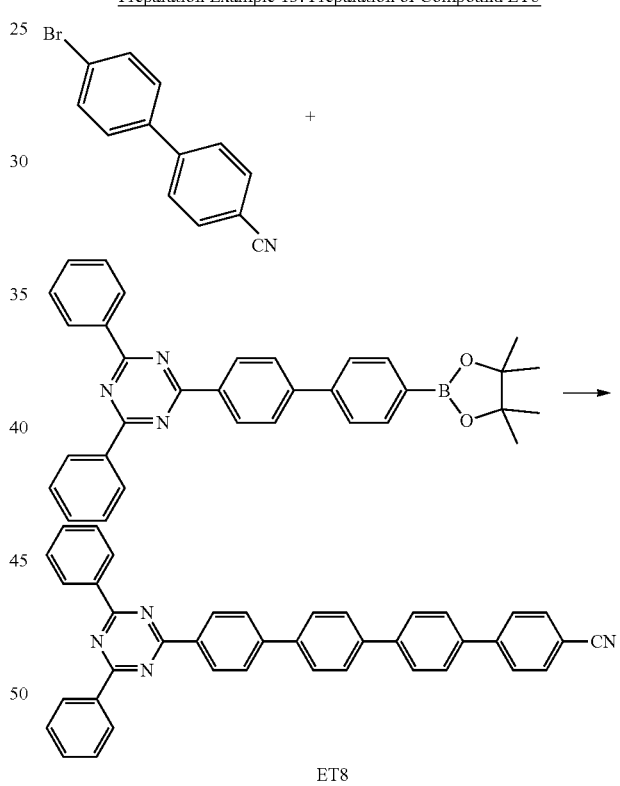

ET8

A compound of Chemical Formula ET8 was prepared in the same manner as in Preparation Example 1 except that the above-described compounds were used as each starting material.
MS [M+H]⁺=563

Example 1-1

A glass substrate on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum depositor.

On the transparent ITO electrode prepared as above, a hole injection layer was famed by thermal vacuum depositing the following HI-A compound to a thickness of 600 Å. A hole transfer layer was formed on the hole injection layer by vacuum depositing the following HAT compound (50 Å) and the following HT-A compound (60 Å) in consecutive order.

Subsequently, a light emitting layer was formed on the hole transfer layer to a film thickness of 200 Å by vacuum depositing the following BH compound and the following BD Compound in a weight ratio of 25:1.

A hole blocking layer was formed on the light emitting layer to a thickness of 50 Å by vacuum depositing Compound EC1. On the hole blocking layer, an electron injection and transfer layer was formed to a thickness of 300 Å by vacuum depositing Compound ET1 and the following LiQ compound in a weight ratio of 1:1. A cathode was formed on the electron injection and transfer layer by depositing lithium fluoride (LiF) to a thickness of 10 Å and aluminum to a thickness of 1,000 Å in consecutive order.

In the above-mentioned process, the deposition rates of the organic materials were maintained at 0.4 Å/sec to 0.9 Å/sec, the deposition rates of the lithium fluoride and the aluminum of the cathode were maintained at 0.3 Å/sec and 2 Å/sec, respectively, and the degree of vacuum during the deposition was maintained at $1\times10^{-7}$ torr to $5\times10^{-5}$ torr, and as a result, an organic light emitting device was manufactured.

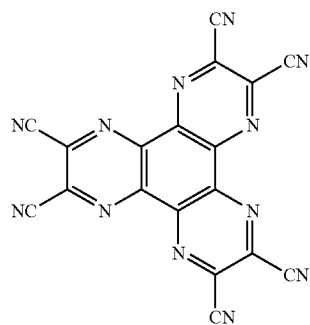

HAT

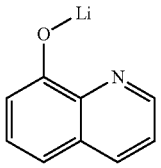

LiQ

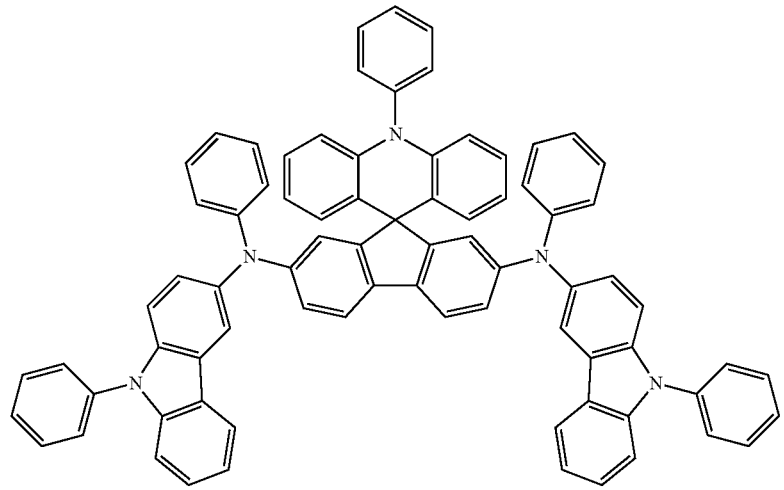

HI-A

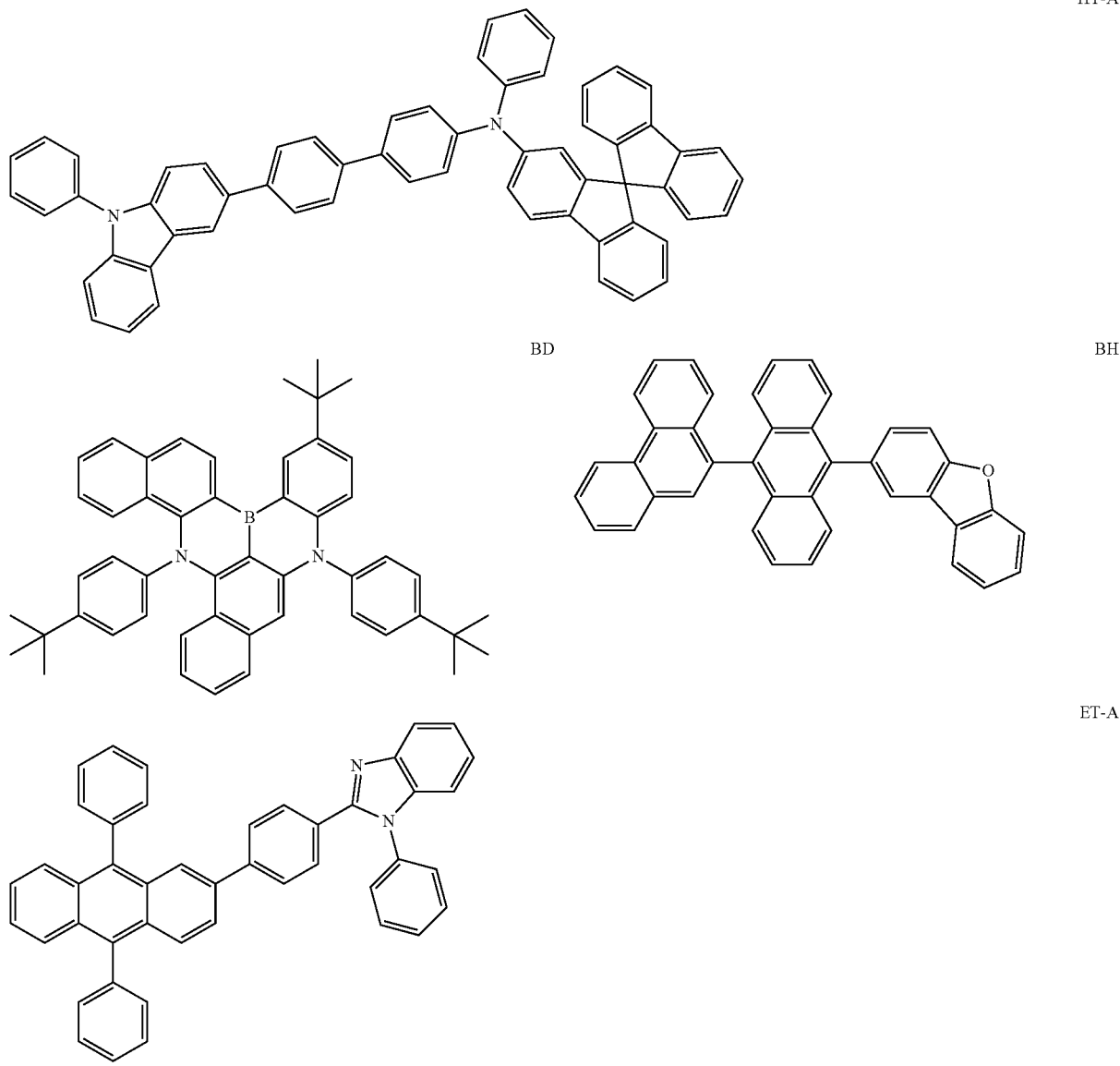

Examples 1-2 to 1-24 and Comparative Examples 1-1 to 1-14

Organic light emitting devices were manufactured in the same manner as in Example 1-1 except that compounds of the following Table 1 were used instead of Compounds EC1 and ET1.

For the organic light emitting devices manufactured in Examples 1-1 to 1-24 and Comparative Examples 1-1 to 1-14, driving voltage and light emission efficiency were measured at current density of 10 mA/cm², and time taken for luminance decreasing to 90% compared to its initial luminance (T90) was measured at current density of 20 mA/cm². The results are shown in the following Table 1.

TABLE 1

| Compound | | | Voltage (V@ 10 mA/ cm$^2$) | Efficiency (cd/A@ 10 mA/ cm$^2$) | Color Coordinate (x, y) | Lifetime (h) (T90 at 20 mA/ cm$^2$) |
|---|---|---|---|---|---|---|
| Example 1-1 | EC1 | ET1 | 4.1 | 5.65 | (0.135, 0.088) | 332 |
| Example 1-2 | EC1 | ET2 | 4.23 | 5.48 | (0.135, 0.089) | 384 |
| Example 1-3 | EC1 | ET3 | 4.26 | 5.39 | (0.135, 0.087) | 391 |
| Example 1-4 | EC1 | ET4 | 4.13 | 5.62 | (0.133, 0.088) | 325 |
| Example 1-5 | EC1 | ET5 | 4.15 | 5.63 | (0.135, 0.089) | 320 |
| Example 1-6 | EC1 | ET6 | 4.11 | 5.70 | (0.135, 0.087) | 294 |
| Example 1-7 | EC1 | ET7 | 4.1 | 5.69 | (0.135, 0.088) | 281 |
| Example 1-8 | EC1 | ET8 | 4.2 | 5.55 | (0.133, 0.088) | 367 |
| Example 1-9 | EC2 | ET1 | 4.14 | 5.59 | (0.135, 0.089) | 342 |
| Example 1-10 | EC2 | ET2 | 4.27 | 5.43 | (0.135, 0.087) | 396 |
| Example 1-11 | EC2 | ET3 | 4.30 | 5.34 | (0.135, 0.087) | 403 |
| Example 1-12 | EC2 | ET4 | 4.17 | 5.56 | (0.133, 0.088) | 335 |
| Example 1-13 | EC3 | ET5 | 4.36 | 5.35 | (0.135, 0.088) | 326 |
| Example 1-14 | EC3 | ET6 | 4.32 | 5.42 | (0.133, 0.088) | 300 |
| Example 1-15 | EC3 | ET7 | 4.31 | 5.41 | (0.135, 0.089) | 287 |

TABLE 1-continued

| Compound | | Voltage (V@ 10 mA/ cm$^2$) | Efficiency (cd/A@ 10 mA/ cm$^2$) | Color Coordinate (x, y) | Lifetime (h) (T90 at 20 mA/ cm$^2$) |
|---|---|---|---|---|---|
| Example 1-16 | EC3 ET8 | 4.41 | 5.27 | (0.135, 0.087) | 374 |
| Example 1-17 | EC4 ET1 | 4.06 | 5.71 | (0.135, 0.088) | 299 |
| Example 1-18 | EC4 ET2 | 4.19 | 5.53 | (0.133, 0.088) | 346 |
| Example 1-19 | EC4 ET3 | 4.22 | 5.44 | (0.135, 0.089) | 352 |
| Example 1-20 | EC4 ET4 | 4.09 | 5.68 | (0.135, 0.087) | 293 |
| Example 1-21 | EC5 ET5 | 4.23 | 5.46 | (0.135, 0.088) | 339 |
| Example 1-22 | EC5 ET6 | 4.19 | 5.53 | (0.135, 0.089) | 312 |
| Example 1-23 | EC5 ET7 | 4.18 | 5.52 | (0.135, 0.087) | 298 |
| Example 1-24 | EC5 ET8 | 4.28 | 5.38 | (0.133, 0.088) | 389 |
| Comparative Example 1-1 | EC1 ET-A | 4.55 | 4.97 | (0.135, 0.089) | 73 |
| Comparative Example 1-2 | EC2 ET-A | 4.60 | 4.92 | (0.135, 0.087) | 75 |
| Comparative Example 1-3 | EC3 ET-A | 4.78 | 4.72 | (0.135, 0.088) | 75 |
| Comparative Example 1-4 | EC4 ET-A | 4.51 | 5.02 | (0.133, 0.088) | 66 |
| Comparative Example 1-5 | EC5 ET-A | 4.64 | 4.82 | (0.135, 0.089) | 75 |
| Comparative Example 1-6 | ET-A ET1 | 4.63 | 5.09 | (0.135, 0.087) | 63 |
| Comparative Example 1-7 | ET-A ET2 | 4.78 | 4.93 | (0.135, 0.088) | 73 |
| Comparative Example 1-8 | ET-A ET3 | 4.81 | 4.85 | (0.135, 0.088) | 74 |
| Comparative Example 1-9 | ET-A ET4 | 4.67 | 5.06 | (0.133, 0.088) | 62 |
| Comparative Example 1-10 | ET-A ET5 | 4.69 | 5.07 | (0.135, 0.089) | 61 |
| Comparative Example 1-11 | ET-A ET6 | 4.64 | 5.13 | (0.135, 0.088) | 56 |
| Comparative Example 1-12 | ET-A ET7 | 4.63 | 5.12 | (0.135, 0.088) | 53 |
| Comparative Example 1-13 | ET-A ET8 | 4.75 | 5.00 | (0.135, 0.087) | 70 |
| Comparative Example 1-14 | ET-A ET-A | 4.69 | 4.72 | (0.135, 0.087) | 64 |

From Table 1, it was seen that the organic light emitting device using both Chemical Formula 1 and Chemical Formula 2 according to the present specification exhibited properties of low driving voltage, high efficiency and long lifetime compared to the organic light emitting device using only Chemical Formula 1 or only Chemical Formula 2. Particularly, it was identified that Examples 1-1 to 1-24 had a lifetime increasing by up to approximately 660% compared to Comparative Examples 1-1 to 1-14.

Example 2-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a first hole injection layer was formed by thermal vacuum depositing the following HI-A compound to a thickness of 600 Å. A first hole transfer layer was formed on the first hole injection layer by vacuum depositing the following HAT compound (50 Å) and the following HT-A compound (60 Å) in consecutive order.

Subsequently, a first light emitting layer was formed on the first hole transfer layer to a film thickness of 200 Å by vacuum depositing the following BH compound and the following BD Compound in a weight ratio of 25:1.

A first hole blocking layer was formed on the first light emitting layer to a thickness of 50 Å by vacuum depositing Compound EC1. On the first hole blocking layer, a first electron injection and transfer layer was formed to a thickness of 200 Å by vacuum depositing Compound ET1 and the following LiQ compound in a weight ratio of 1:1.

An electron charge generating layer was formed on the first electron injection and transfer layer to a film thickness of 100 Å by vacuum depositing Compound ET-C and lithium compound in a weight ratio of 100:2. On the electron charge generating layer, a second hole injection layer was formed by thermal vacuum depositing the following HI-A compound to a thickness of 100 Å.

A second hole transfer layer was formed on the second hole injection layer by vacuum depositing the following HAT compound (50 Å) and the following HT-A compound (60 Å) in consecutive order.

Subsequently, a second light emitting layer was formed on the second hole transfer layer to a film thickness of 200 Å by vacuum depositing the following BH compound and the following BD Compound in a weight ratio of 25:1.

A second hole blocking layer was formed on the second light emitting layer to a thickness of 50 Å by vacuum depositing Compound EC1. On the second hole blocking layer, a second electron injection and transfer layer was formed to a thickness of 200 Å by vacuum depositing Compound ET1 and the following LiQ compound in a weight ratio of 1:1. A cathode was formed on the second electron injection and transfer layer by depositing lithium fluoride (LiF) to a thickness of 10 Å and aluminum to a thickness of 1,000 Å in consecutive order.

In the above-mentioned process, the deposition rates of the organic materials were maintained at 0.4 Å/sec to 0.9 Å/sec, the deposition rates of the lithium fluoride and the aluminum of the cathode were maintained at 0.3 Å/sec and 2 Å/sec, respectively, and the degree of vacuum during the deposition was maintained at $1\times10^{-7}$ torr to $5\times10^{-5}$ torr, and as a result, an organic light emitting device was manufactured.

215  216
HAT 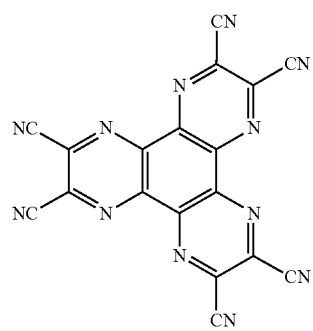
LiQ 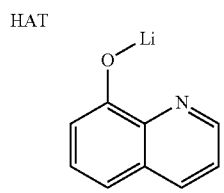
HI-A 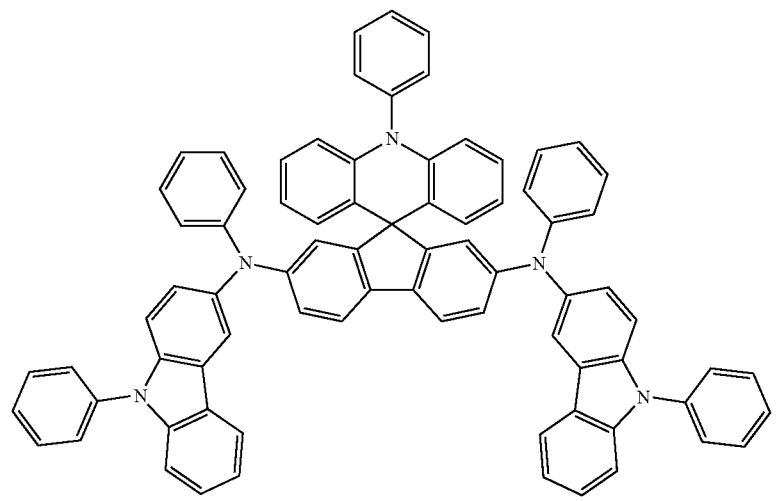
HT-A 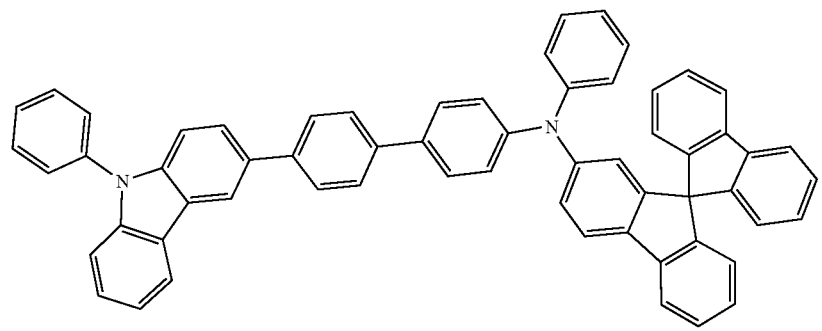
BD 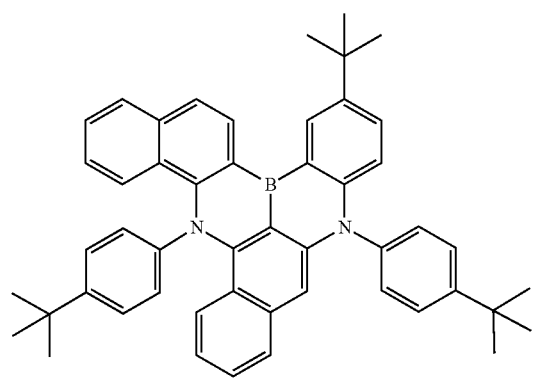
BH 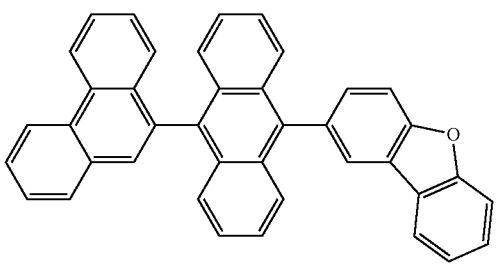

ET-A

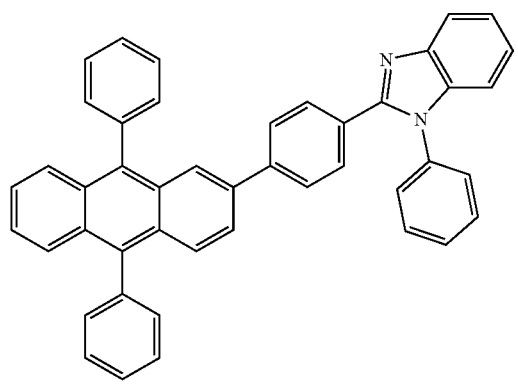

ET-C

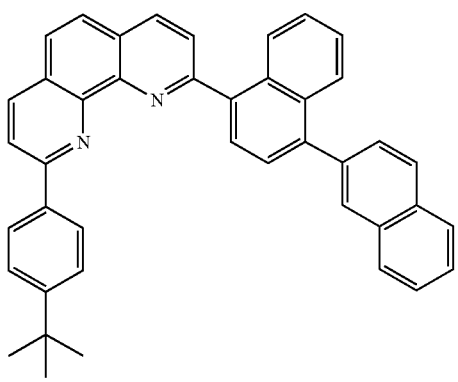

Examples 2-2 to 2-24 and Comparative Examples 2-1 to 2-14

Organic light emitting devices were manufactured in the same manner as in Example 2-1 except that compounds of the following Table 2 were used instead of Compounds EC1 and ET1.

For the organic light emitting devices manufactured in Examples 2-1 to 2-24 and Comparative Examples 2-1 to 2-14, driving voltage and light emission efficiency were measured at current density of 10 mA/cm$^2$, and time taken for luminance decreasing to 90% compared to its initial luminance (T90) was measured at current density of 20 mA/cm$^2$. The results are shown in the following Table 2.

TABLE 2

| Compound | | | Voltage (V@ 10 mA/ cm$^2$) | Efficiency (cd/A@ 10 mA/ cm$^2$) | Color Coordinate (x, y) | Lifetime (h) (T90 at 20 mA/ cm$^2$) |
|---|---|---|---|---|---|---|
| Example 2-1 | EC1 | ET1 | 8.14 | 13.00 | (0.137, 0.124) | 266 |
| Example 2-2 | EC1 | ET2 | 8.40 | 12.60 | (0.137, 0.124) | 307 |
| Example 2-3 | EC1 | ET3 | 8.46 | 12.40 | (0.137, 0.123) | 313 |
| Example 2-4 | EC1 | ET4 | 8.20 | 12.93 | (0.137, 0.125) | 260 |
| Example 2-5 | EC1 | ET5 | 8.24 | 12.95 | (0.137, 0.124) | 256 |
| Example 2-6 | EC1 | ET6 | 8.16 | 13.11 | (0.137, 0.124) | 235 |
| Example 2-7 | EC1 | ET7 | 8.14 | 13.09 | (0.137, 0.123) | 225 |
| Example 2-8 | EC1 | ET8 | 8.34 | 12.77 | (0.137, 0.125) | 294 |
| Example 2-9 | EC2 | ET1 | 8.22 | 12.87 | (0.137, 0.124) | 274 |
| Example 2-10 | EC2 | ET2 | 8.48 | 12.48 | (0.137, 0.124) | 316 |
| Example 2-11 | EC2 | ET3 | 8.54 | 12.27 | (0.137, 0.123) | 322 |
| Example 2-12 | EC2 | ET4 | 8.28 | 12.80 | (0.137, 0.125) | 268 |
| Example 2-13 | EC3 | ET5 | 8.65 | 12.30 | (0.137, 0.124) | 261 |
| Example 2-14 | EC3 | ET6 | 8.57 | 12.45 | (0.137, 0.124) | 240 |
| Example 2-15 | EC3 | ET7 | 8.55 | 12.43 | (0.137, 0.123) | 229 |
| Example 2-16 | EC3 | ET8 | 8.75 | 12.13 | (0.137, 0.125) | 299 |
| Example 2-17 | EC4 | ET1 | 8.06 | 13.12 | (0.137, 0.124) | 239 |
| Example 2-18 | EC4 | ET2 | 8.31 | 12.73 | (0.137, 0.124) | 276 |
| Example 2-19 | EC4 | ET3 | 8.37 | 12.52 | (0.137, 0.123) | 282 |
| Example 2-20 | EC4 | ET4 | 8.12 | 13.06 | (0.137, 0.125) | 234 |
| Example 2-21 | EC5 | ET5 | 8.40 | 12.56 | (0.137, 0.124) | 271 |
| Example 2-22 | EC5 | ET6 | 8.32 | 12.72 | (0.137, 0.124) | 249 |
| Example 2-23 | EC5 | ET7 | 8.30 | 12.69 | (0.137, 0.124) | 238 |
| Example 2-24 | EC5 | ET8 | 8.50 | 12.38 | (0.137, 0.125) | 311 |
| Comparative Example 2-1 | EC1 | ET-A | 9.03 | 9.94 | (0.137, 0.124) | 56 |
| Comparative Example 2-2 | EC2 | ET-A | 9.12 | 9.84 | (0.137, 0.124) | 58 |
| Comparative Example 2-3 | EC3 | ET-A | 9.49 | 9.45 | (0.137, 0.124) | 57 |
| Comparative Example 2-4 | EC4 | ET-A | 8.94 | 10.04 | (0.137, 0.125) | 51 |
| Comparative Example 2-5 | EC5 | ET-A | 9.21 | 9.65 | (0.137, 0.124) | 57 |
| Comparative Example 2-6 | ET-A | ET1 | 9.20 | 10.17 | (0.137, 0.124) | 49 |
| Comparative Example 2-7 | ET-A | ET2 | 9.49 | 9.86 | (0.137, 0.123) | 56 |
| Comparative Example 2-8 | ET-A | ET3 | 9.56 | 9.70 | (0.137, 0.123) | 57 |
| Comparative Example 2-9 | ET-A | ET4 | 9.26 | 10.12 | (0.137, 0.124) | 48 |
| Comparative Example 2-10 | ET-A | ET5 | 9.31 | 10.13 | (0.137, 0.124) | 47 |
| Comparative Example 2-11 | ET-A | ET6 | 9.22 | 10.26 | (0.137, 0.123) | 43 |
| Comparative Example 2-12 | ET-A | ET7 | 9.20 | 10.24 | (0.137, 0.125) | 41 |
| Comparative Example 2-13 | ET-A | ET8 | 9.42 | 9.99 | (0.137, 0.124) | 54 |
| Comparative Example 2-14 | ET-A | ET-A | 9.30 | 9.45 | (0.137, 0.124) | 49 |

From Table 2, it was seen that the organic light emitting device using both Chemical Formula 1 and Chemical Formula 2 according to the present specification exhibited properties of low driving voltage, high efficiency and long lifetime compared to the organic light emitting device using only Chemical Formula 1 or only Chemical Formula 2. Particularly, it was identified that Examples 2-1 to 2-24 had a lifetime increasing by up to approximately 680% compared to Comparative Examples 2-1 to 2-14.

Example 3

Dipole moment (Debye) values of Chemical Formulae EC1 to EC5, ET1 to ET8, and ET-A according to one embodiment of the present specification are listed in the following Table 3.

TABLE 3

| Chemical Formula | Dipole Moment (Debye) |
|---|---|
| EC1 | 0.70 |
| EC2 | 0.93 |

TABLE 3-continued

| Chemical Formula | Dipole Moment (Debye) |
|---|---|
| EC3 | 0.22 |
| EC4 | 2.54 |
| EC5 | 2.69 |
| ET1 | 3.83 |
| ET2 | 5.28 |
| ET3 | 5.78 |
| ET4 | 6.02 |
| ET5 | 4.66 |
| ET6 | 5.38 |
| ET7 | 5.89 |
| ET8 | 5.54 |
| ET-A | 3.61 |

The dipole moment (Debye) was obtained using Gaussian 03, a quantum chemistry calculation program manufactured by Gaussian, Inc. of the USA, and, using a density functional theory (DFT), a calculated value of triplet energy was obtained by a time-dependent density functional theory (TD-DFT) for the optimized structure using B3LYP as a function and 6-31G* as a basis function. By the relation of $P_{ET} > P_{Eb}$ in Table 3, a phenomenon of over-injection of the amount of the electrons transferred to the light emitting layer can be controlled, and as a result, high efficiency and long lifetime are obtained in the organic light emitting device.

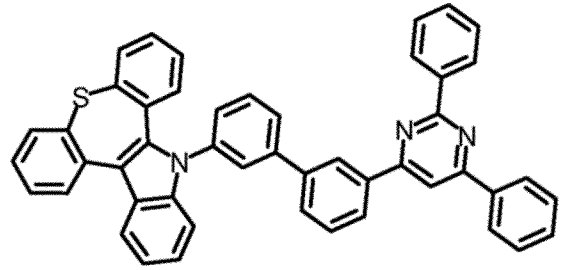

The invention claimed is:

1. An organic light emitting device comprising:
   a first electrode;
   a second electrode provided opposite to the first electrode; and
   a first organic material layer and a second organic material layer provided between the first electrode and the second electrode,
   wherein the first organic material layer is a hole blocking layer or an electron control layer and includes a compound of the following Chemical Formula 1,
   the second organic material layer includes a compound of the following Chemical Formula 2, and
   a dipole moment value of the second organic material layer is larger than a dipole moment value of the first organic material layer:

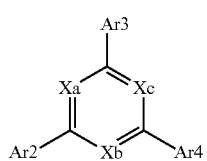

[Chemical Formula 1]

wherein in Chemical Formula 1:
at least one of Xa to Xc is N, and the rest are CR;
R is hydrogen, deuterium, a cyano group, a nitrile group, a substituted or unsubstituted silyl group, a substituted or unsubstituted alkyl group, a substituted or unsubstituted haloalkyl group, a substituted or unsubstituted cycloalkyl group, a substituted or unsubstituted alkenyl group, a substituted or unsubstituted aryl group, or a substituted or unsubstituted heterocyclic group; and Ar2 to Ar4 are each independently a substituted or unsubstituted aryl group or a substituted or unsubstituted heterocyclic group;

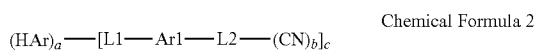

Chemical Formula 2 wherein in Chemical Formula 2:
HAr is a substituted or unsubstituted heterocyclic group including one or more Ns;
L1 and L2 are each independently a direct bond, a substituted or unsubstituted arylene group, or a substituted or unsubstituted divalent heterocyclic group;
Ar1 is a direct bond, —O—, a substituted or unsubstituted arylene group, or a substituted or unsubstituted divalent heterocyclic group;
a to c are each an integer of 1 to 3; and
when a to c are each 2 or greater, the structures in the two or more parentheses are the same as or different from each other.

2. The organic light emitting device of claim 1, wherein Chemical Formula 1 is the following Chemical Formula 101:

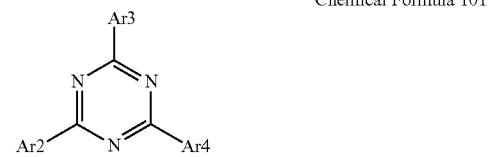

Chemical Formula 101 wherein in Chemical Formula 101:
Ar2 to Ar4 have the same definitions as in Chemical Formula 1.

3. The organic light emitting device of claim 1, wherein Chemical Formula 1 is any one of the following Chemical Formulae 1-1 to 1-3:

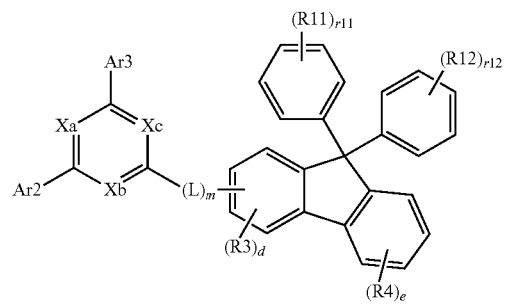

Chemical Formula 1-1

Chemical Formula 1-2

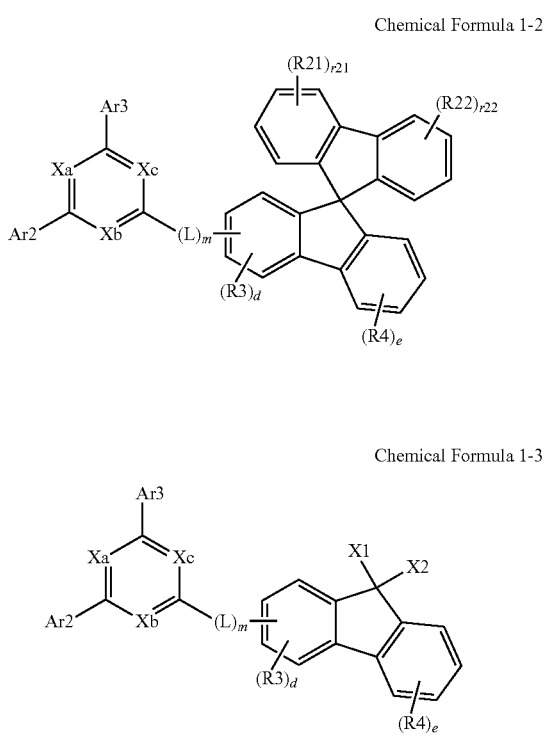

Chemical Formula 1-3 wherein in Chemical Formulae 1-1 to 1-3:
Xa to Xc, Ar2 and Ar3 have the same definitions as in Chemical Formula 1;
L is substituted or unsubstituted phenylene, substituted or unsubstituted biphenylylene, or substituted or unsubstituted terphenylene;
R3, R4, R11, R12, R21 and R22 are the same as or different from each other, and each independently is hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted arylphosphine group, or a substituted or unsubstituted phosphine oxide group, or bond to adjacent groups to form a substituted or unsubstituted ring;
X1 and X2 are the same as or different from each other, and each independently is hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, or a substituted or unsubstituted phosphine oxide group, or bond to adjacent groups to form a substituted or unsubstituted ring;
r11 and r12 are the same as or different from each other, and each independently is an integer of 0 to 5;
r21 and r22 are the same as or different from each other, and each independently is an integer of 0 to 4;
m is an integer of 1 to 3;
d is an integer of 1 to 3;
e is an integer of 1 to 4; and
when r11, r12, r21, r22, m, d and e are each 2 or greater, structures in the parentheses are the same as or different from each other.

4. The organic light emitting device of claim 1, wherein Chemical Formula 1 is any one of the following Chemical Formulae 1-4 to 1-6:

Chemical Formula 1-4

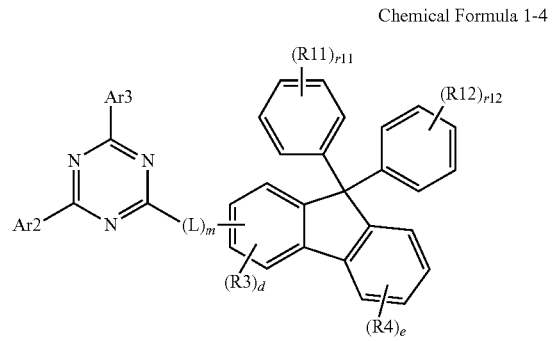

Chemical Formula 1-5

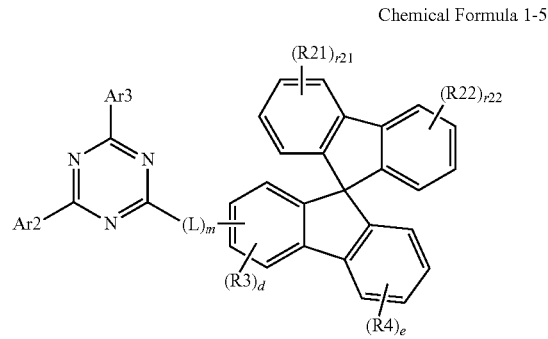

Chemical Formula 1-6

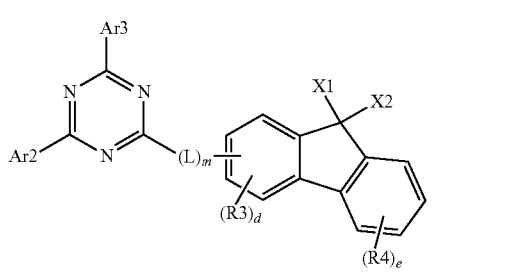

wherein in Chemical Formulae 1-4 to 1-6:
Ar2 and Ar3 have the same definitions as in Chemical Formula 1;
L is substituted or unsubstituted phenylene, substituted or unsubstituted biphenylylene, or substituted or unsubstituted terphenylene;
R3, R4, R11, R12, R21 and R22 are the same as or different from each other, and each independently is hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted arylphosphine group, or a substituted or unsubstituted phosphine oxide group, or bond to adjacent groups to form a substituted or unsubstituted ring;
X1 and X2 are the same as or different from each other, and each independently is hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, substituted or unsubstituted arylheteroarylamine group, a substituted or unsubstituted arylphosphine group, or a substituted or unsubstituted phosphine oxide group, or bond to adjacent groups to form a substituted or unsubstituted ring;
r11 and r12 are the same as or different from each other, and each independently is an integer of 0 to 5;
r21 and r22 are the same as or different from each other, and each independently is an integer of 0 to 4;
m is an integer of 1 to 3;
d is an integer of 1 to 3;
e is an integer of 1 to 4; and
when r11, r12, r21, r22, m, d and e are each 2 or greater, structures in the parentheses are the same as or different from each other.

5. The organic light emitting device of claim 1, wherein Ar2 to Ar4 are the same as or different from each other, and each independently is —L11-Ar11;
the L11s are the same as or different from each other, and each independently is a direct bond or a substituted or unsubstituted arylene group; and
the Ar11s are the same as or different from each other, and each independently is a substituted or unsubstituted aryl group or a substituted or unsubstituted heterocyclic group.

6. The organic light emitting device claim 1, wherein HAr is the following Chemical Formula 2-1:

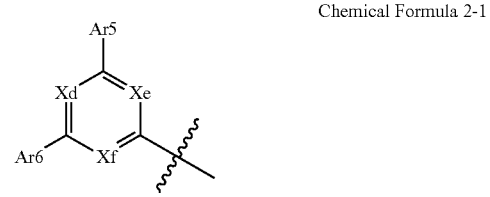

Chemical Formula 2-1 wherein in Chemical Formula 2-1:
Ar5 and Ar6 are a substituted or unsubstituted aryl group or a substituted or unsubstituted heterocyclic group, or bond to adjacent groups to form a ring; and
at least one of Xd to Xf is N, and the rest are CH.

7. The organic light emitting device of claim 1, wherein the compound of Chemical Formula 1 is selected from among the following compounds:

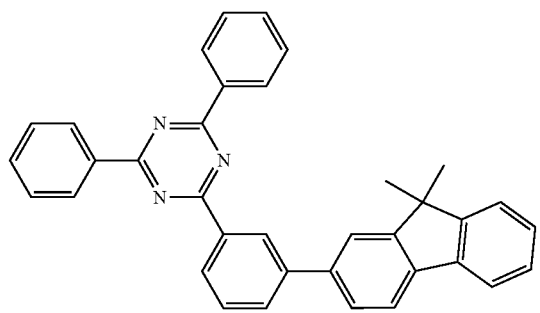

225
-continued
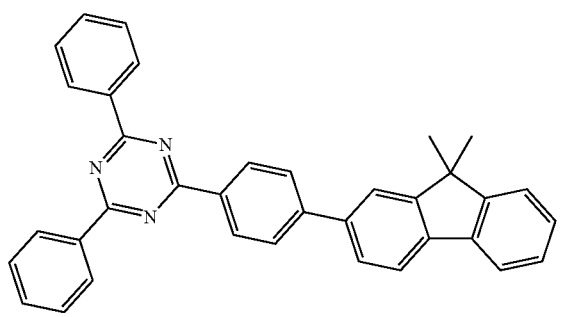
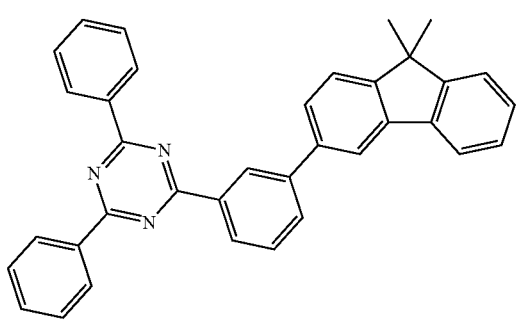
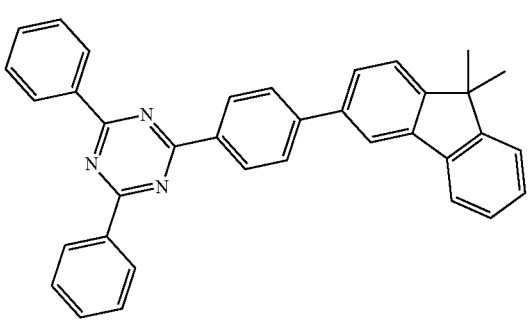
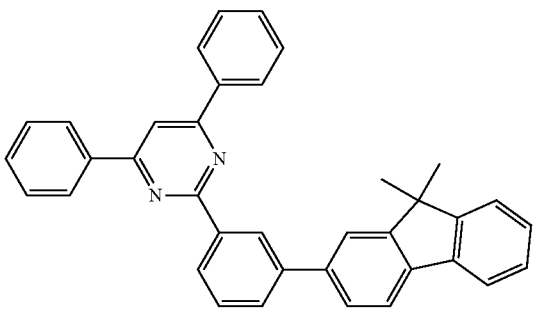
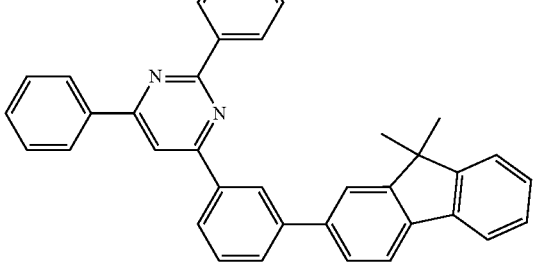
226
-continued
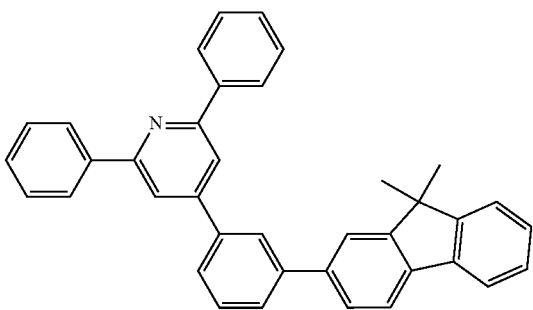
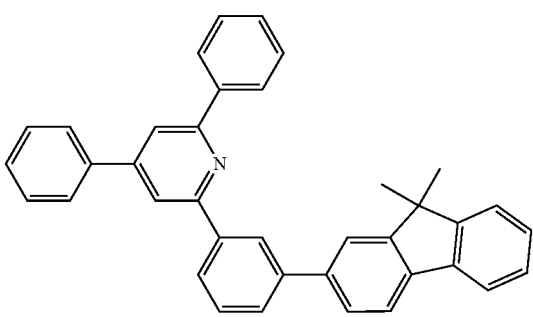
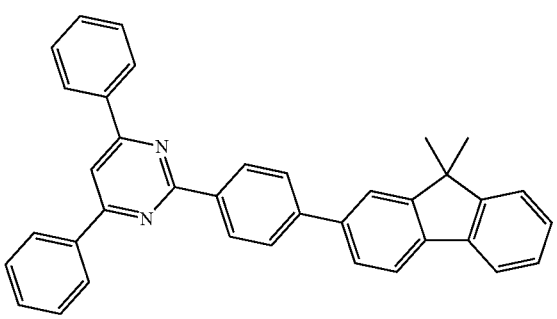
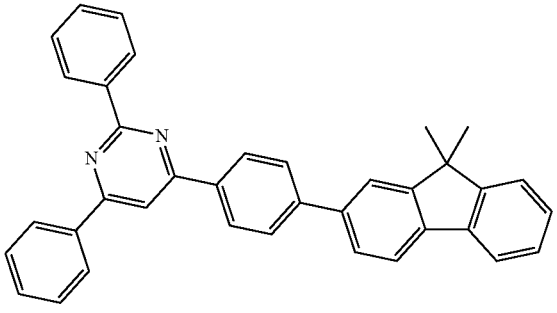
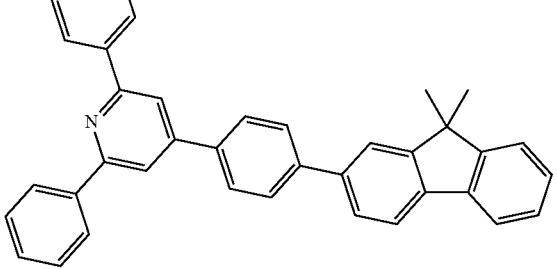

227
-continued
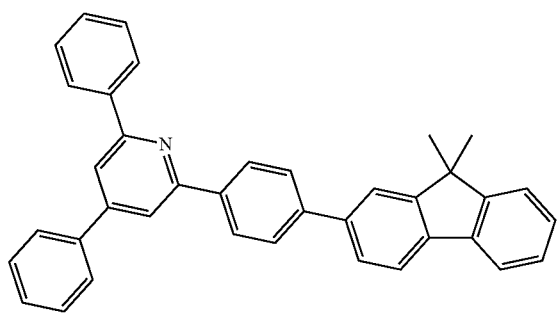
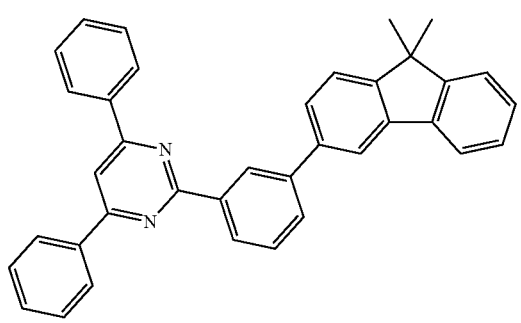
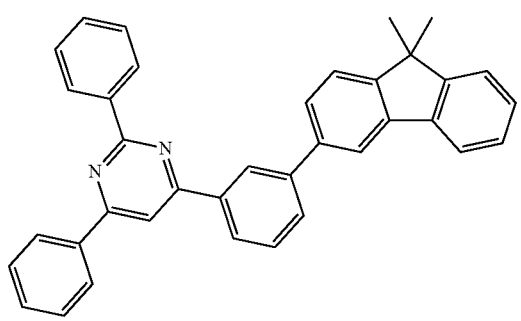
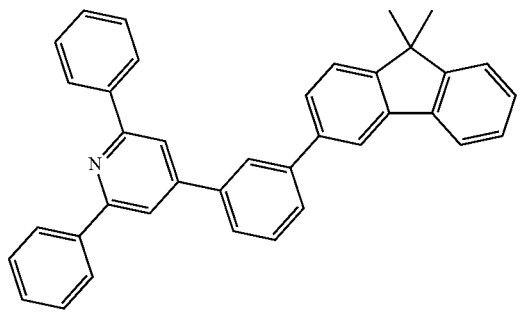
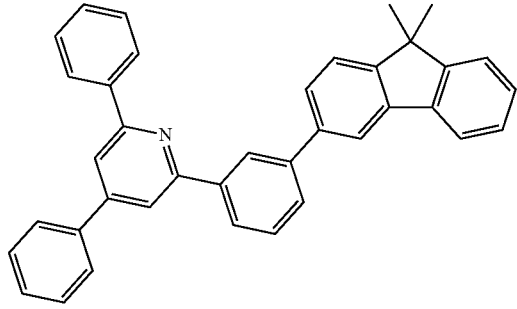
228
-continued
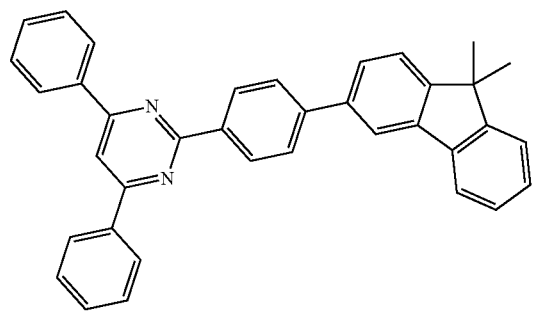
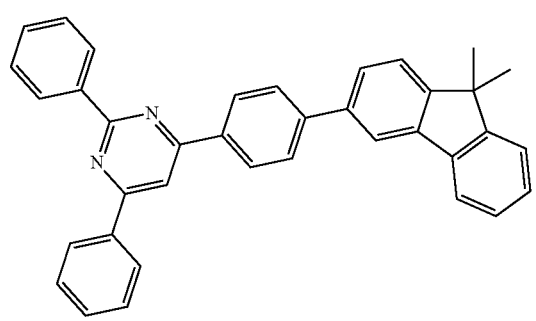
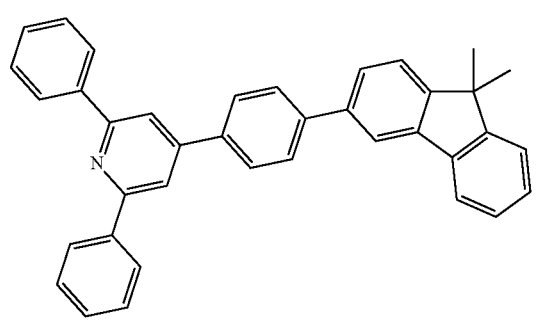
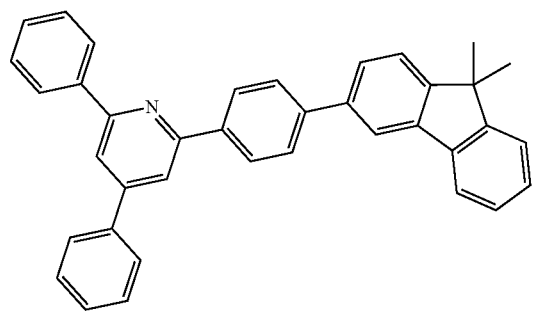
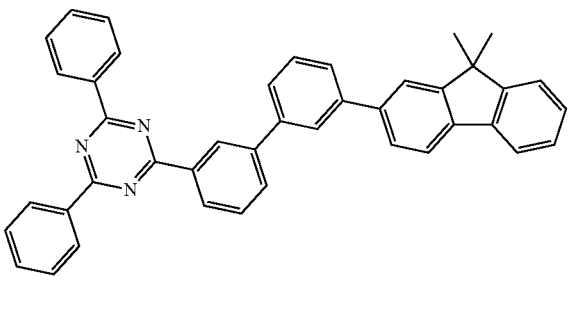

229
-continued
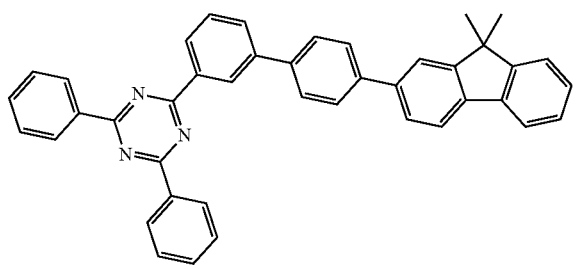
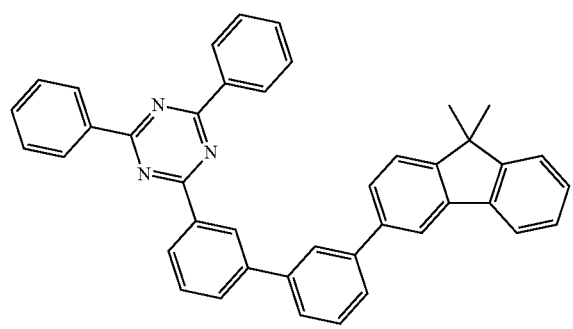
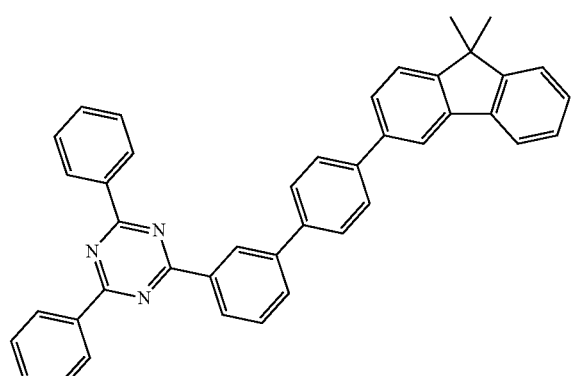
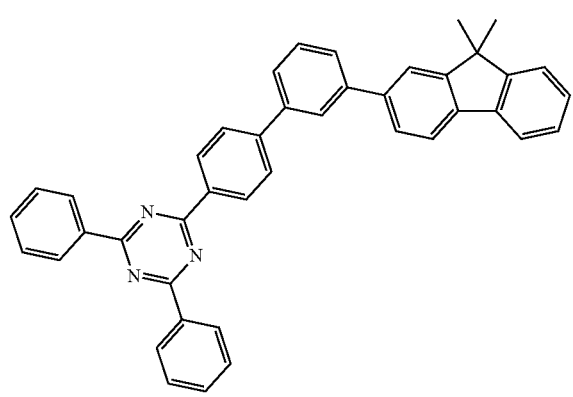
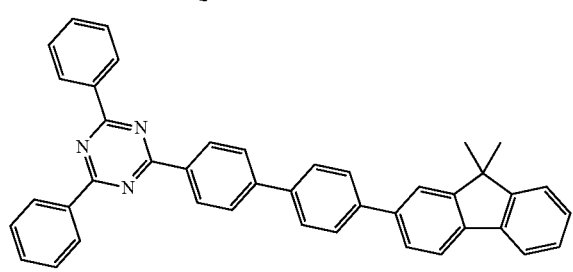
230
-continued
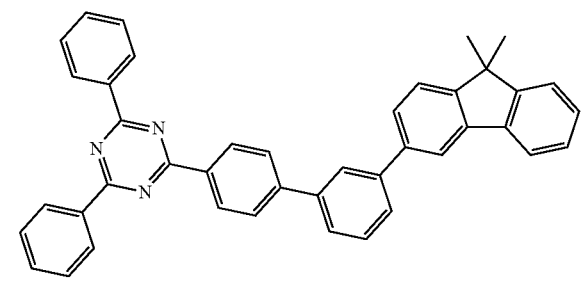
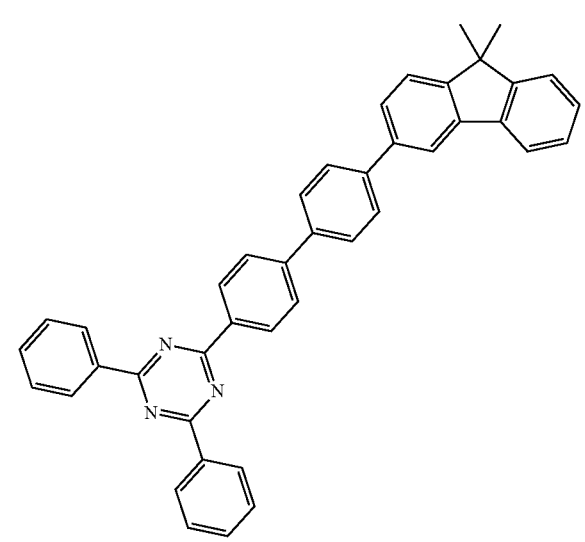
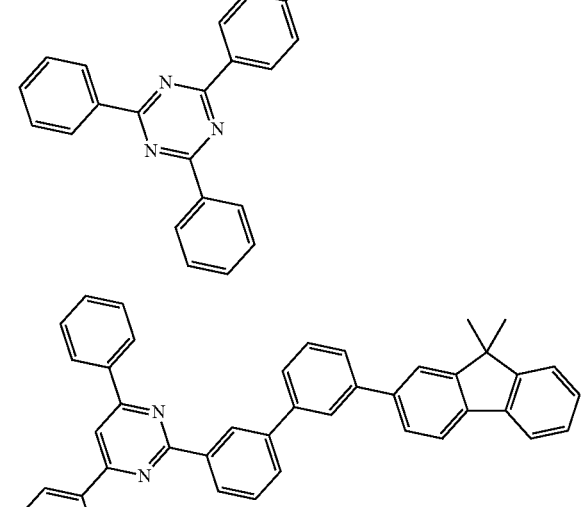
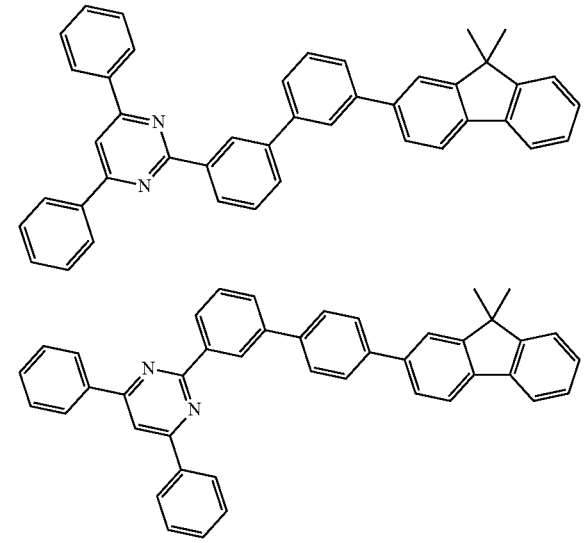
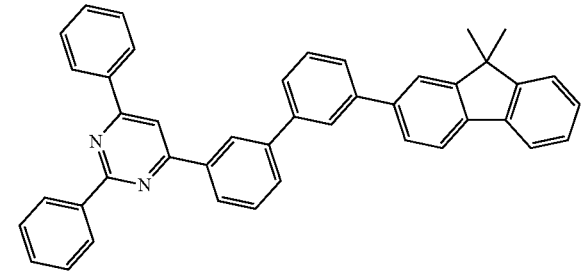

231
-continued
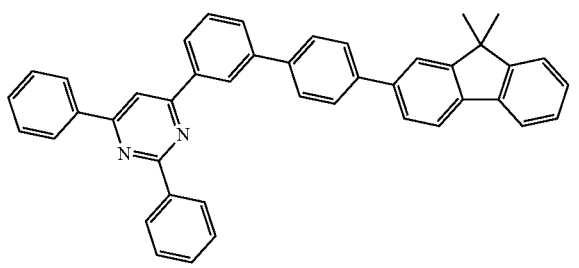
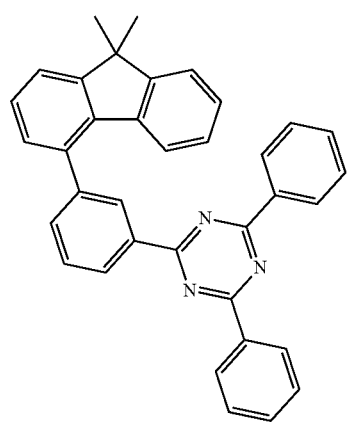
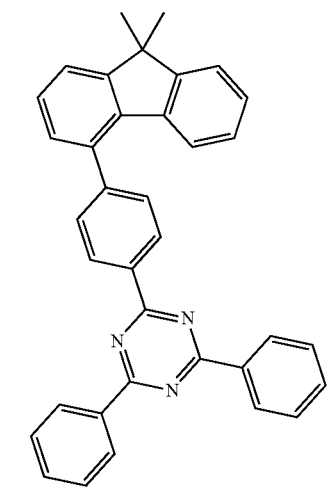
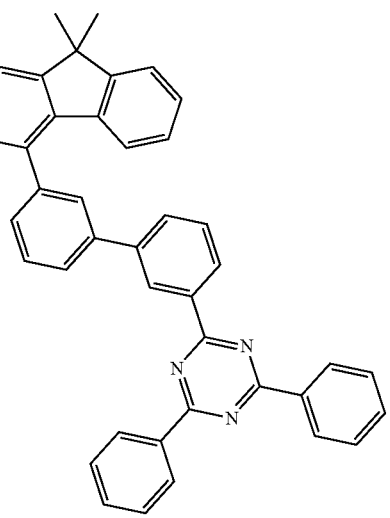
232
-continued
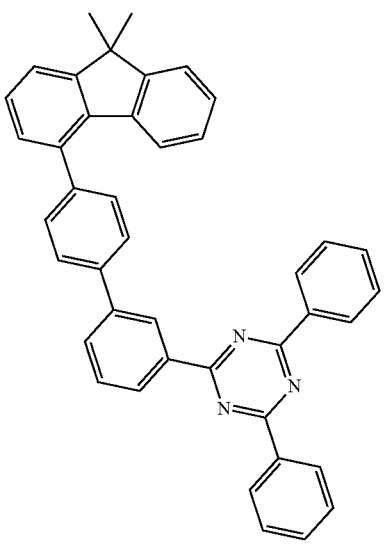
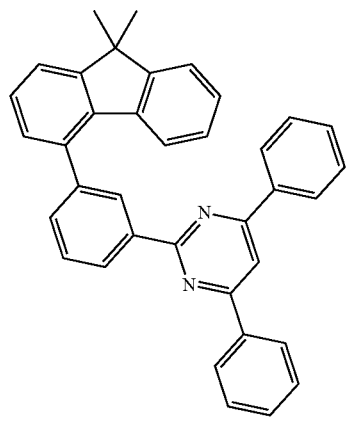
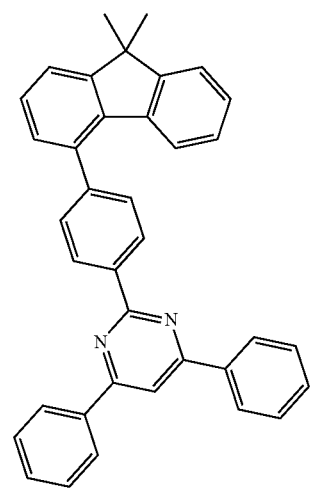

233
-continued
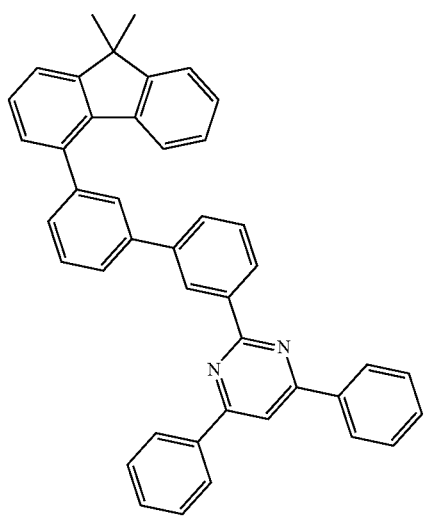
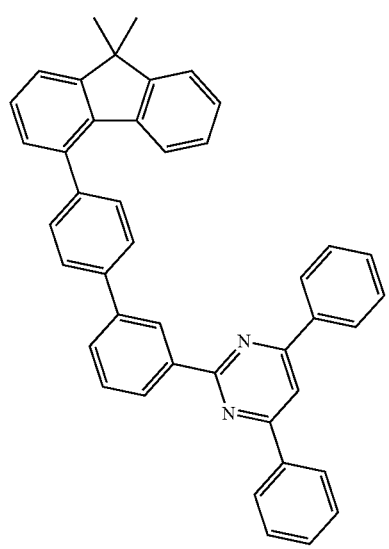
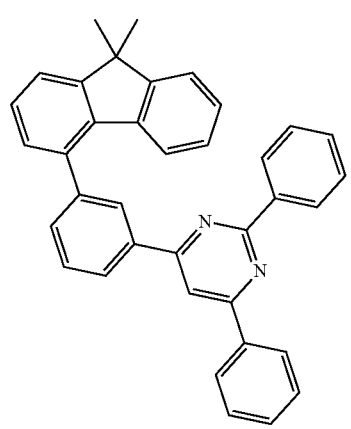
234
-continued
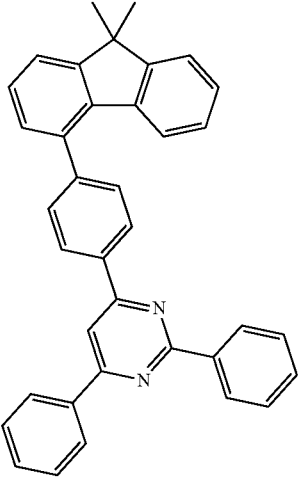
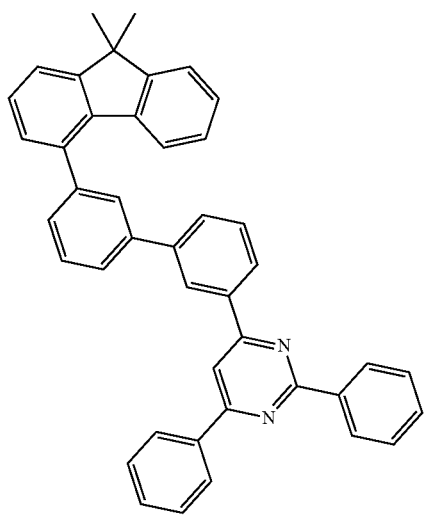
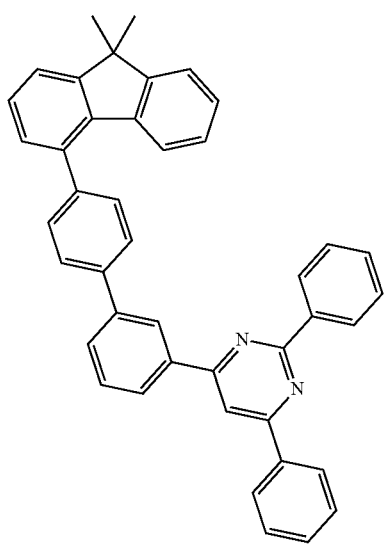

235
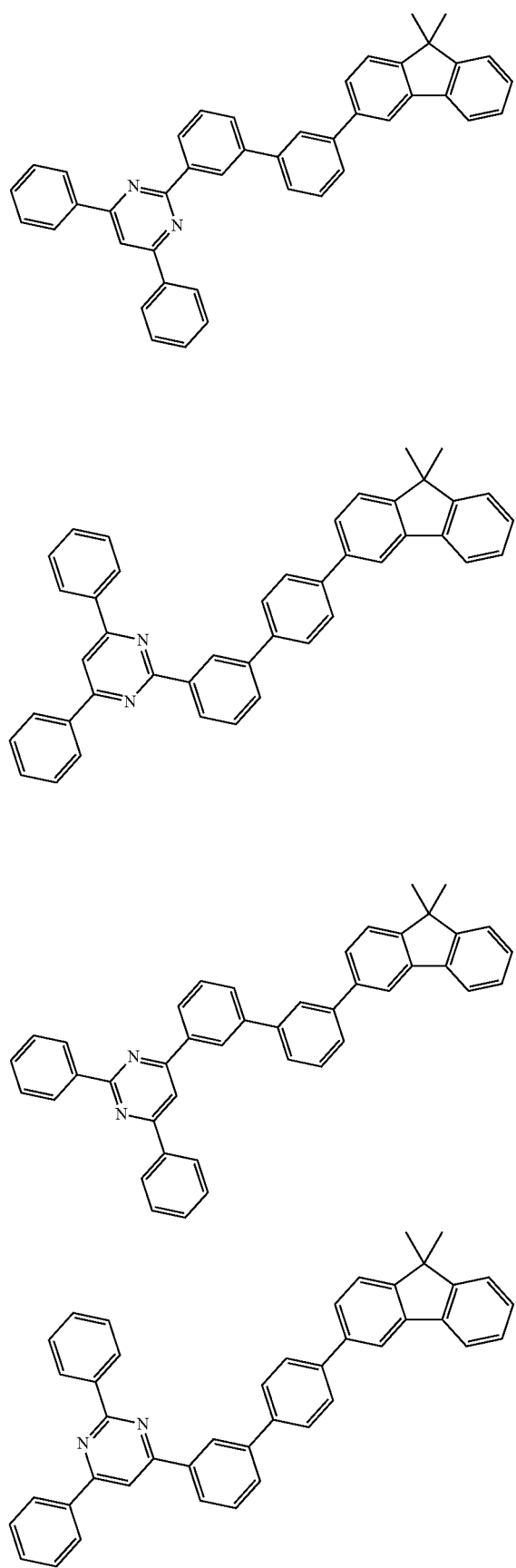
236
-continued
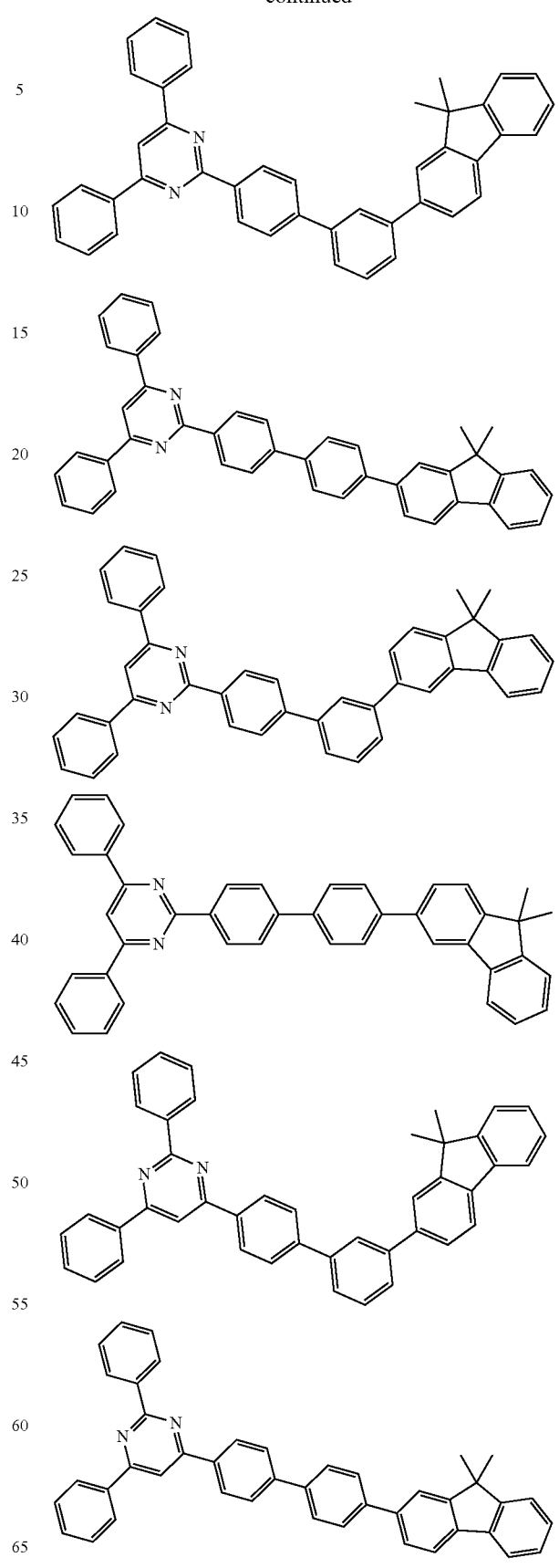

237
-continued
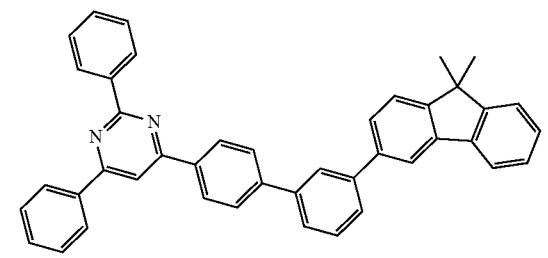
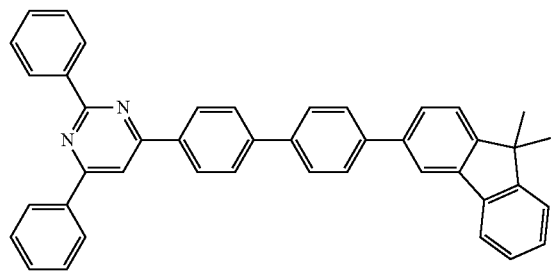
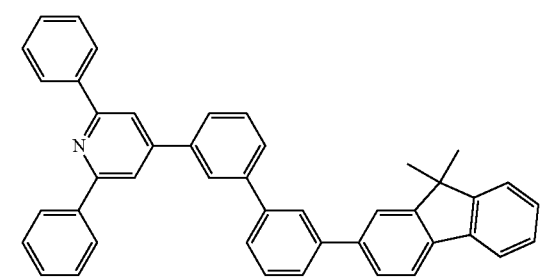
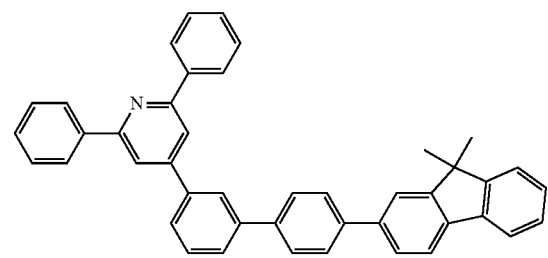
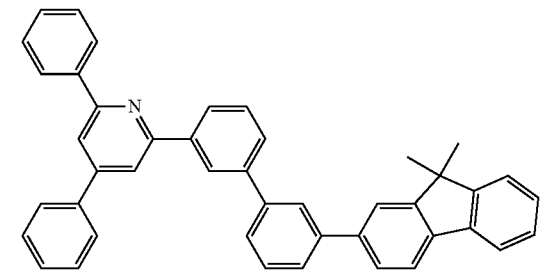
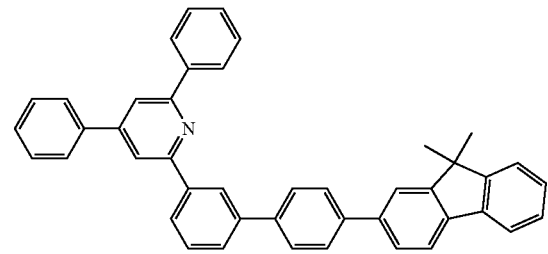
238
-continued
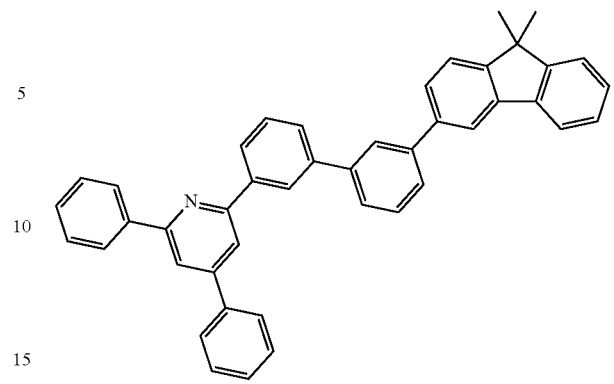
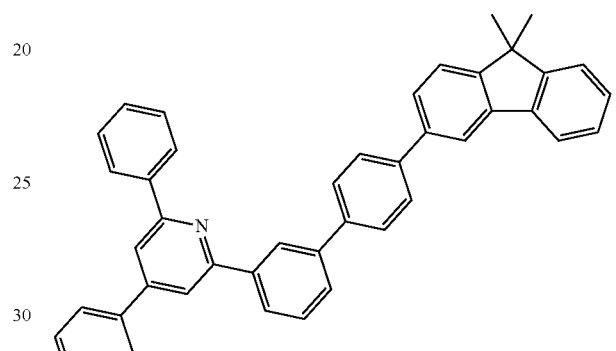
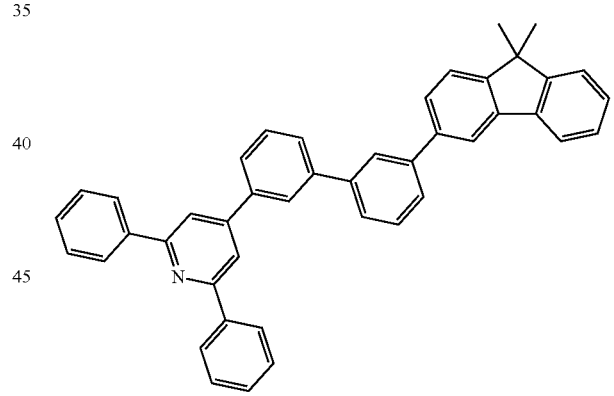
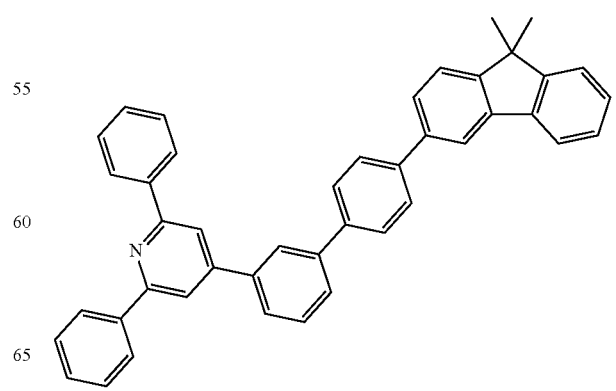

239
-continued
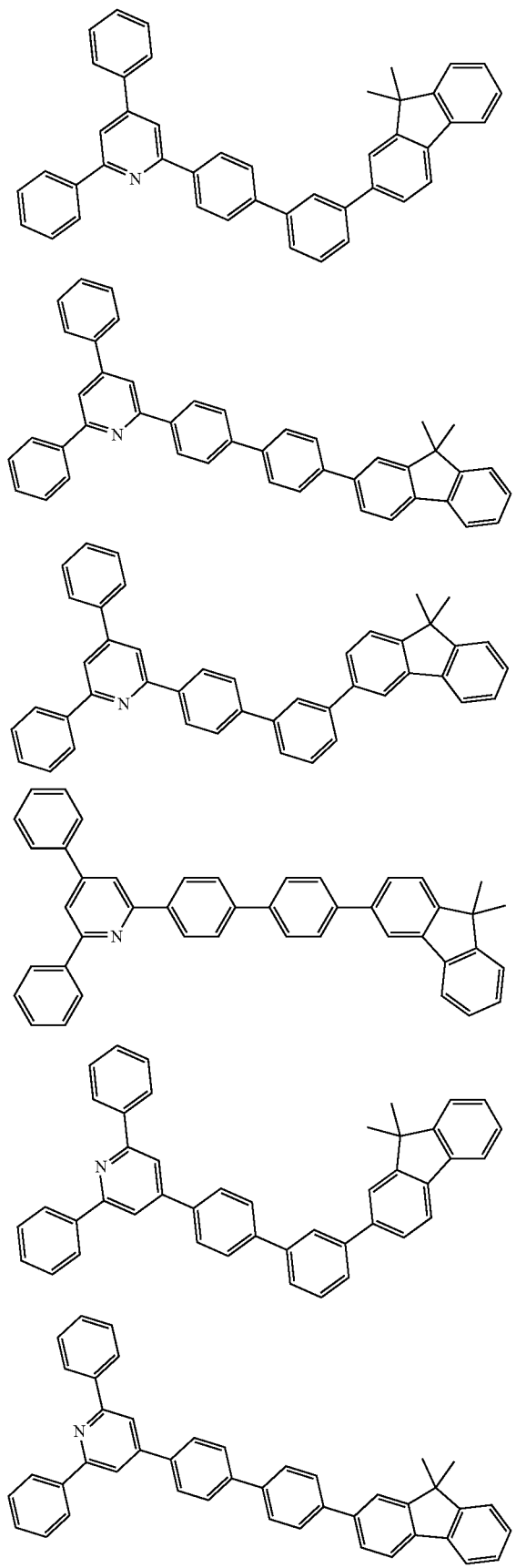
240
-continued
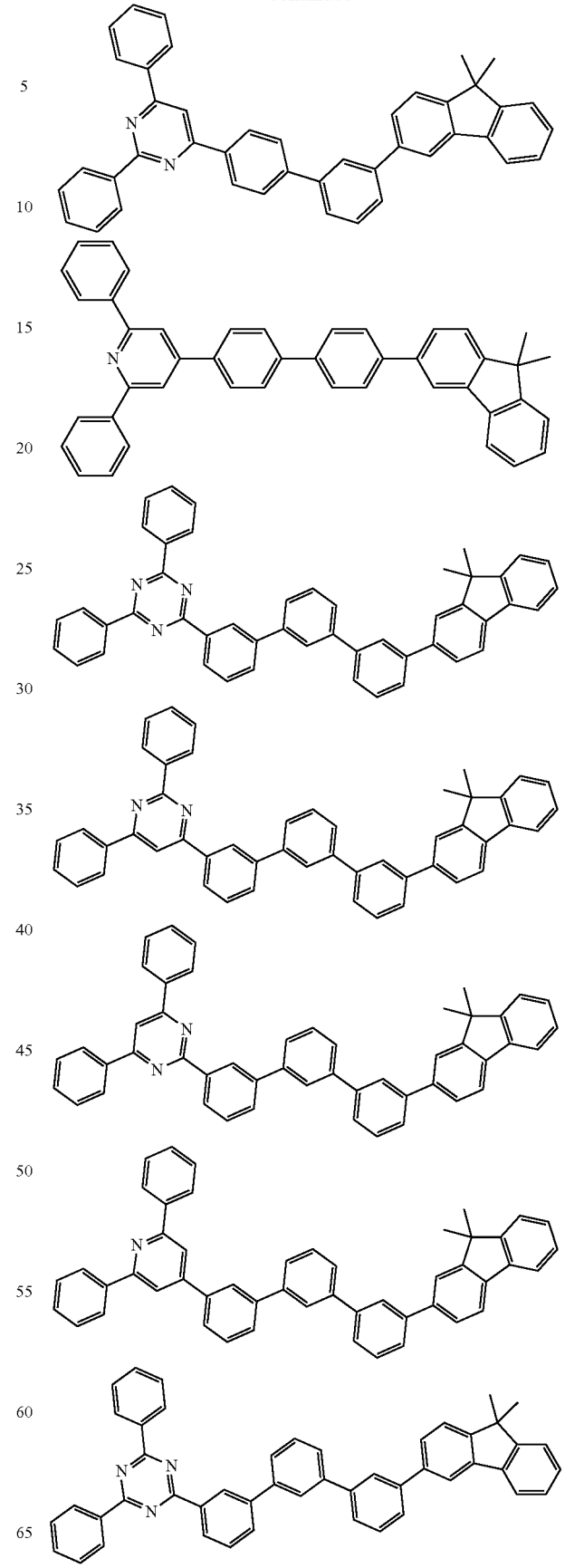

241
-continued
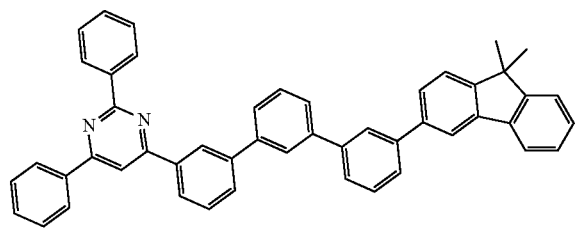
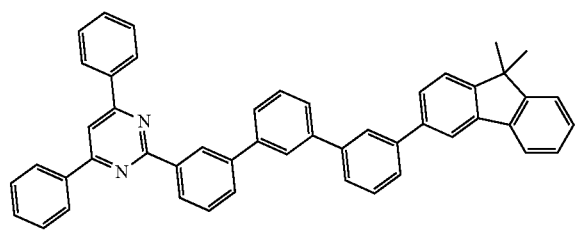
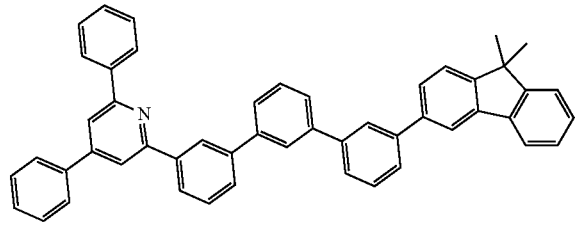
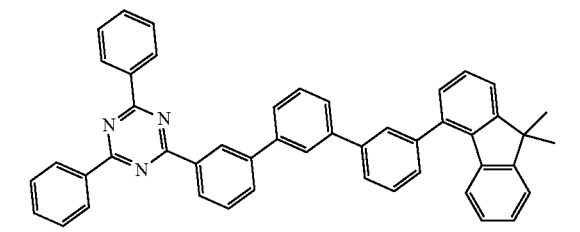
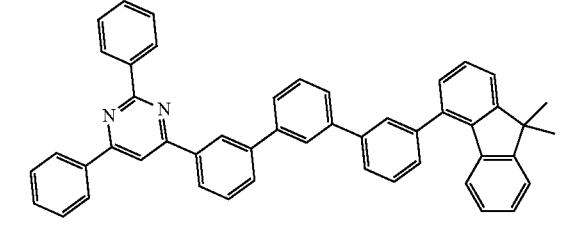
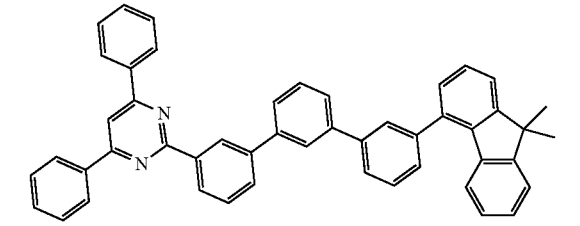
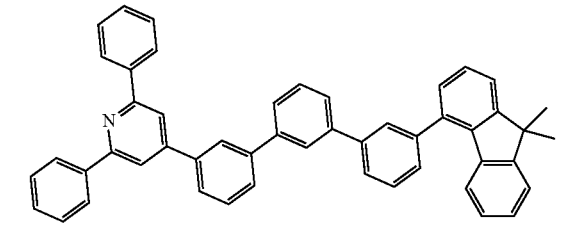
242
-continued
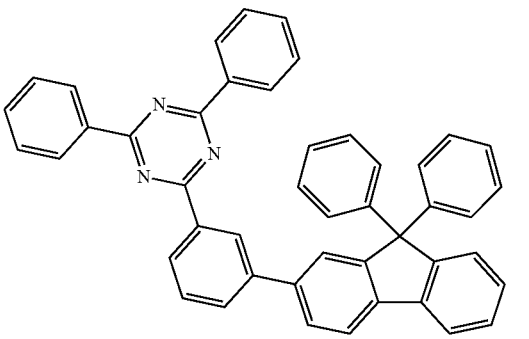
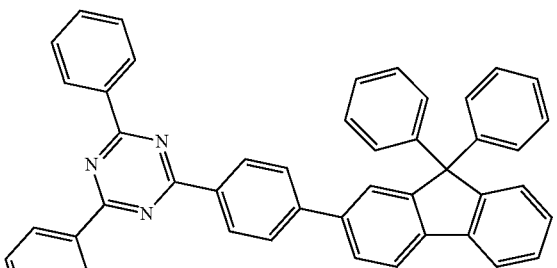
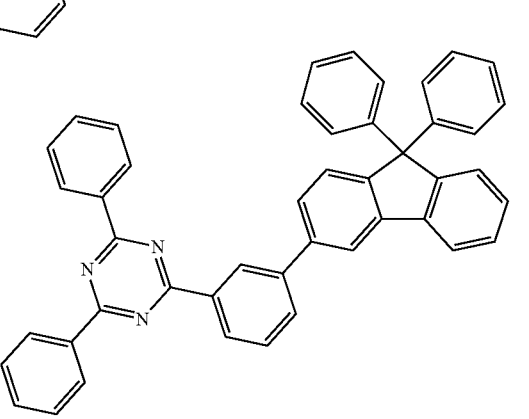
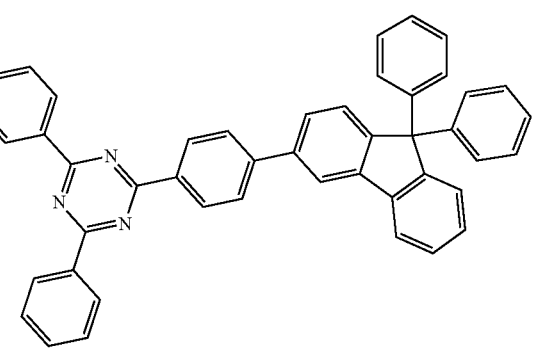
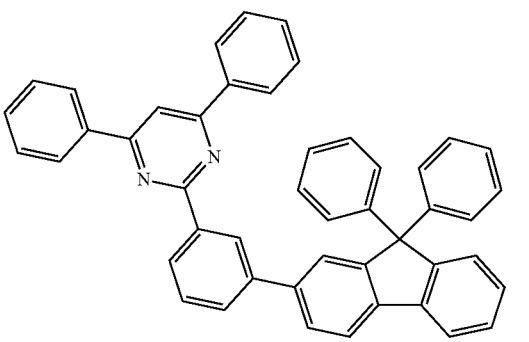

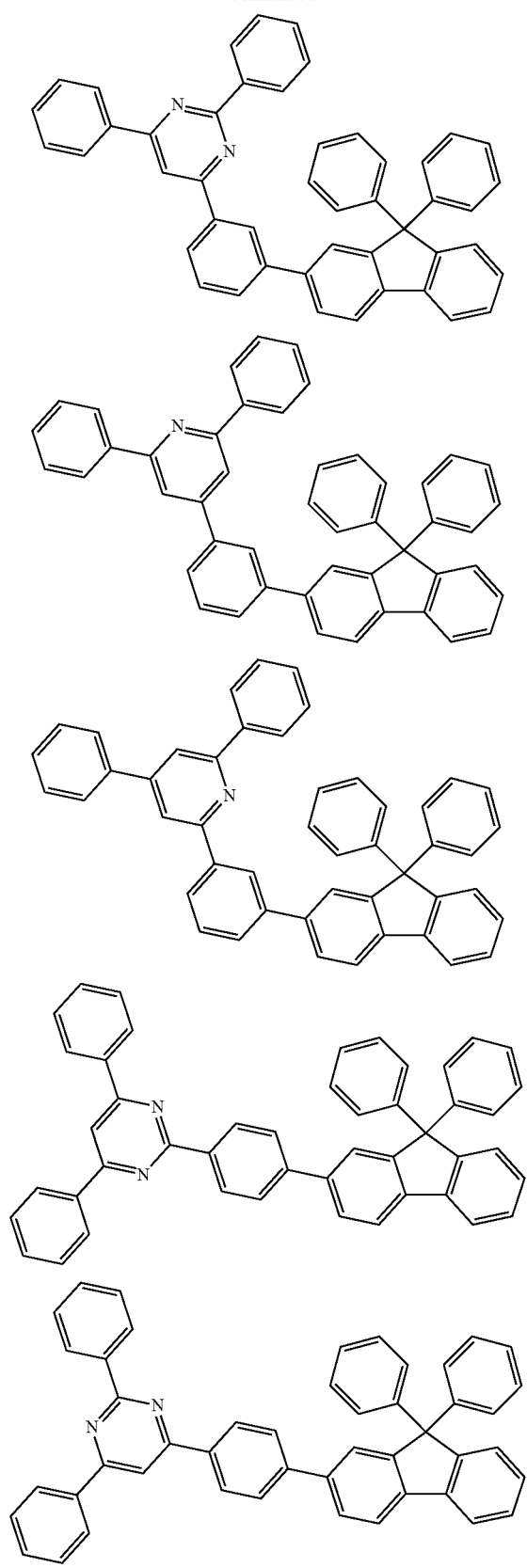
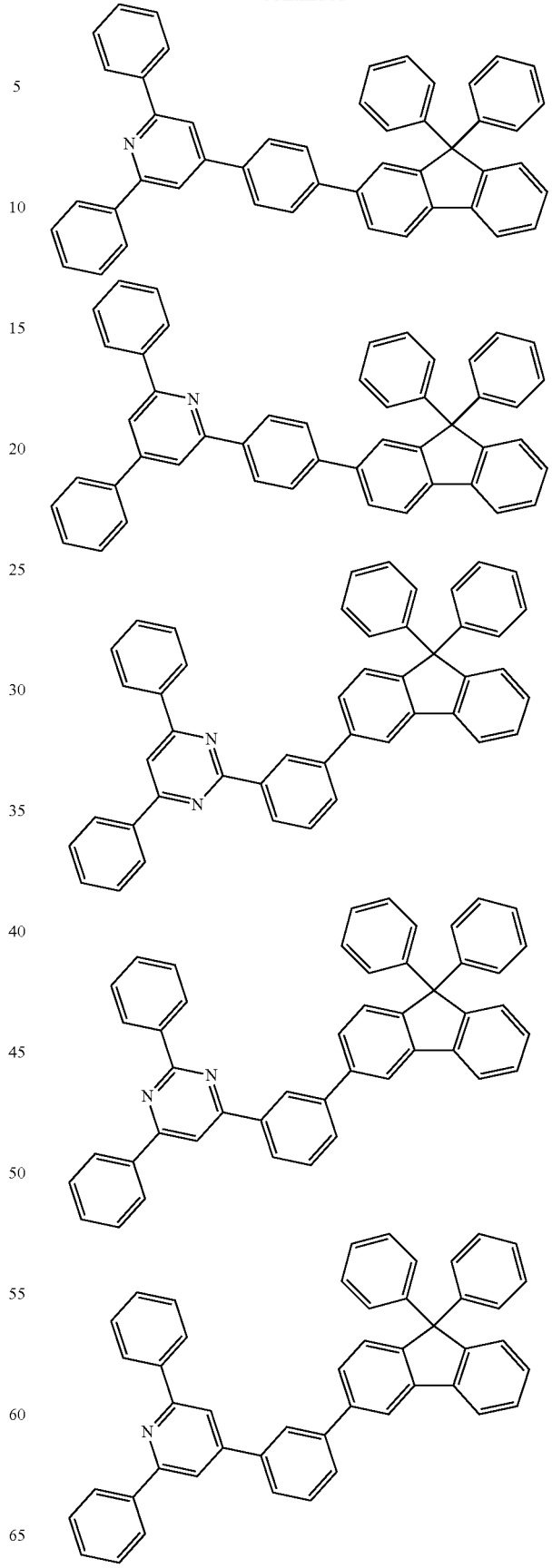

245
-continued
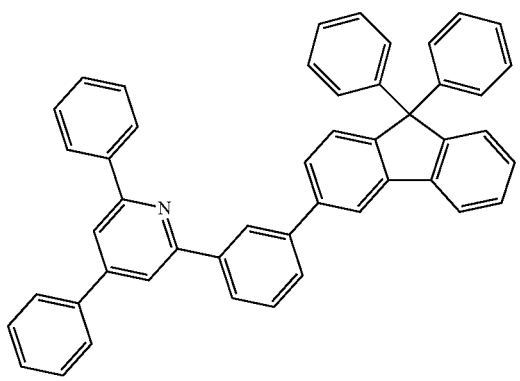
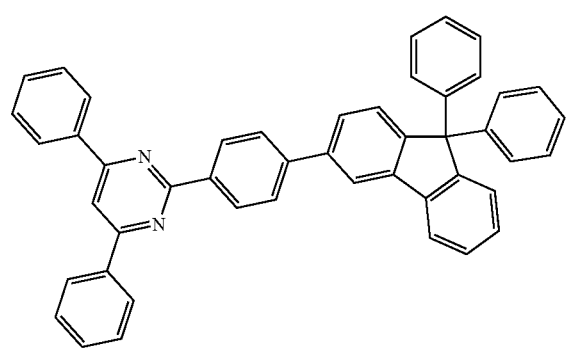
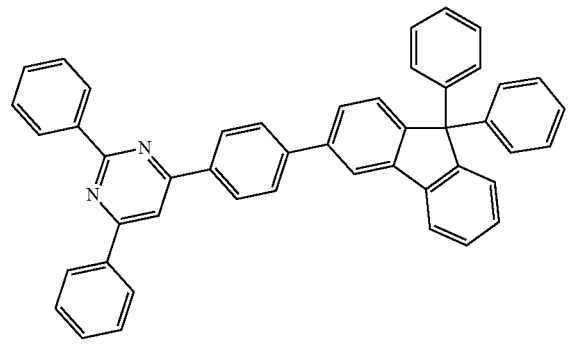
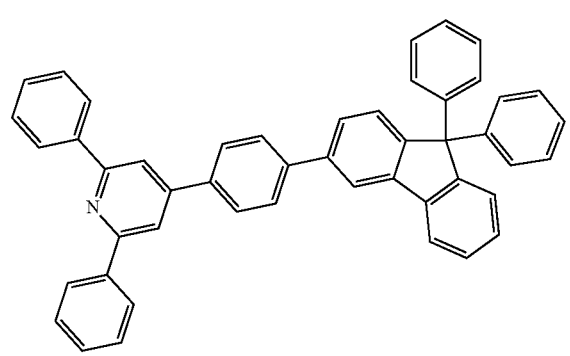
246
-continued
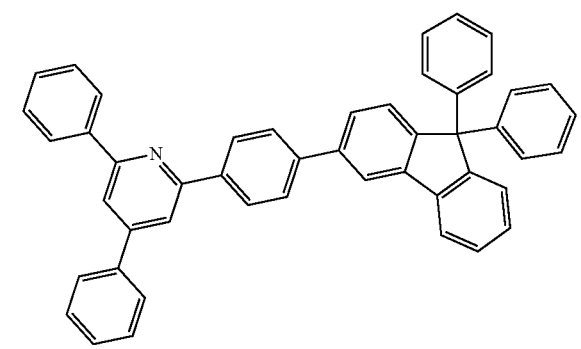
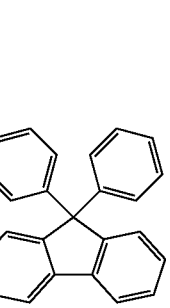
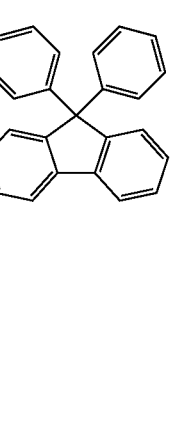

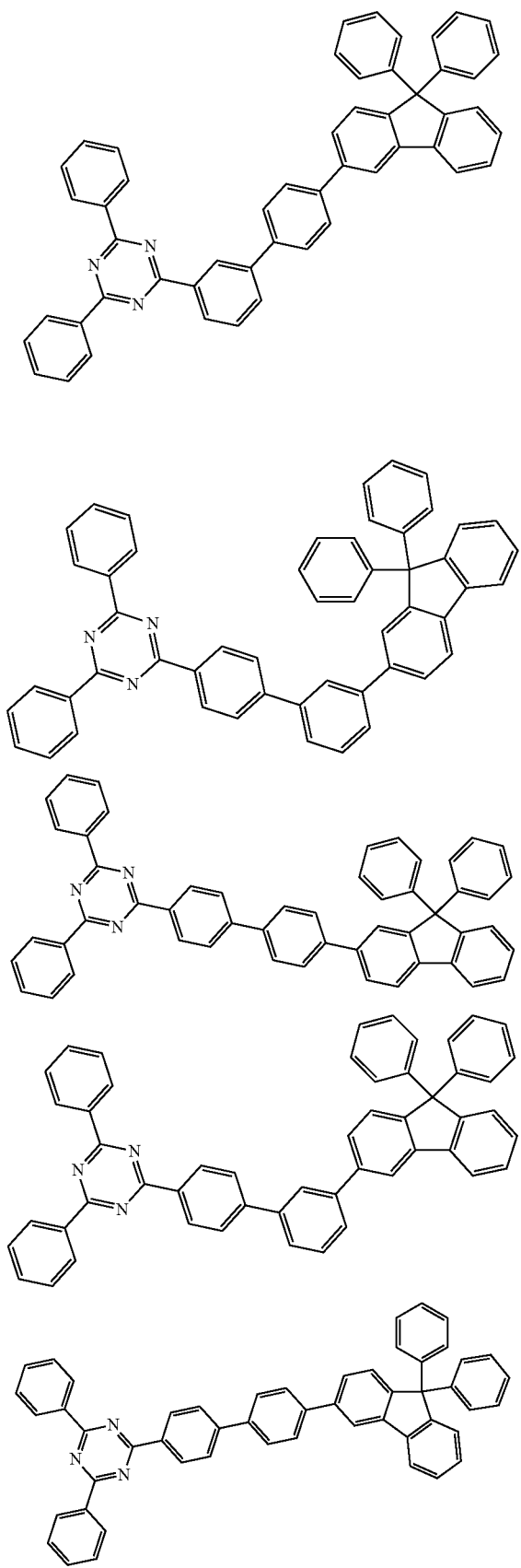
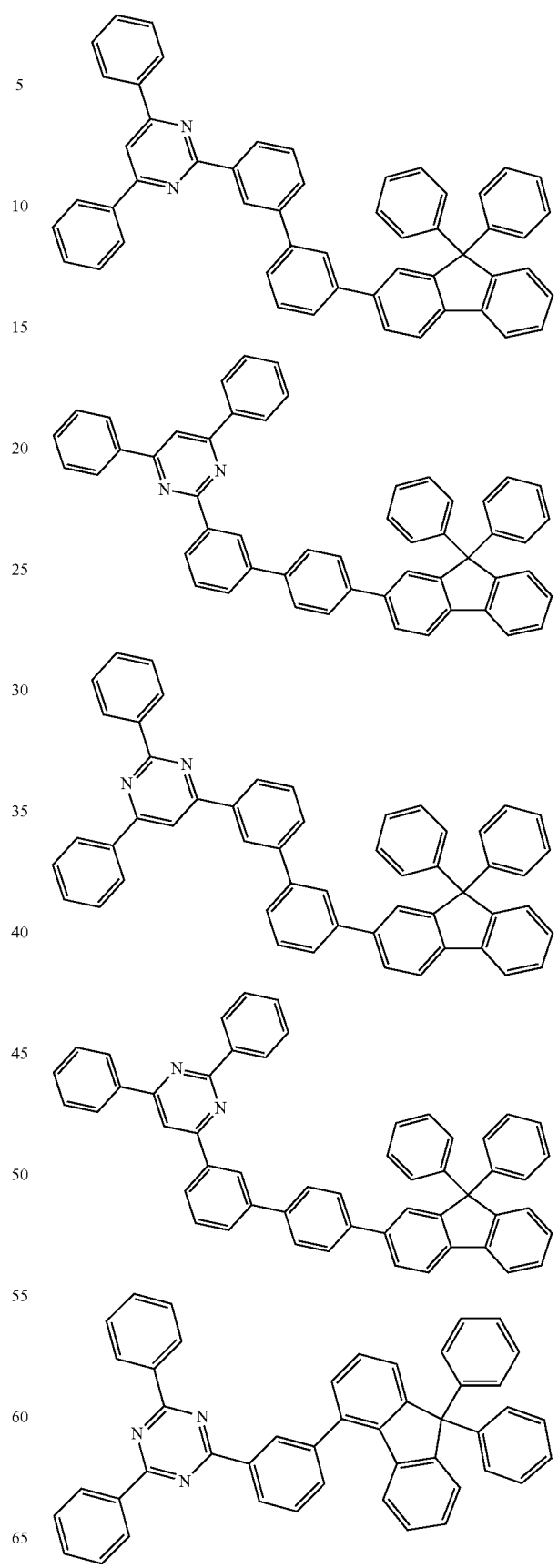

249
-continued
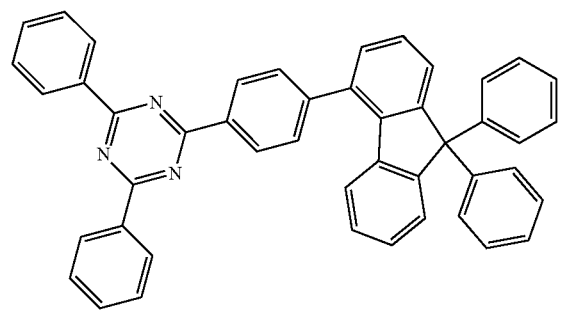
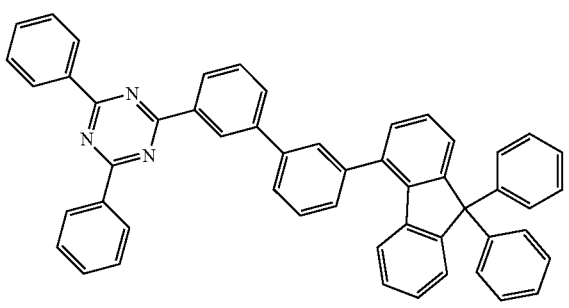
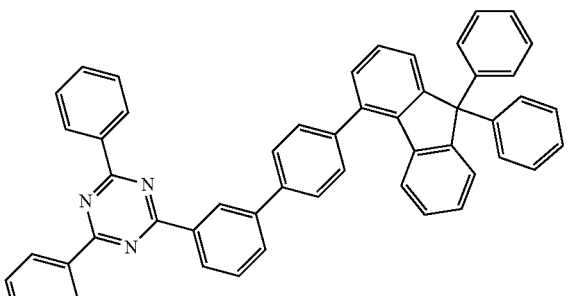
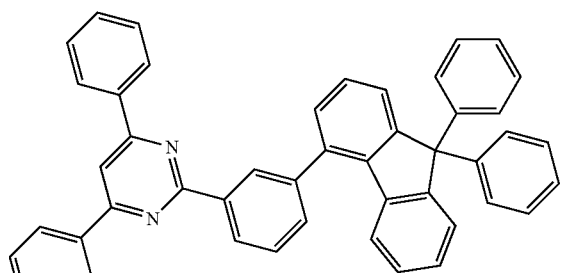
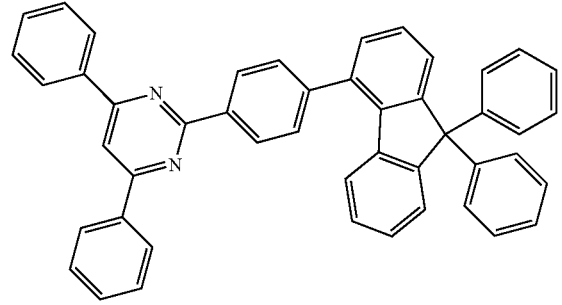
250
-continued
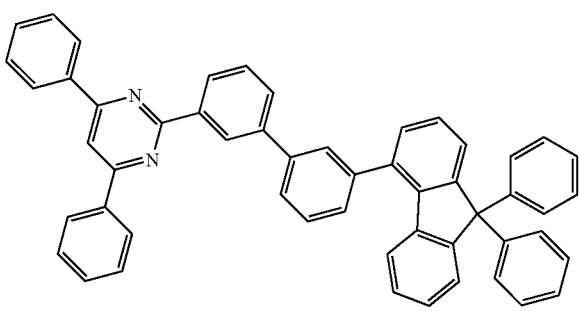
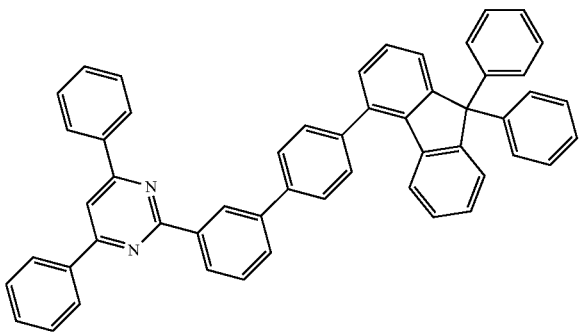
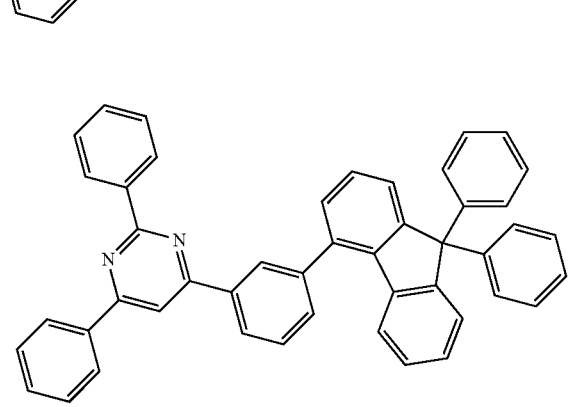
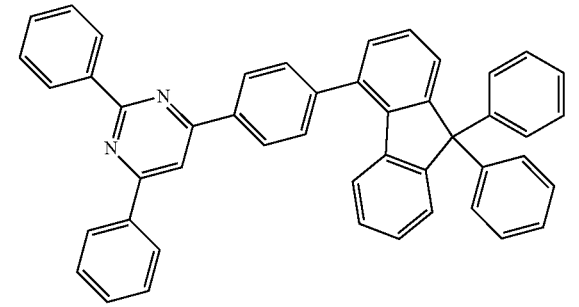
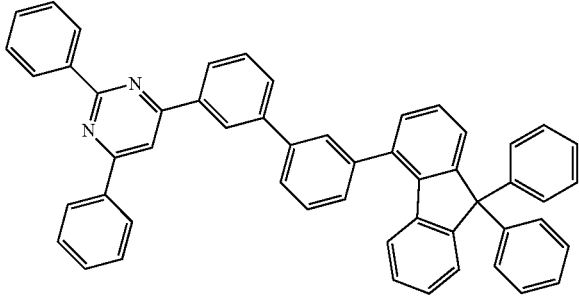

251
-continued
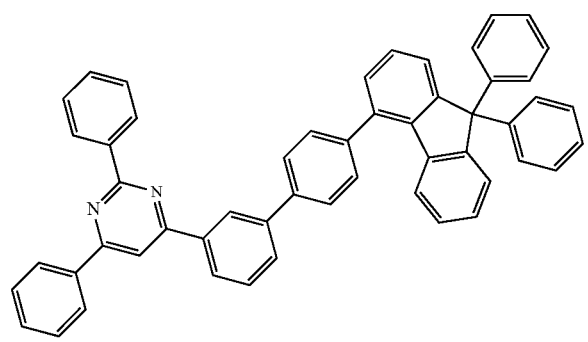
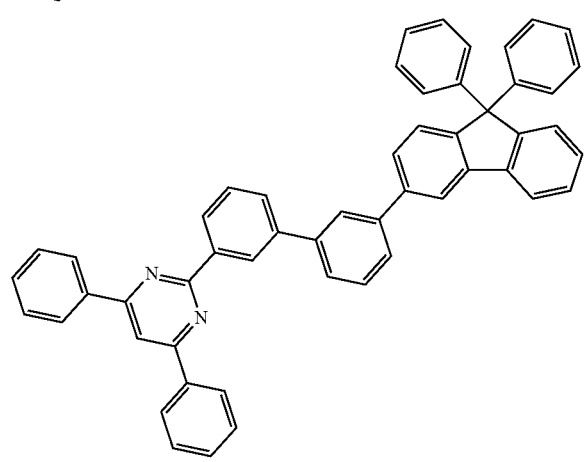
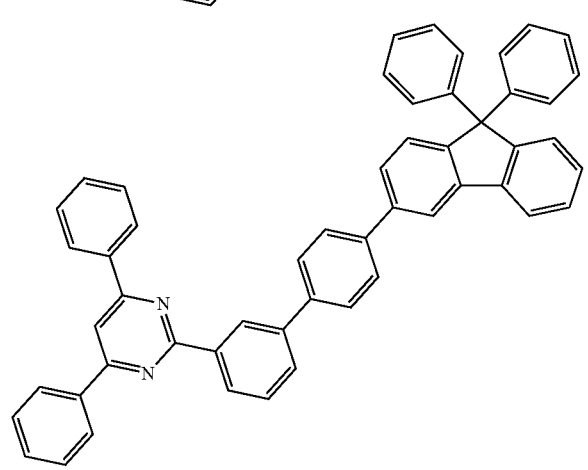
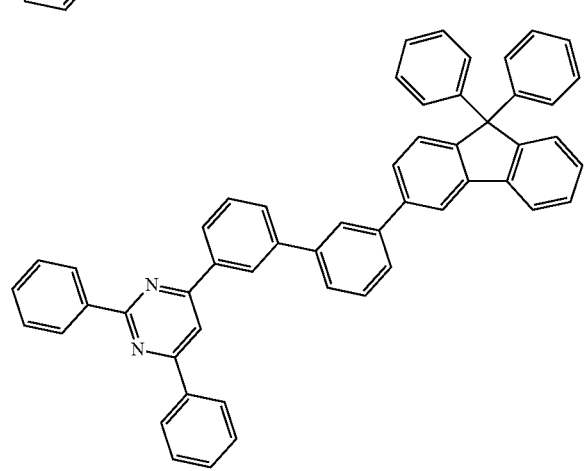
252
-continued
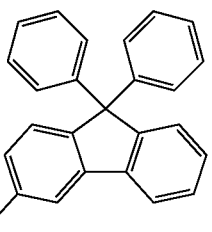
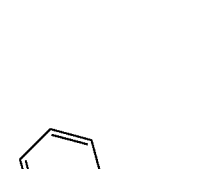
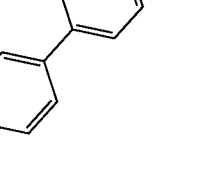
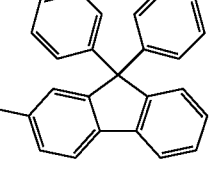
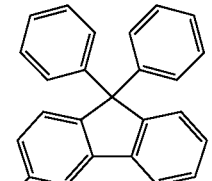

253
-continued
254
-continued
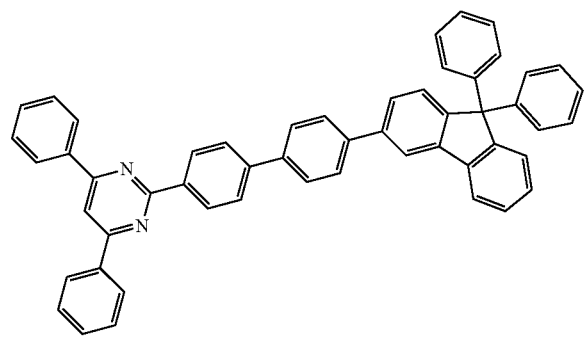
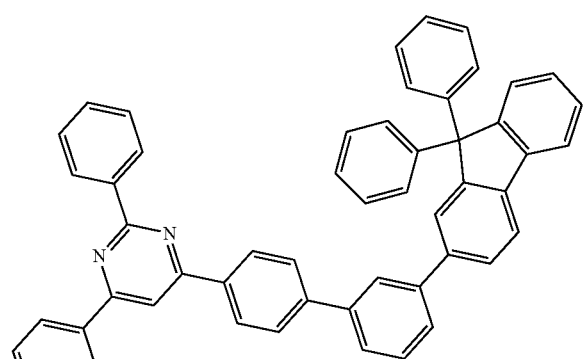
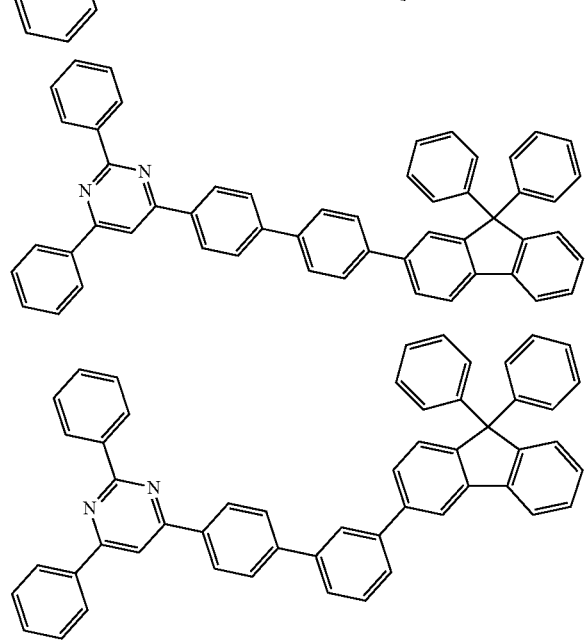
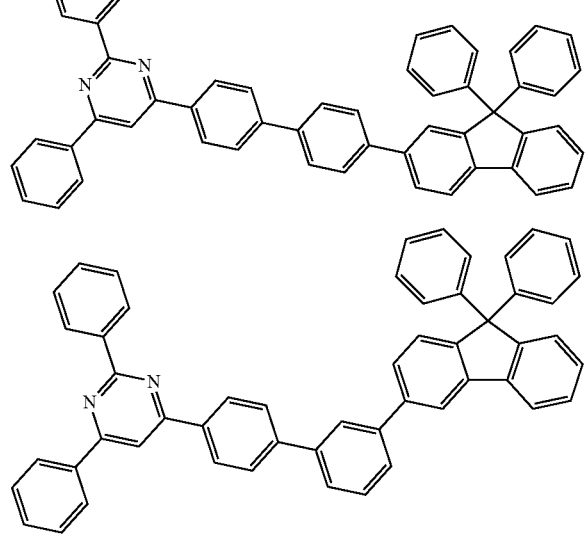
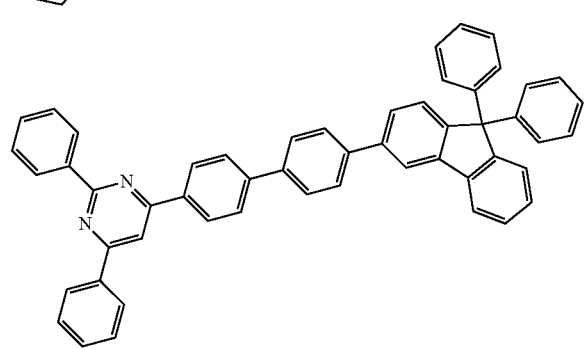
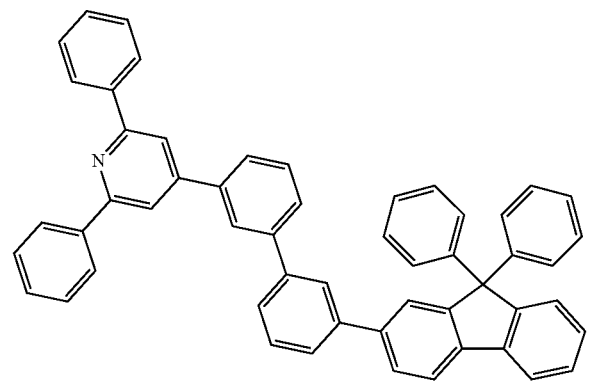
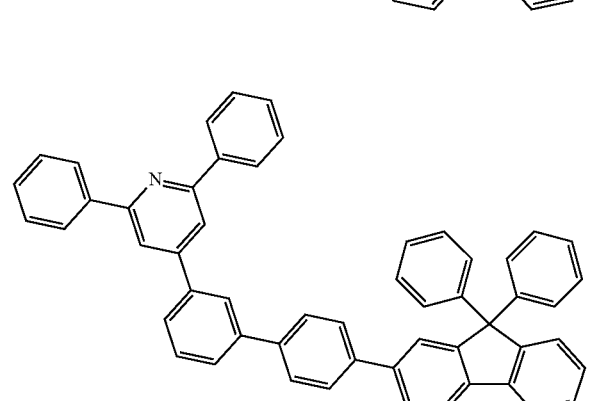
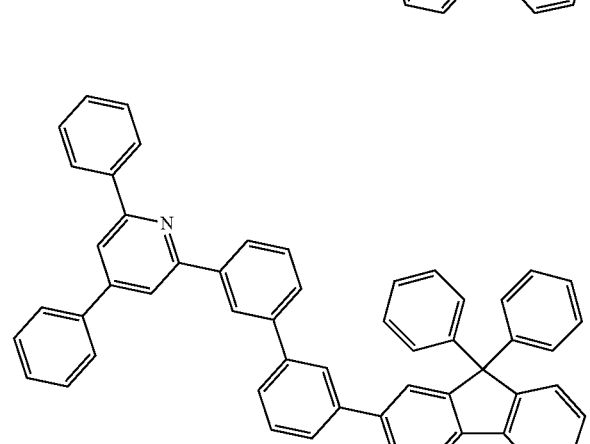
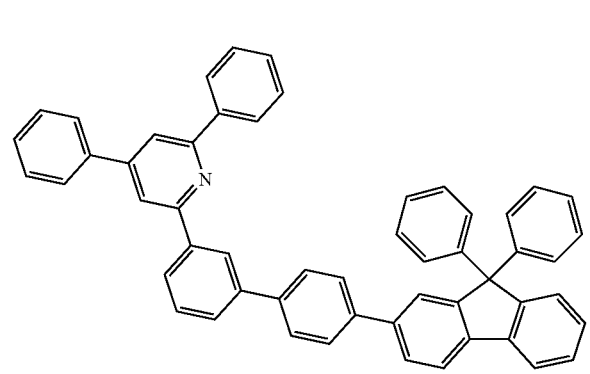

255
-continued
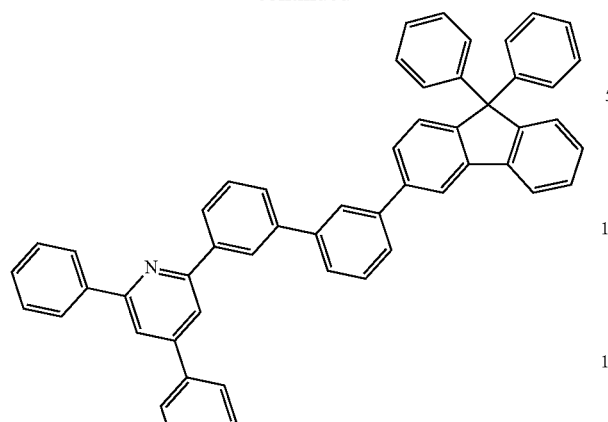
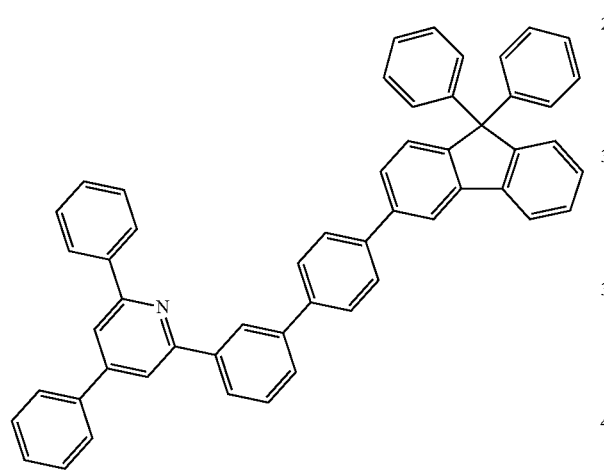
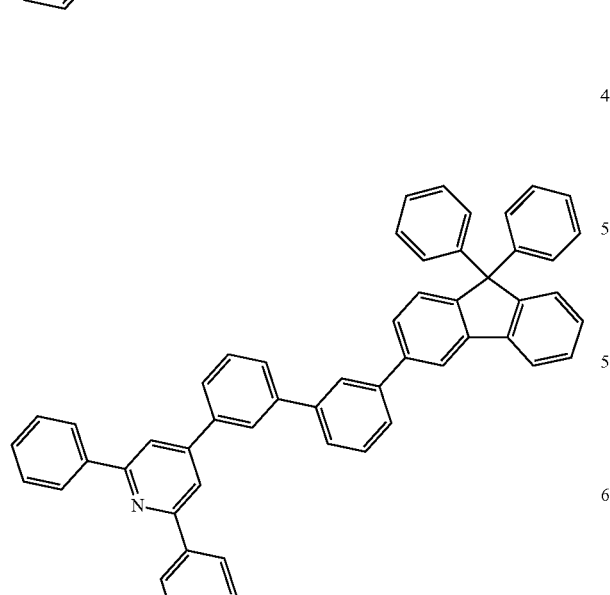
256
-continued
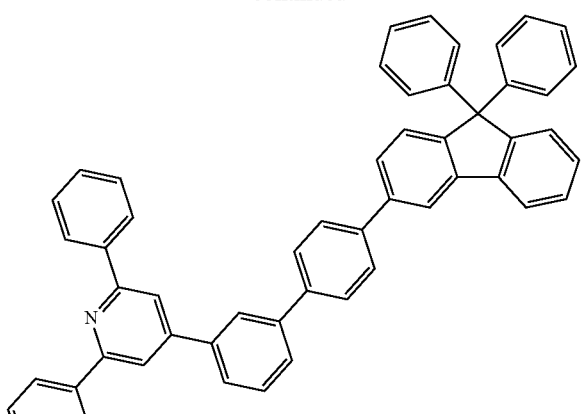
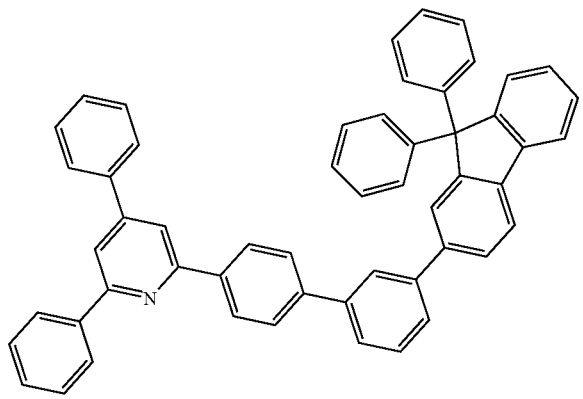
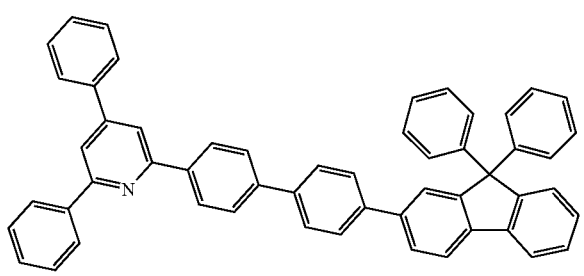
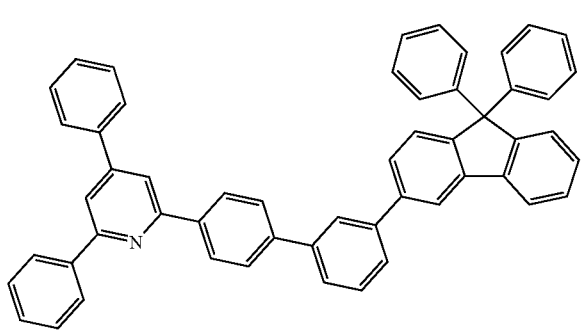

257
-continued
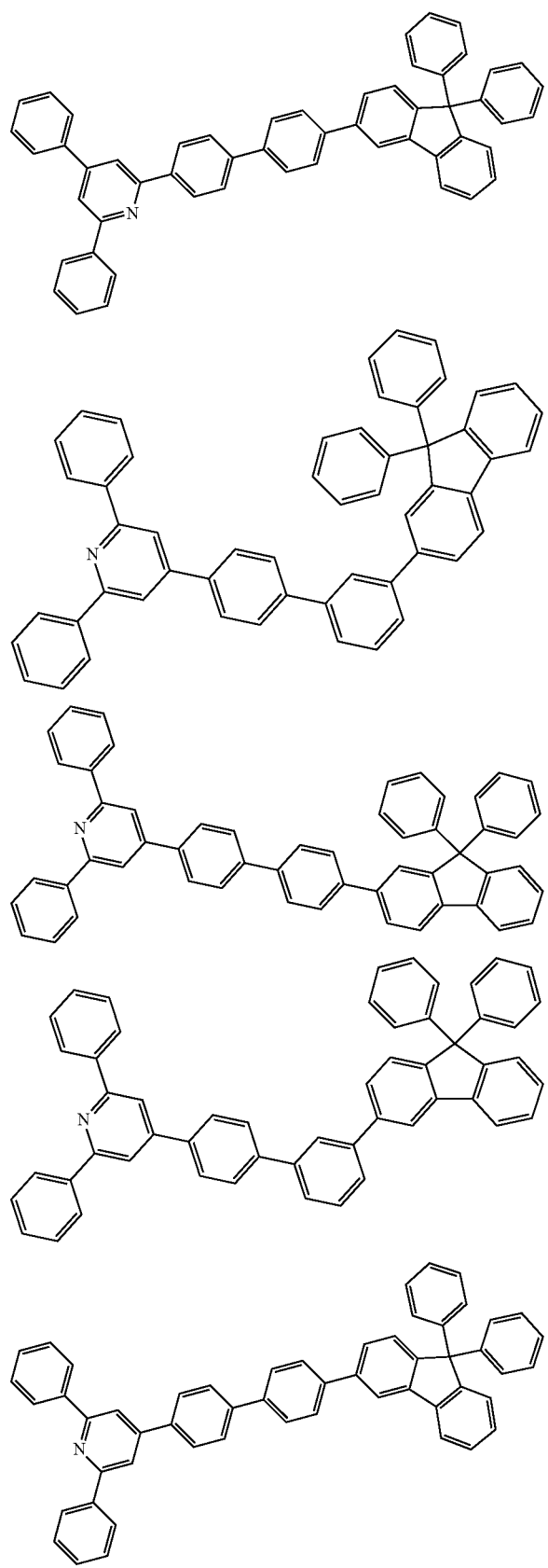
258
-continued
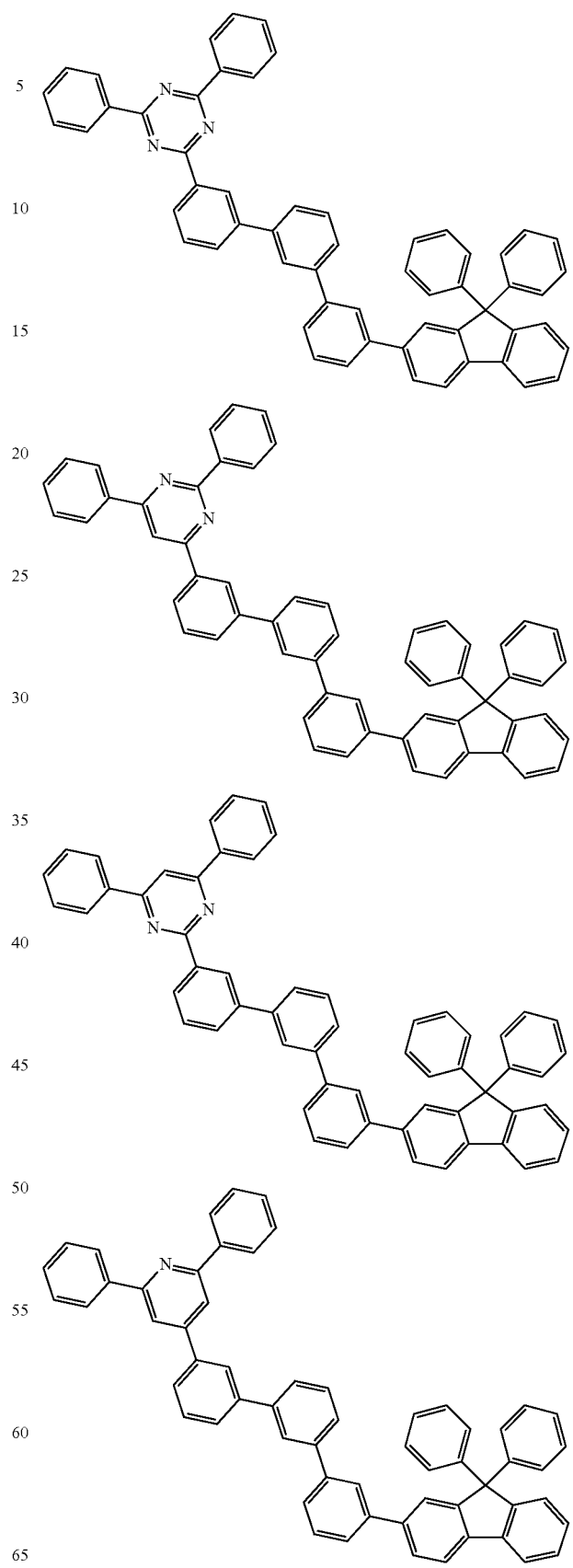

259
-continued
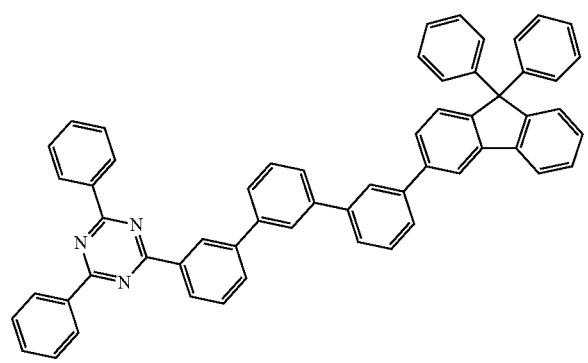
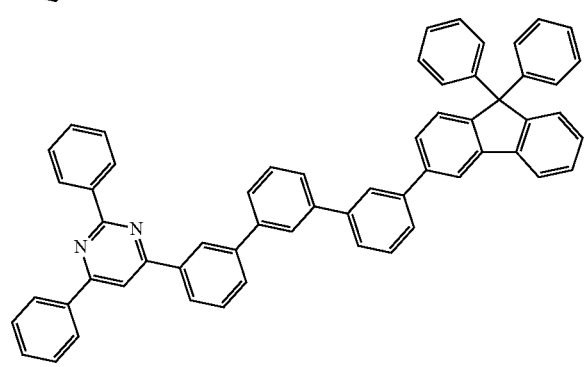
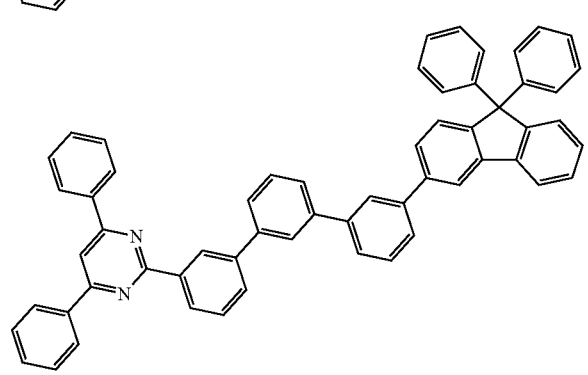
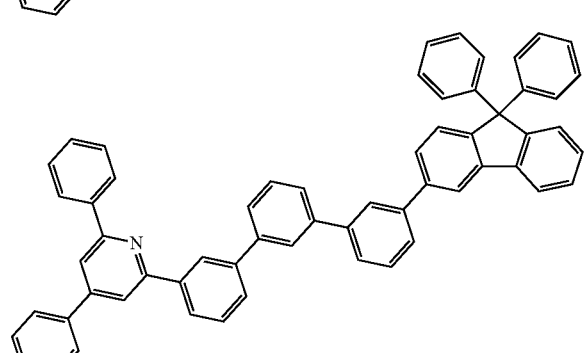
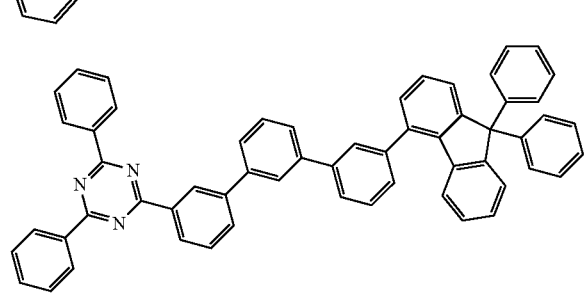
260
-continued
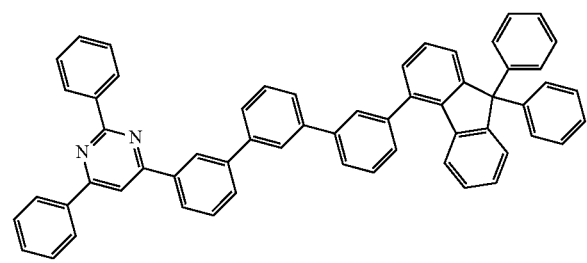
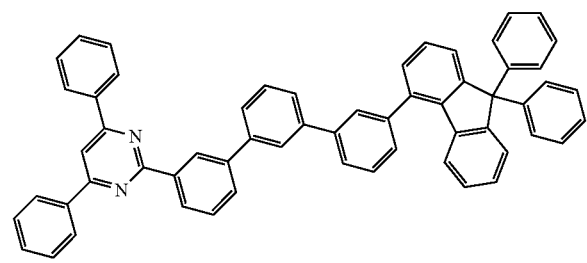
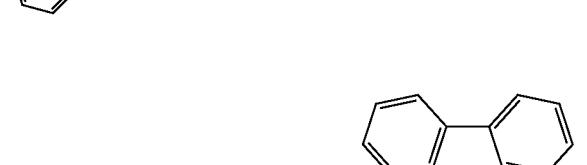
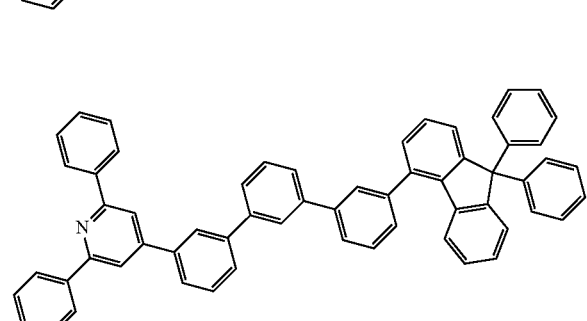
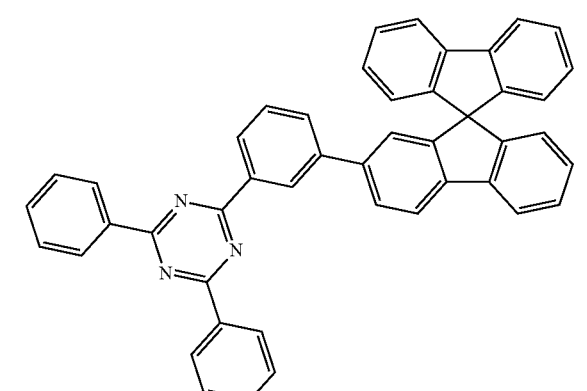
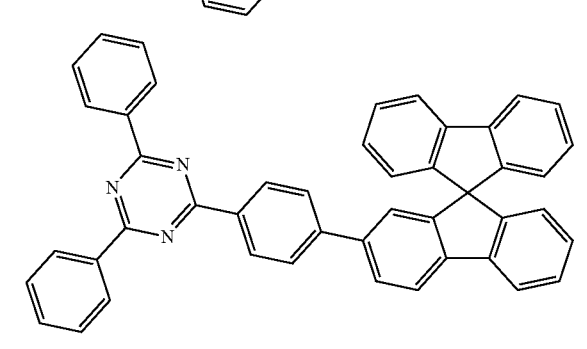

261
-continued
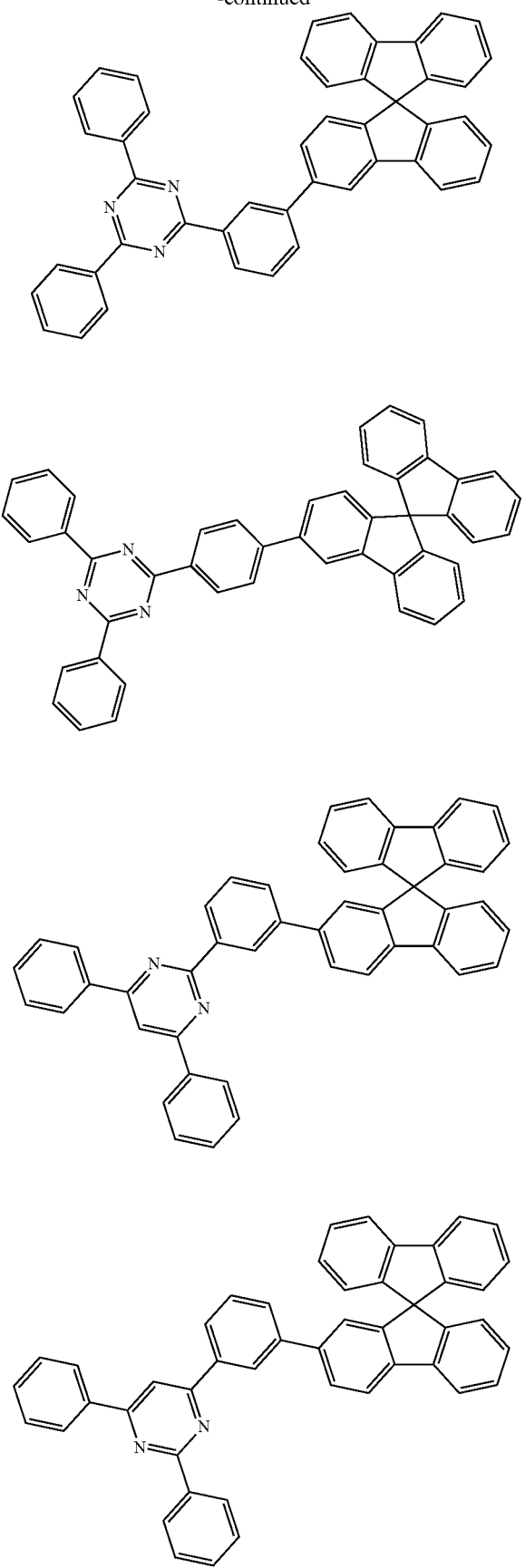
262
-continued
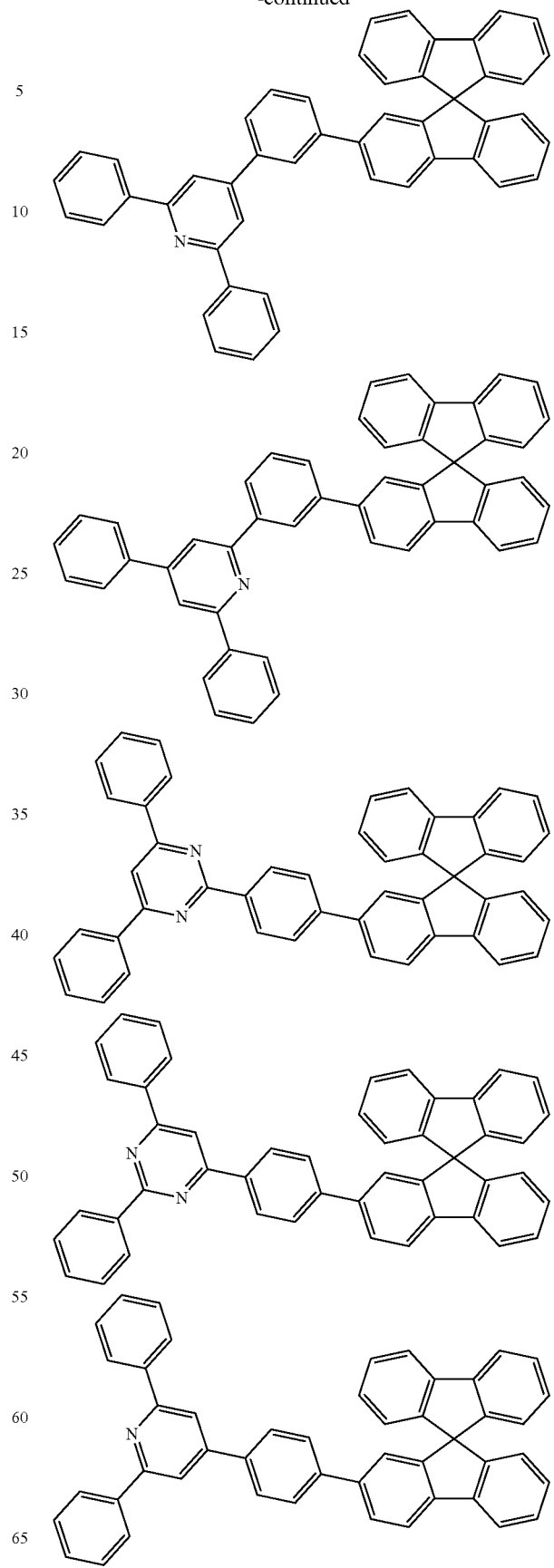

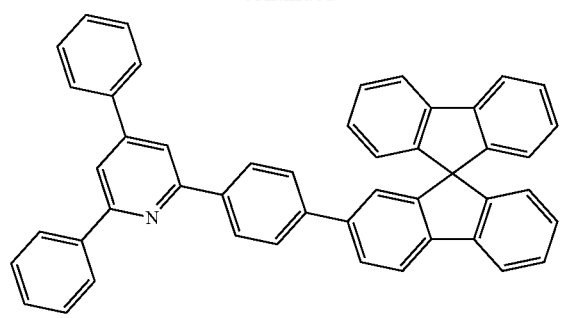
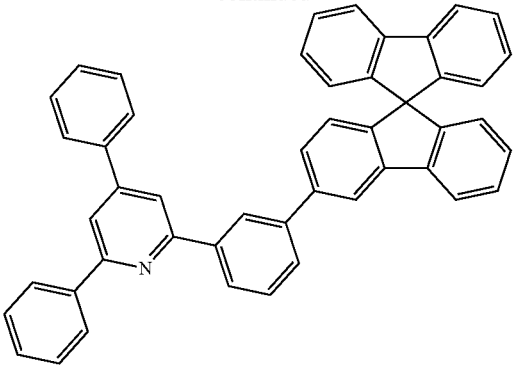
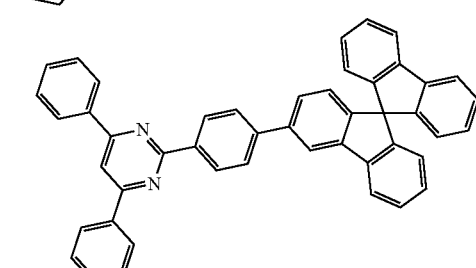
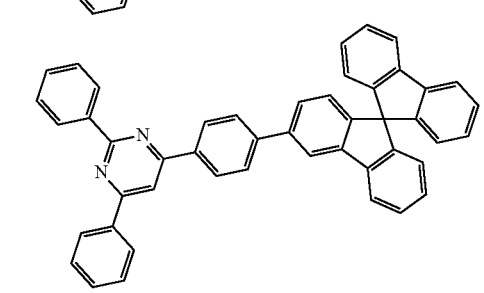
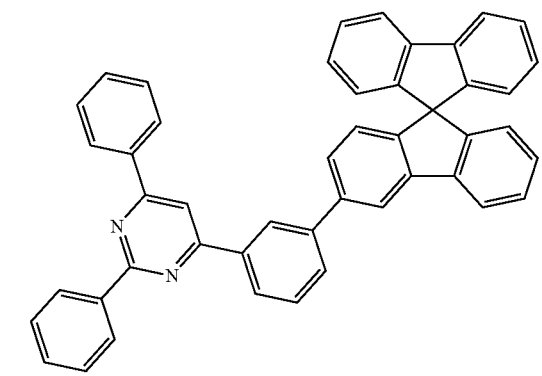
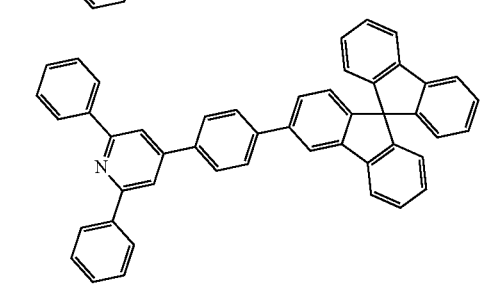
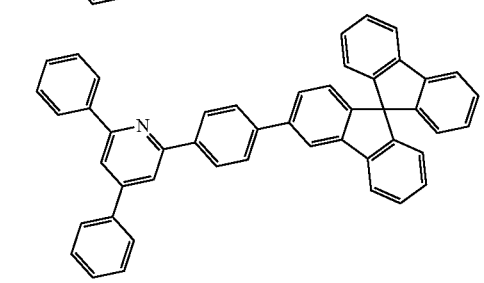
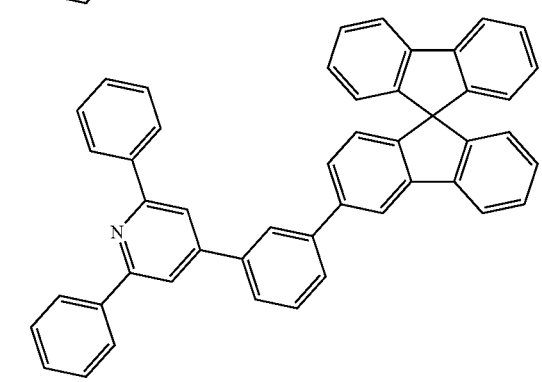
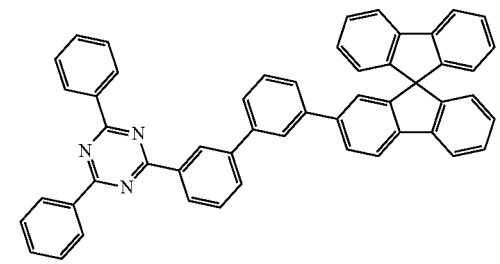

265
-continued
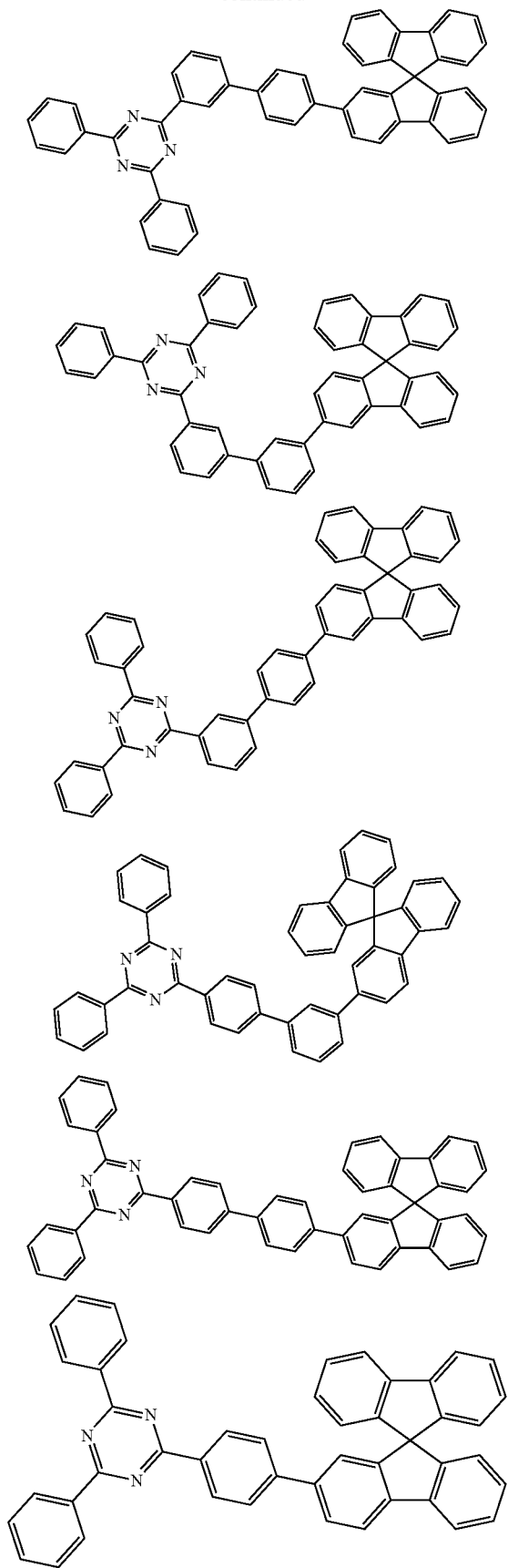
266
-continued
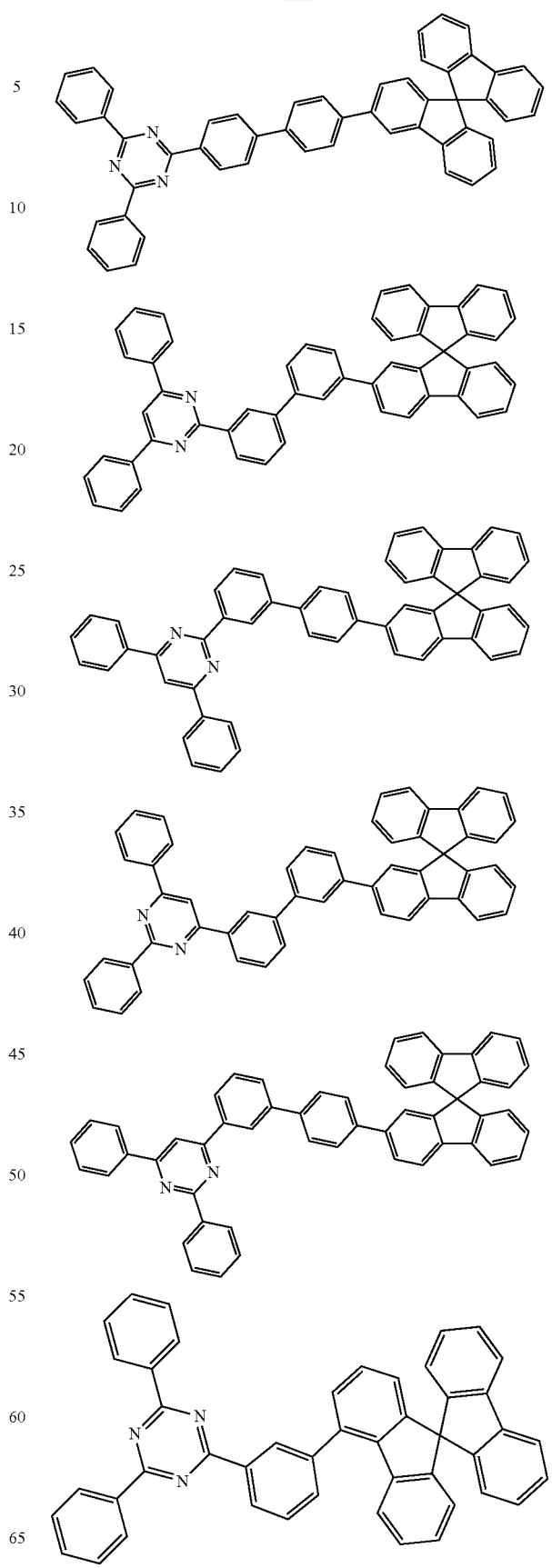

267
-continued
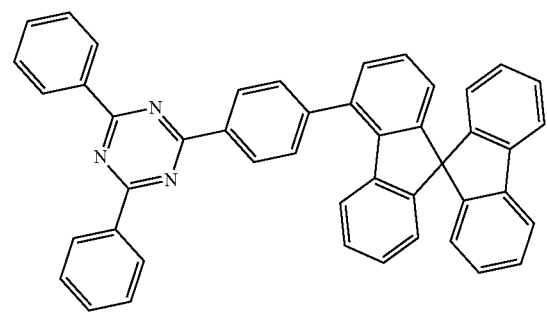
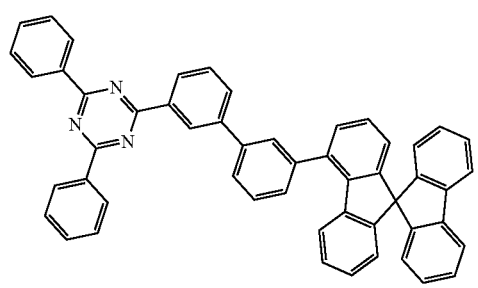
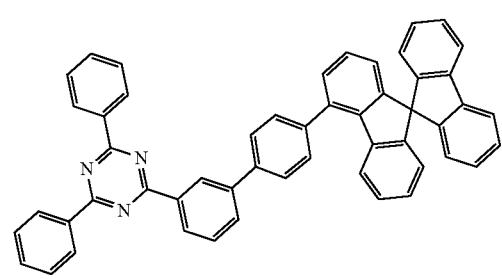
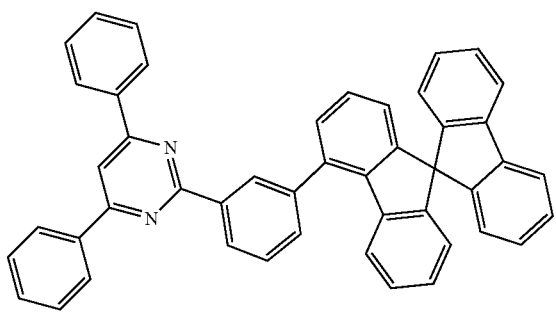
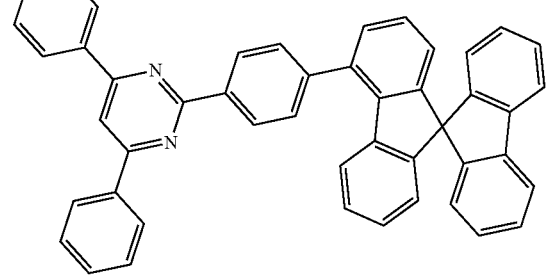
268
-continued
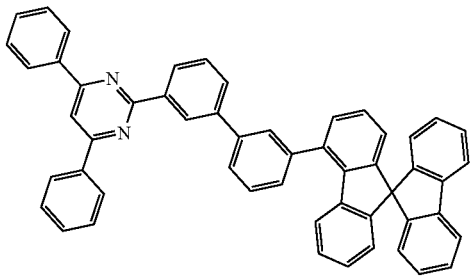
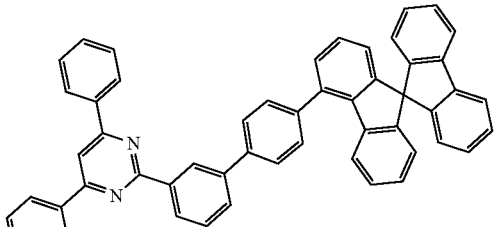
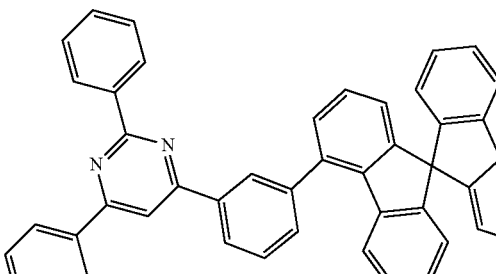
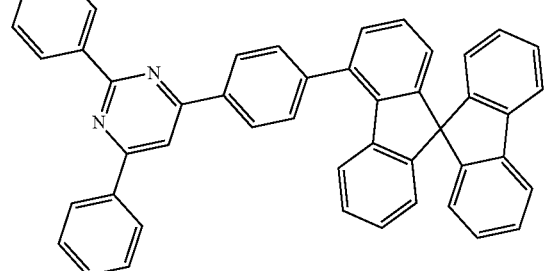
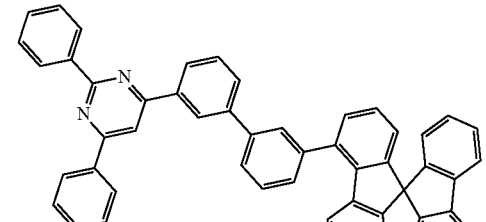
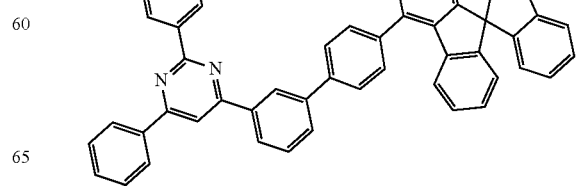

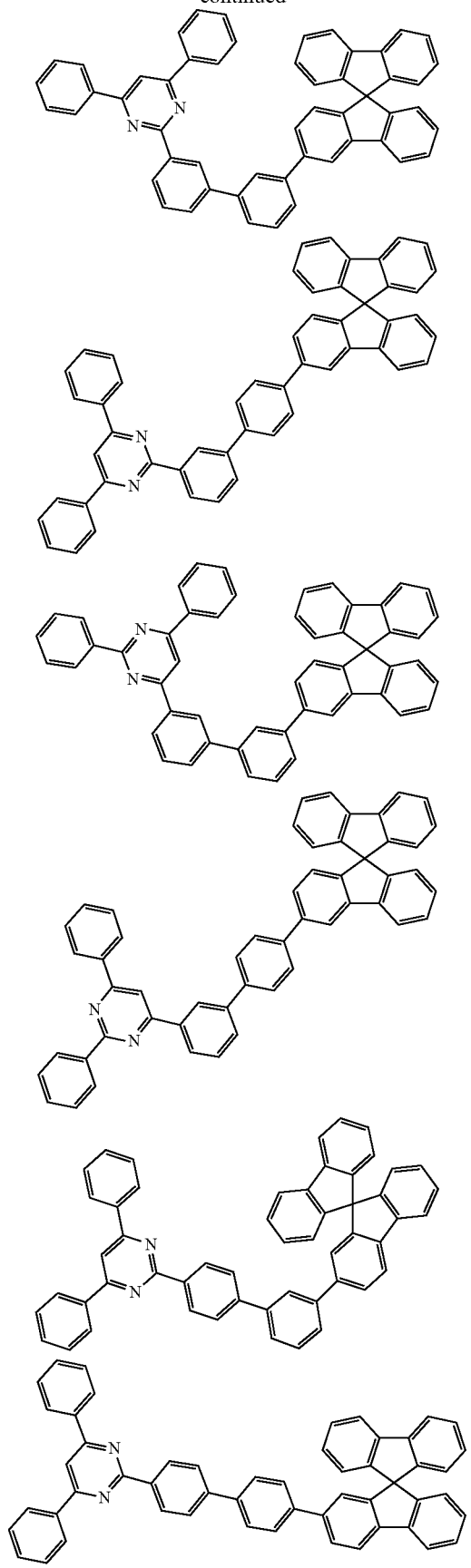
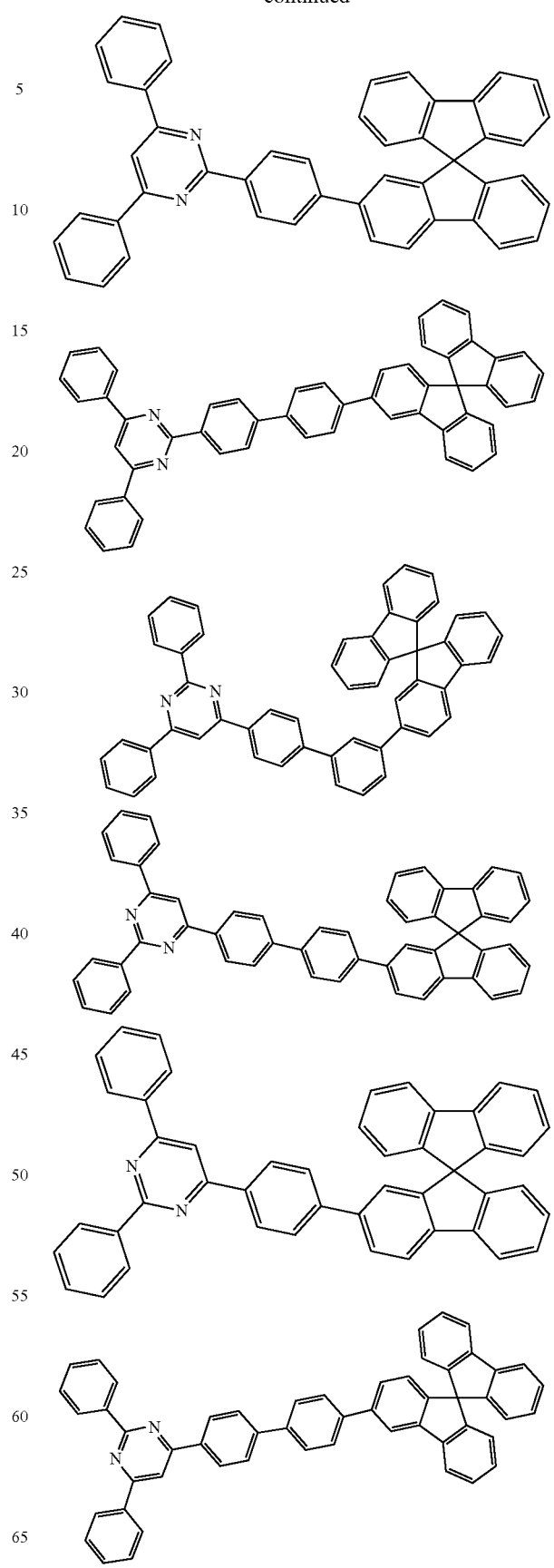

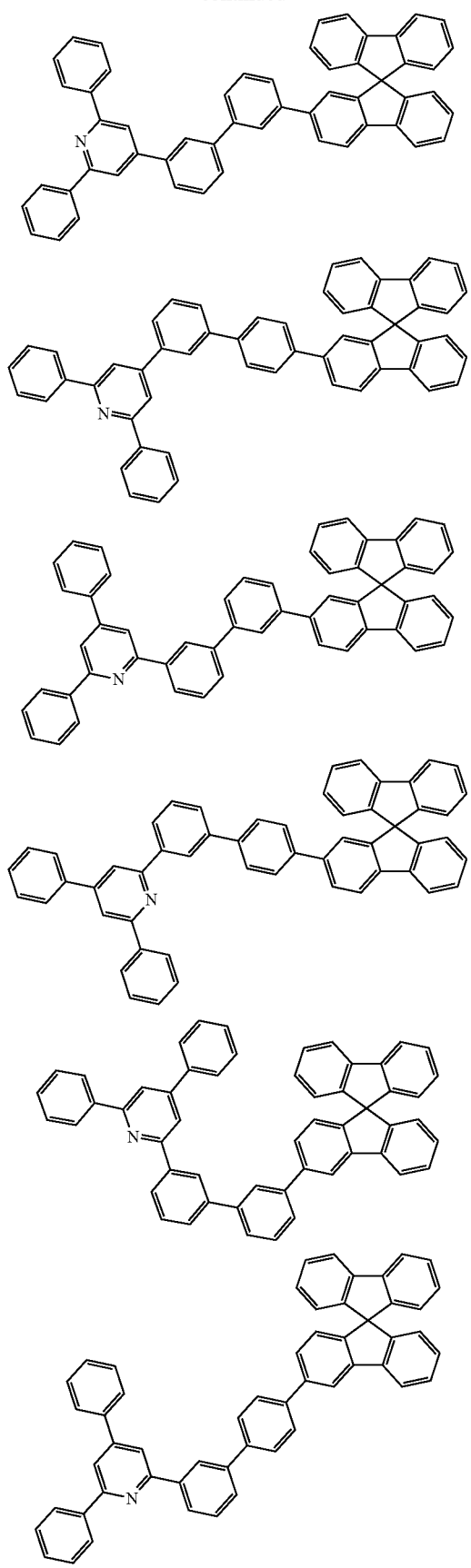
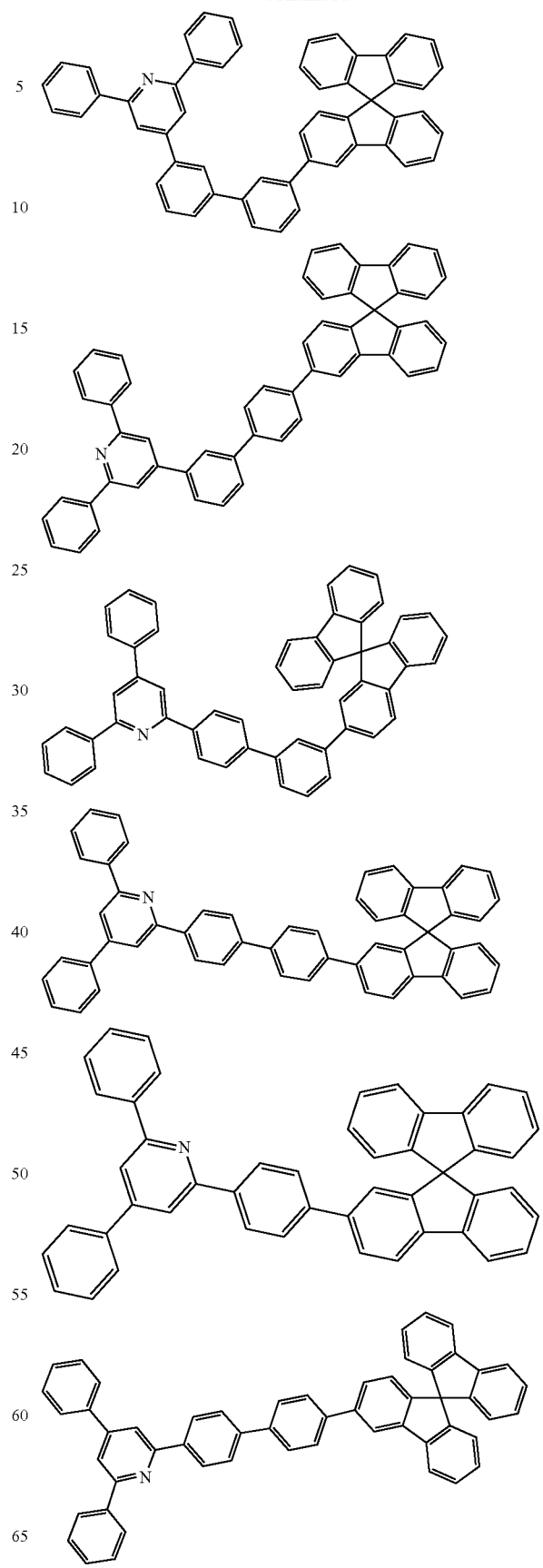

273
-continued
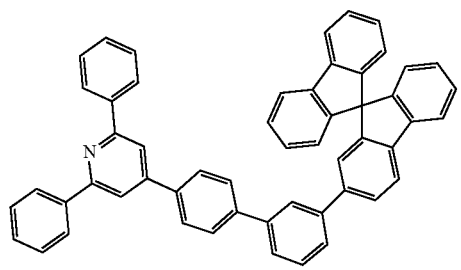
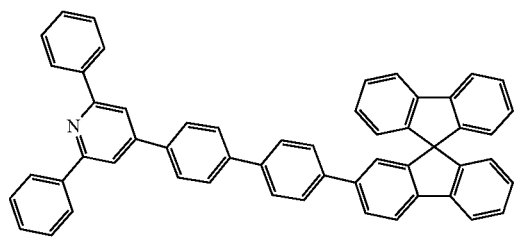
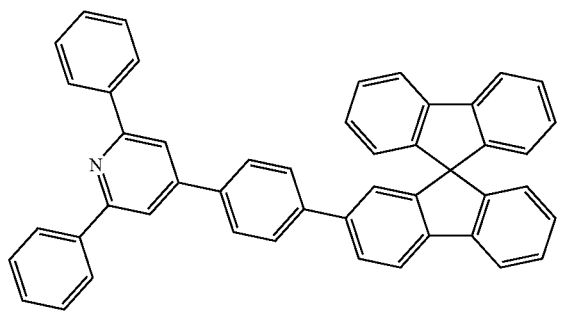
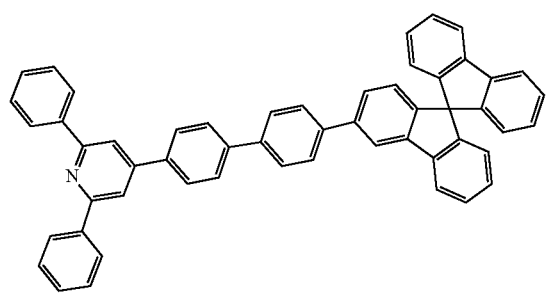
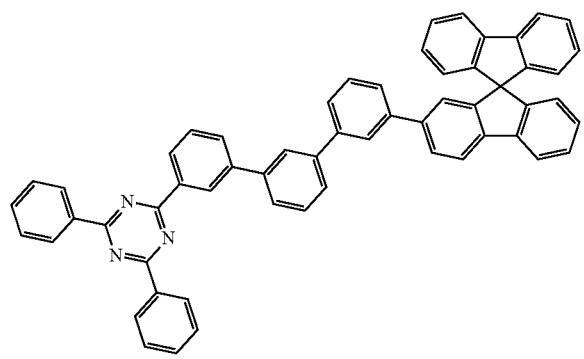
274
-continued
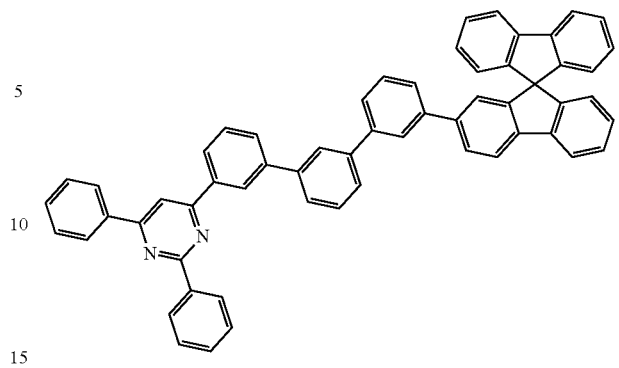
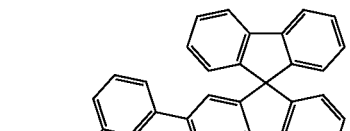
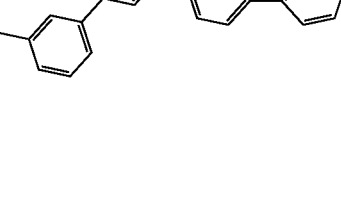
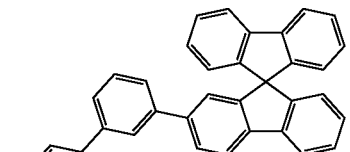
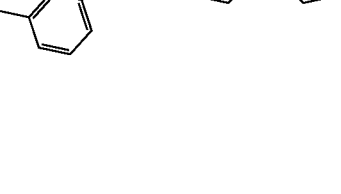

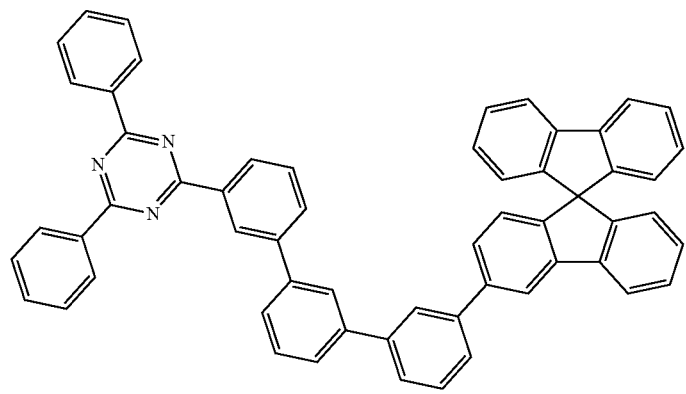
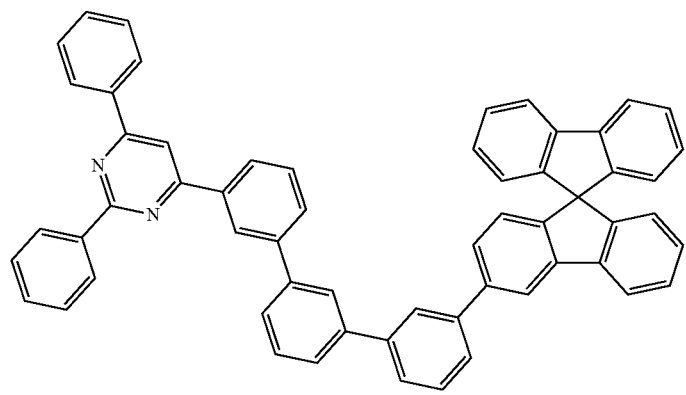
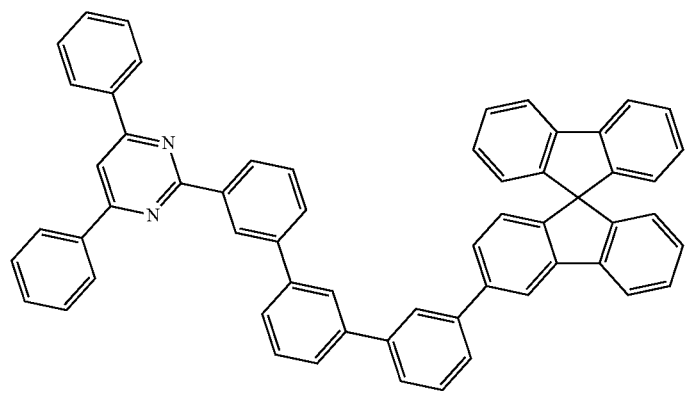
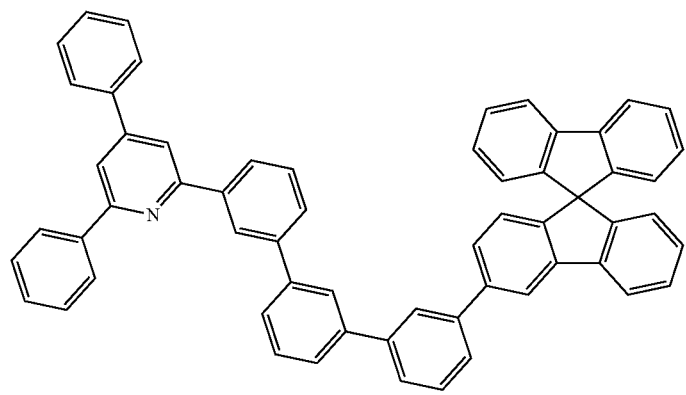

-continued
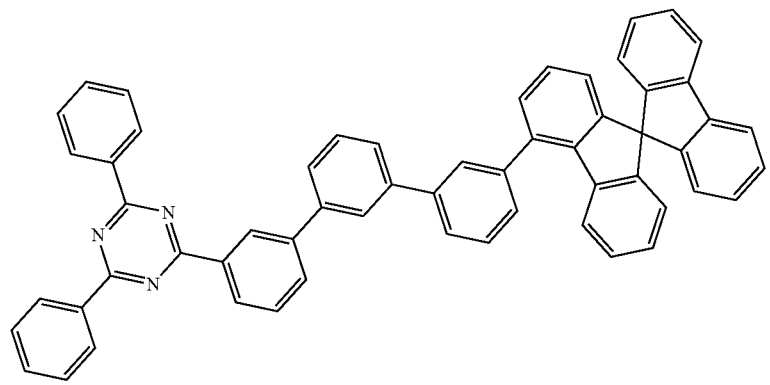
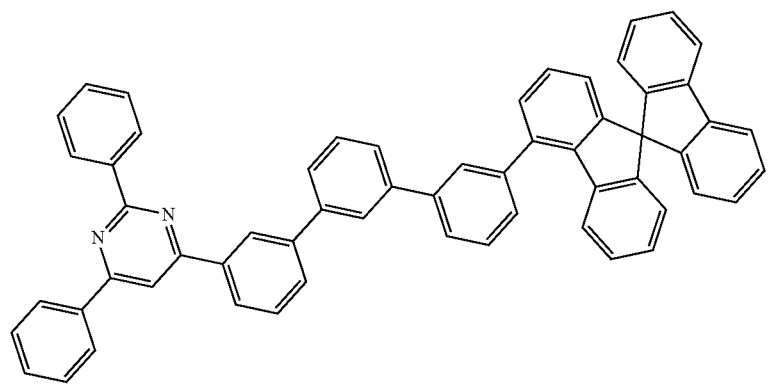
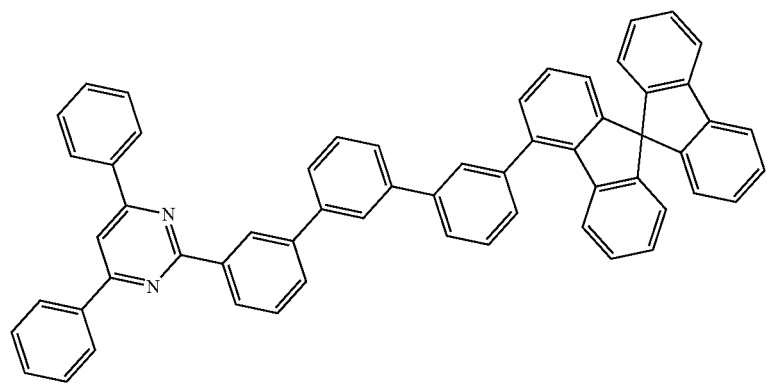
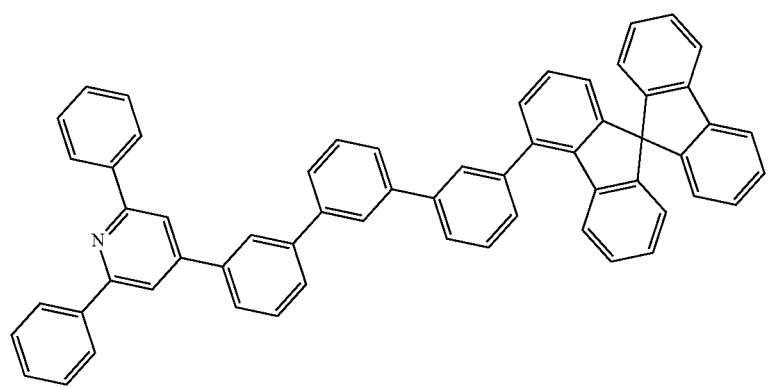

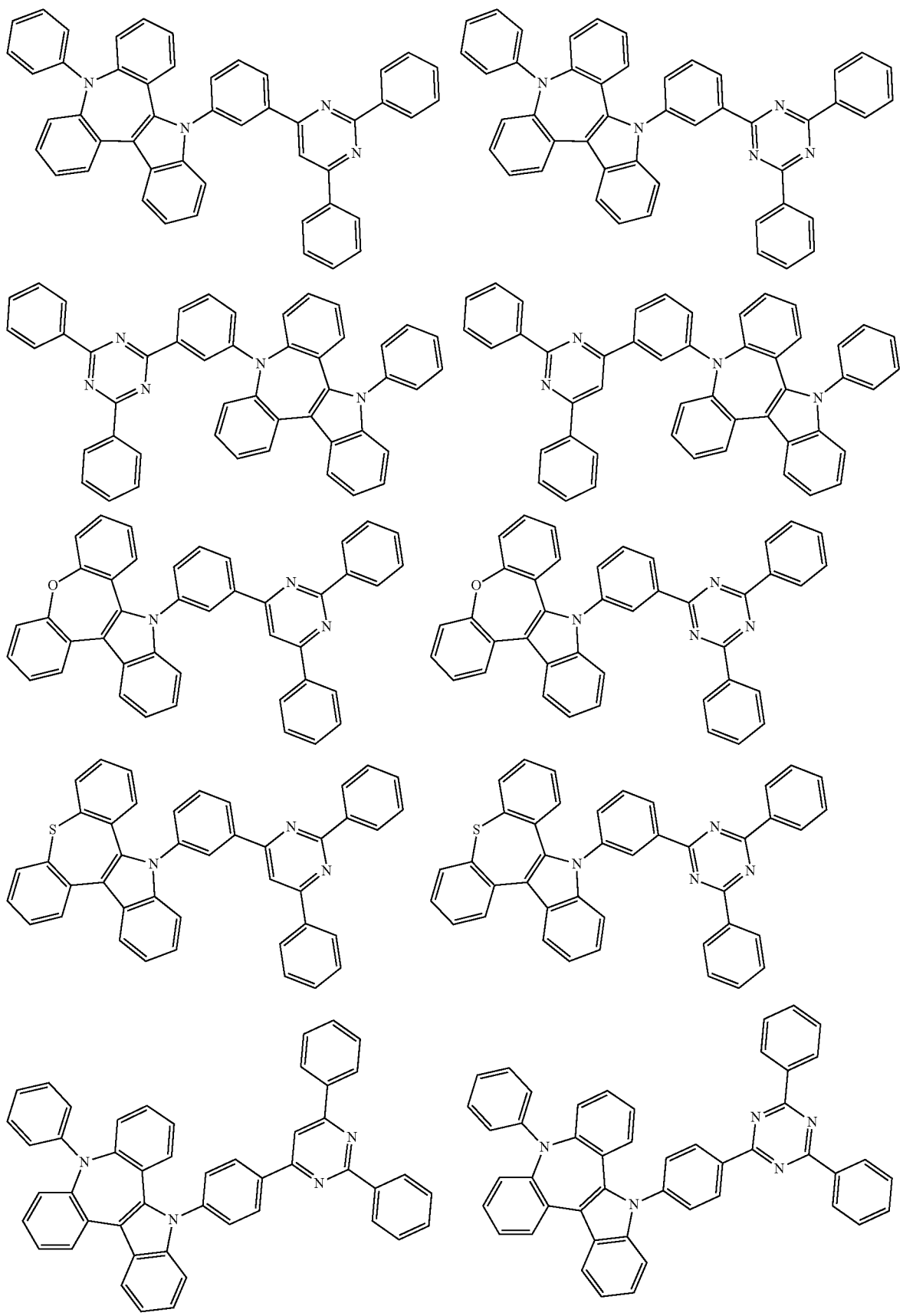

281
-continued
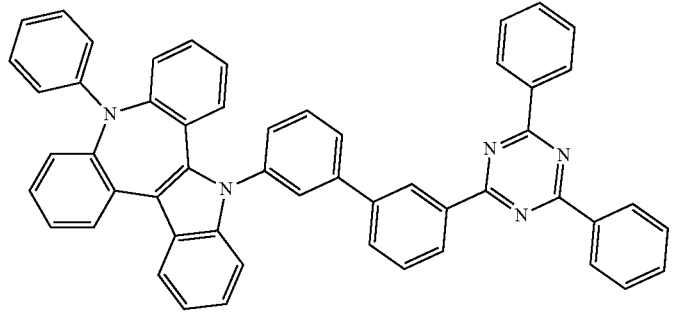
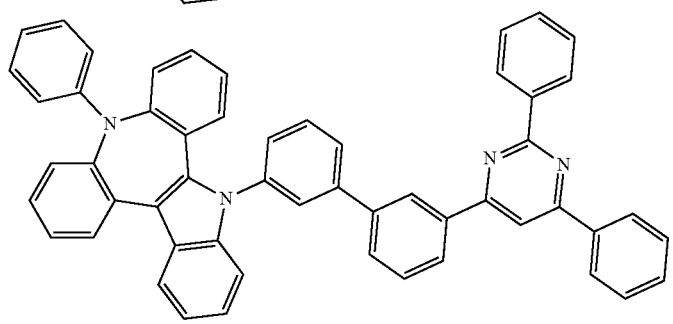
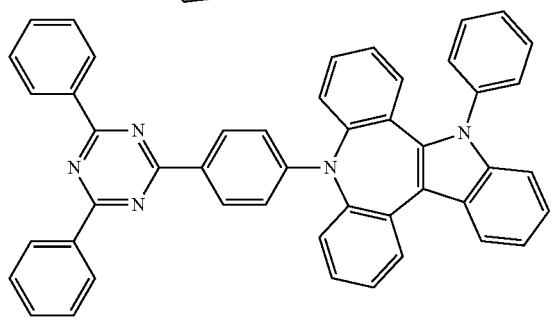
282
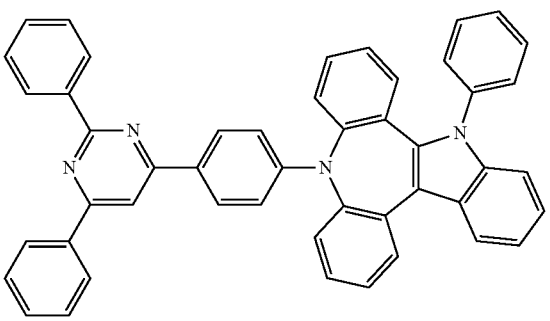
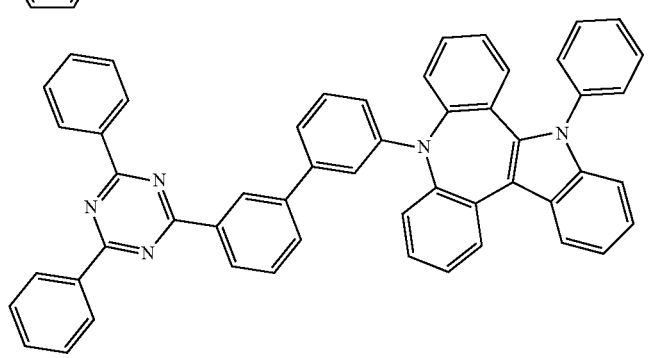
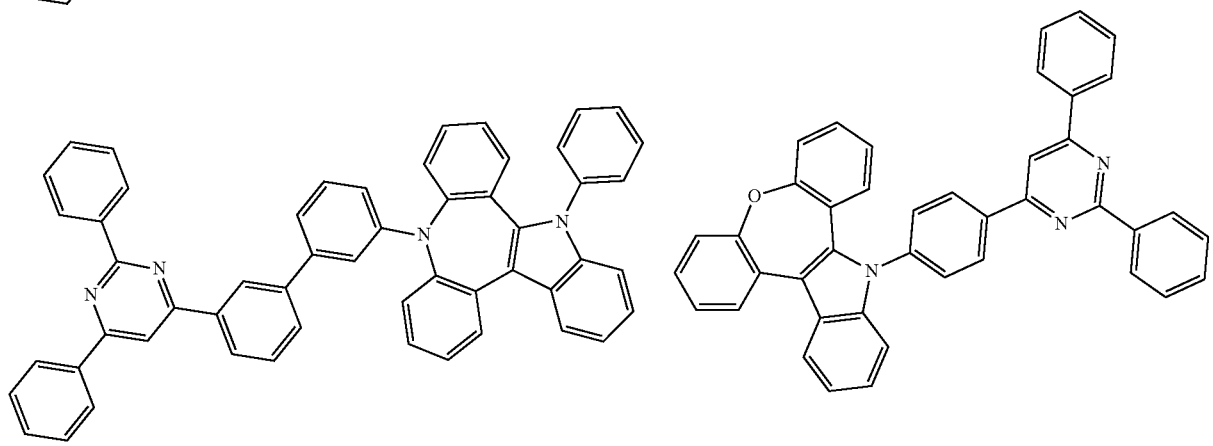

283 284
-continued
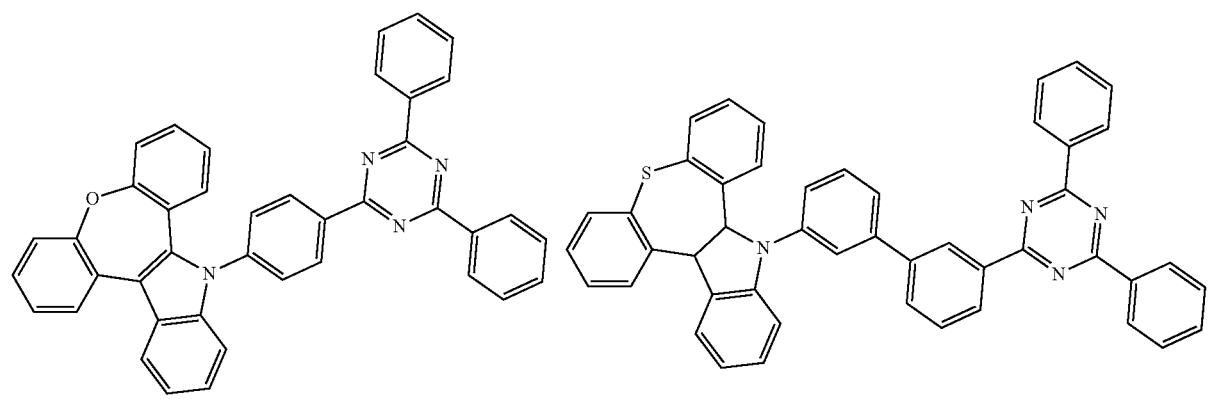
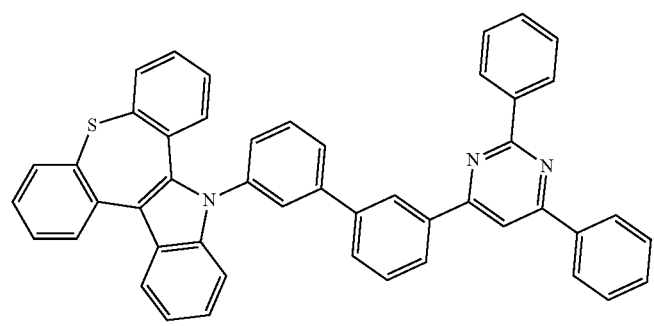
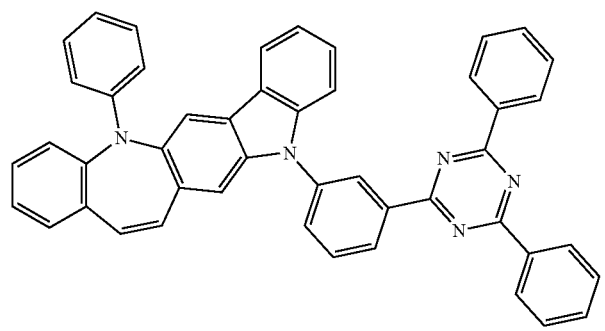
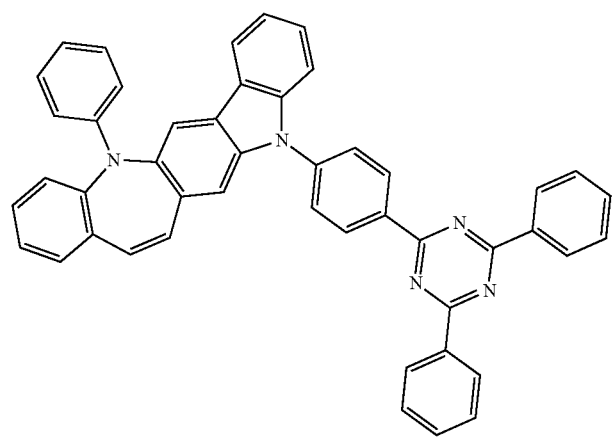

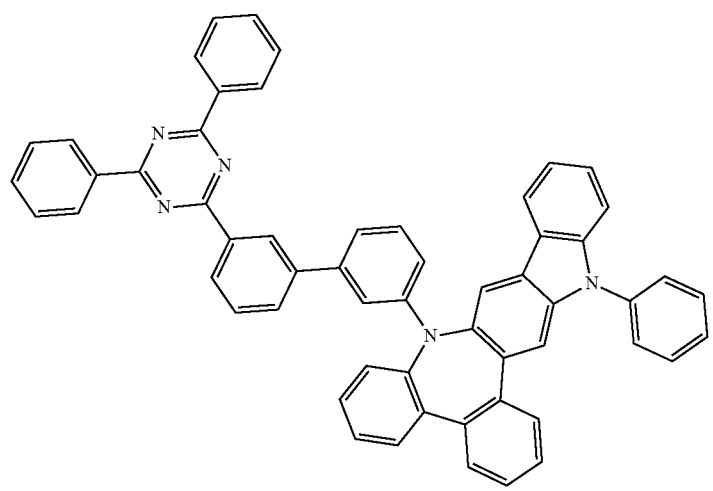
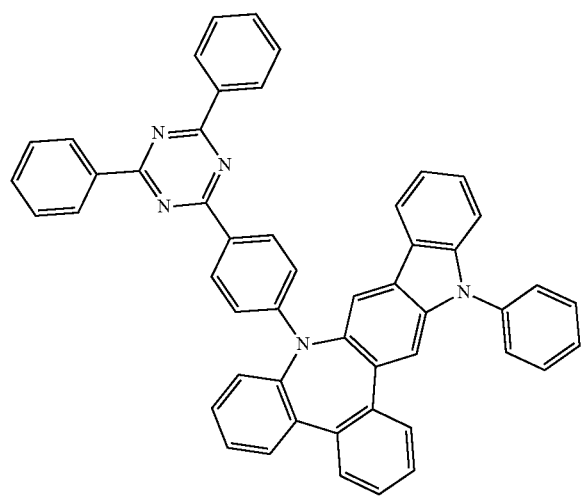
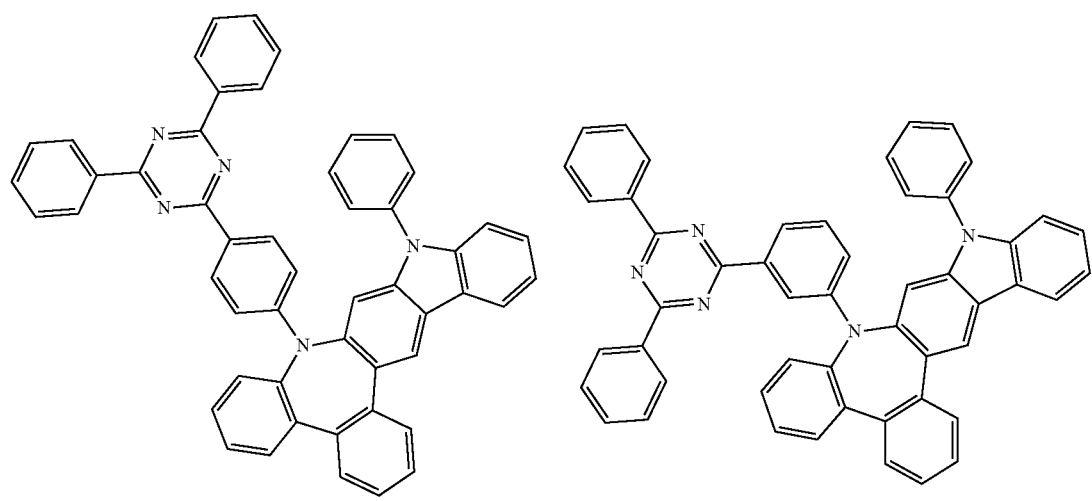

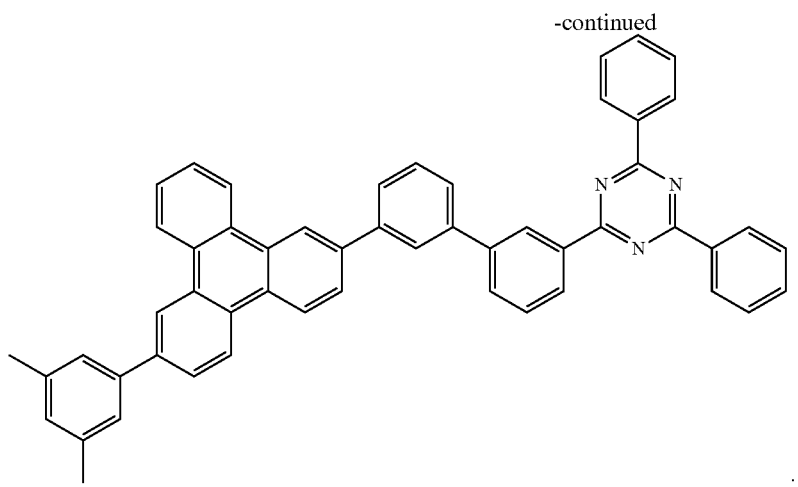
8. The organic light emitting device of claim 1, wherein the compound of Chemical Formula 2 is selected from among the following compounds:
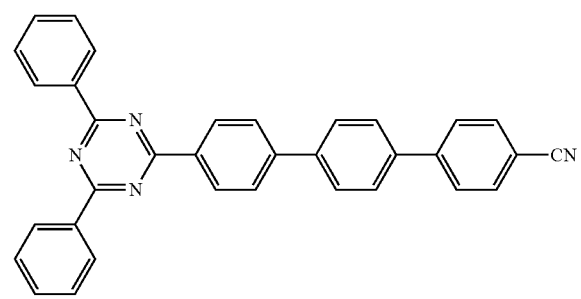
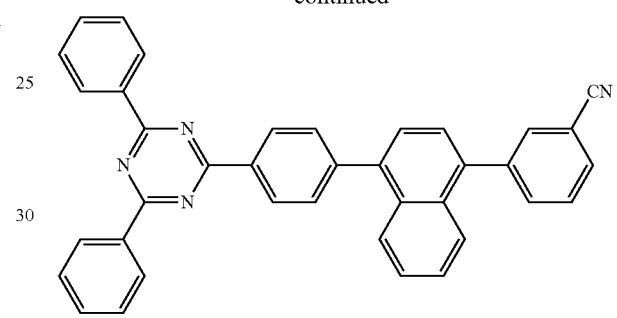
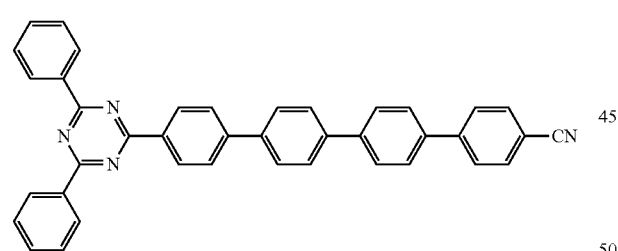
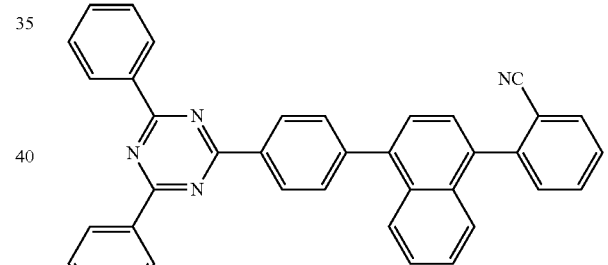
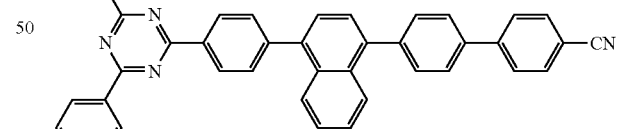
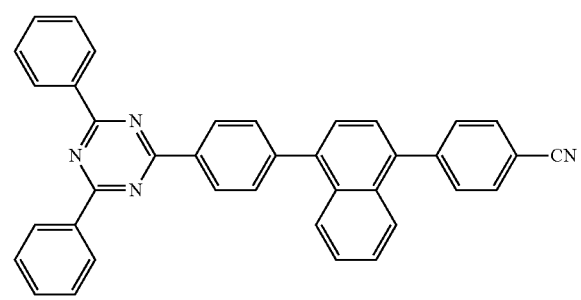
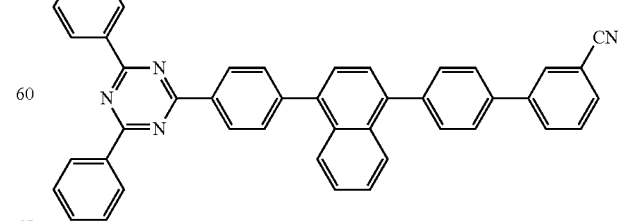

289
-continued
290
-continued
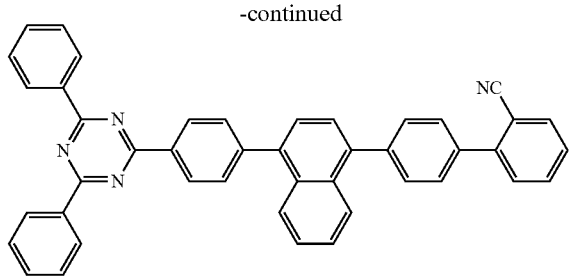
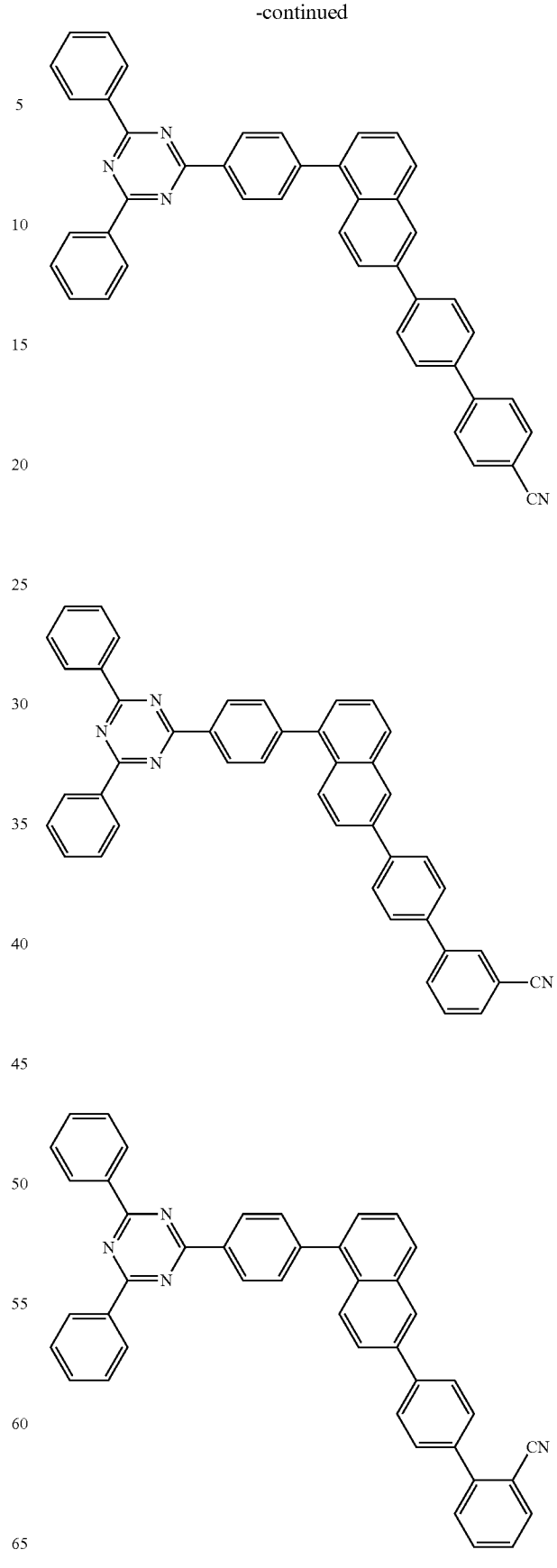

291
-continued
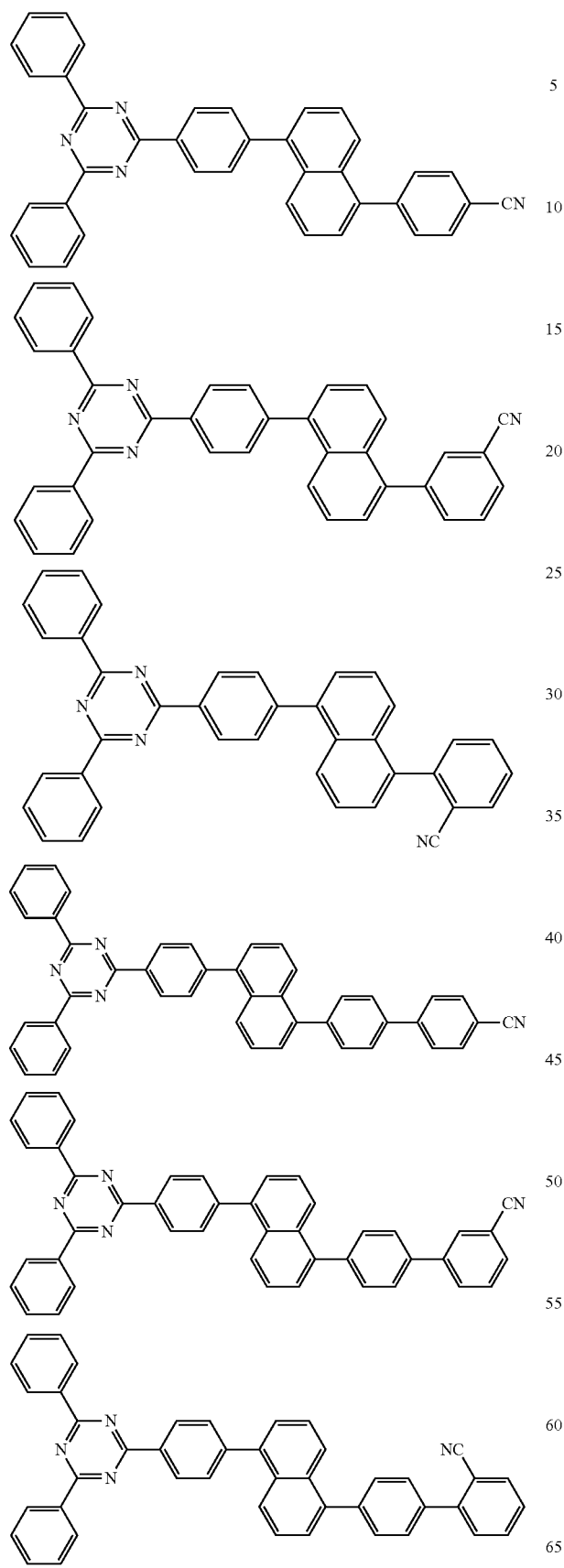
292
-continued
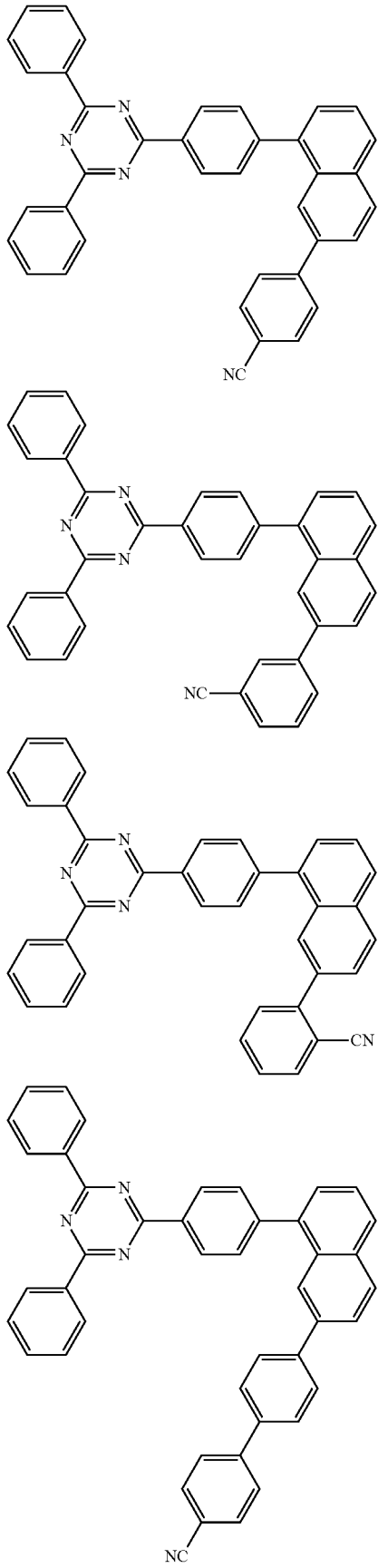

293
-continued
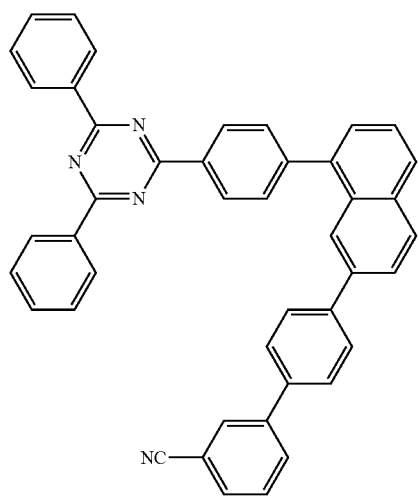
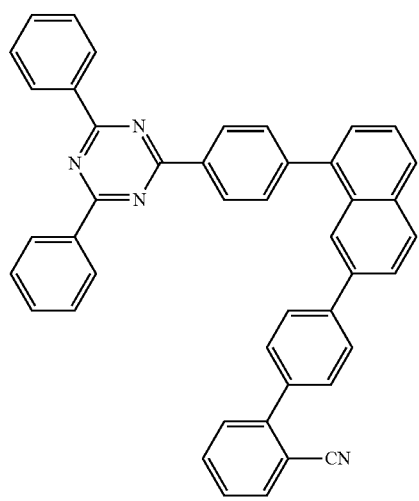
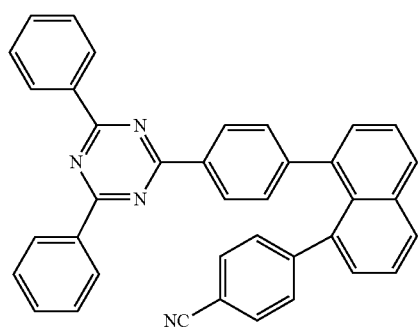
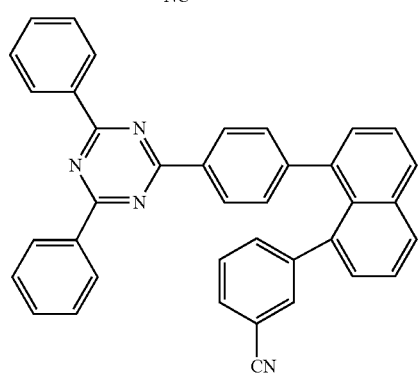
294
-continued
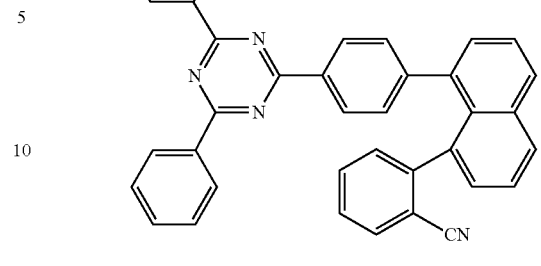
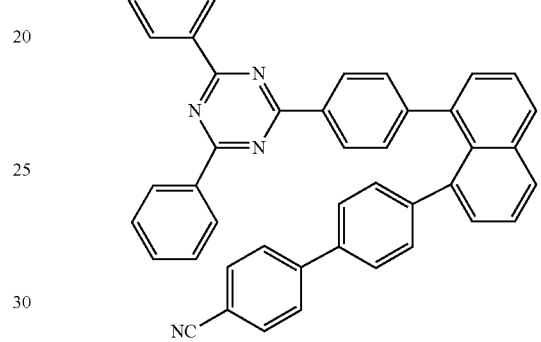
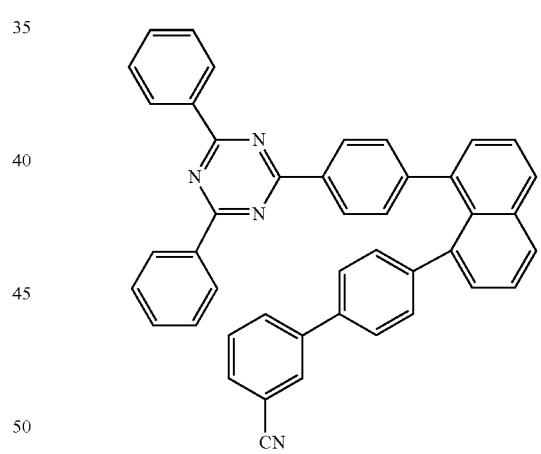
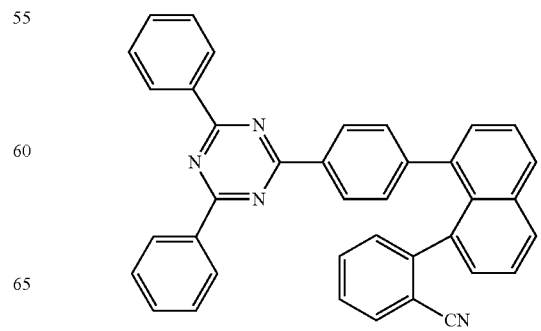

-continued
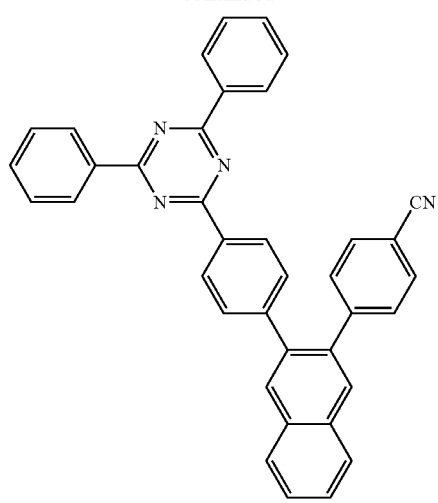
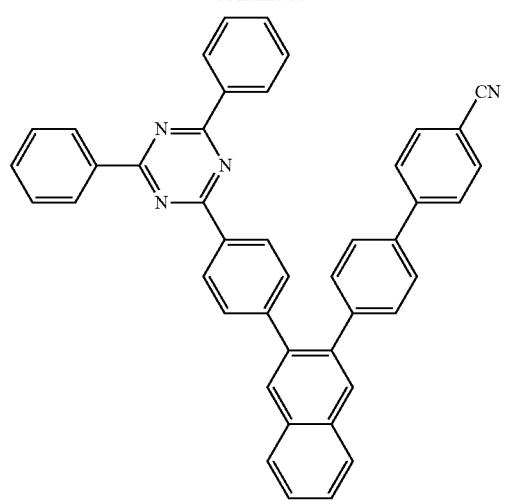
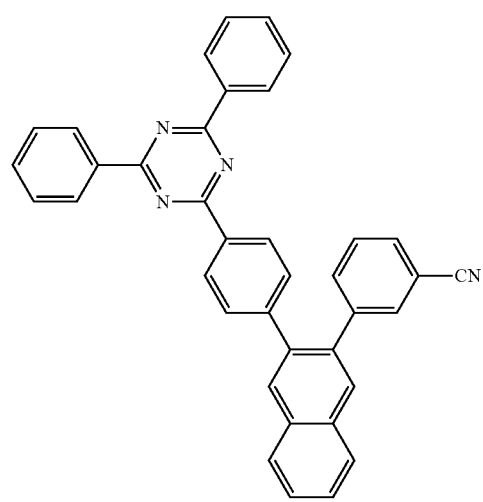
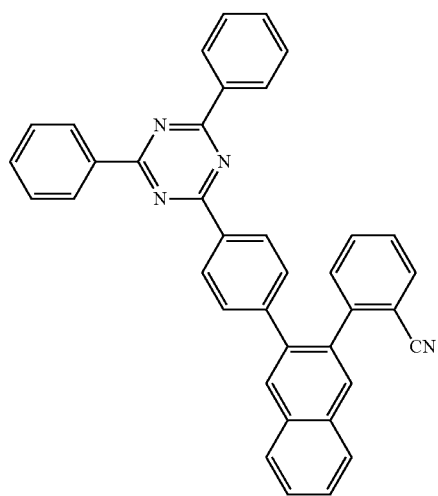
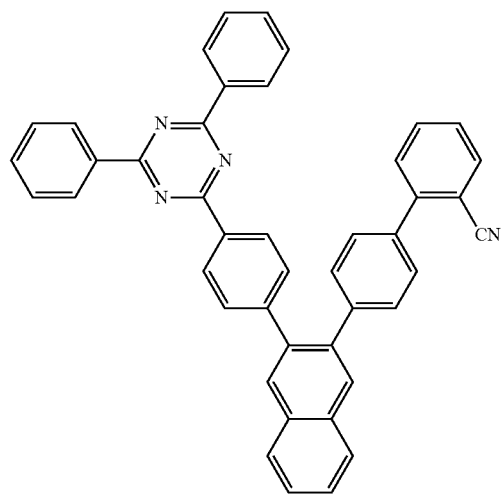

-continued
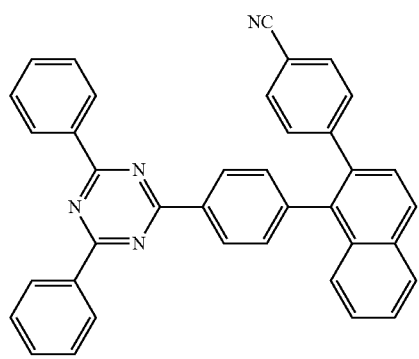
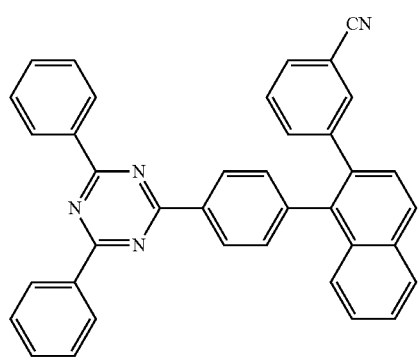
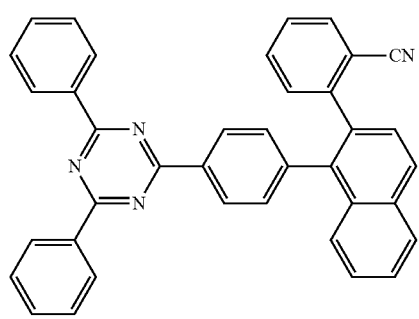
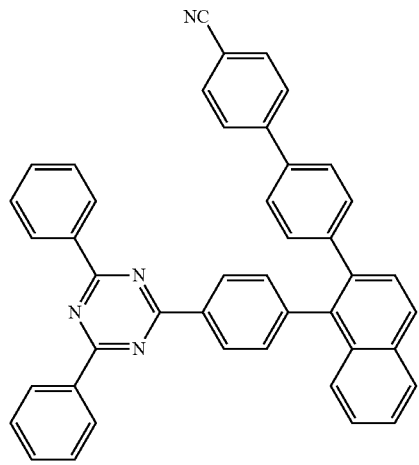
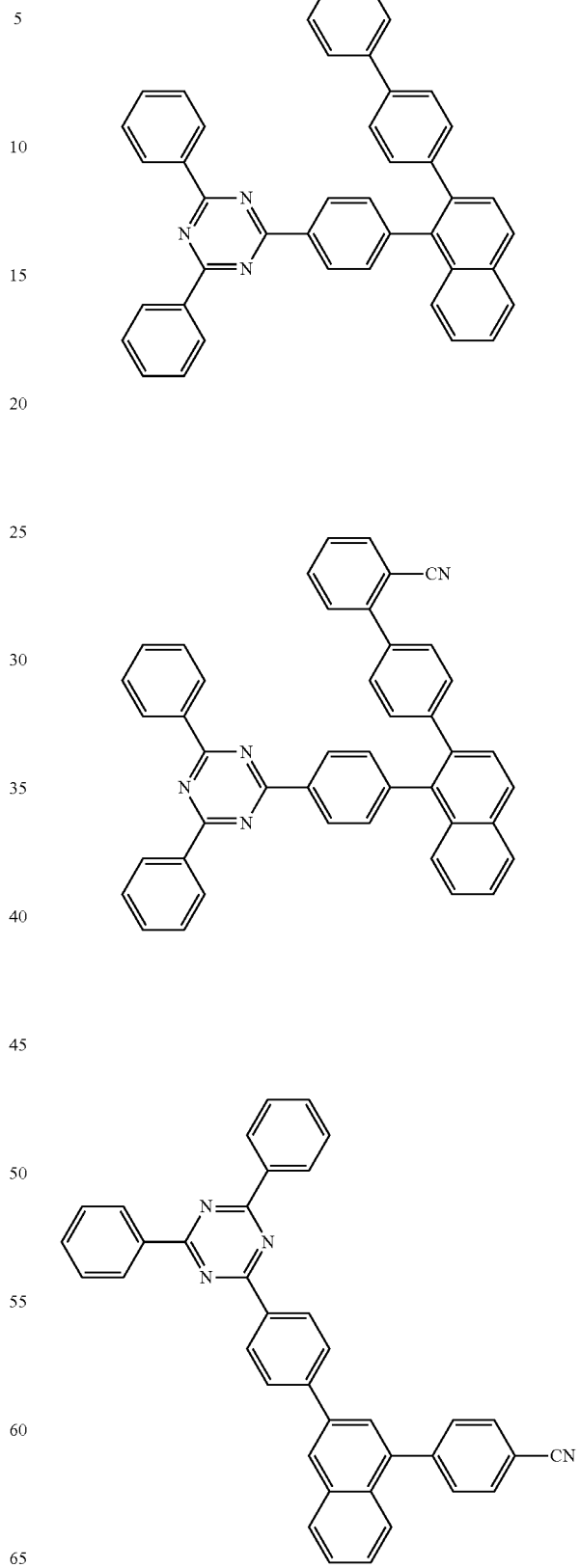

299
-continued
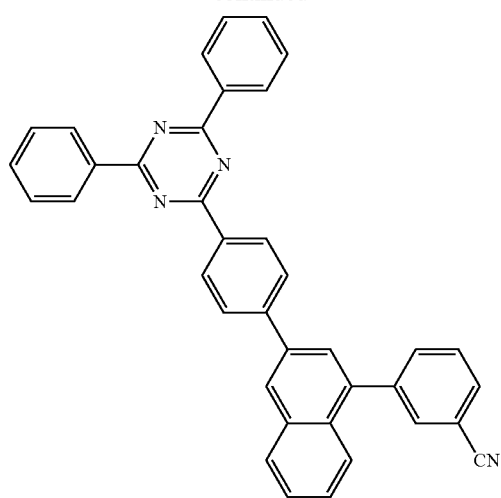
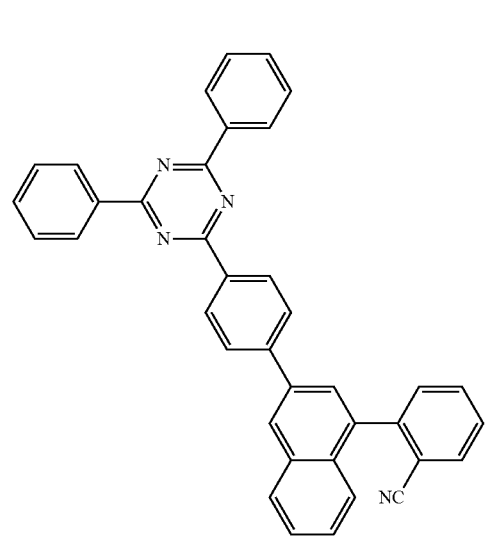
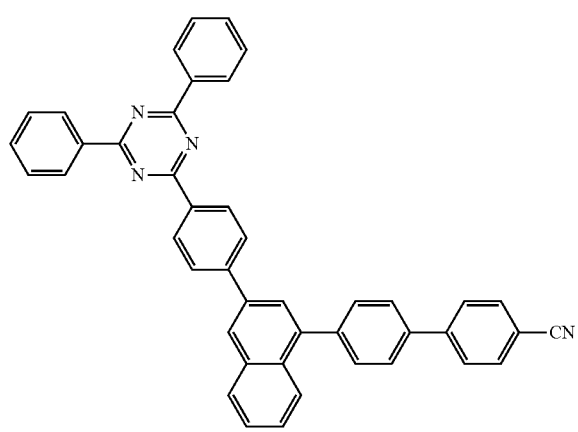
300
-continued
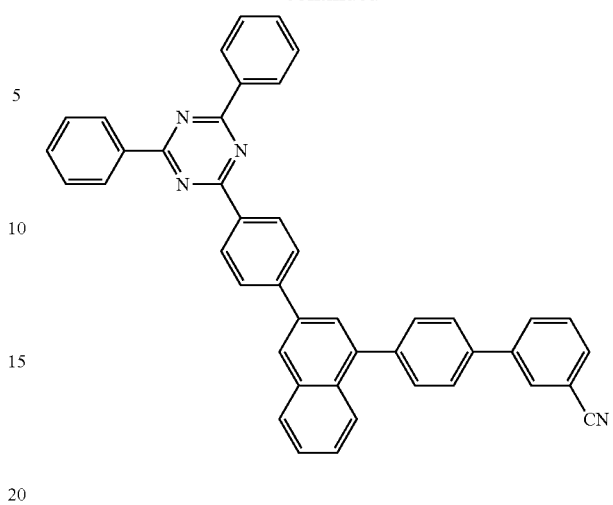
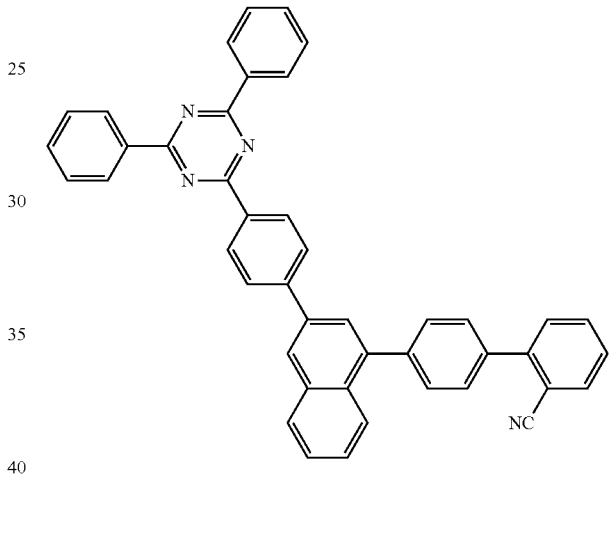
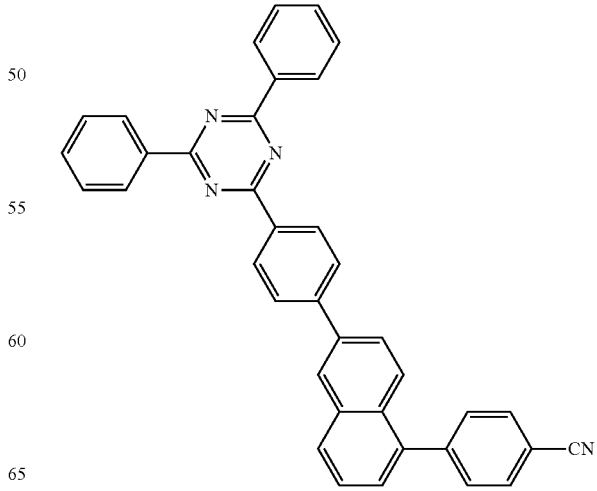

301
-continued
302
-continued
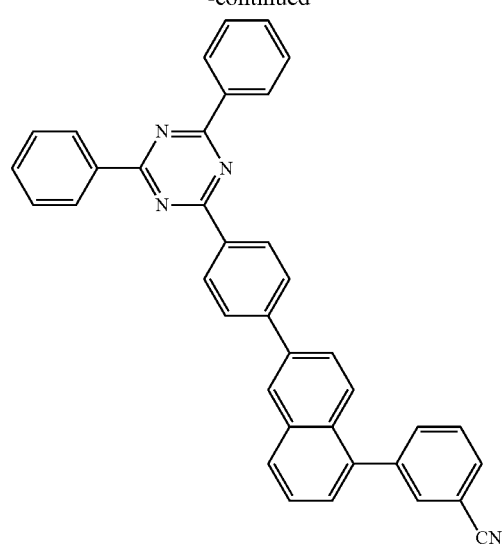
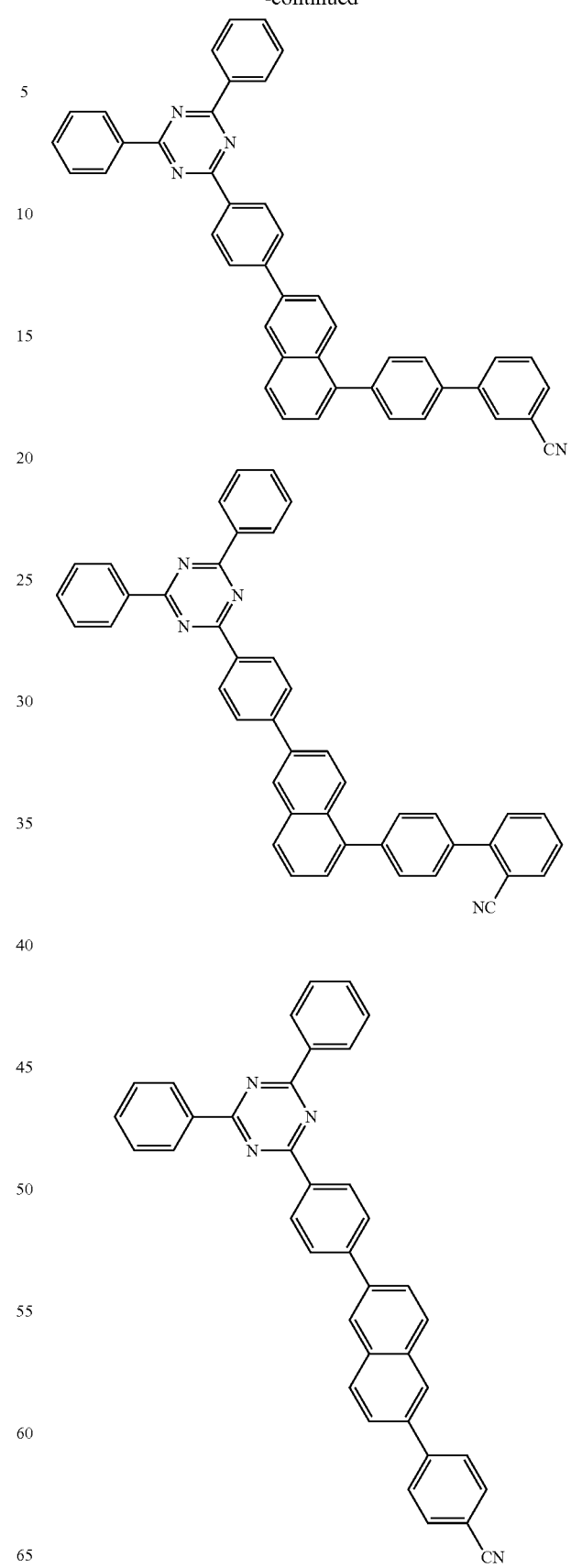

303
-continued
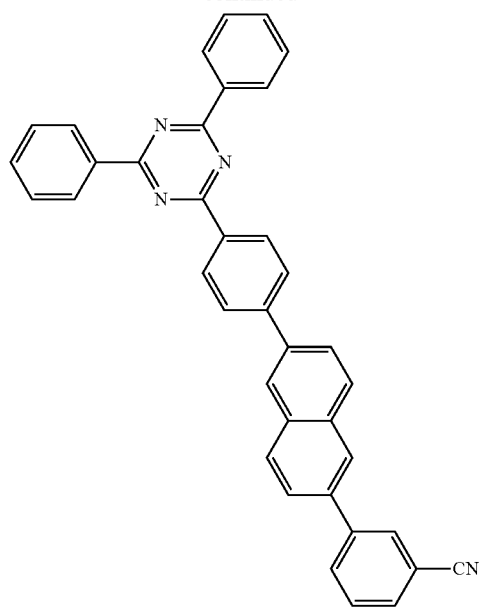
304
-continued
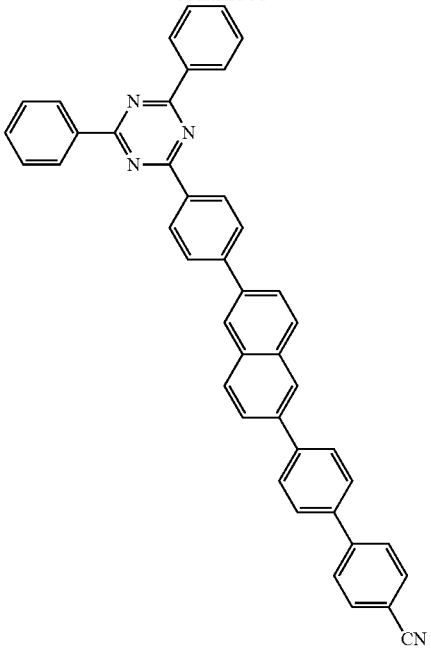
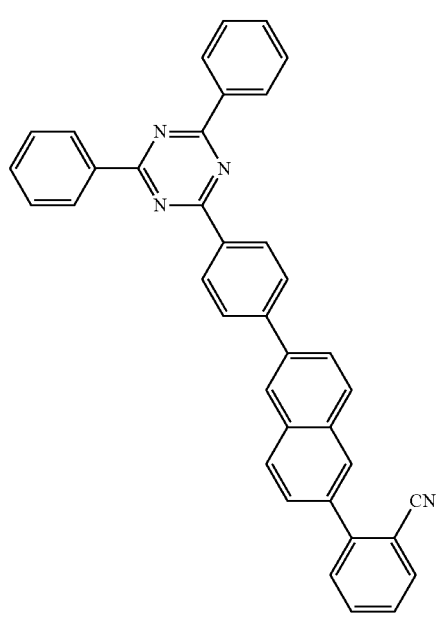
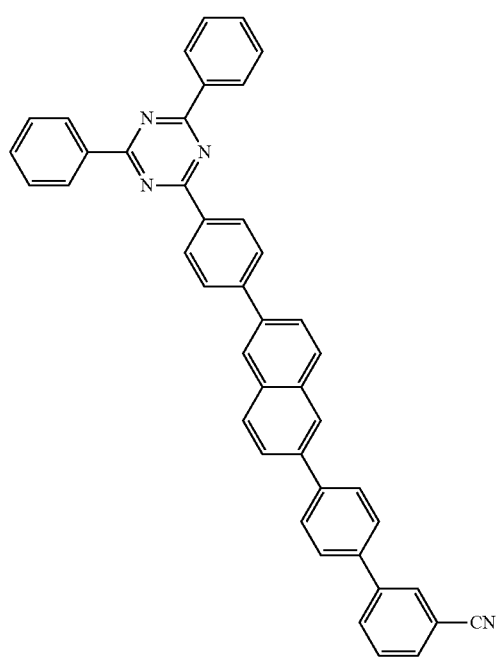

305
-continued
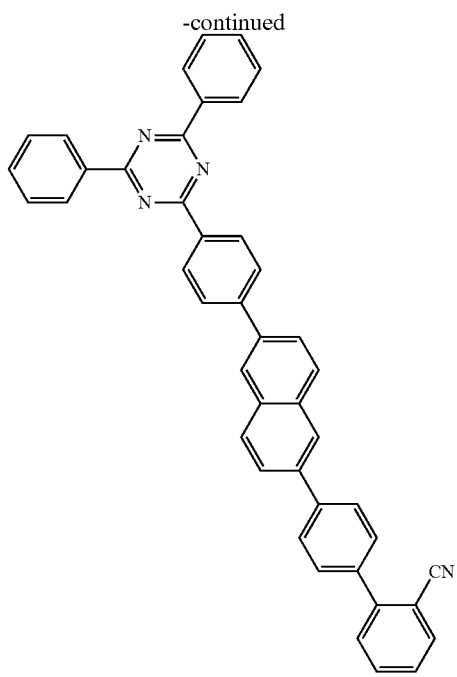
306
-continued
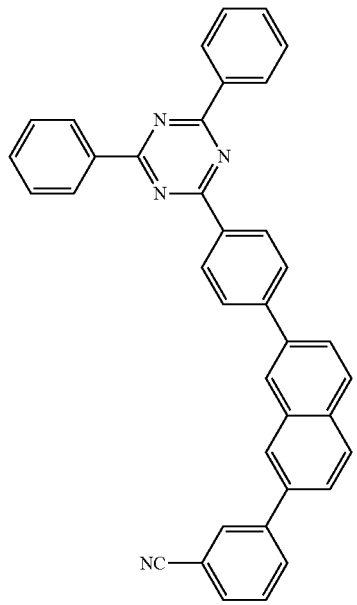
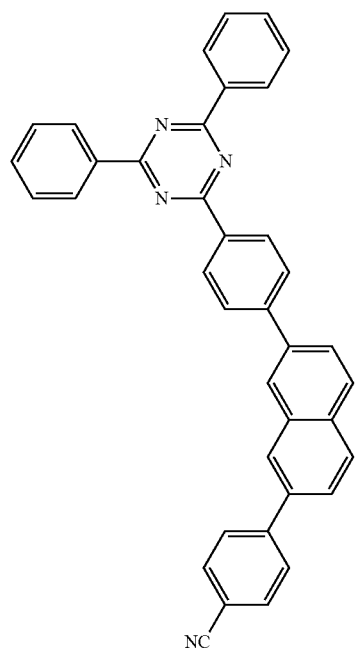
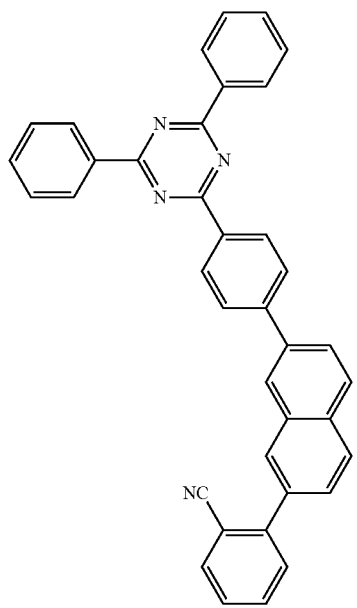

307
-continued
308
-continued
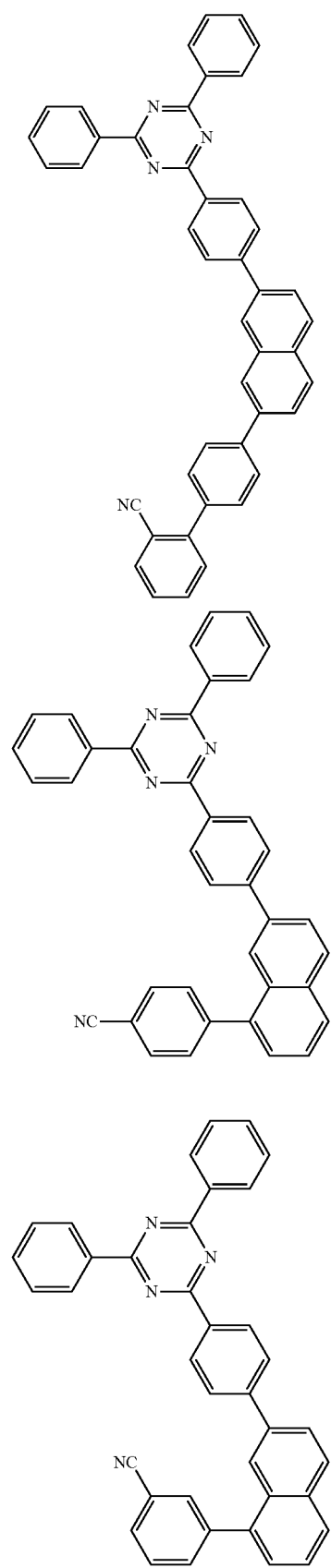

309
-continued
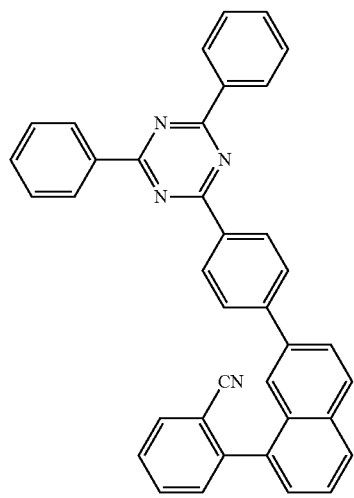
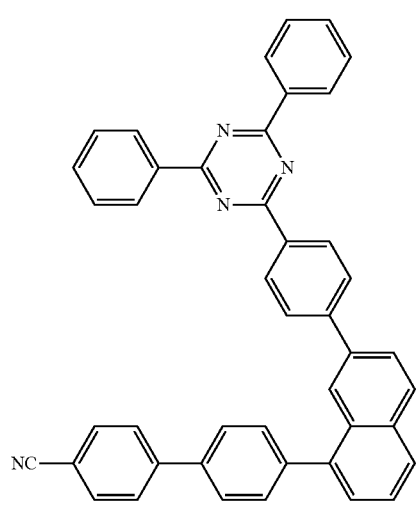
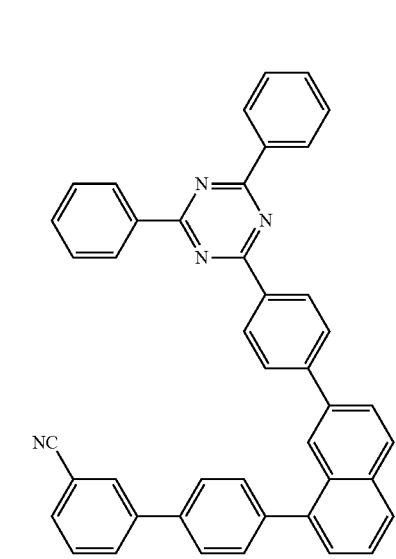
310
-continued
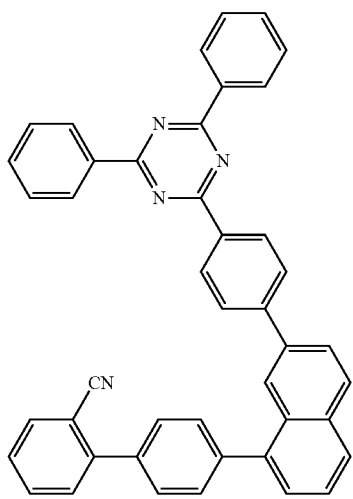
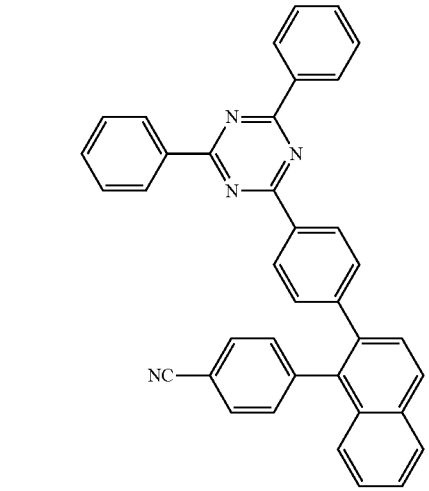
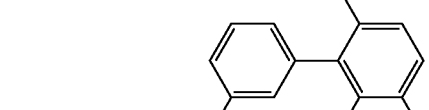

311
-continued
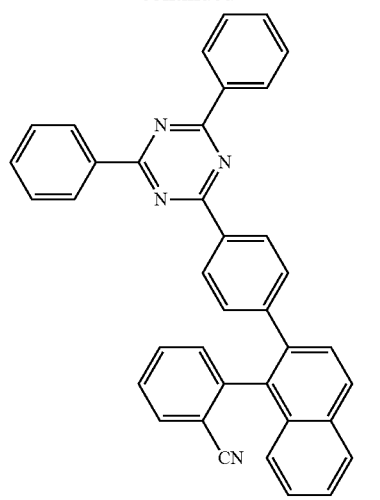
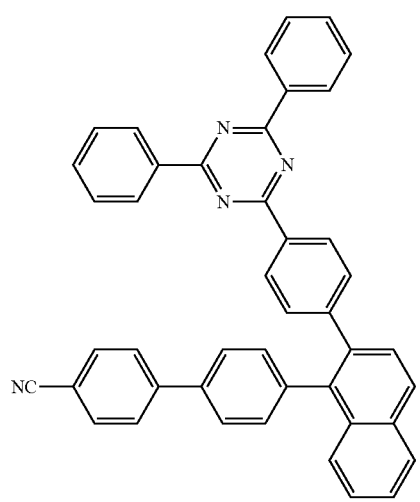
312
-continued
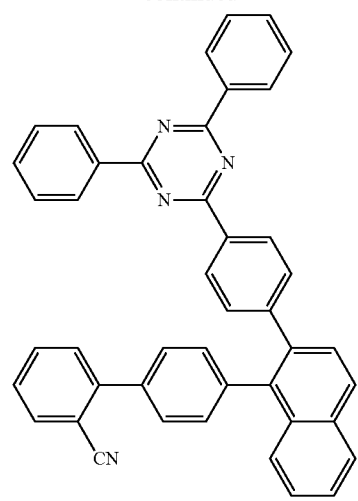
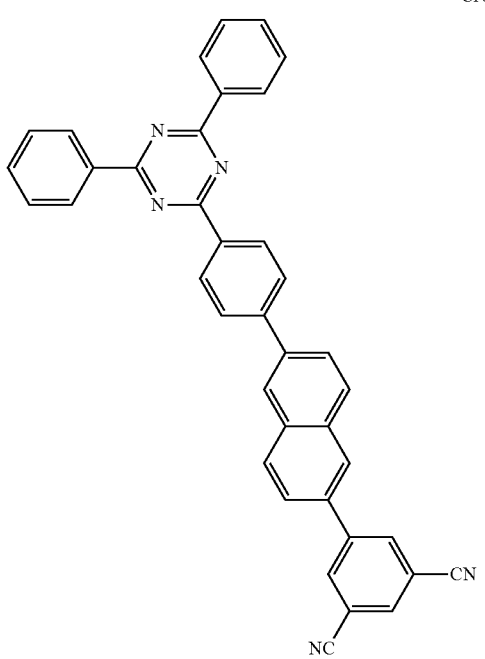

313
-continued
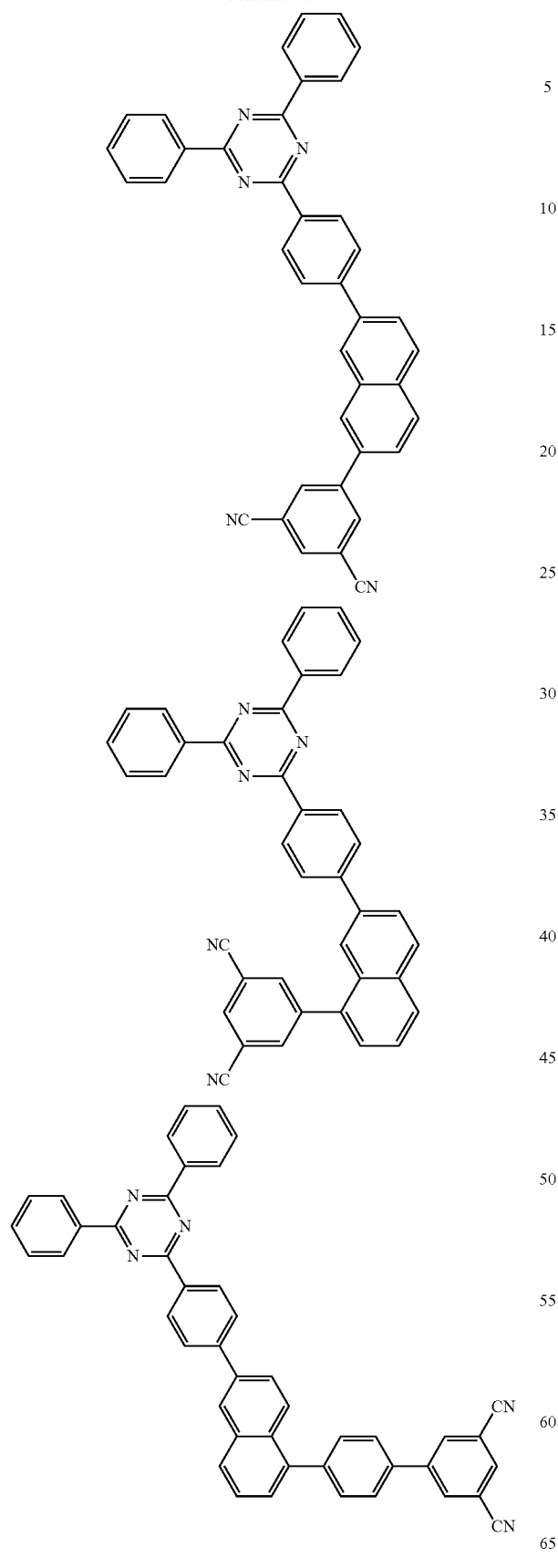
314
-continued
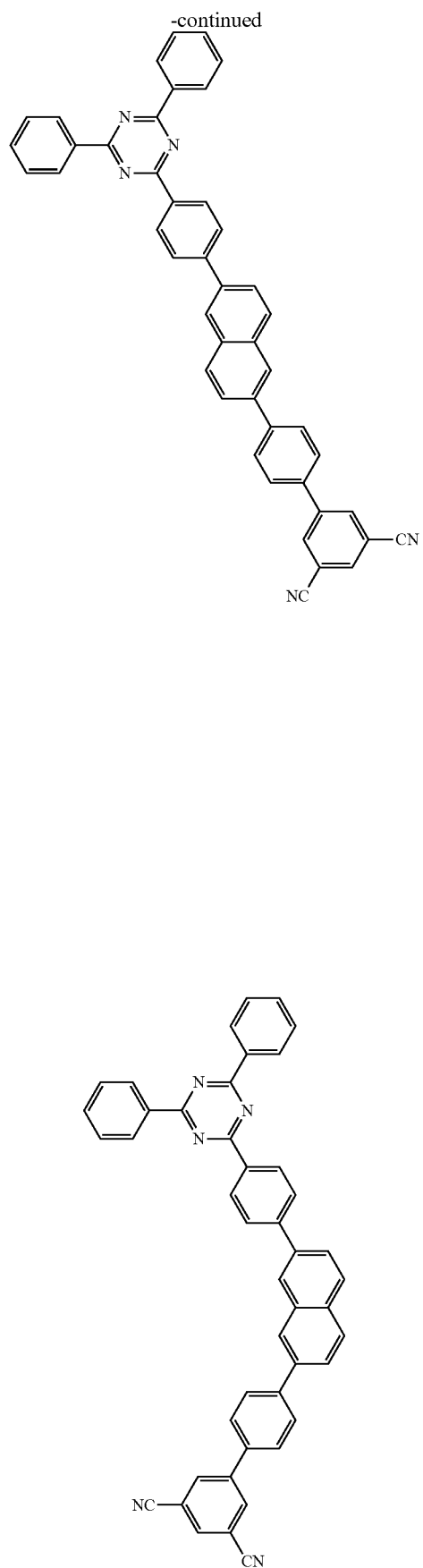

315
-continued
316
-continued
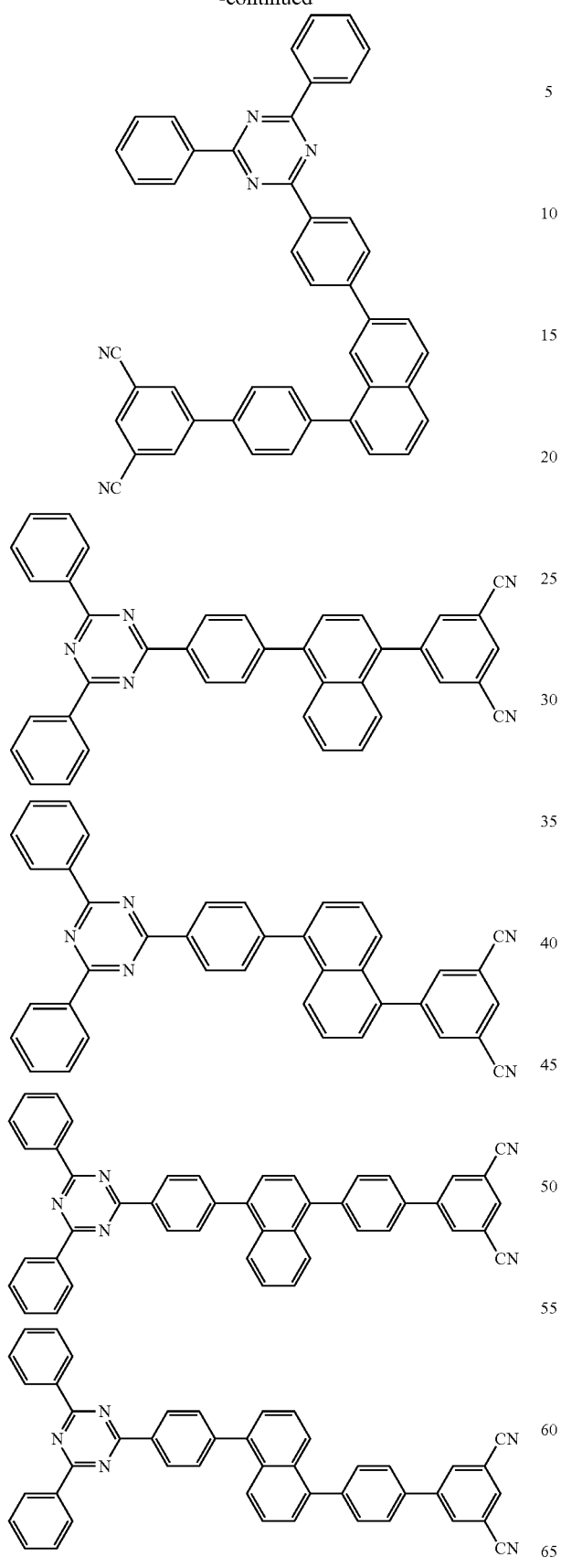
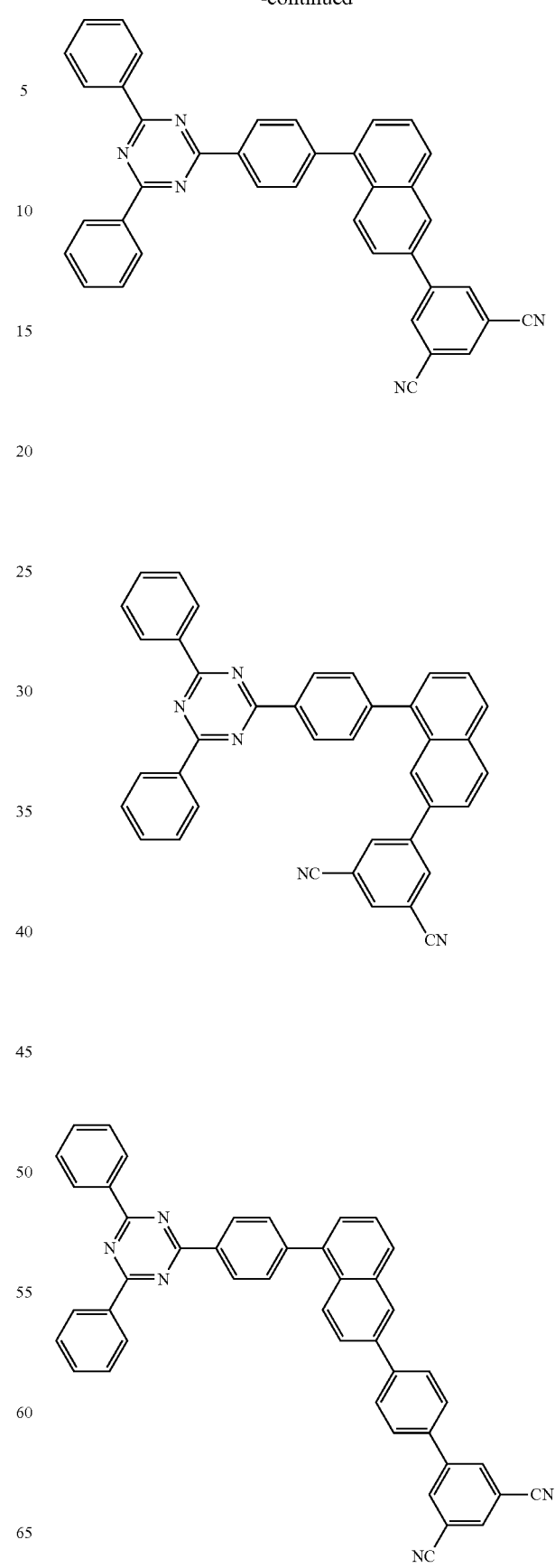

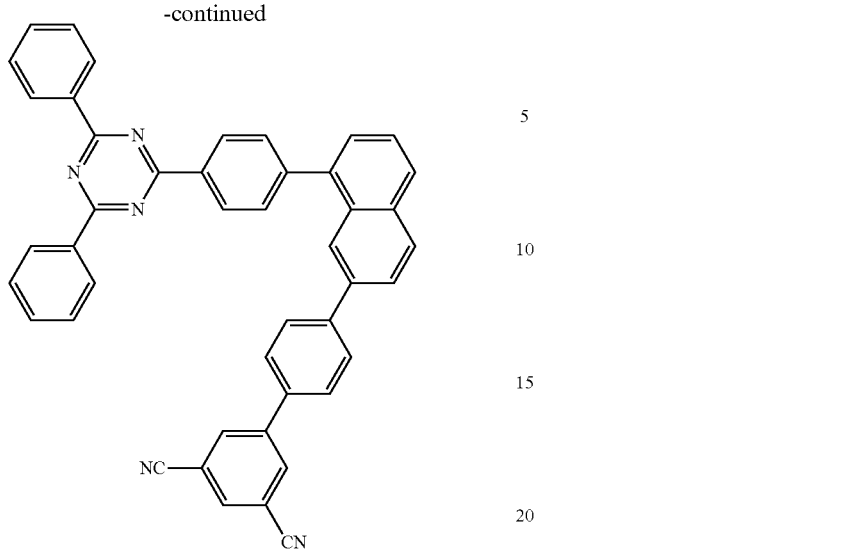
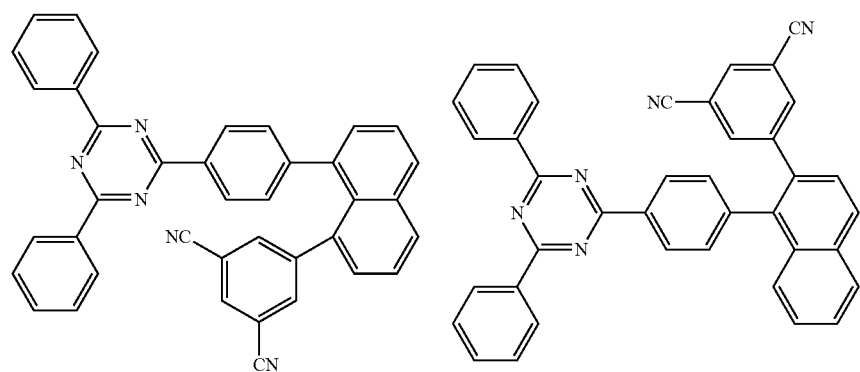
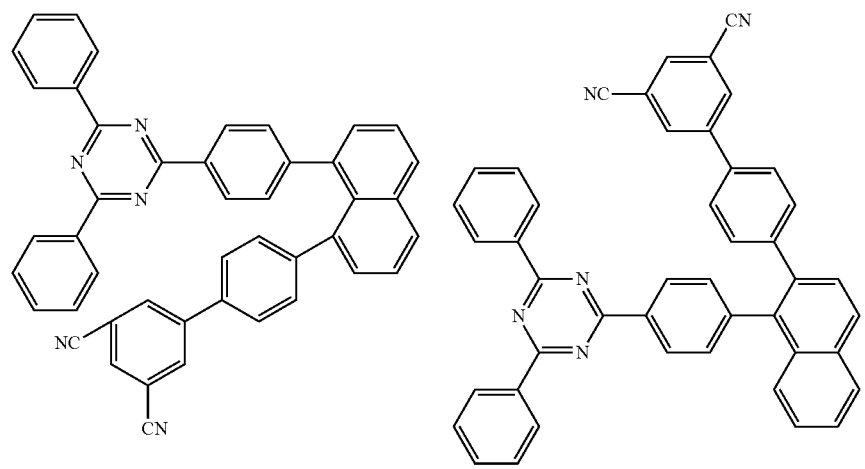

319
320
-continued
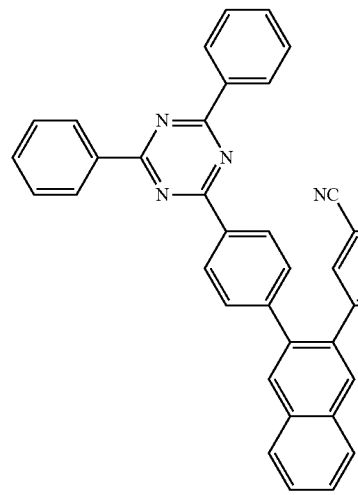
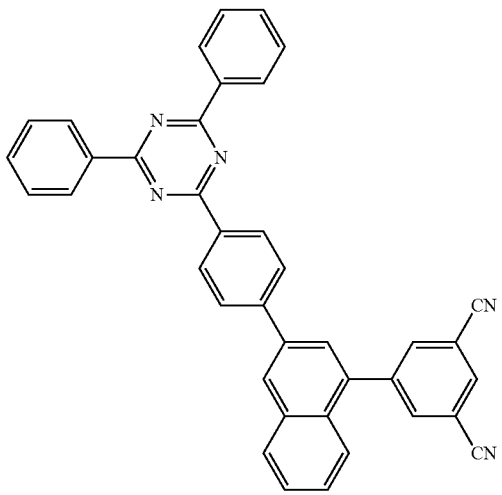
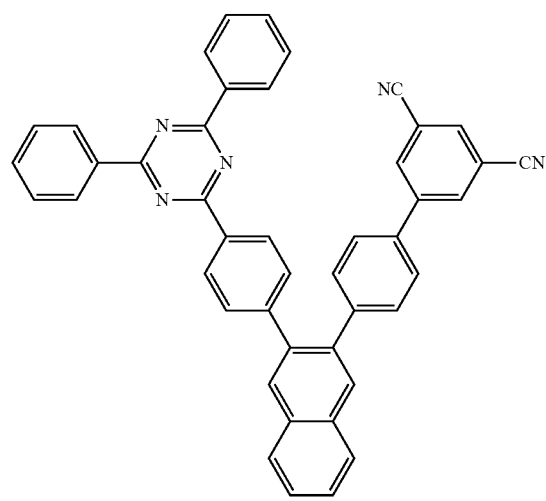
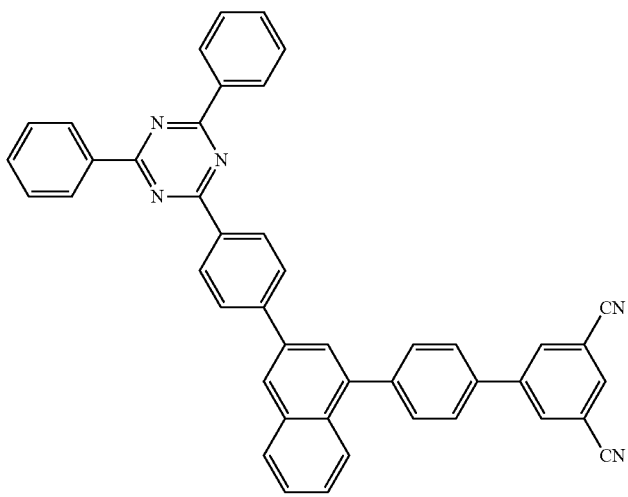
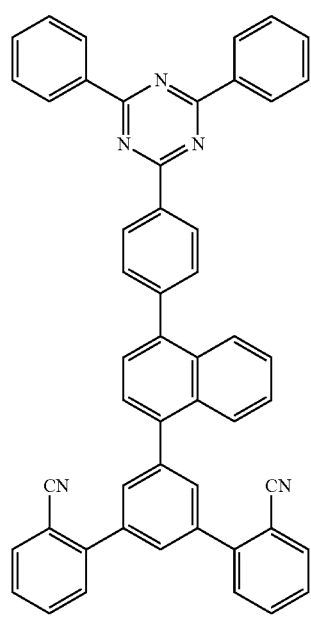
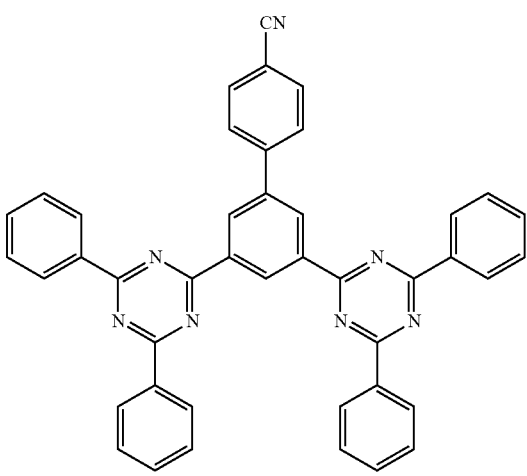

321 322
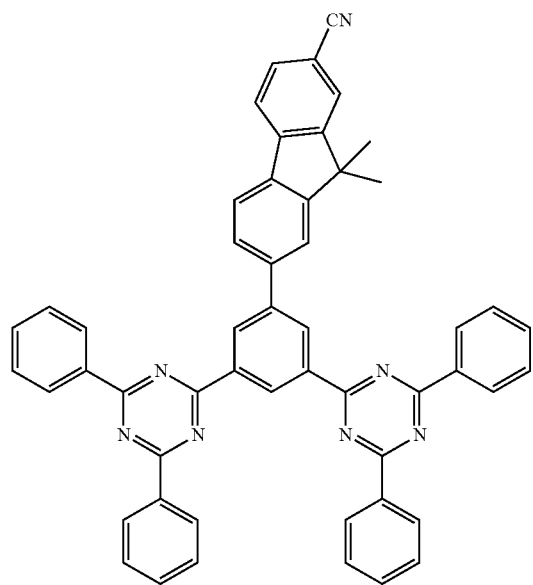 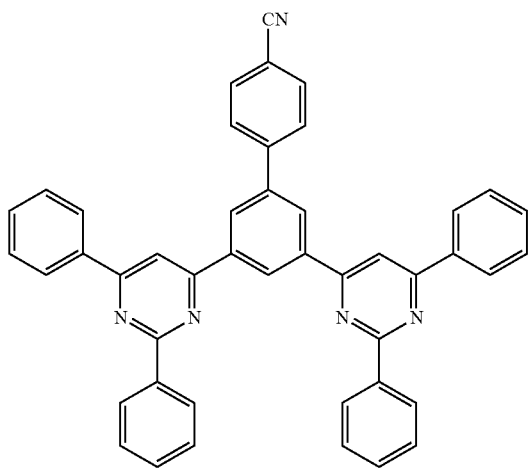
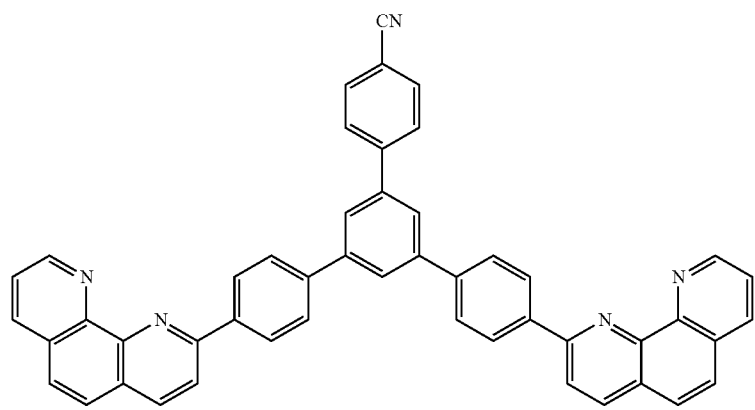
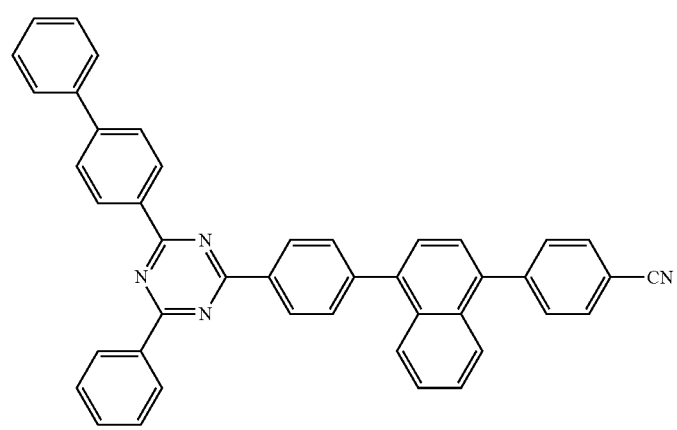

-continued
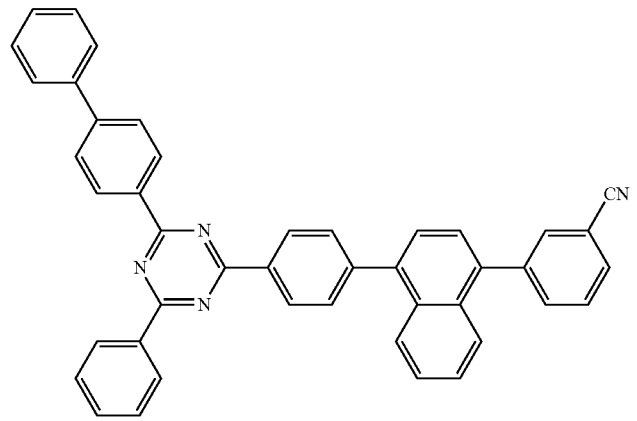
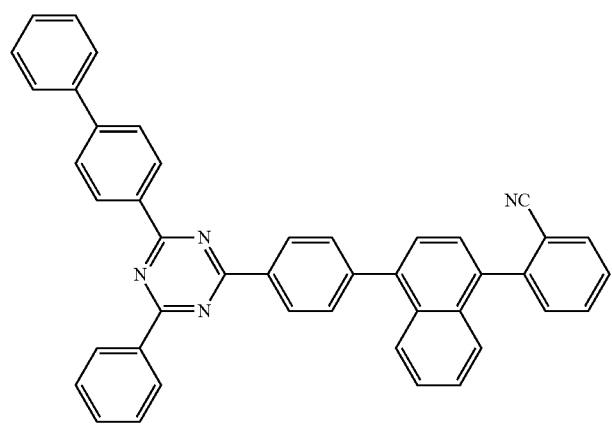
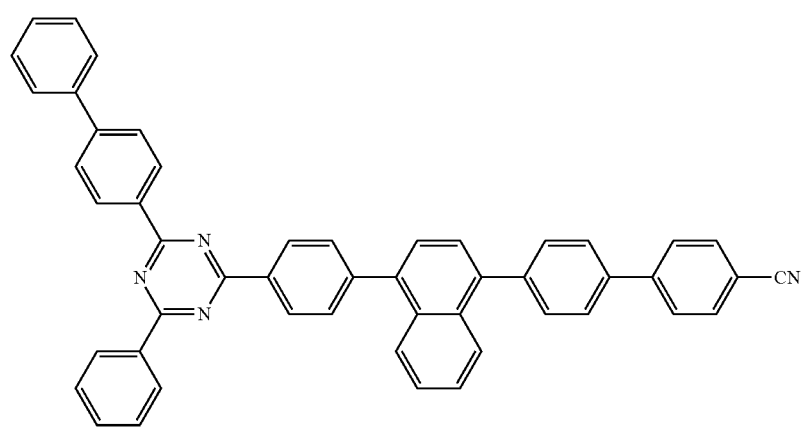
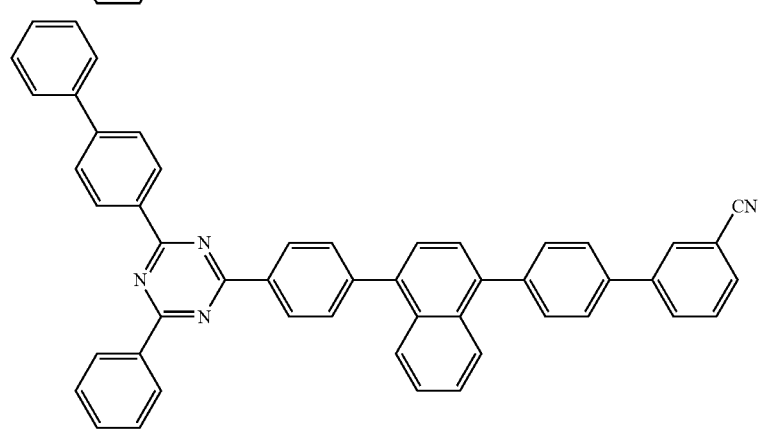

325 326
-continued
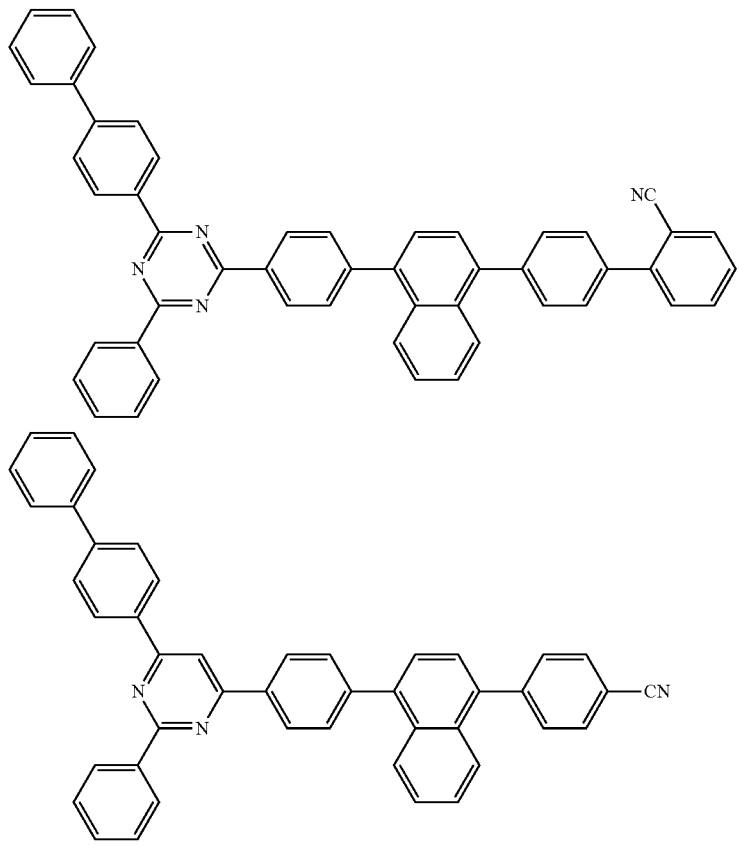
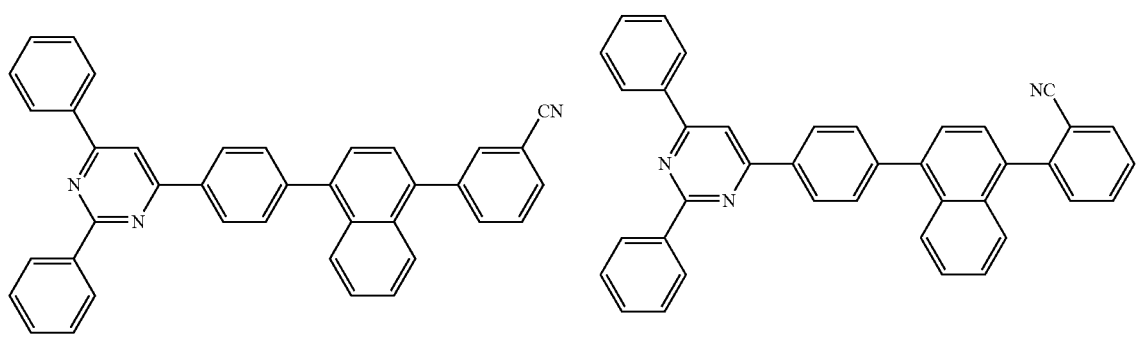
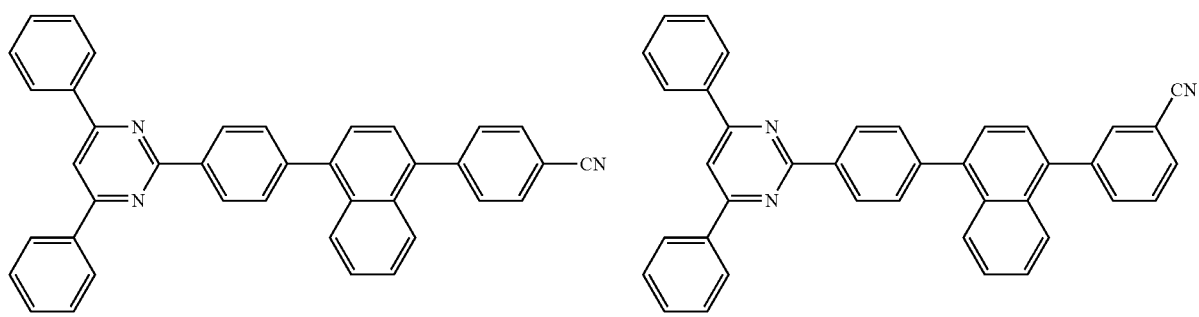

-continued
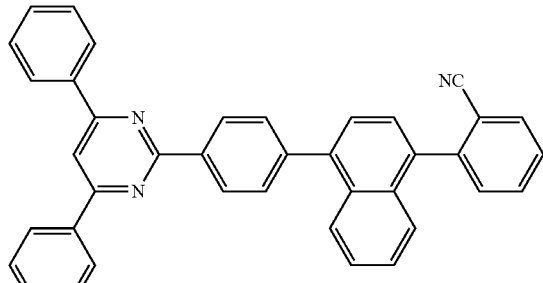
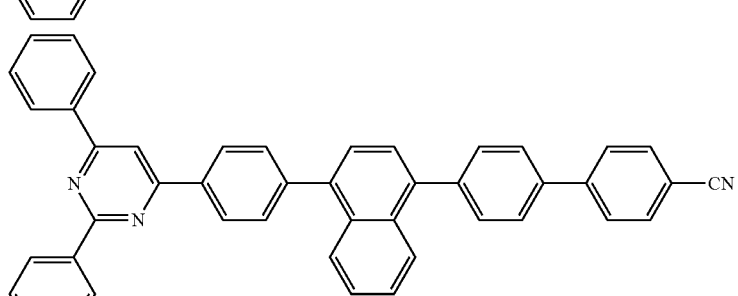
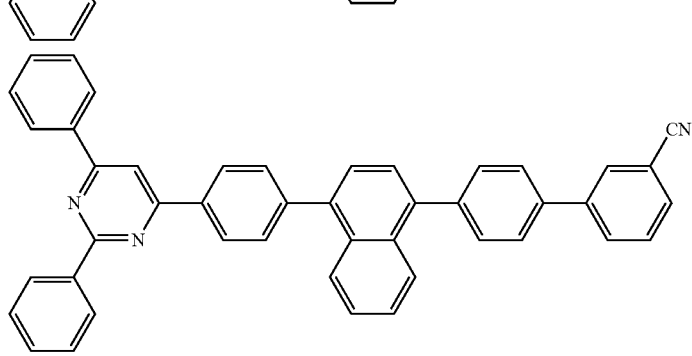
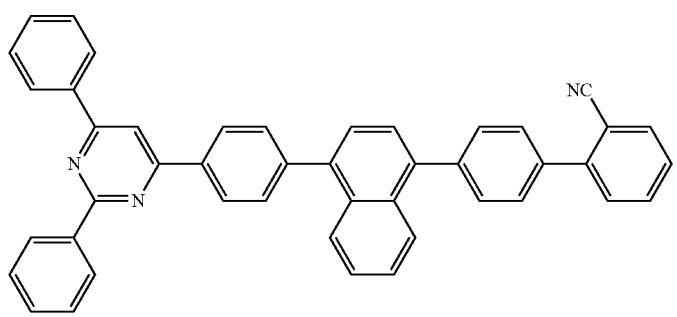
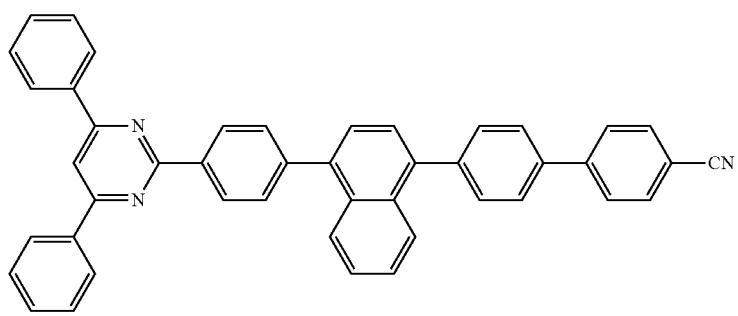

-continued
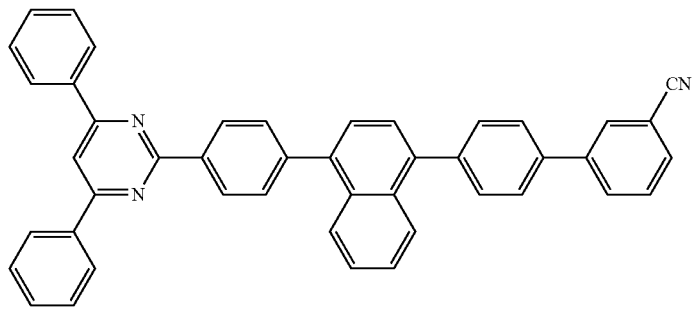
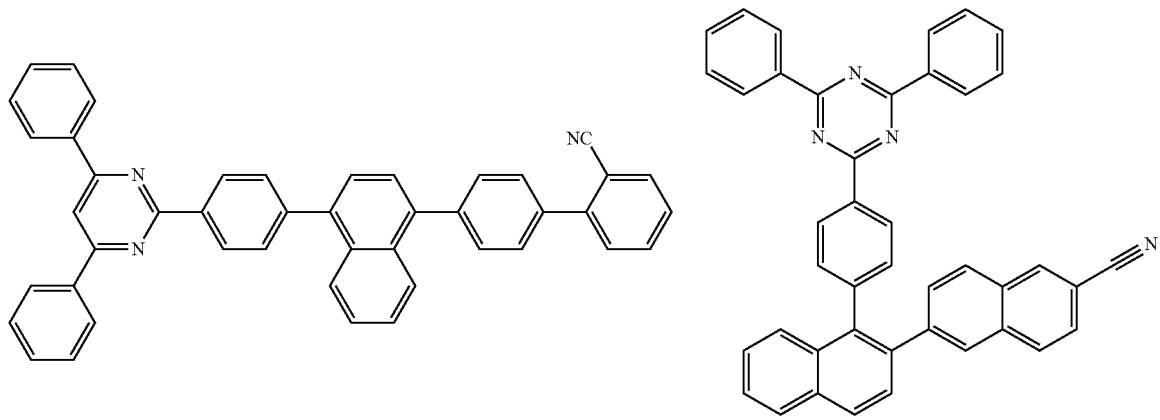
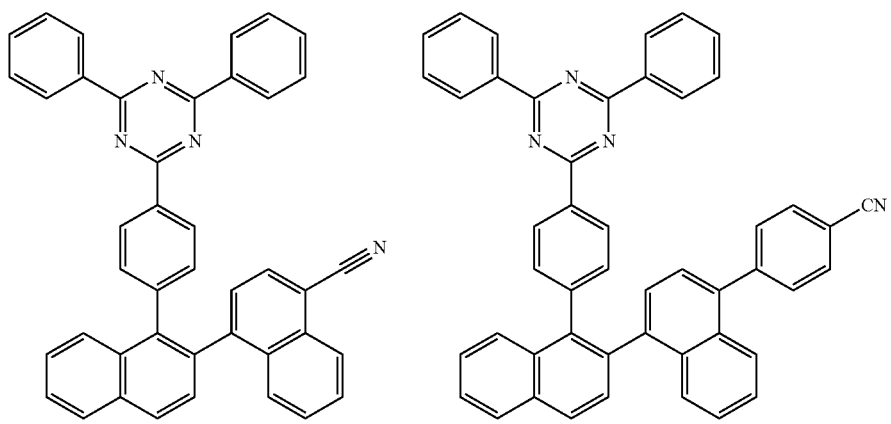

-continued
331
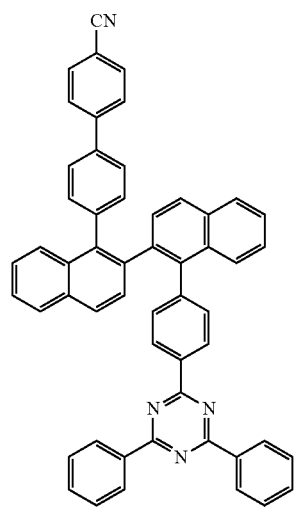 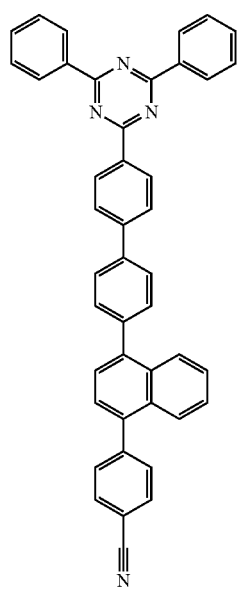 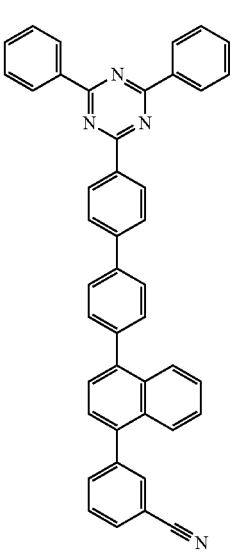
332
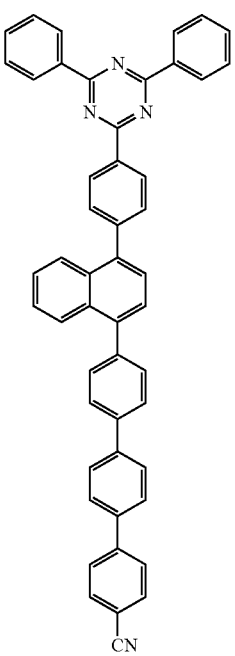
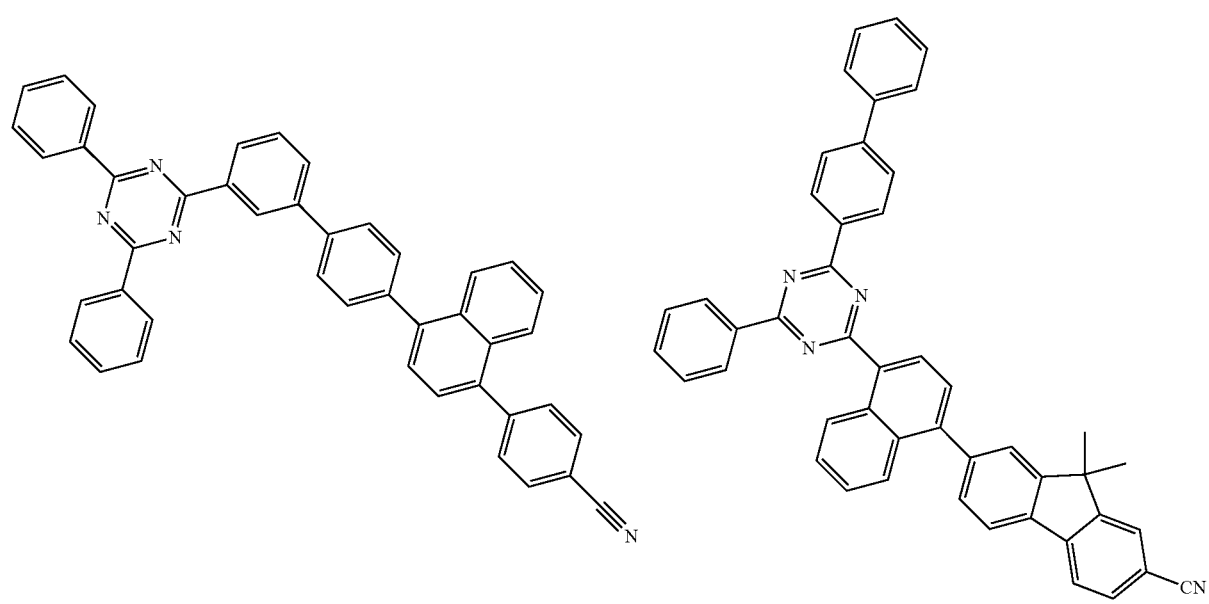

333
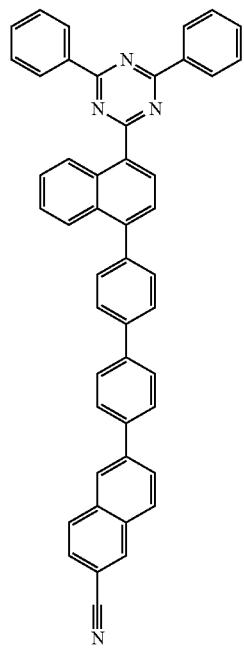
334
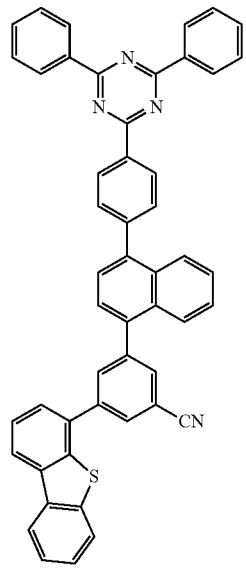
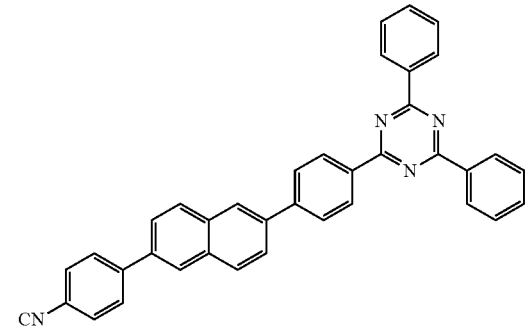
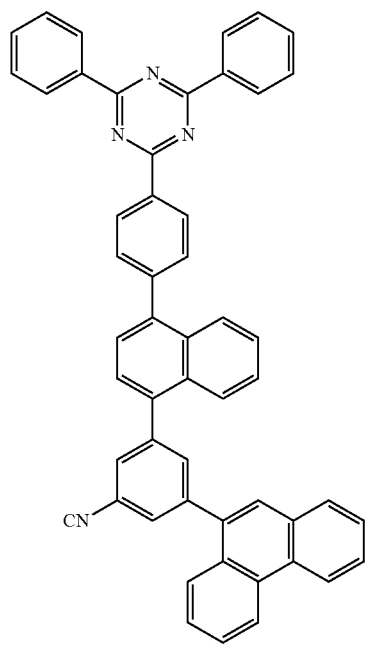
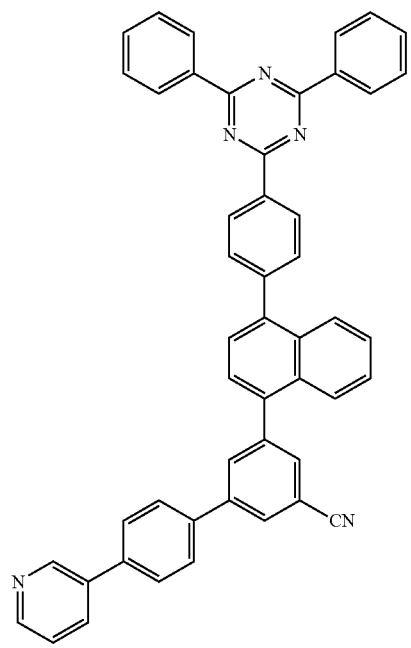
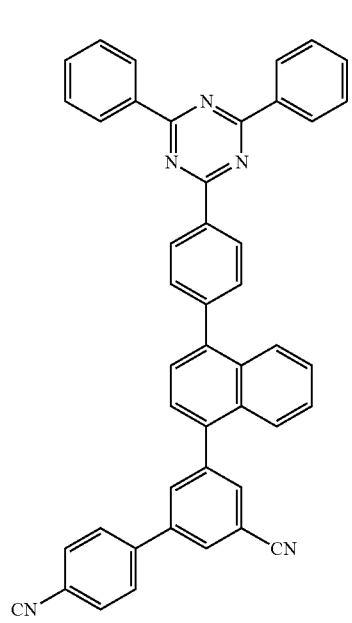

335
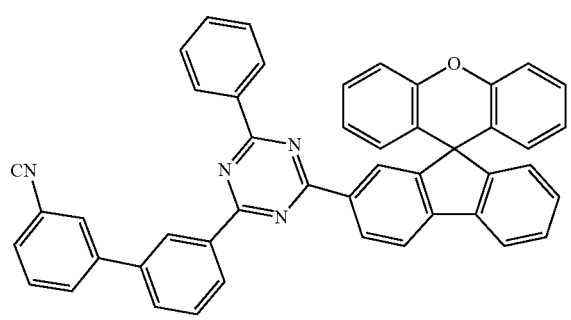
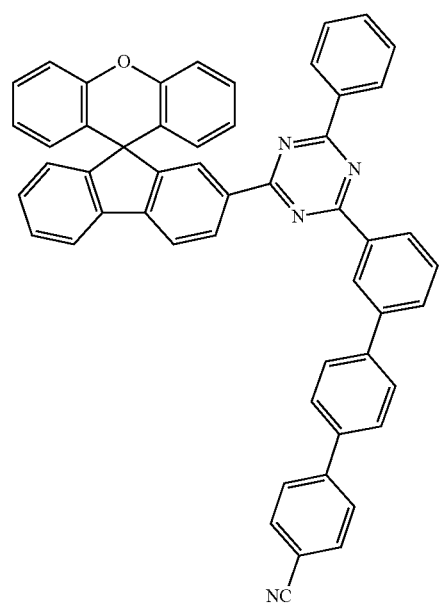
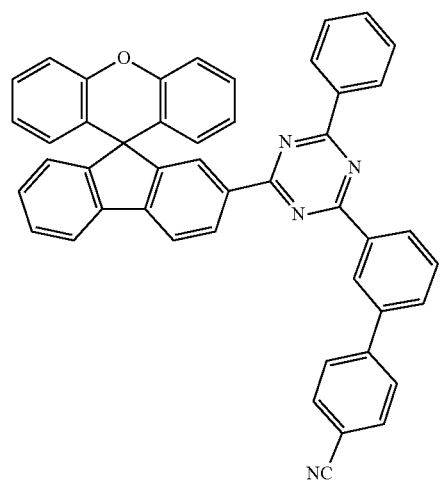
336
-continued
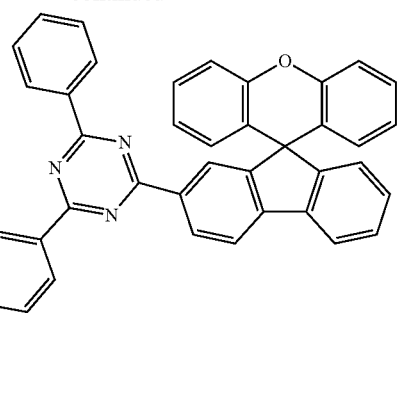
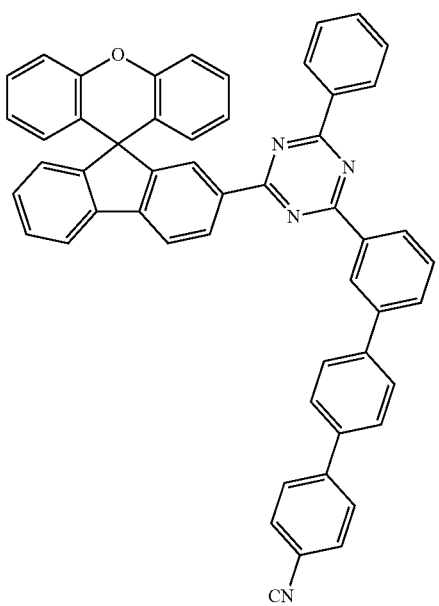
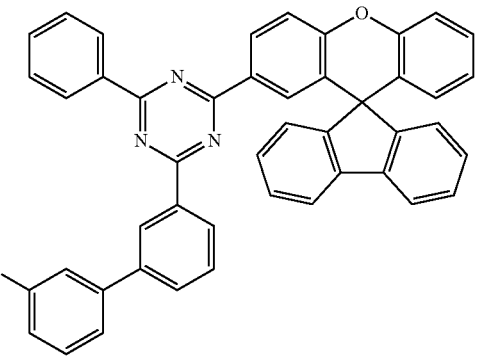

337
-continued
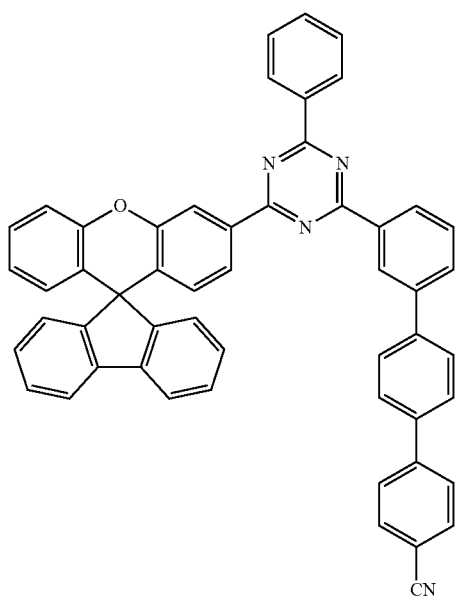
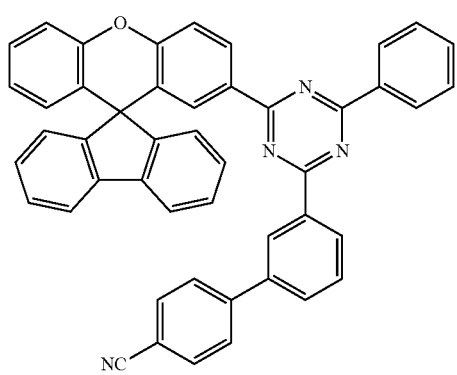
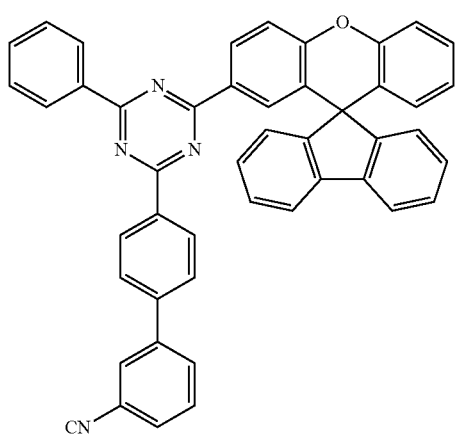
338
-continued
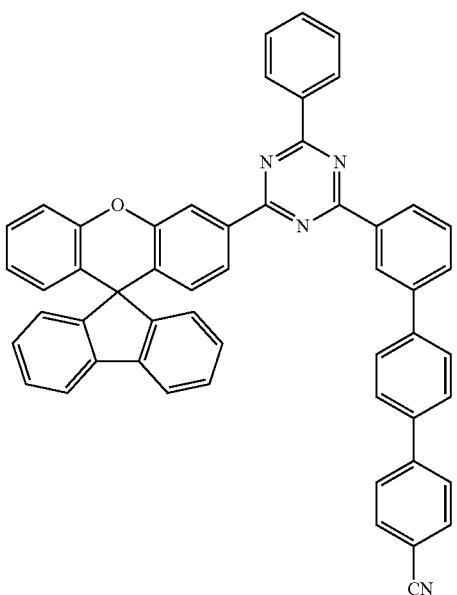

339
-continued
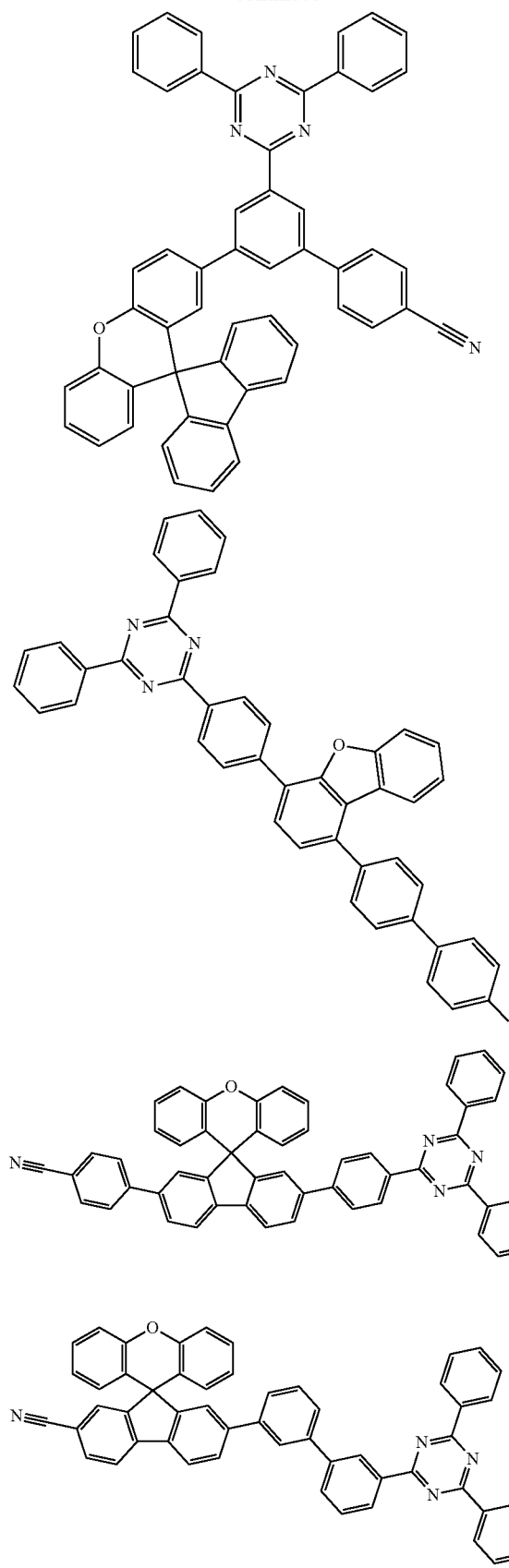
340
-continued
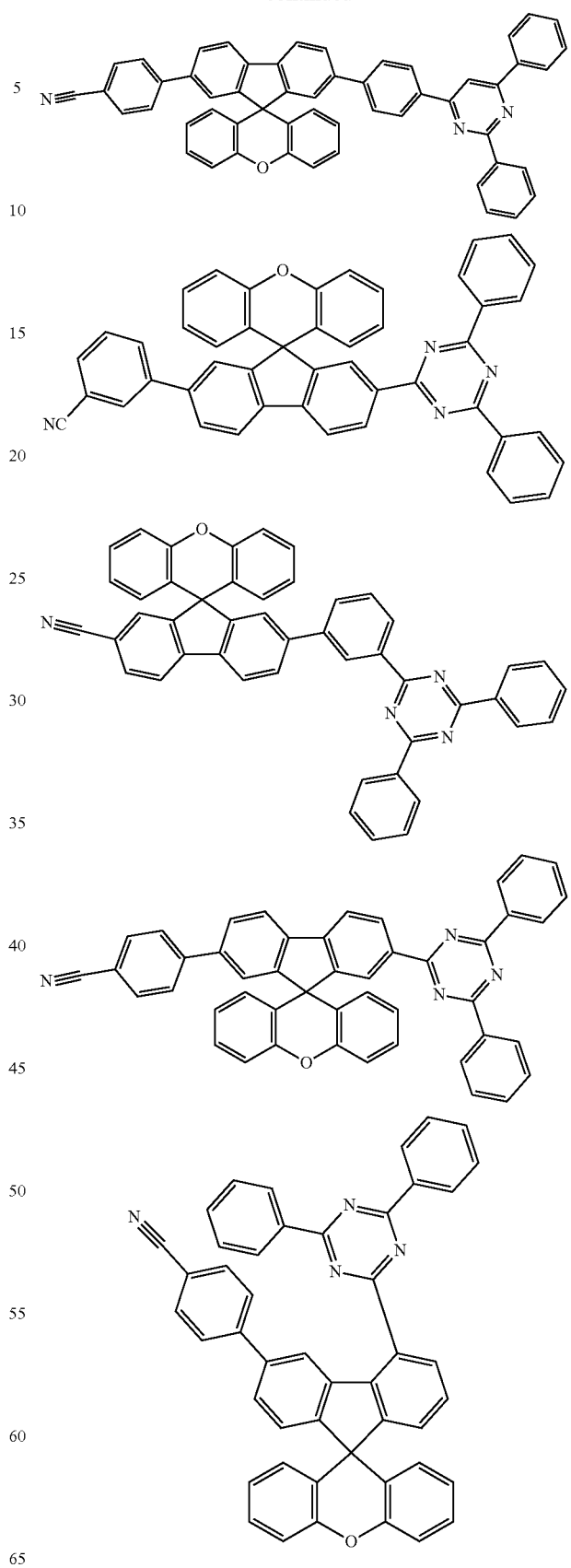

341
-continued
342
-continued
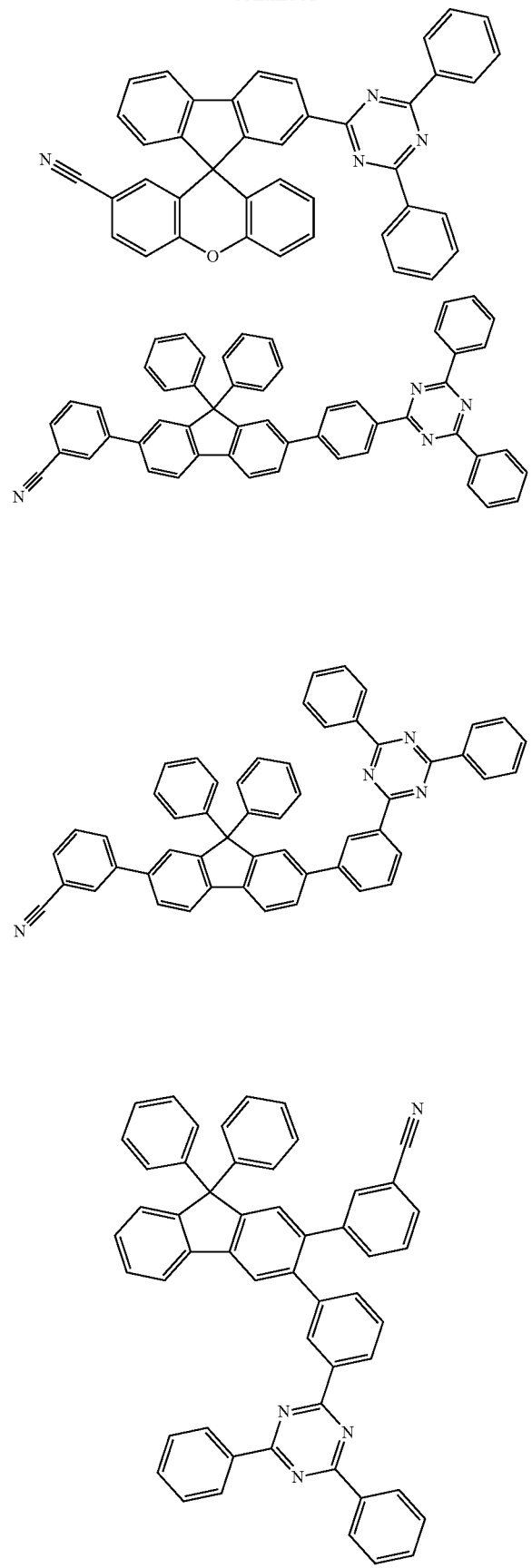
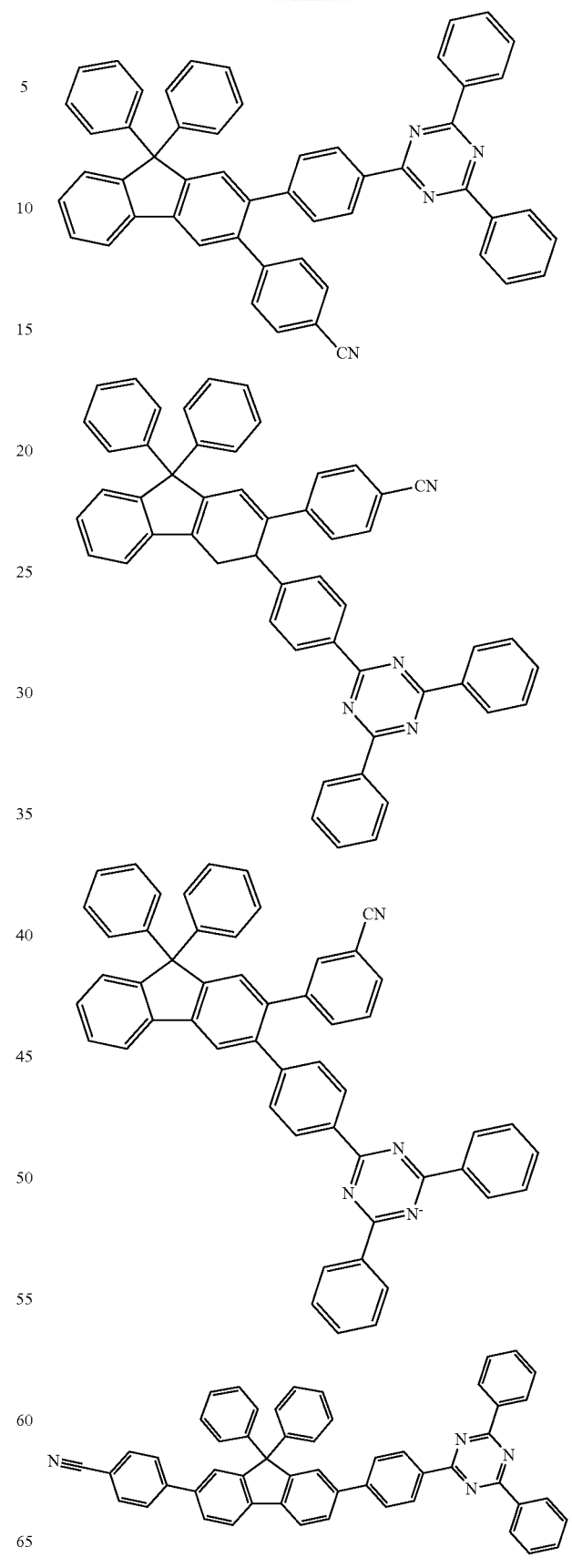

343
-continued
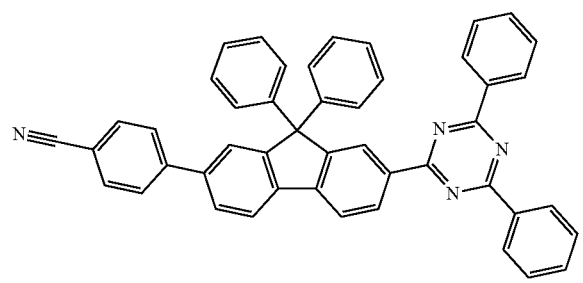
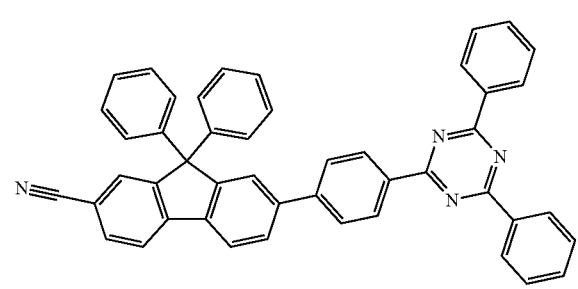
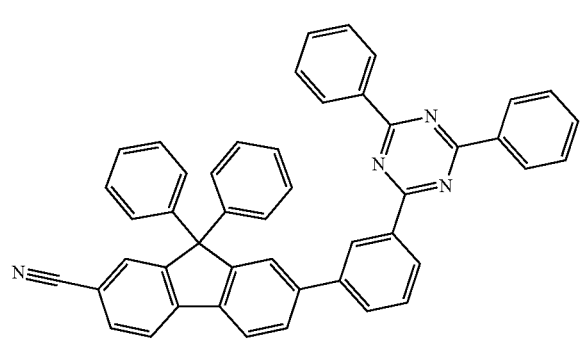
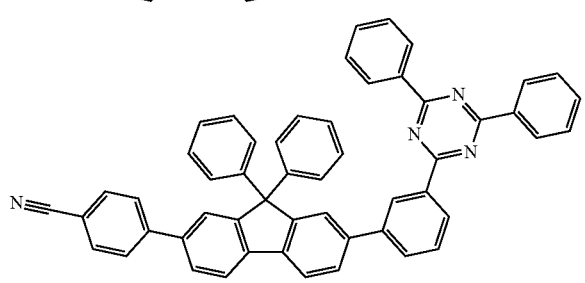
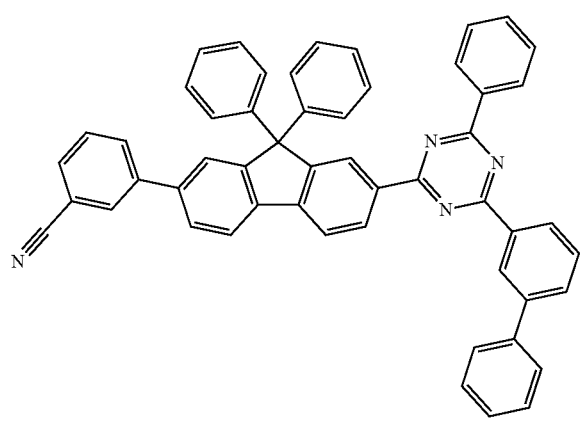
344
-continued
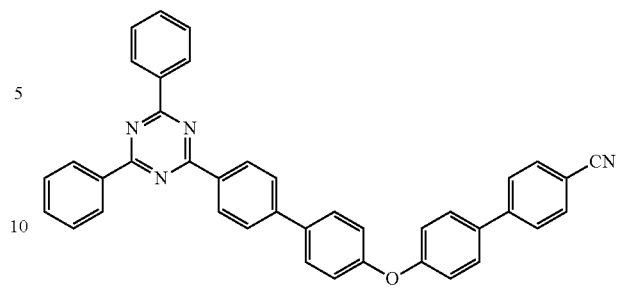
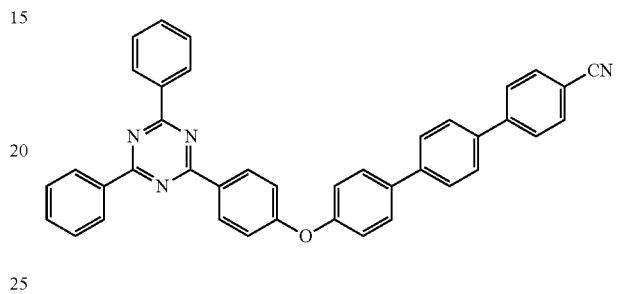
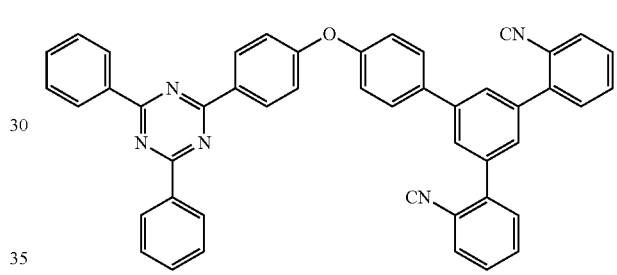
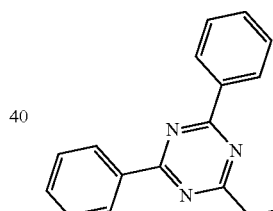

345
-continued
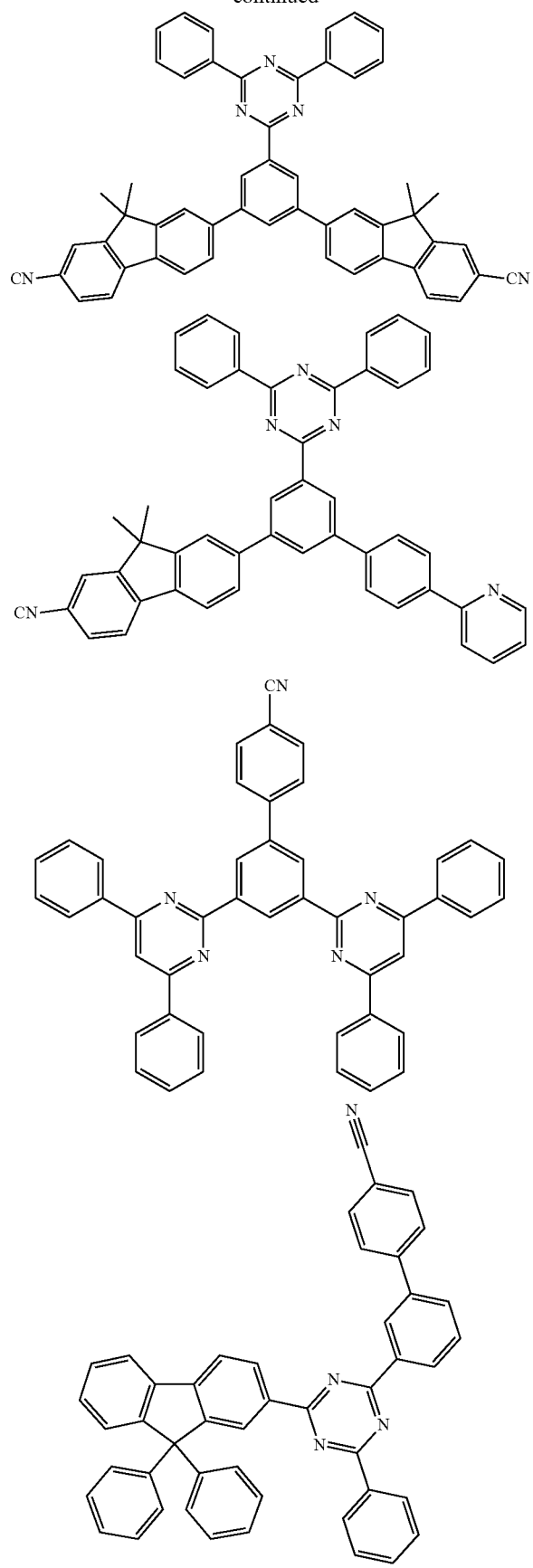
346
-continued
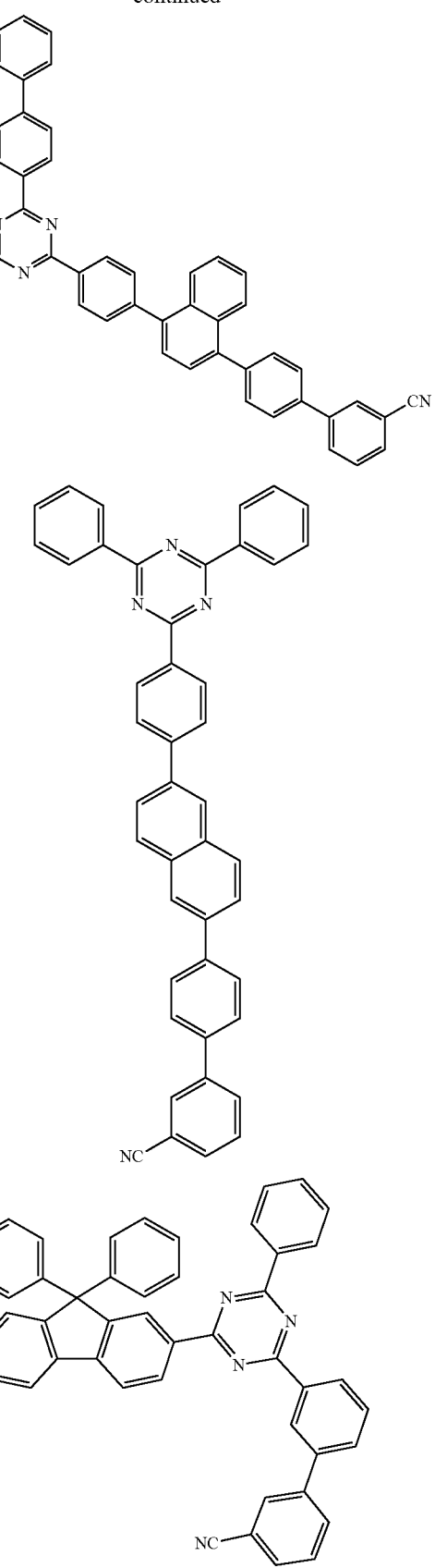

-continued

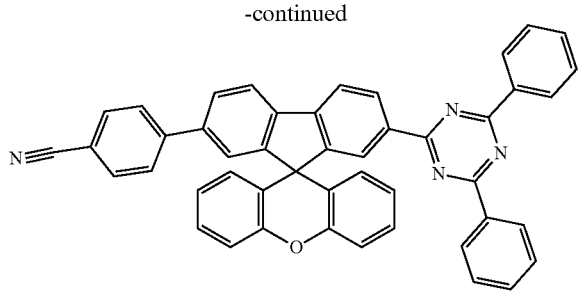

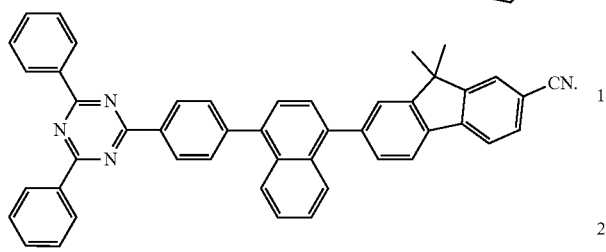

9. The organic light emitting device of claim 1, wherein the compound of Chemical Formula 1 and the compound of Chemical Formula 2 satisfy the following Equation 1:

$$|P_{El}| > |P_{Eb}|  \quad \text{<Equation 1>}$$

wherein in Equation 1:

$|P_{Eb}|$ means an absolute value of a dipole moment of the compound of Chemical Formula 1; and $|P_{El}|$ means an absolute value of a dipole moment of the compound of Chemical Formula 2.

10. An organic light emitting device comprising:
a first electrode;
a second electrode provided opposite to the first electrode; and
a first organic material layer and a second organic material layer provided between the first electrode and the second electrode,
wherein the first organic material layer includes a compound of the following Chemical Formula 1,
the second organic material layer is an electron transfer layer and includes a compound of the following Chemical Formula 2, and
a dipole moment value of the second organic material layer is larger than a dipole moment value of the first organic material layer:

[Chemical Formula 1]

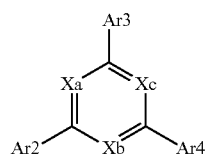

wherein in Chemical Formula 1:
at least one of Xa to Xc is N, and the rest are CR;
R is hydrogen, deuterium, a cyano group, a nitrile group, a substituted or unsubstituted silyl group, a substituted or unsubstituted alkyl group, a substituted or unsubstituted haloalkyl group, a substituted or unsubstituted cycloalkyl group, a substituted or unsubstituted alkenyl group, a substituted or unsubstituted aryl group, or a substituted or unsubstituted heterocyclic group; and Ar2 to Ar4 are each independently a substituted or unsubstituted aryl group or a substituted or unsubstituted heterocyclic group;

Chemical Formula 2

$$(HAr)_a\text{---}[L1\text{---}Ar1\text{---}L2\text{---}(CN)_b]_c$$

wherein in Chemical Formula 2:
HAr is a substituted or unsubstituted heterocyclic group including one or more Ns;
L1 and L2 are each independently a direct bond, a substituted or unsubstituted arylene group, or a substituted or unsubstituted divalent heterocyclic group;
Ar1 is a direct bond, —O—, a substituted or unsubstituted arylene group, or a substituted or unsubstituted divalent heterocyclic group;
a to c are each an integer of 1 to 3; and
when a to c are each 2 or greater, the structures in the two or more parentheses are the same as or different from each other.

11. An organic light emitting device comprising:
a first electrode;
a second electrode provided opposite to the first electrode;
two or more light emitting layers between the first electrode and the second electrode, wherein the light emitting layers each independently includes a fluorescent dopant or a phosphorescent dopant; and
a first organic material layer and a second organic material layer provided between the first electrode and the second electrode,
wherein the first organic material layer includes a compound of the following Chemical Formula 1,
the second organic material layer includes a compound of the following Chemical Formula 2, and
a dipole moment value of the second organic material layer is larger than a dipole moment value of the first organic material layer:

[Chemical Formula 1]

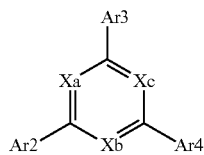

wherein in Chemical Formula 1:
at least one of Xa to Xc is N, and the rest are CR;
R is hydrogen, deuterium, a cyano group, a nitrile group, a substituted or unsubstituted silyl group, a substituted or unsubstituted alkyl group, a substituted or unsubstituted haloalkyl group, a substituted or unsubstituted cycloalkyl group, a substituted or unsubstituted alkenyl group, a substituted or unsubstituted aryl group, or a substituted or unsubstituted heterocyclic group; and
Ar2 to Ar4 are each independently a substituted or unsubstituted aryl group or a substituted or unsubstituted heterocyclic group;

Chemical Formula 2

$$(HAr)_a\text{---}[L1\text{---}Ar1\text{---}L2\text{---}(CN)_b]_c$$

wherein in Chemical Formula 2:

HAr is a substituted or unsubstituted heterocyclic group including one or more Ns;

L1 and L2 are each independently a direct bond, a substituted or unsubstituted arylene group, or a substituted or unsubstituted divalent heterocyclic group;

Ar1 is a direct bond, —O—, a substituted or unsubstituted arylene group, or a substituted or unsubstituted divalent heterocyclic group;

a to c are each an integer of 1 to 3; and when a to c are each 2 or greater, the structures in the two or more parentheses are the same as or different from each other.

12. The organic light emitting device of claim 11, comprising three or more light emitting layers between the first electrode and the second electrode, wherein the light emitting layers each includes a blue fluorescent light emitting layer.

13. The organic light emitting device of claim 12, wherein the three or more light emitting layers are provided consecutively in a direction from the first electrode to the second electrode direction.

14. The organic light emitting device of claim 11, wherein:

Chemical Formula 1 is any one of the following Chemical Formulae 1-1 to 1-3:

Chemical Formula 1-1

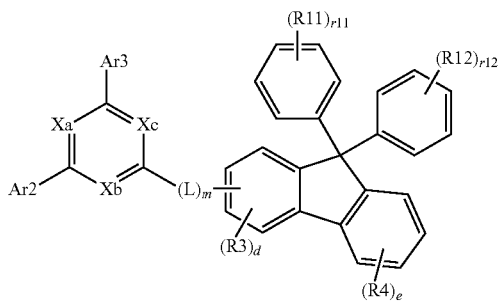

Chemical Formula 1-2

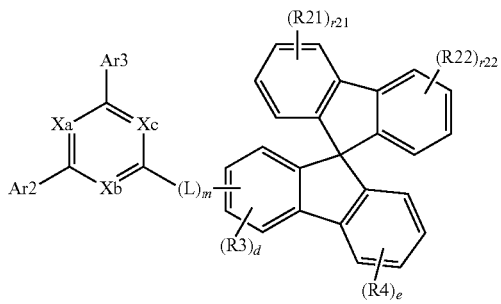

Chemical Formula 1-3

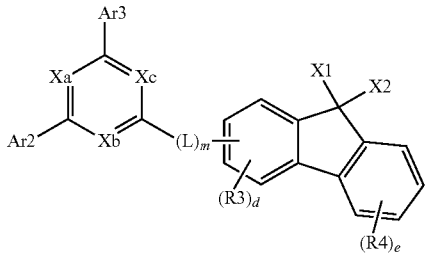

wherein in Chemical Formulae 1-1 to 1-3:

Xa to Xc, Ar2 and Ar3 have the same definitions as in Chemical Formula 1;

L is substituted or unsubstituted phenylene, substituted or unsubstituted biphenylylene, or substituted or unsubstituted terphenylene;

R3, R4, R11, R12, R21 and R22 are the same as or different from each other, and each independently is hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted arylphosphine group, or a substituted or unsubstituted phosphine oxide group, or bond to adjacent groups to form a substituted or unsubstituted ring;

X1 and X2 are the same as or different from each other, and each independently is hydrogen, deuterium, a halogen group, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, or a substituted or unsubstituted phosphine oxide group, or bond to adjacent groups to form a substituted or unsubstituted ring;

r11 and r12 are the same as or different from each other, and each independently is an integer of 0 to 5;

r21 and r22 are the same as or different from each other, and each independently is an integer of 0 to 4;

m is an integer of 1 to 3;

d is an integer of 1 to 3;

e is an integer of 1 to 4; and when r11, r12, r21, r22, m, d and e are each 2 or greater, structures in the parentheses are the same as or different from each other; and HAr is the following Chemical Formula 2-1:

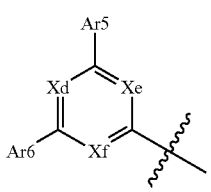

Chemical Formula 2-1 wherein in Chemical Formula 2-1:

Ar5 and Ar6 are a substituted or unsubstituted aryl group or a substituted or unsubstituted heterocyclic group, or bond to adjacent groups to form a ring; and at least one of Xd to Xf is N, and the rest are CH.

15. The organic light emitting device of claim 11, wherein the compound of Chemical Formula 1 is selected from among the following compounds:

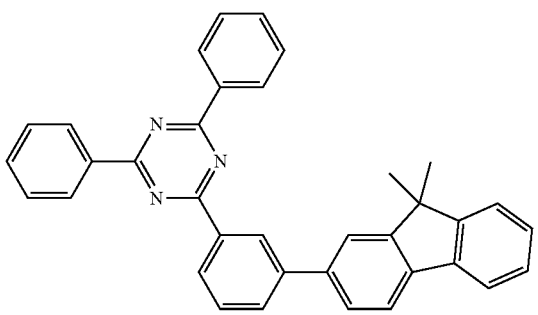

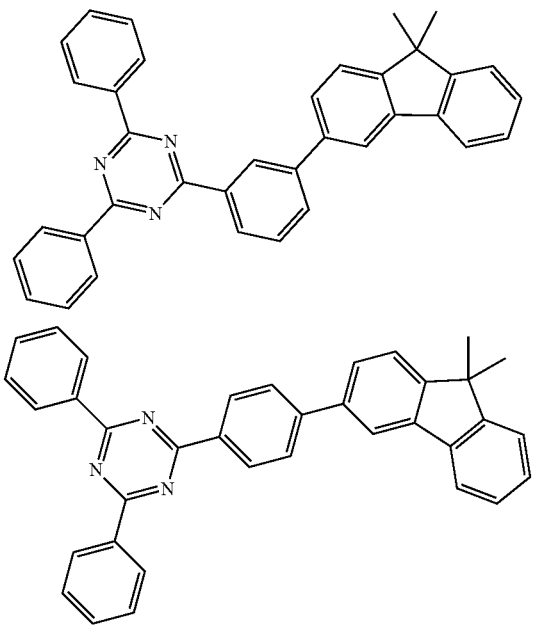

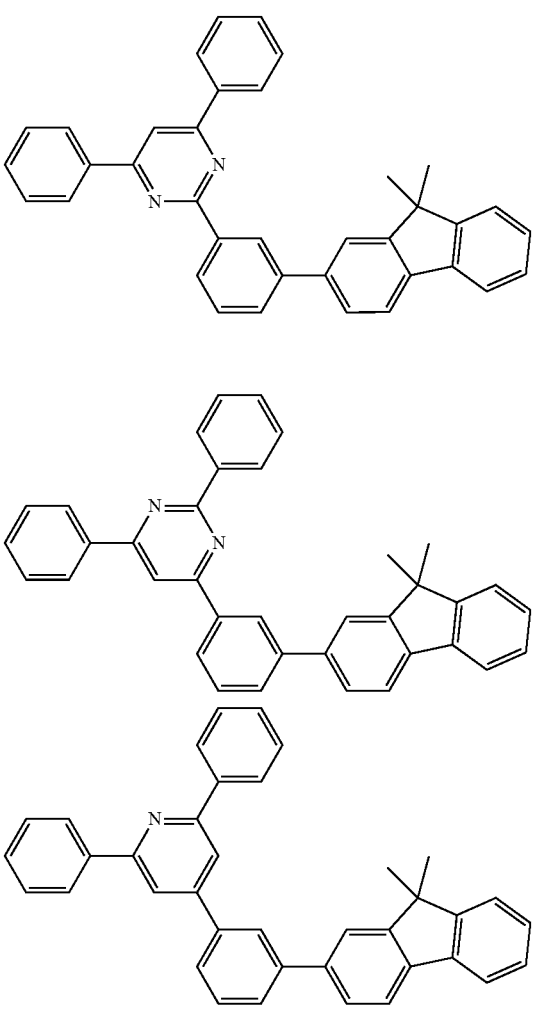

353
-continued
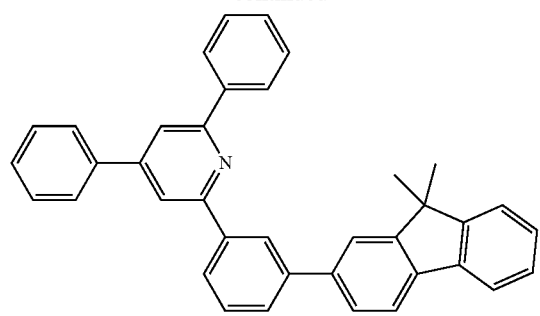
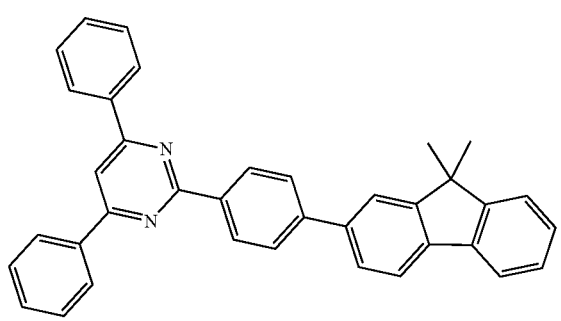
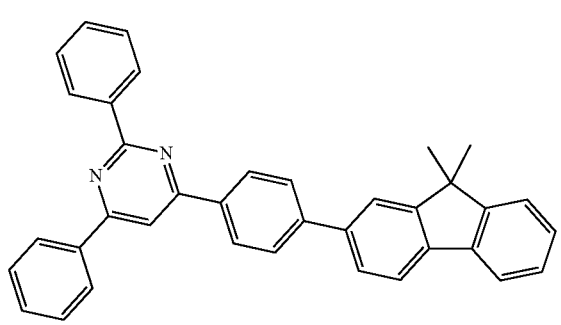
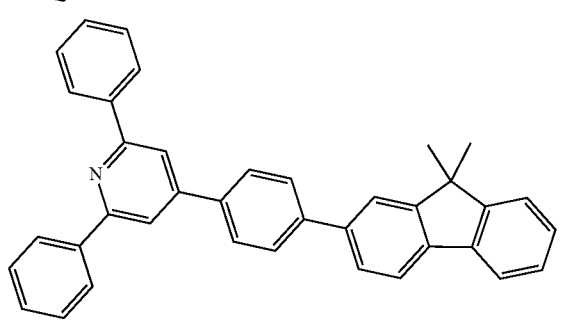
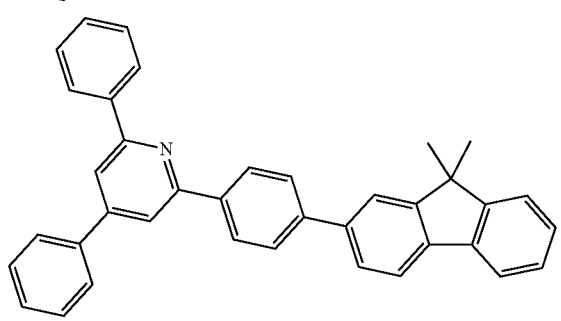
354
-continued
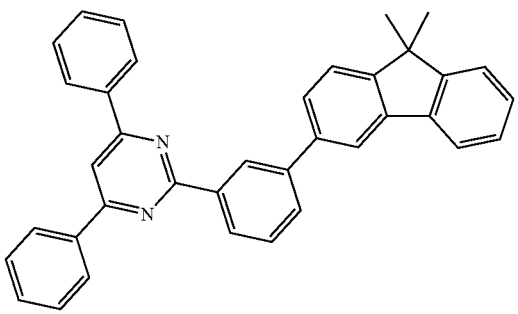
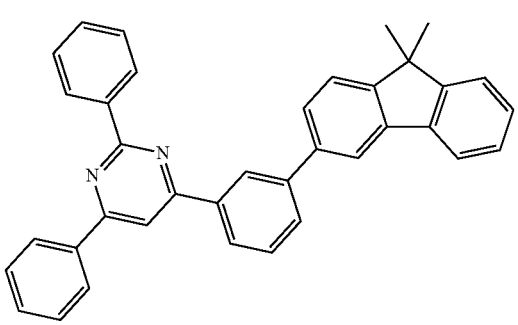
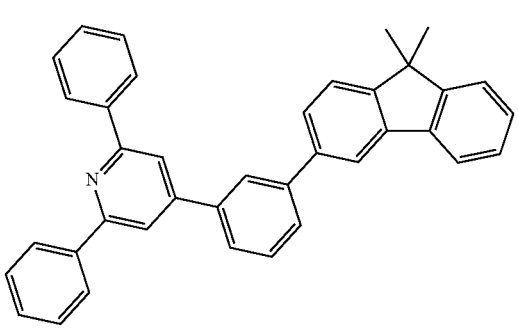
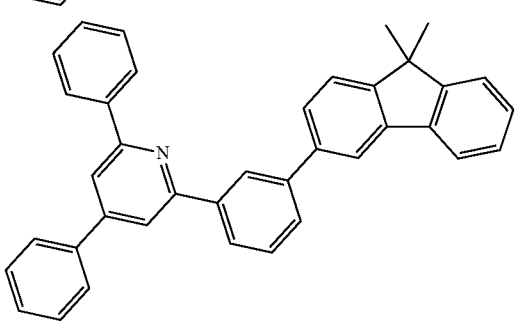
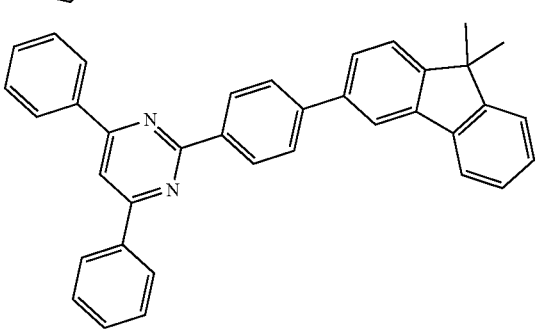

355
-continued
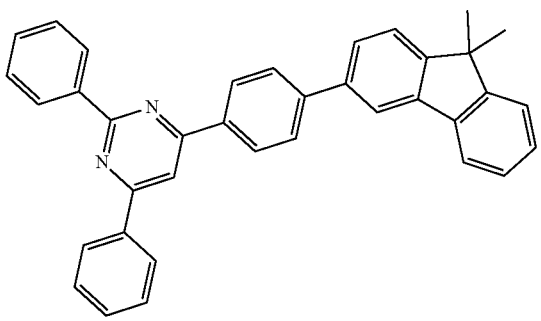
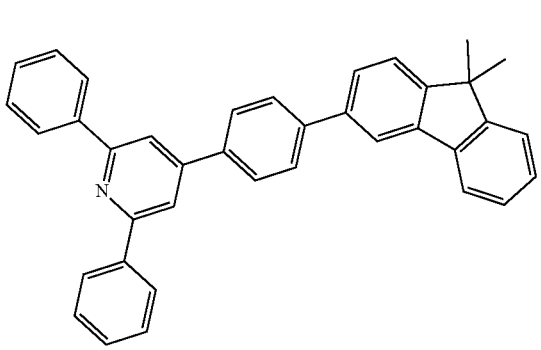
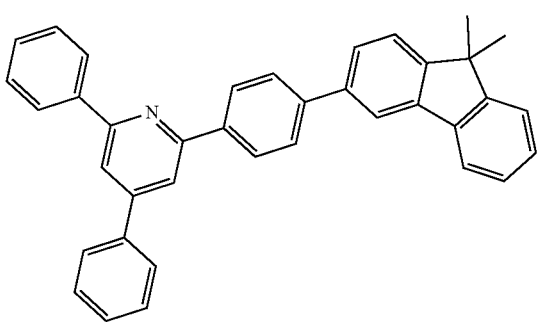
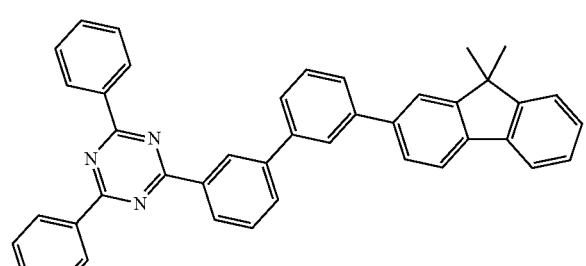
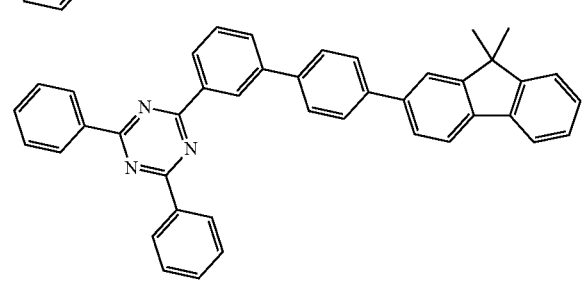
356
-continued
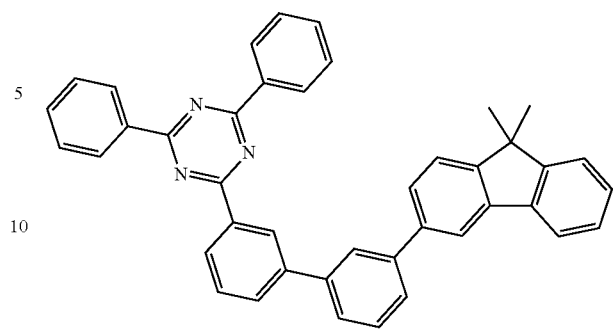
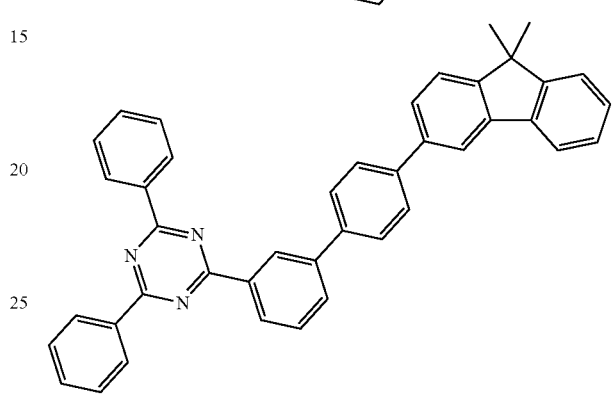
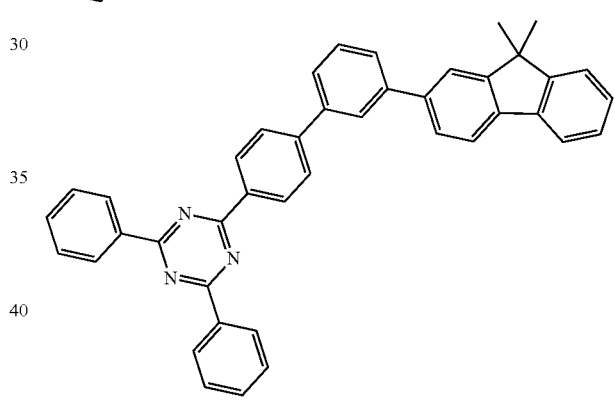
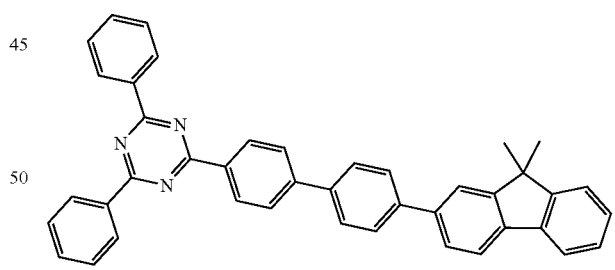
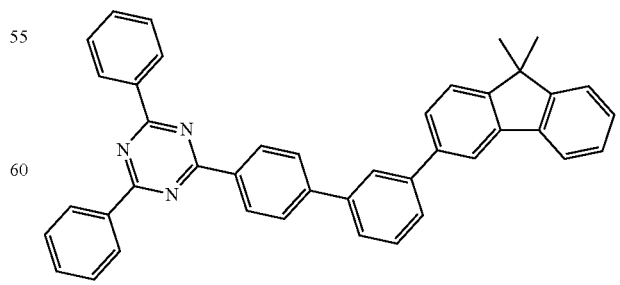

357
-continued
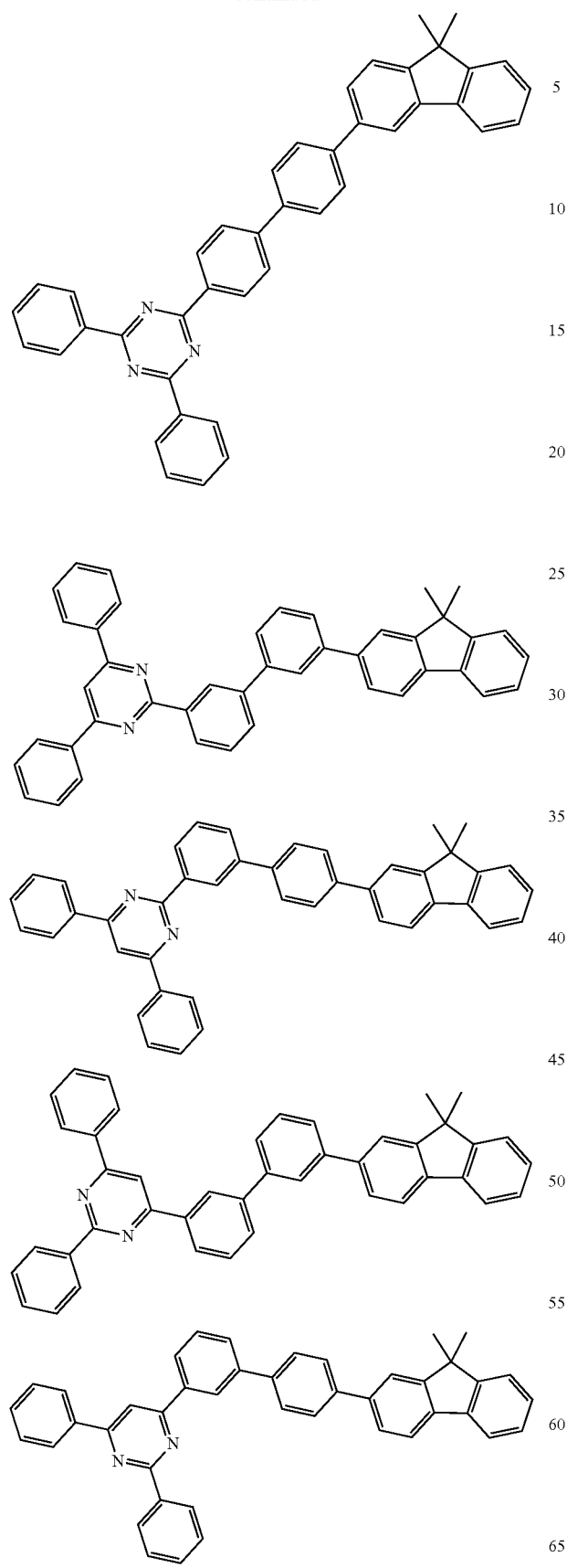
358
-continued
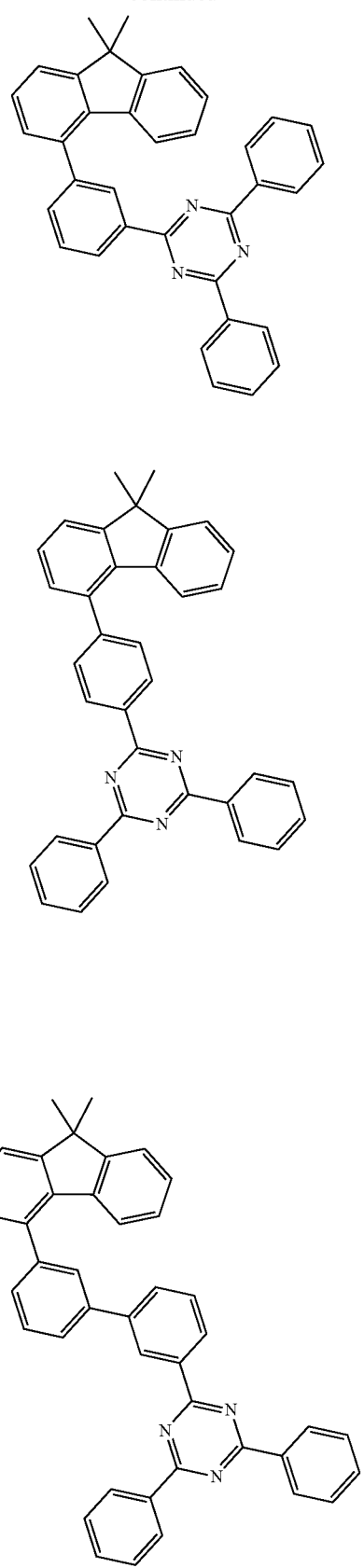

359
-continued
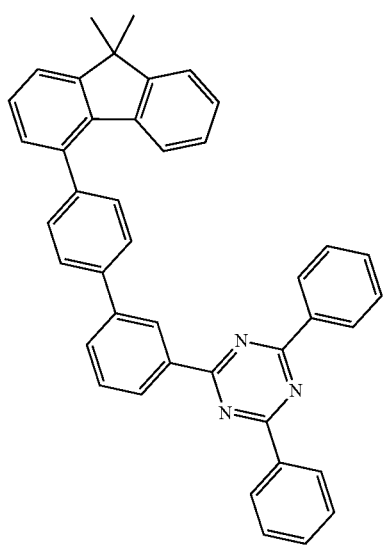 [SMILES: CC1(C)c2ccccc2-c2c(-c3ccc(-c4cccc(-c5nc(-c6ccccc6)nc(-c6ccccc6)n5)c4)cc3)cccc21]
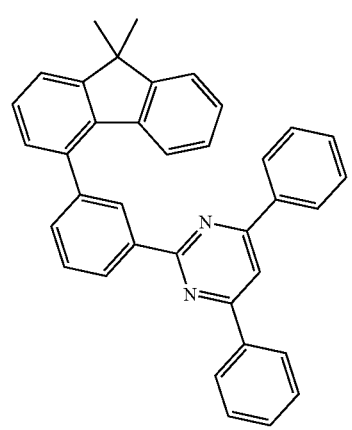
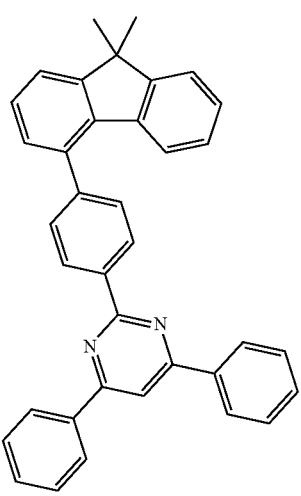
360
-continued
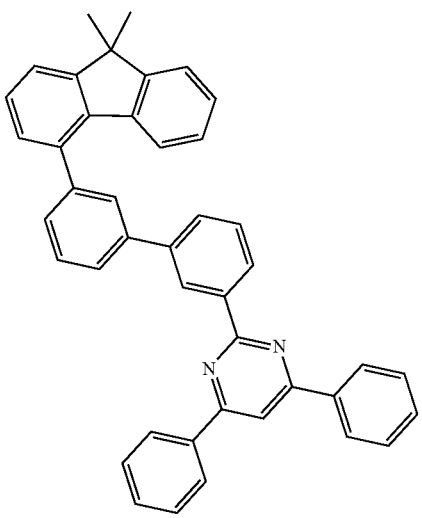
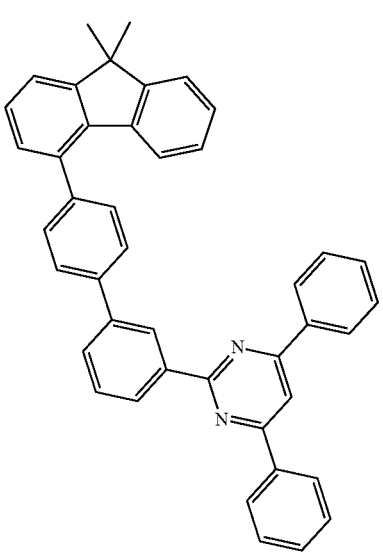 [SMILES: CC1(C)c2ccccc2-c2c(-c3ccc(-c4cccc(-c5nc(-c6ccccc6)cc(-c6ccccc6)n5)c4)cc3)cccc21]
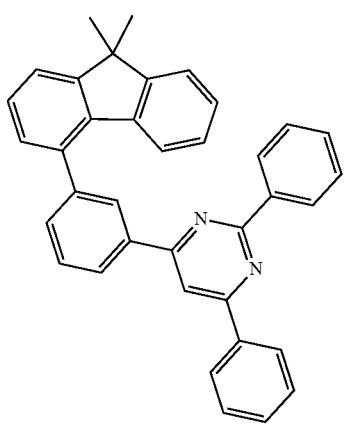

361
-continued
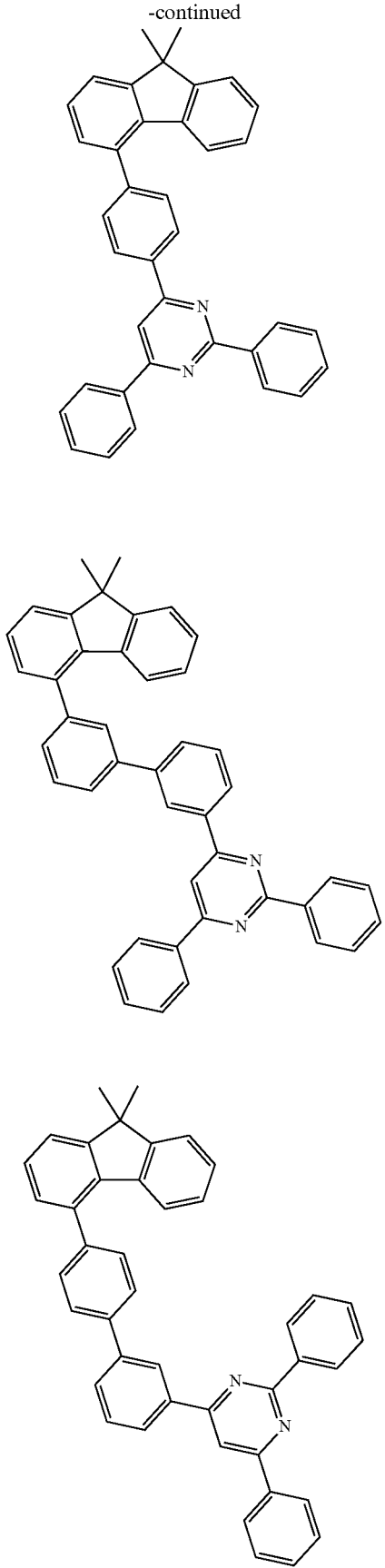
362
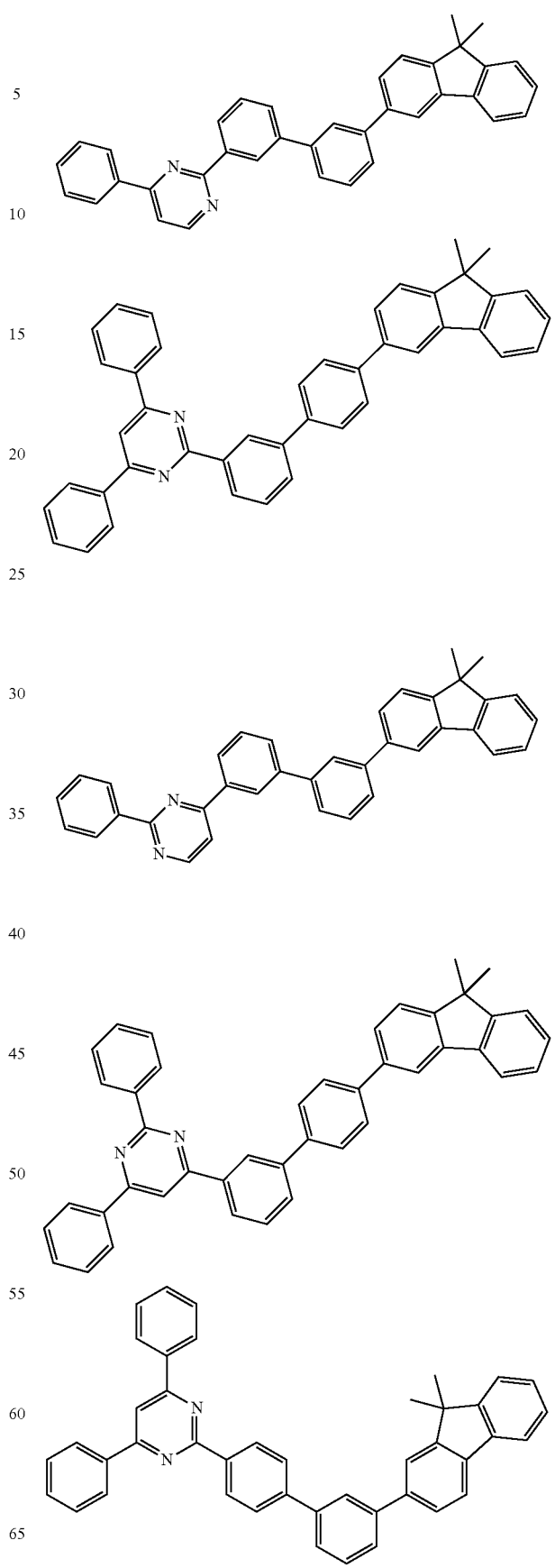

363
-continued
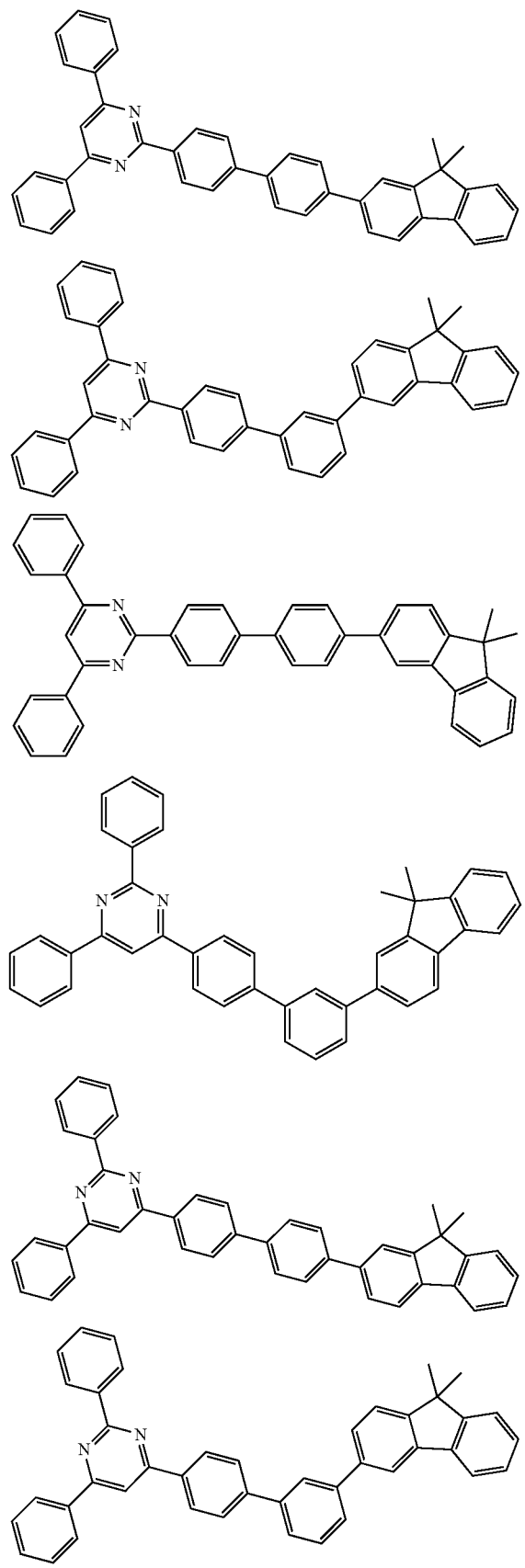
364
-continued
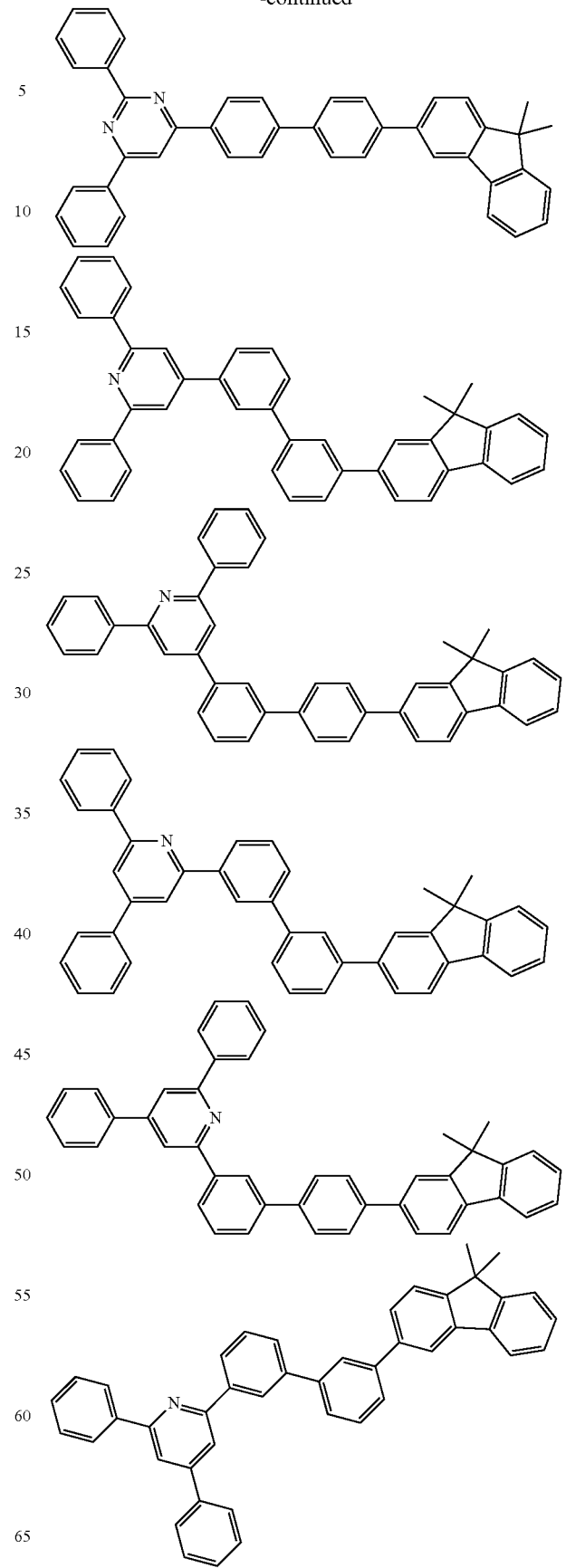

365
-continued
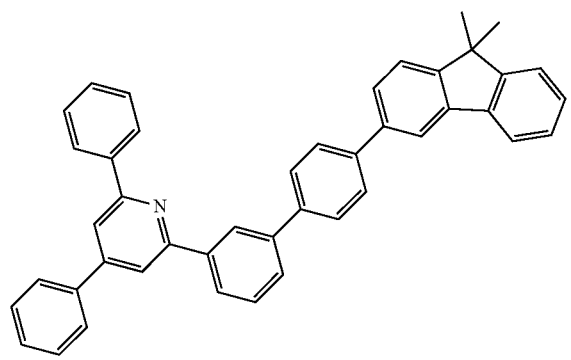
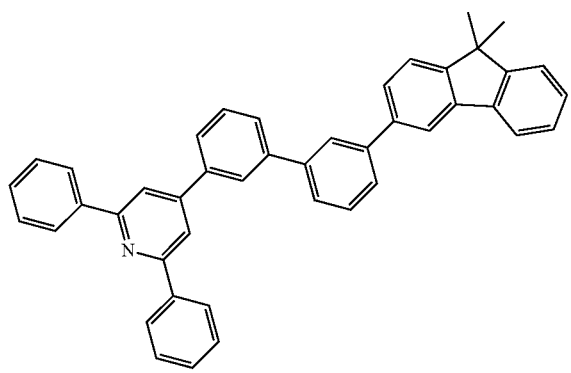
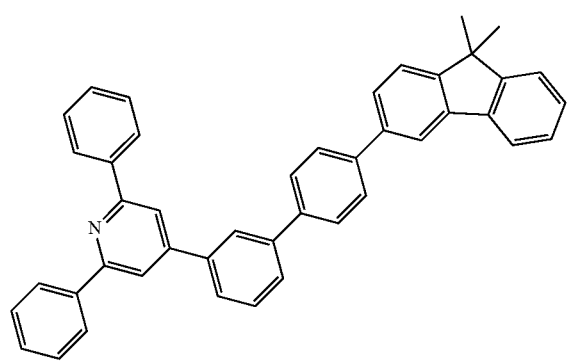
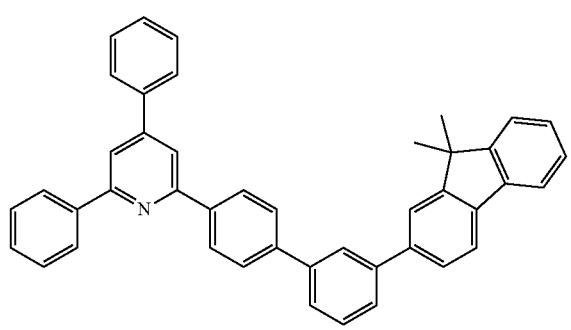
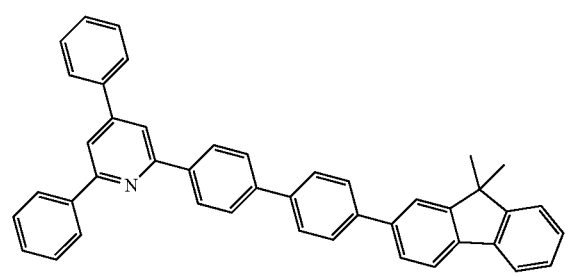
366
-continued
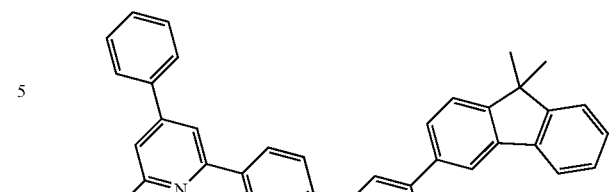
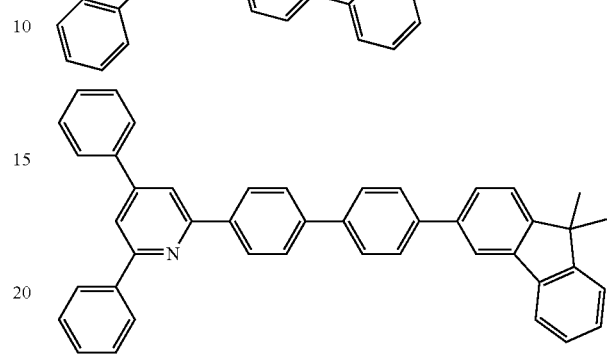
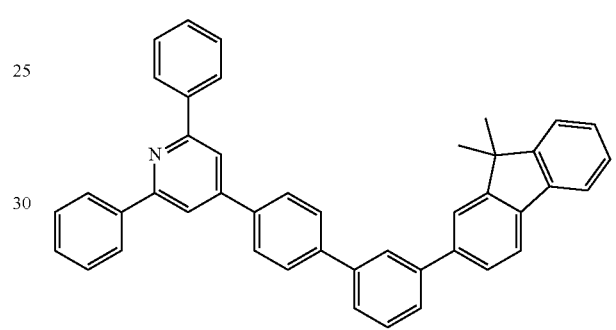
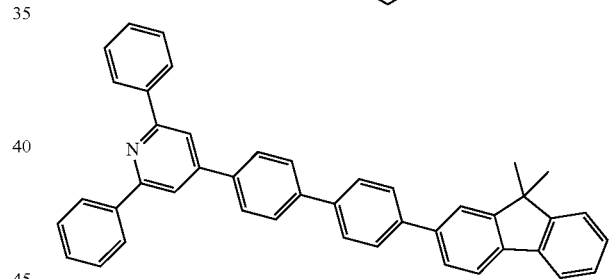
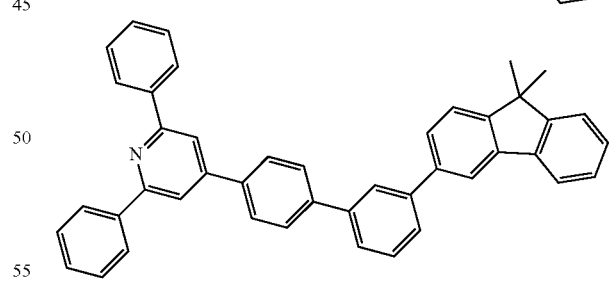
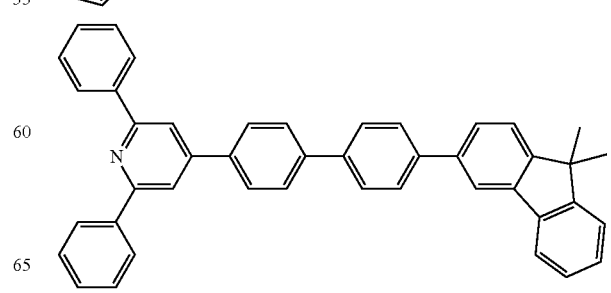

367
-continued
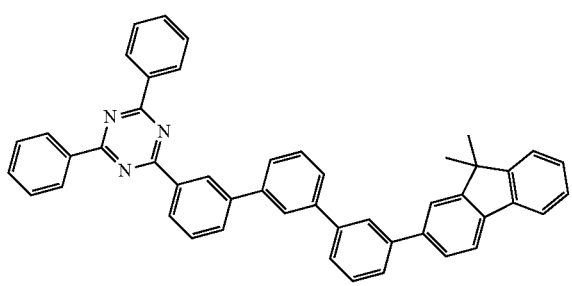
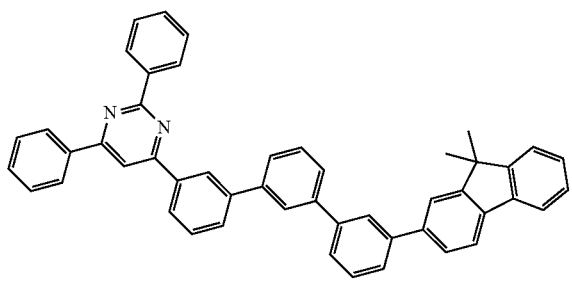
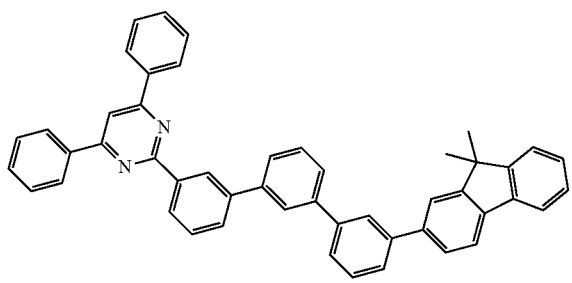
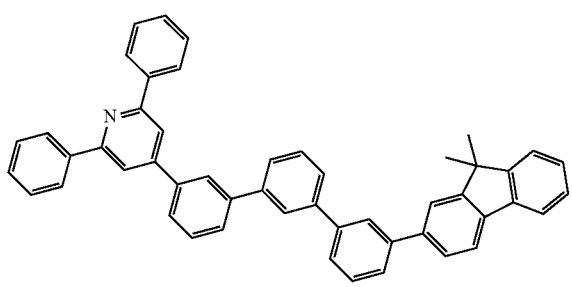
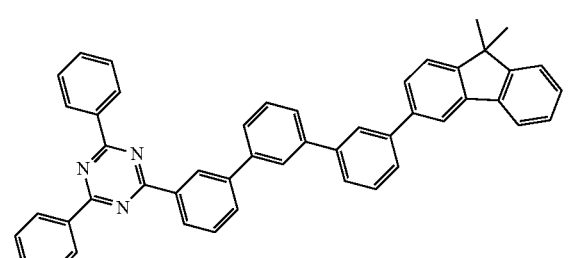
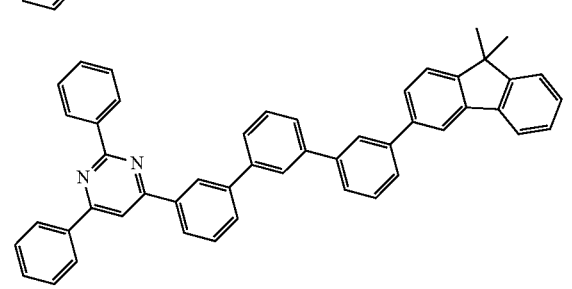
368
-continued
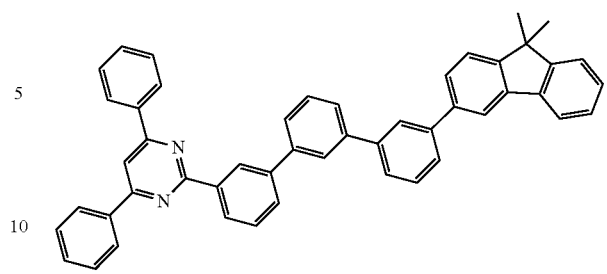
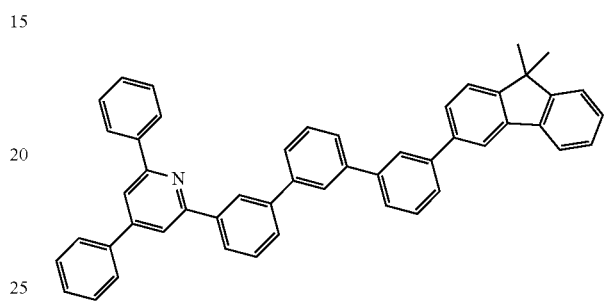
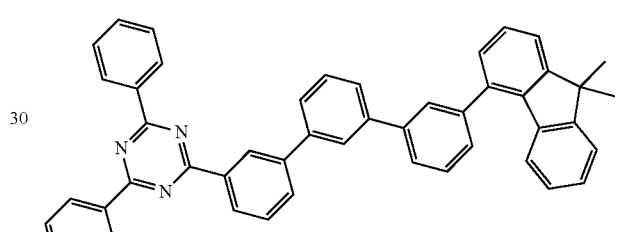
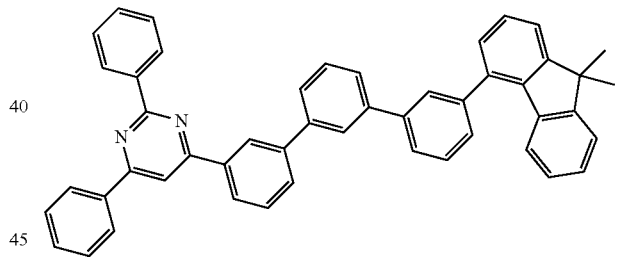
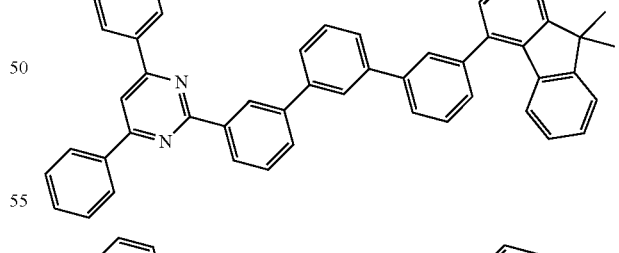
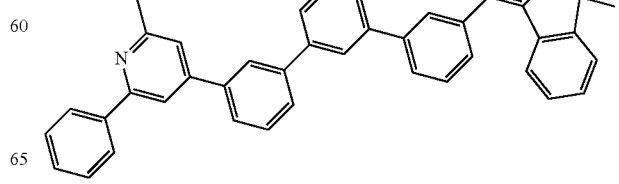

369
-continued
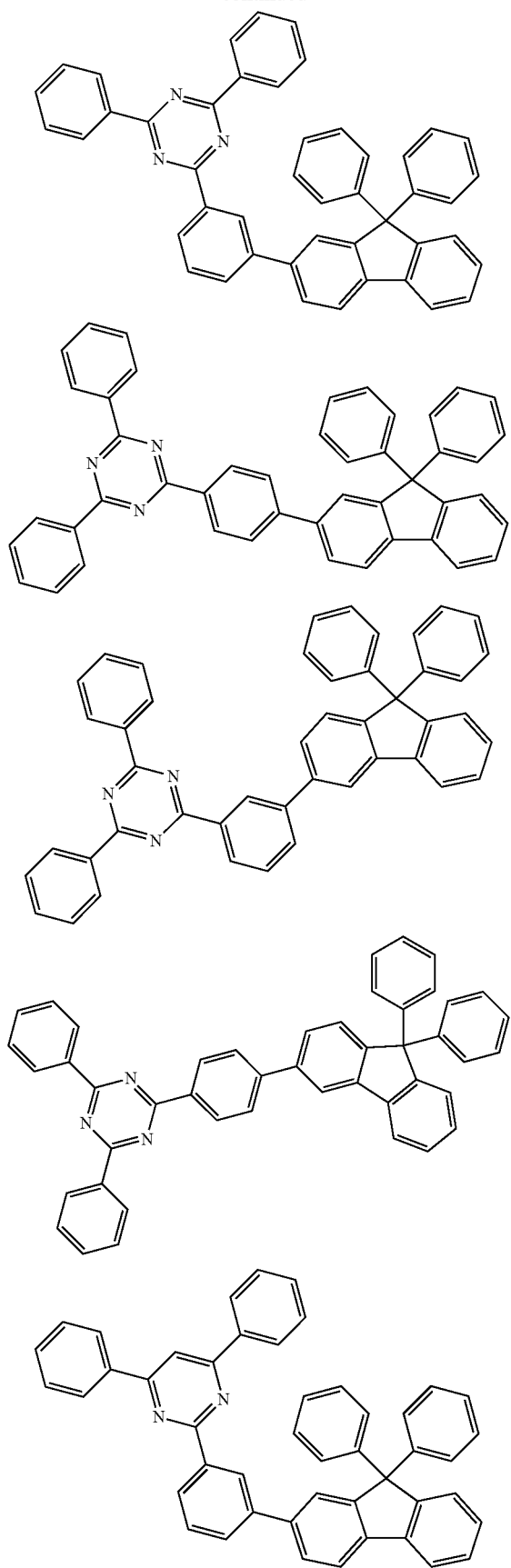
370
-continued
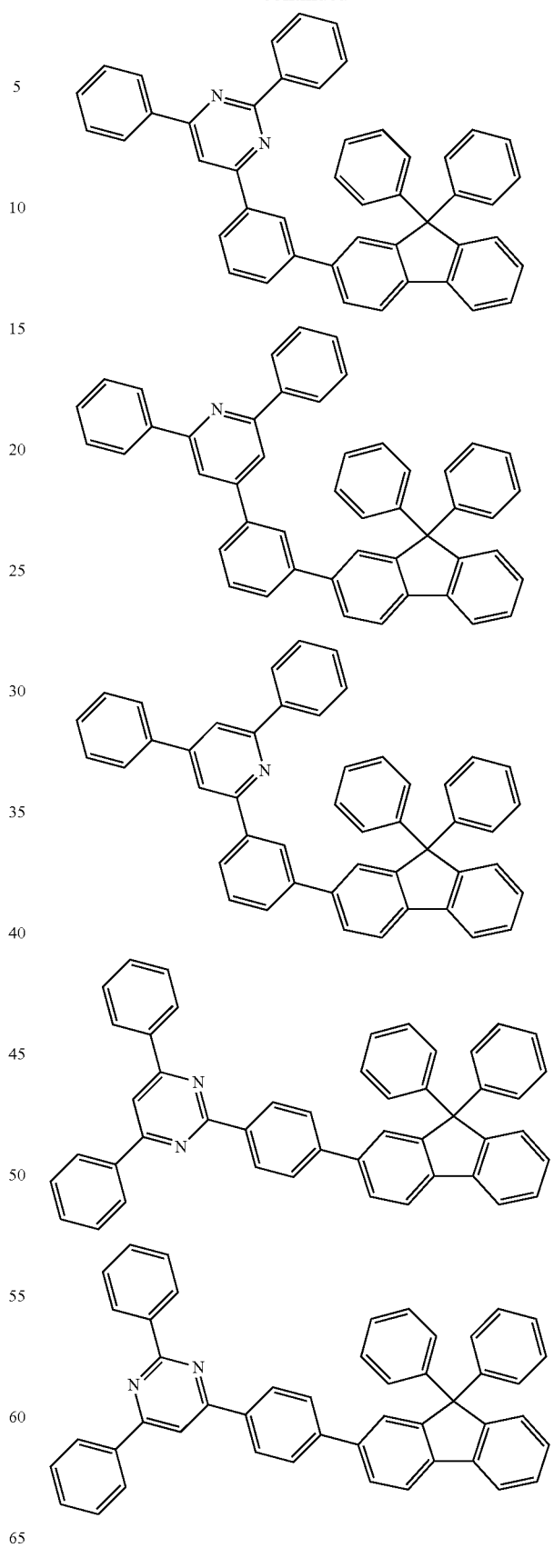

371
-continued
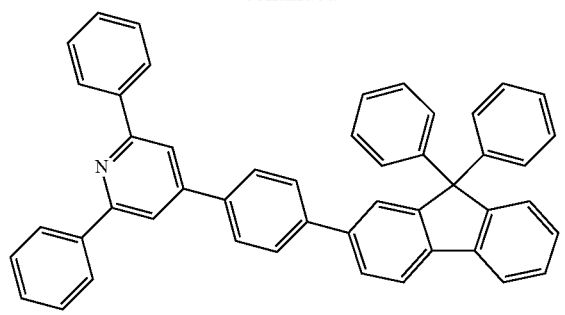
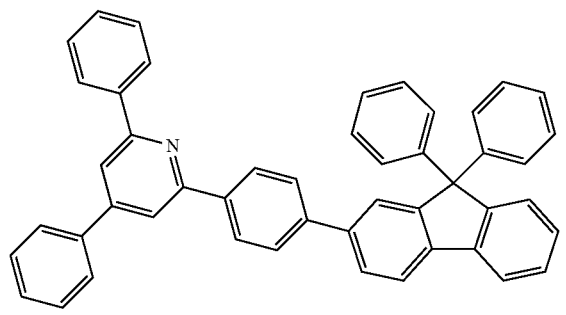
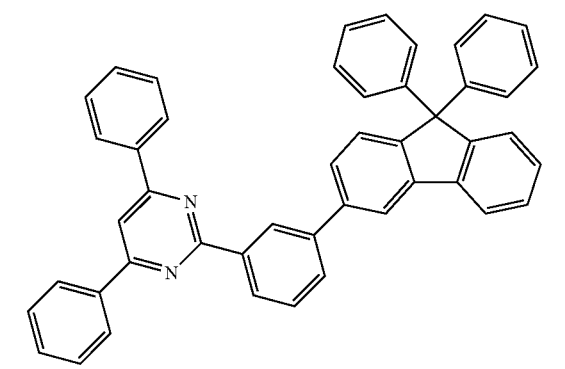
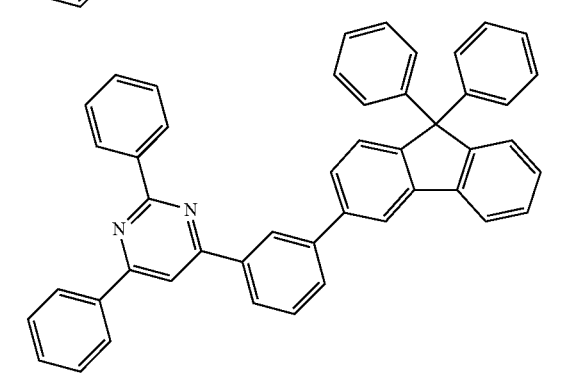
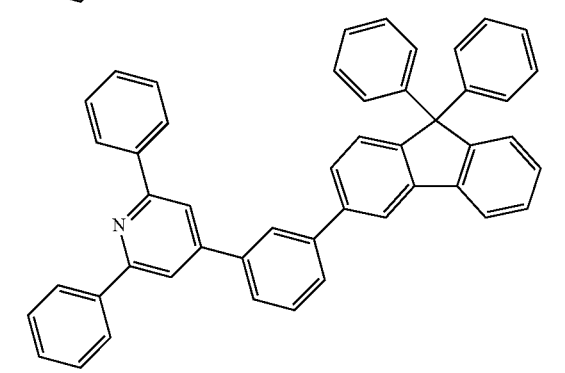
372
-continued
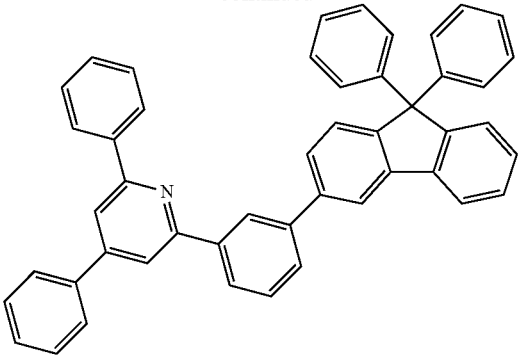
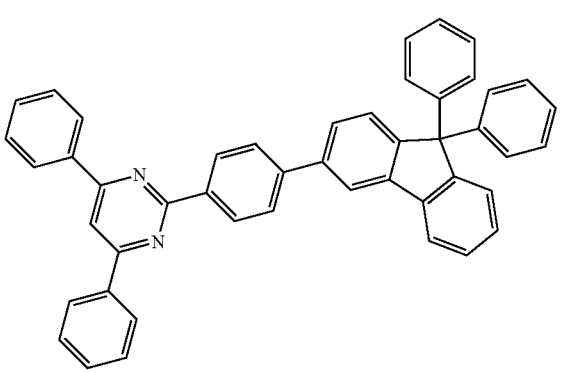
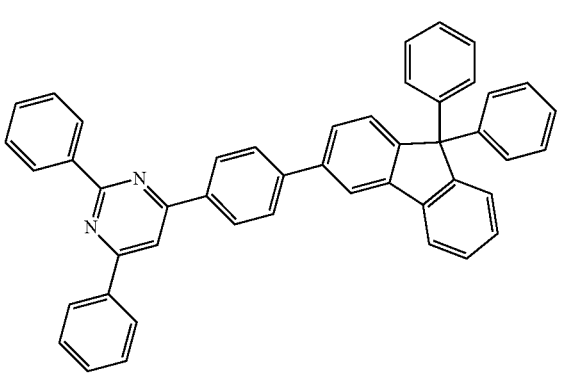
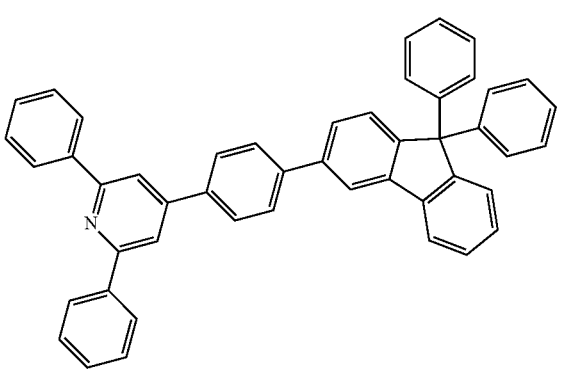

373
-continued
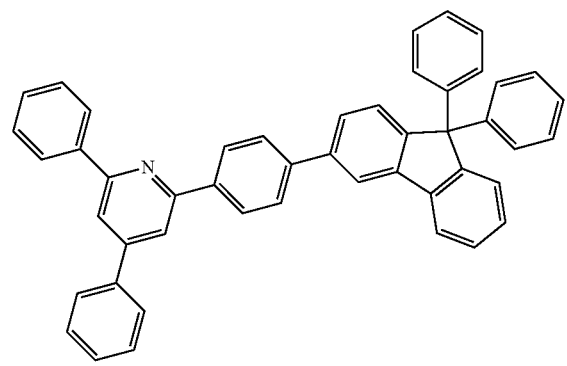
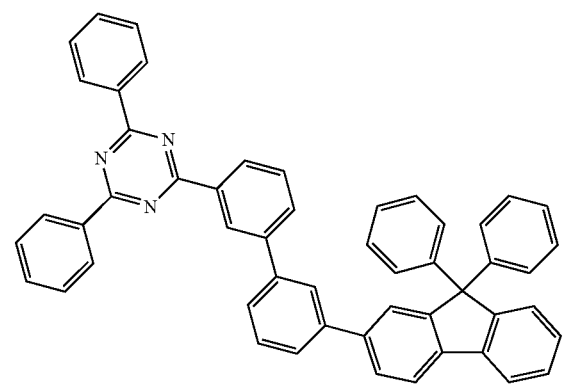
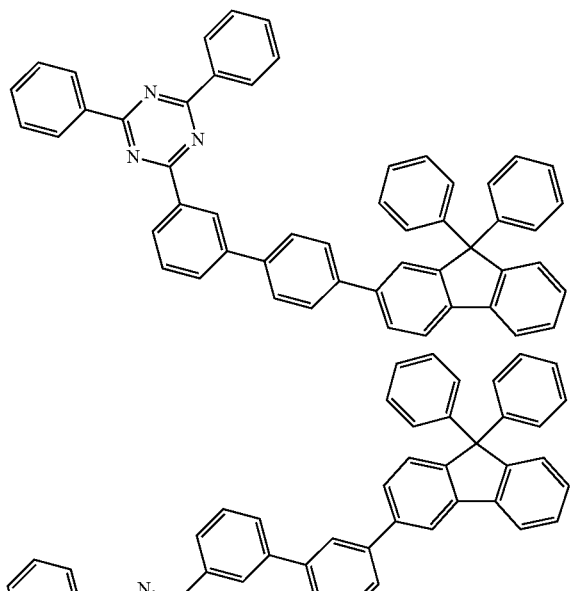
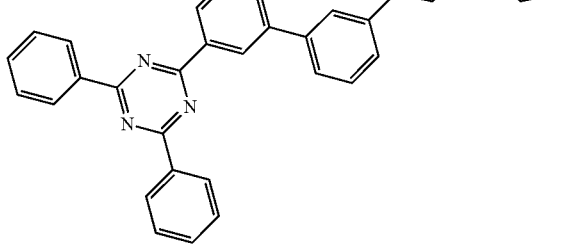
374
-continued
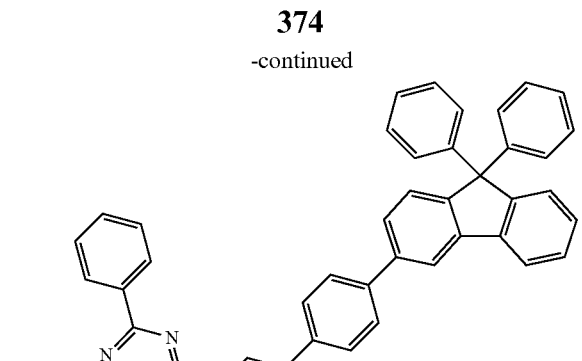
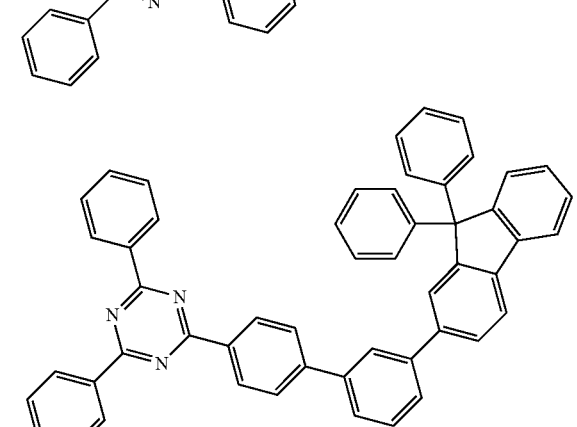
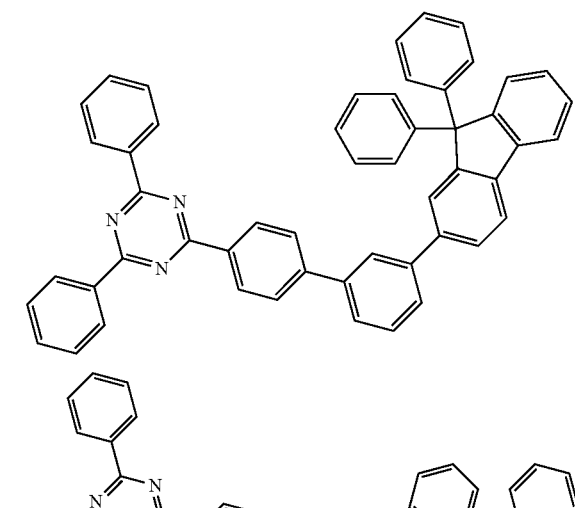
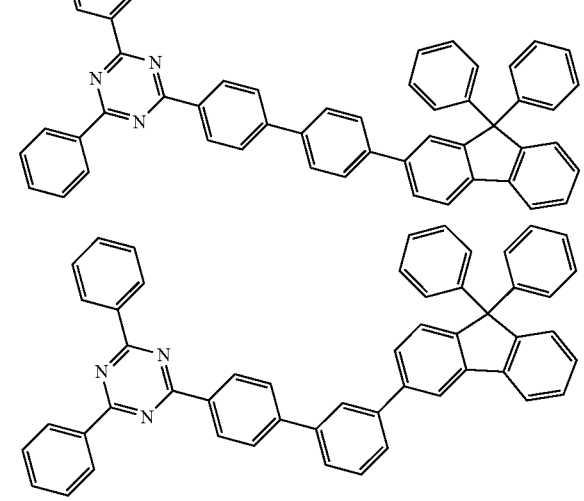
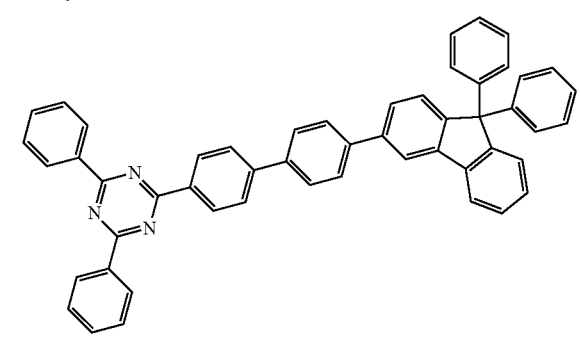

375
-continued
376
-continued
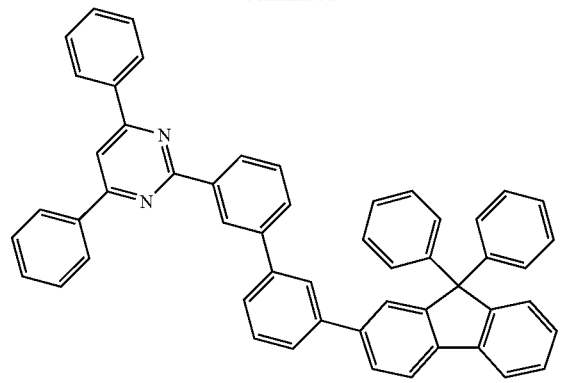
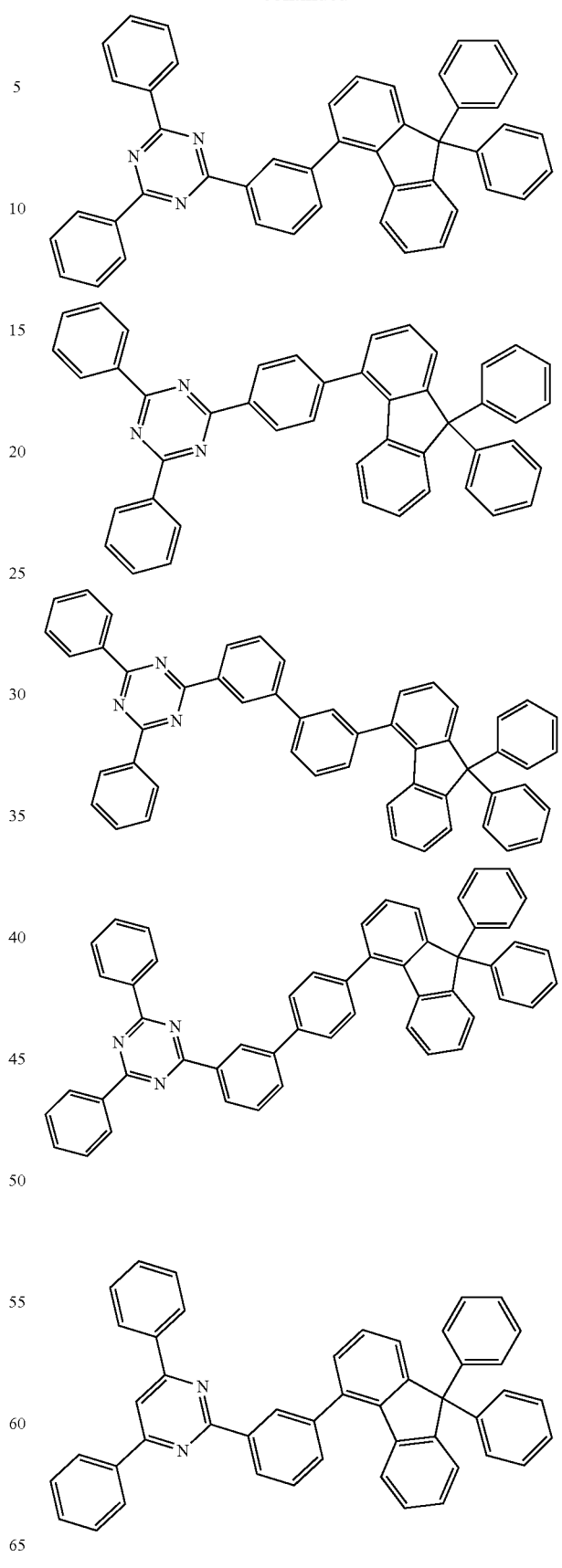

377
-continued
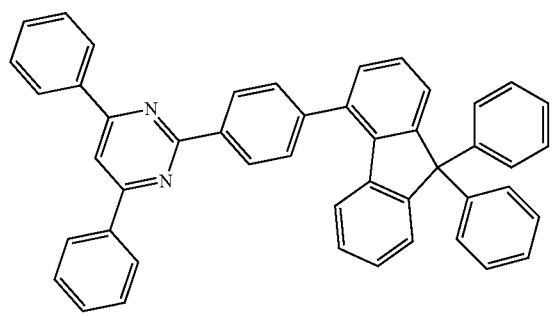
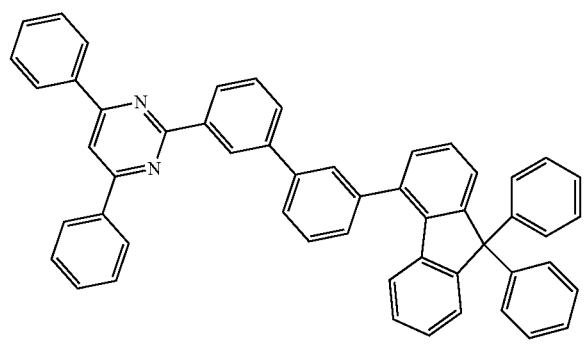
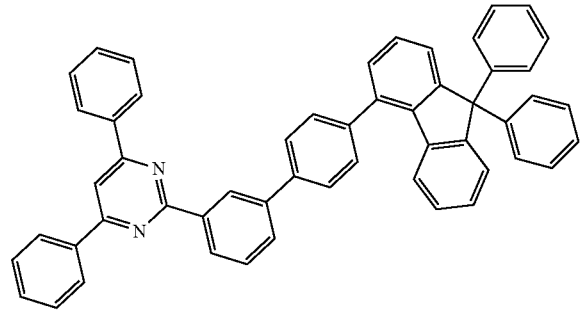
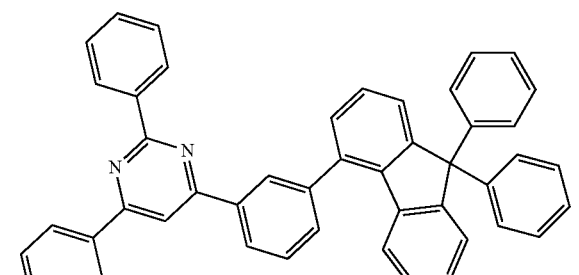
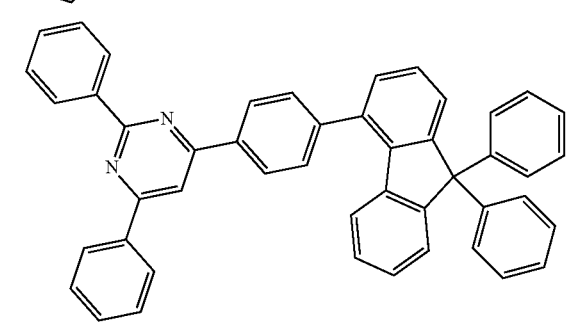
378
-continued
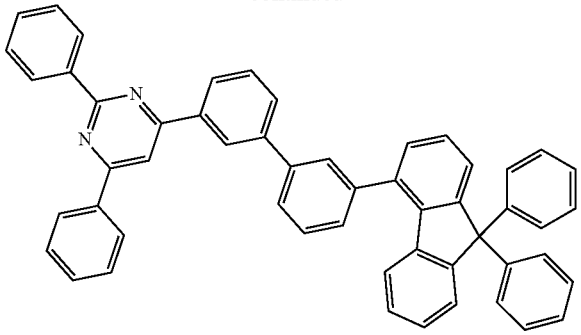
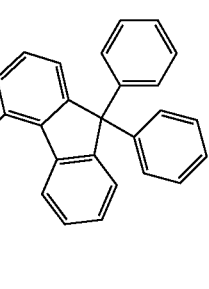
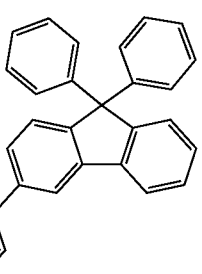
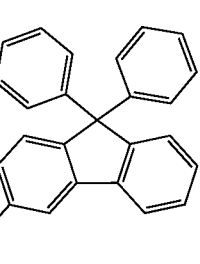

379
-continued
380
-continued
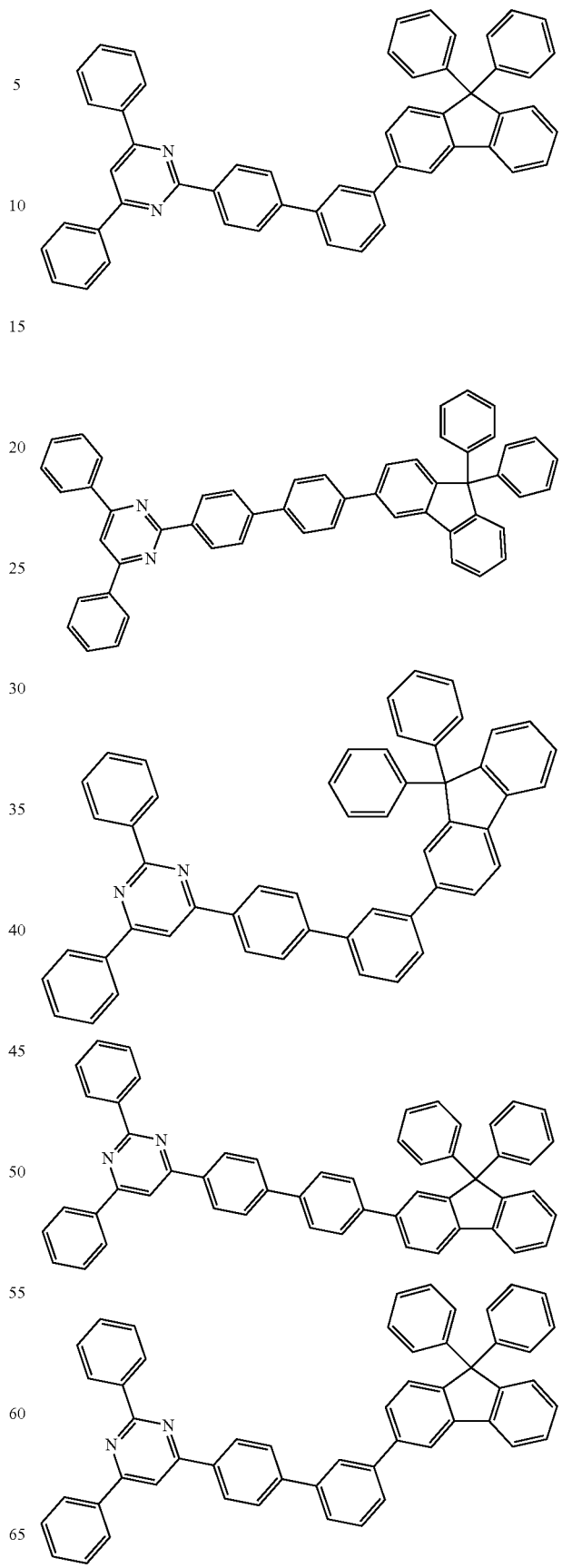

381
-continued
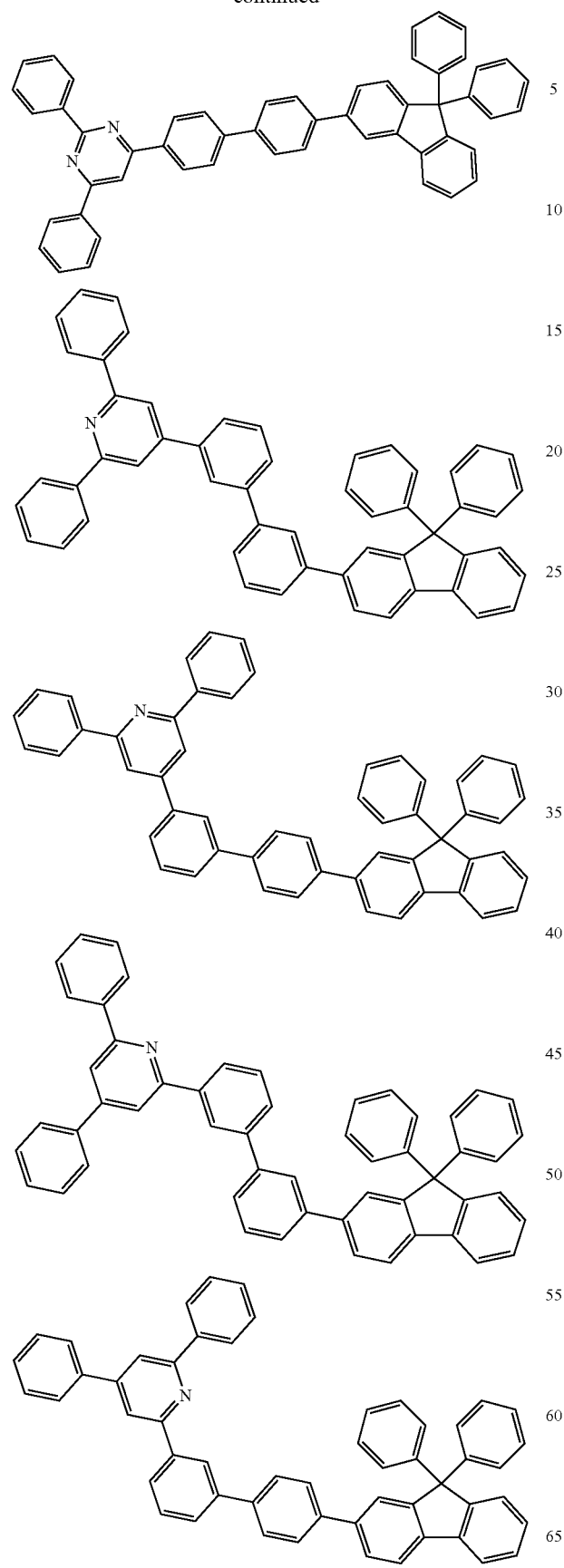
382
-continued
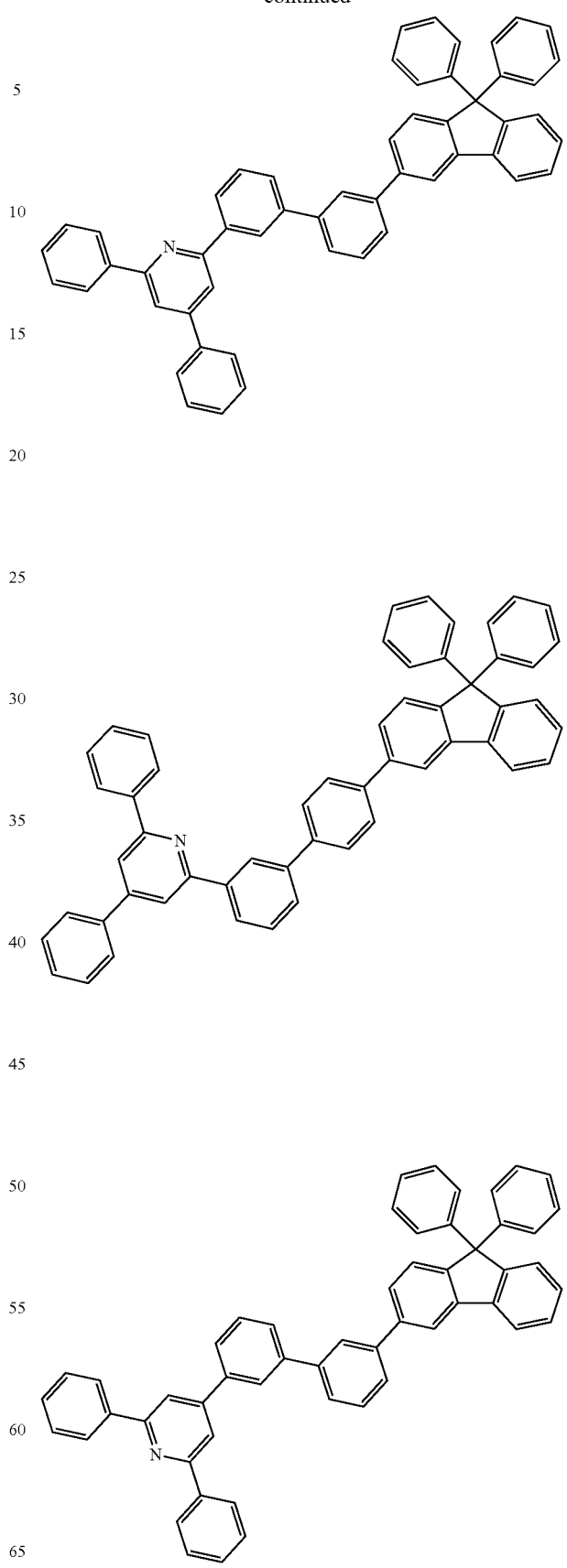

383
-continued
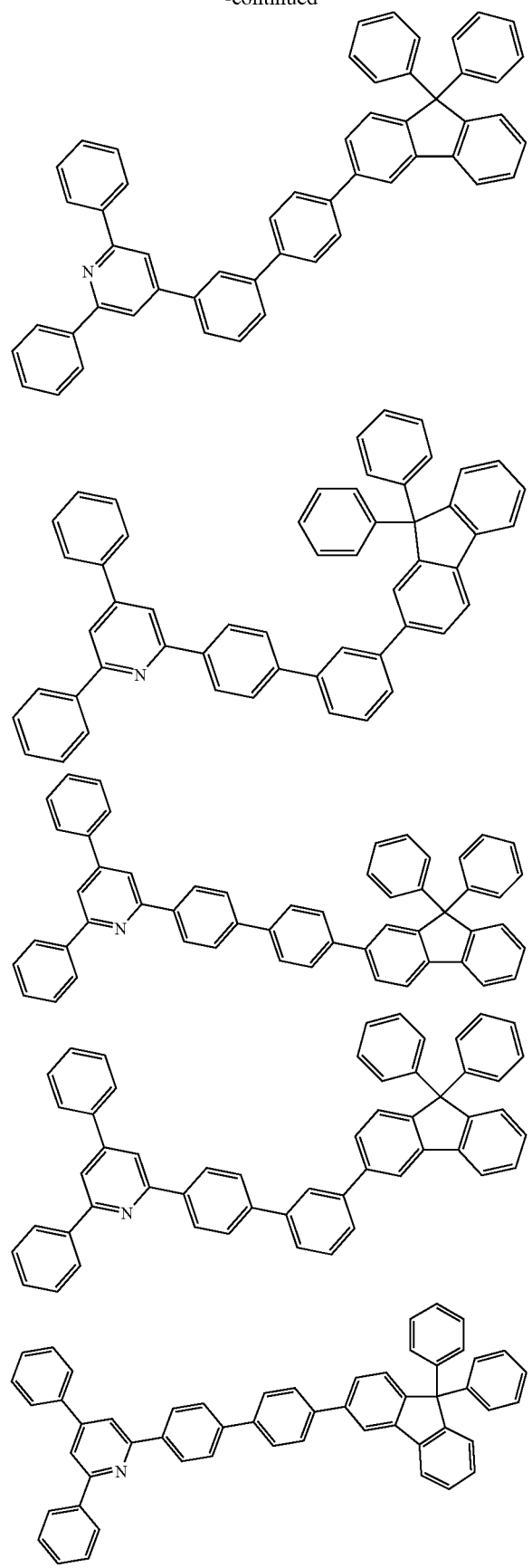
384
-continued
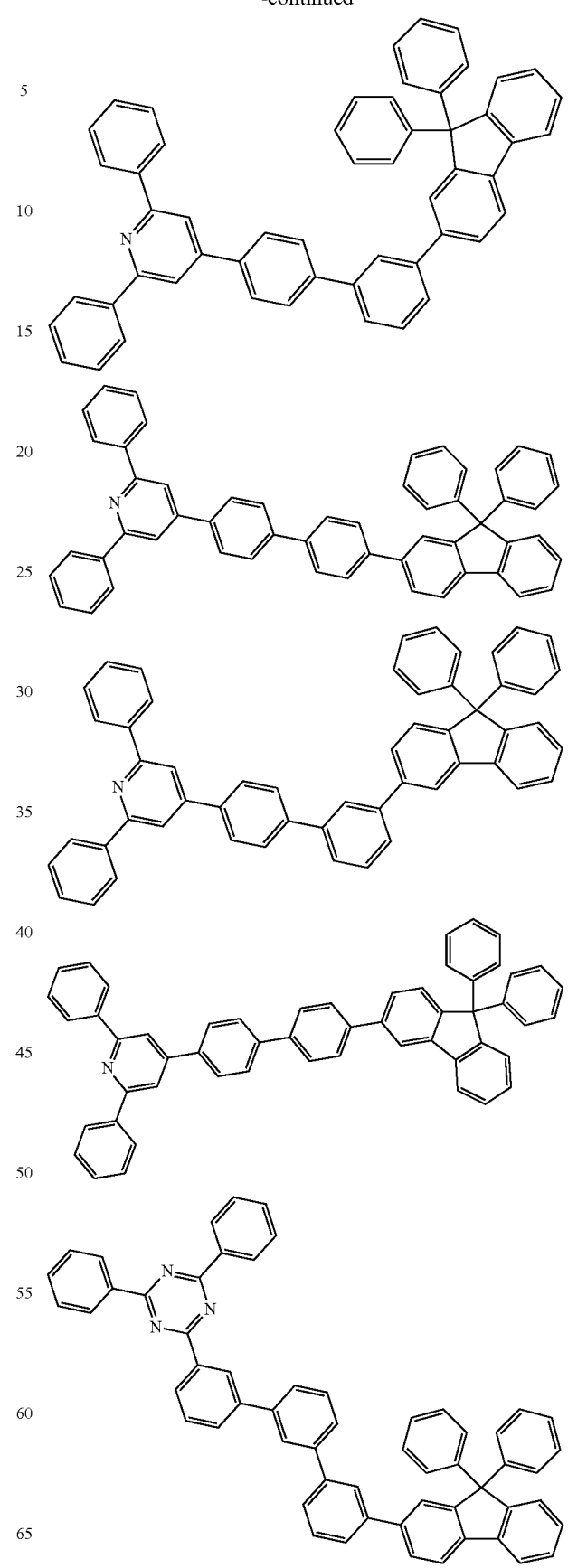

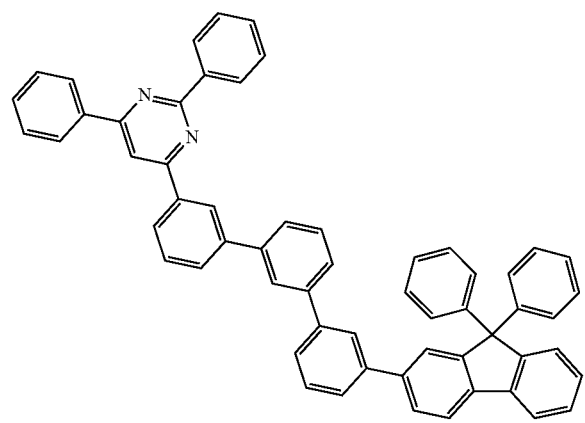
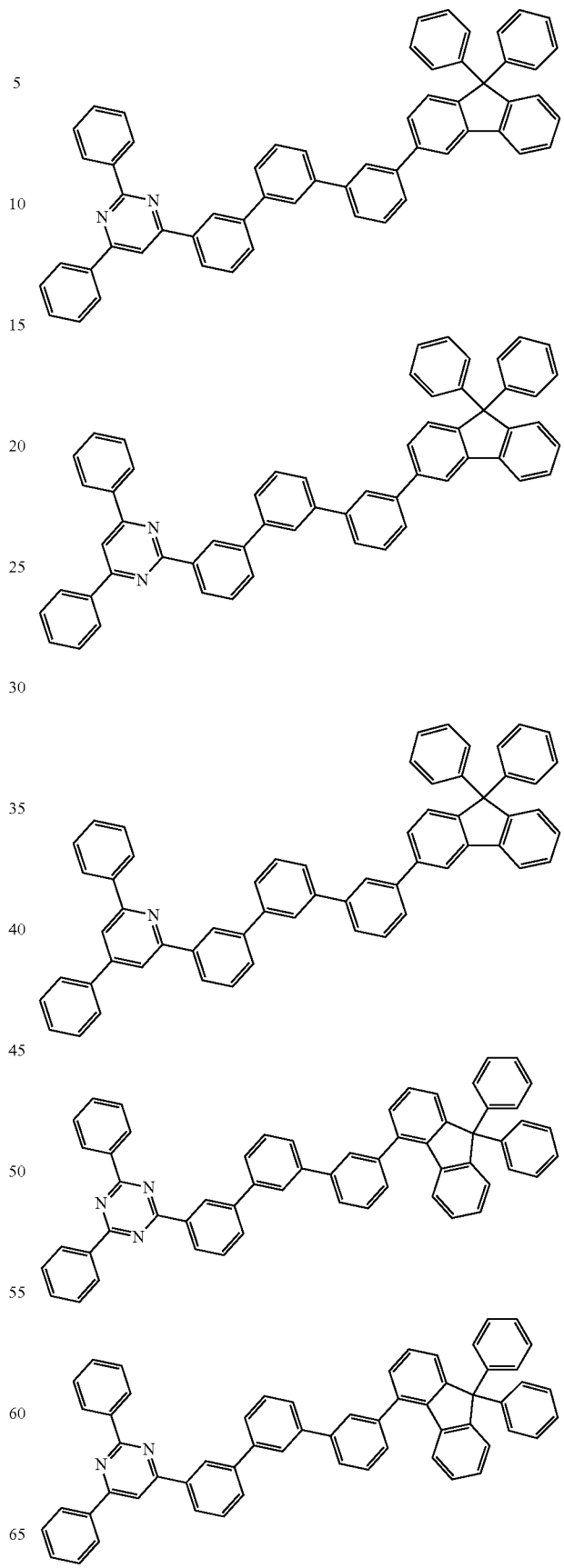

387
-continued
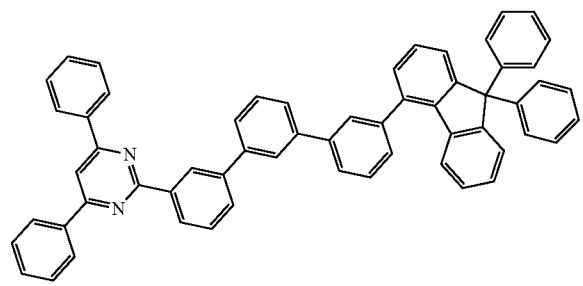

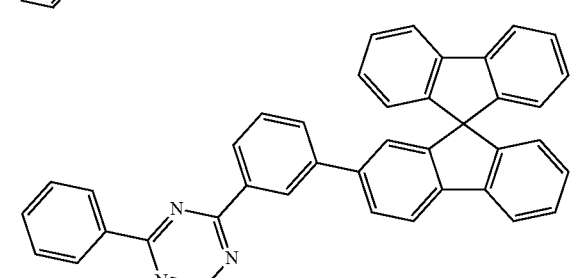
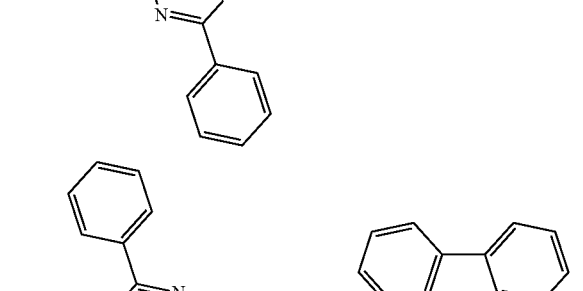
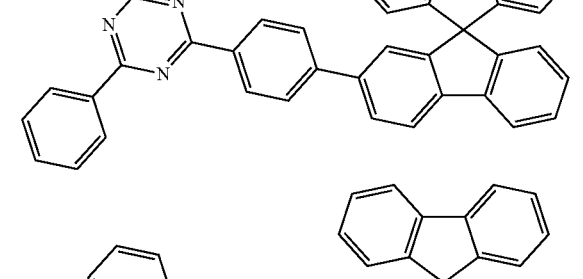
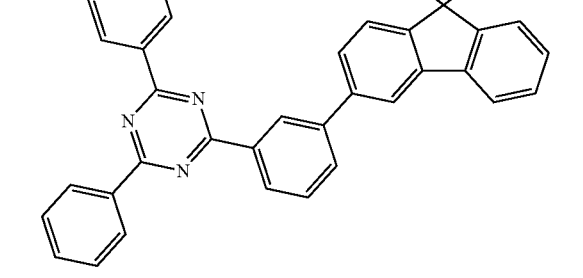
388
-continued
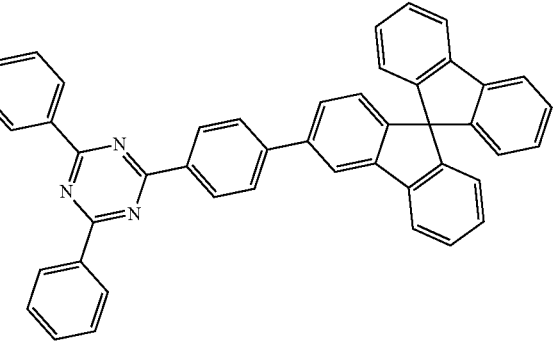
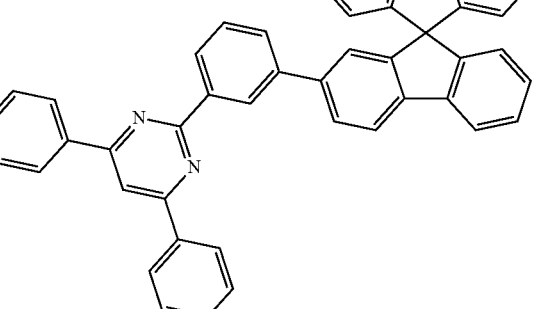
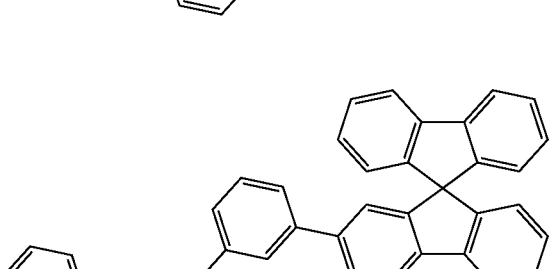
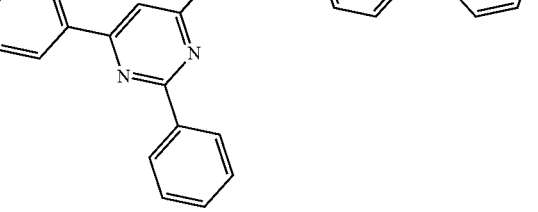
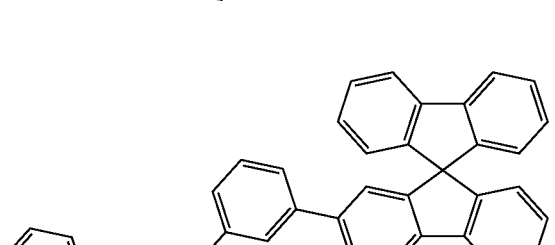
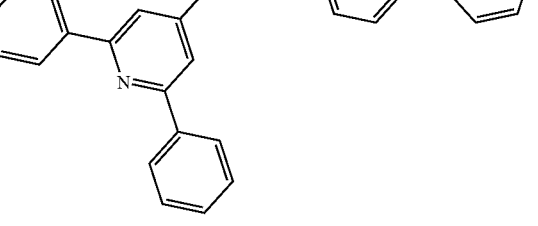

389
-continued
390
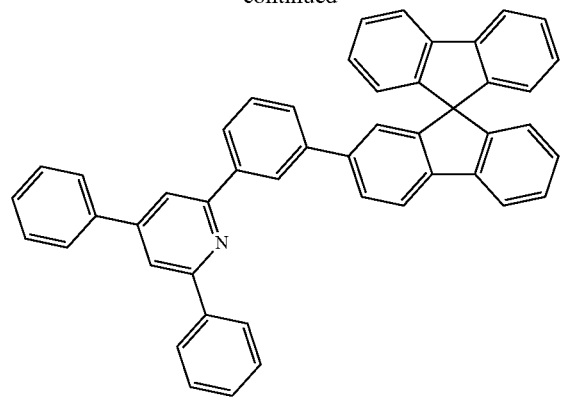
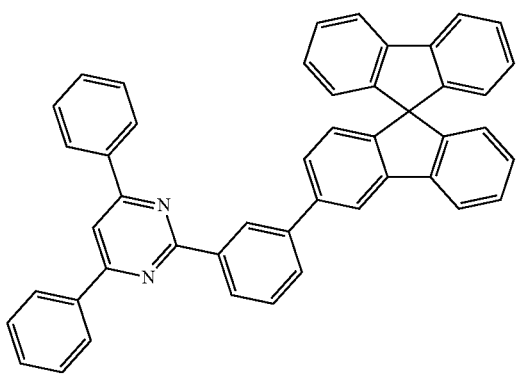
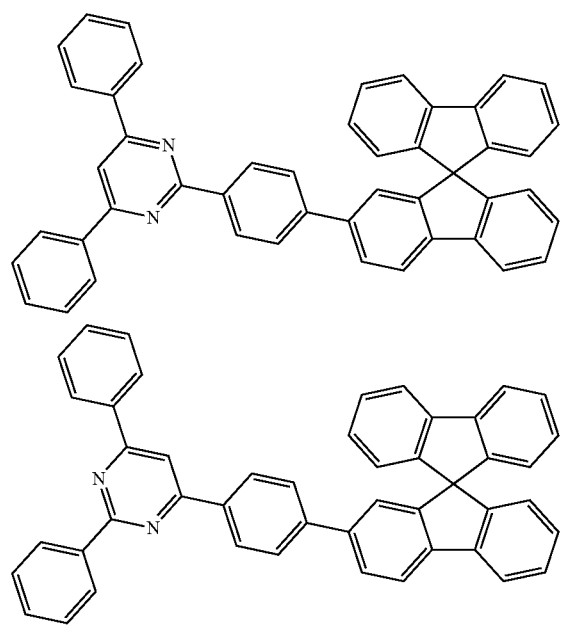
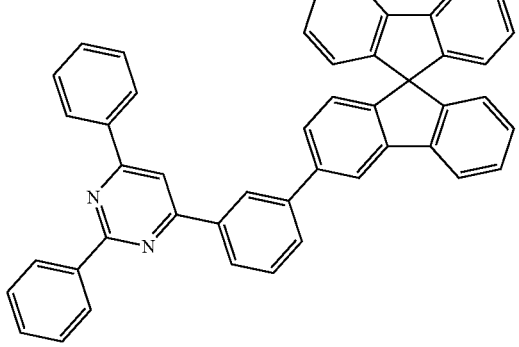
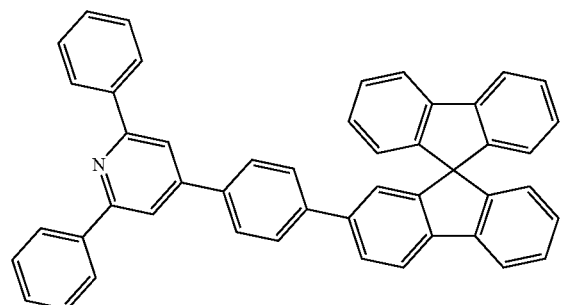

391
-continued
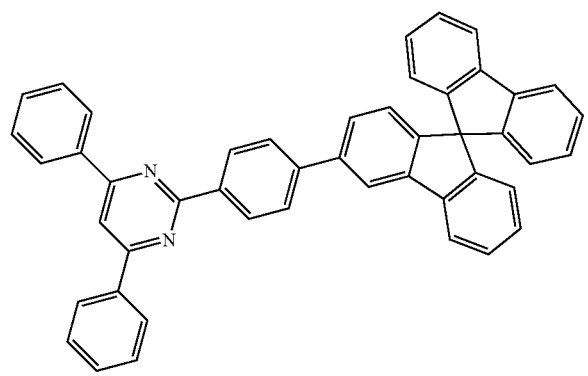
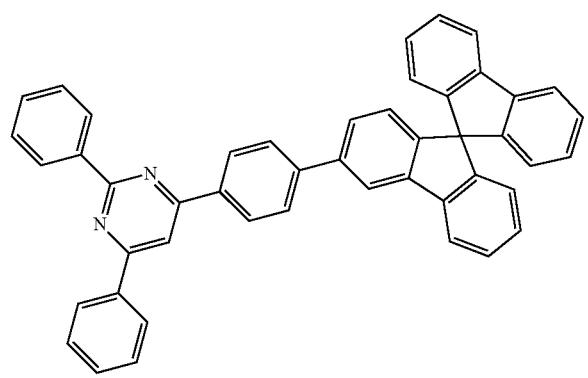
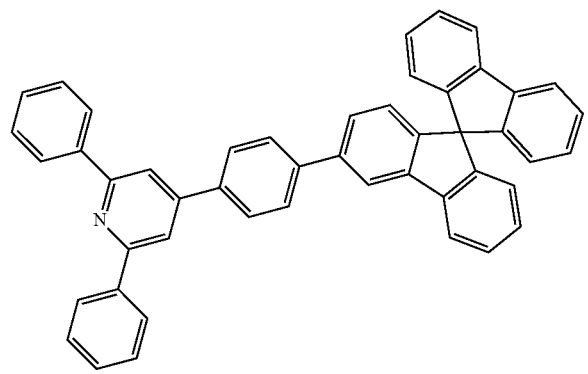
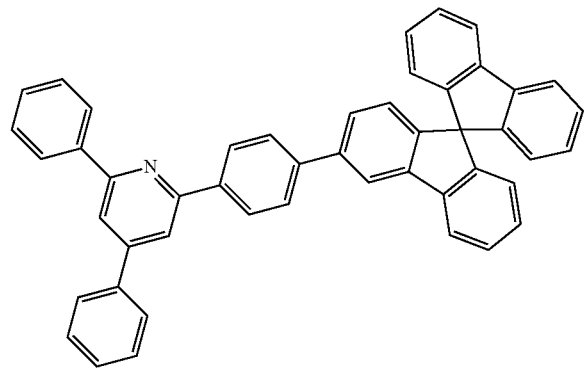
392
-continued
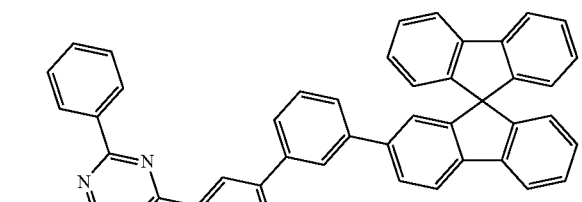
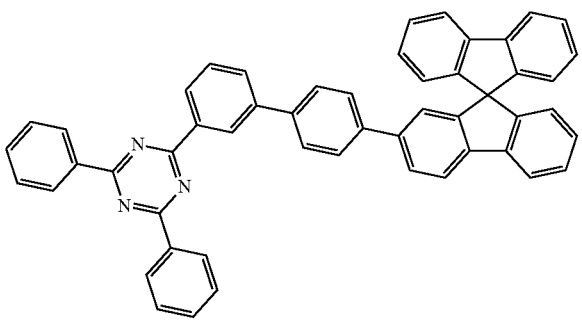
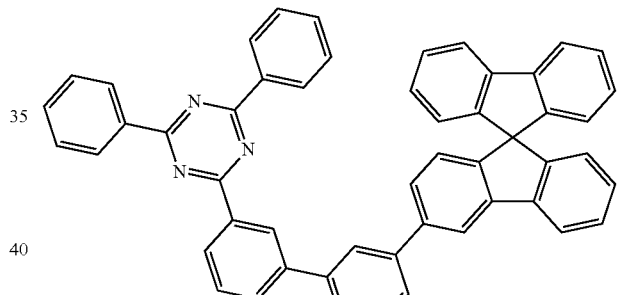
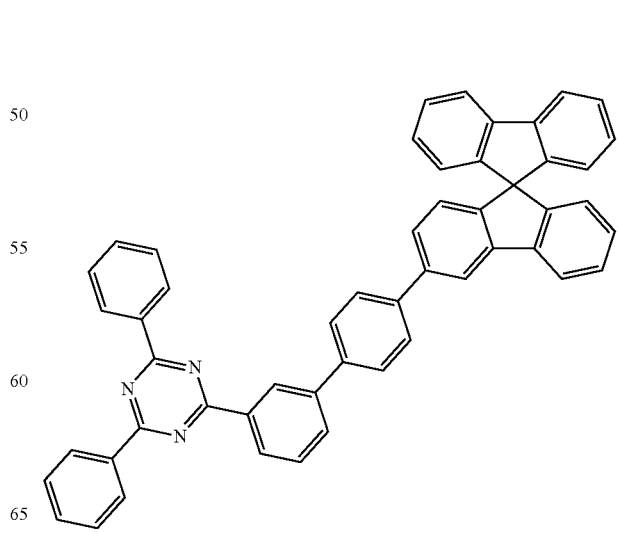

393
-continued
394
-continued
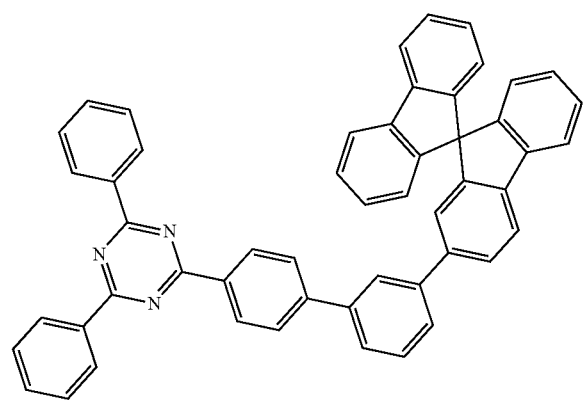
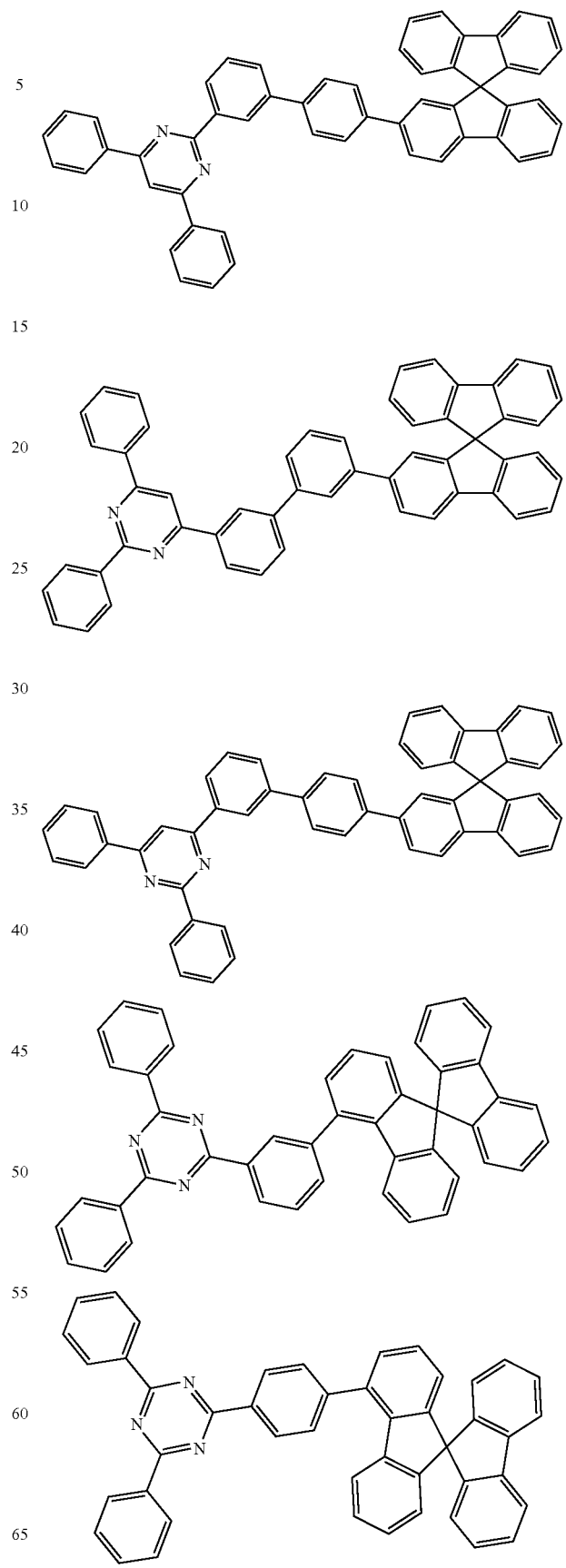

395
-continued
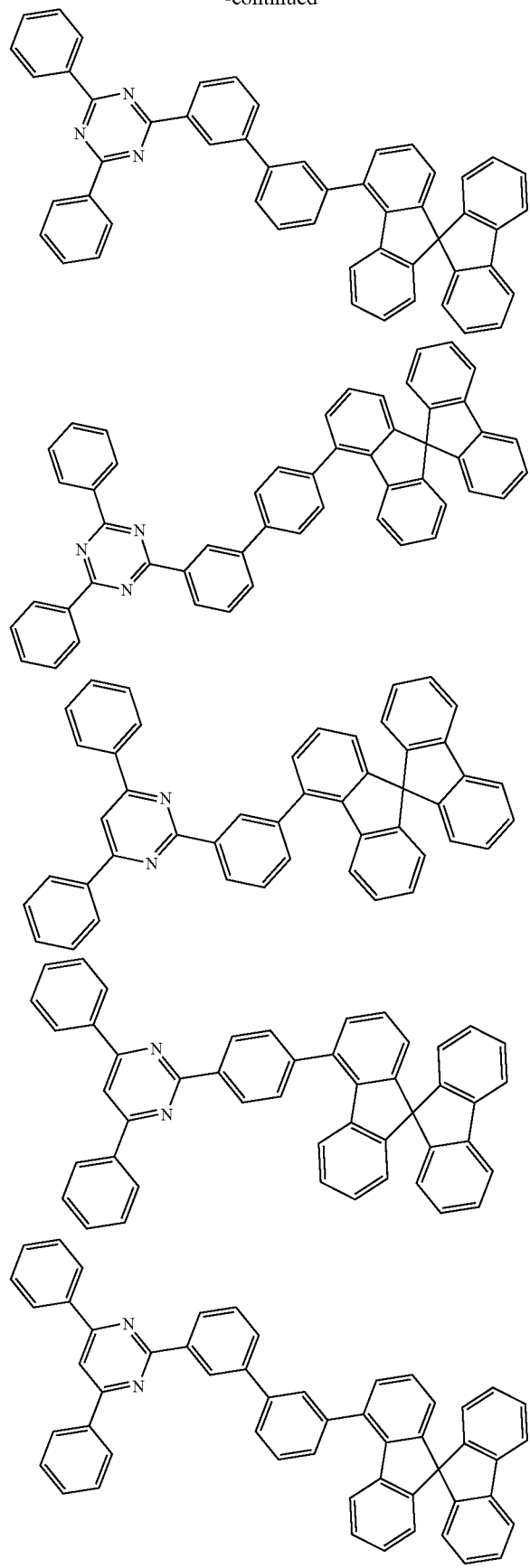
396
-continued
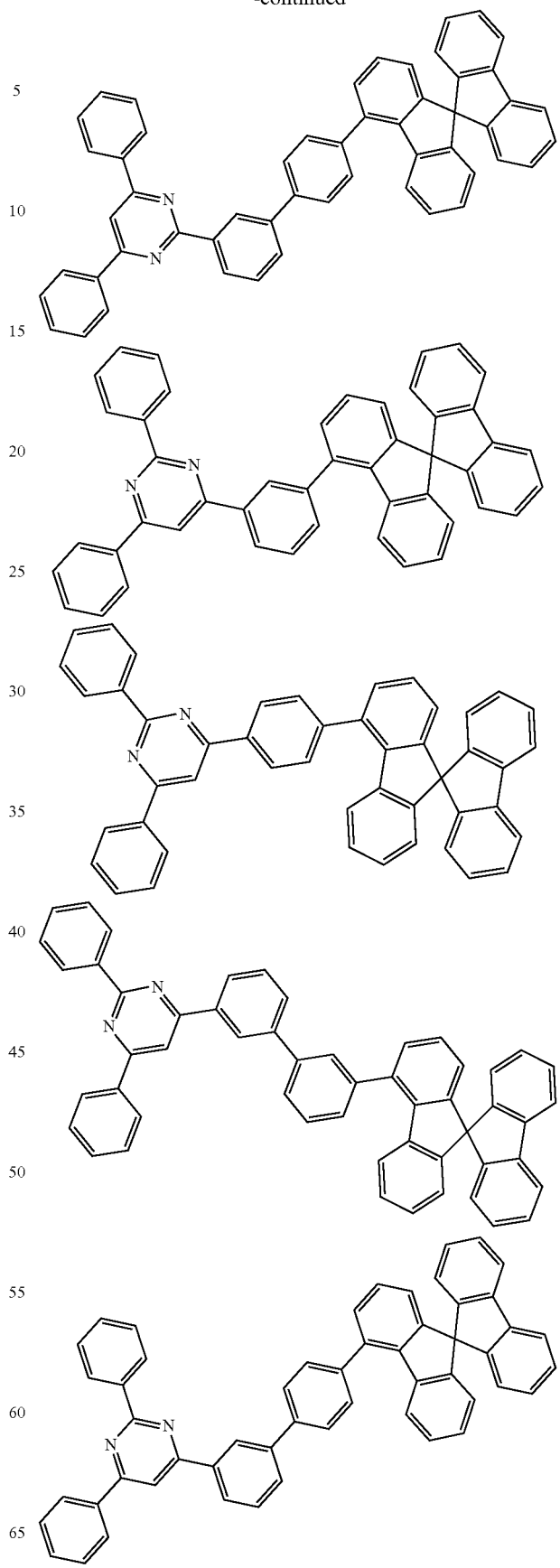

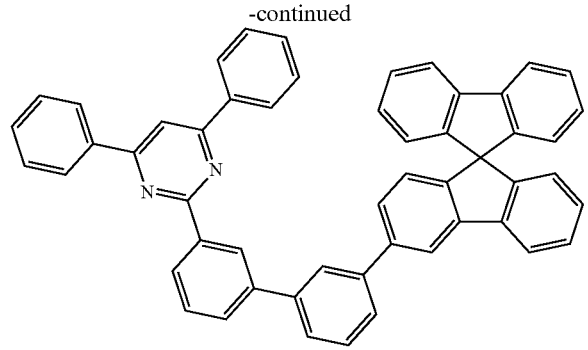
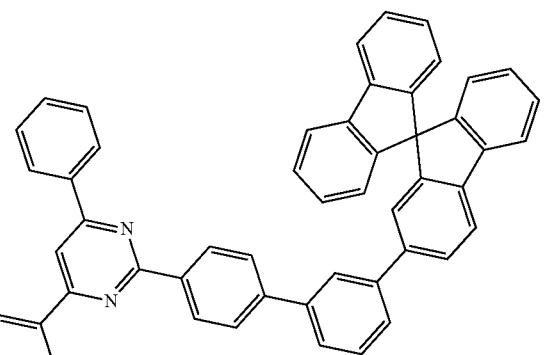

399
-continued
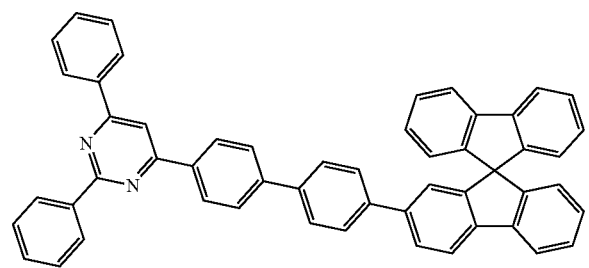
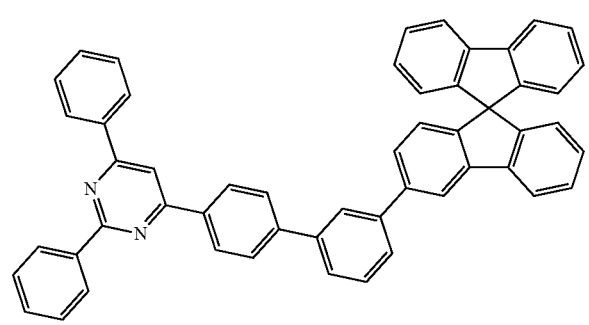
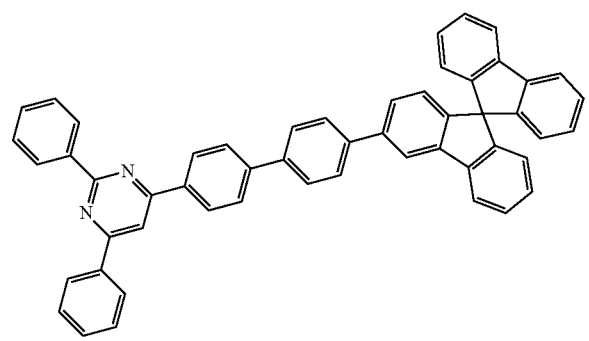
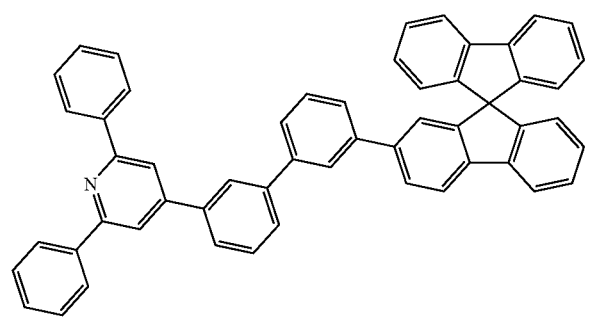
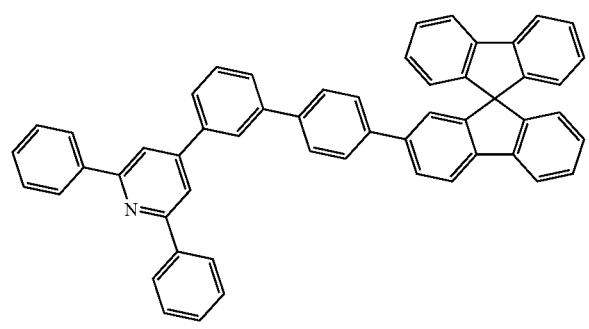
400
-continued
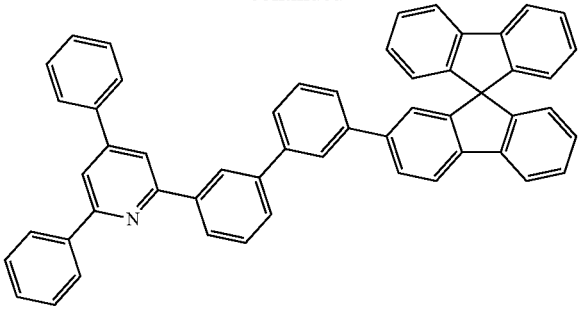
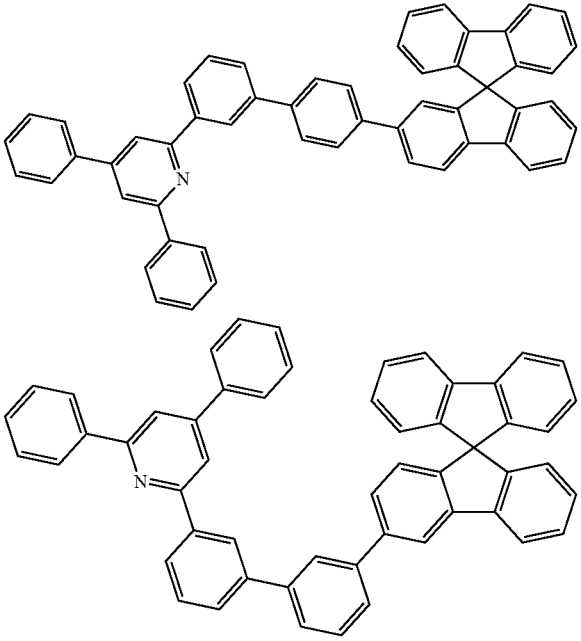
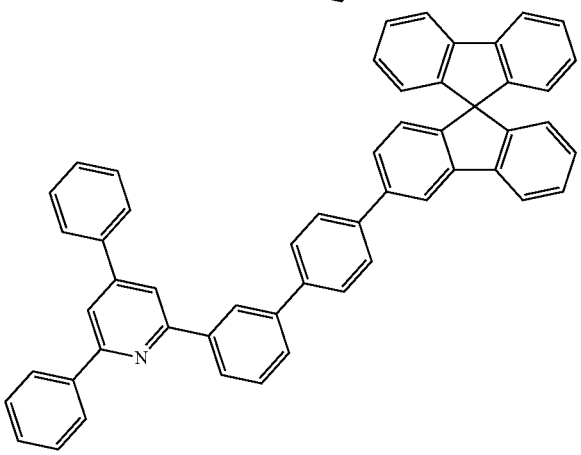
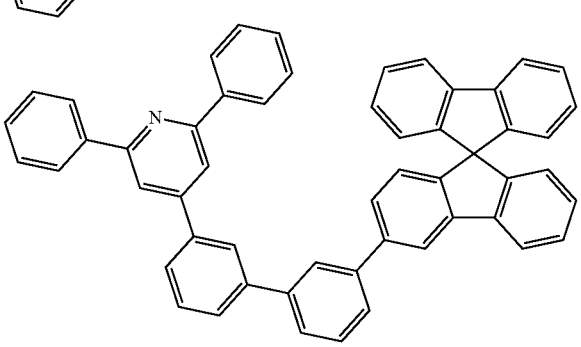

401
-continued
402
-continued
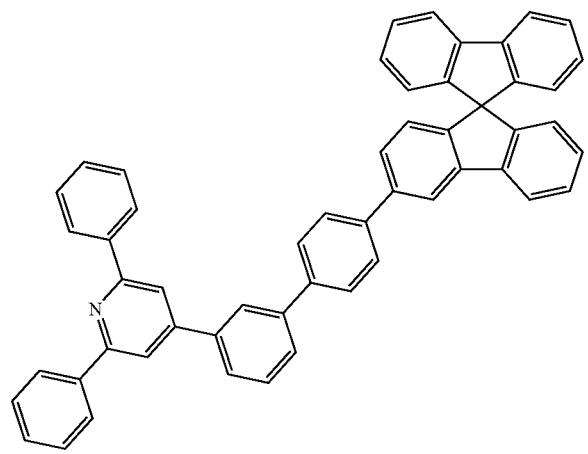
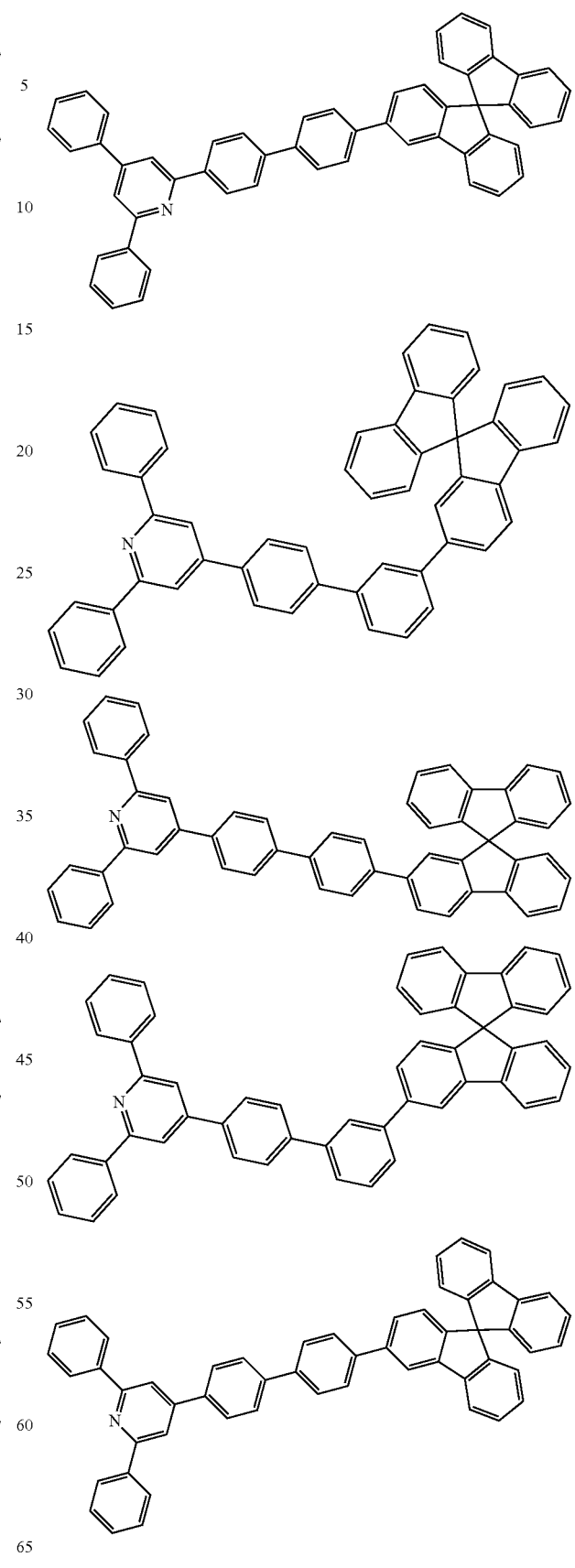

403
-continued
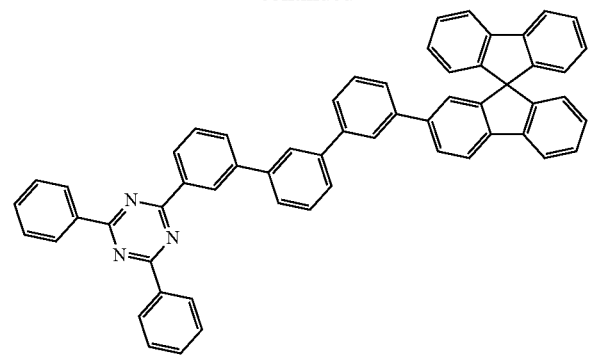
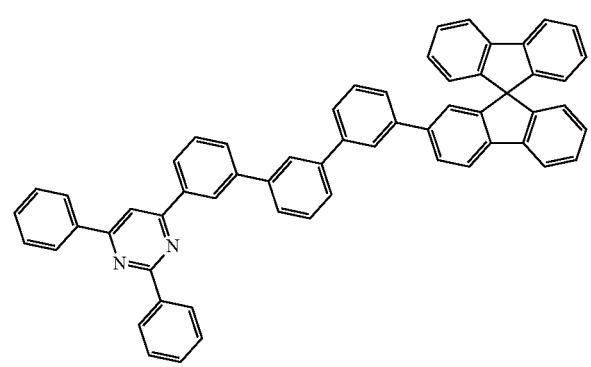
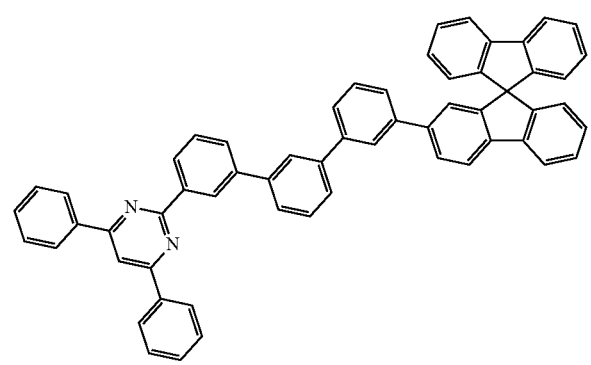
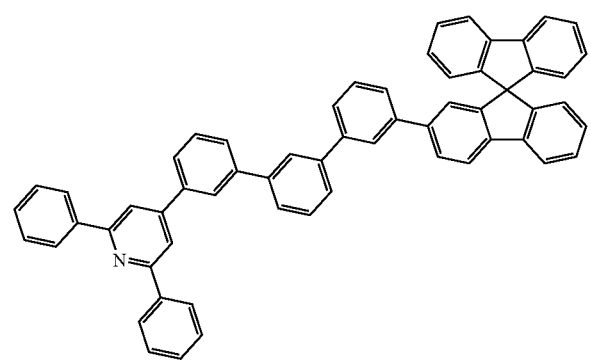
404
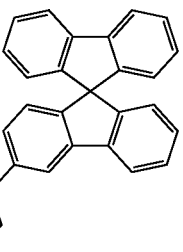
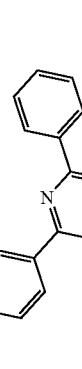
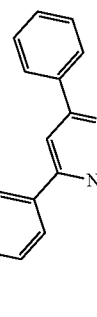
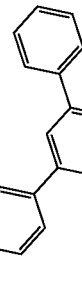
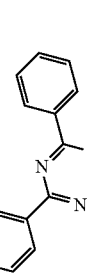

405
-continued
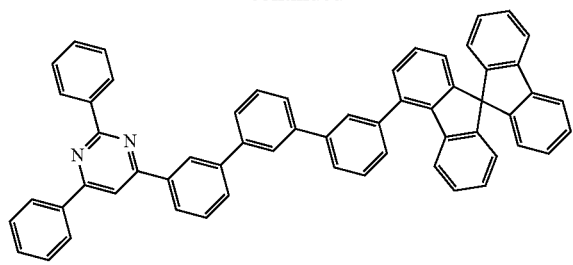
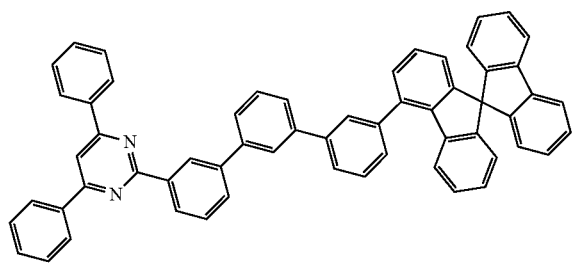
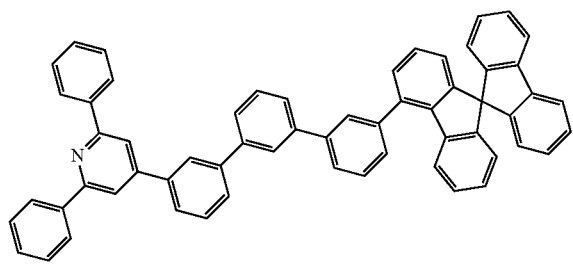
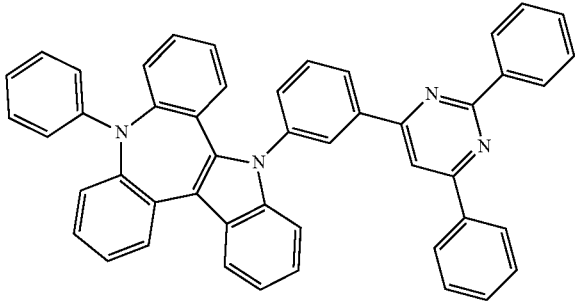
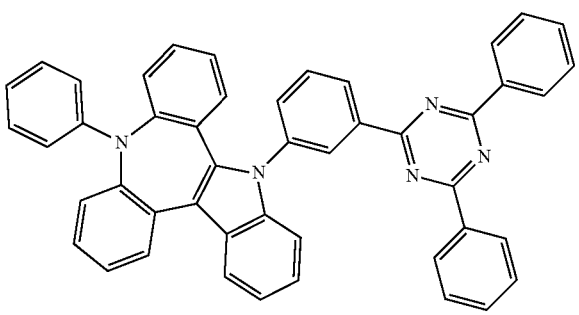
406
-continued
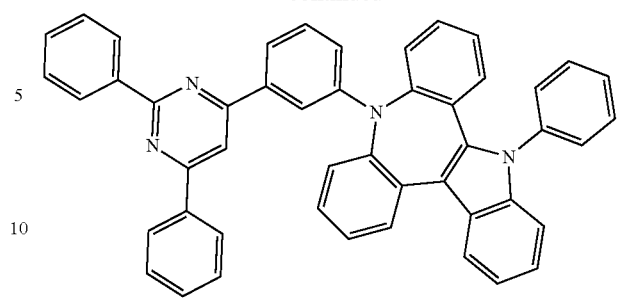
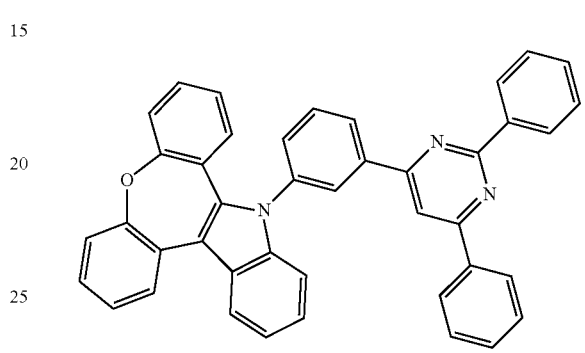
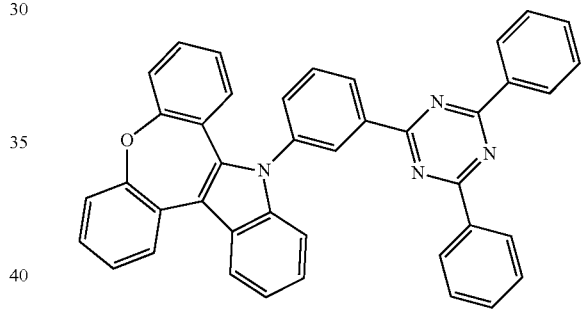
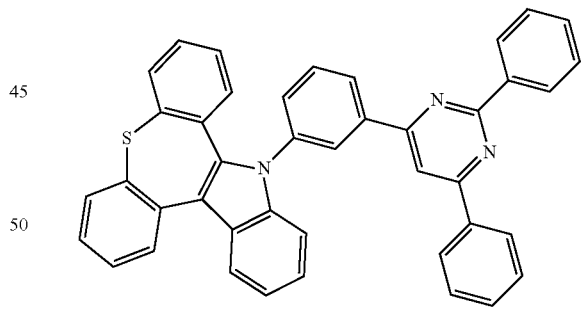
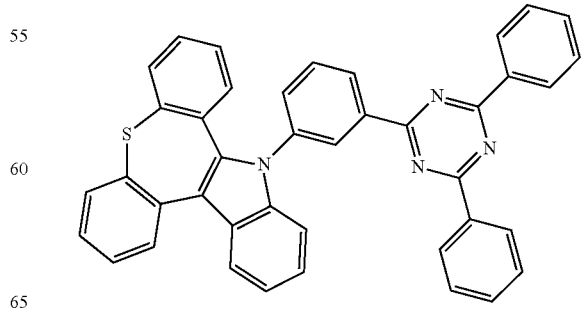

407
-continued
408
-continued
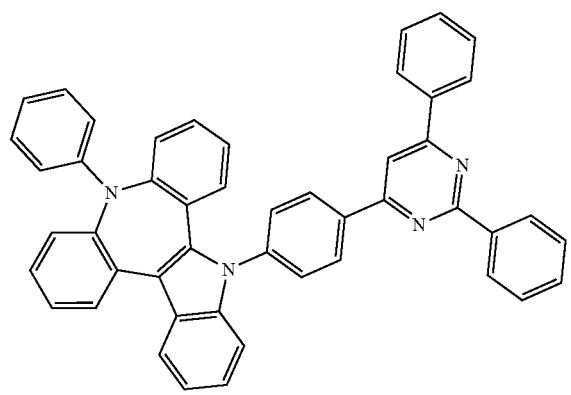
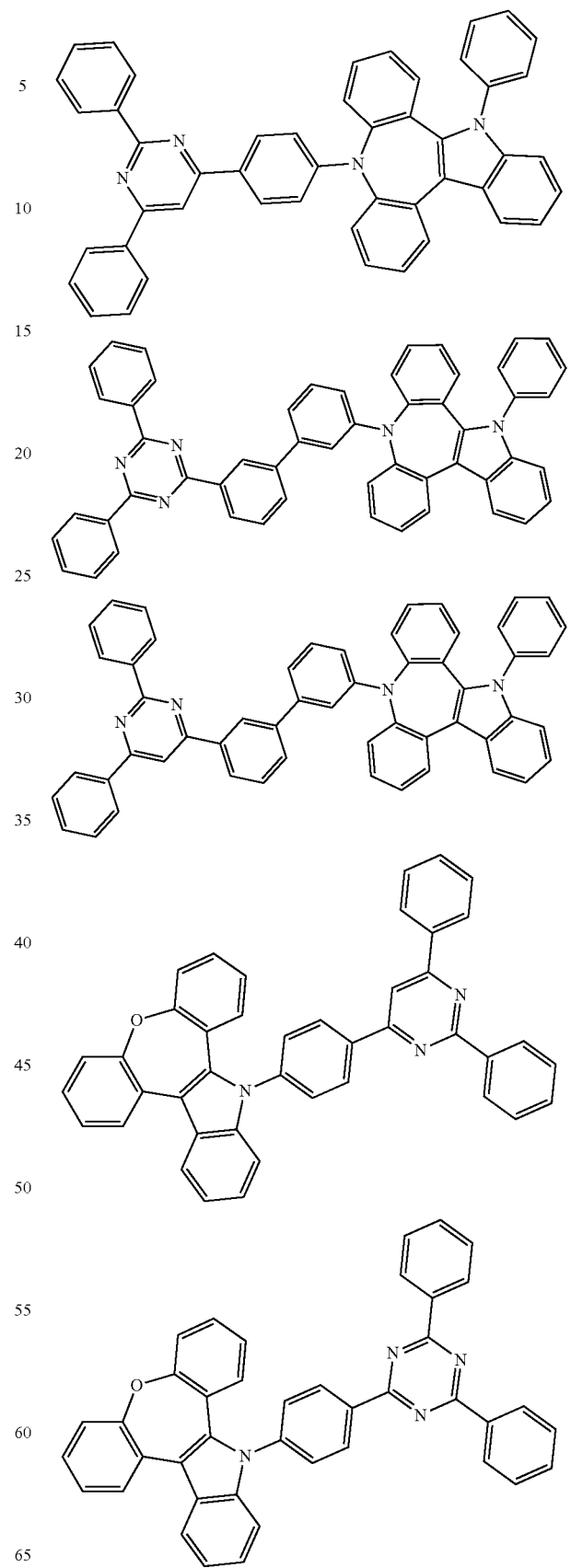

409
-continued
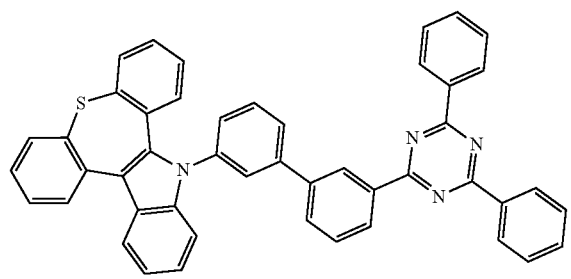
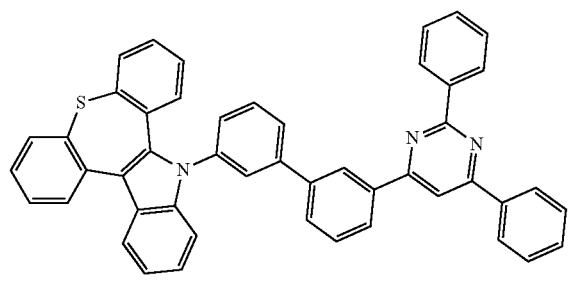
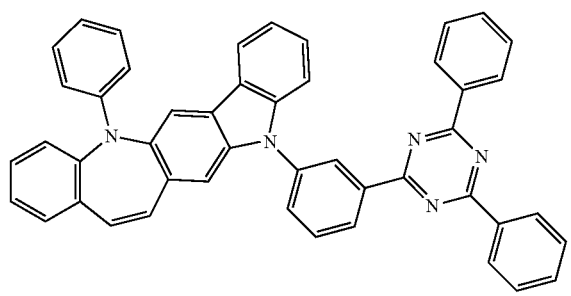
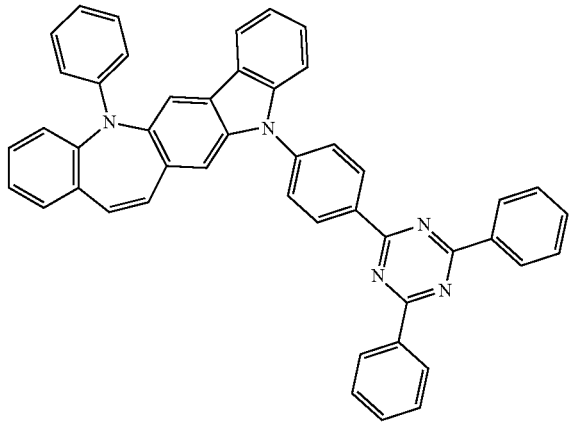
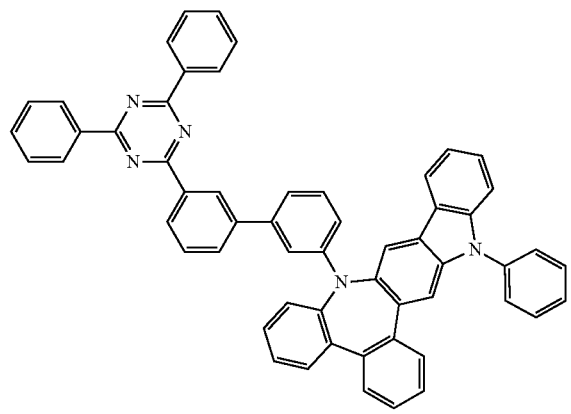
410
-continued
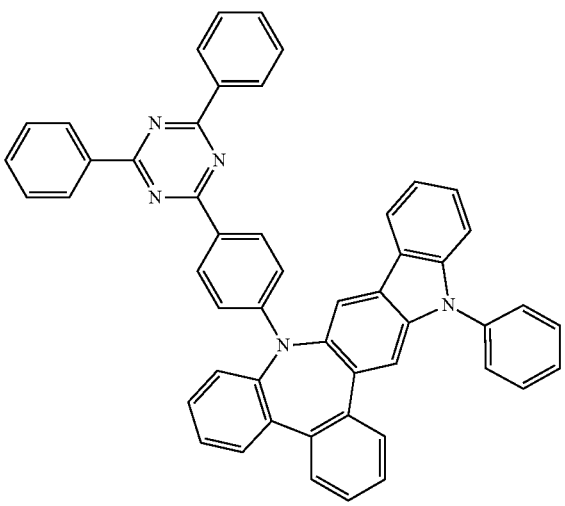
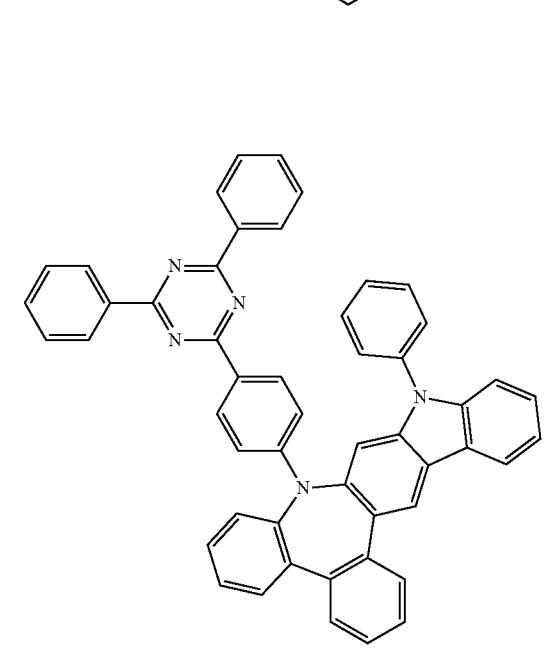
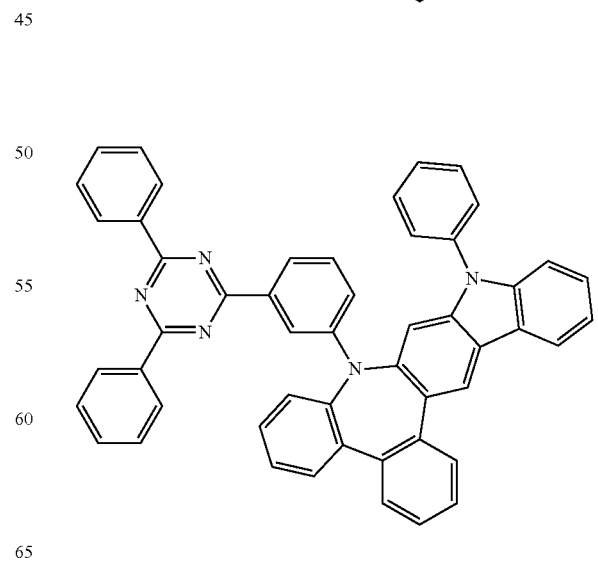

411
-continued
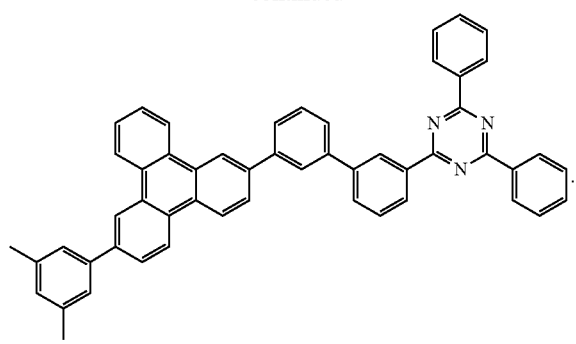
16. The organic light emitting device of claim 11, wherein the compound of Chemical Formula 2 is selected from among the following compounds:
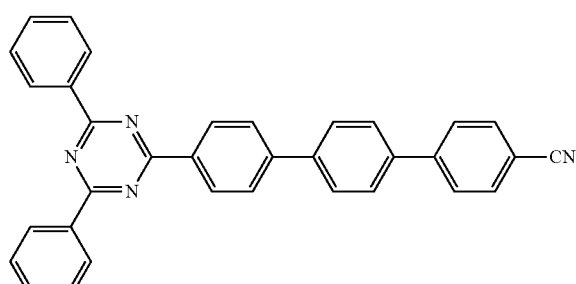
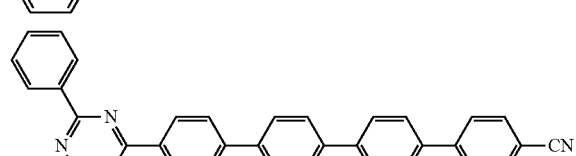
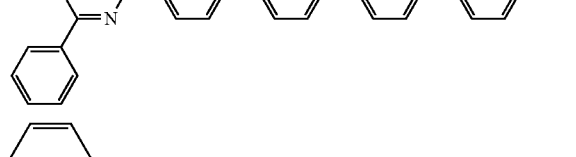
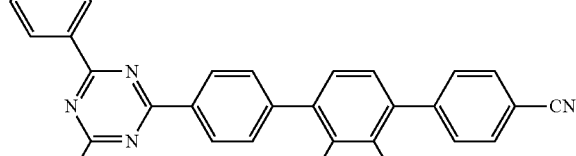
412
-continued
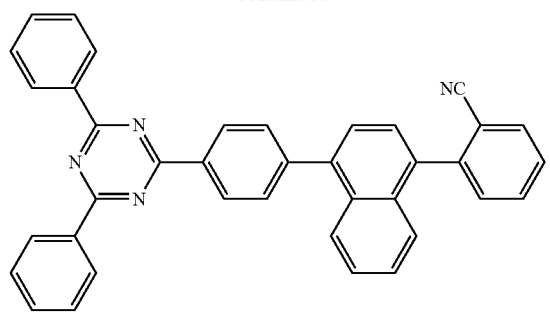
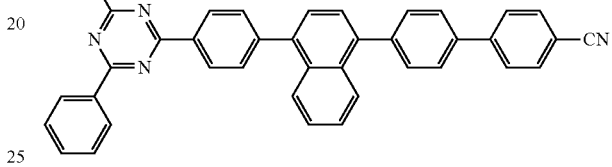
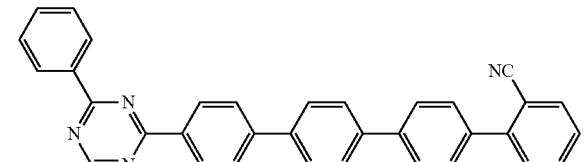
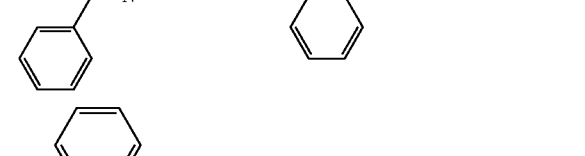
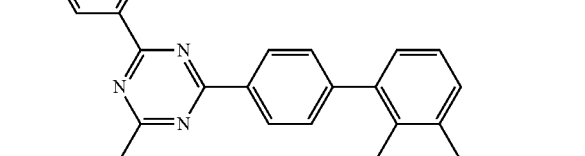

413
-continued
414
-continued
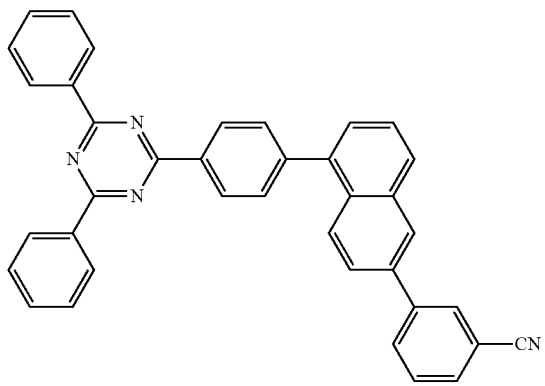
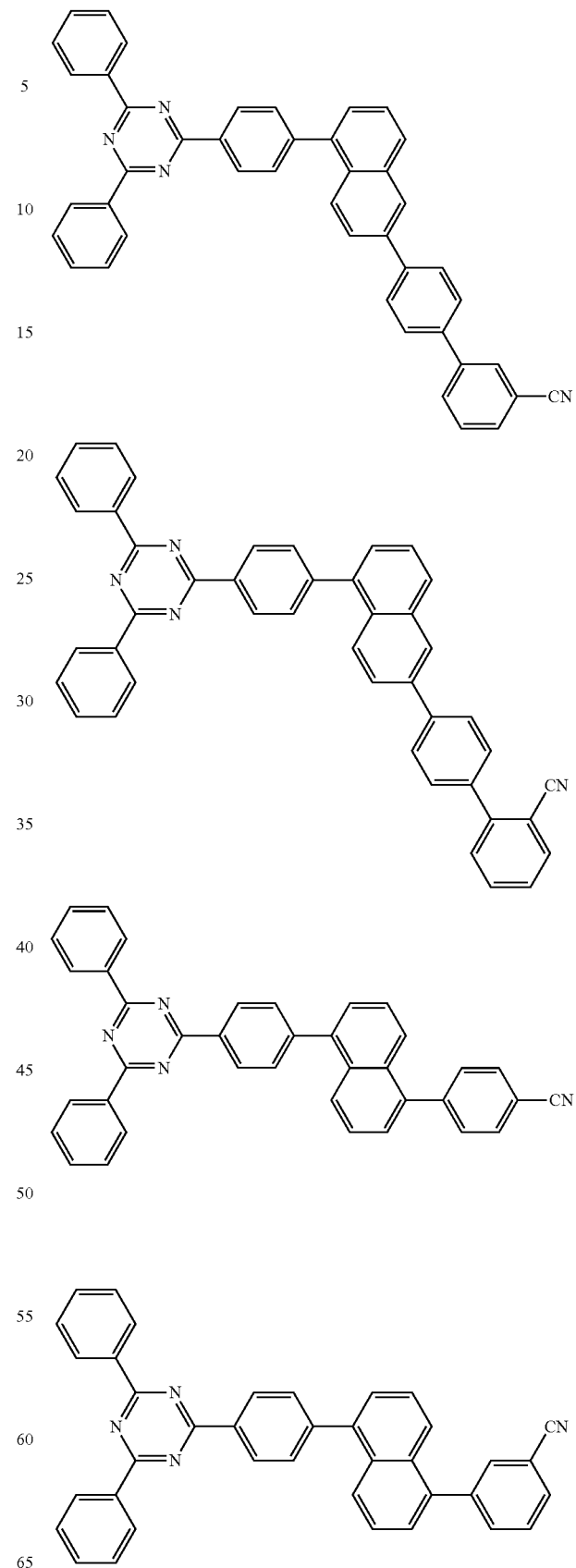

415
-continued
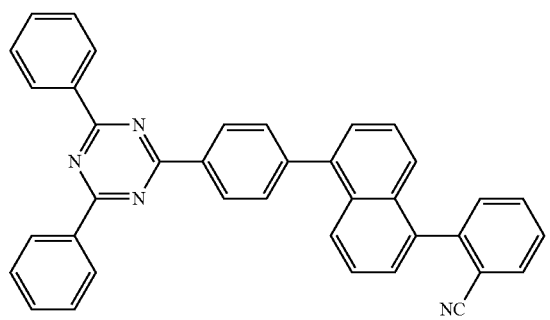
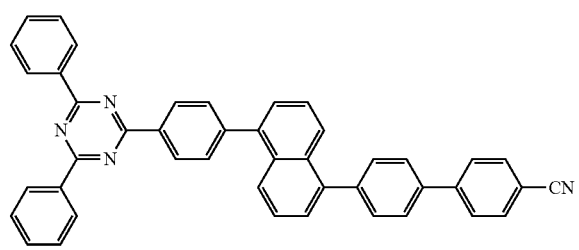
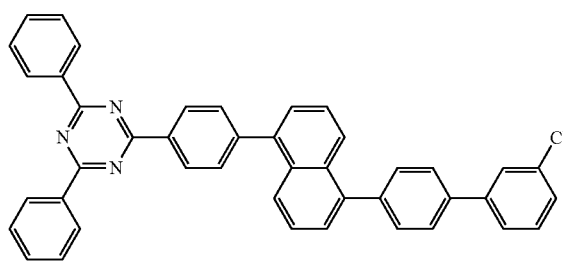
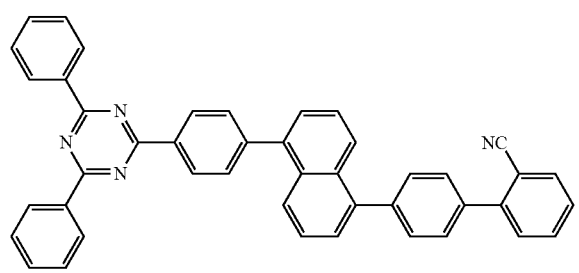
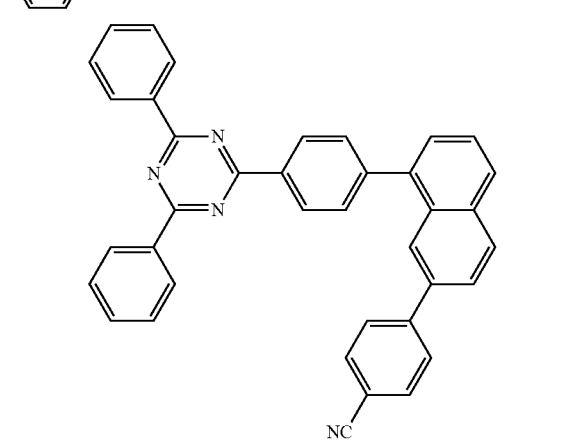
416
-continued
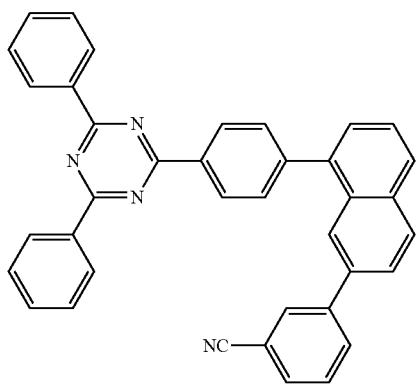
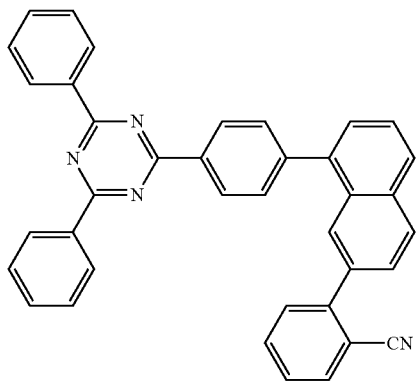
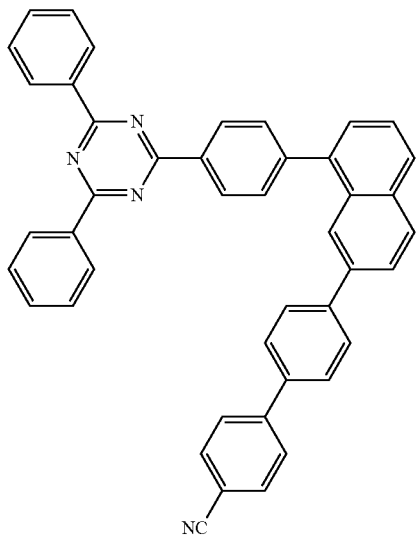

417
-continued
418
-continued
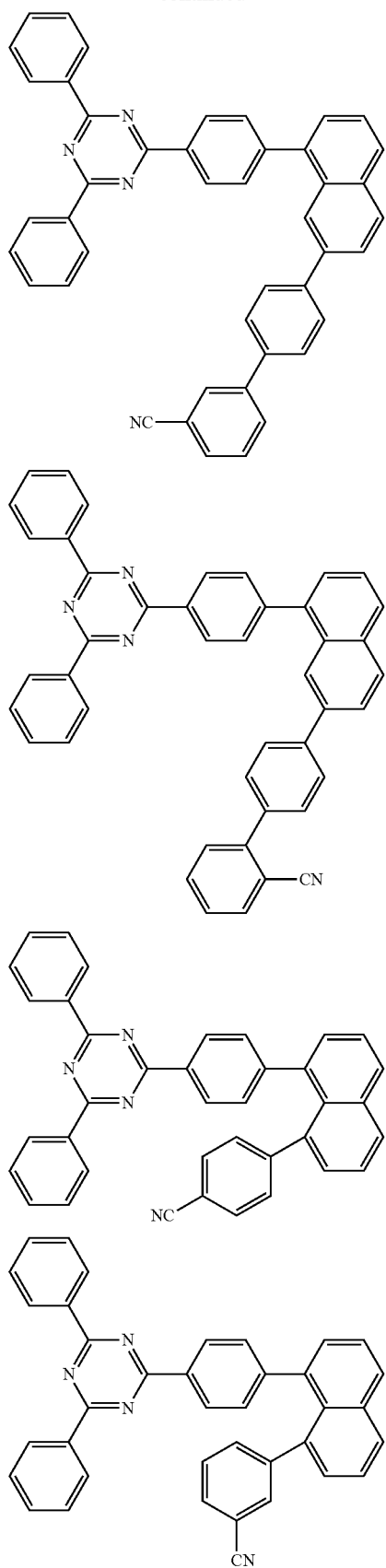
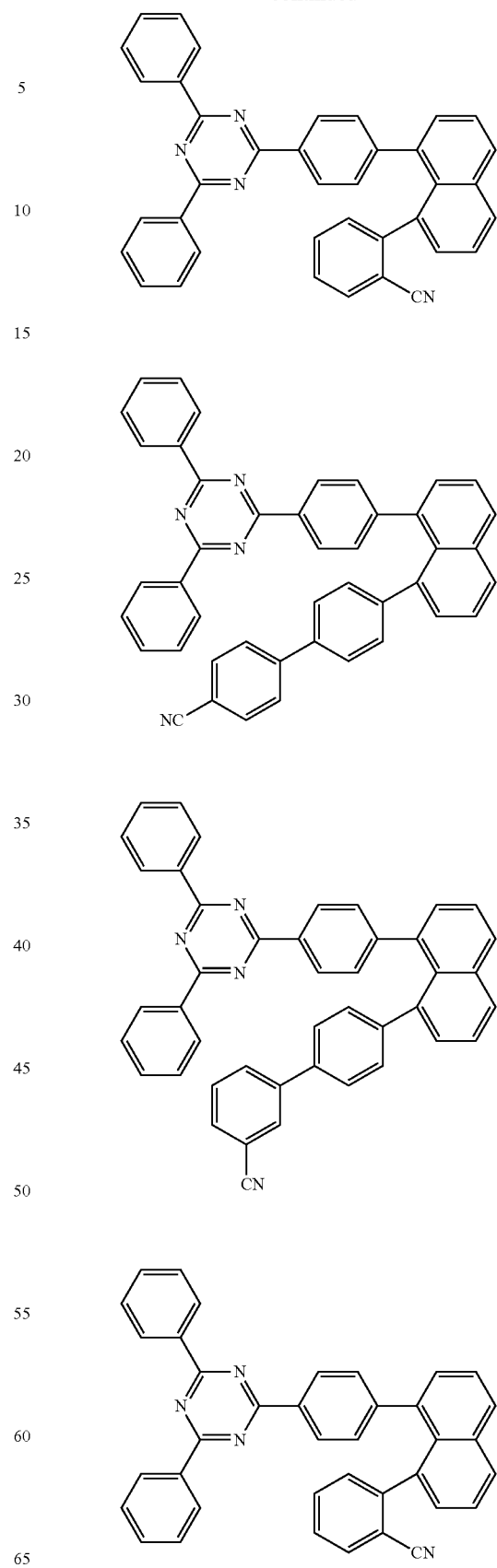

419
-continued
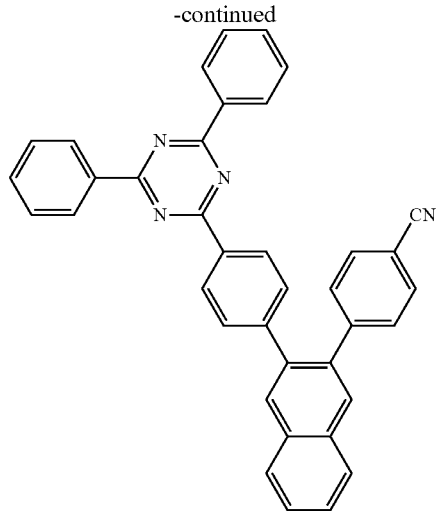
420
-continued
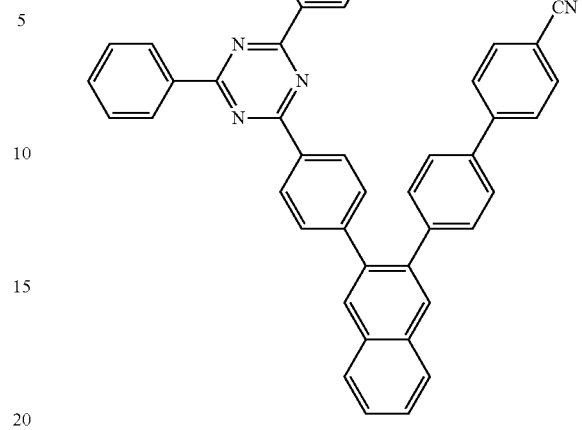
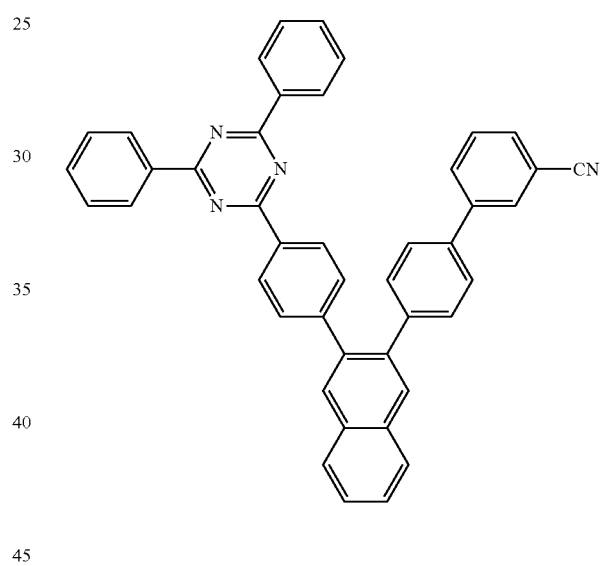
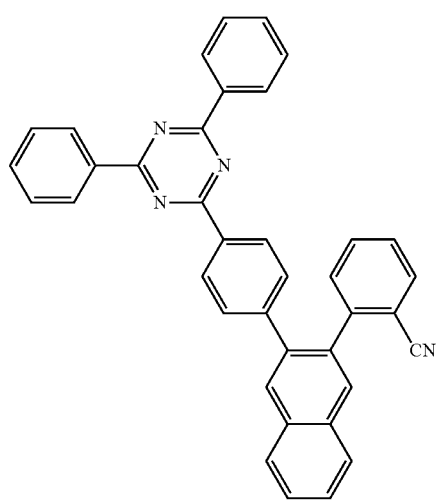
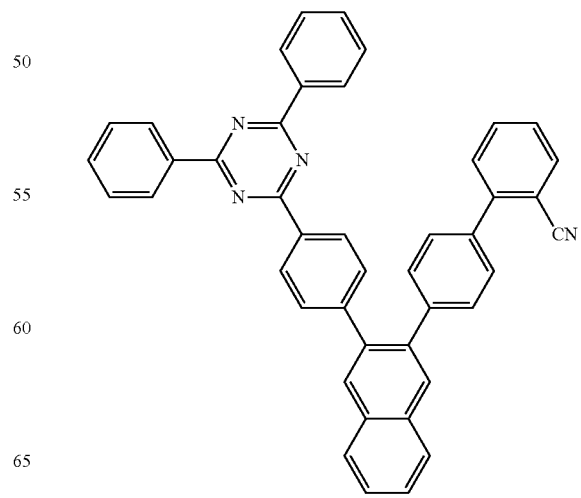

421
-continued
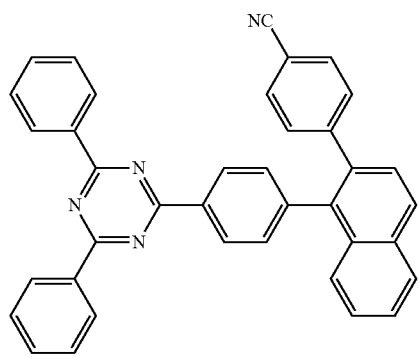
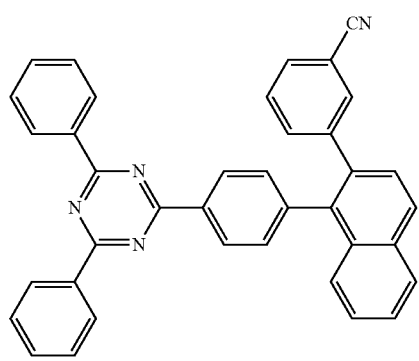
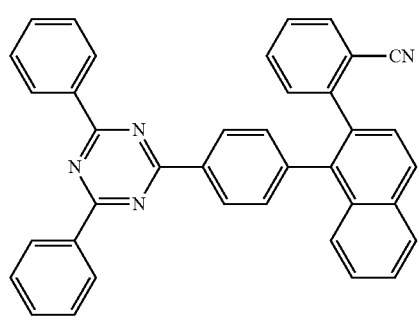
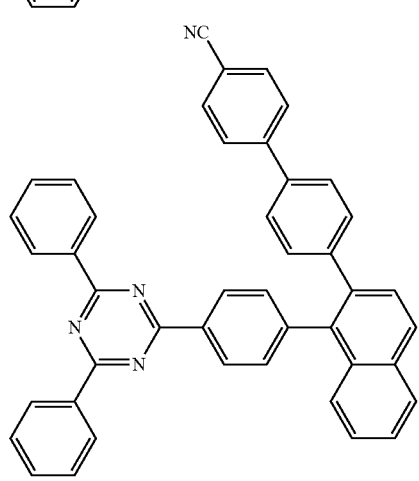
422
-continued
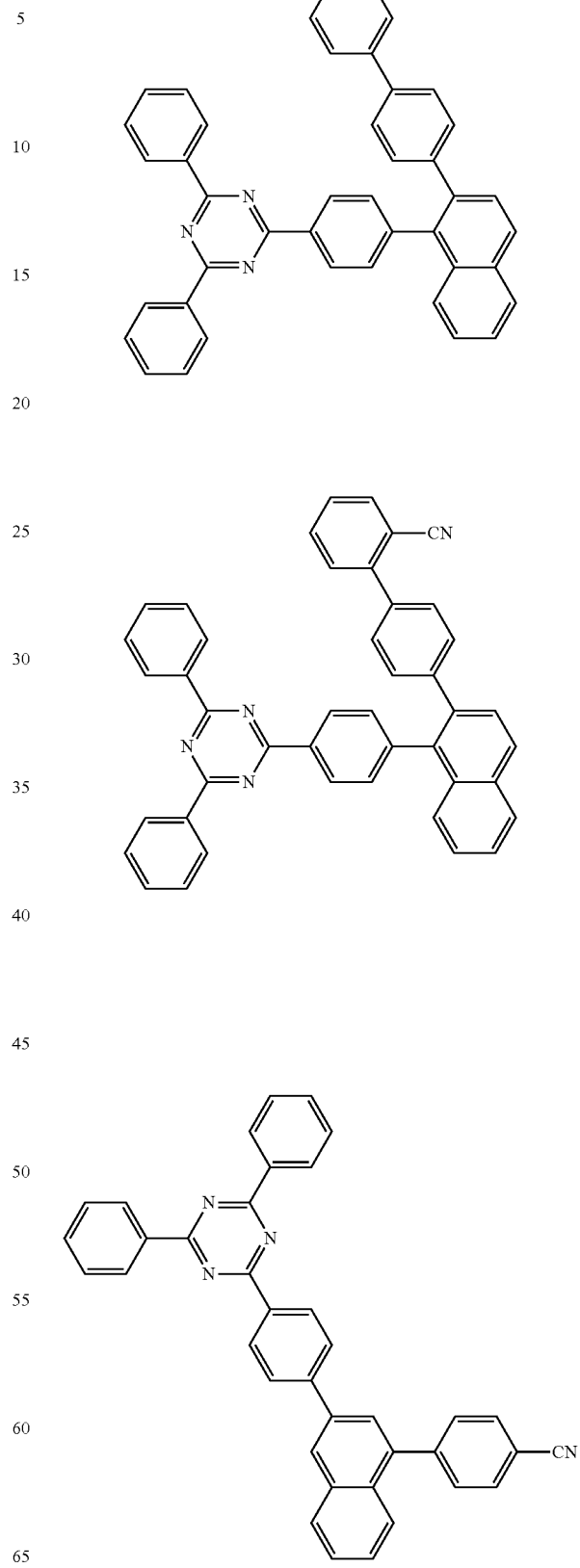

423
-continued
424
-continued
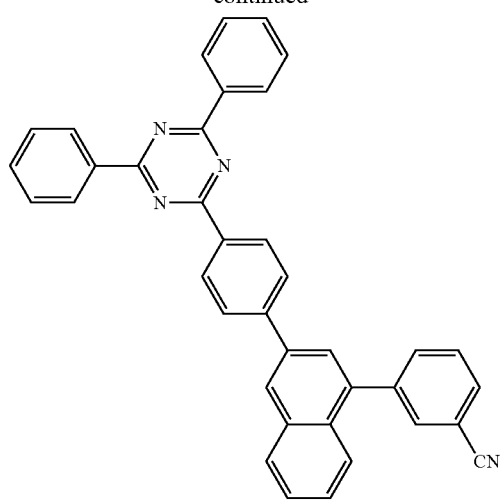
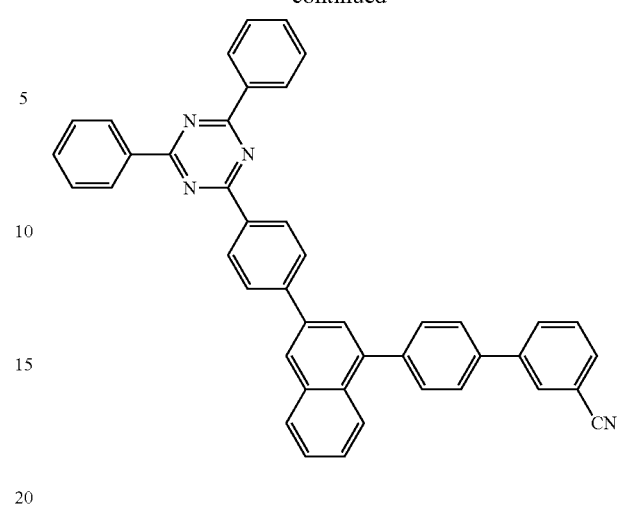
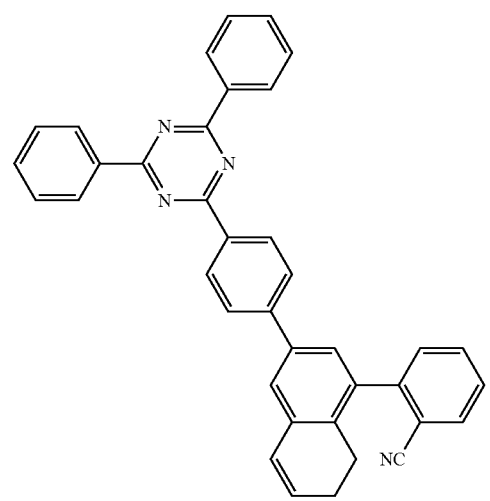
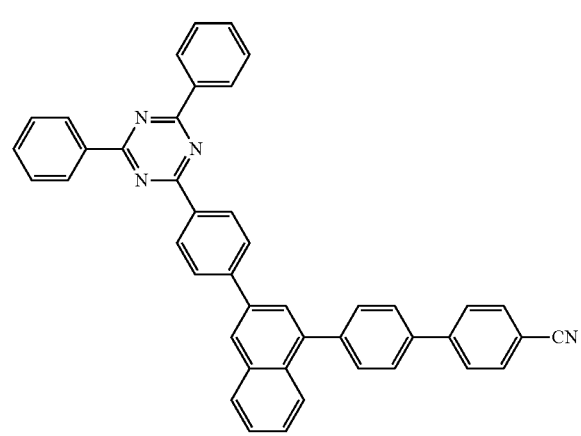

425
-continued
426
-continued
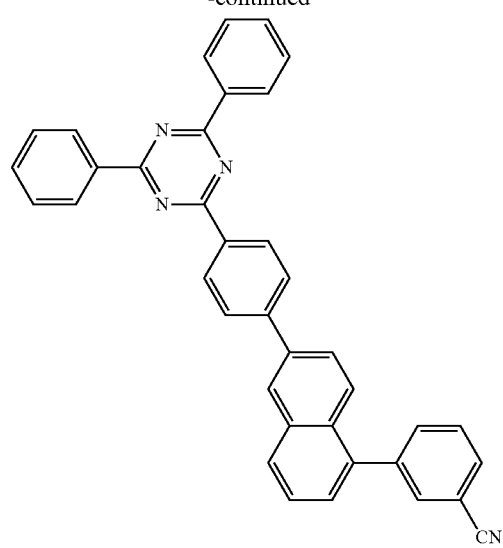
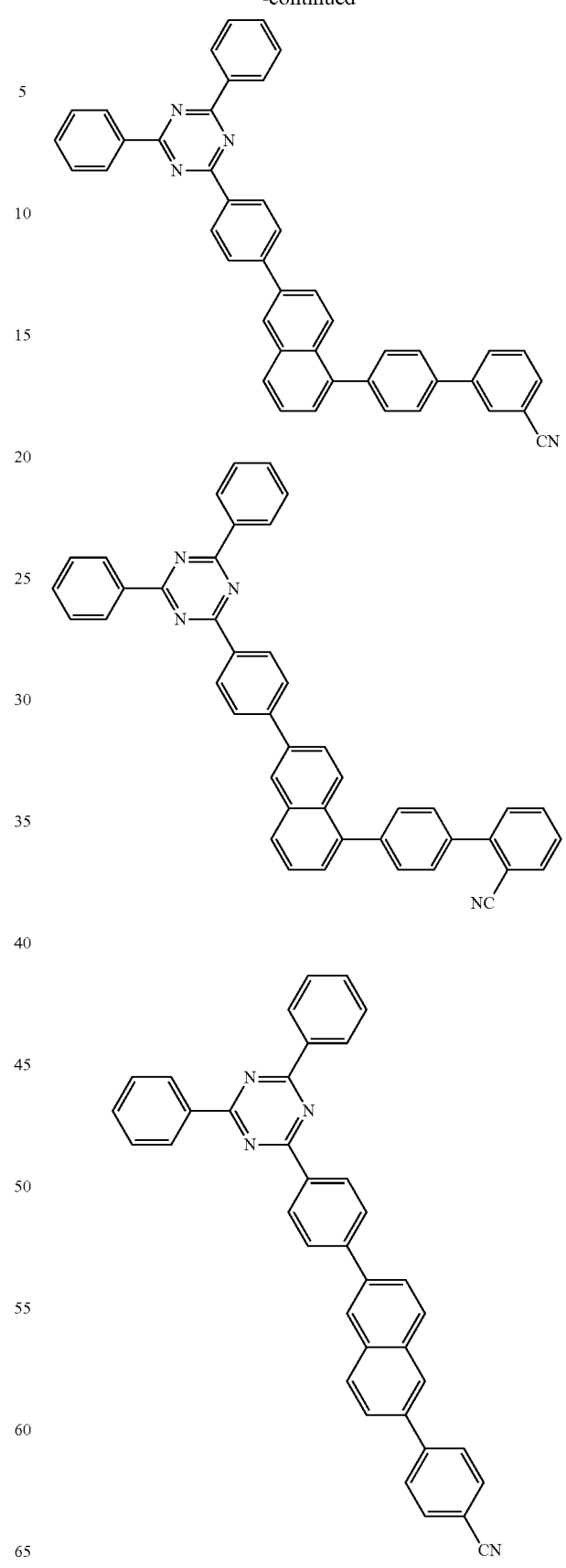

427
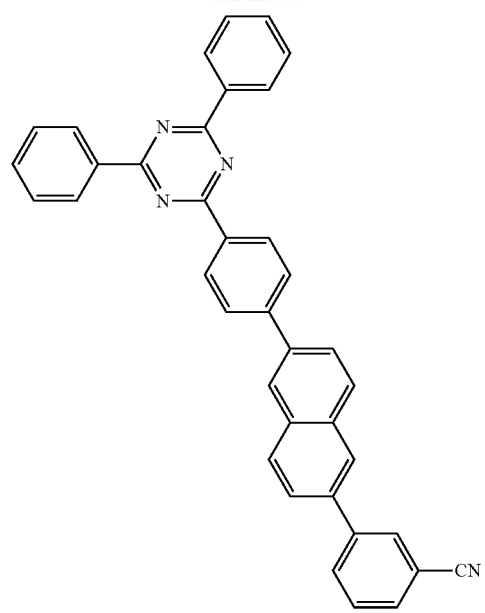
428
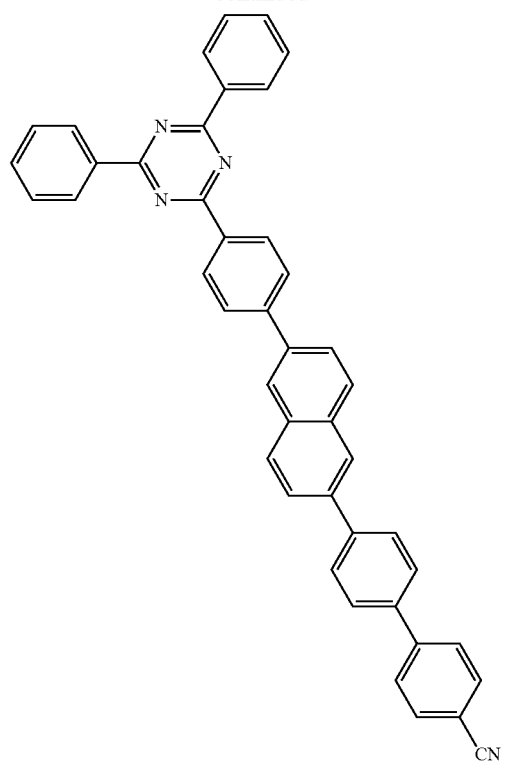
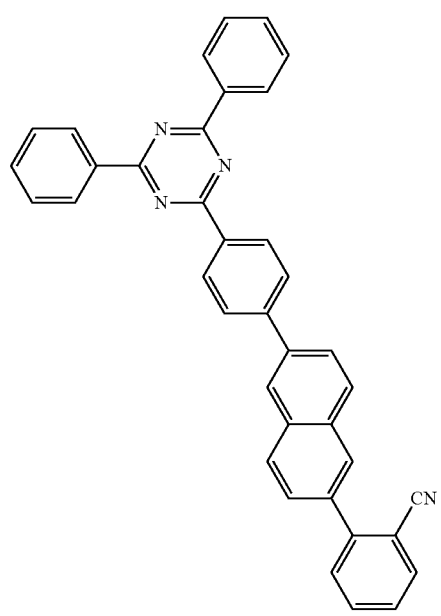

429
-continued
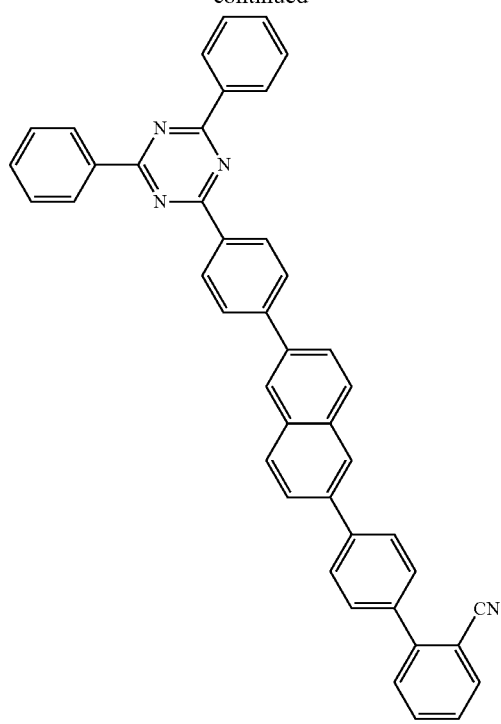
430
-continued
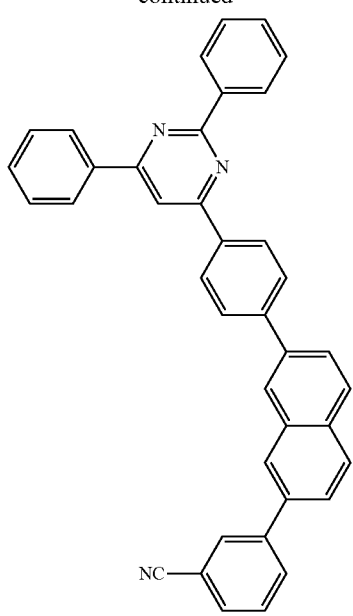
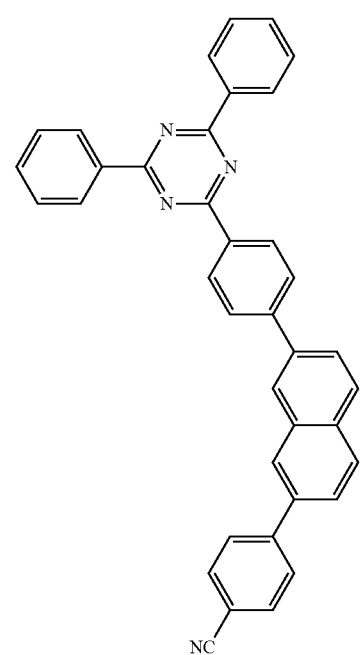
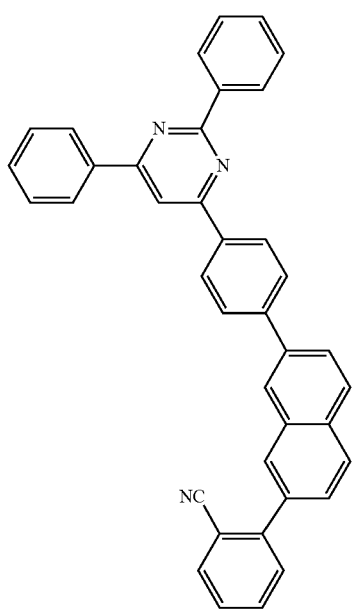

431
-continued
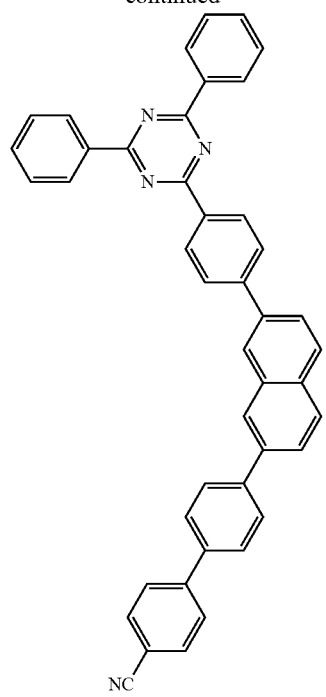
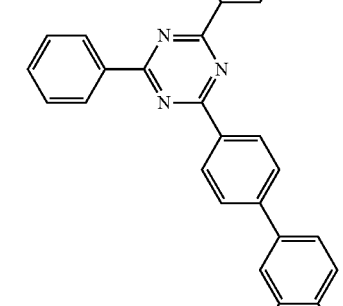
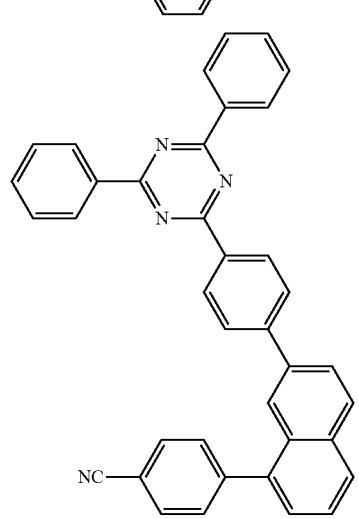
432
-continued
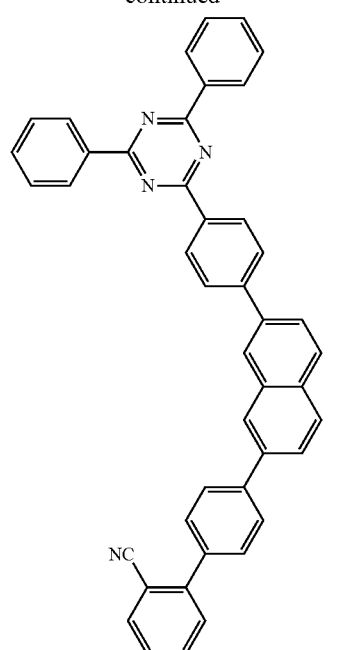
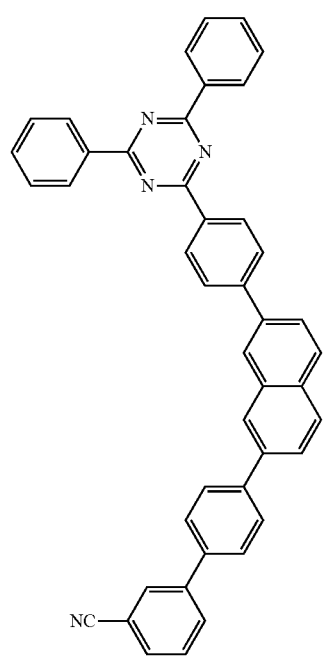

433
-continued
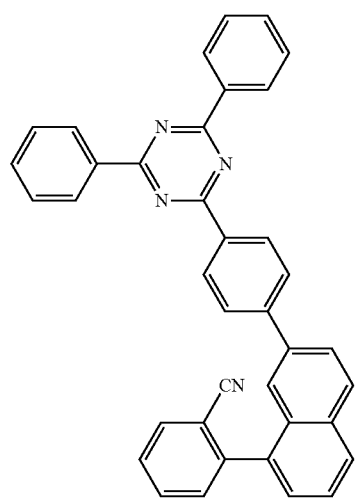
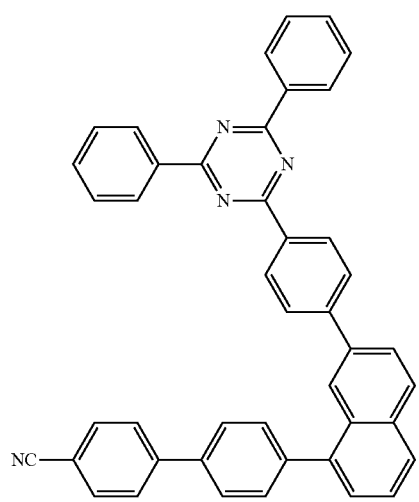
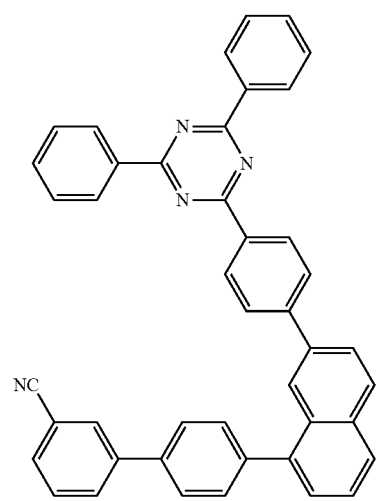
434
-continued
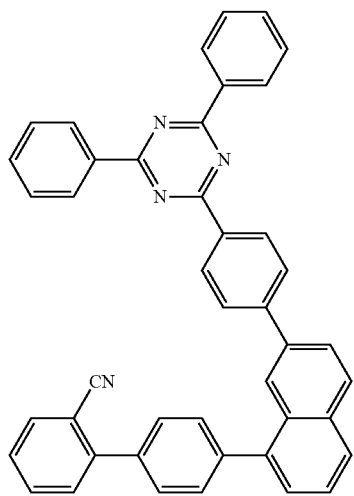
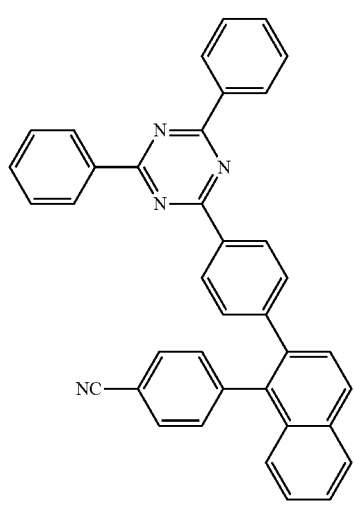
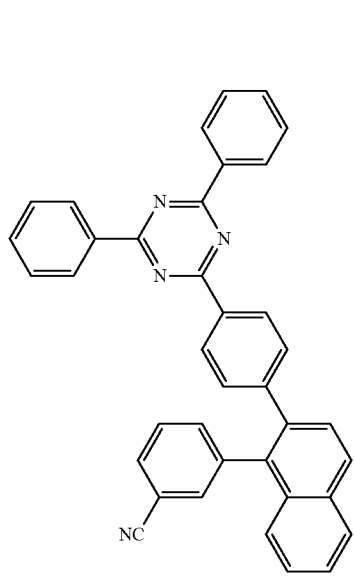

435
-continued
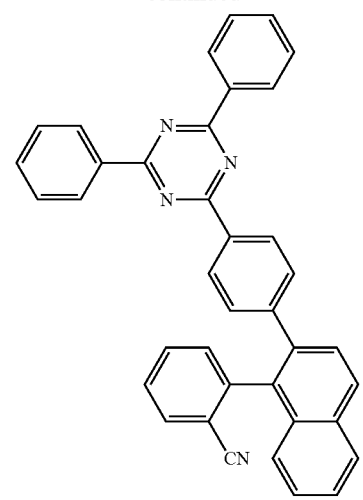
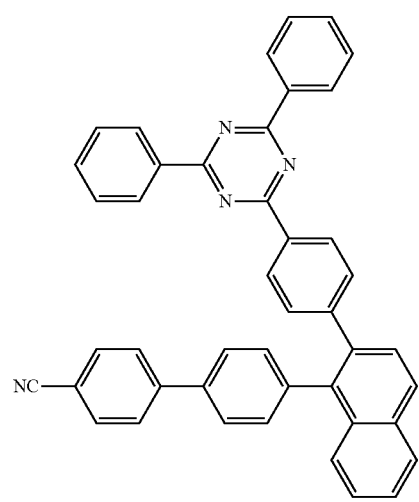
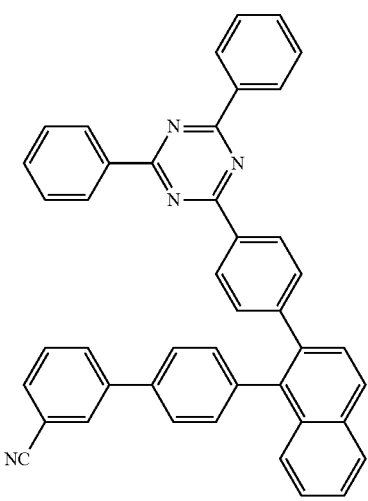
436
-continued
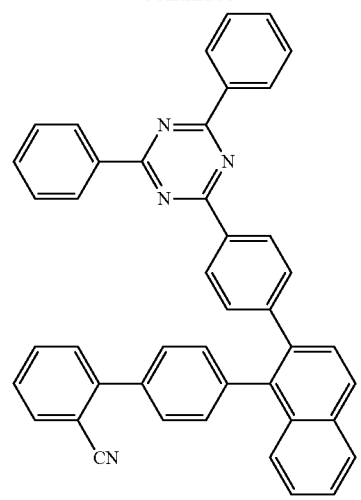
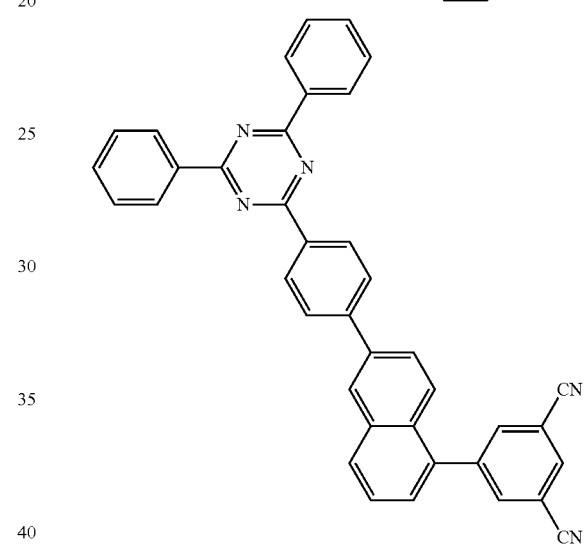
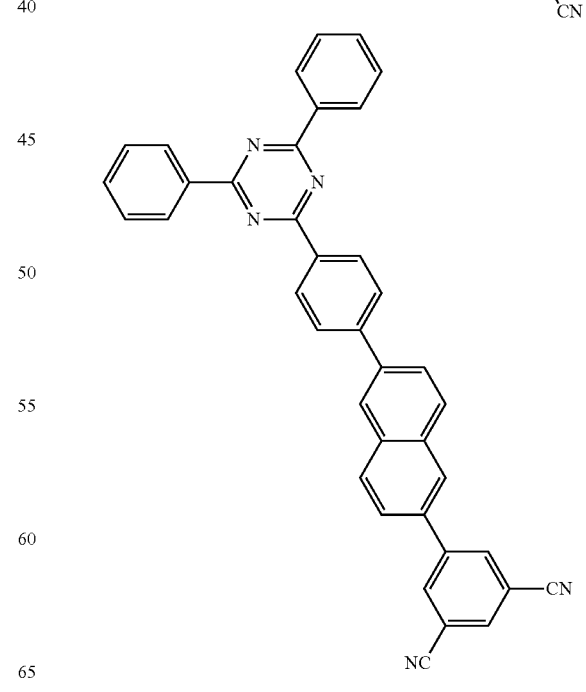

437
-continued

438
-continued

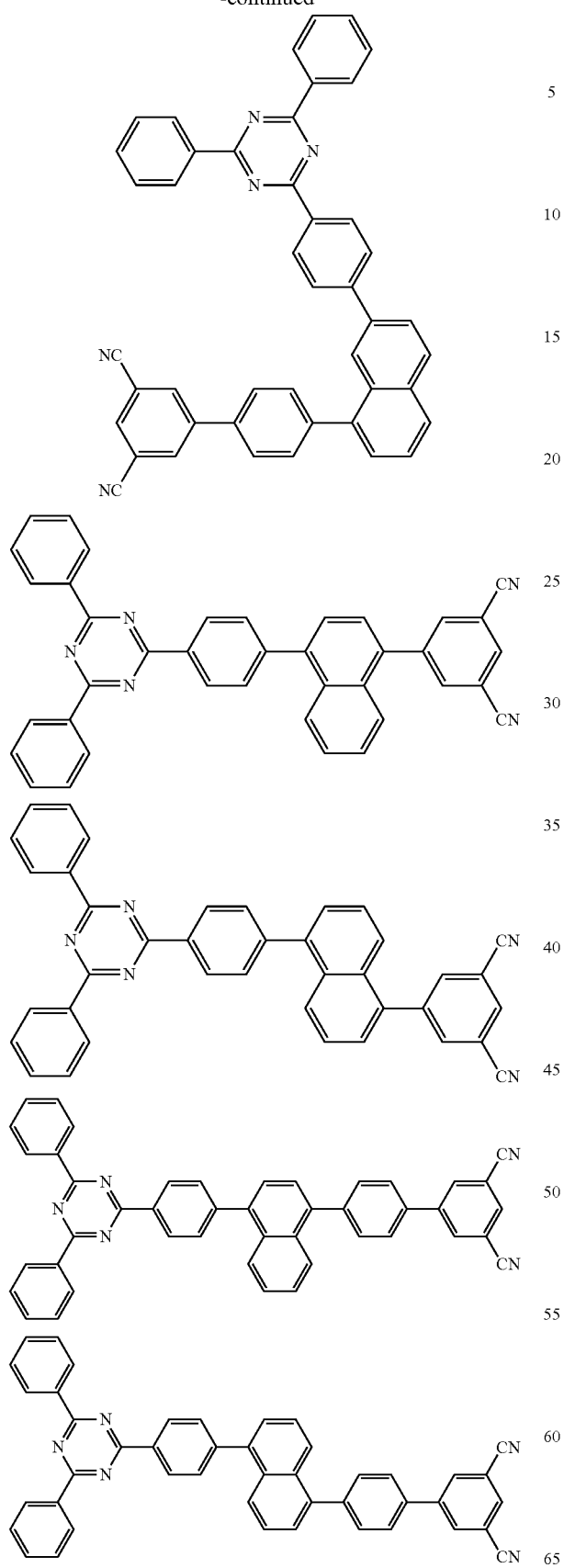
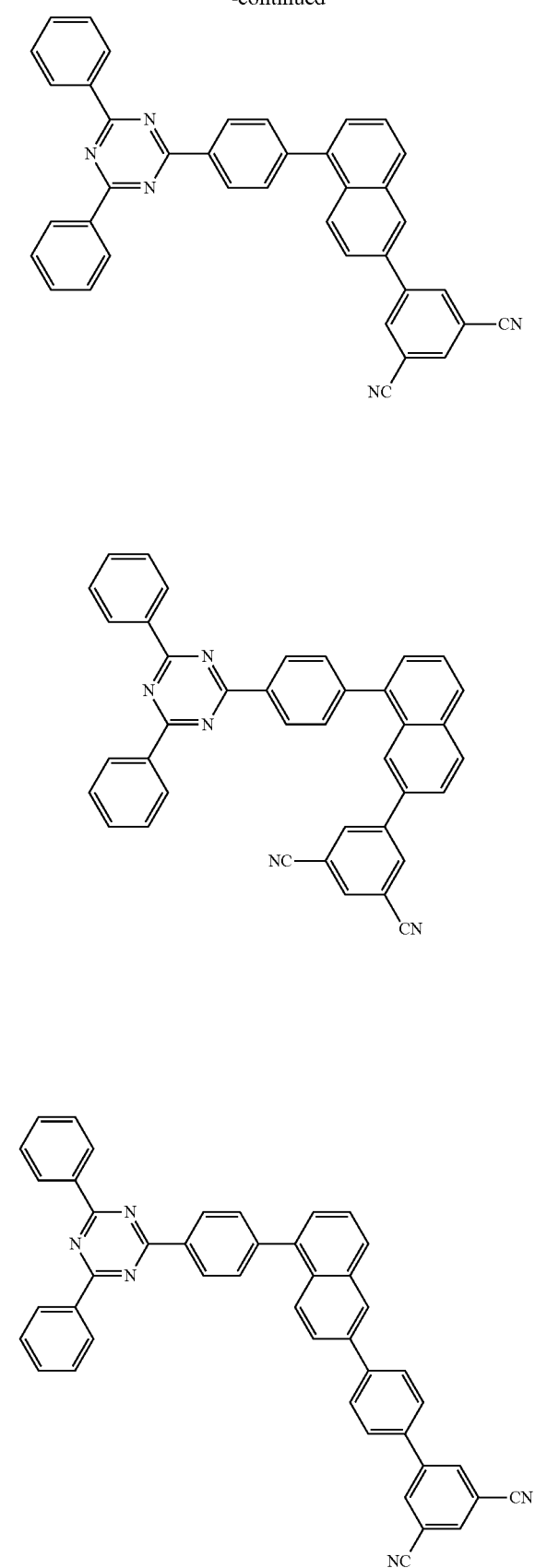

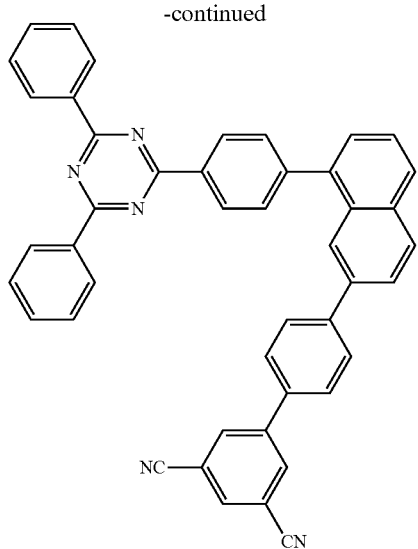
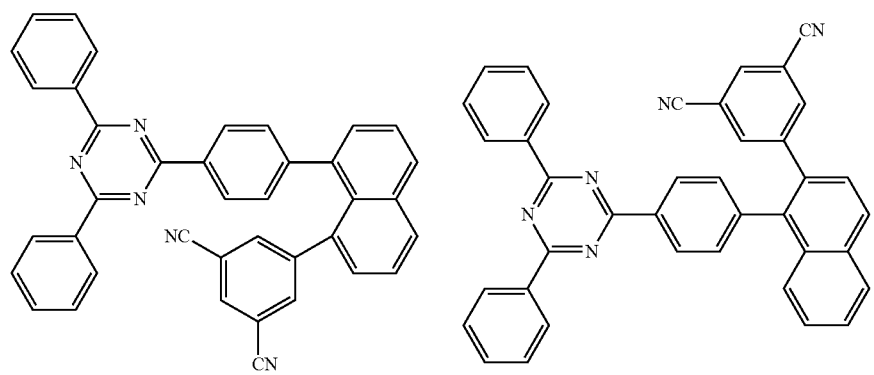
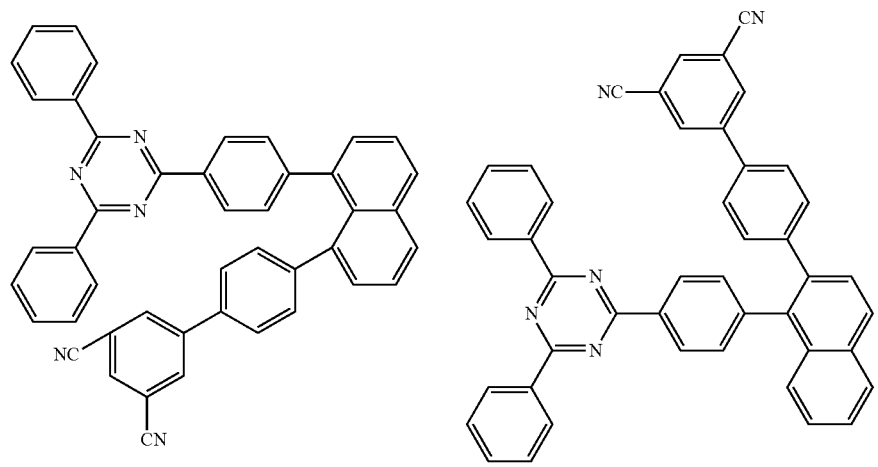

-continued
| 443 | 444 |
|---|---|
| 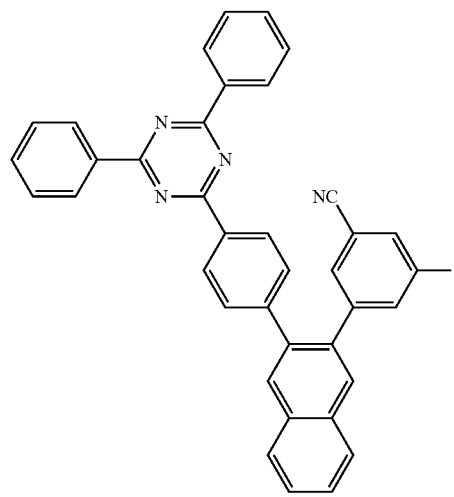 | 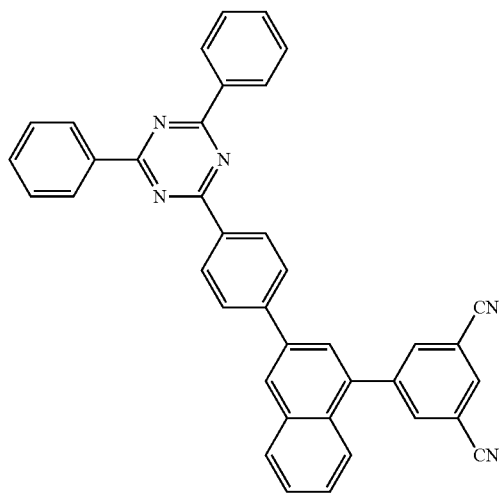 |
| 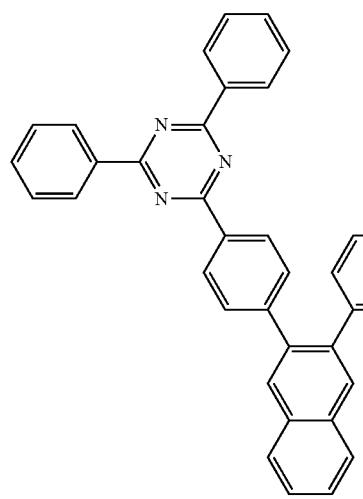 | 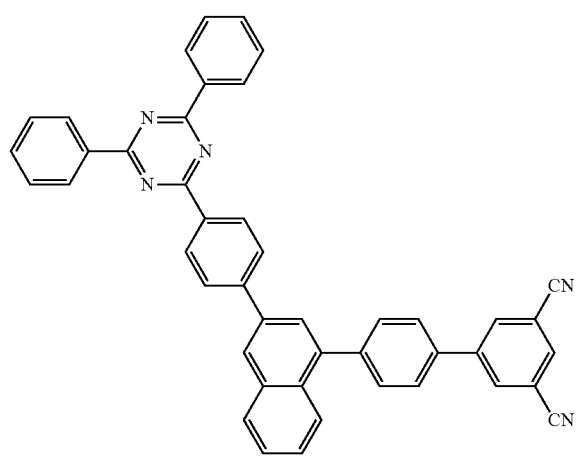 [SMILES: N#Cc1cccc(-c2ccc(-c3cc(-c4ccc(-c5nc(-c6ccccc6)nc(-c6ccccc6)n5)cc4)cc4ccccc34)cc2)c1] |
| 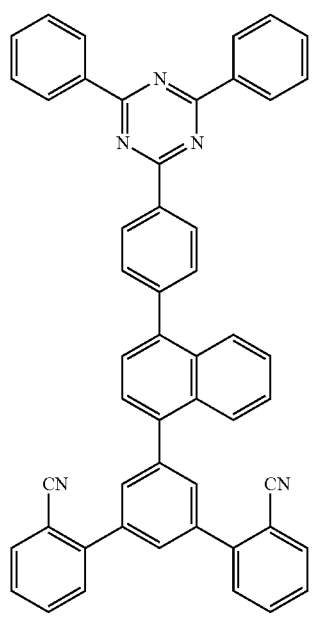 | 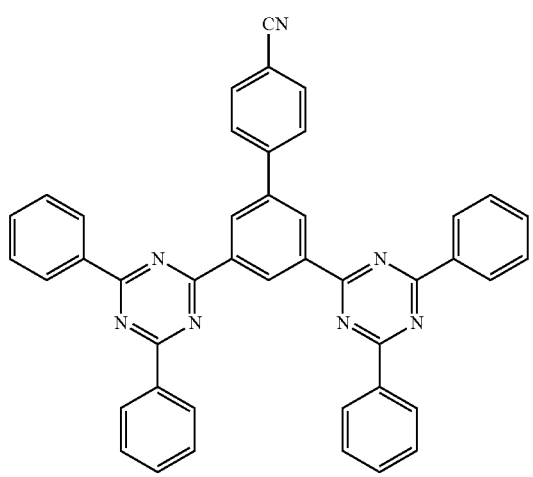 |

445
446
-continued
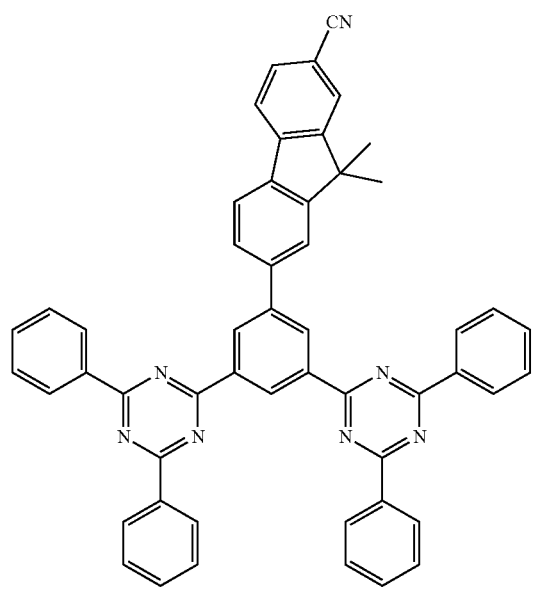
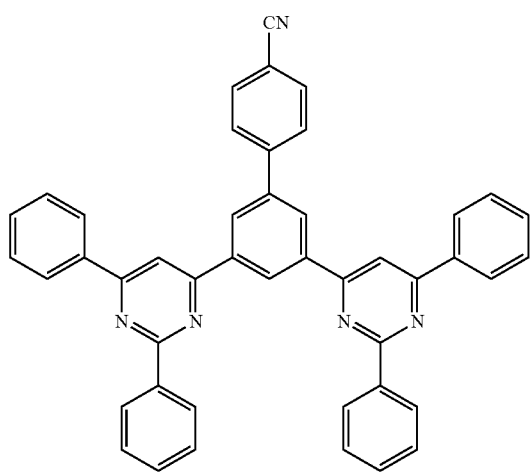
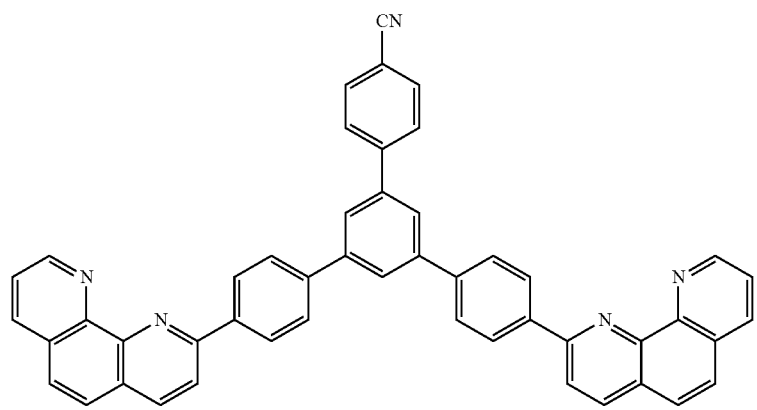
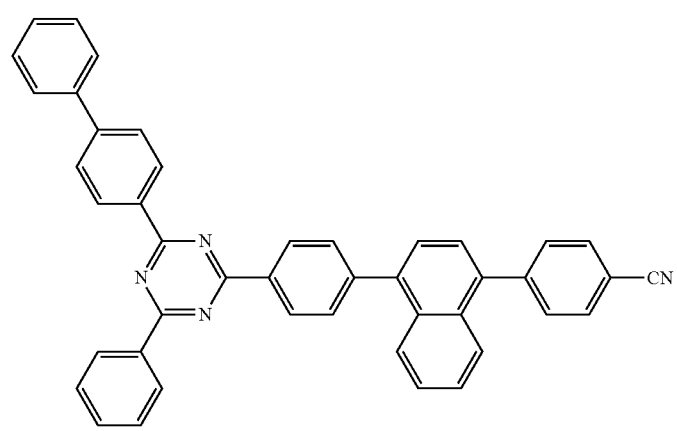

-continued
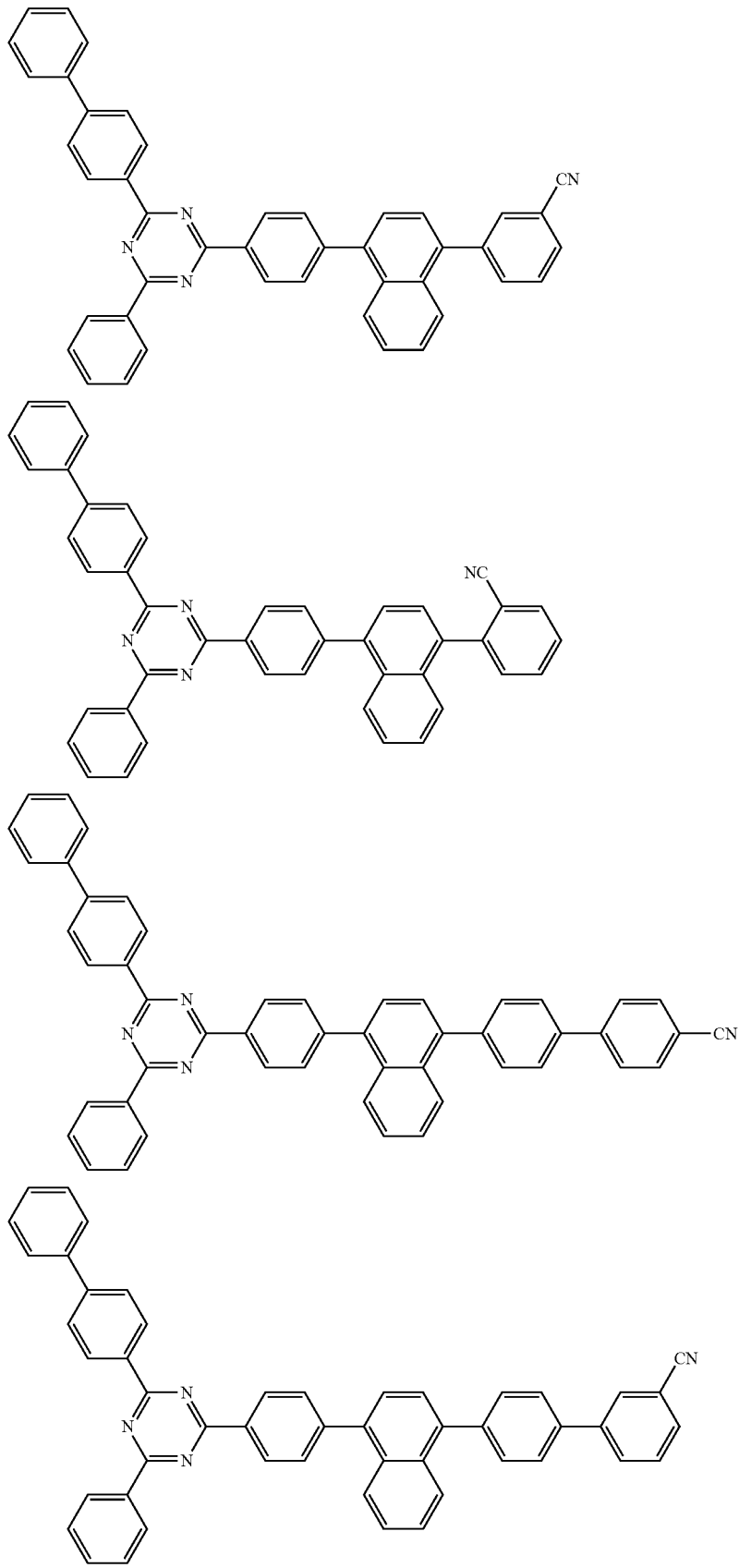

-continued
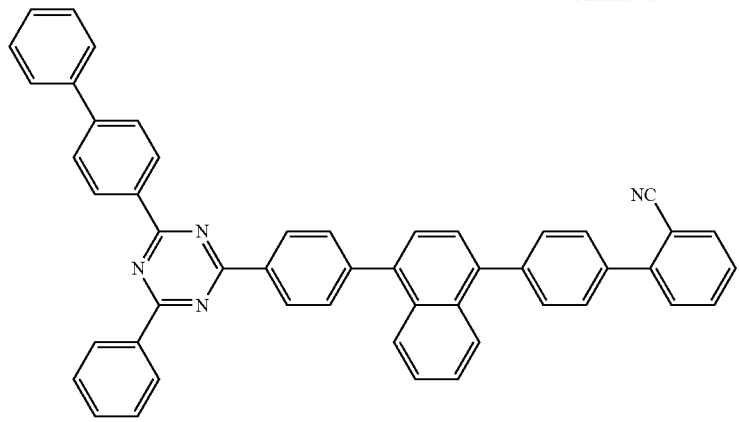
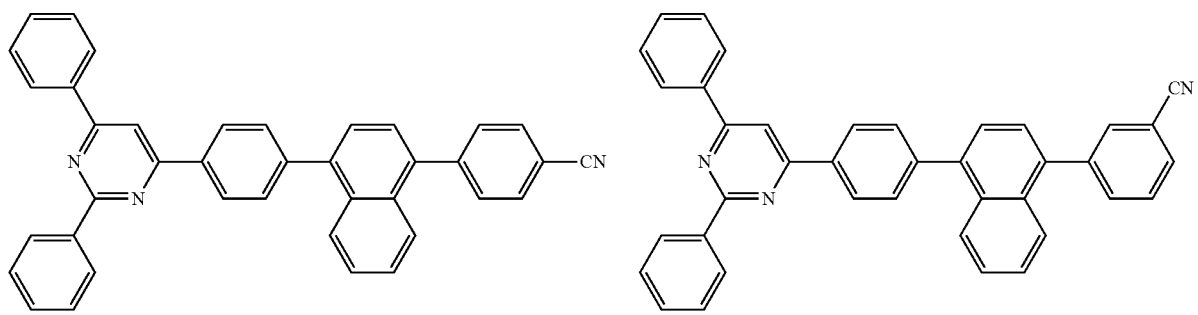
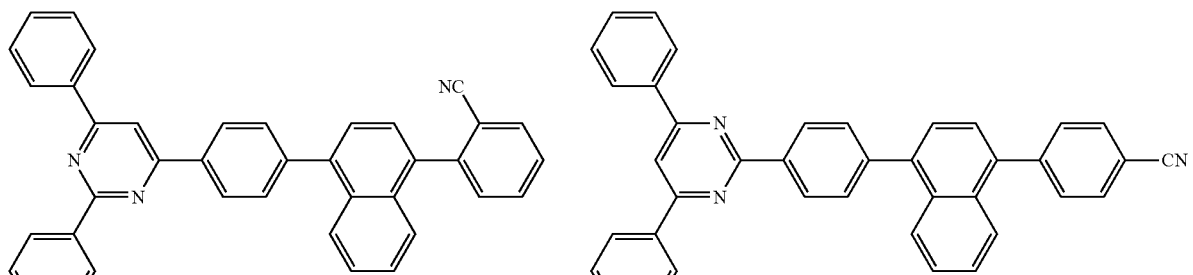
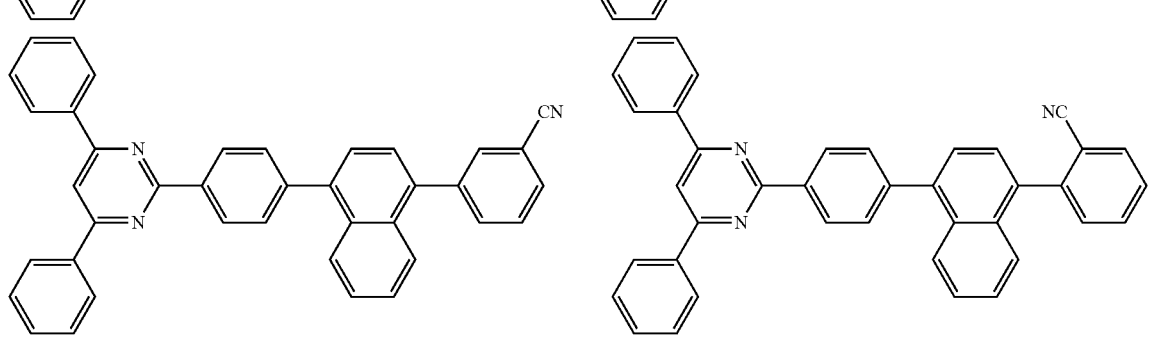
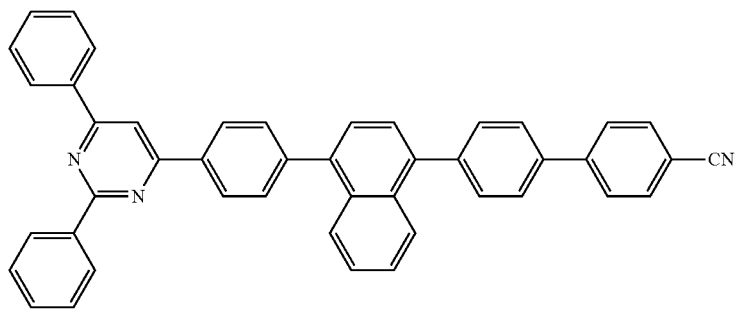

-continued
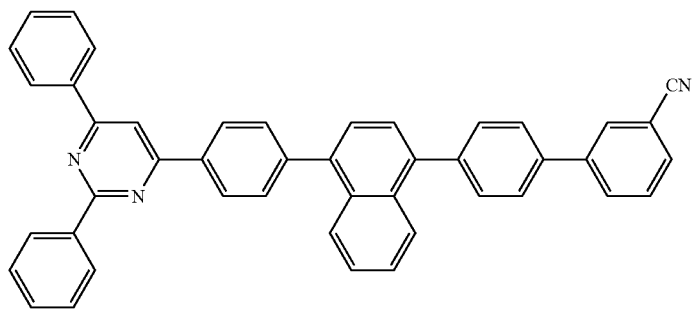
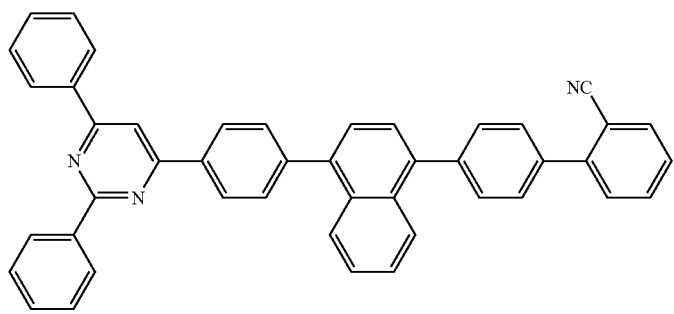
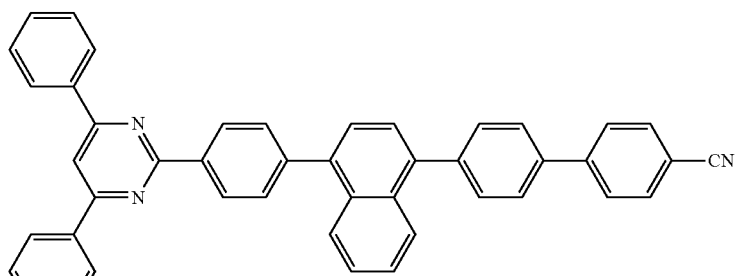
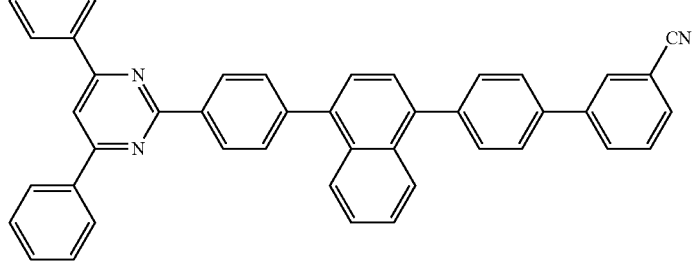
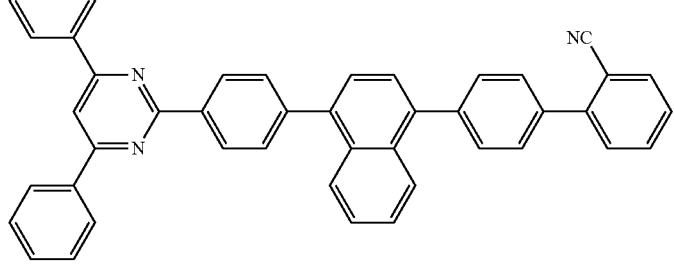

-continued
453
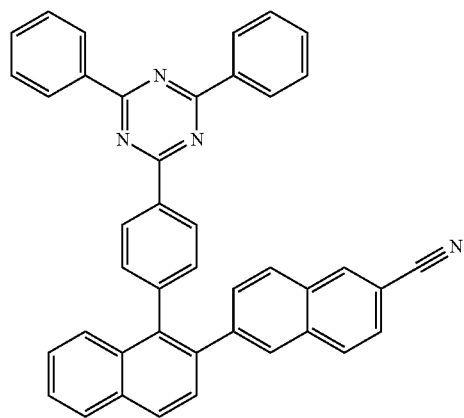
454
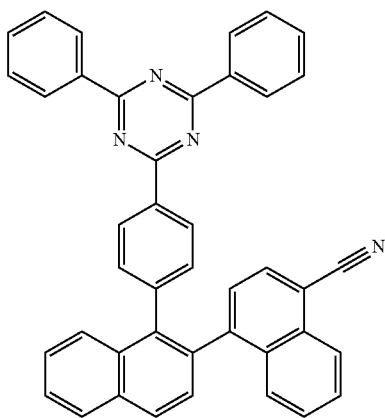
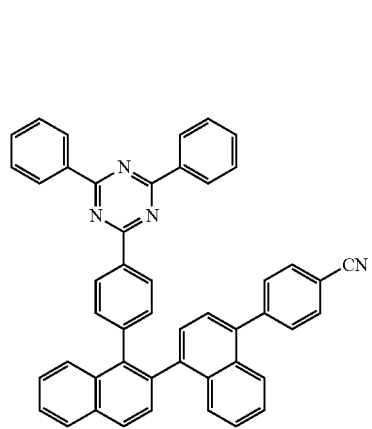
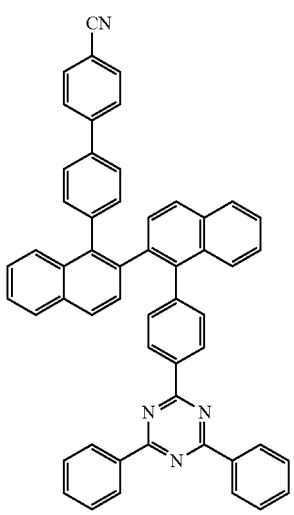
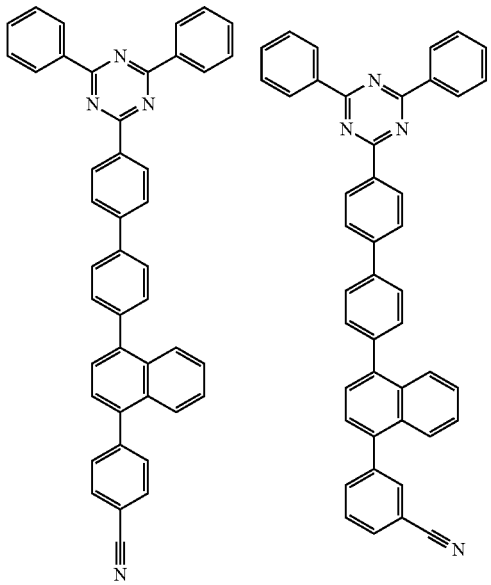
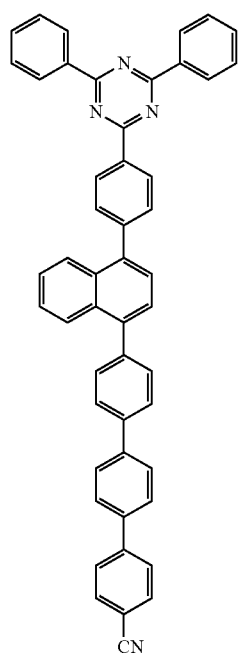
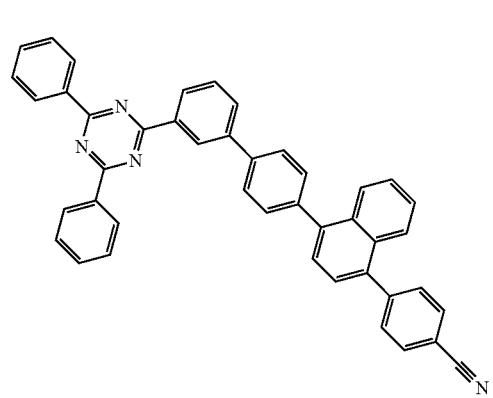

455
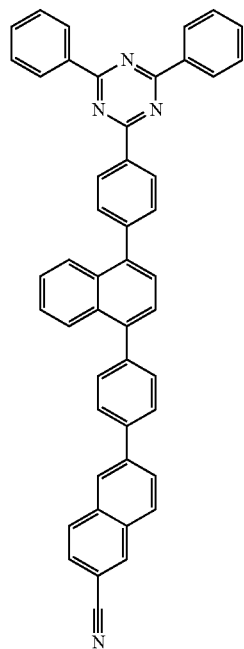
456
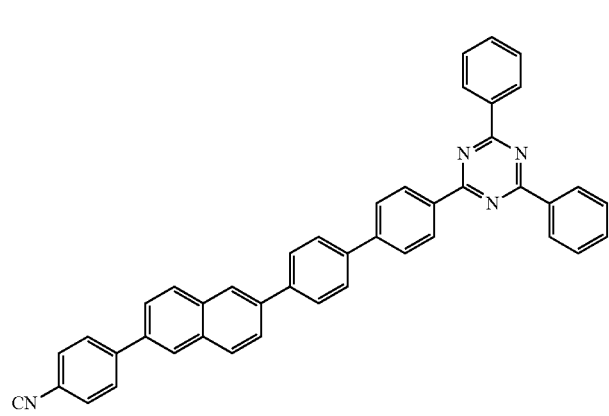
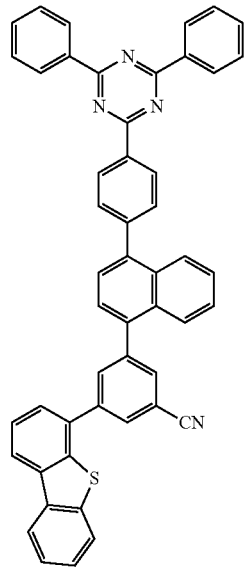
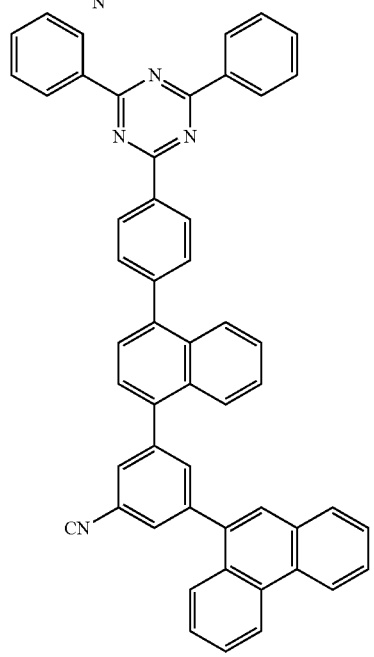
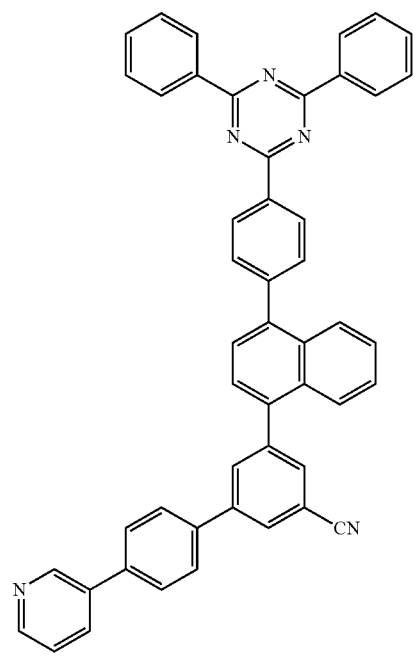
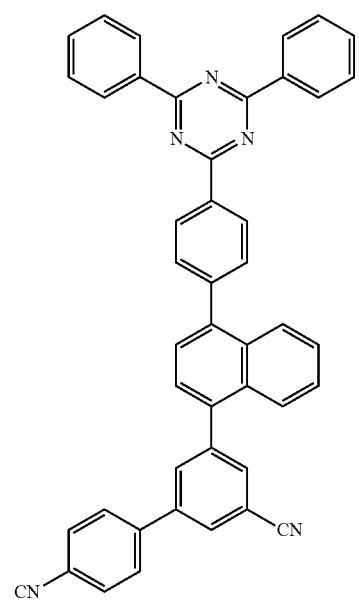
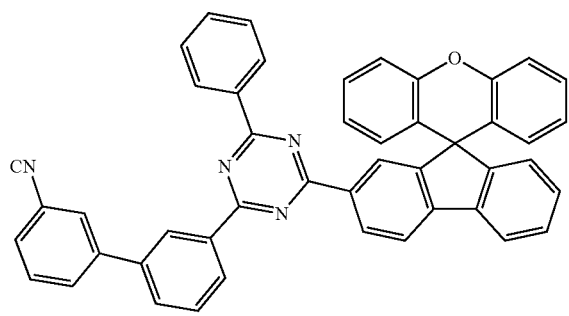

457
-continued
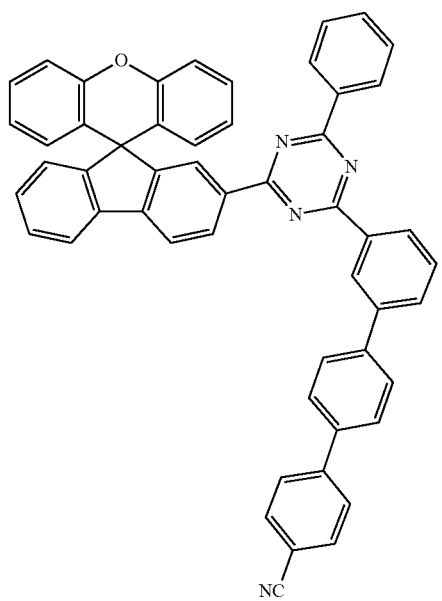
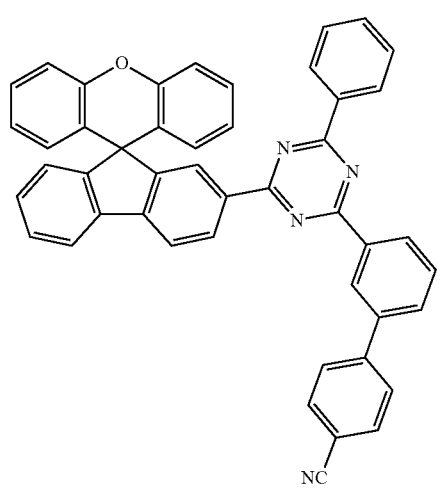
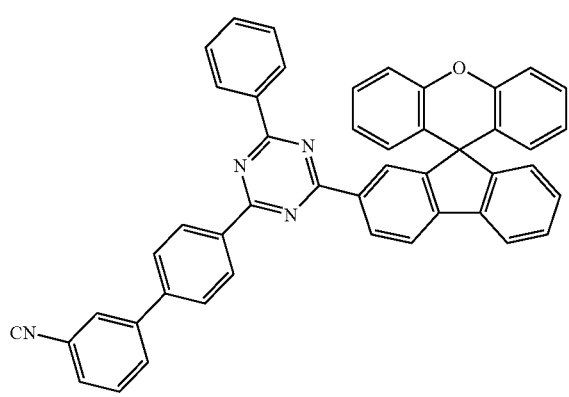
458
-continued
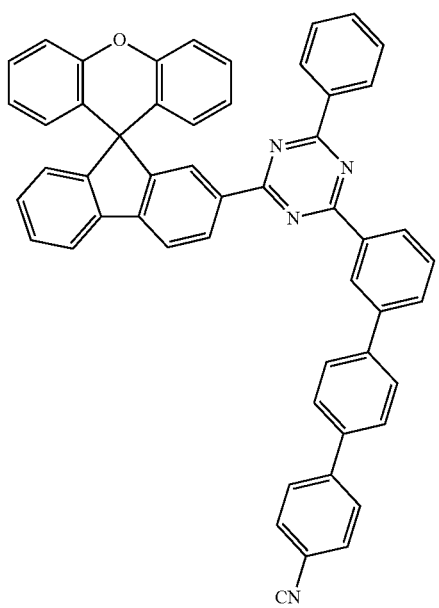
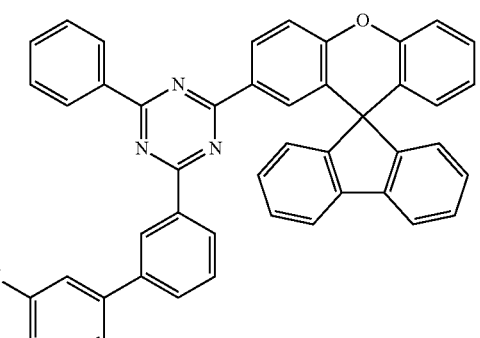
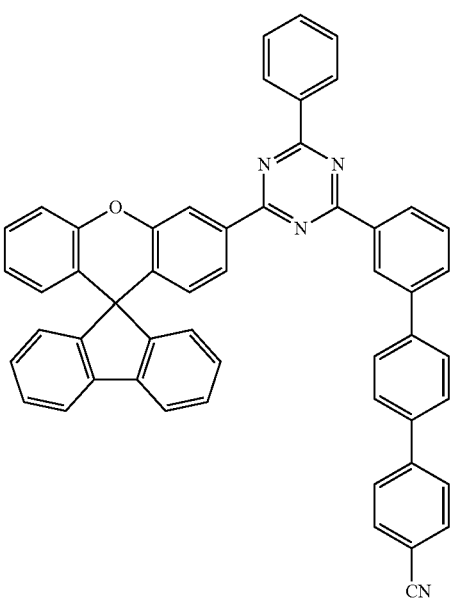

459
-continued
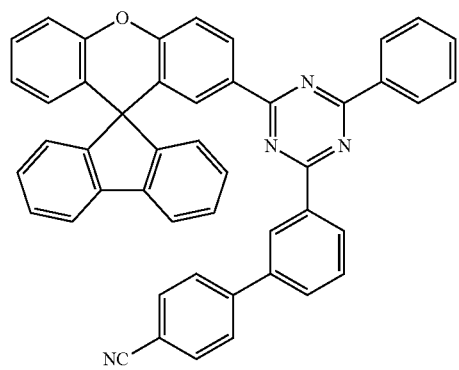
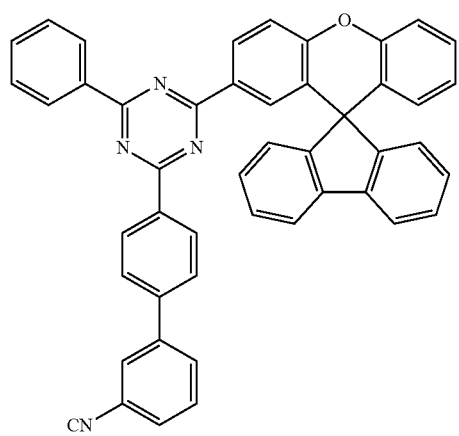
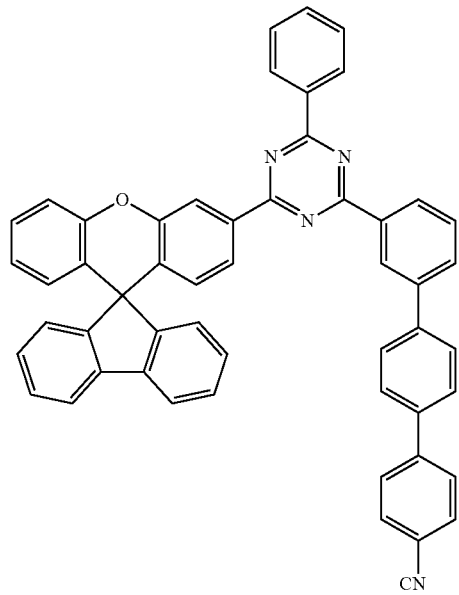
460
-continued
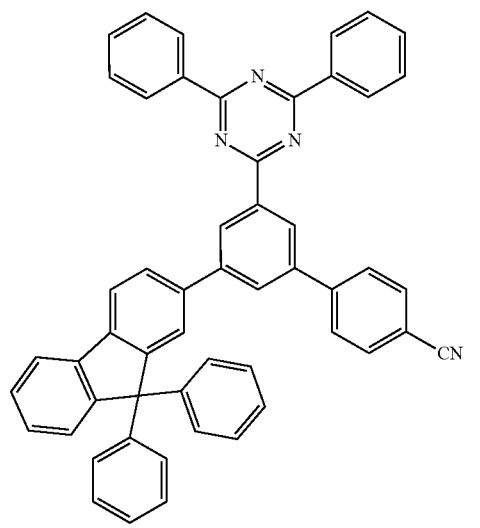
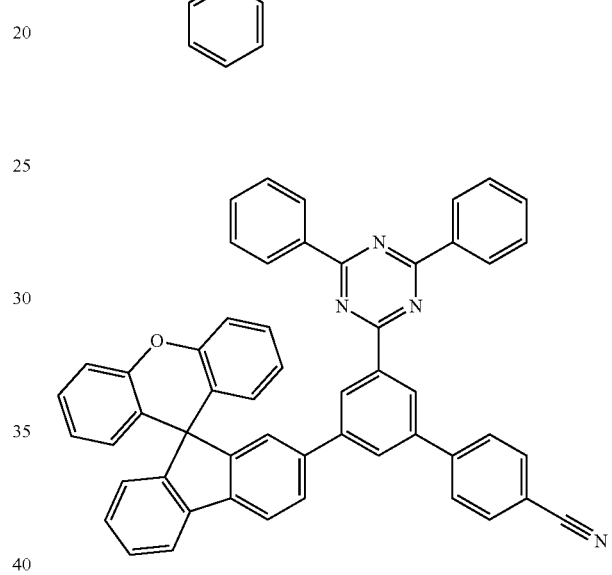
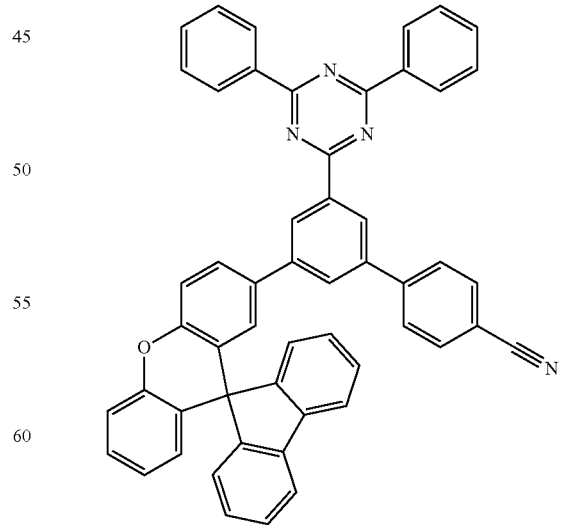

461
-continued
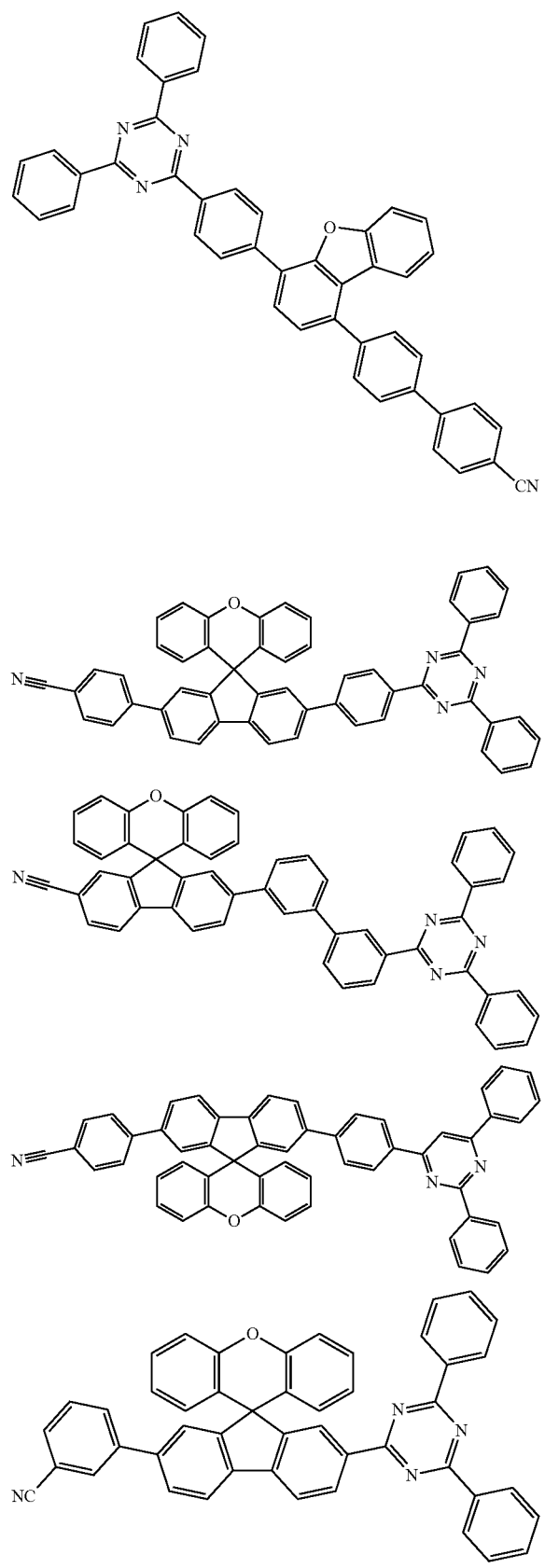
462
-continued
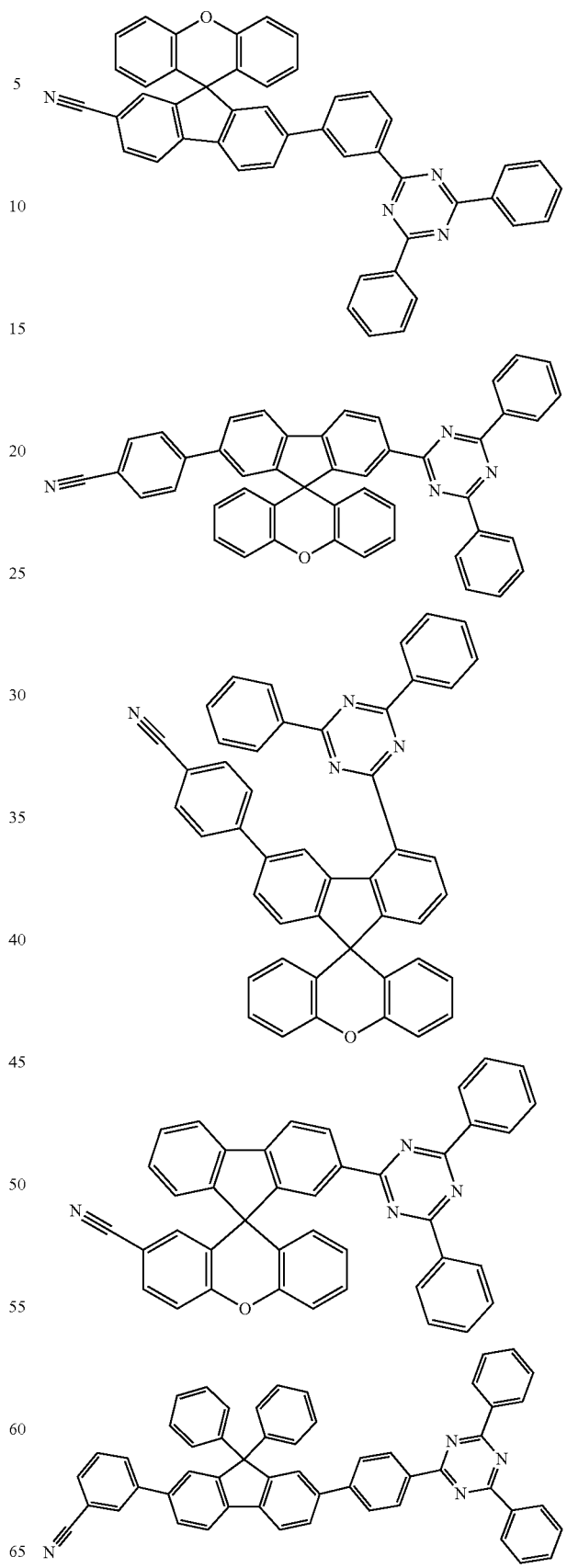

463
-continued
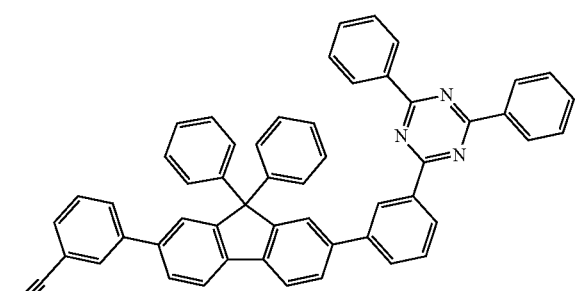
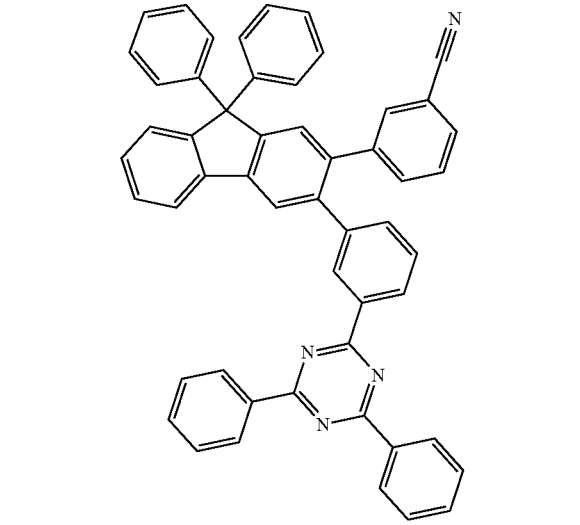
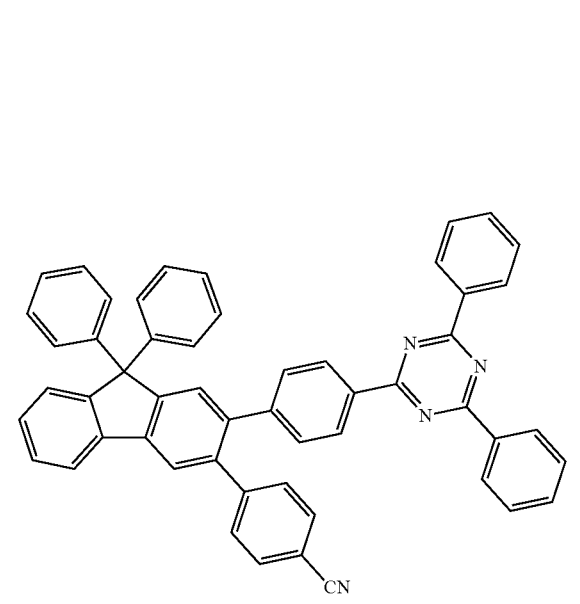
464
-continued
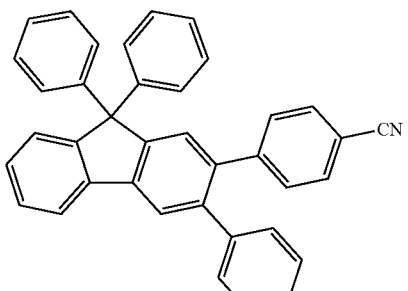
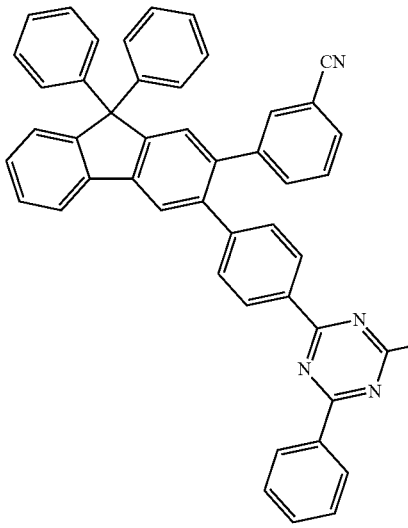
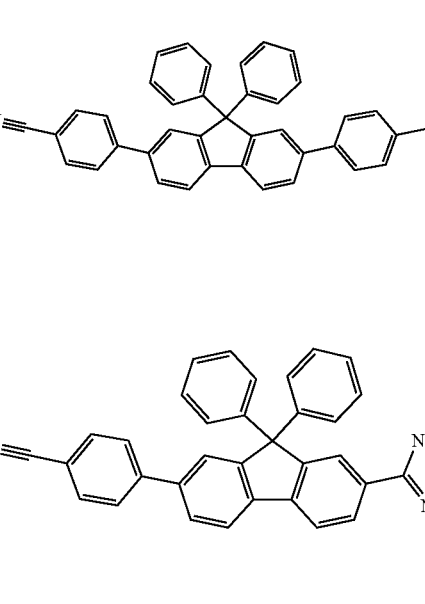
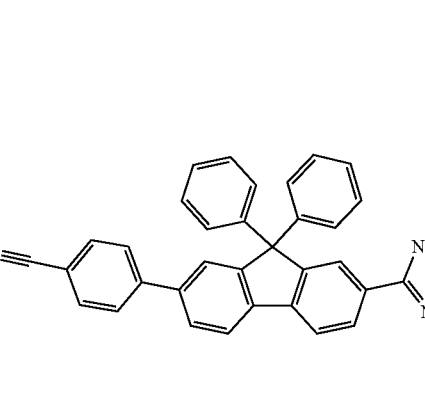

465
-continued
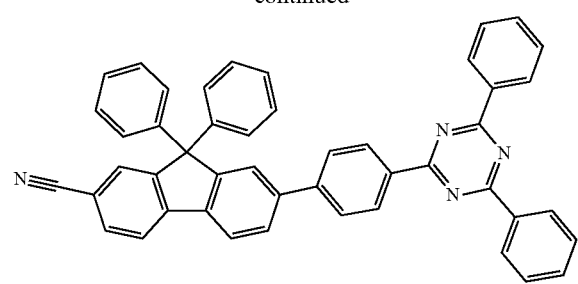
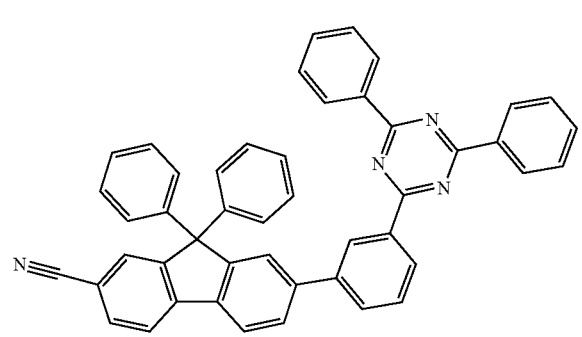
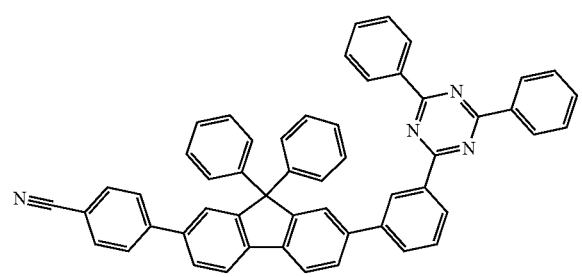
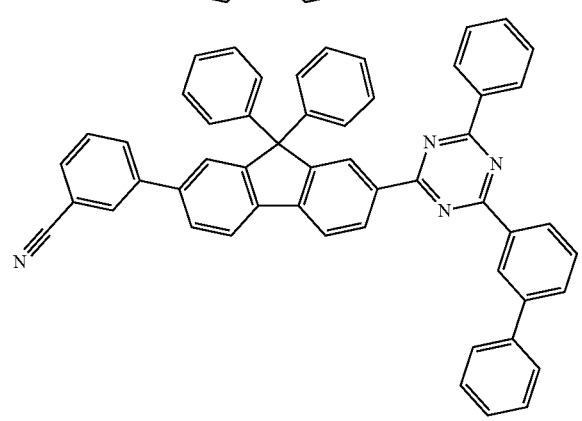
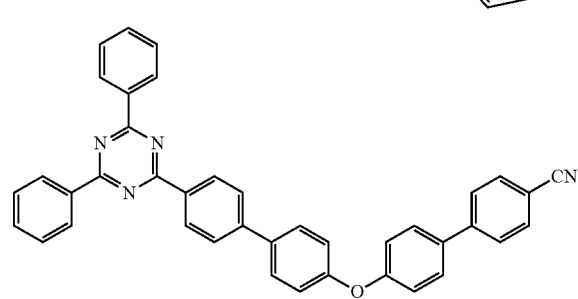
466
-continued
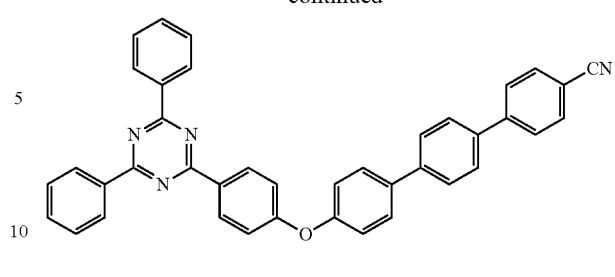
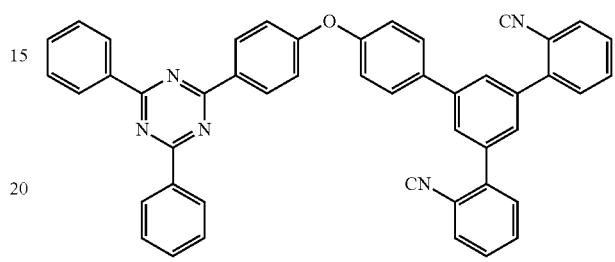
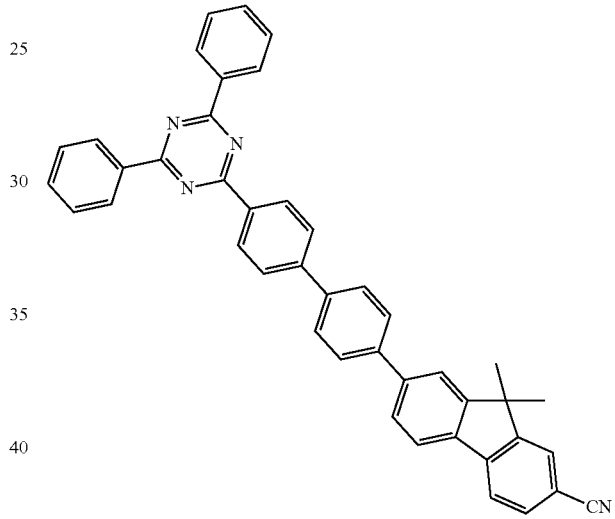
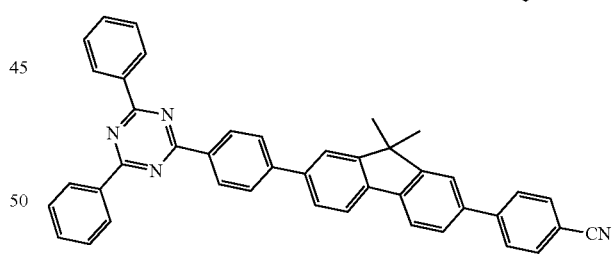
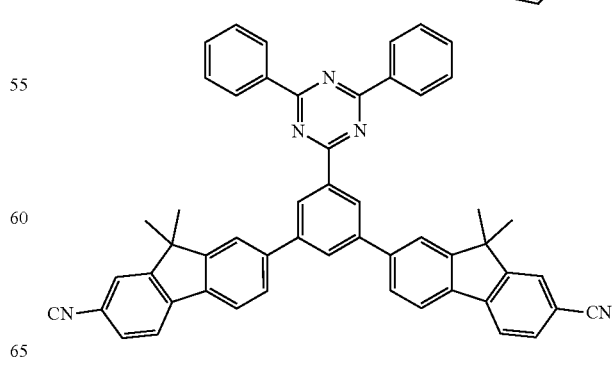

467
-continued
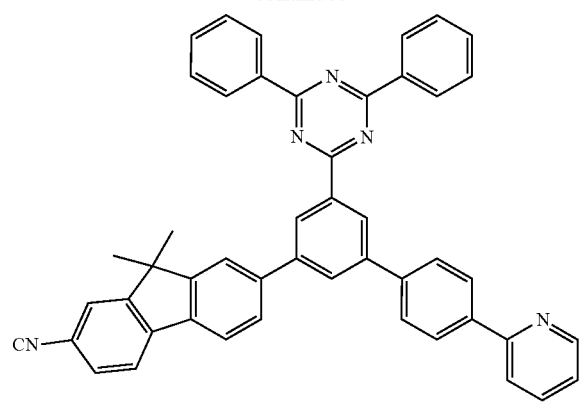
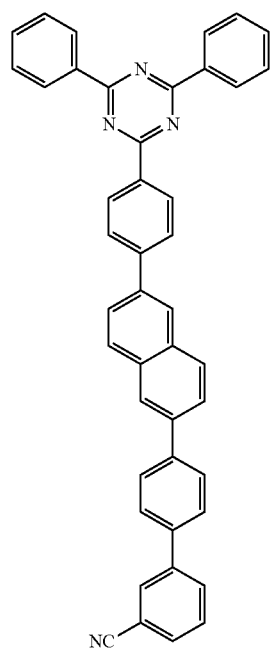
468
-continued
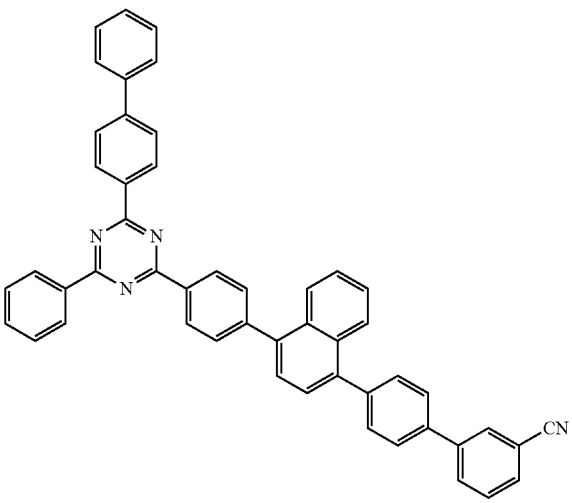
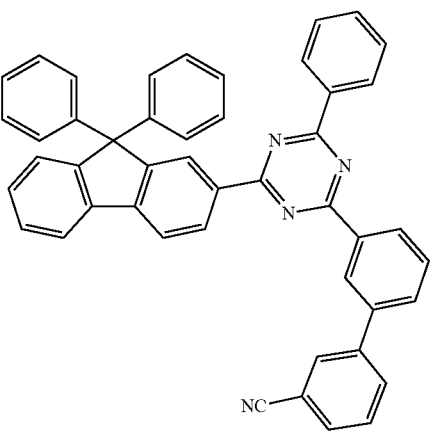

-continued

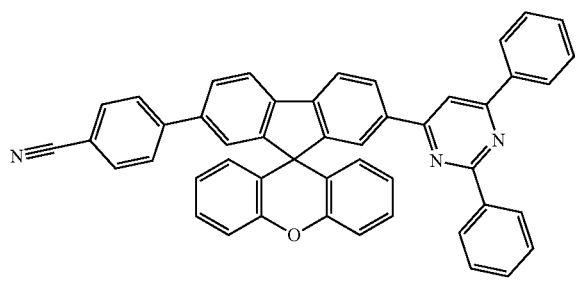

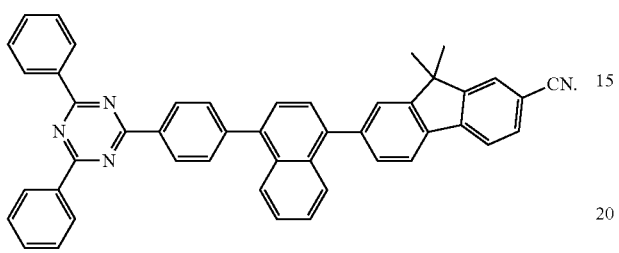

17. The organic light emitting device of claim 11, wherein the compound of Chemical Formula 1 and the compound of Chemical Formula 2 satisfy the following Equation 1:

$|P_{El}| > |P_{Eb}|$  <Equation 1> wherein in Equation 1:

$|P_{Eb}|$ means an absolute value of a dipole moment of the compound of Chemical Formula 1; and $|P_{El}|$ means an absolute value of a dipole moment of the compound of Chemical Formula 2.

18. The organic light emitting device of claim 10, wherein the compound of Chemical Formula 1 is selected from among the following compounds:

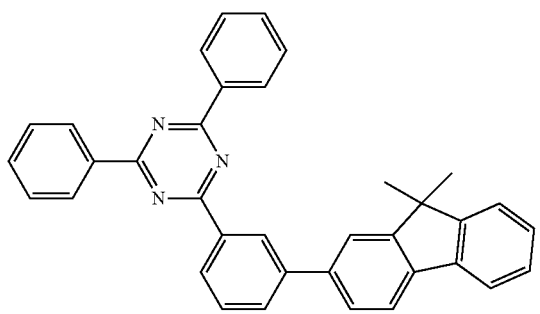

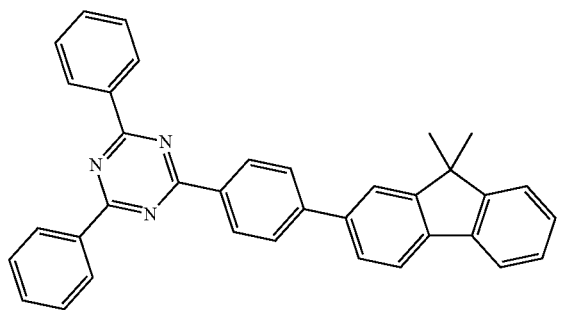

-continued

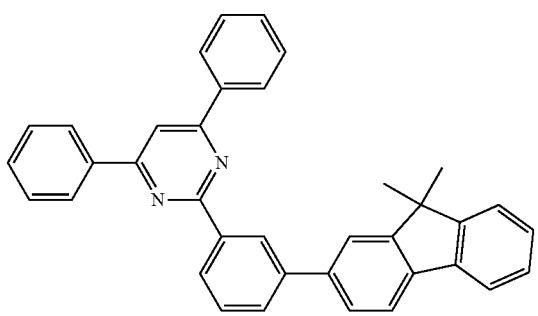

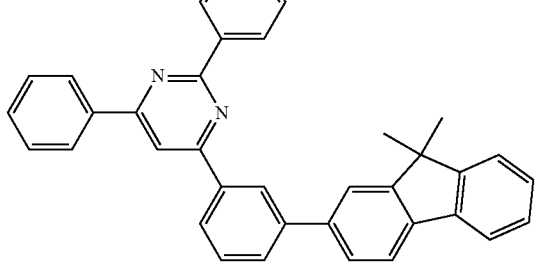

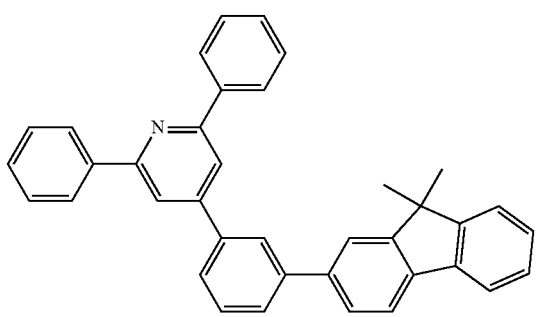

471
-continued
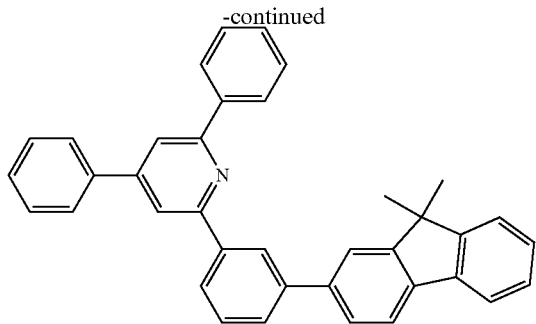
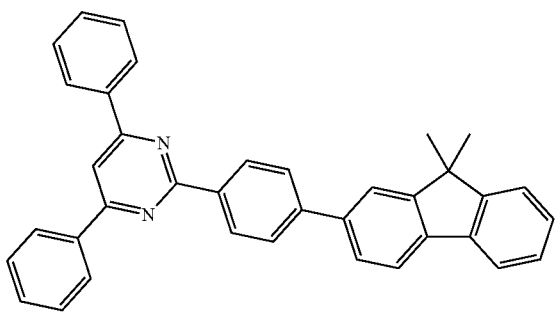
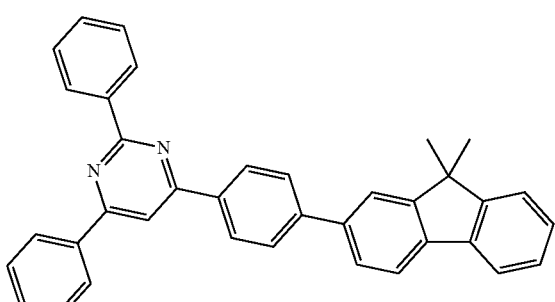
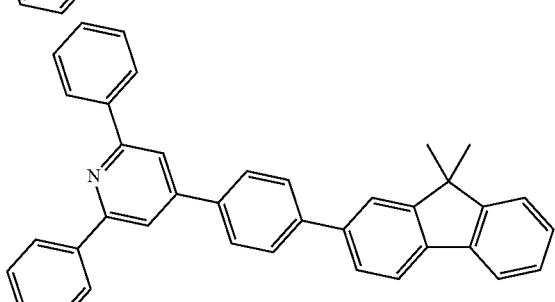
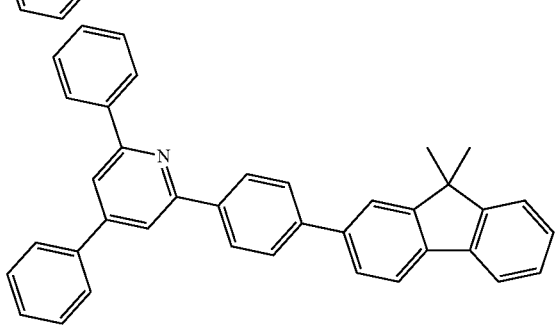
472
-continued
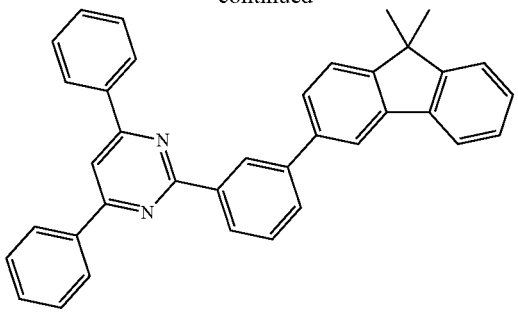
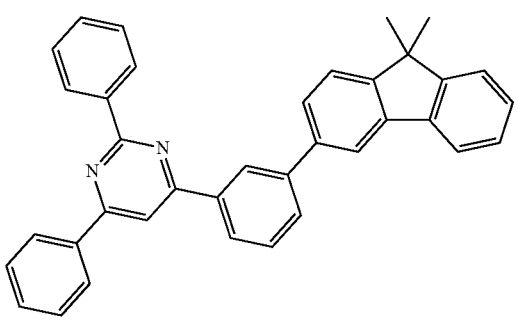
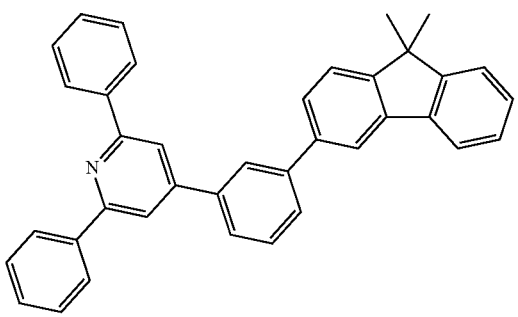
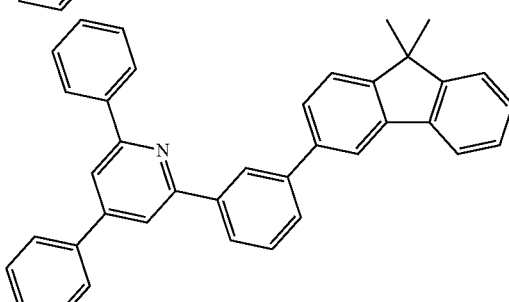
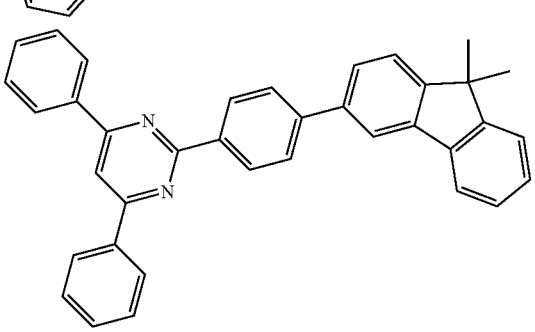

473
-continued
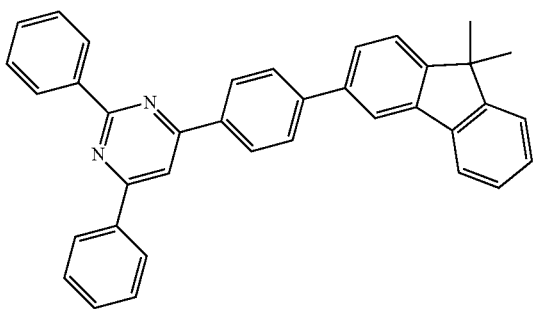
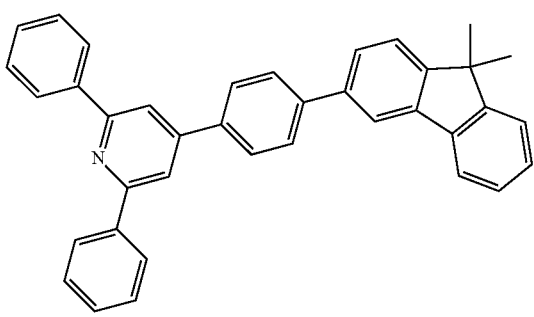
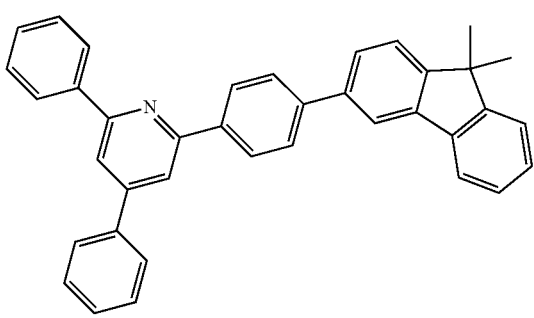
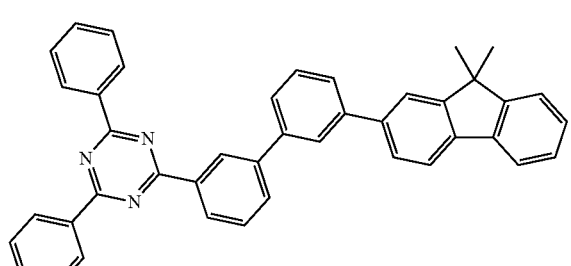
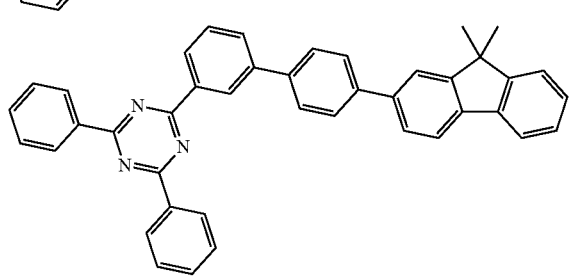
474
-continued
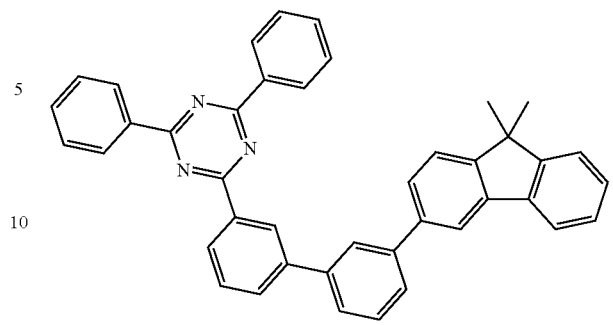
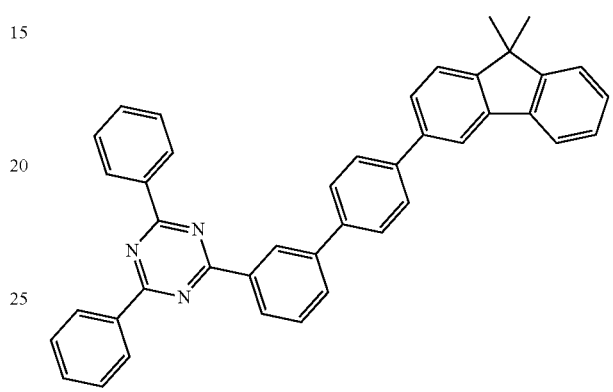
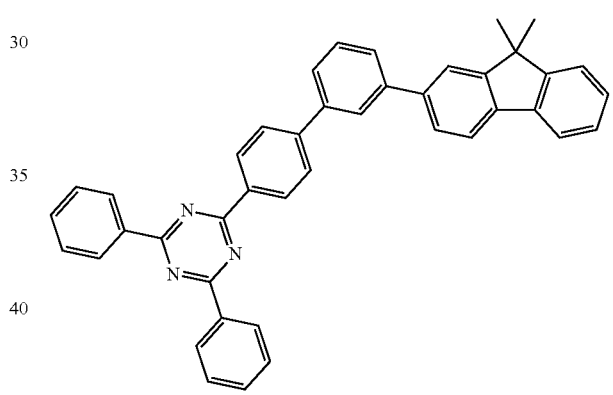
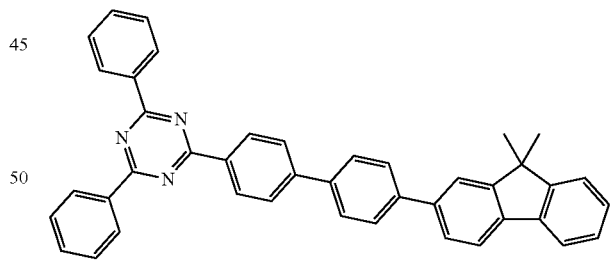
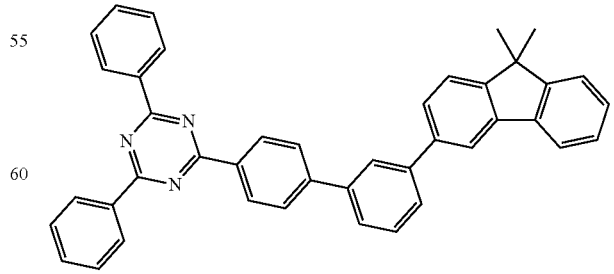

475
-continued
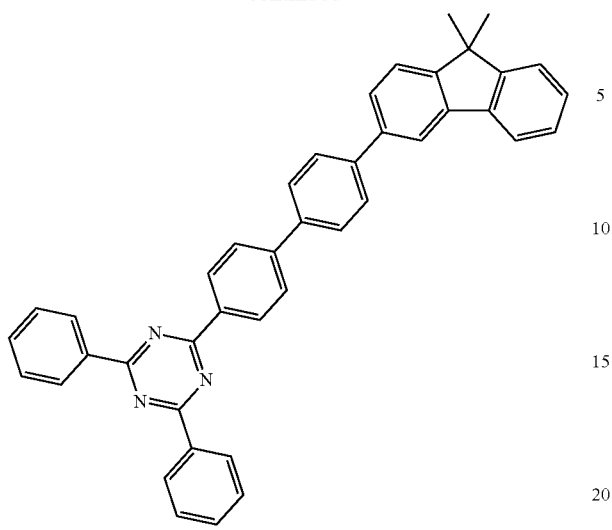
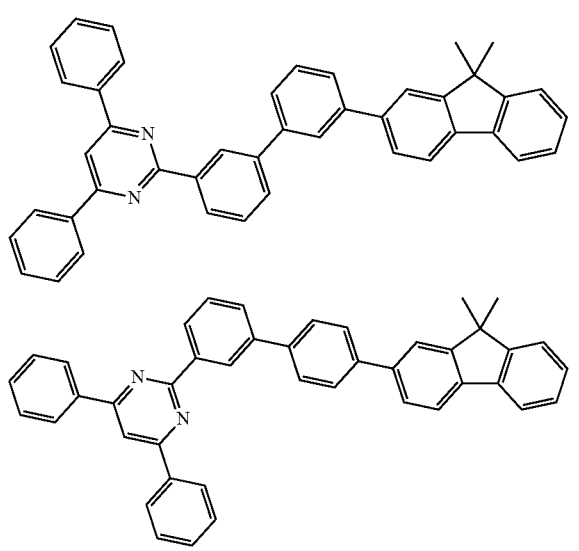
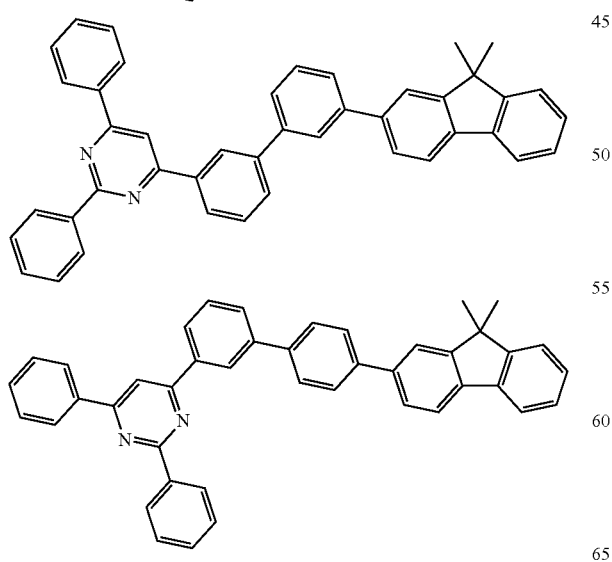
476
-continued
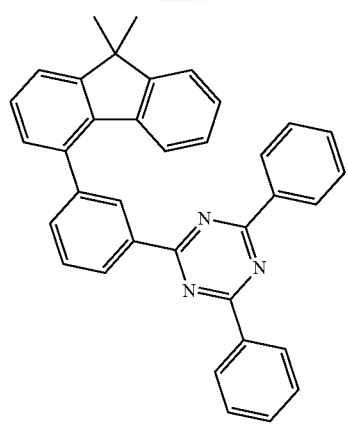
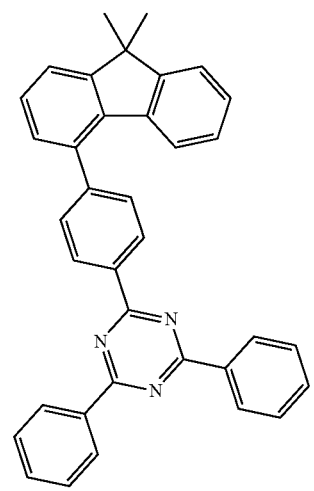
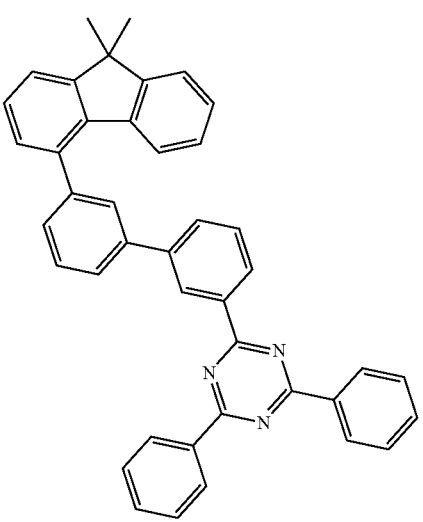

477
-continued
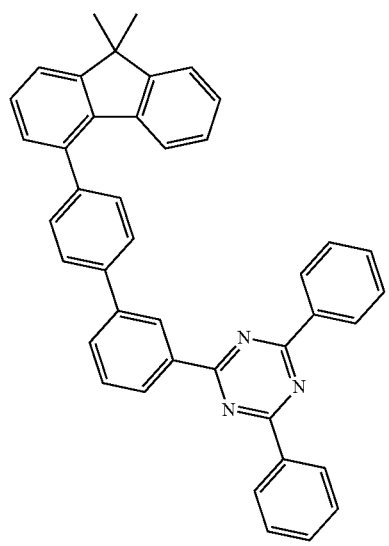
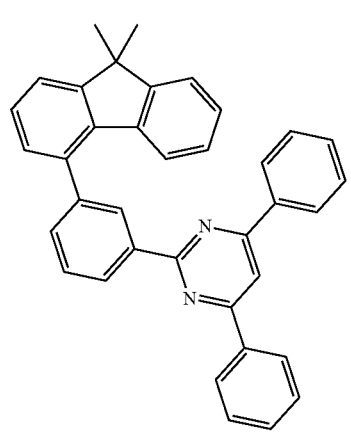
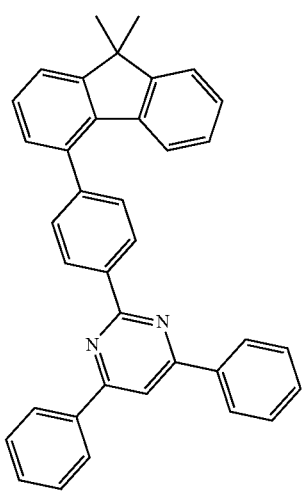
478
-continued
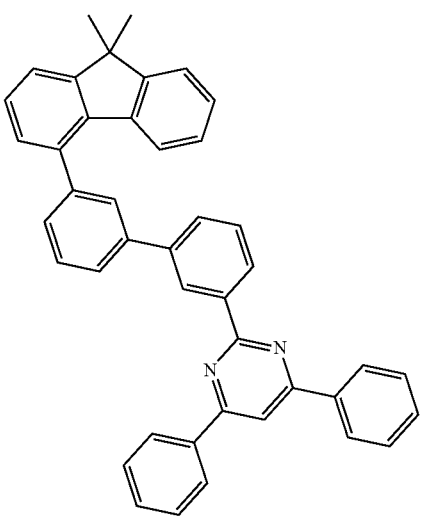
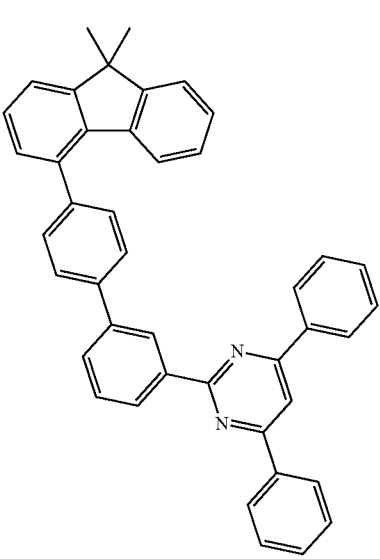
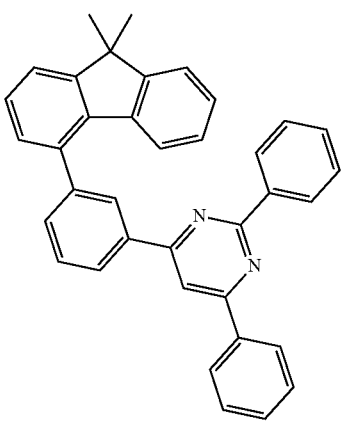

479
-continued
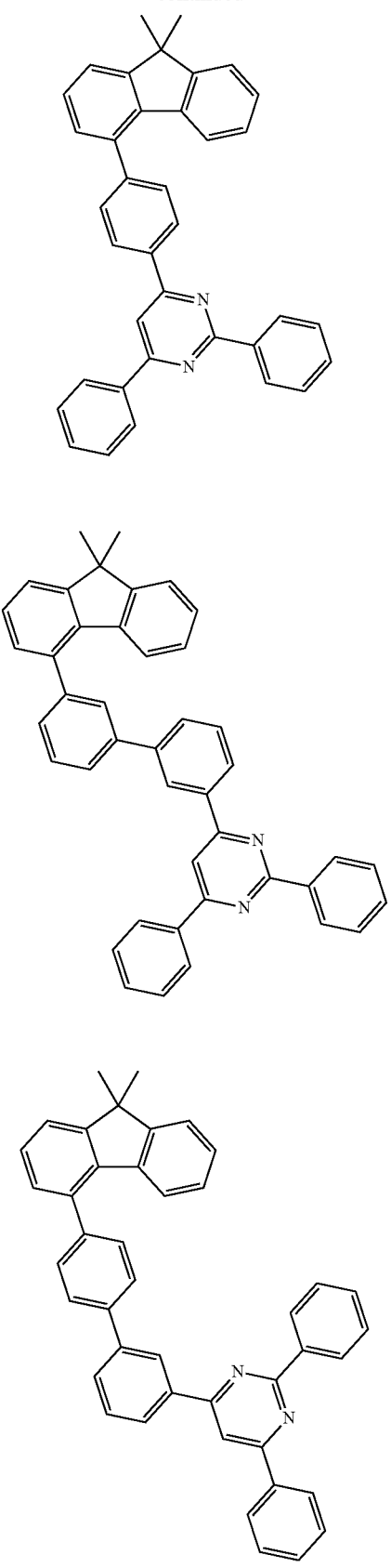
480
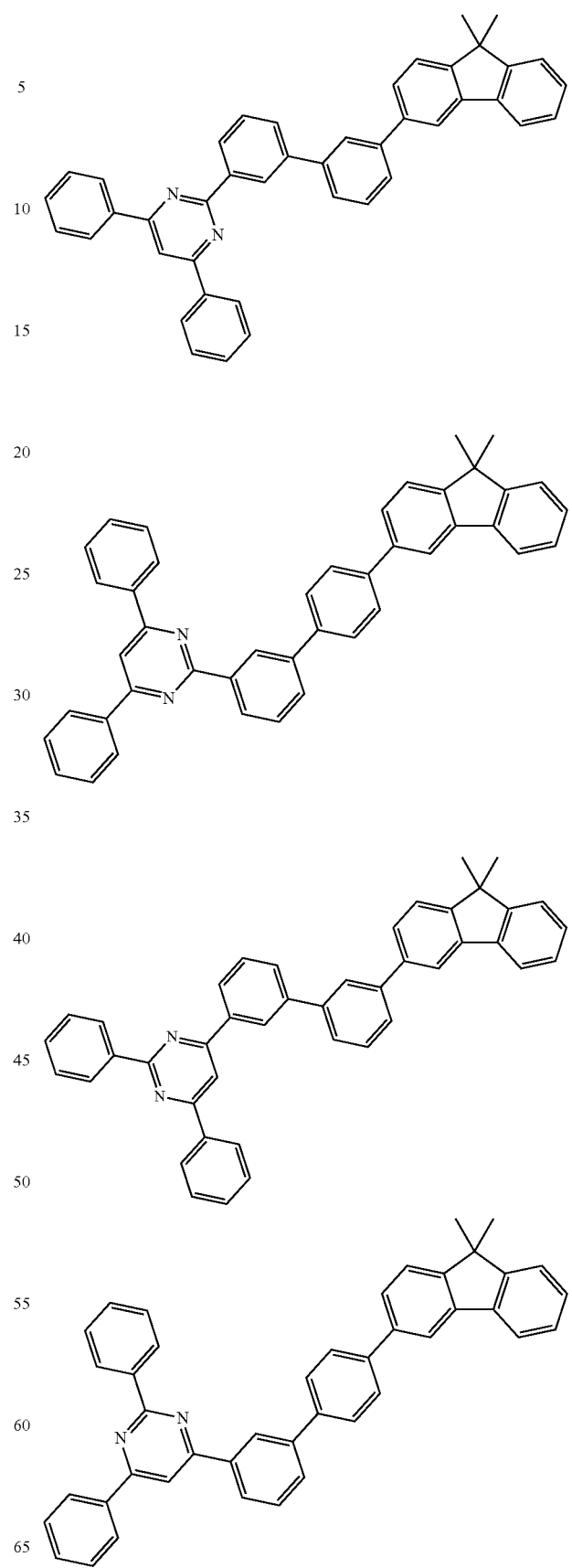

481
-continued
482
-continued
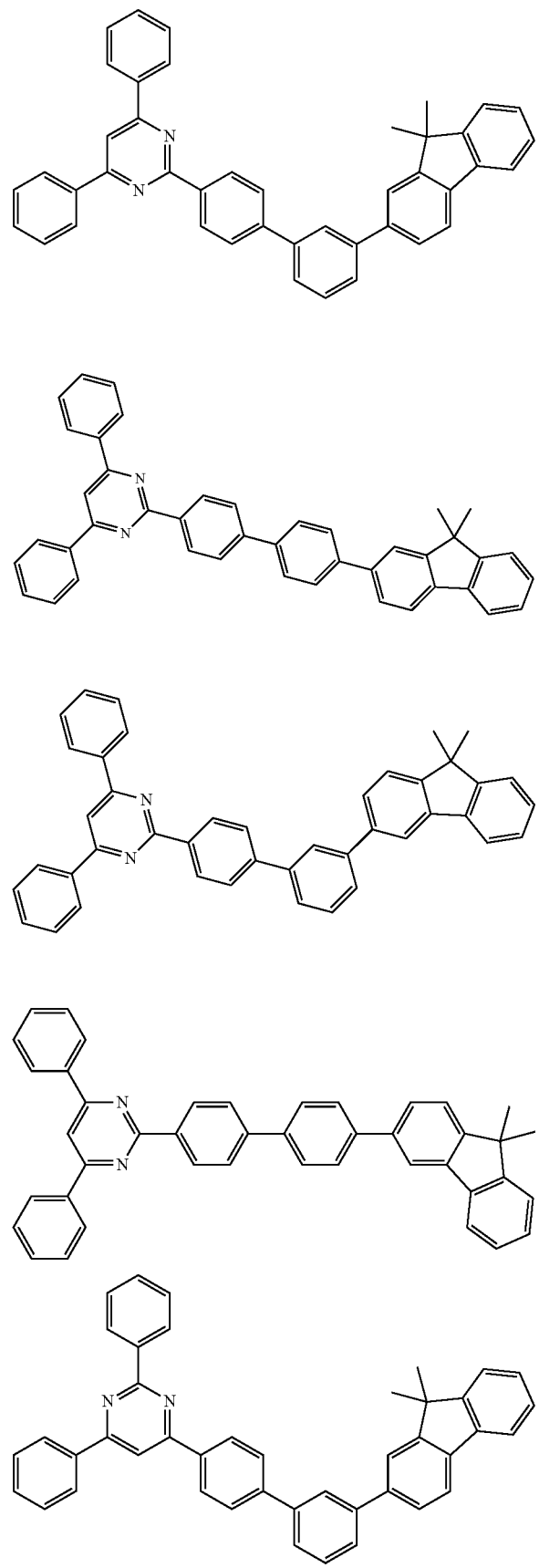
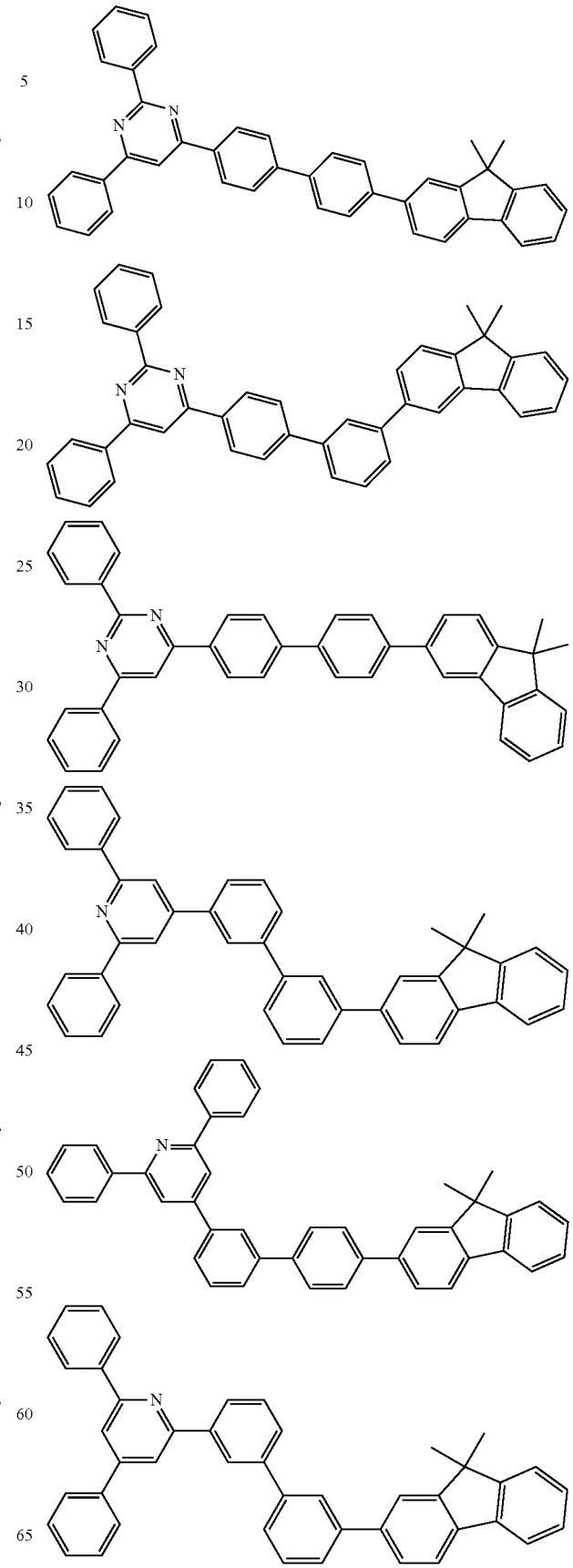

483
-continued
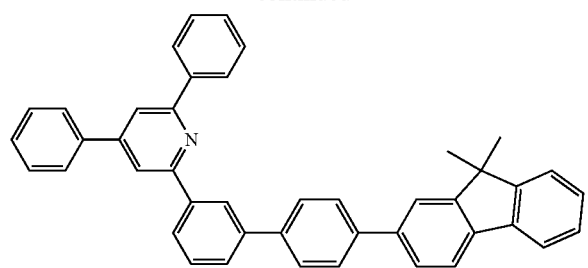
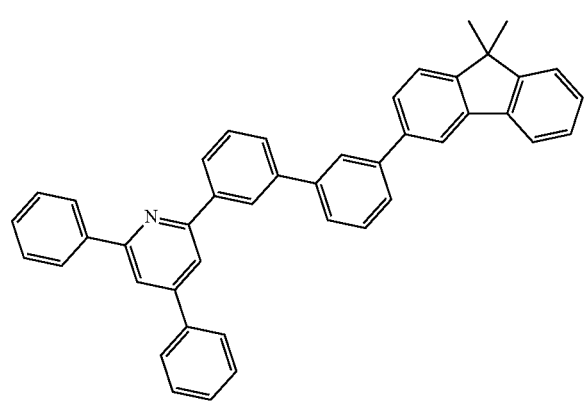
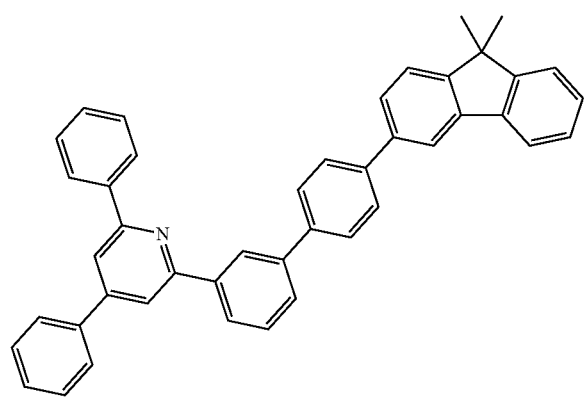
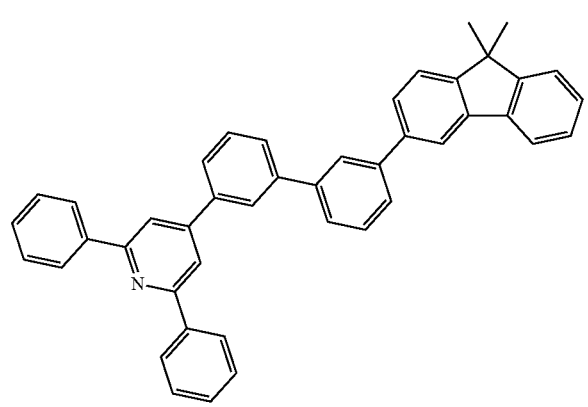
484
-continued
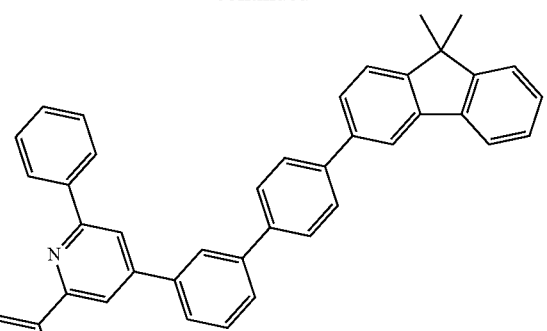
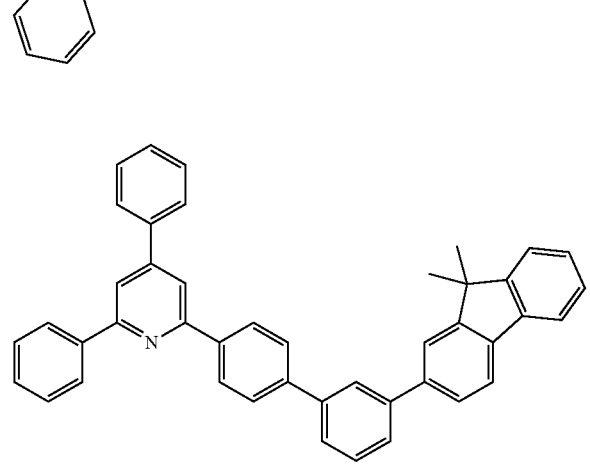
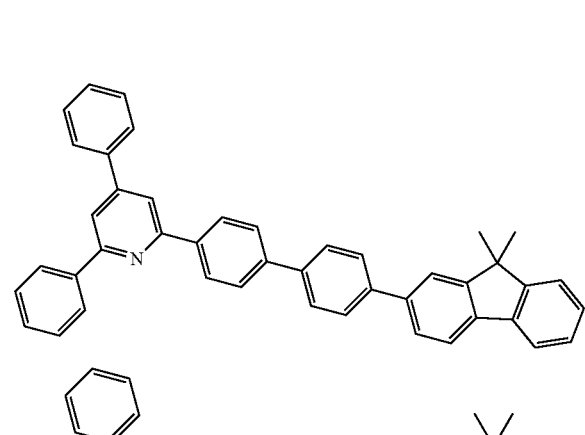
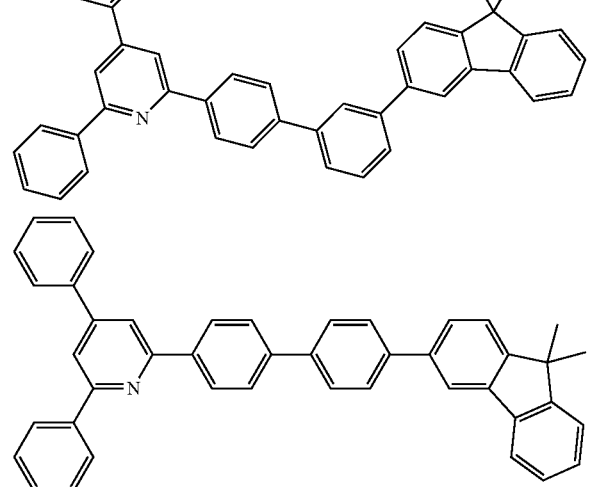

485
-continued
486
-continued
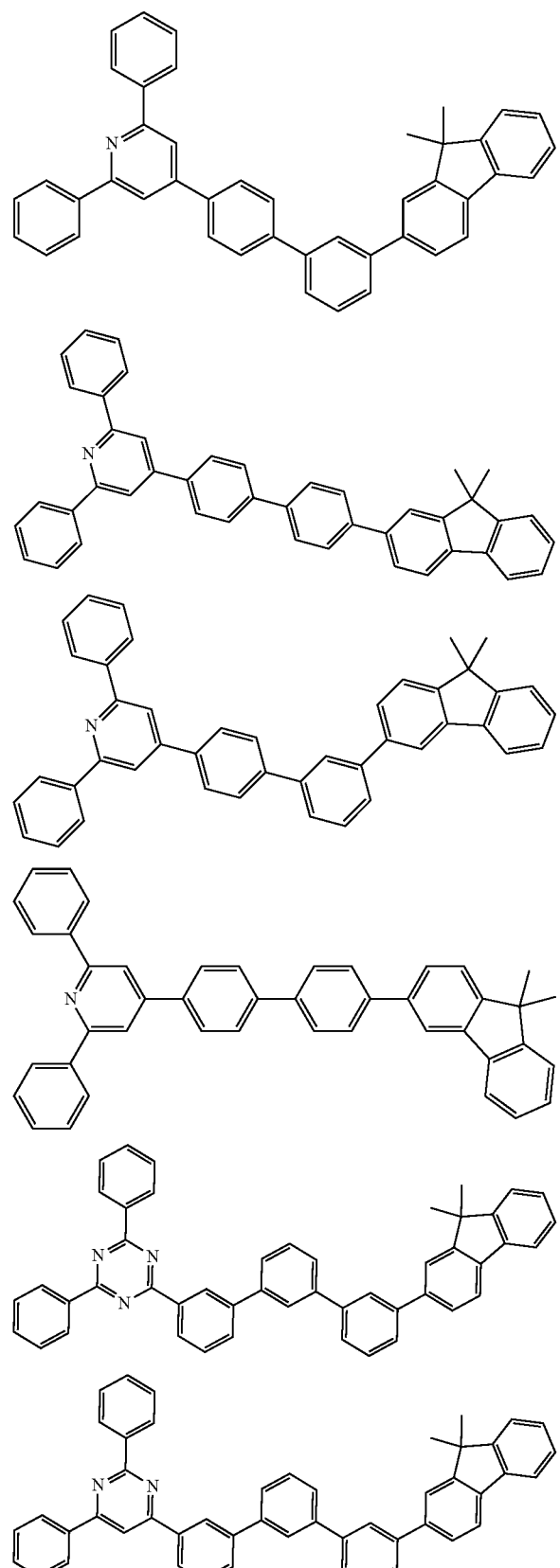
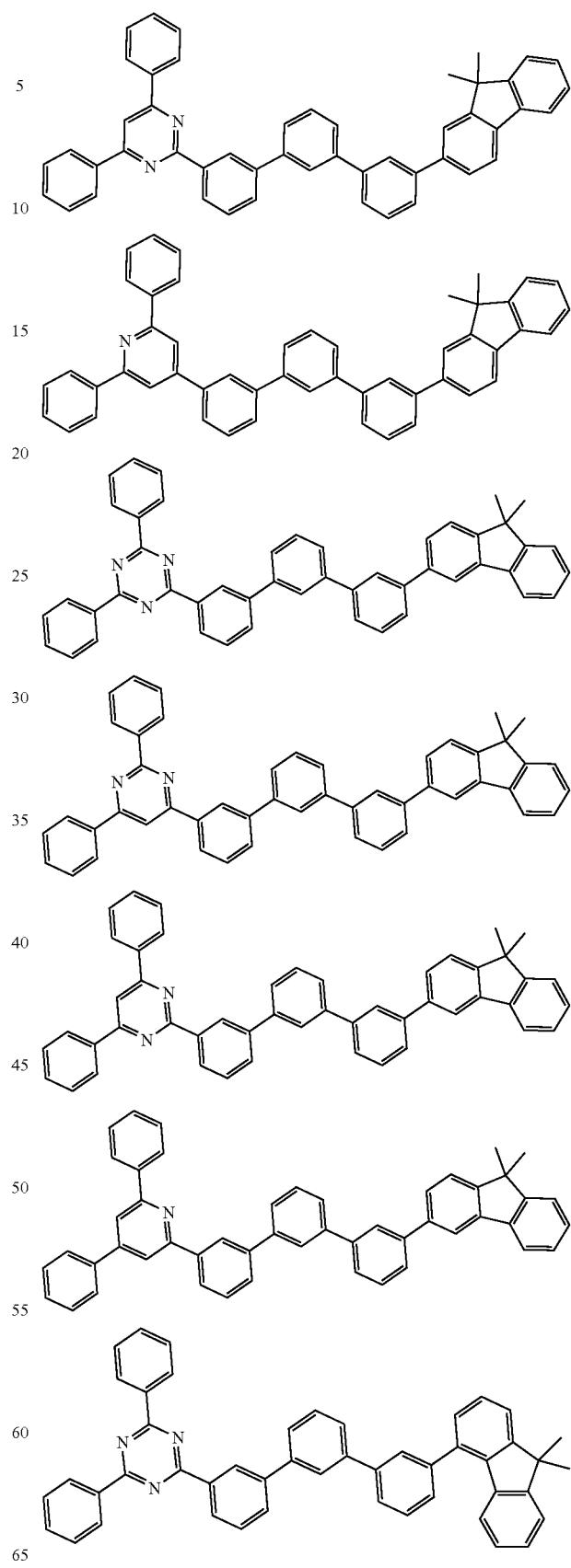

487
-continued
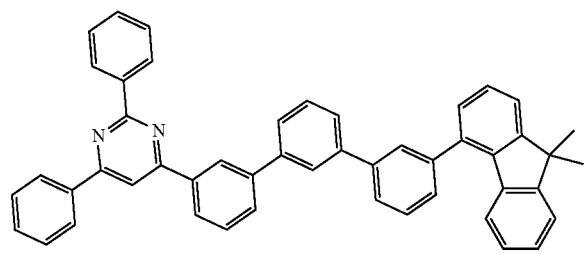
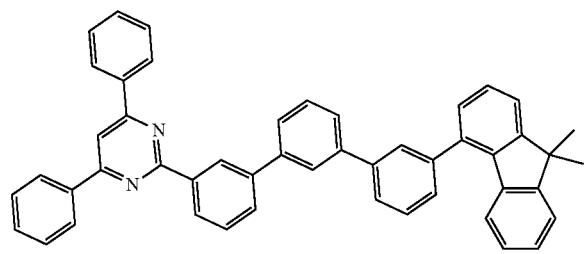
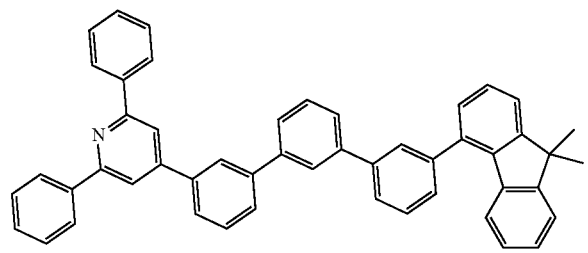
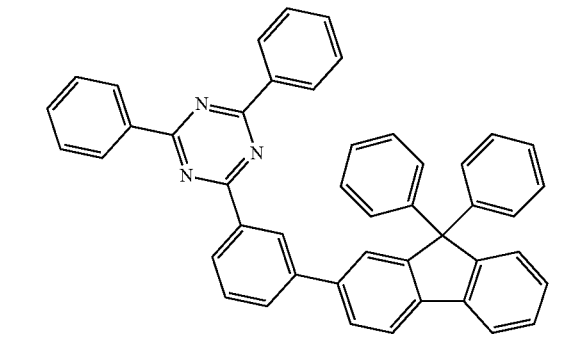
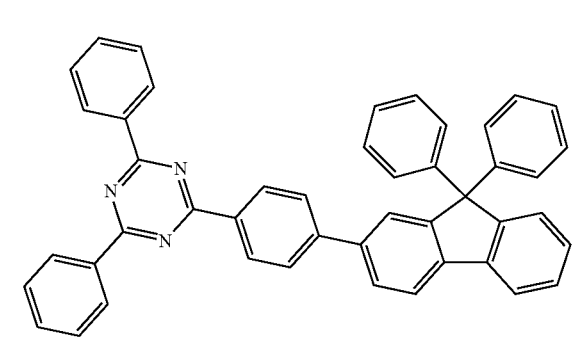
488
-continued
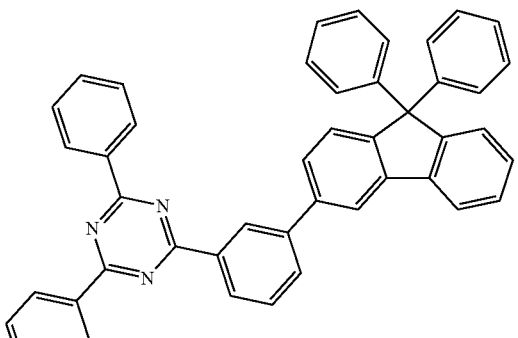
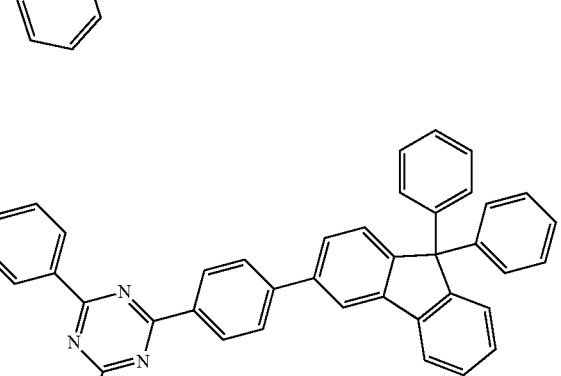
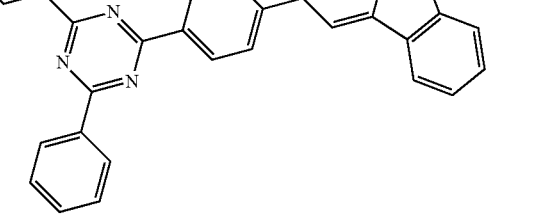
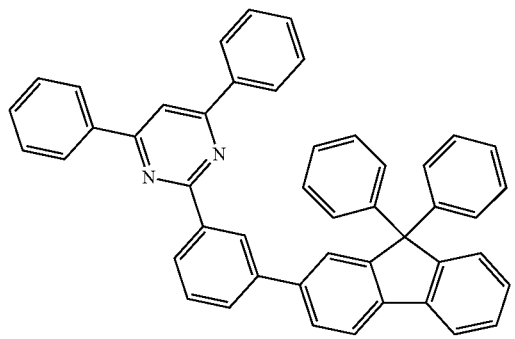
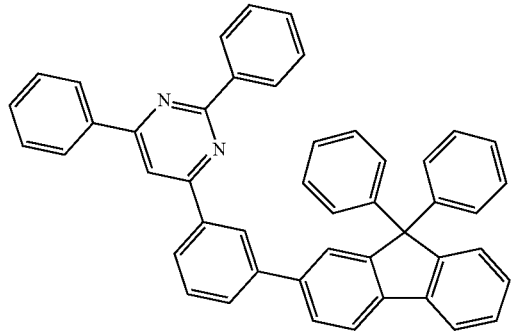

489
-continued
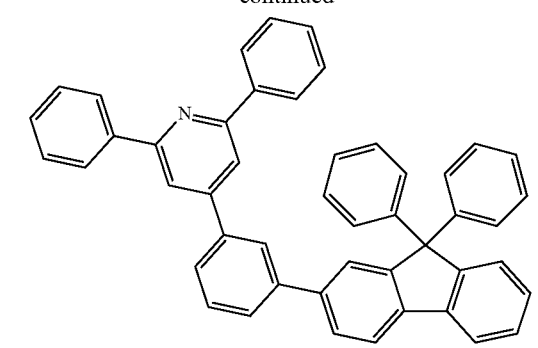
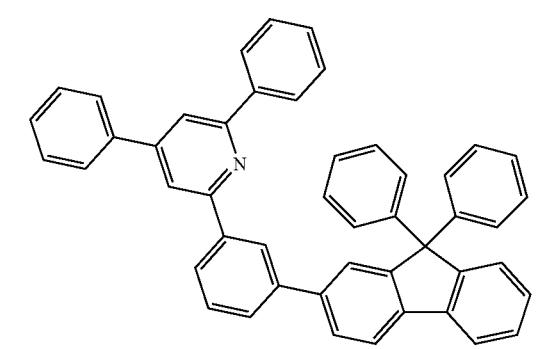
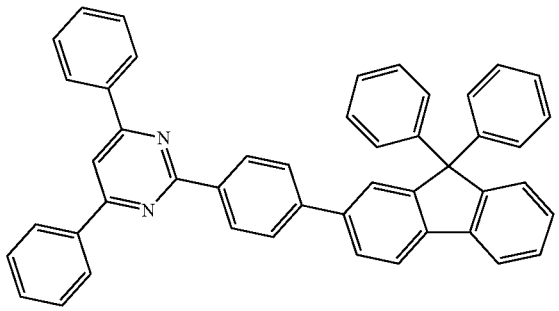
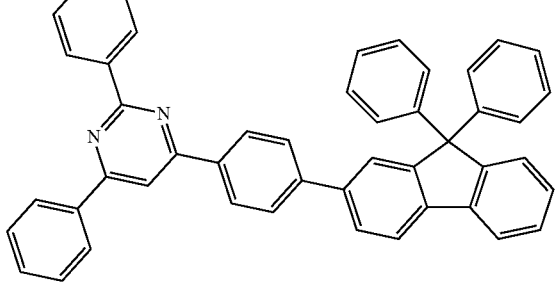
490
-continued
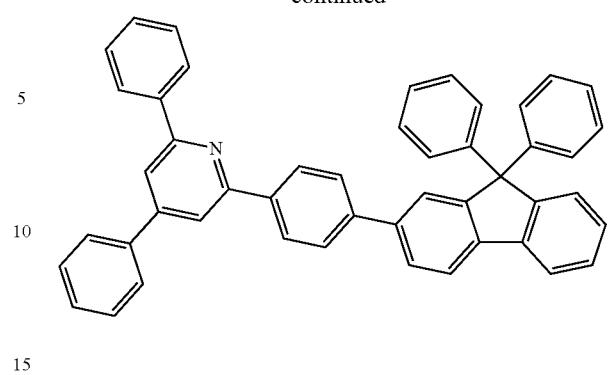
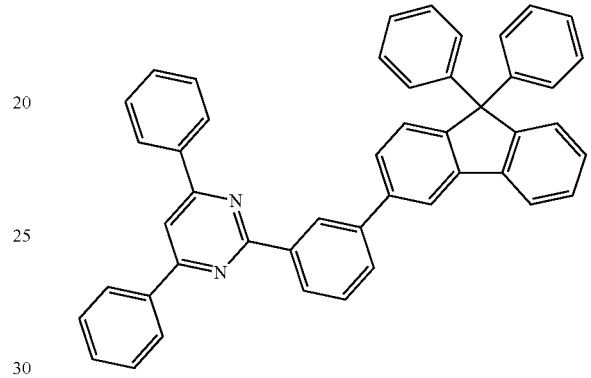
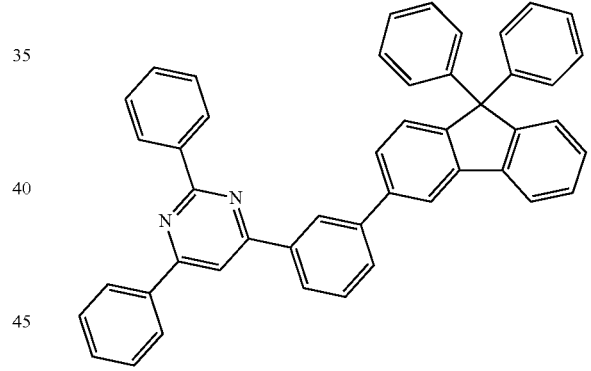
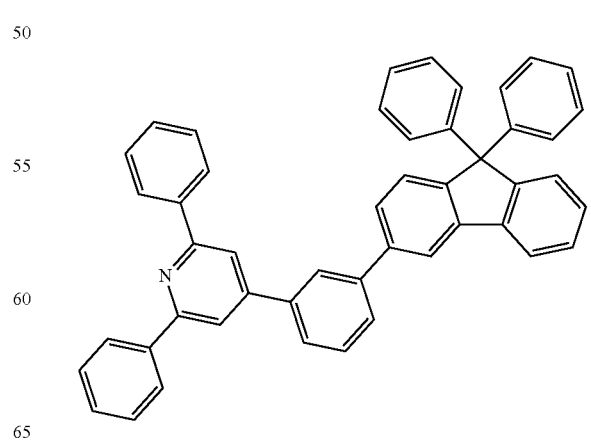

491
-continued
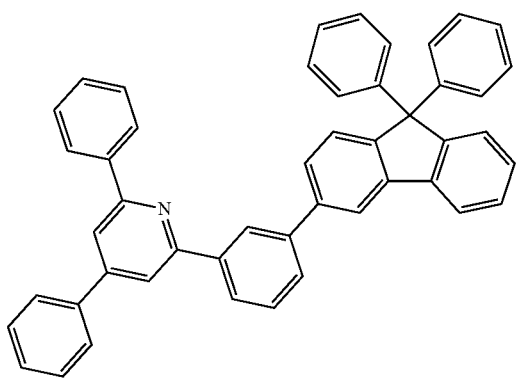
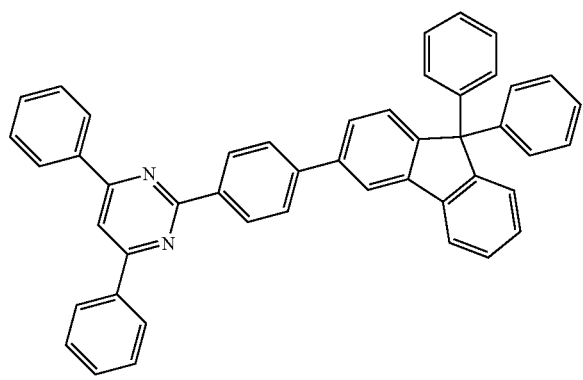
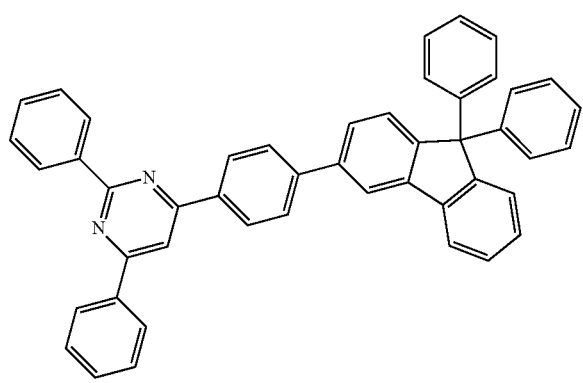
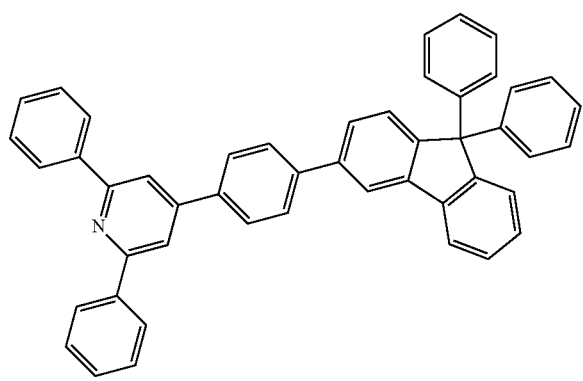
492
-continued
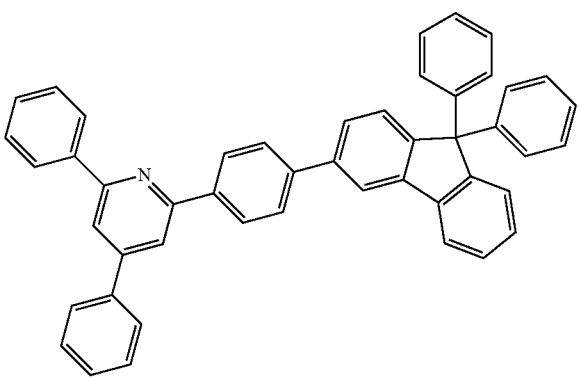
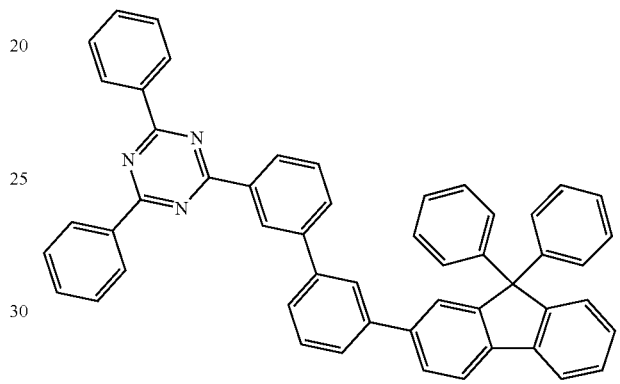

493
-continued
494
-continued
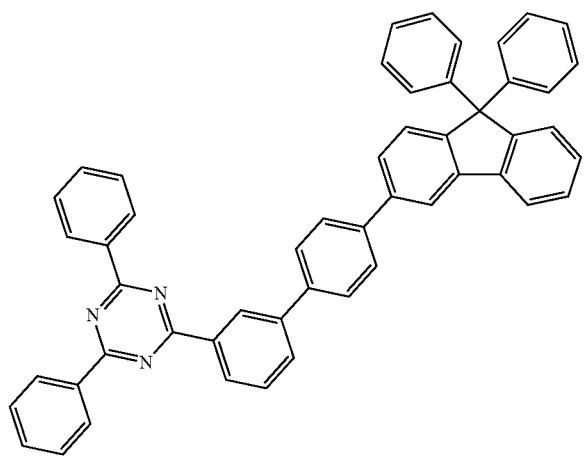
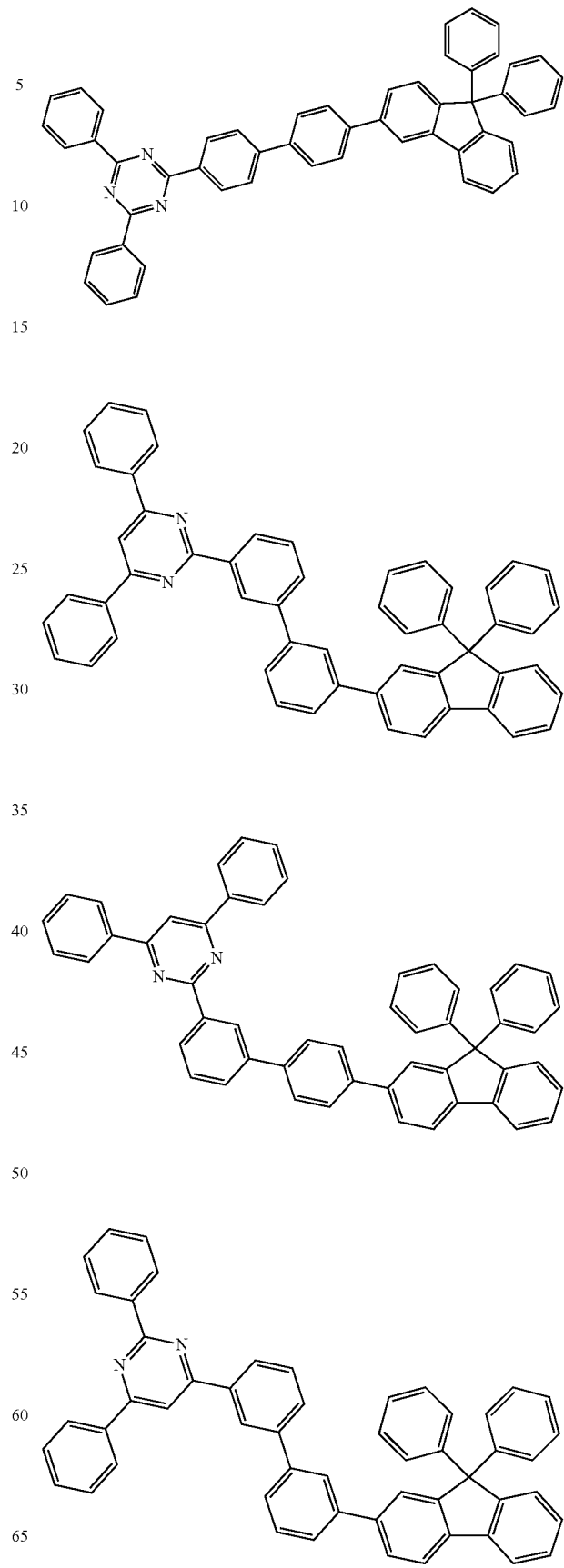

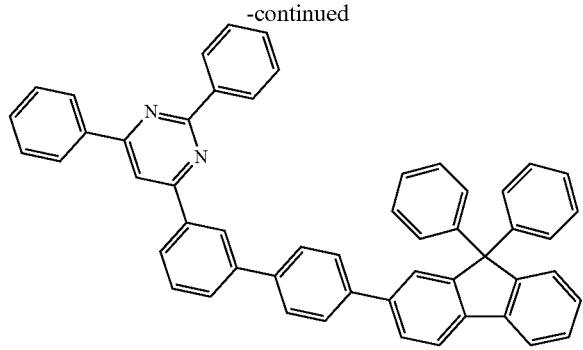
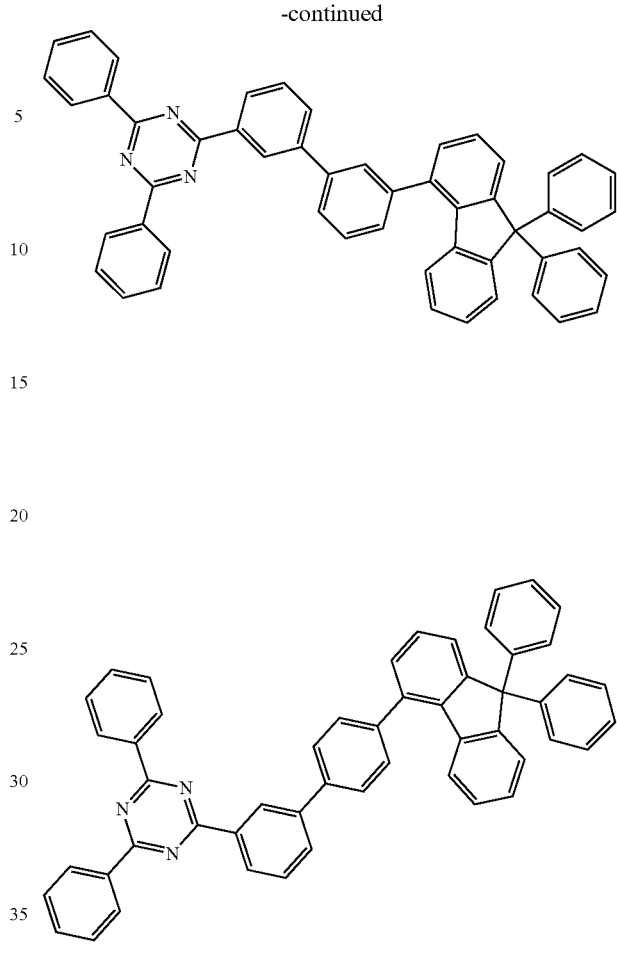
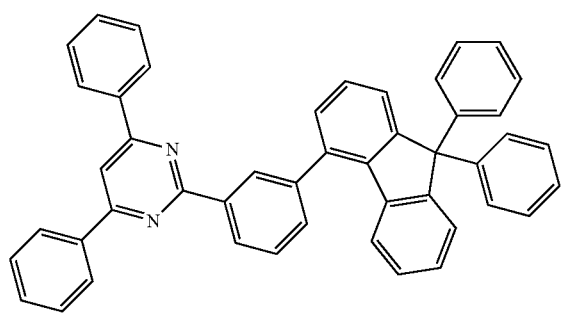
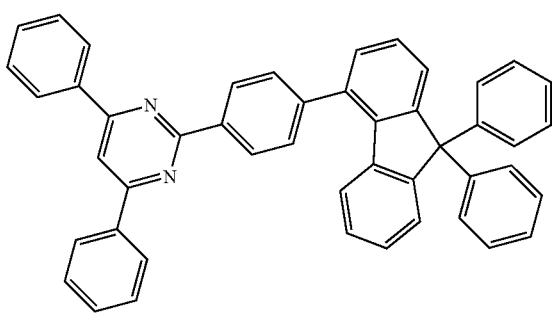
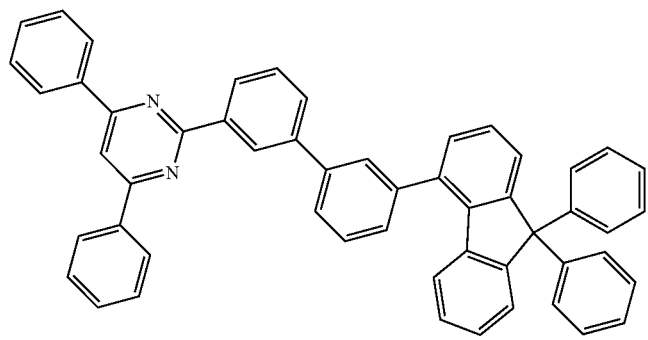

-continued
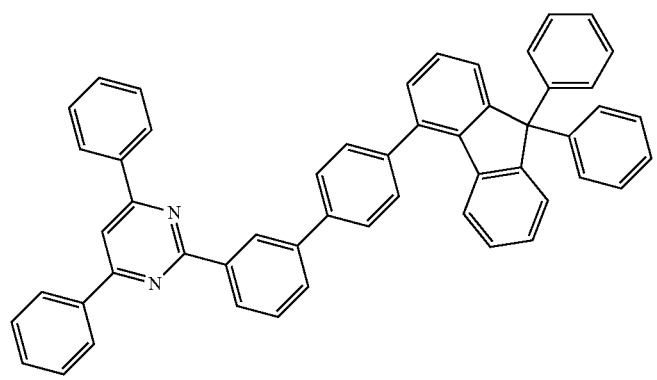
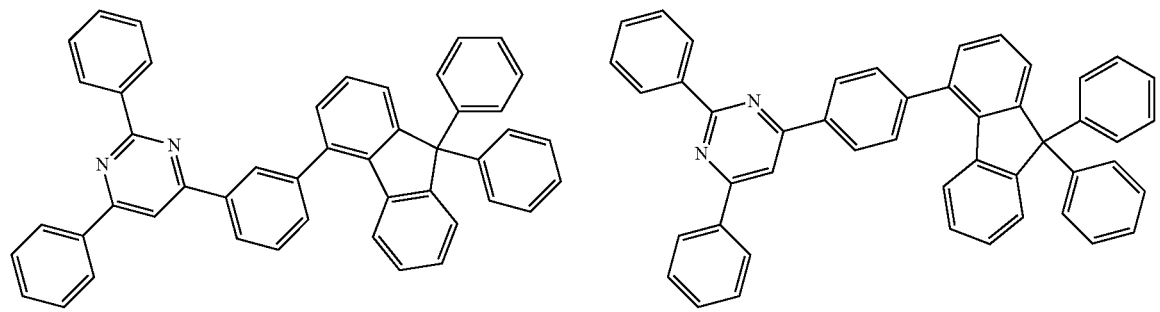
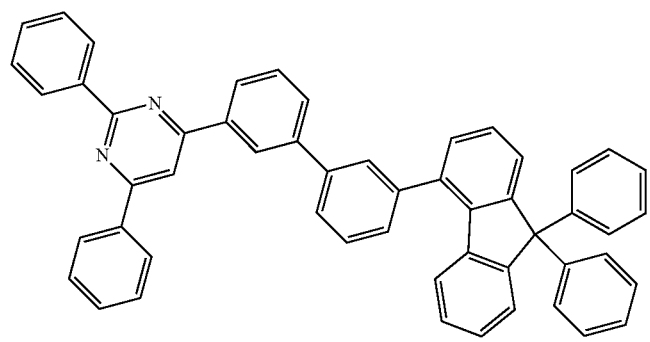
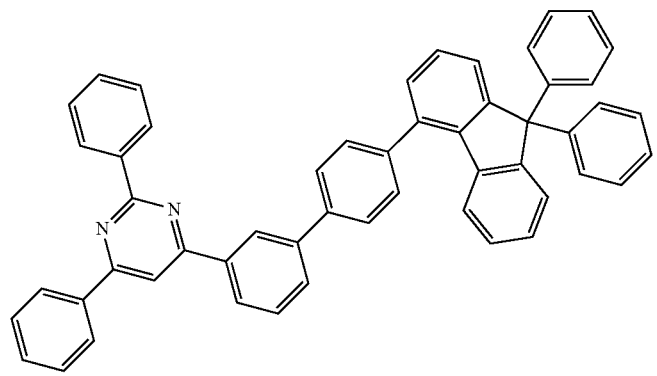

-continued
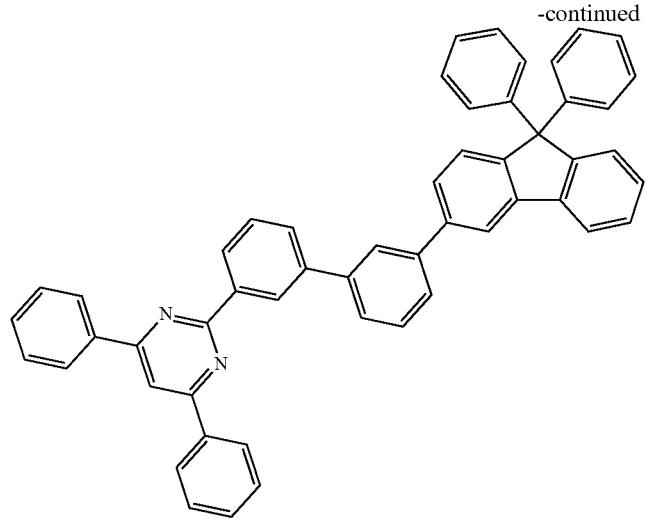
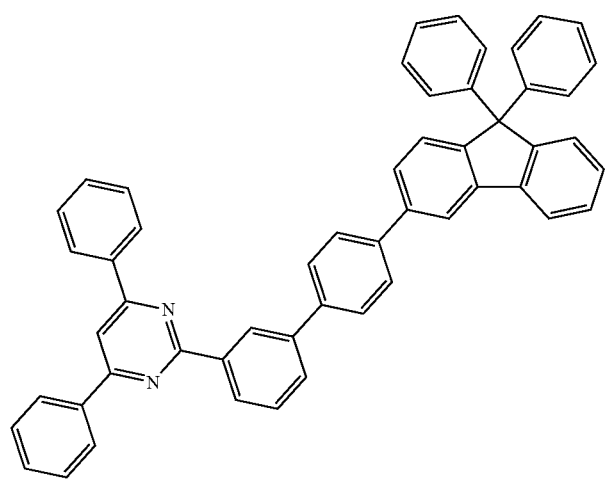
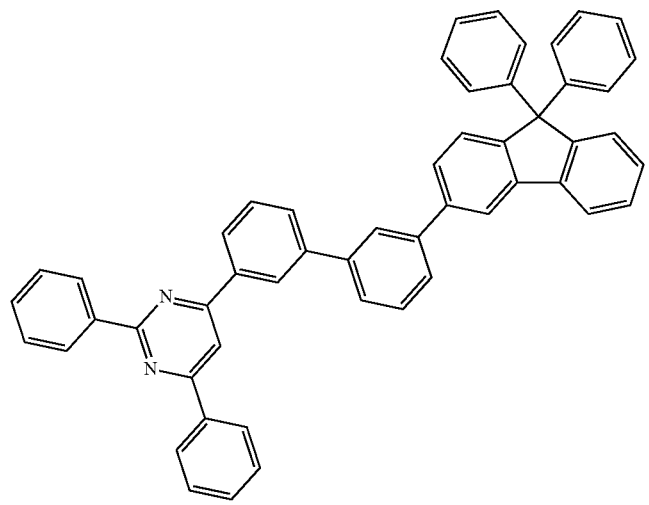

-continued
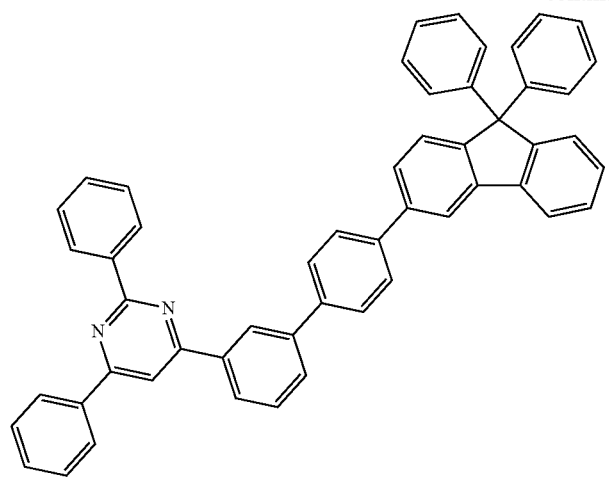
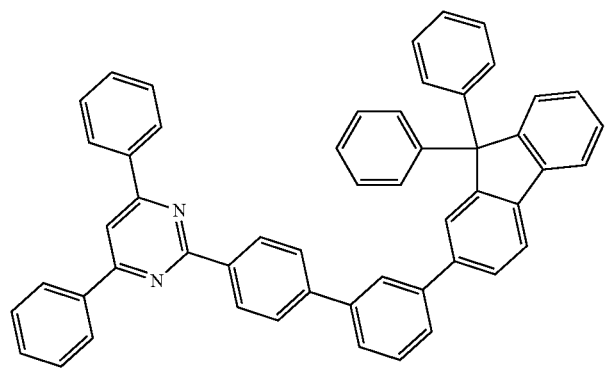
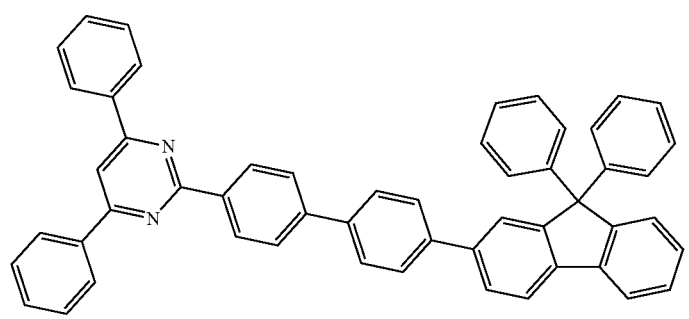
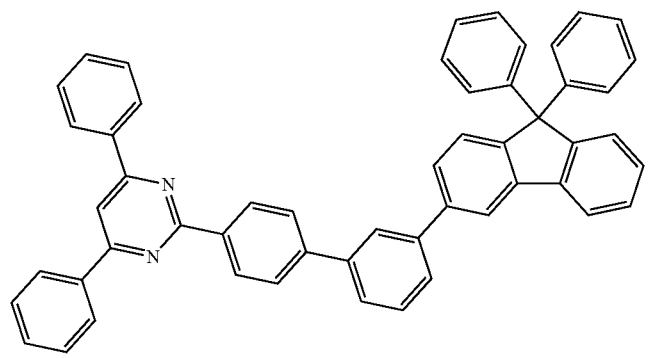

-continued
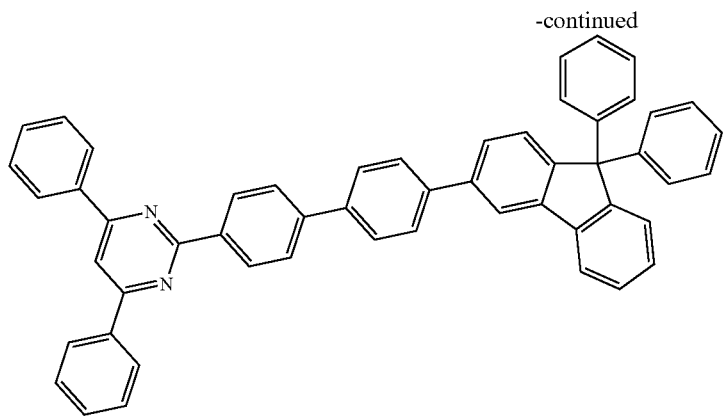
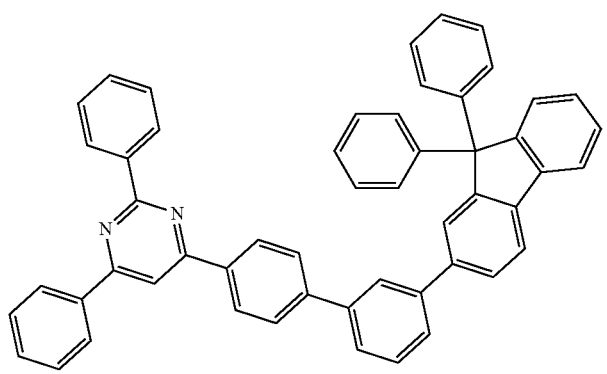
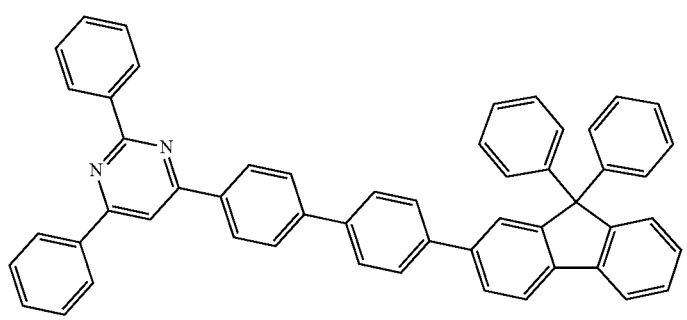
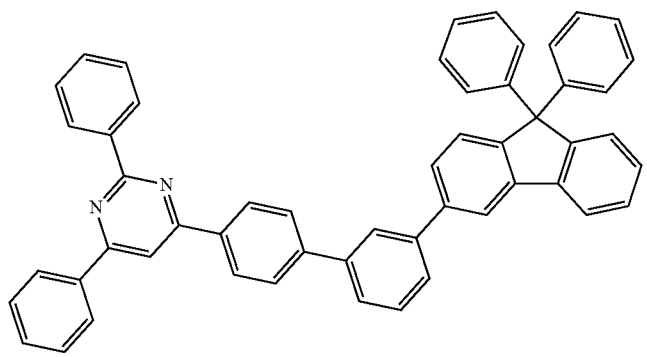

-continued
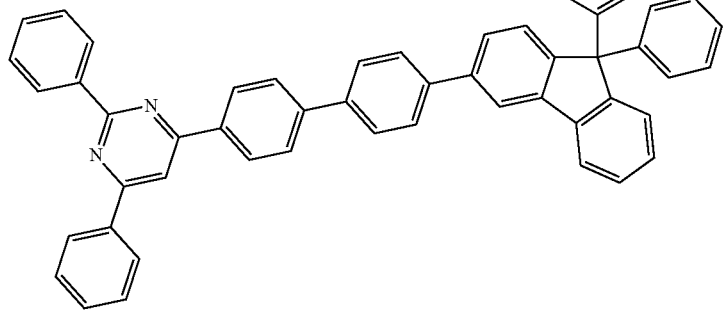
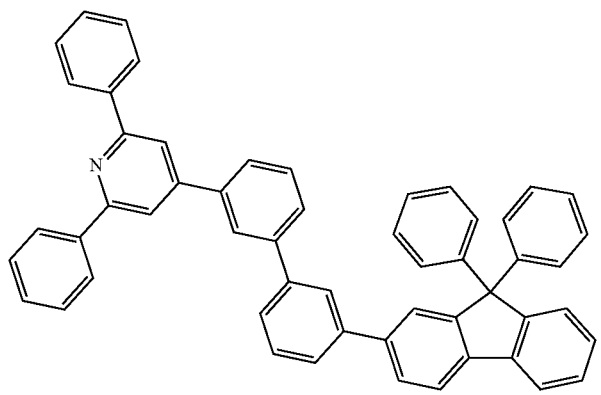
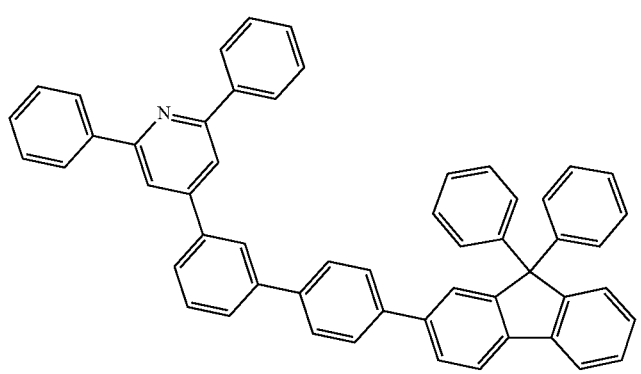
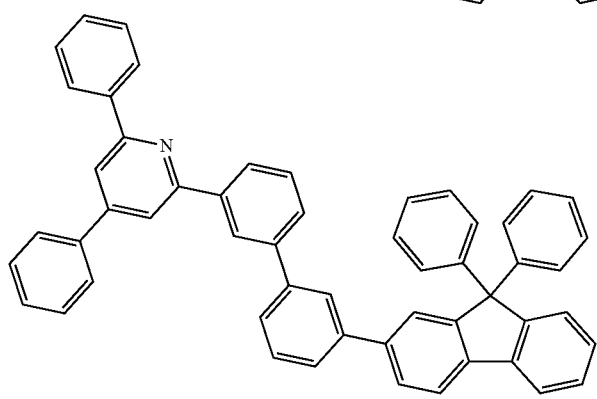

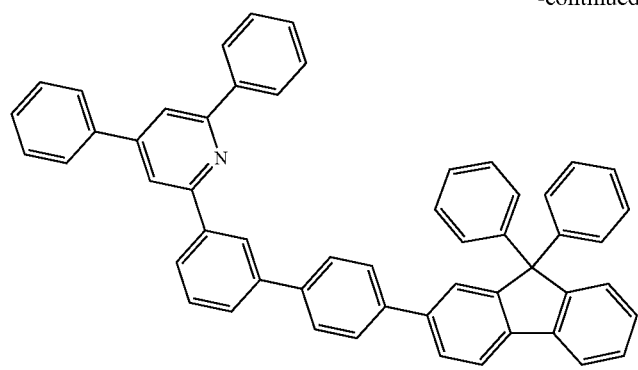
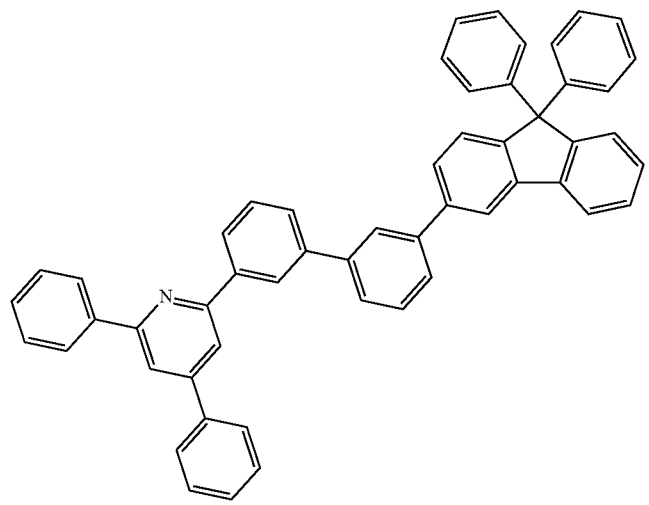
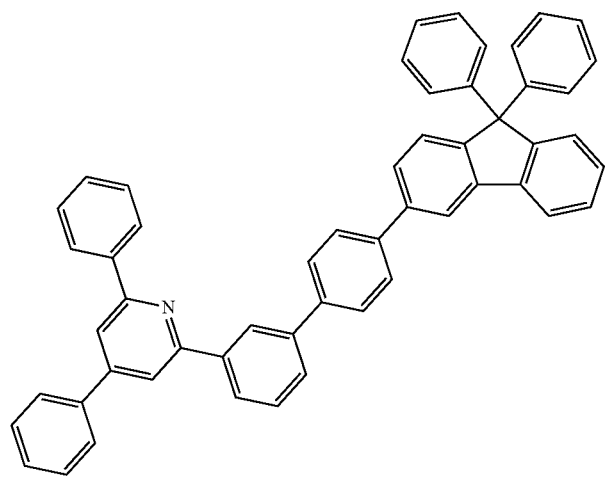

-continued
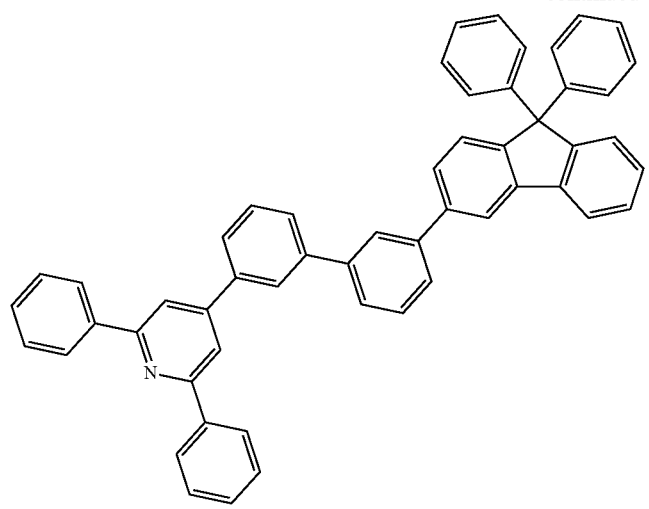
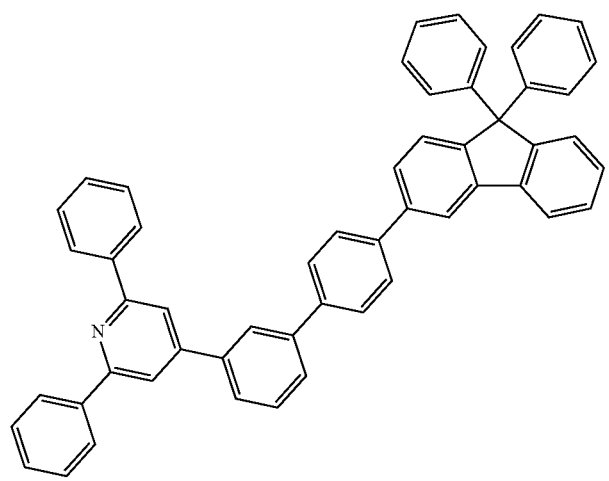
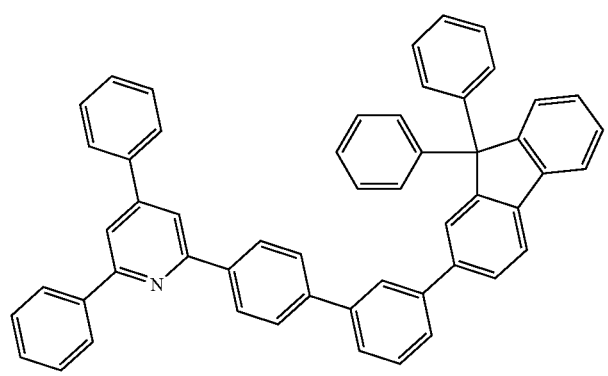
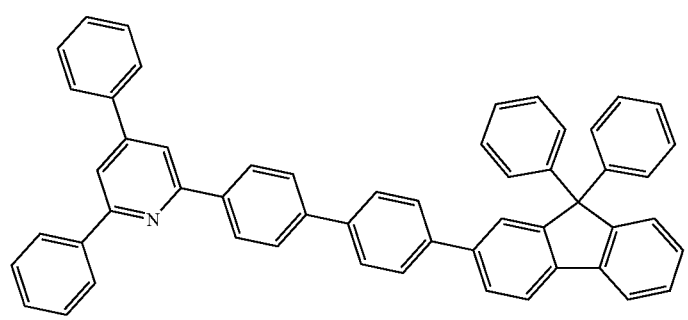

-continued
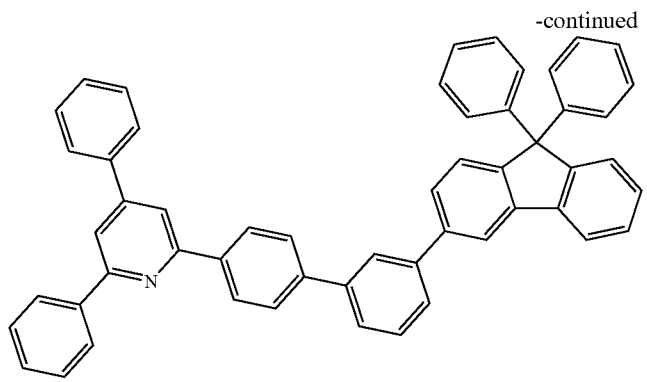
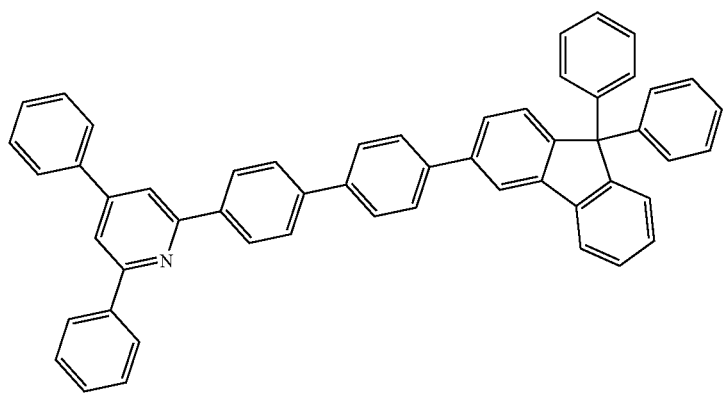
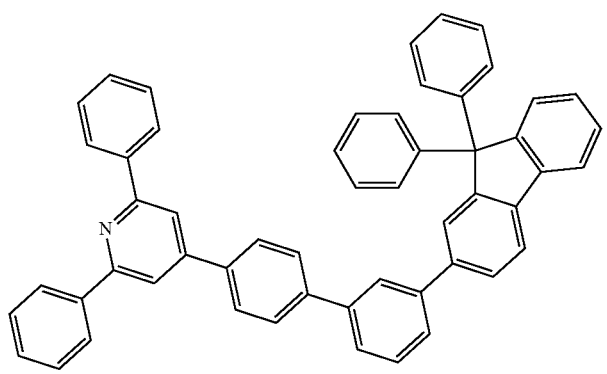
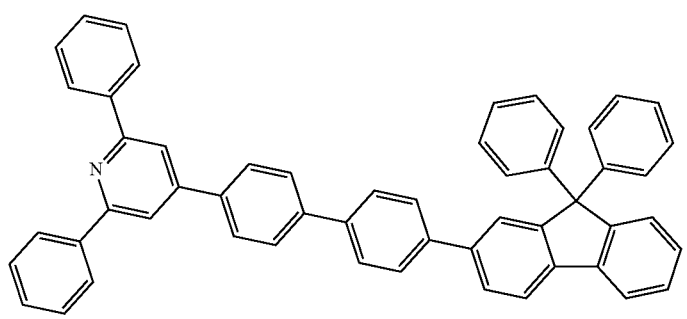

-continued
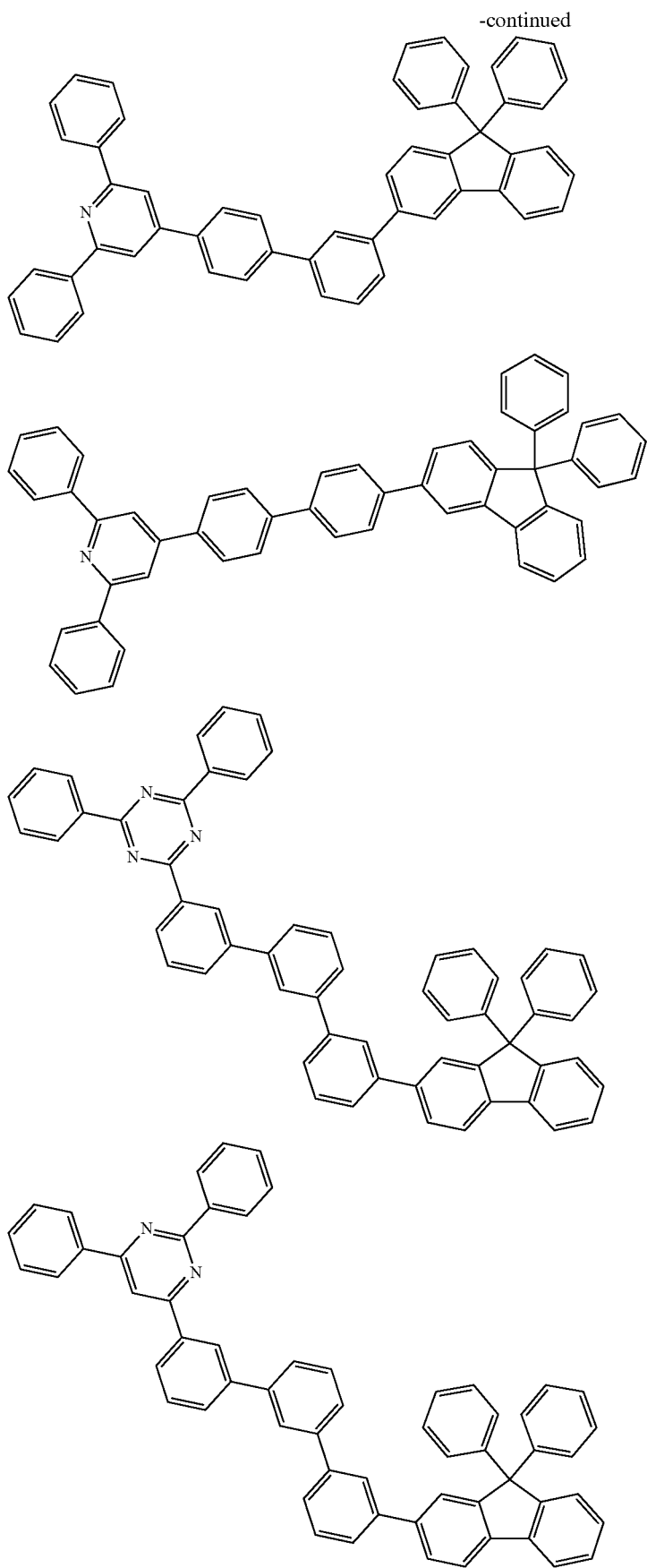

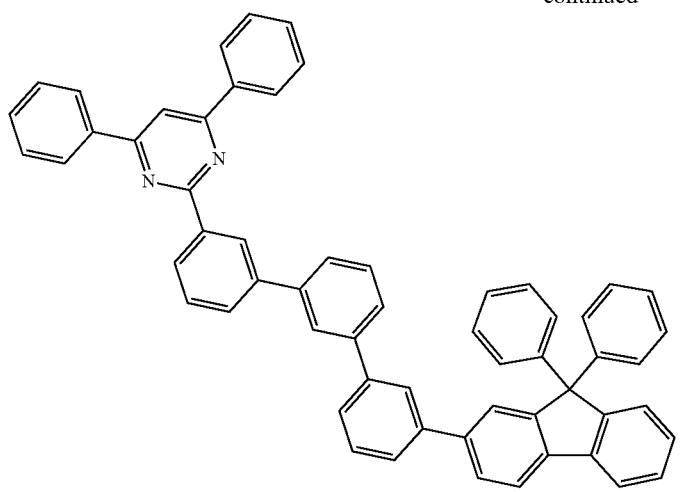
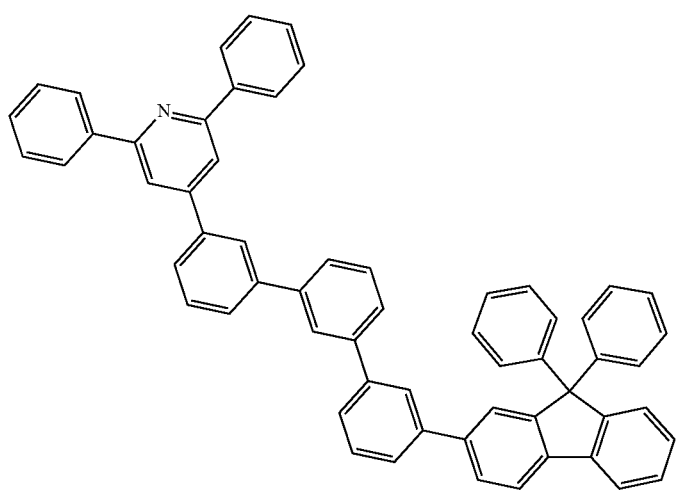
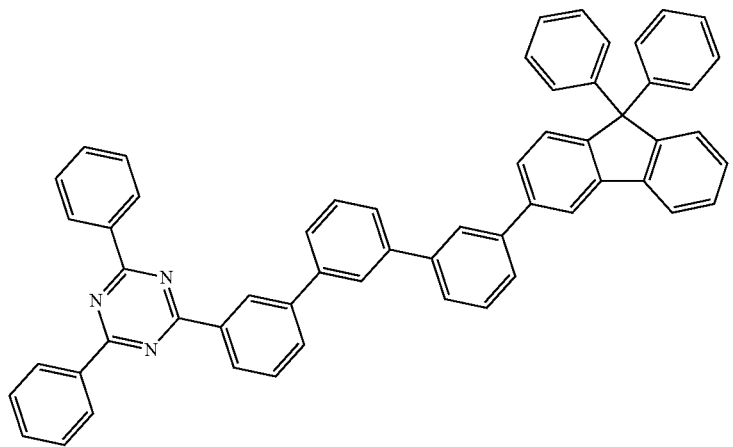

-continued
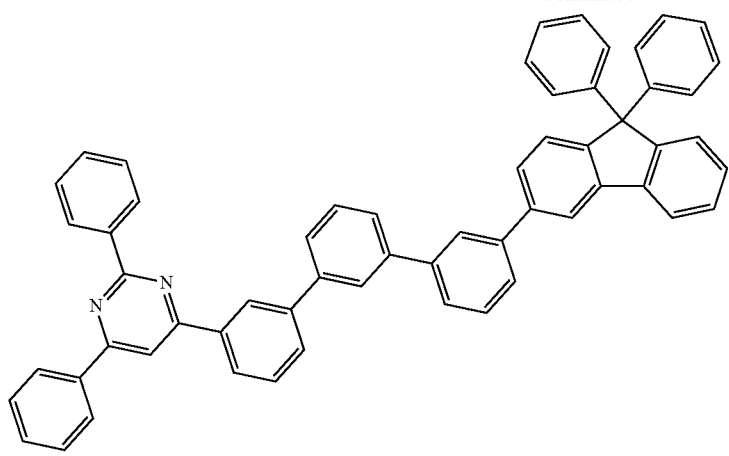
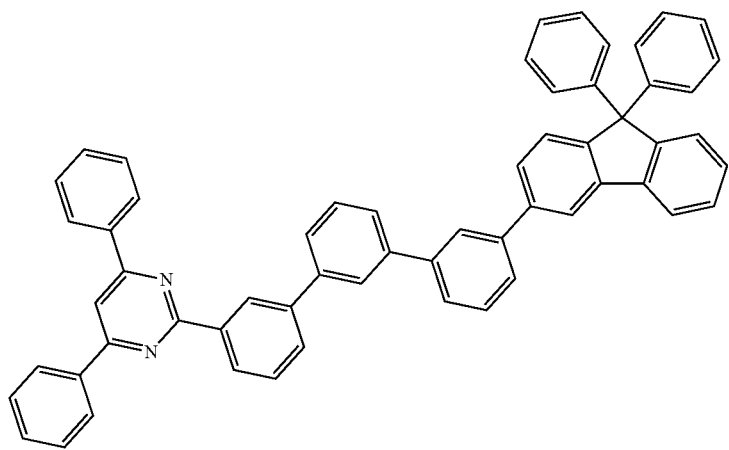
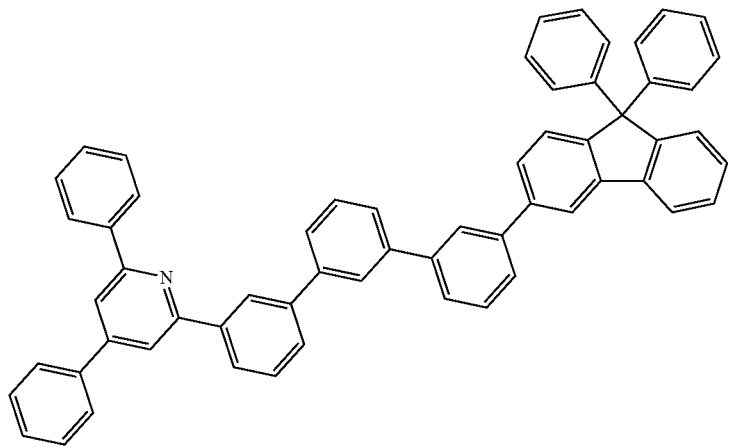
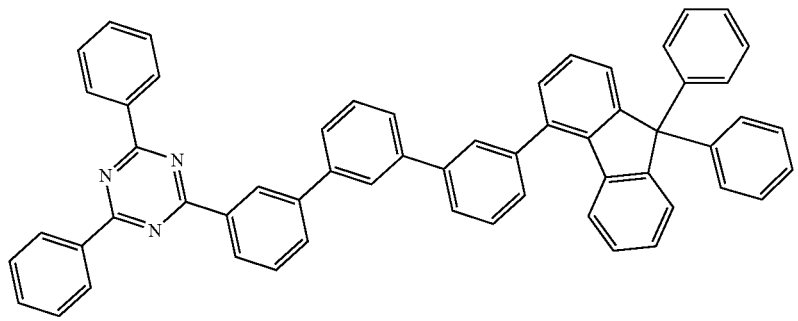

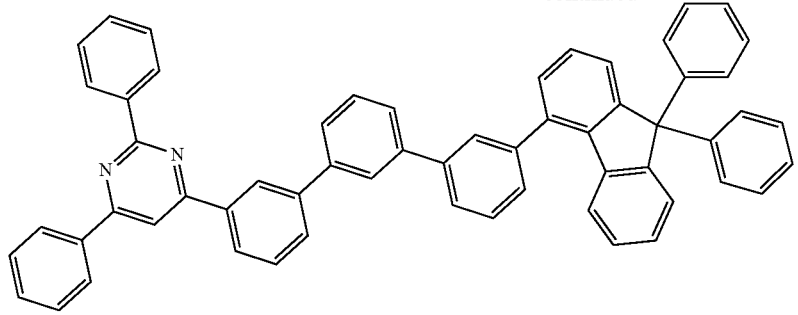
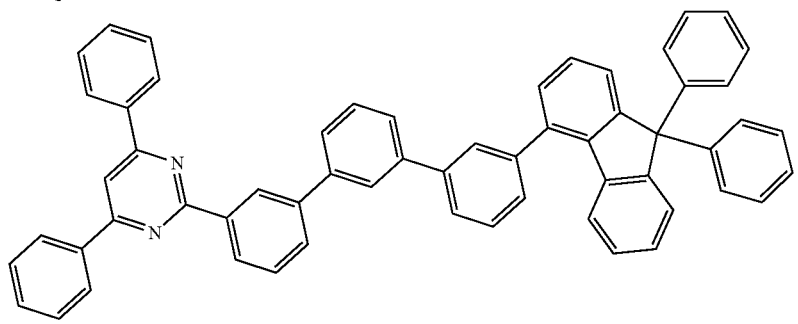
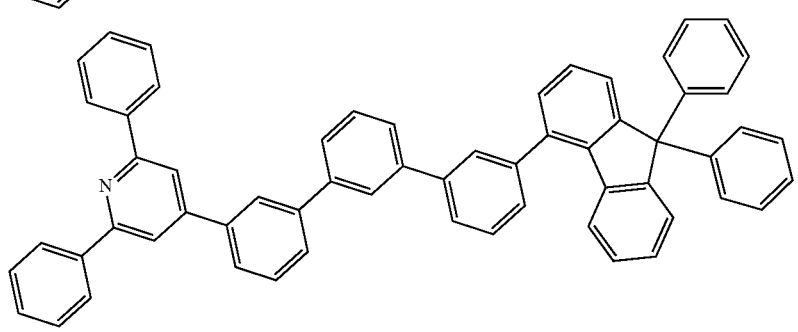
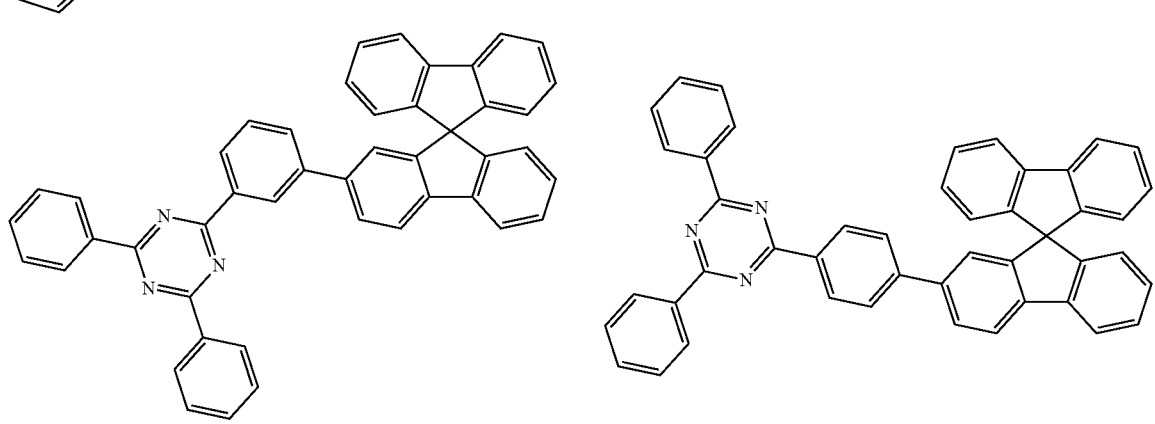
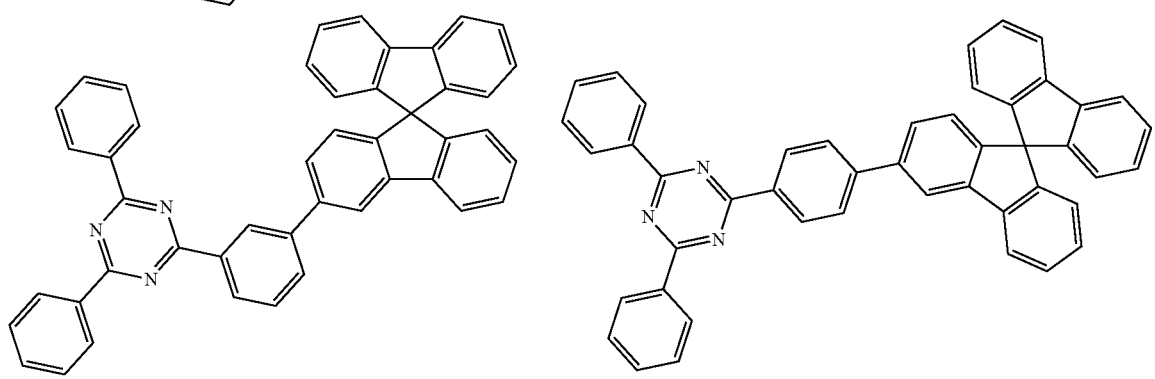

-continued
| 521 | 522 |
|---|---|
| 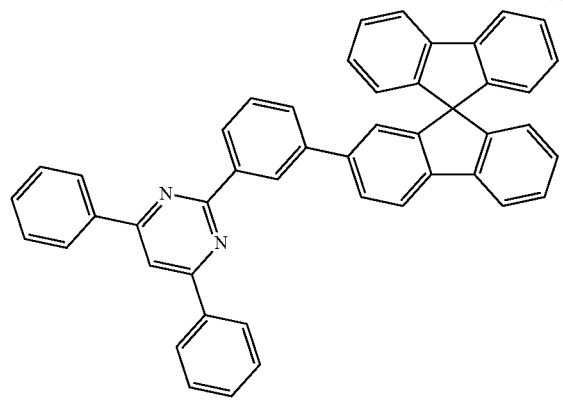 | 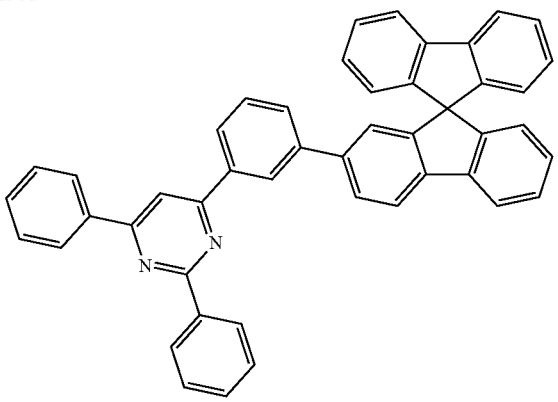 |
| 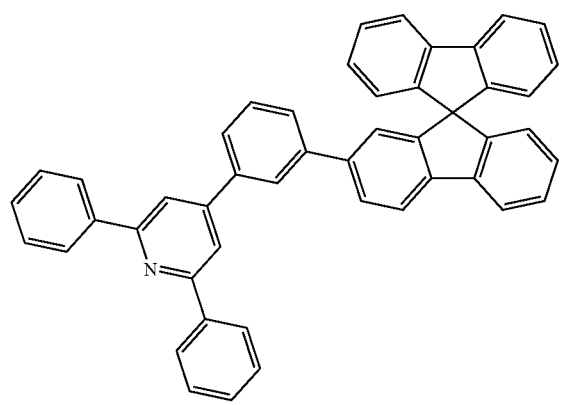 | 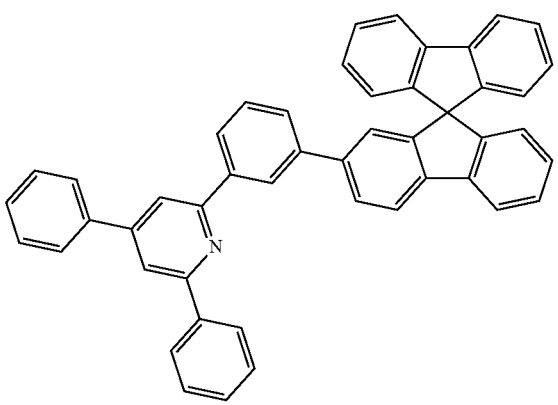 |
| 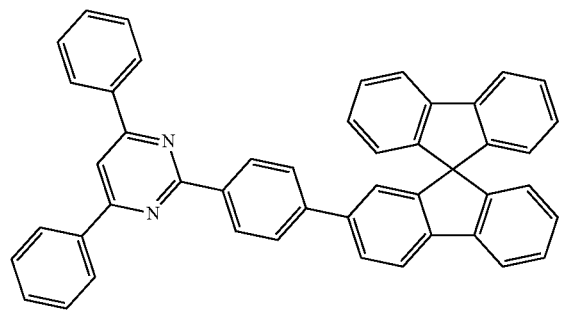 | 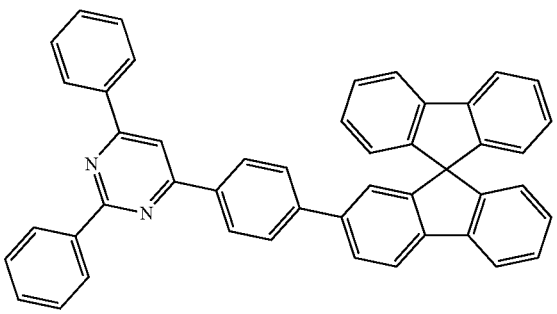 |
| 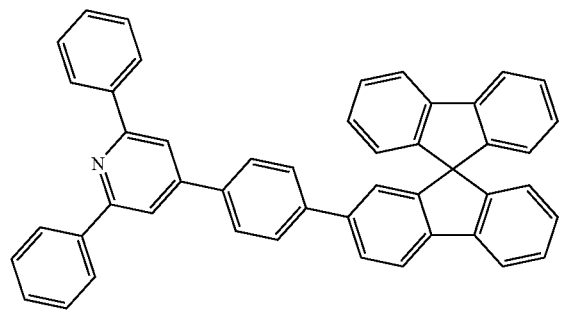 | 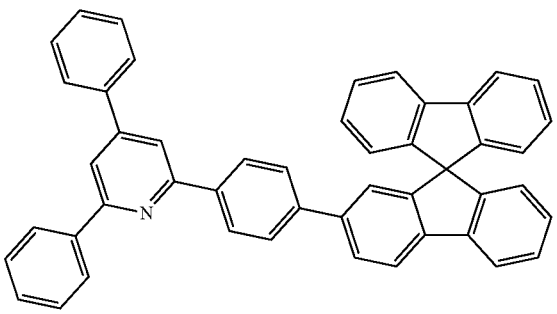 |

523 524
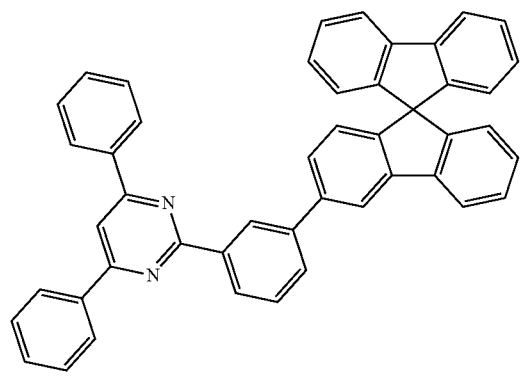 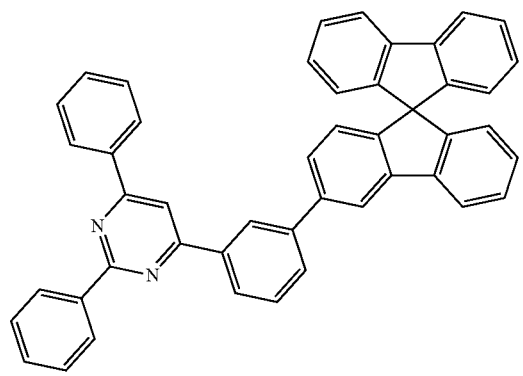
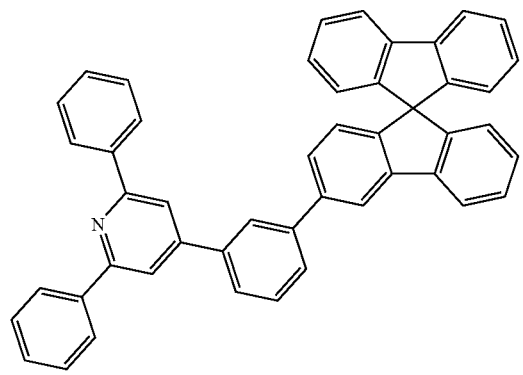 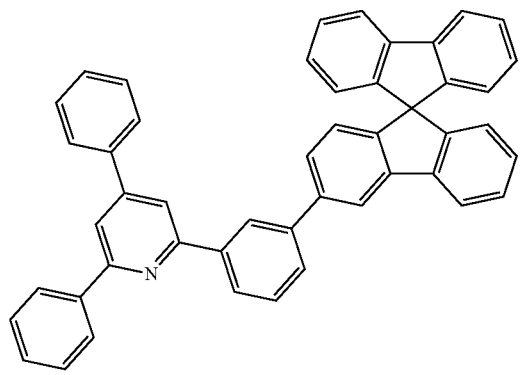
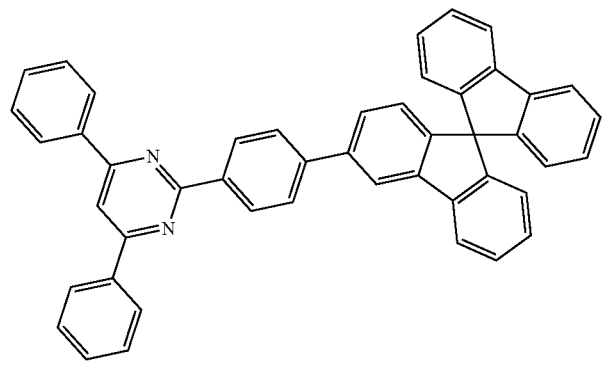
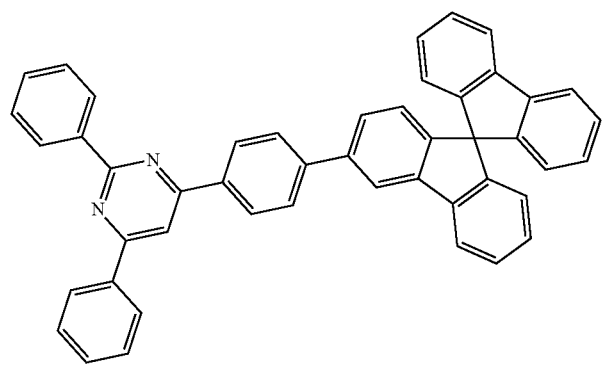

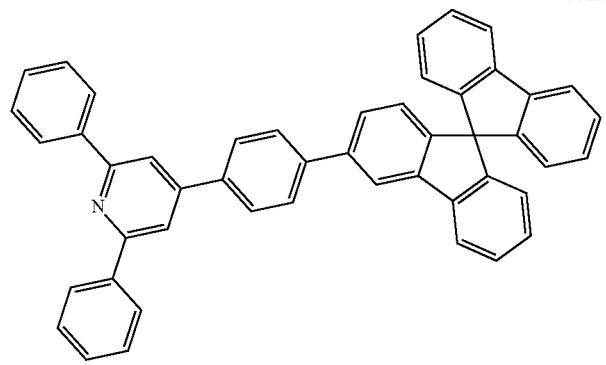
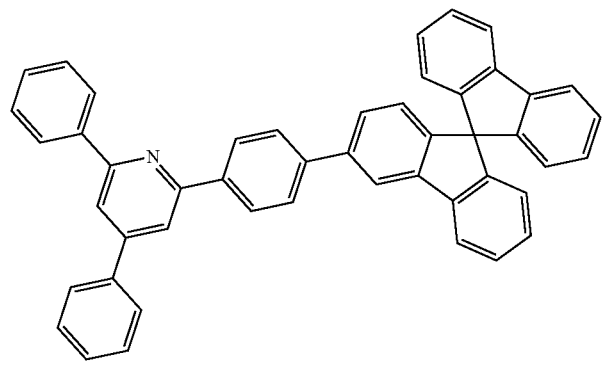
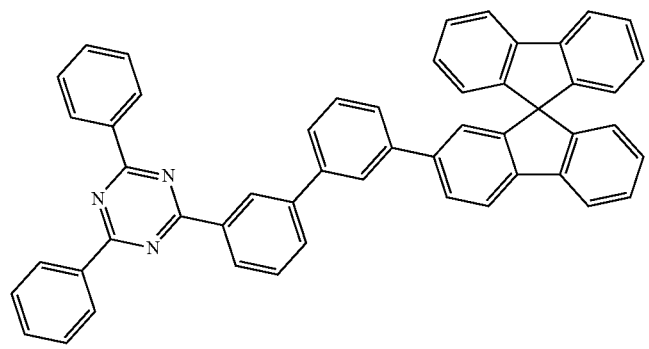
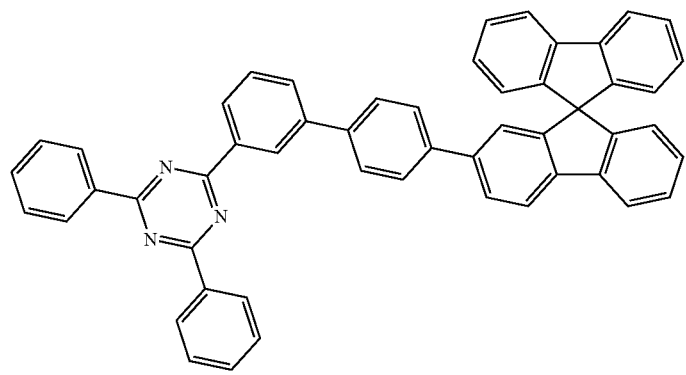

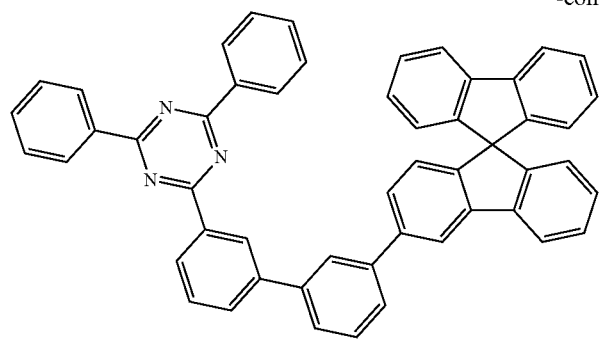
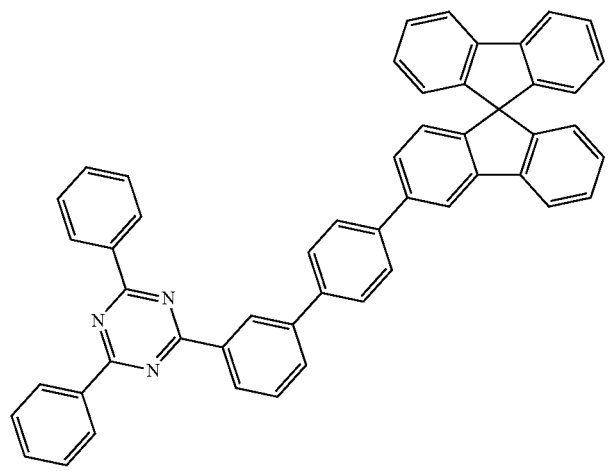
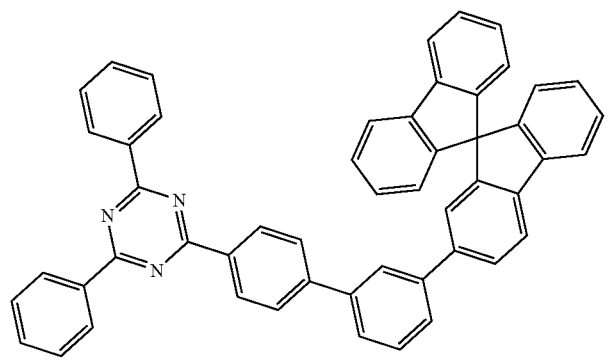
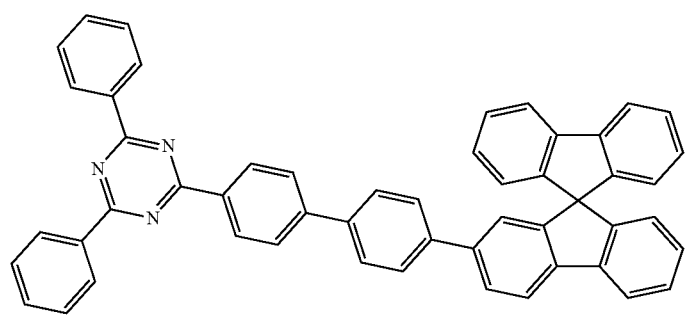

-continued
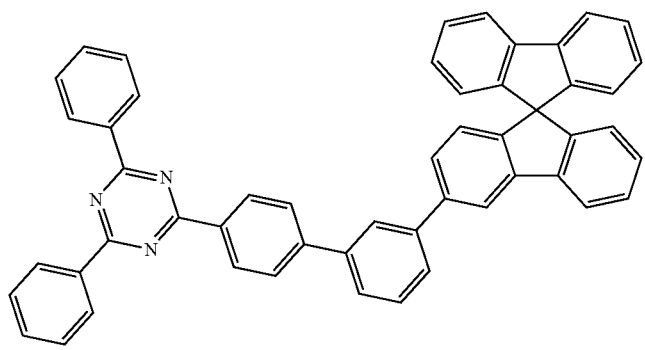
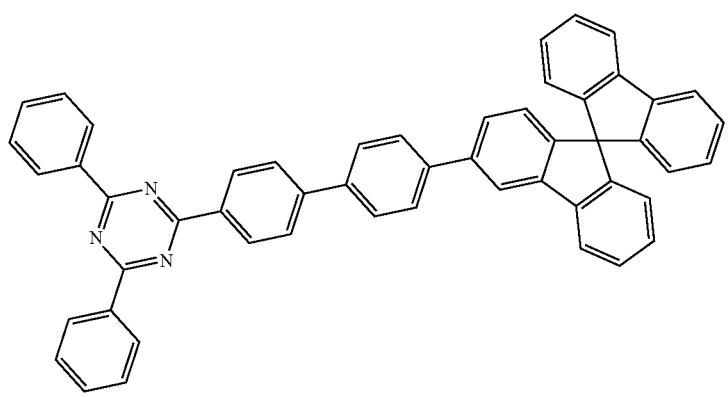
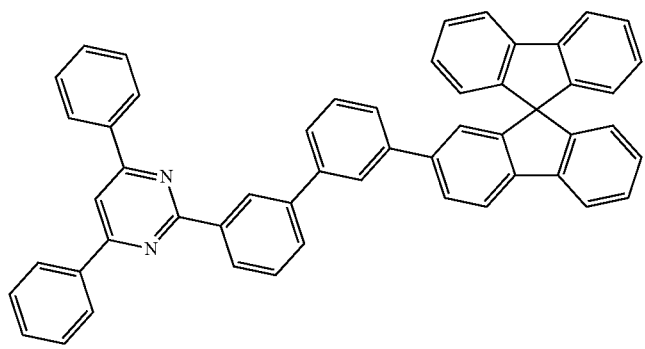
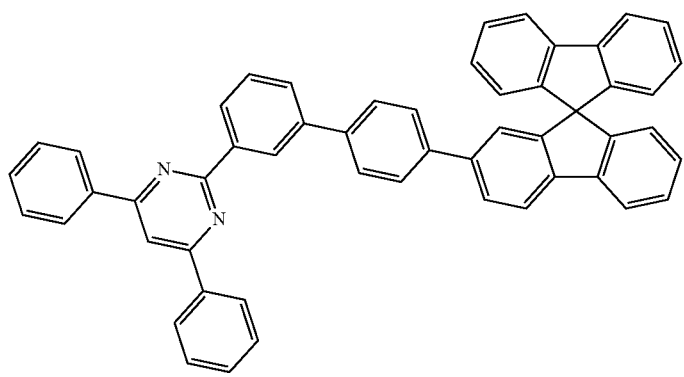

531
-continued
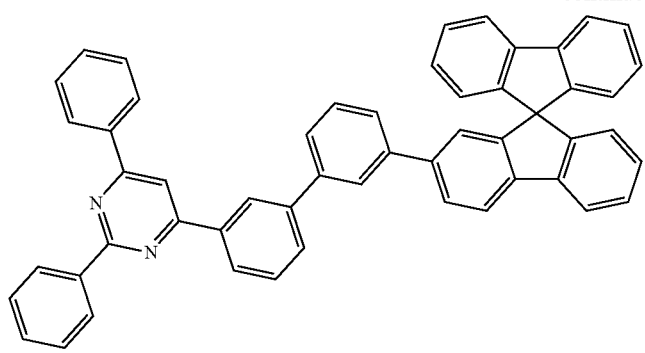
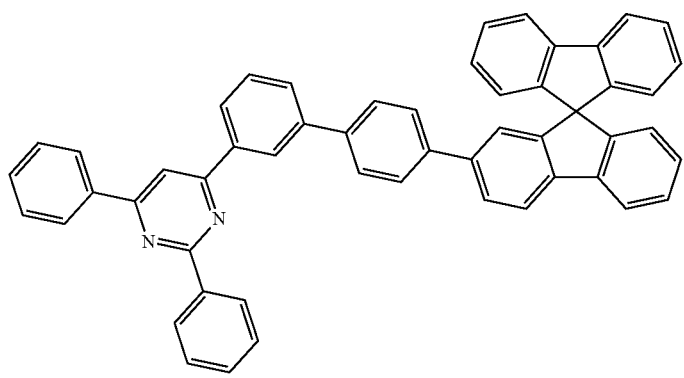
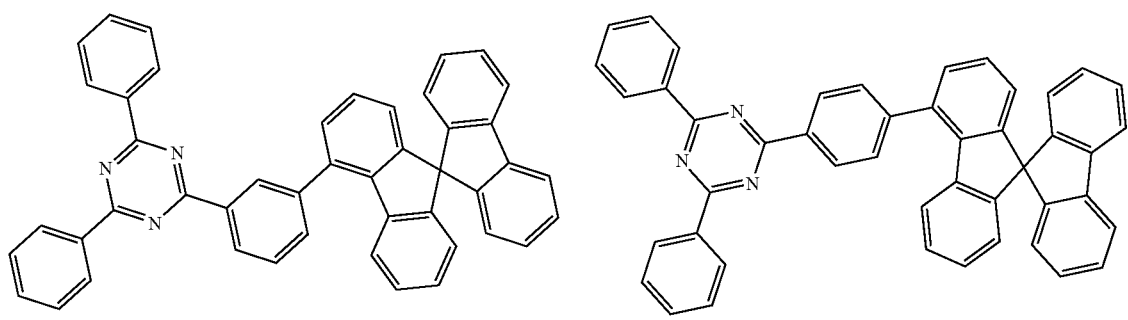
532
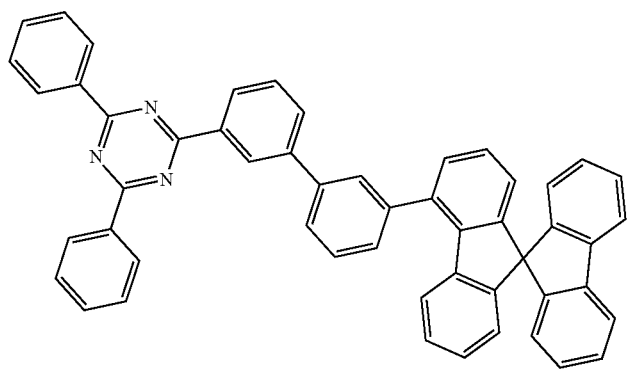

-continued
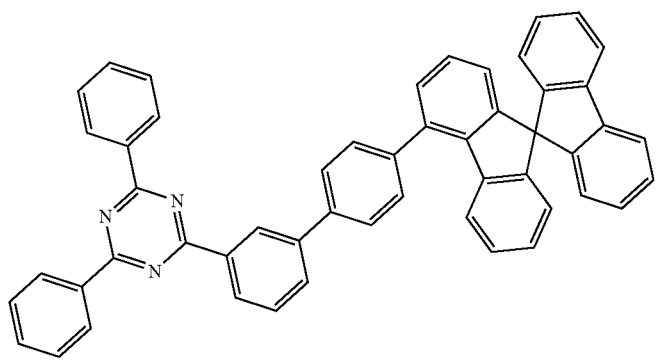
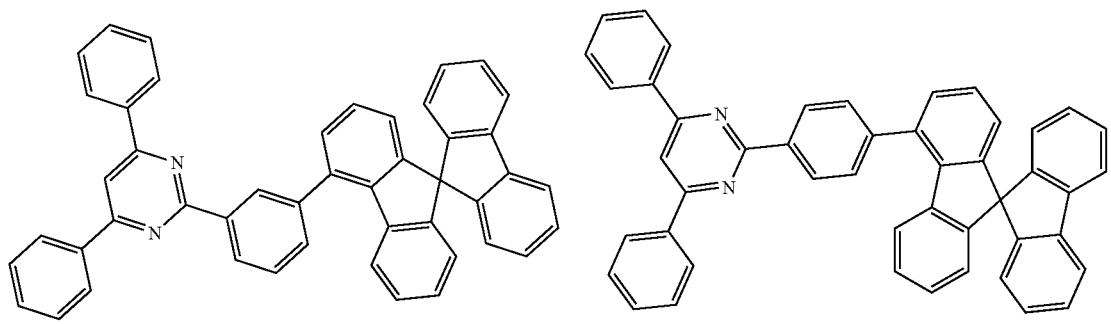
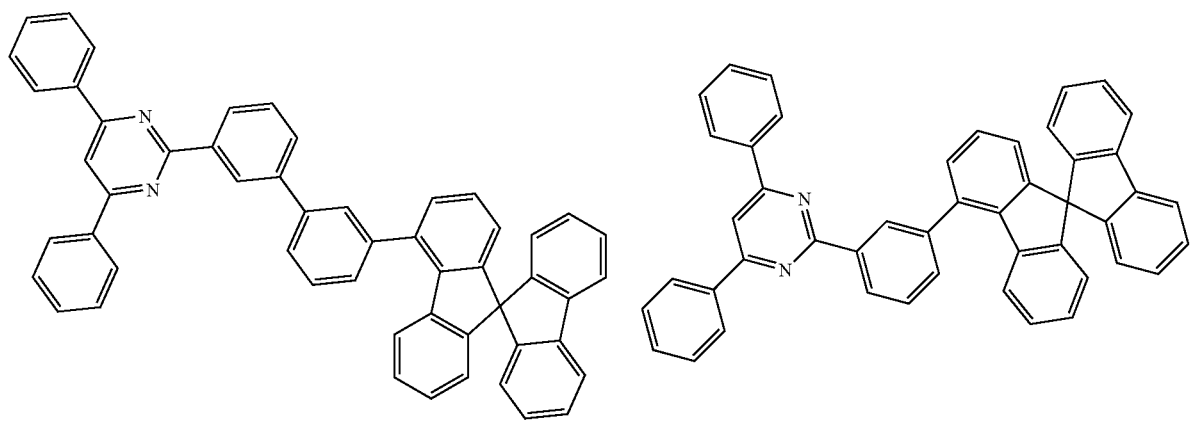
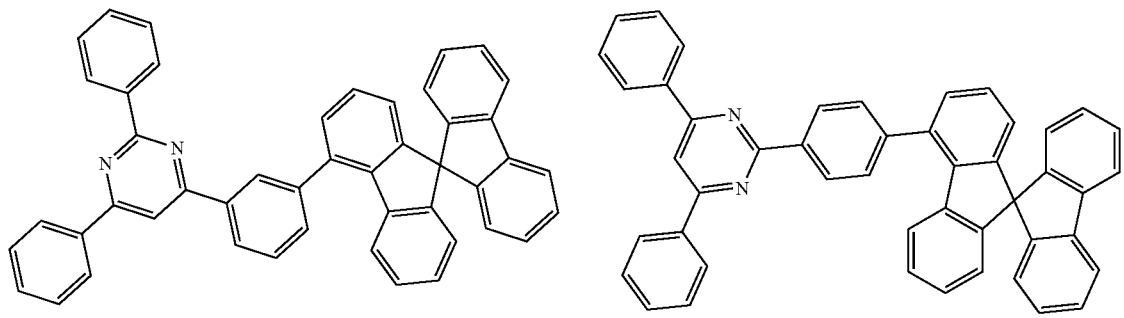

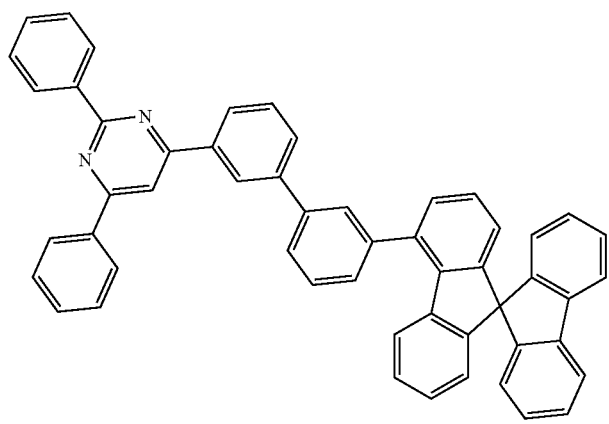
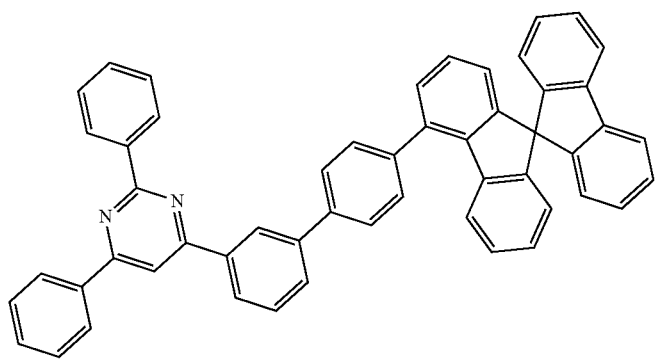
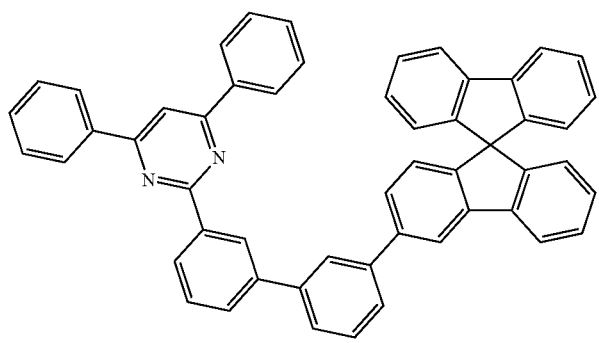
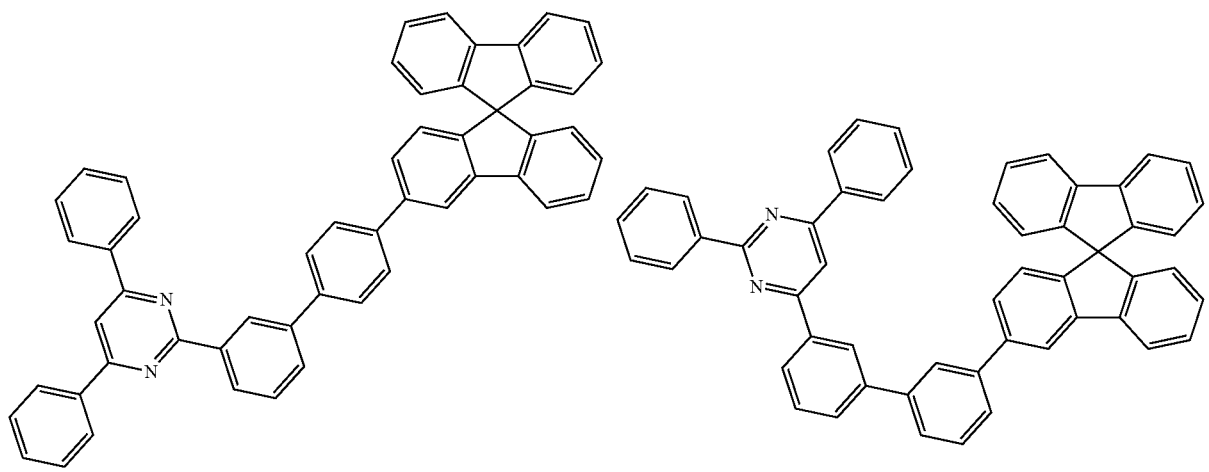

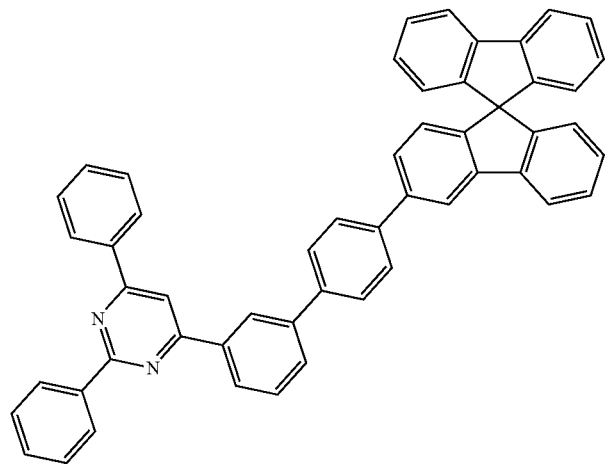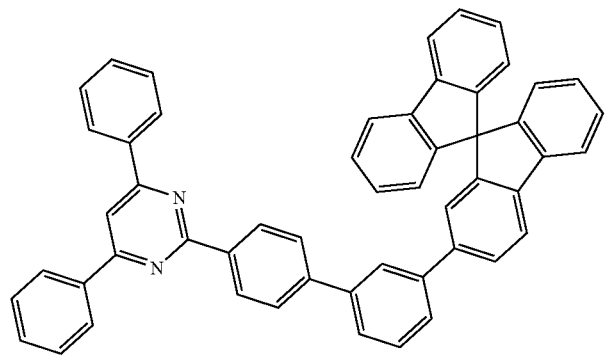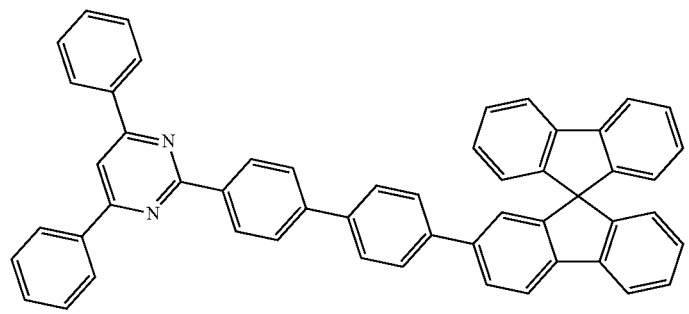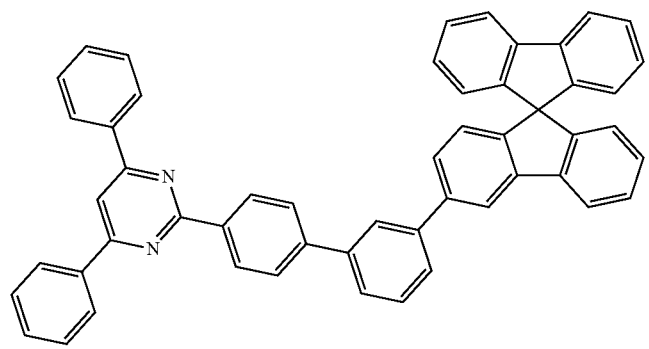

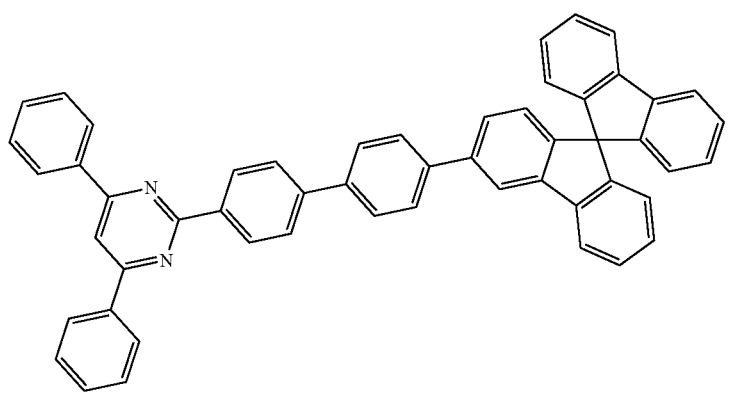
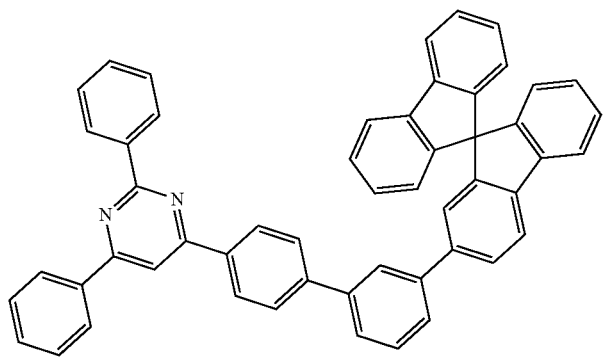
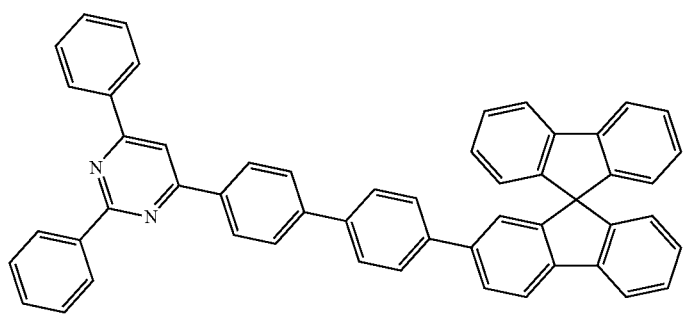
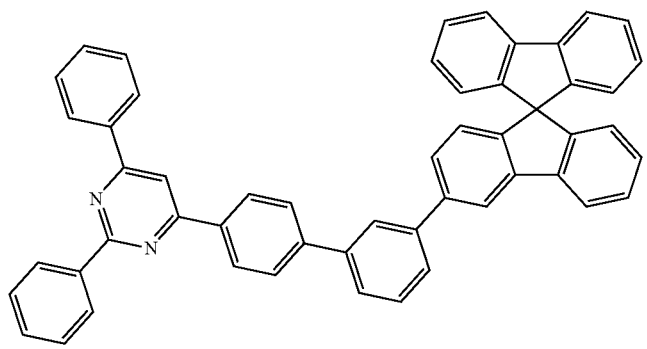

-continued
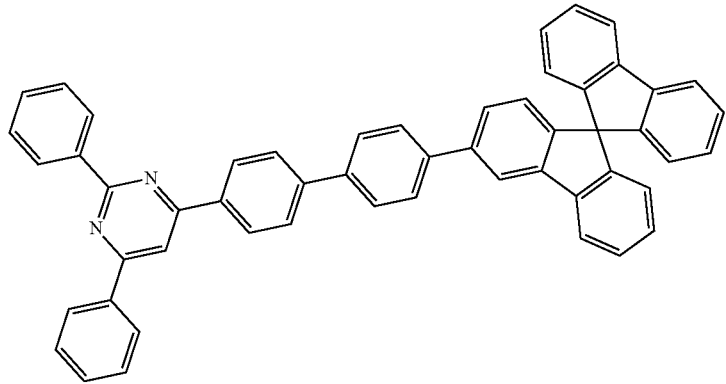
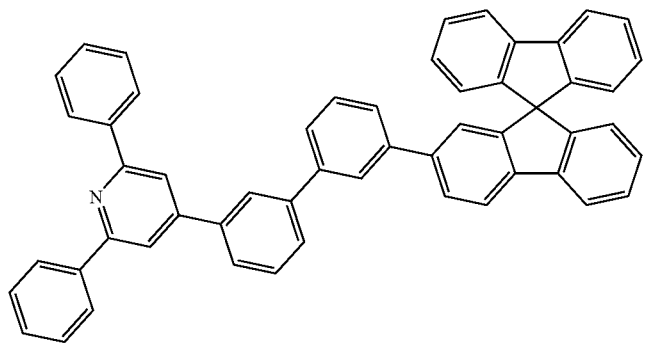
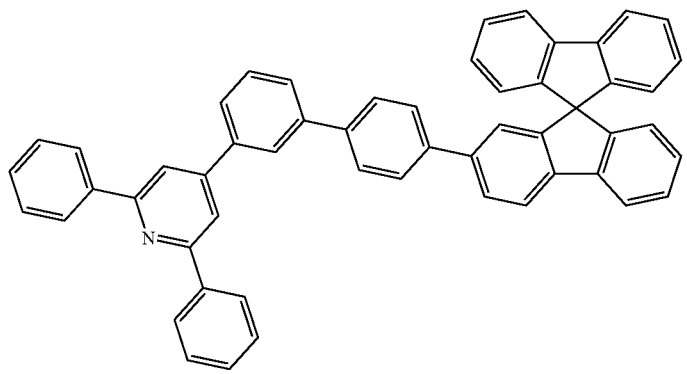
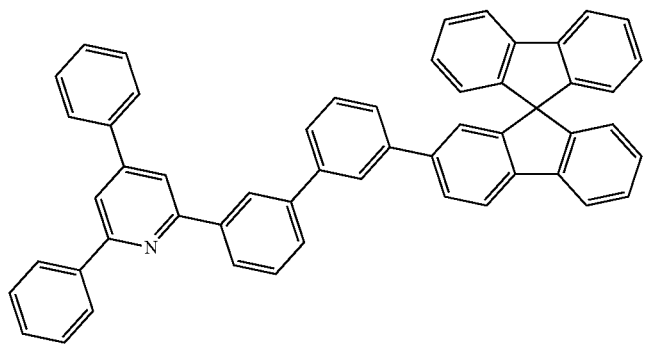

-continued
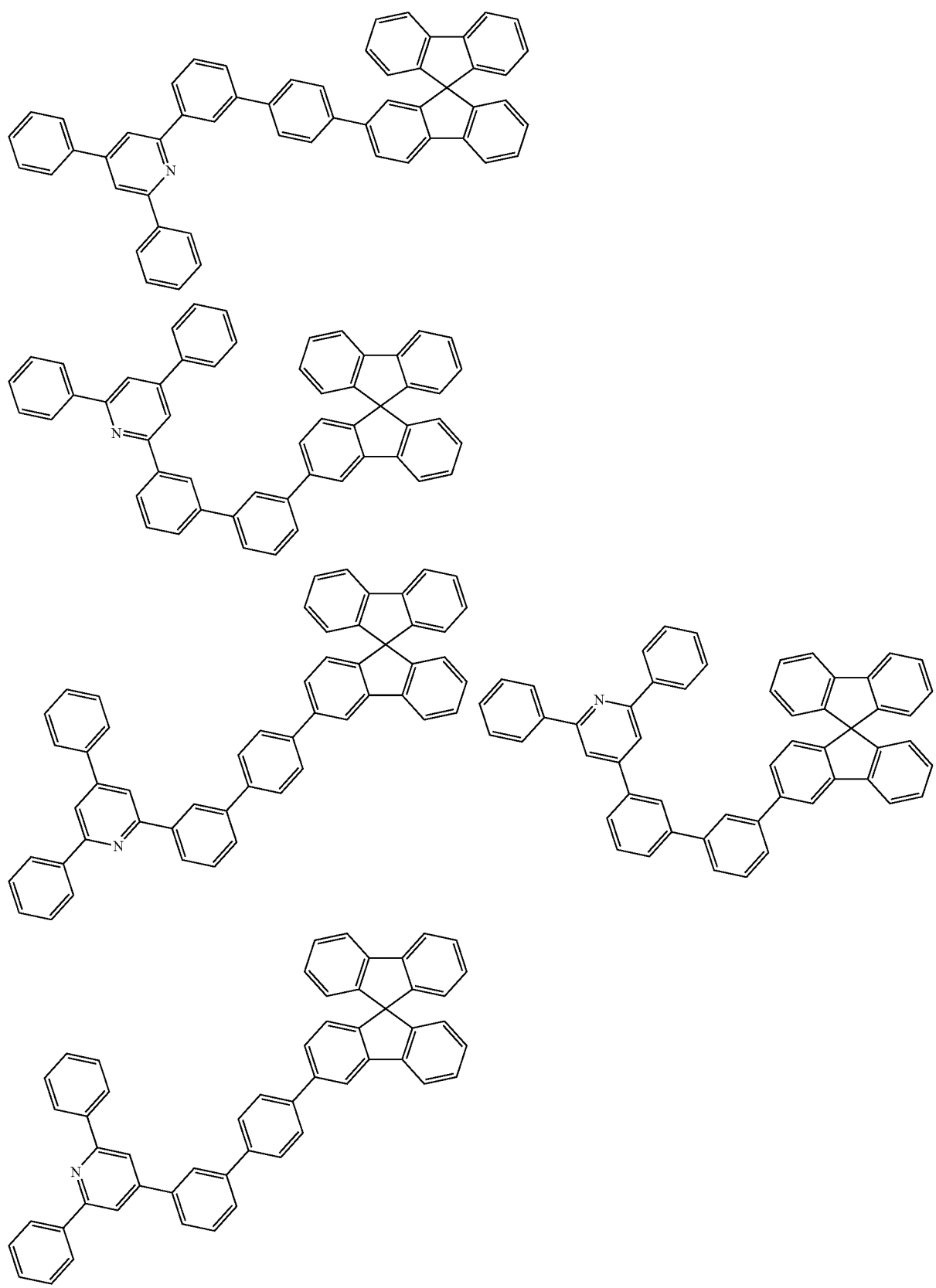

-continued
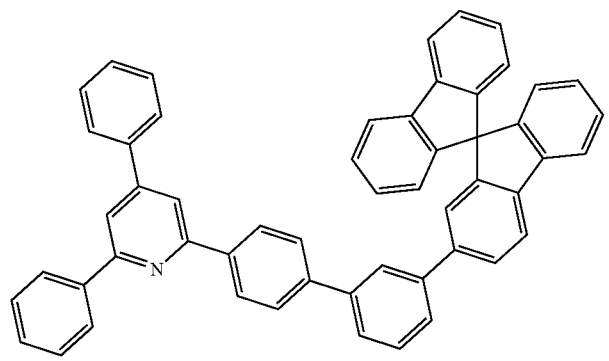
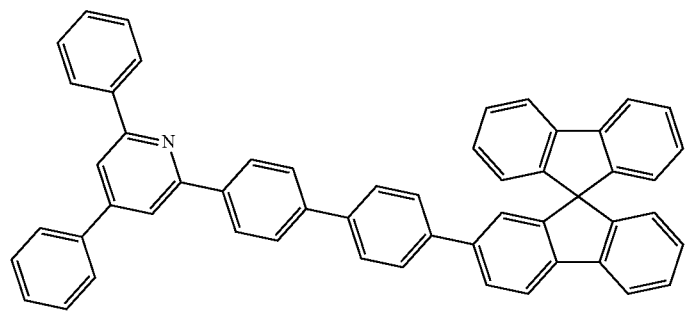
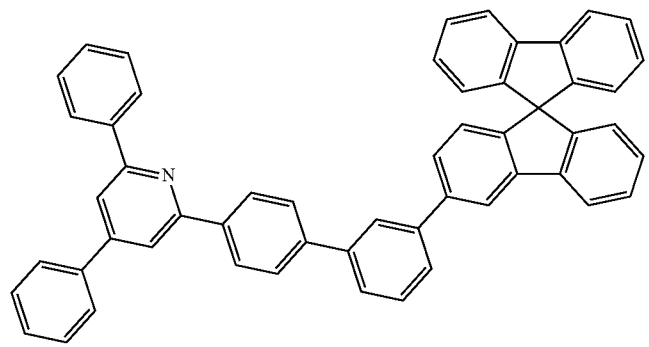
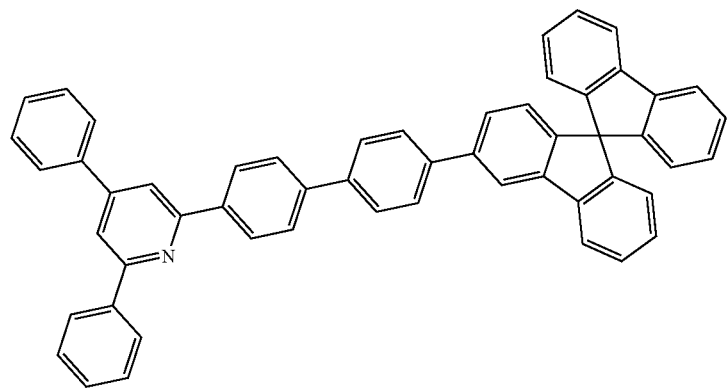

-continued
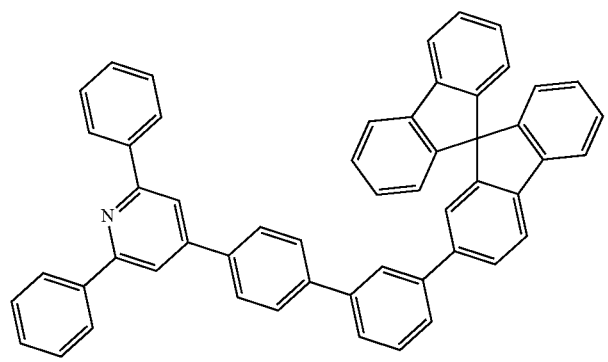
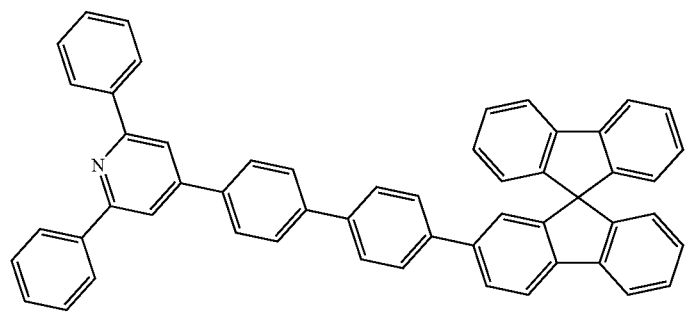
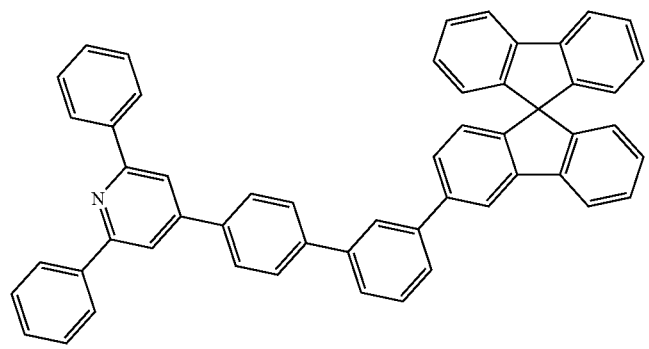
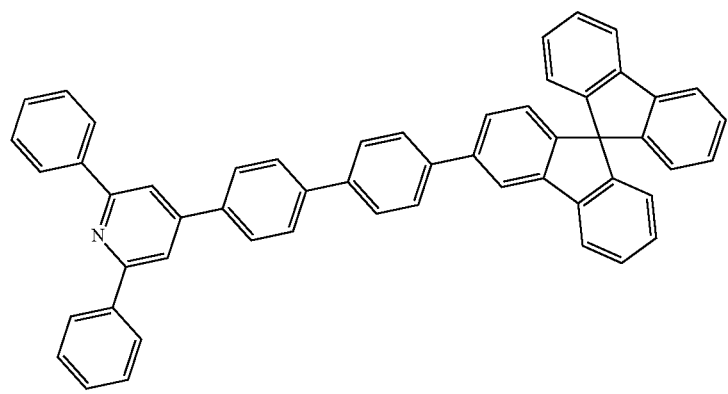

-continued
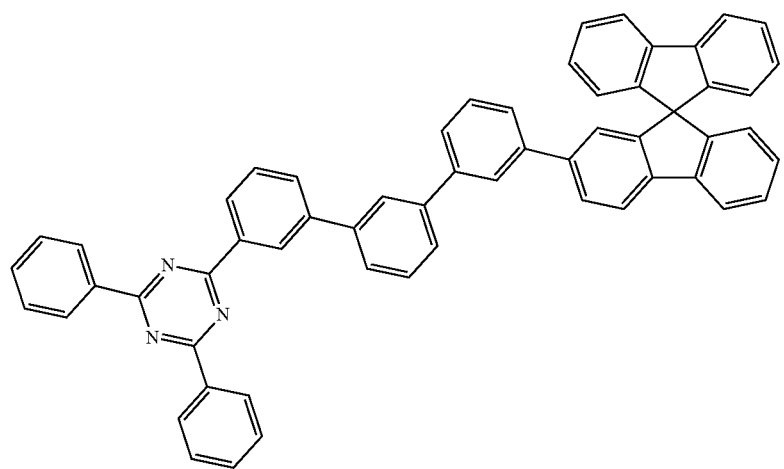
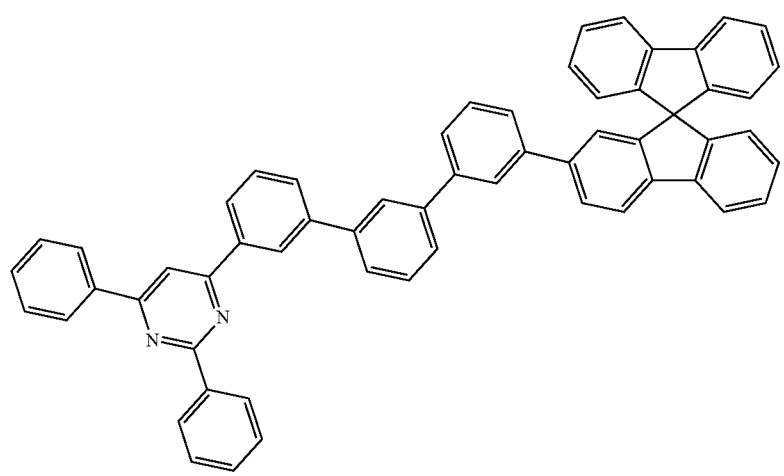
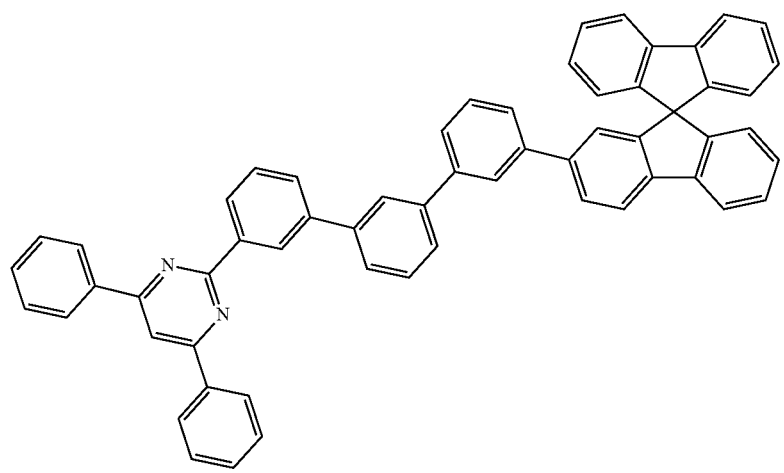

-continued
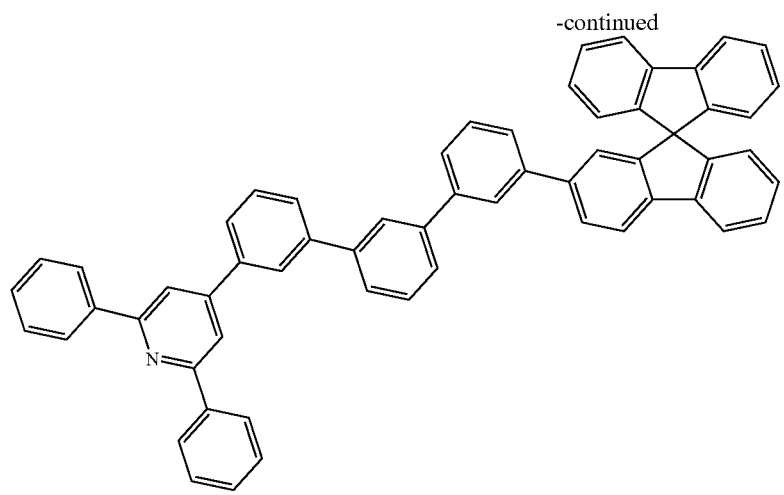
-continued
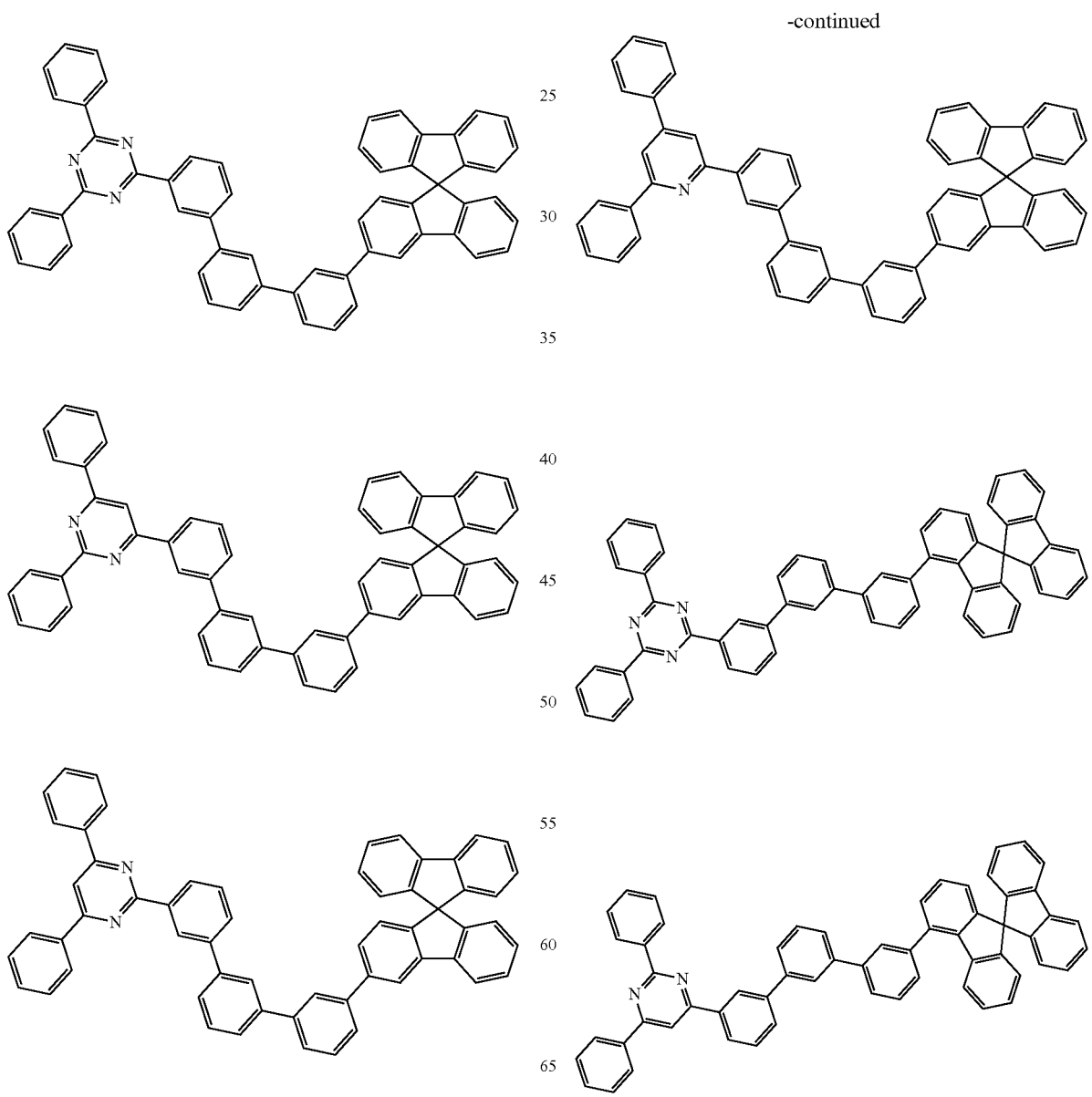

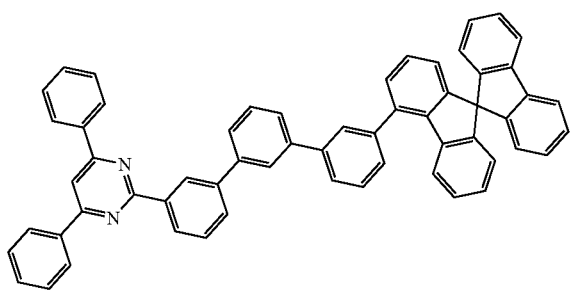
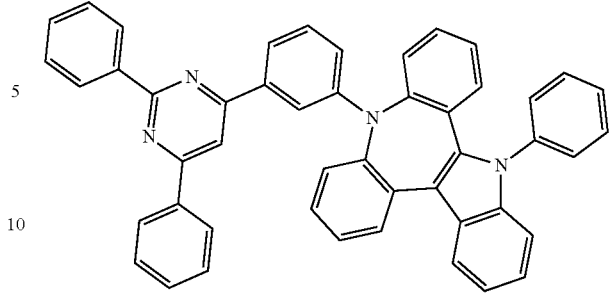
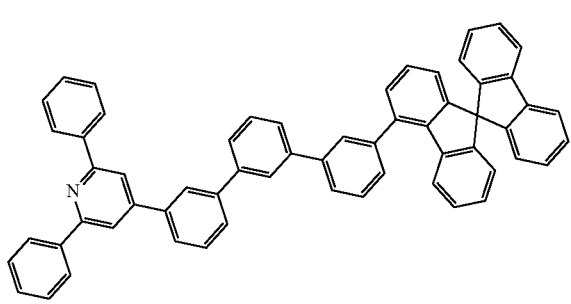
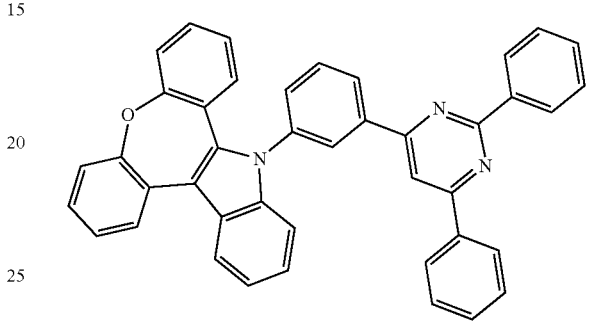
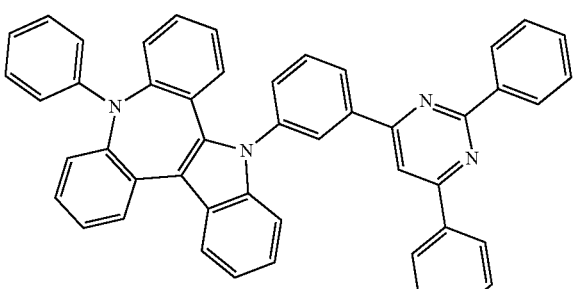
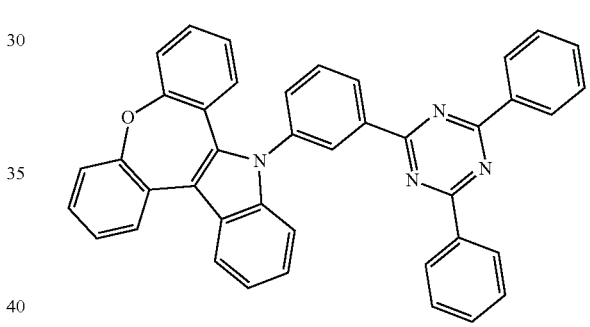
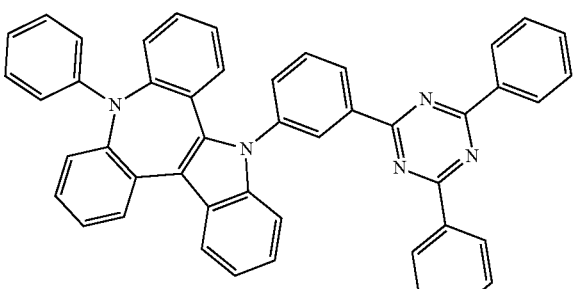
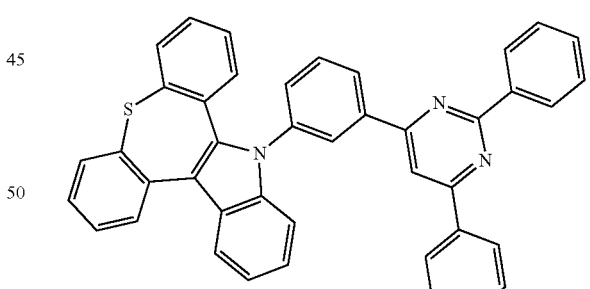
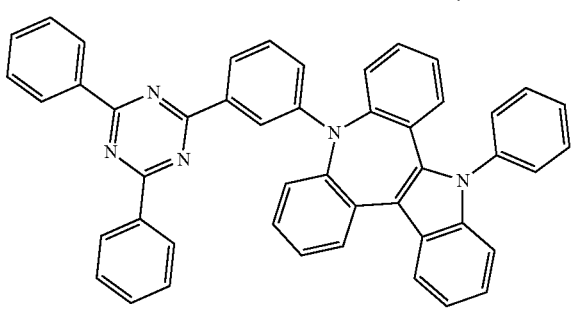
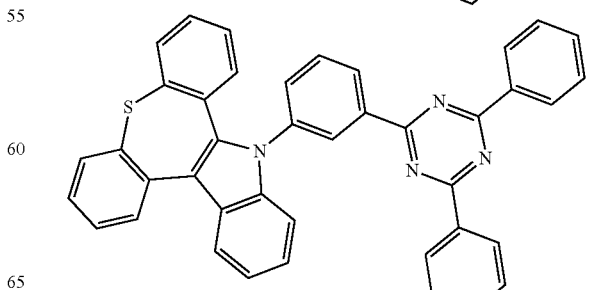

555
-continued
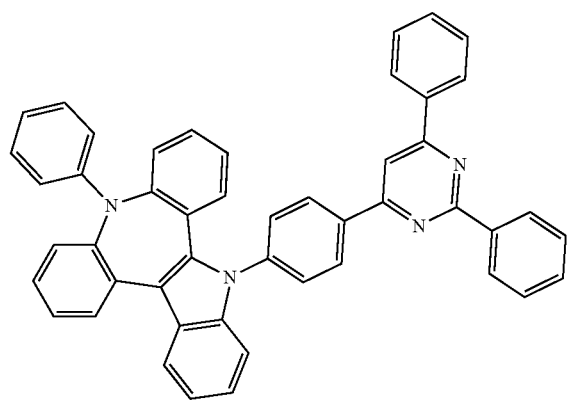
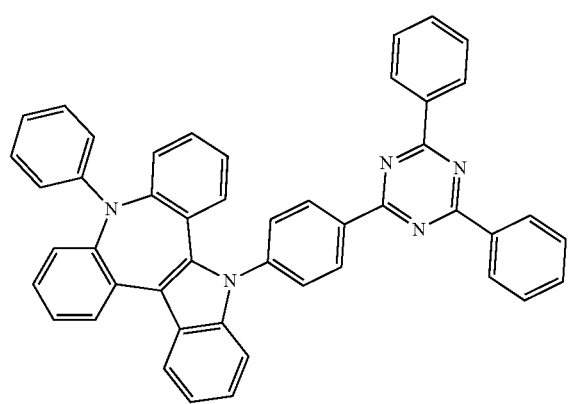
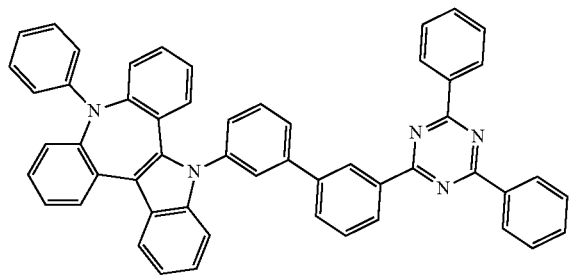
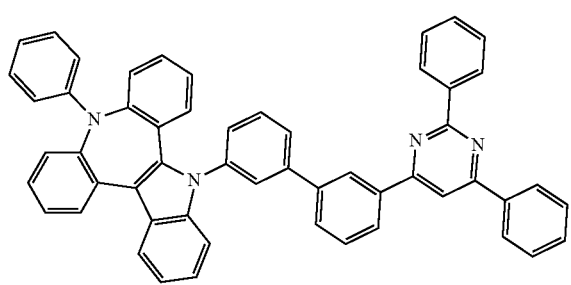
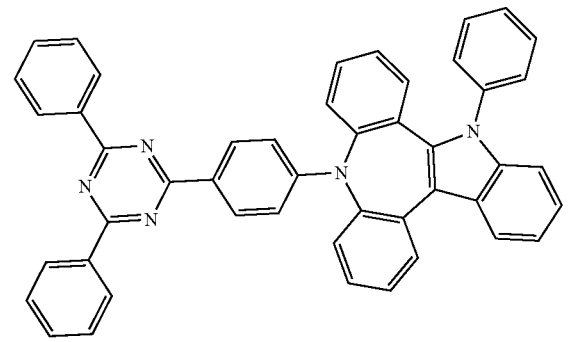
556
-continued
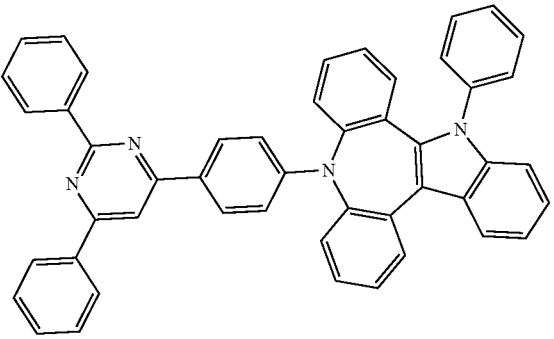
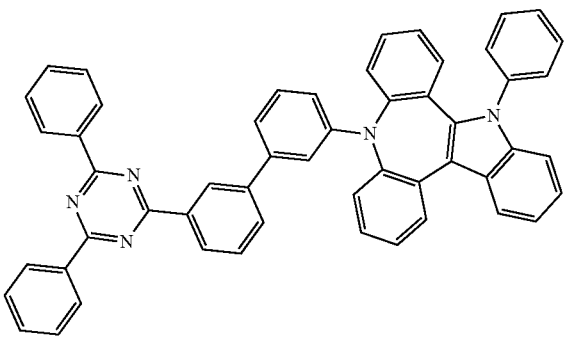
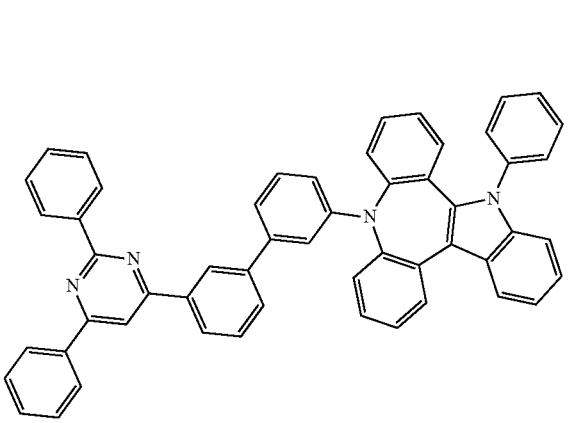
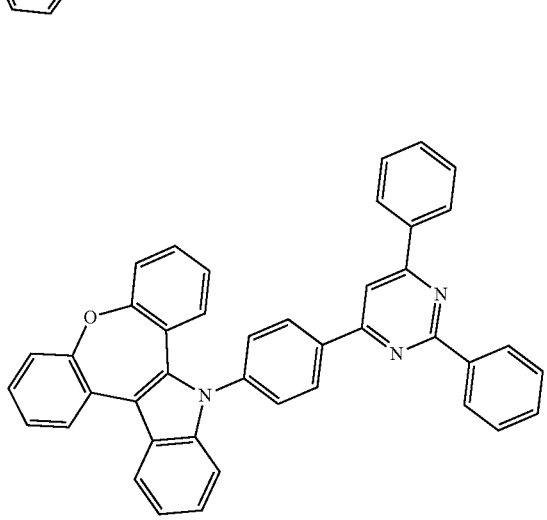

557
-continued
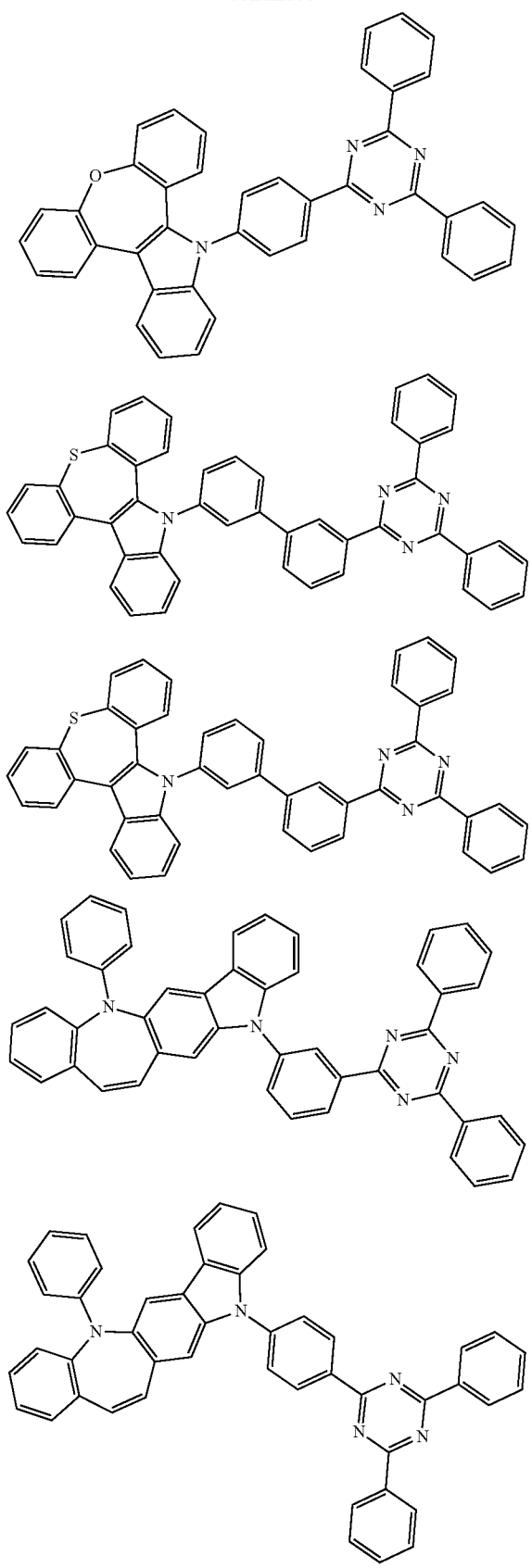
558
-continued
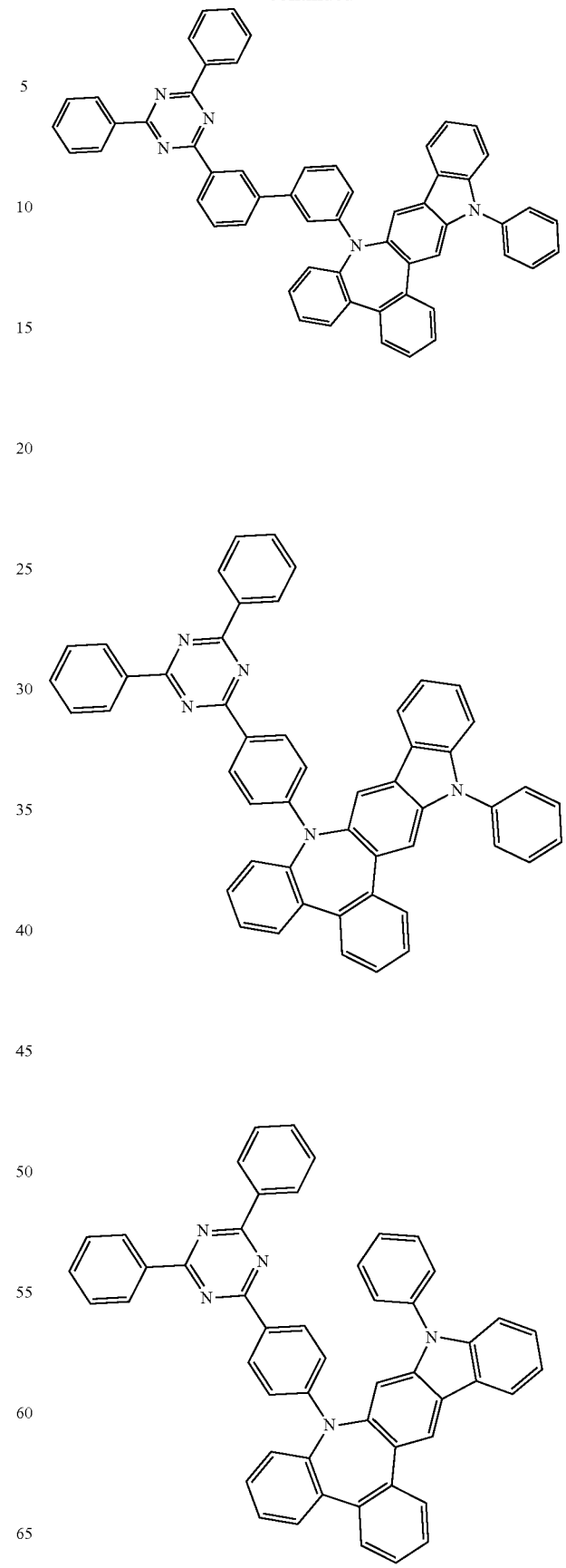

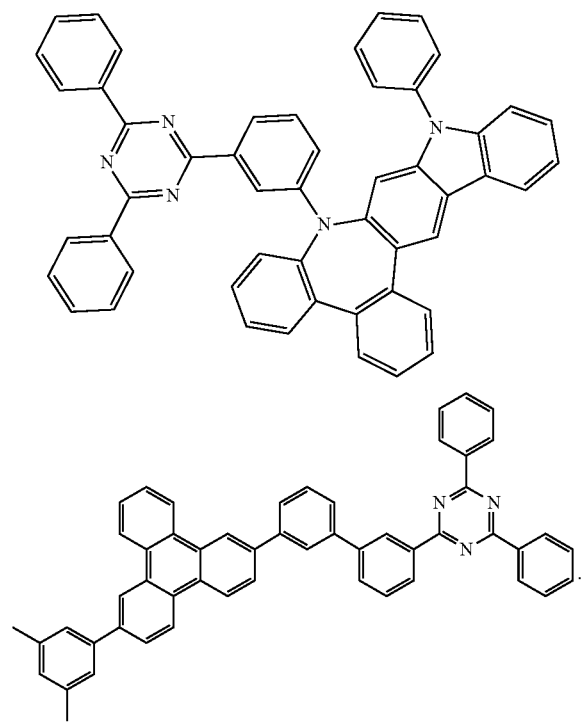
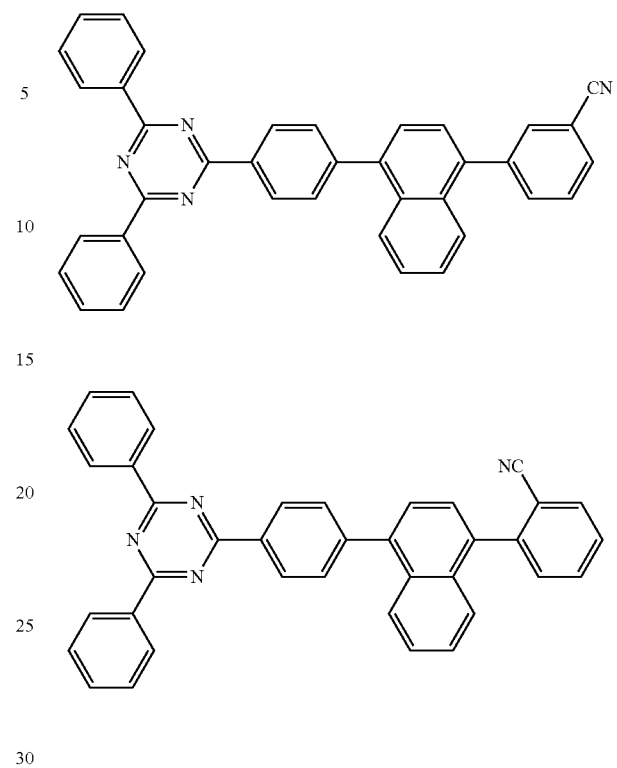
19. The organic light emitting device of claim 10, wherein the compound of Chemical Formula 2 is selected from among the following compounds:
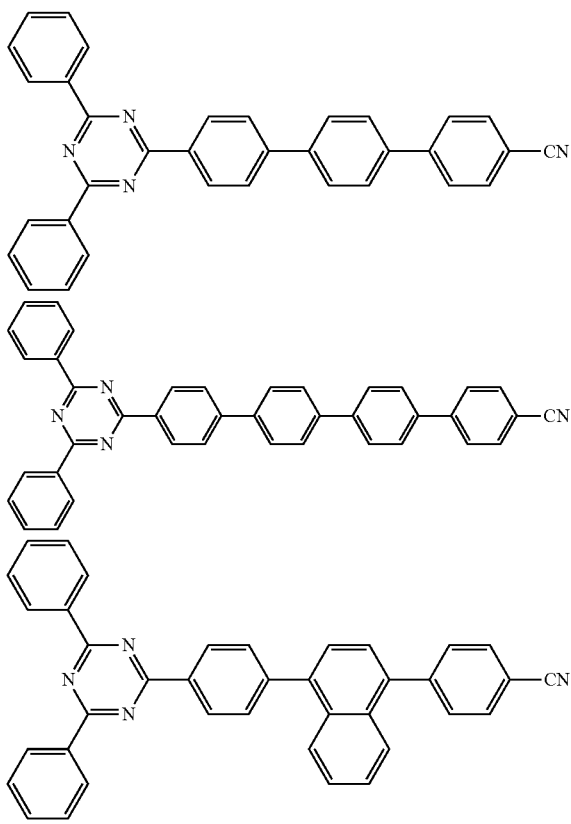
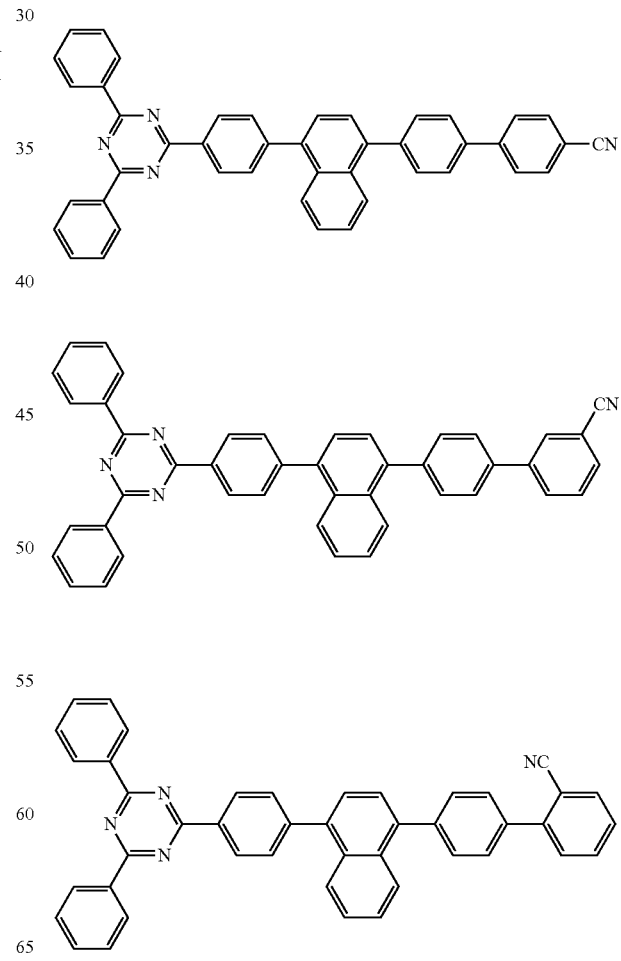

561
-continued
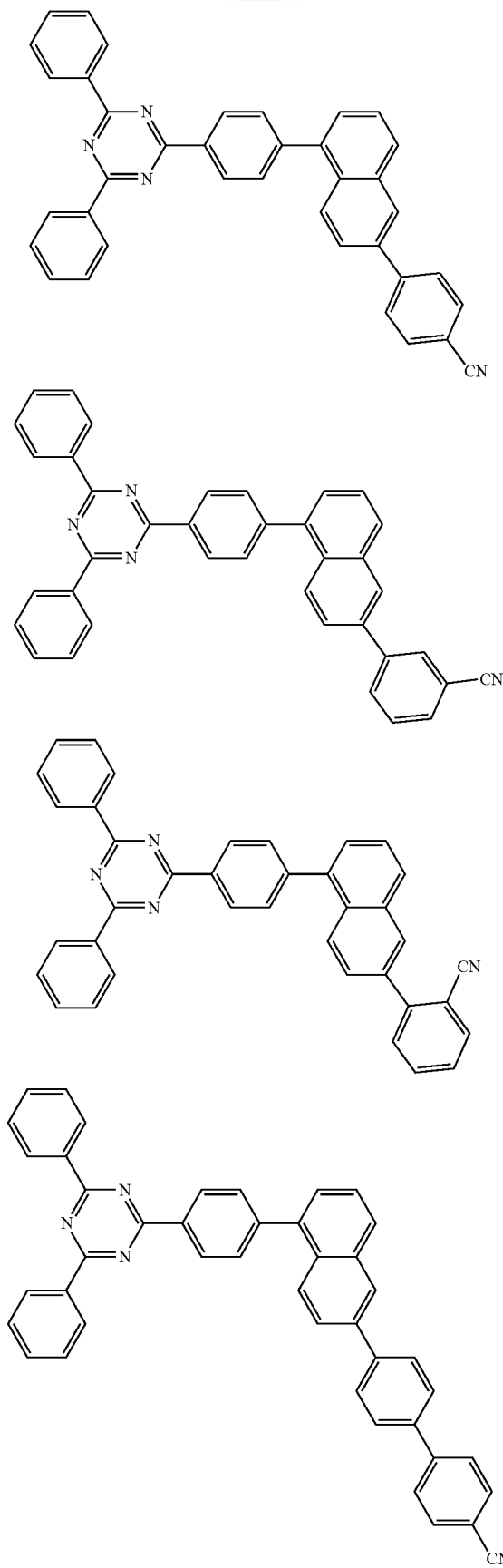
562
-continued
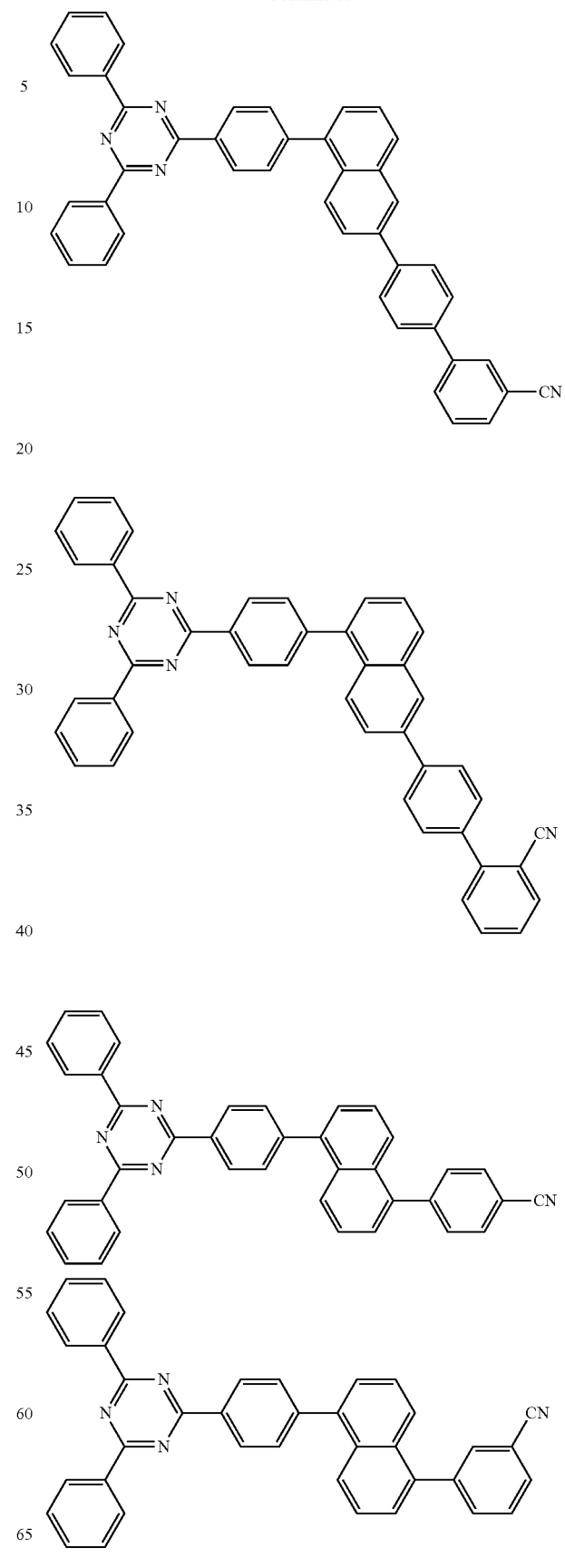

563
-continued
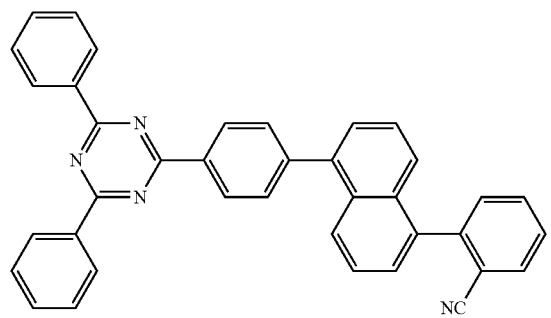
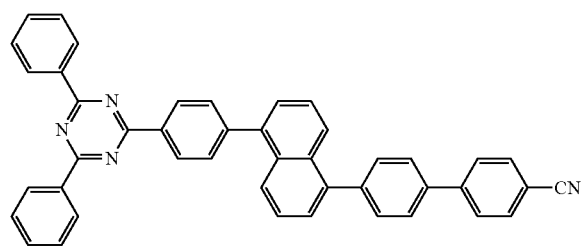
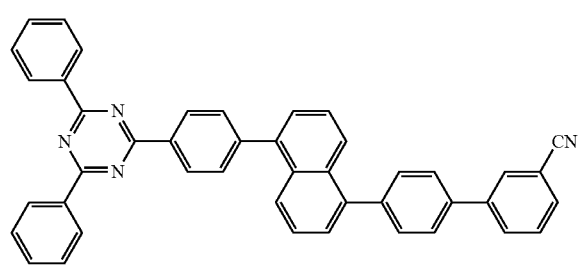
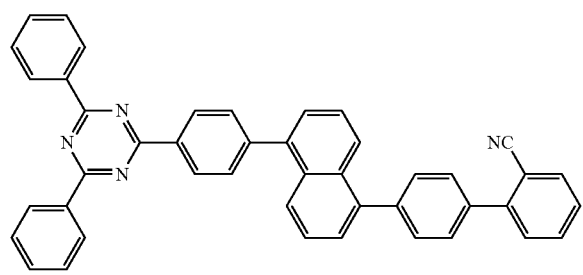
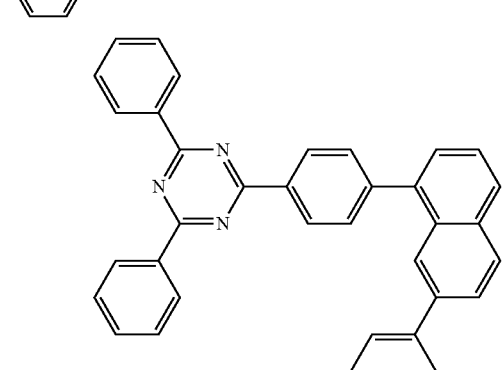
564
-continued
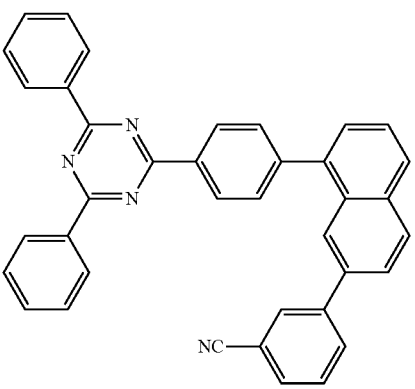
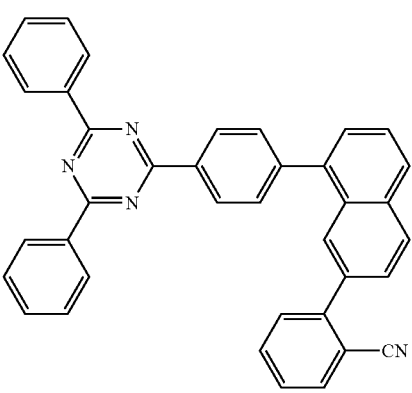
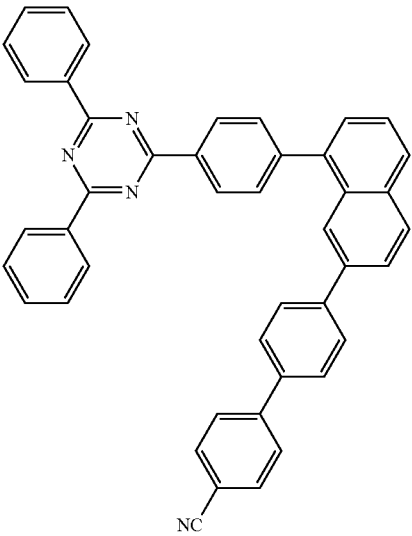

565
-continued
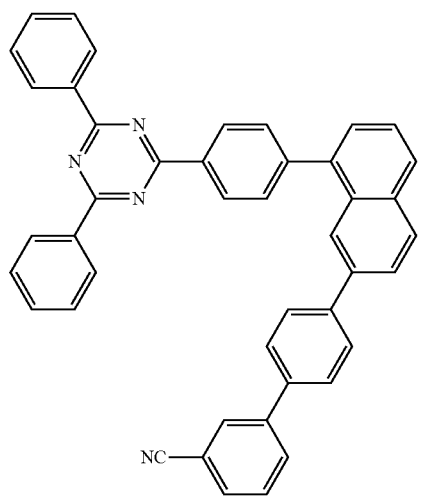
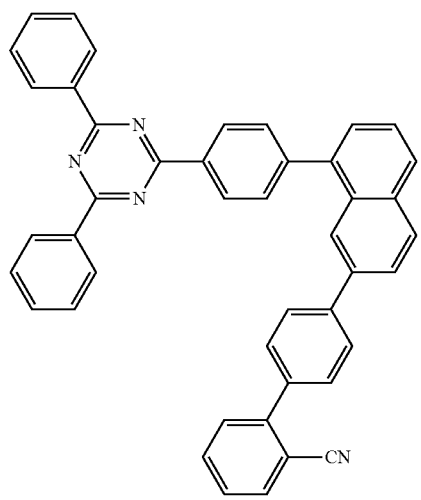
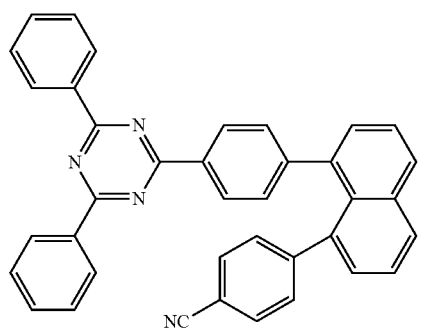
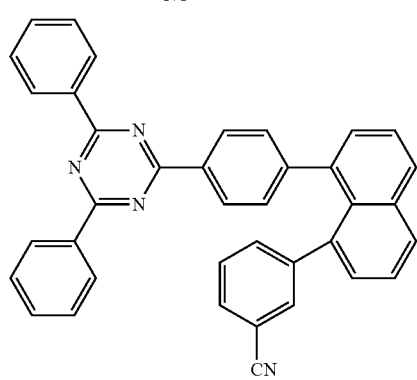
566
-continued
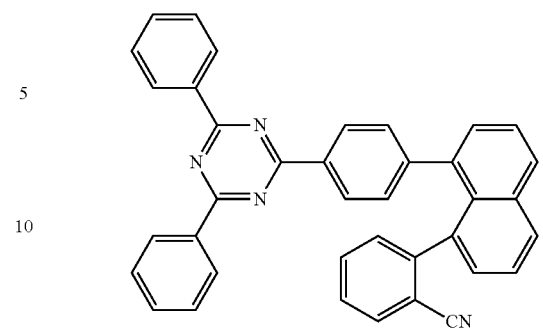
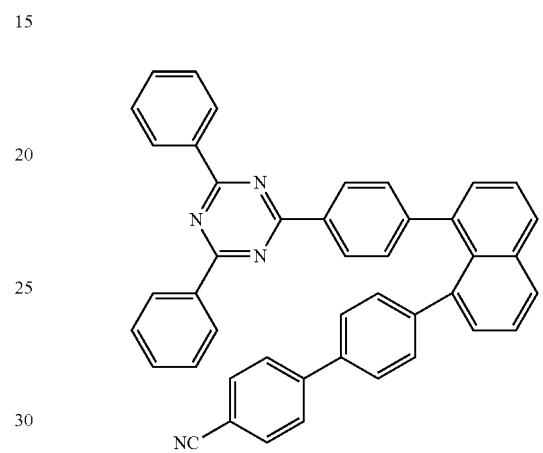
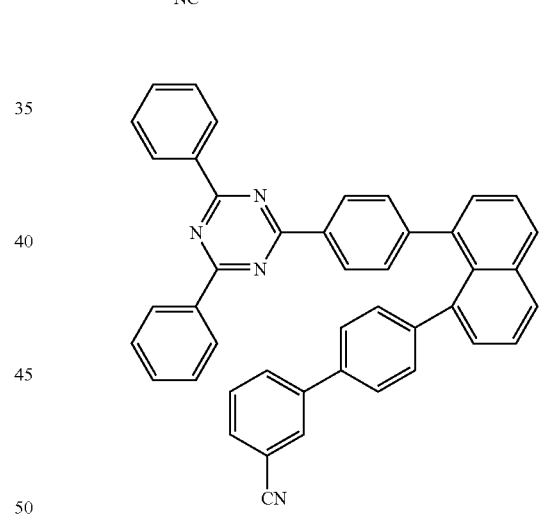
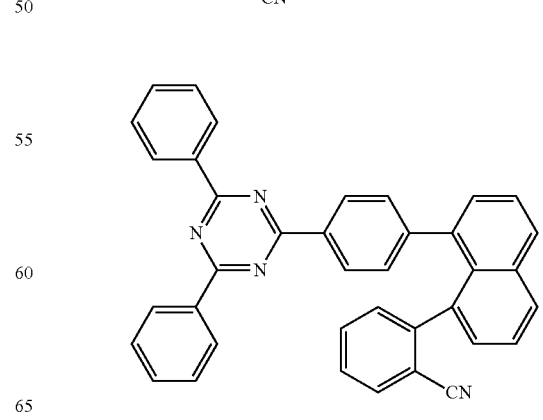

567
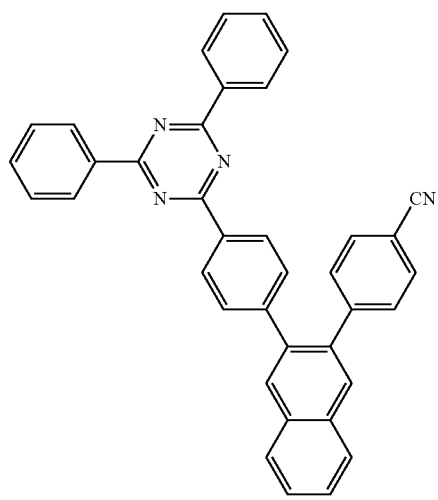
568
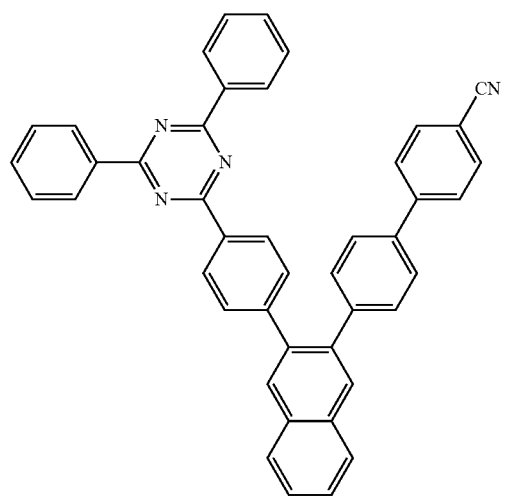
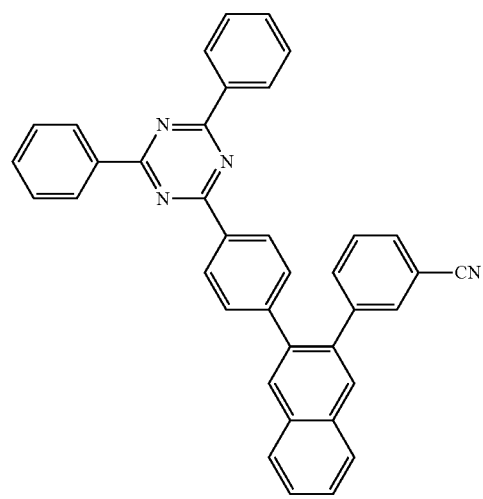
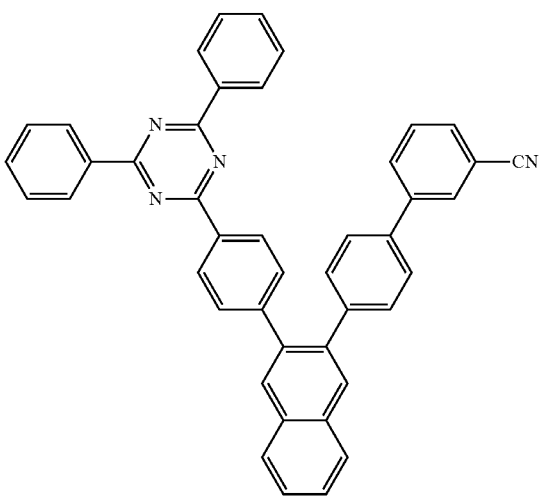
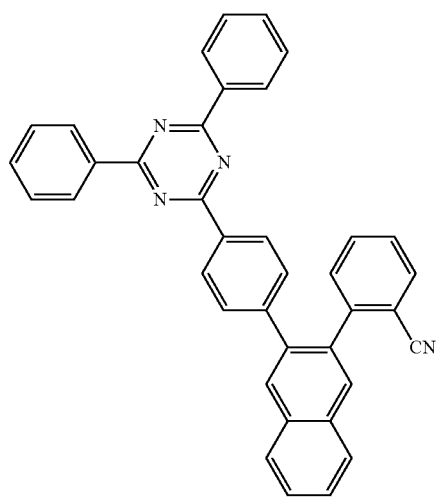

569
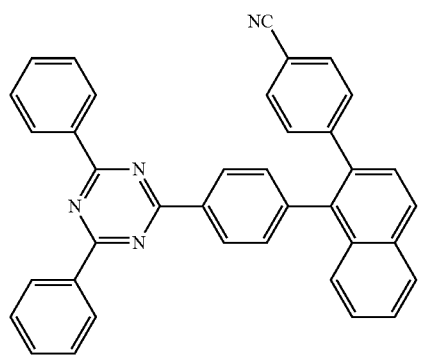
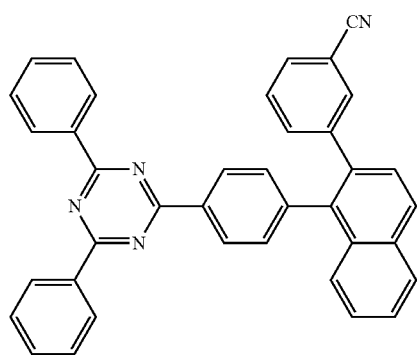
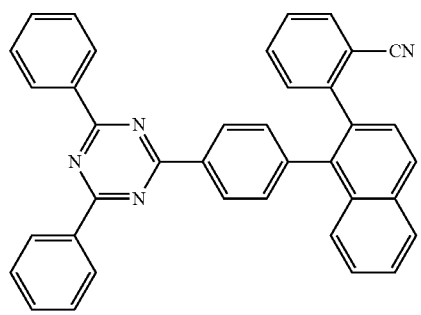
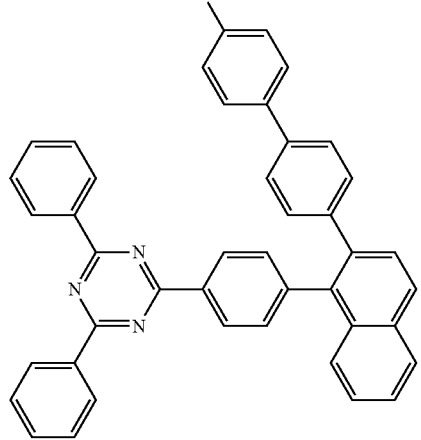
570
-continued
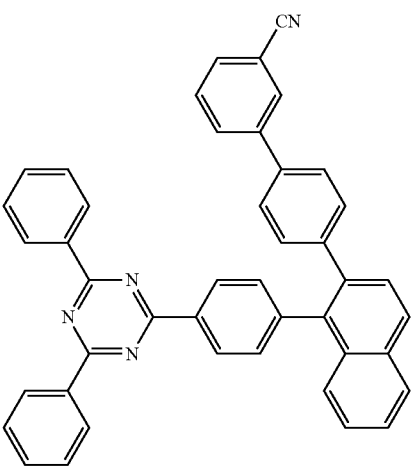
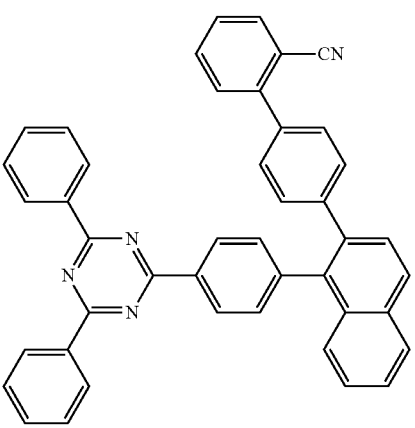
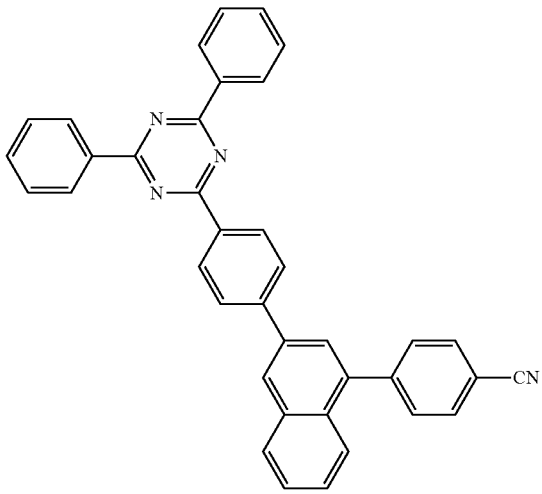

571
-continued
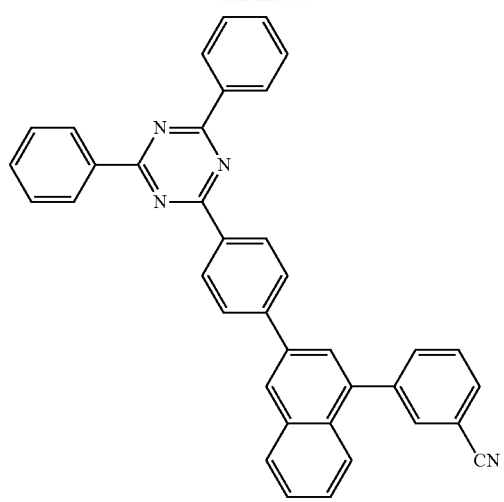
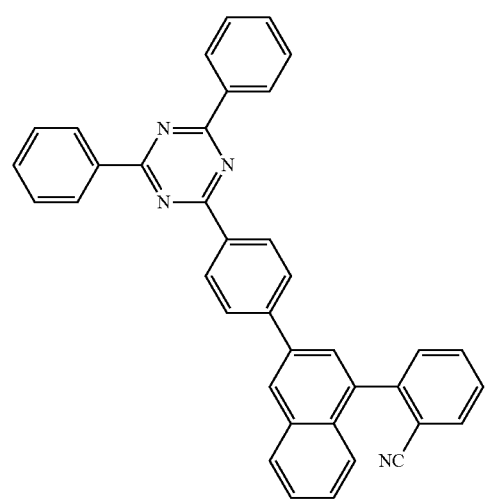
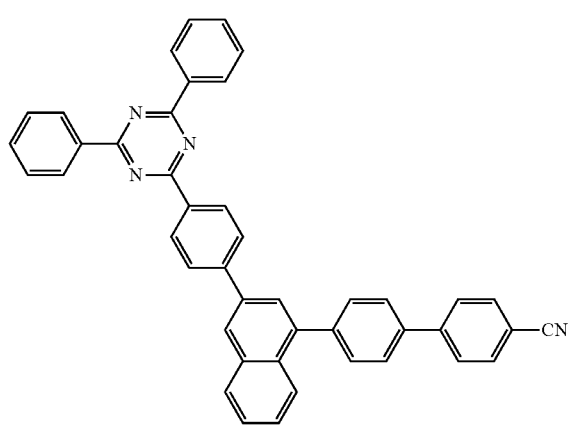
572
-continued
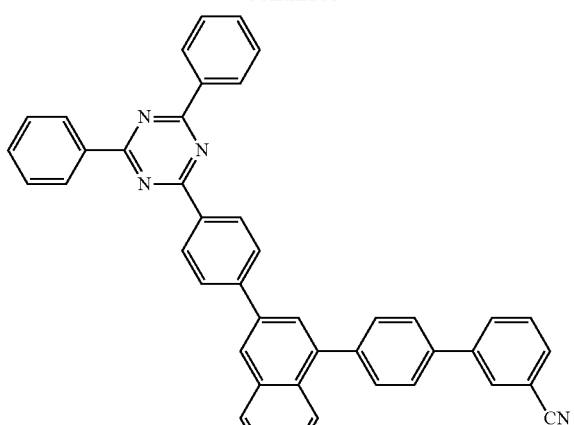
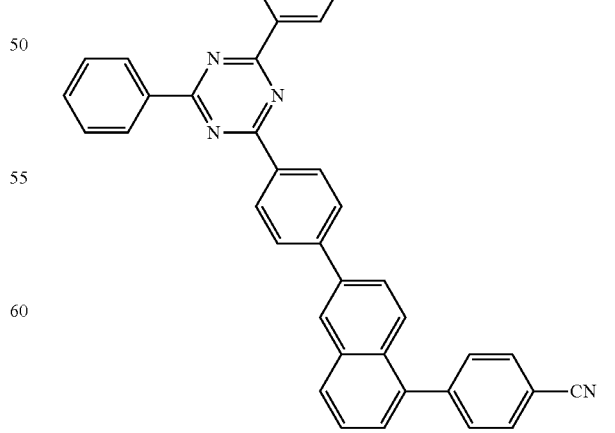

573
-continued
574
-continued
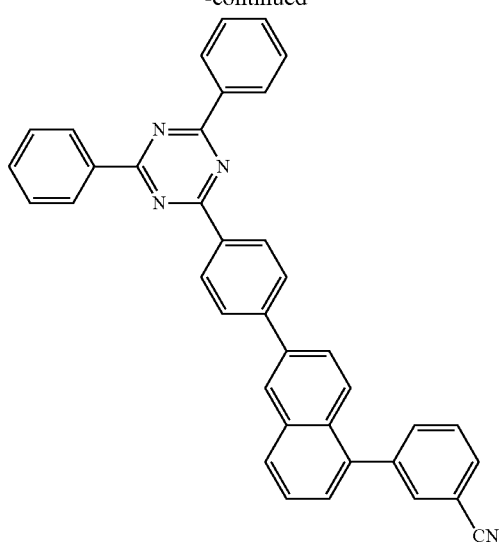
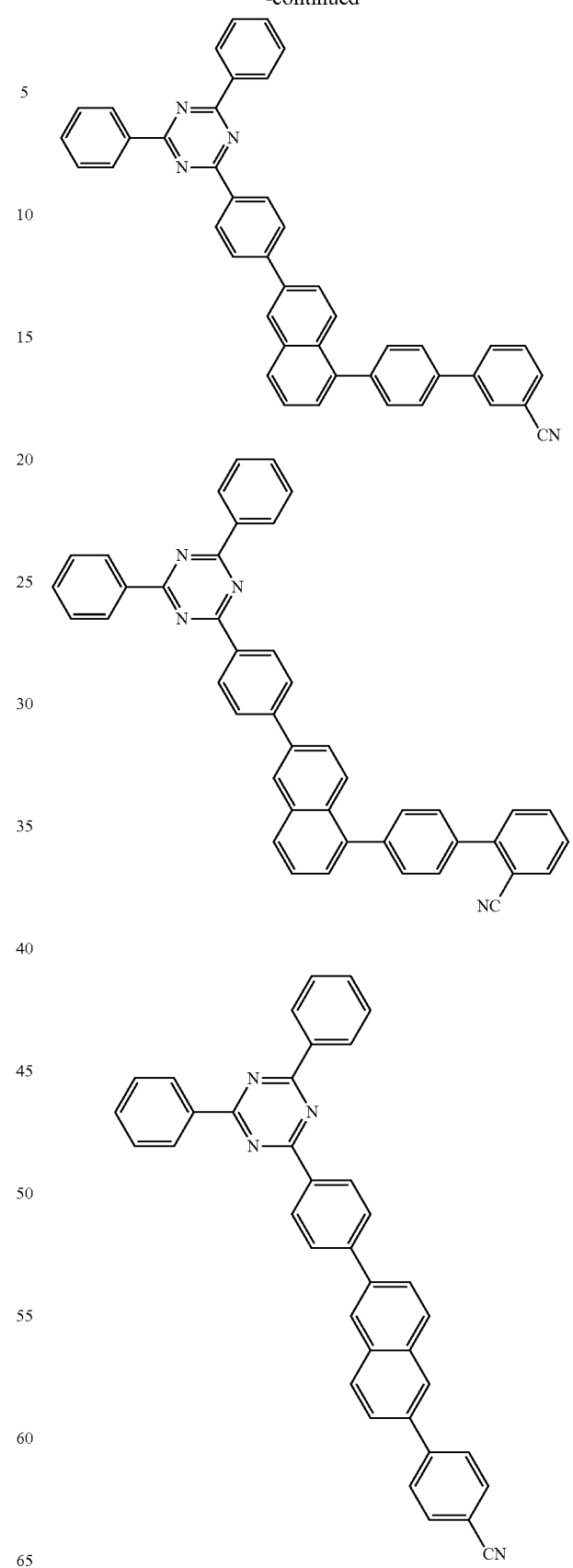

575
-continued
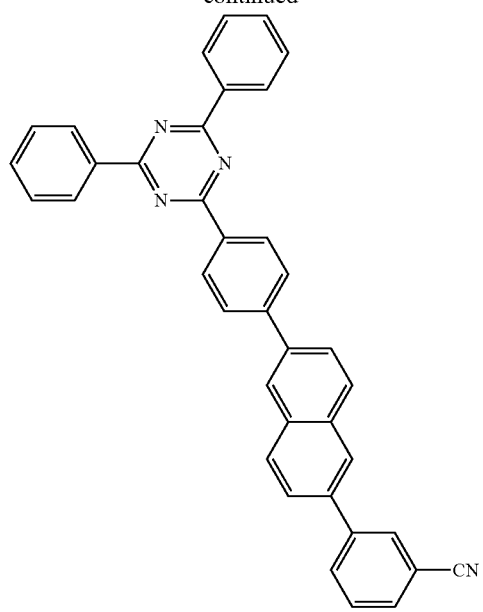
576
-continued
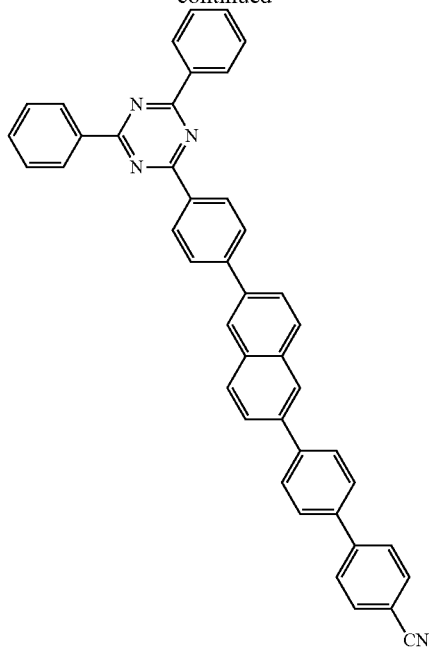
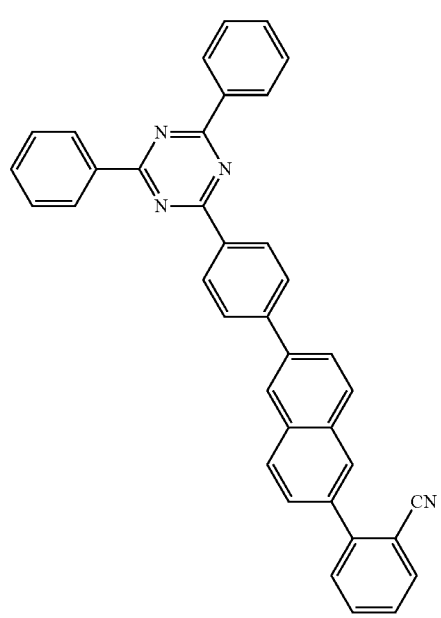
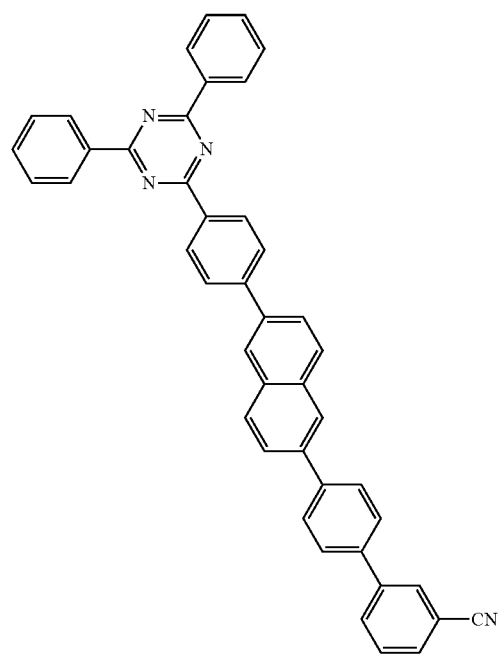 [SMILES: N#Cc1cccc(-c2ccc(-c3ccc4cc(-c5ccc(-c6nc(-c7ccccc7)nc(-c7ccccc7)n6)cc5)ccc4c3)cc2)c1]

577
-continued
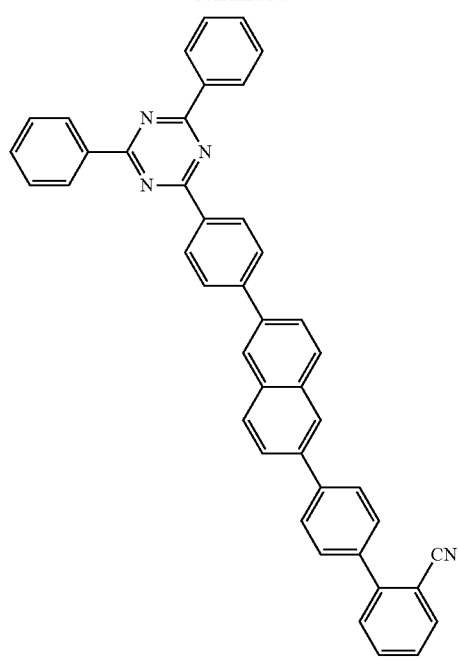
578
-continued
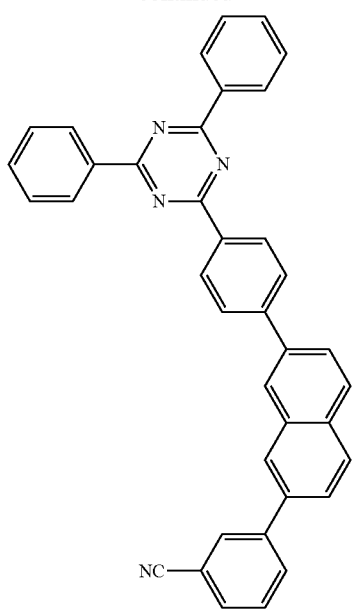
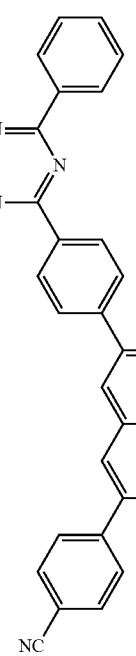
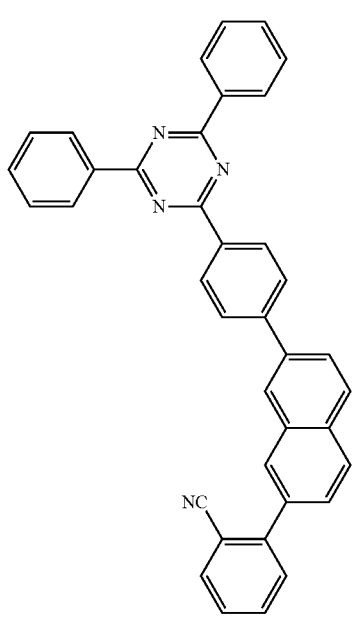

579
-continued
580
-continued
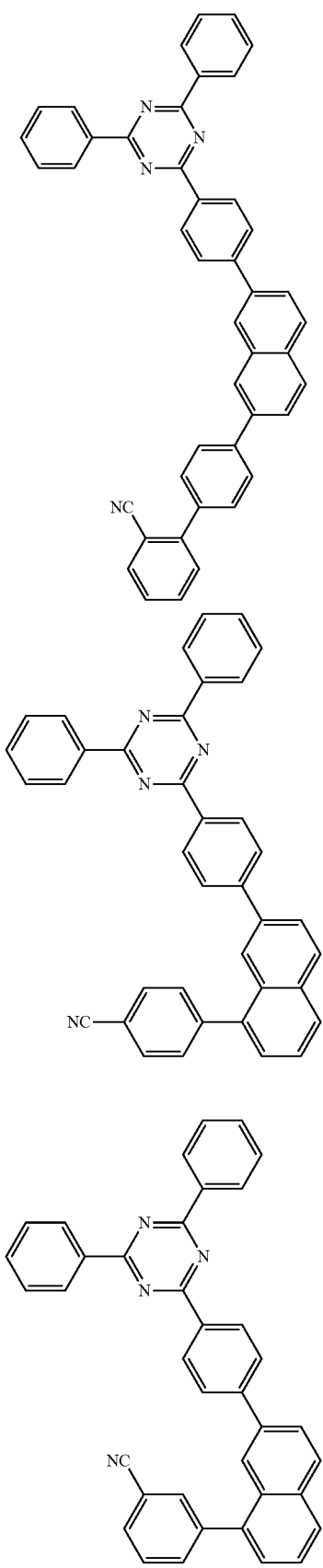

581
-continued
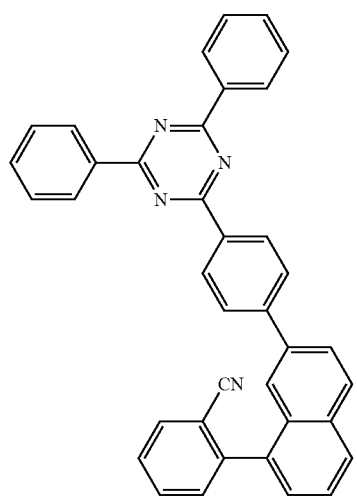
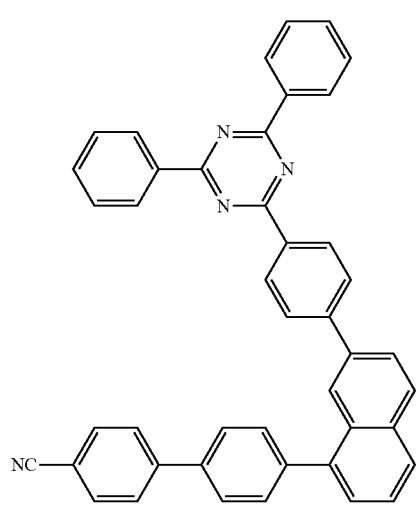
582
-continued
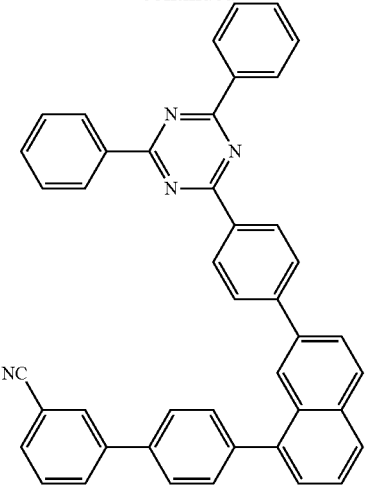
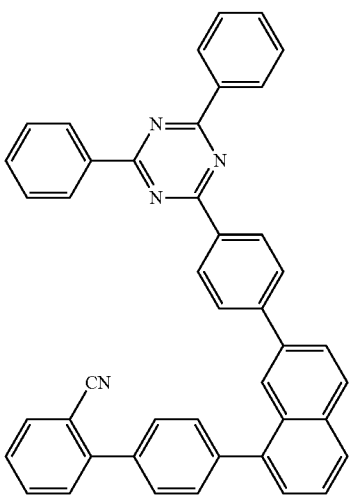 [SMILES: N#Cc1ccccc1-c1ccc(-c2cccc3ccc(-c4ccc(-c5nc(-c6ccccc6)nc(-c6ccccc6)n5)cc4)cc23)cc1]
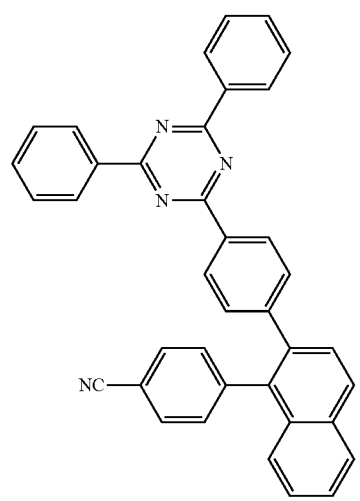

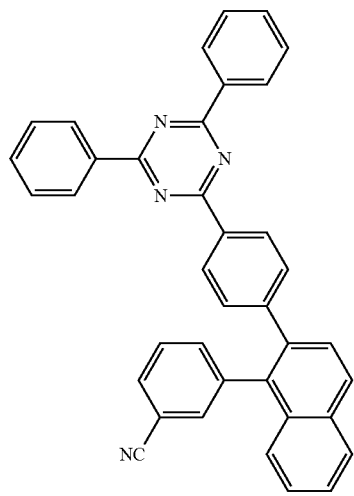
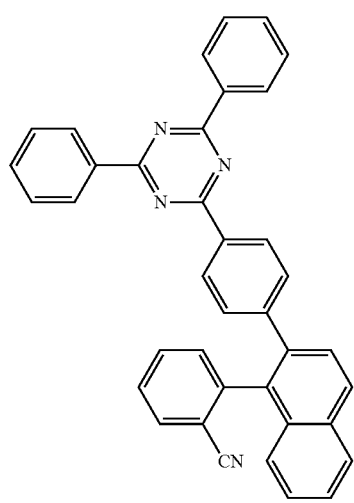
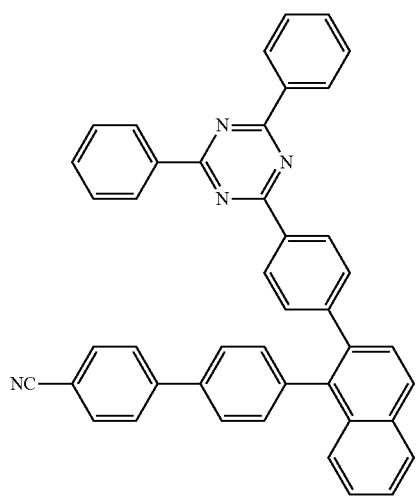

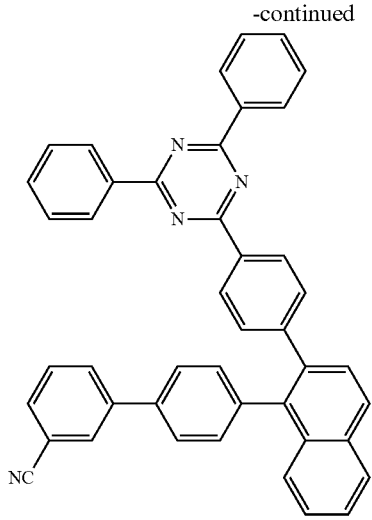
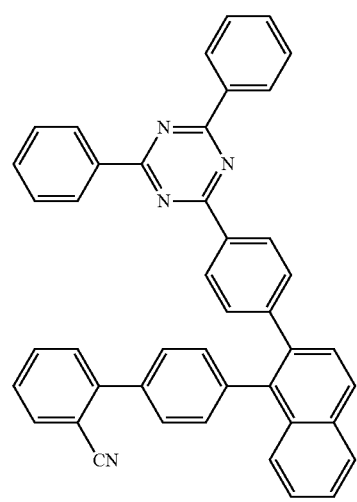
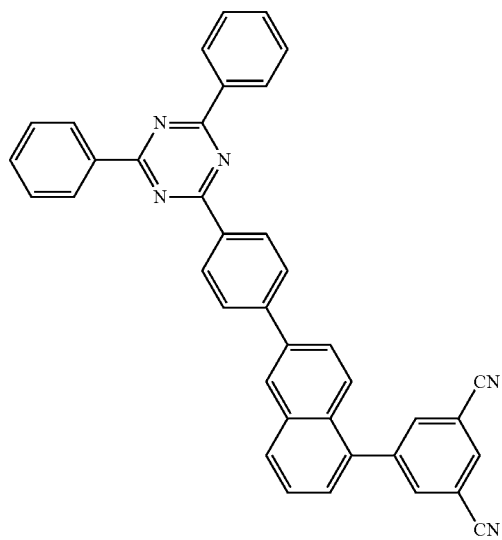

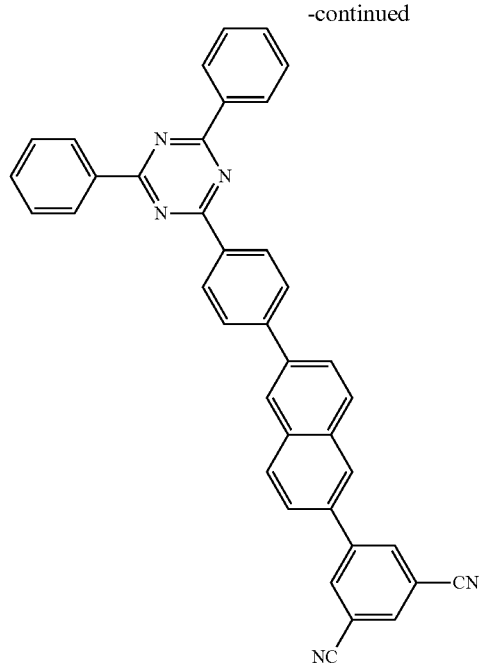
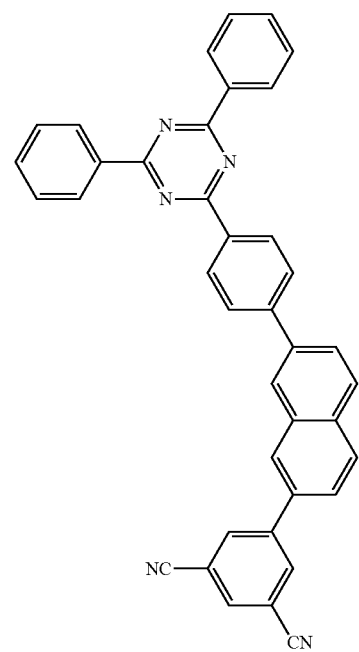

-continued
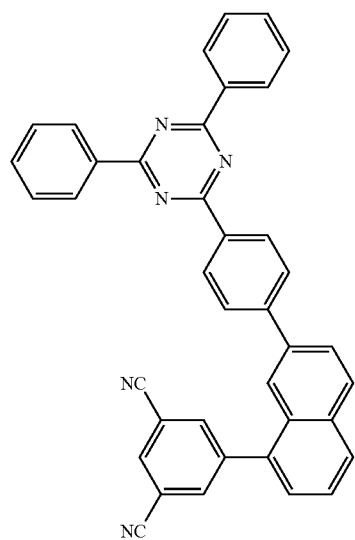
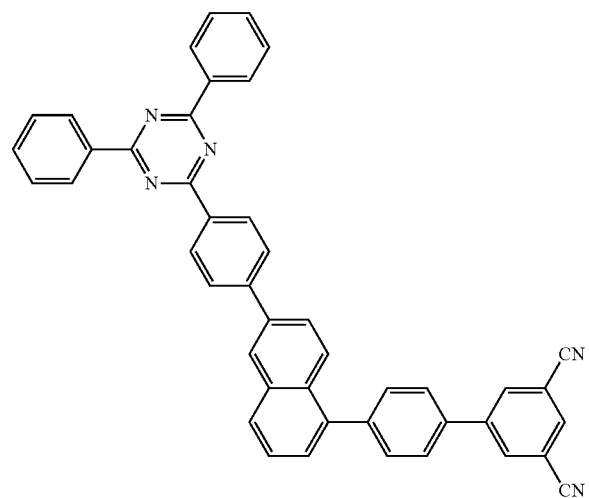

-continued
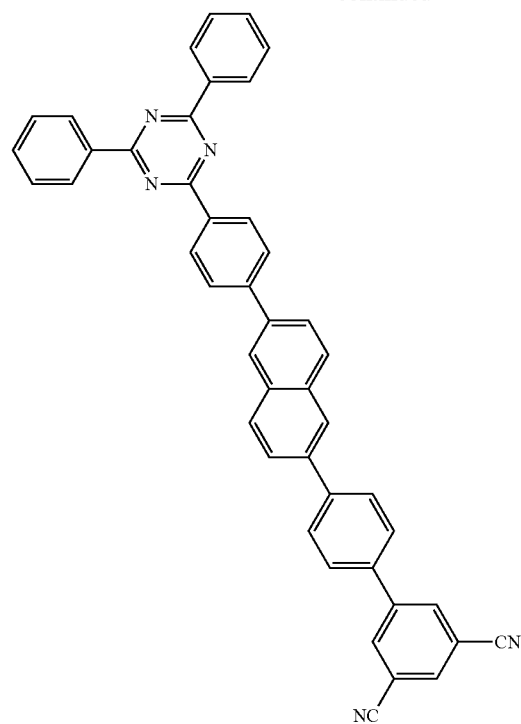
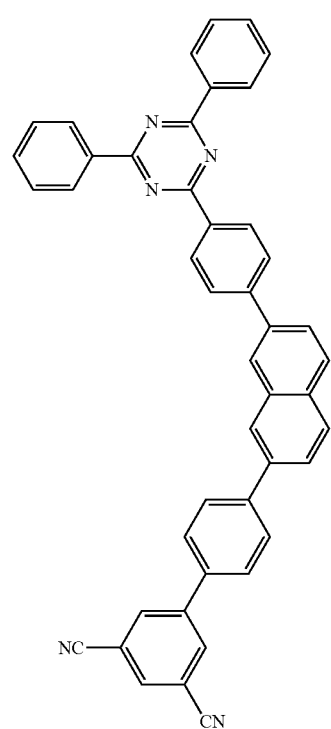

-continued
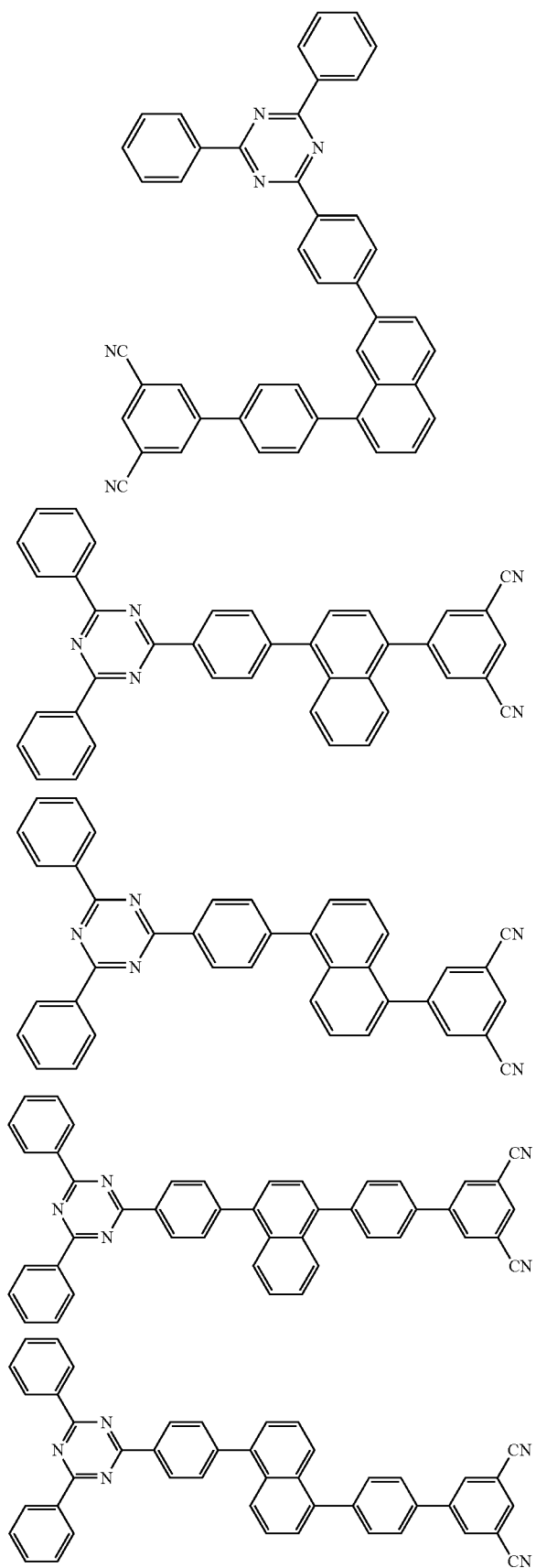

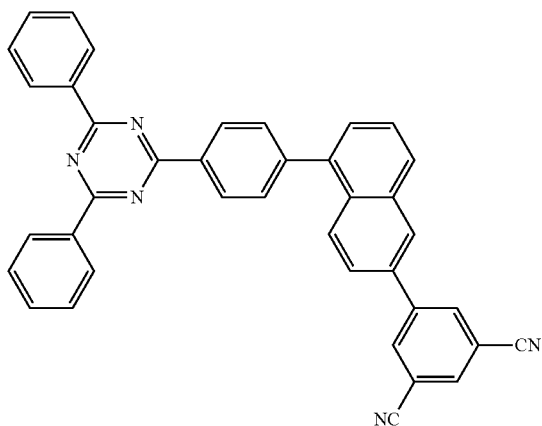
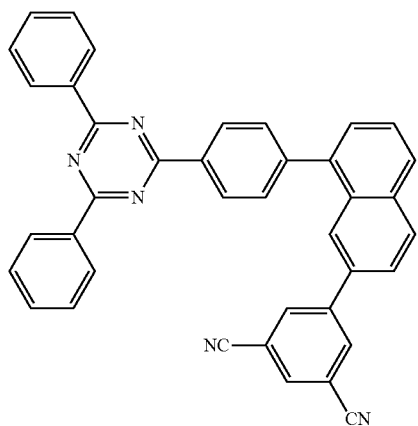
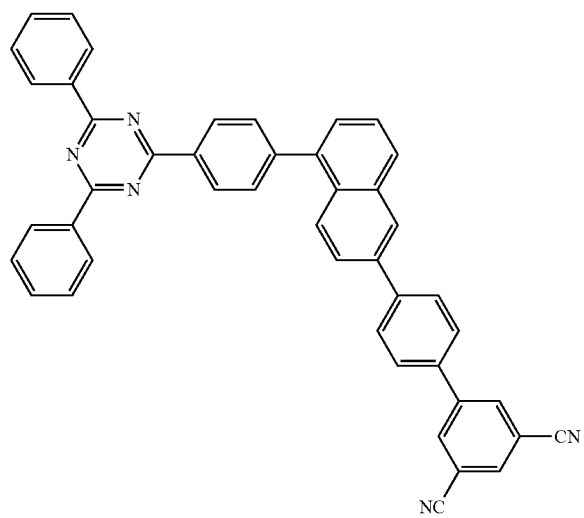

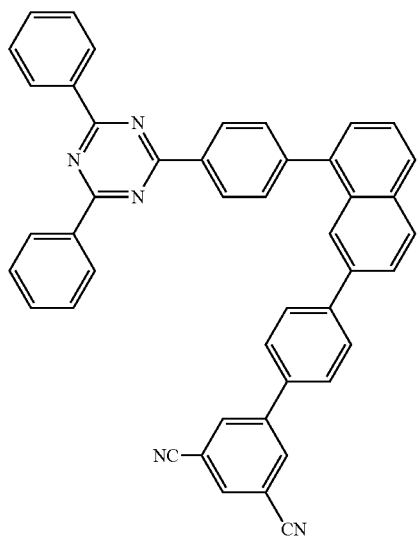
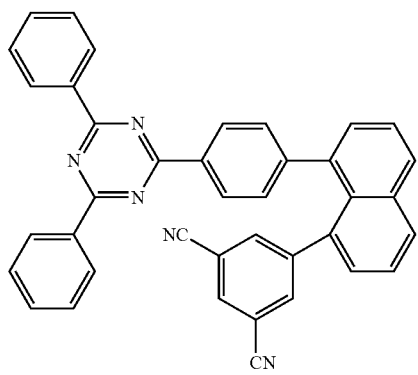
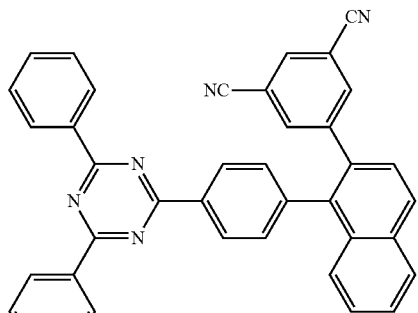
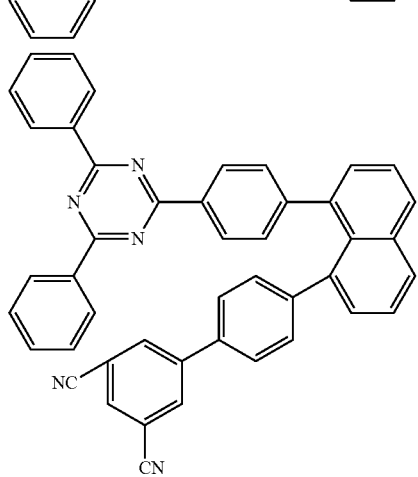

-continued
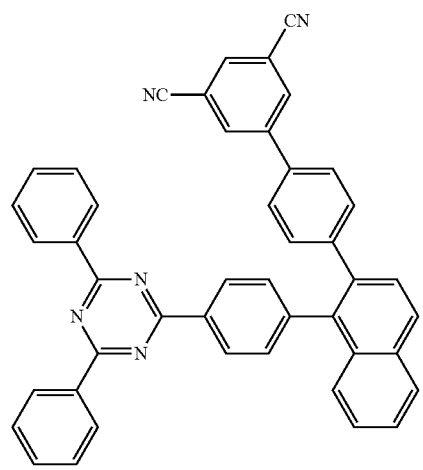
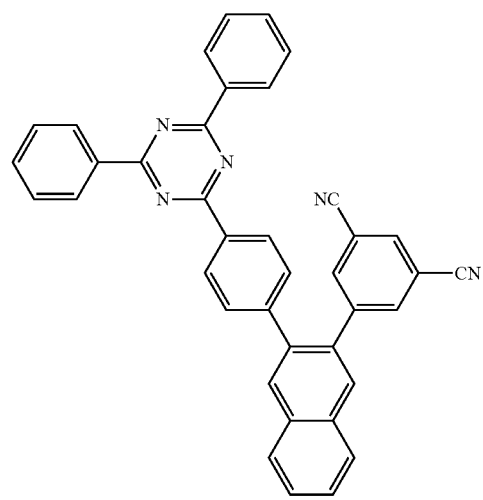
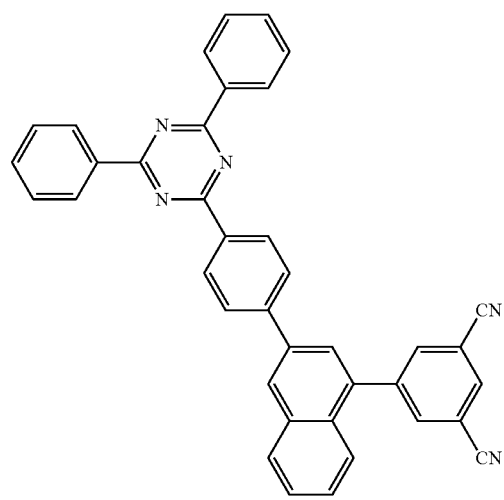

-continued
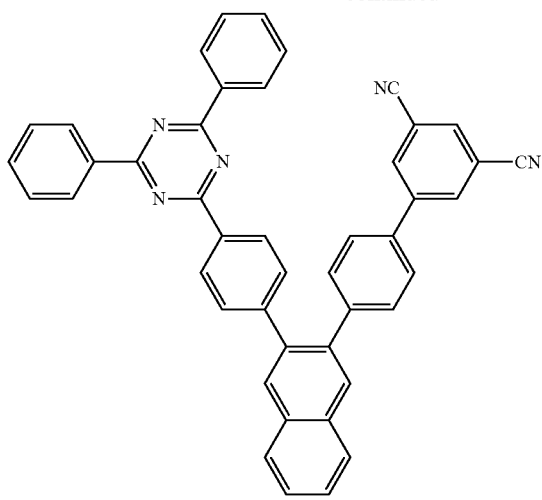
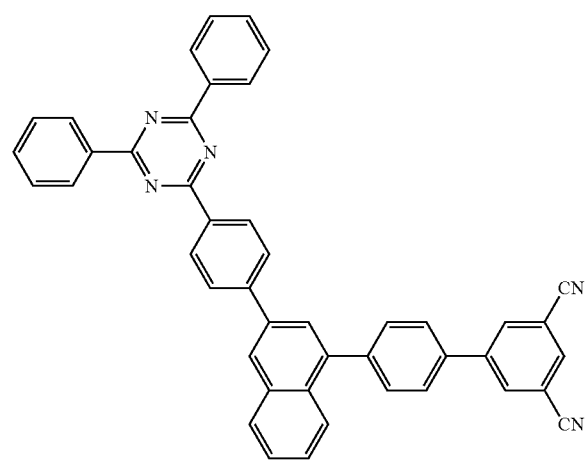
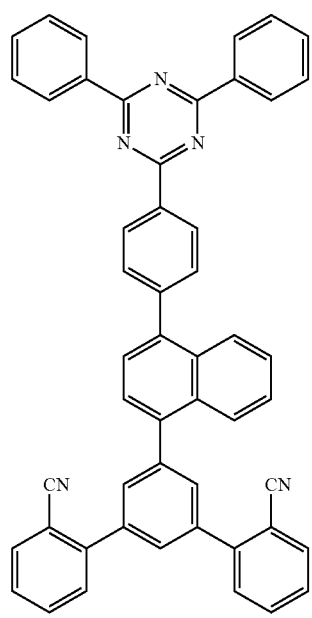

-continued
603
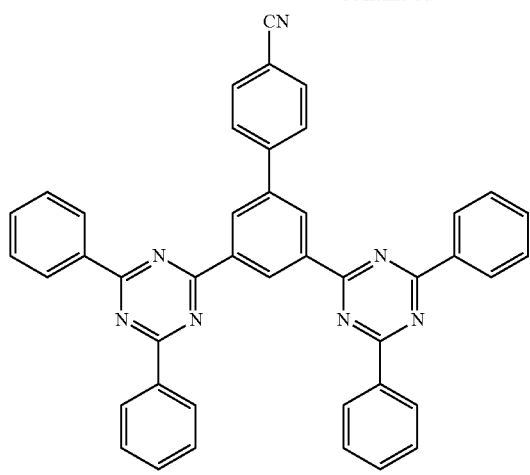
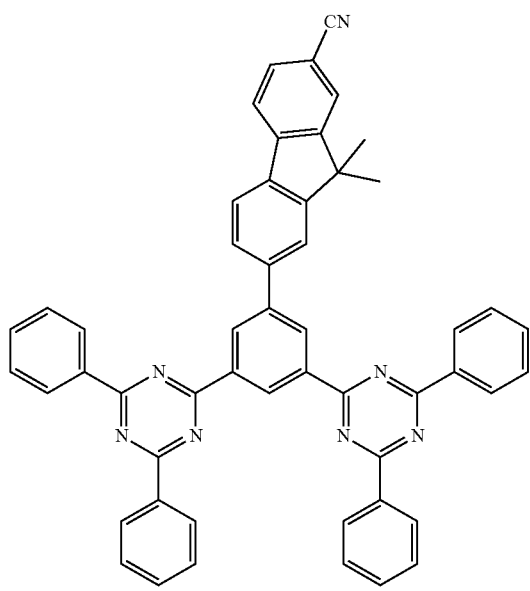
604
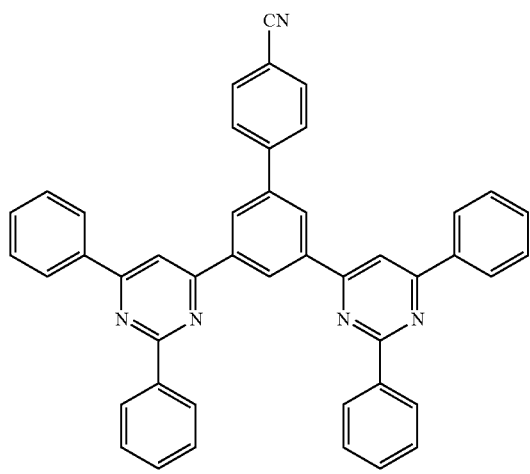

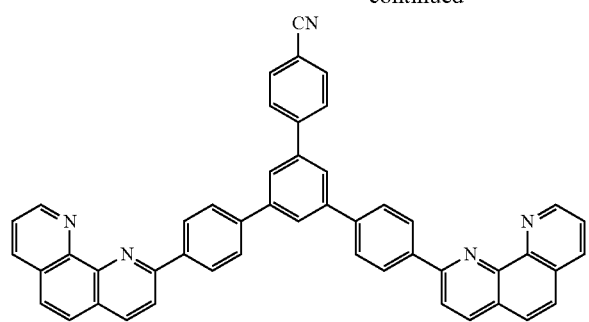
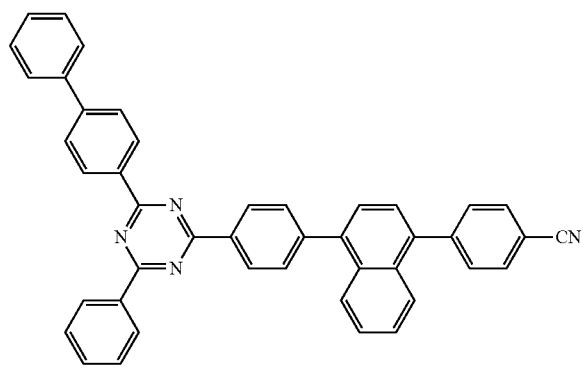
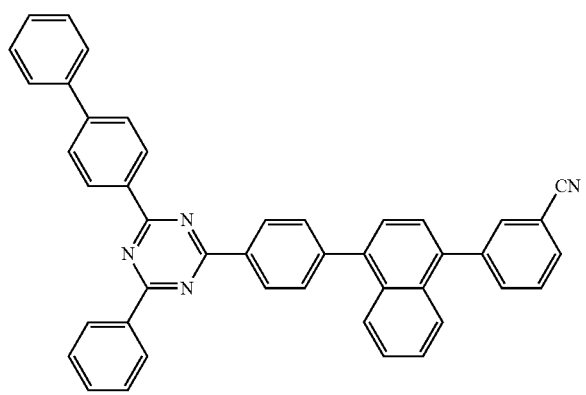
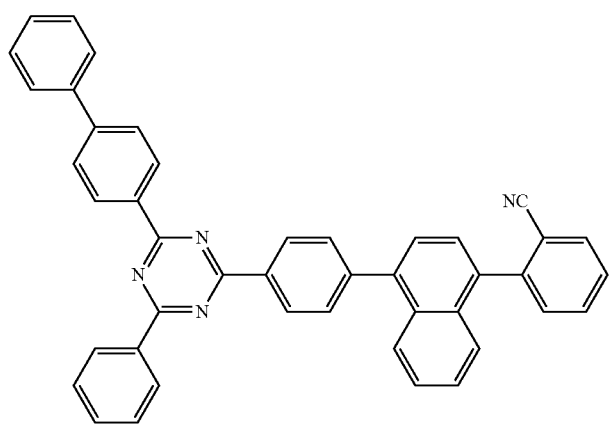

607
-continued
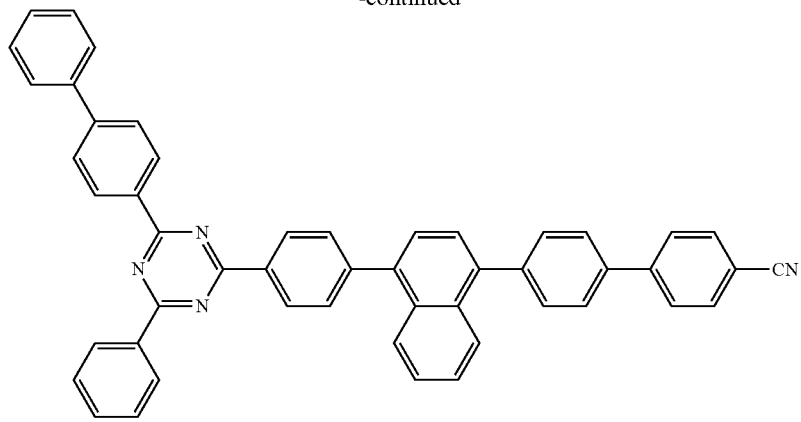
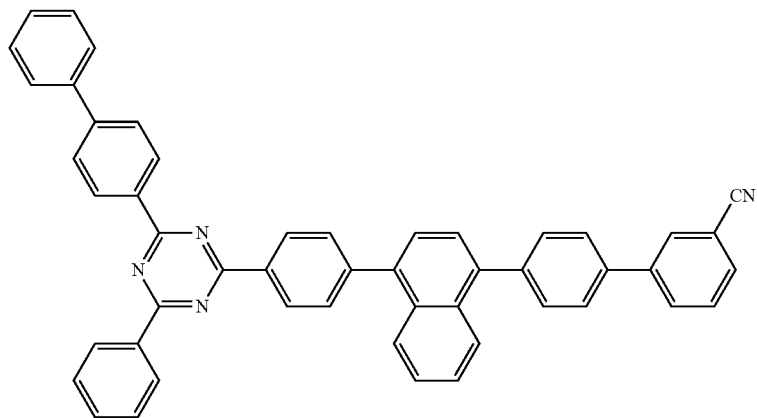
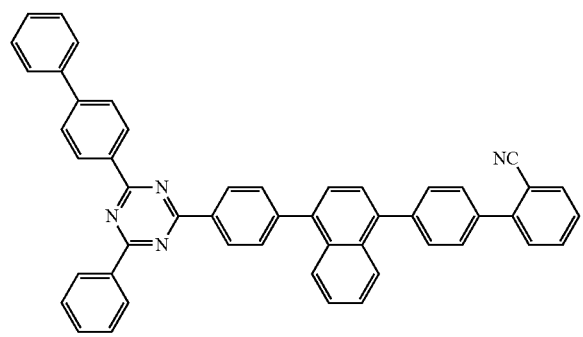 [SMILES: N#Cc1ccccc1-c1ccc(-c2ccc(-c3ccc(-c4nc(-c5ccccc5)nc(-c5ccc(-c6ccccc6)cc5)n4)cc3)c3ccccc23)cc1]
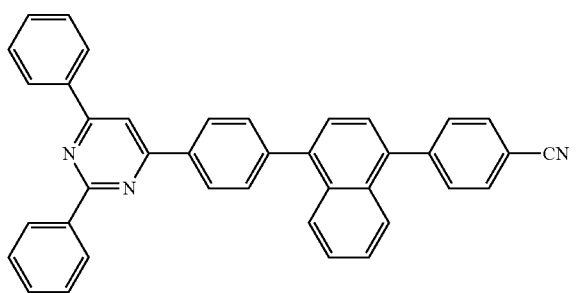
608
-continued
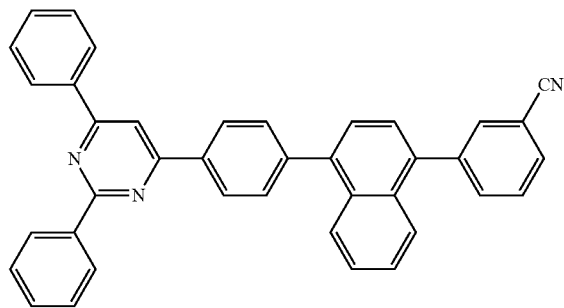

609
-continued
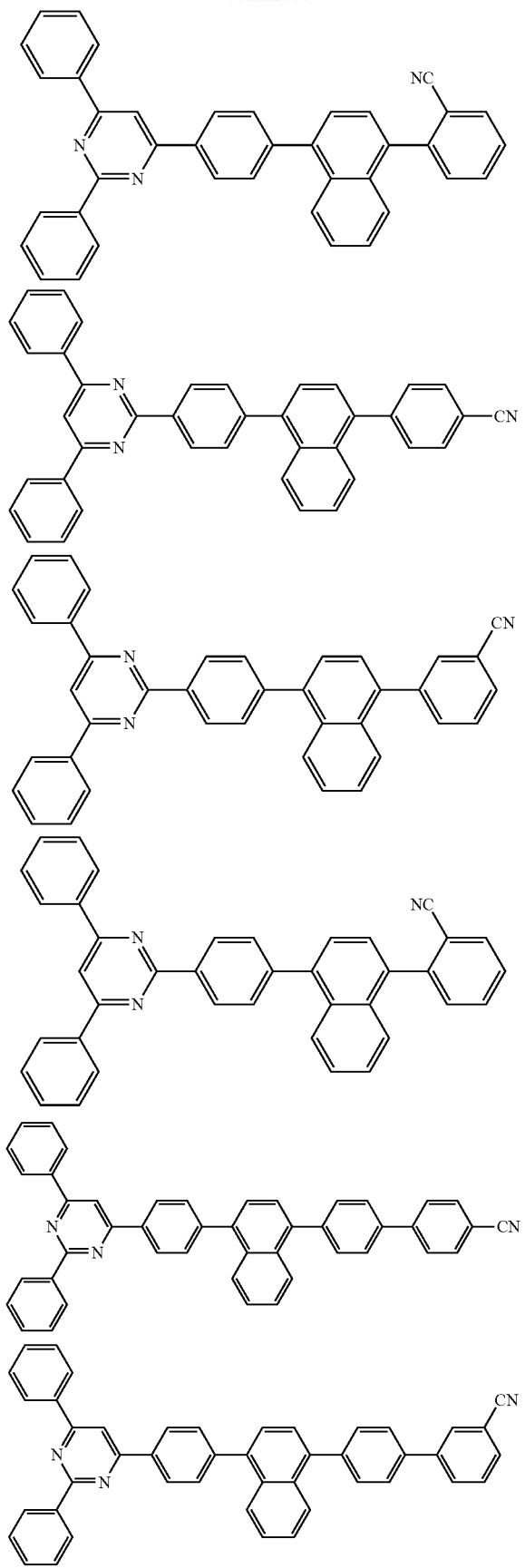
610
-continued
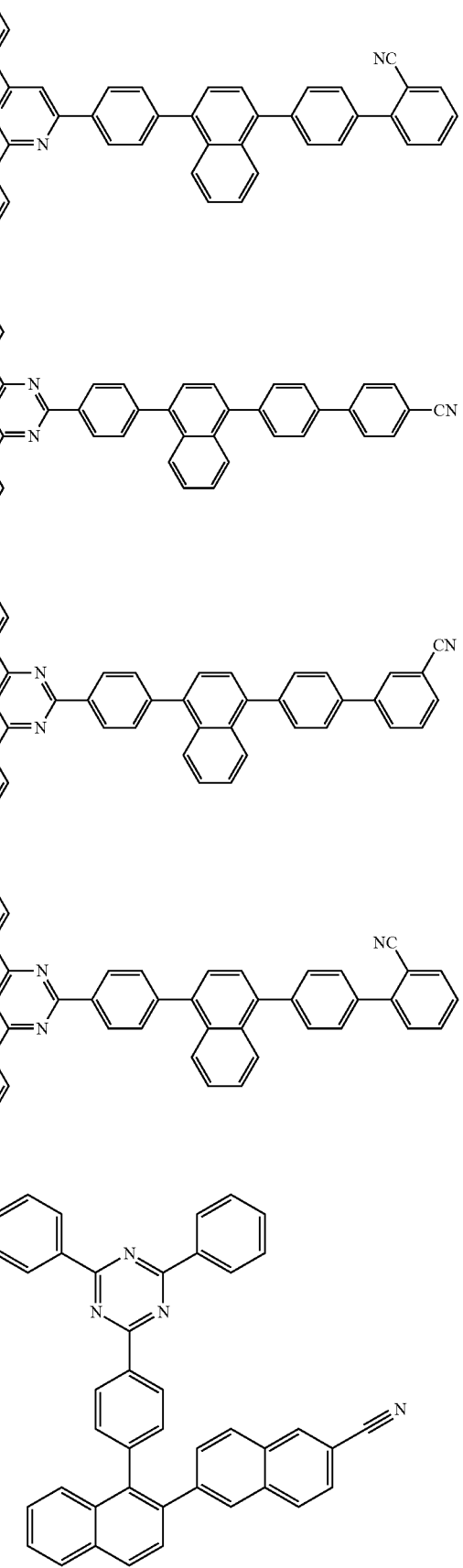

611
-continued
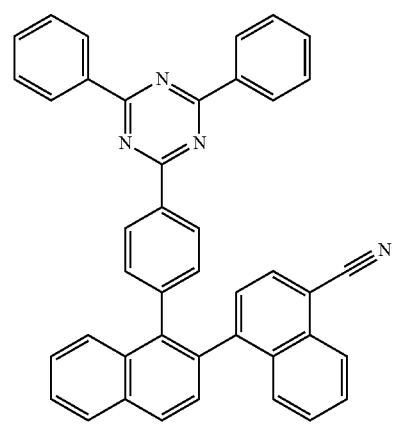
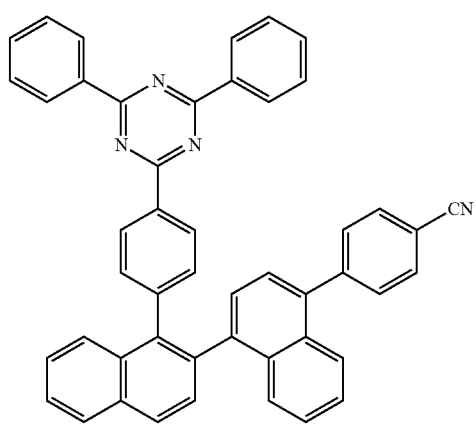
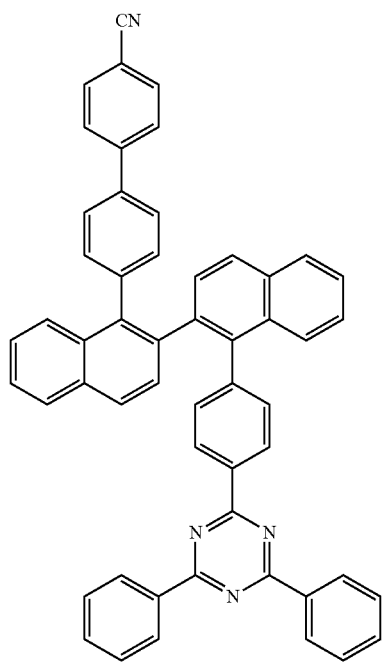
612
-continued
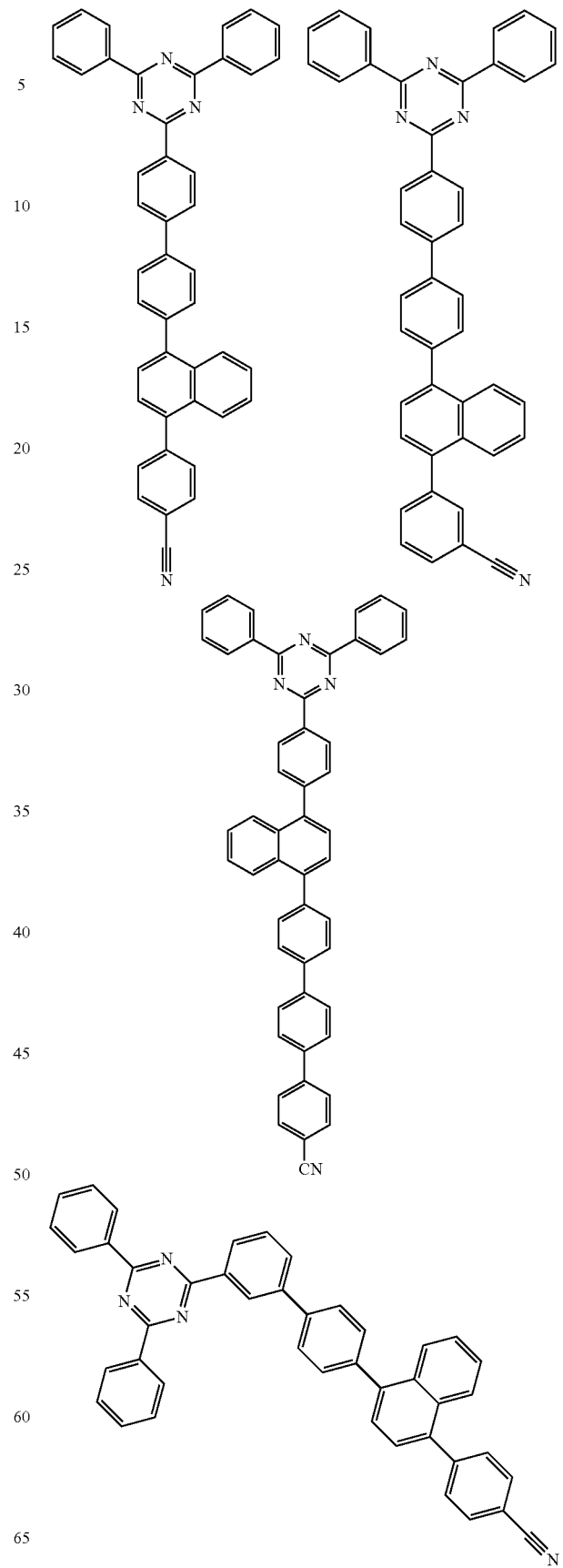

613
-continued
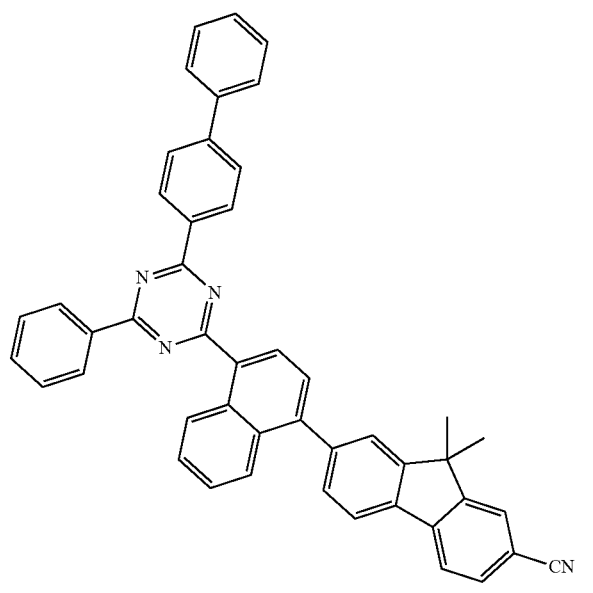
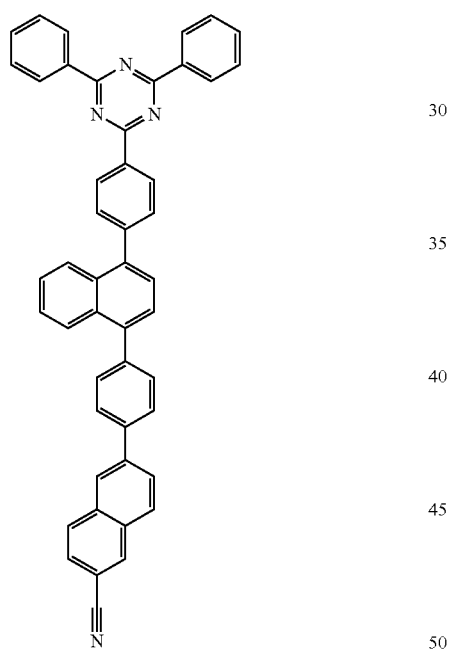
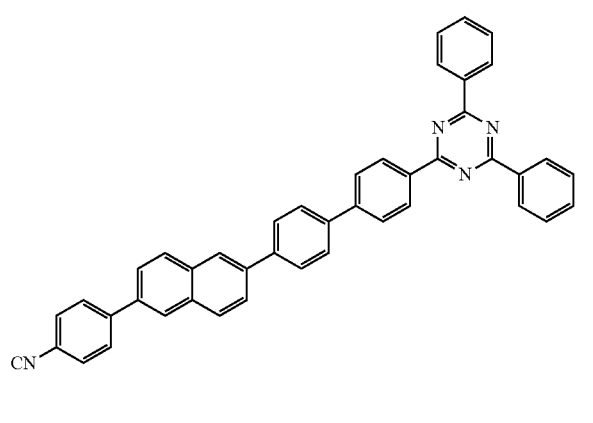
614
-continued
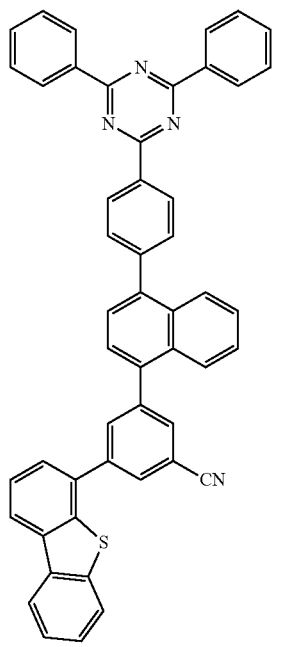
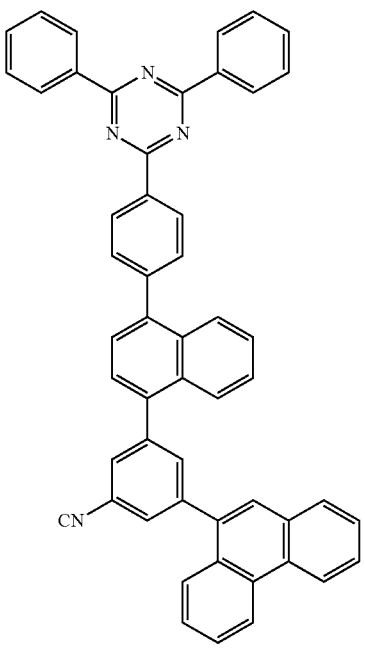

615
-continued
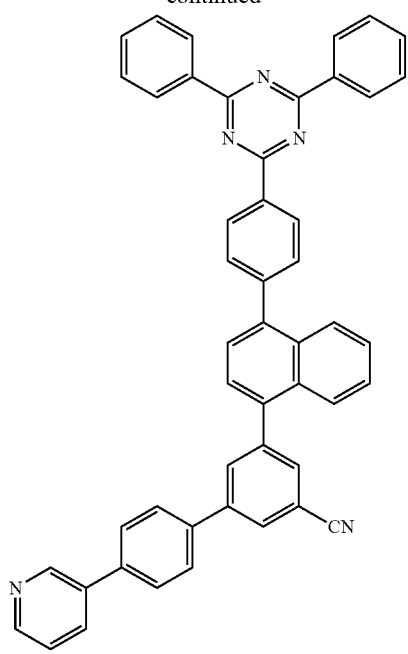
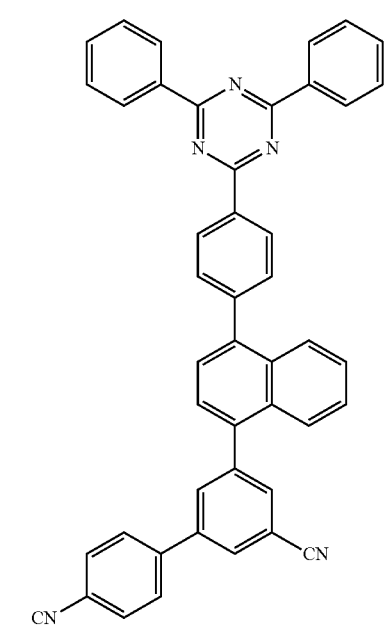
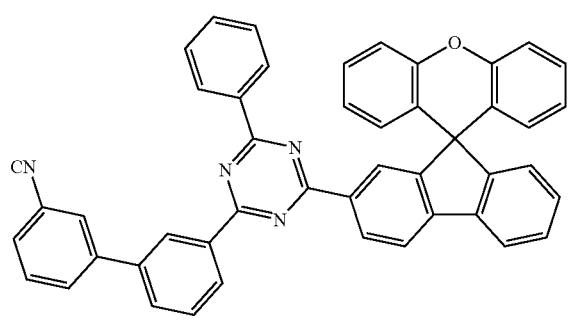
616
-continued
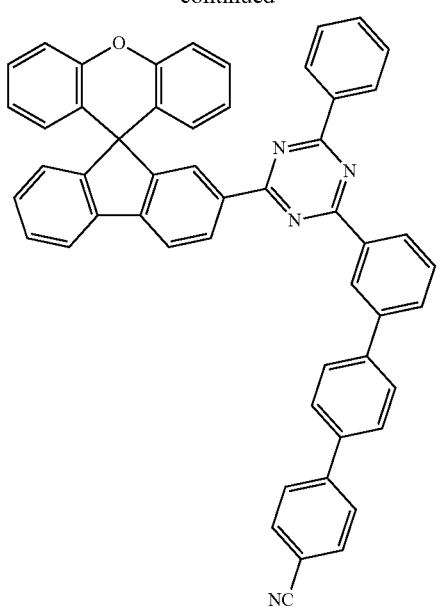
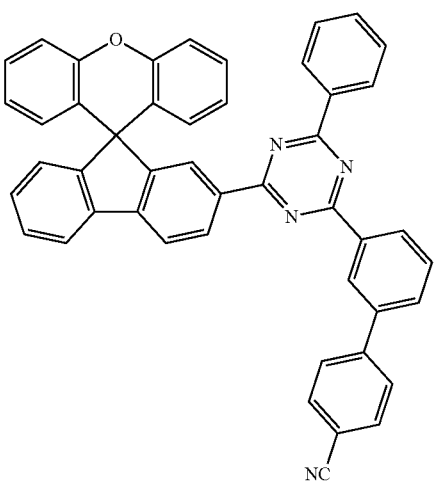
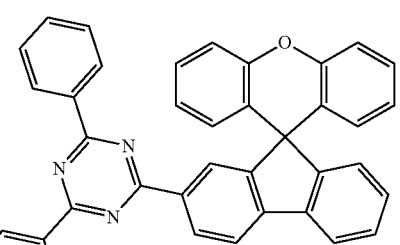

617
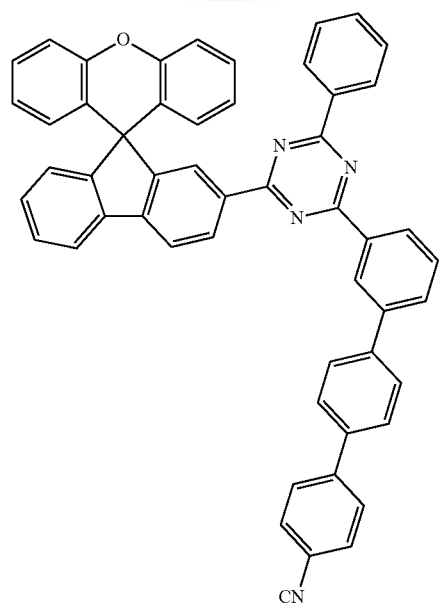
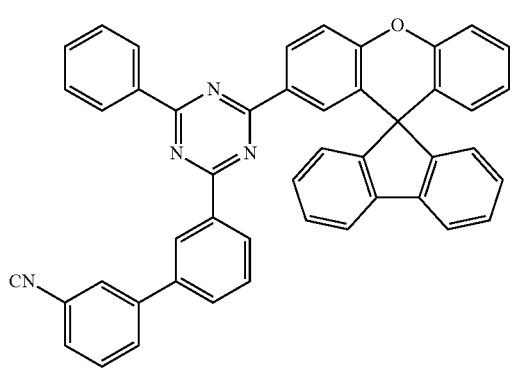
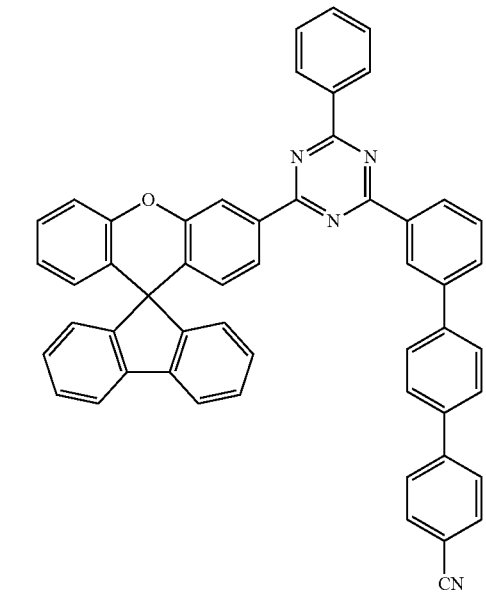
618
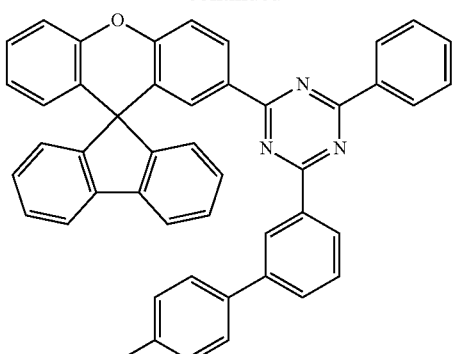
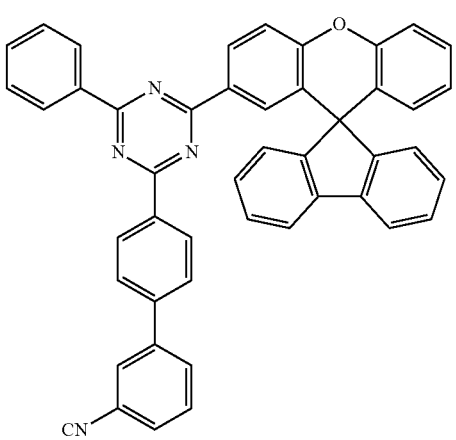
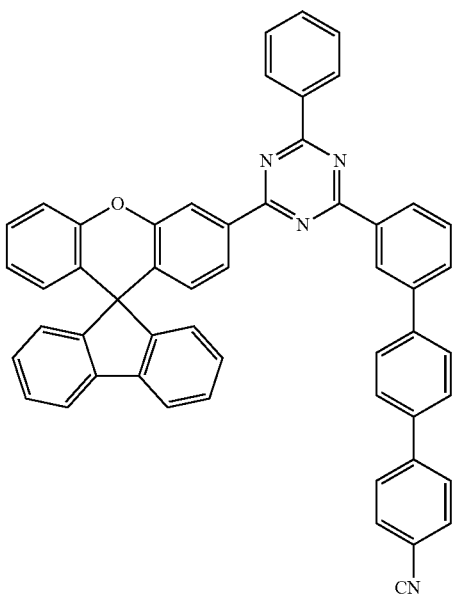

619
-continued
620
-continued
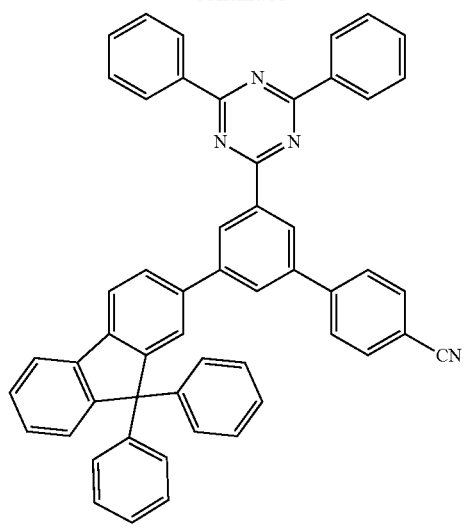
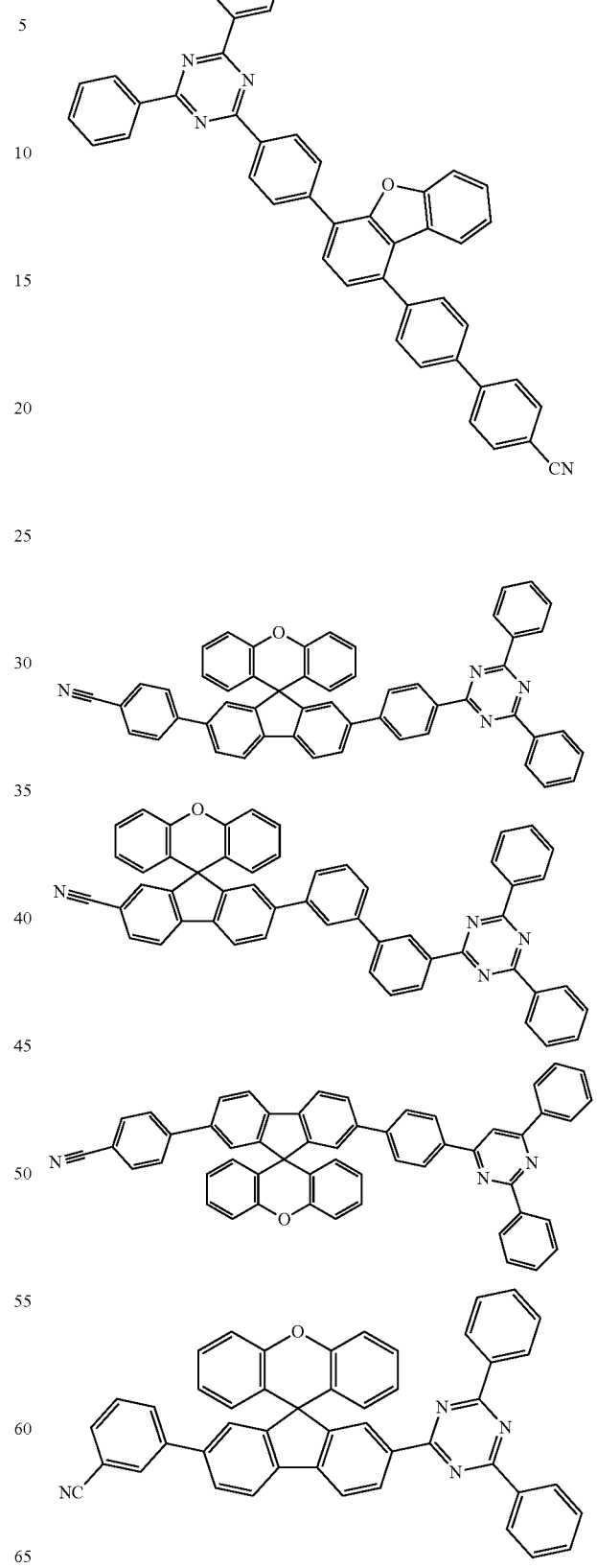

621
-continued
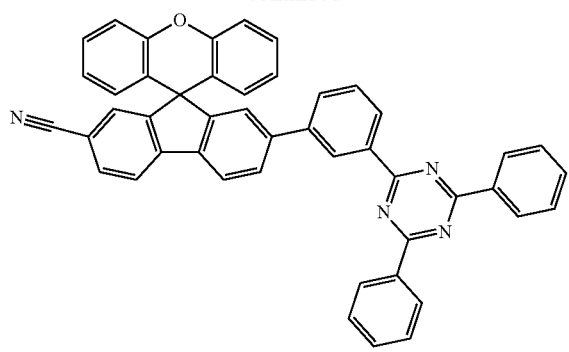
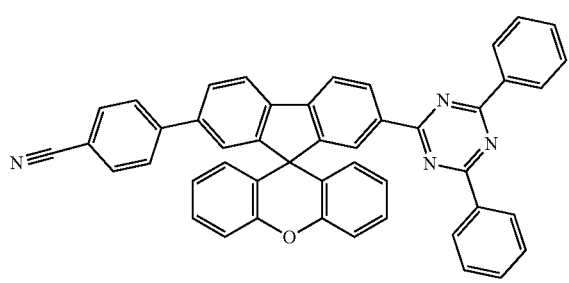
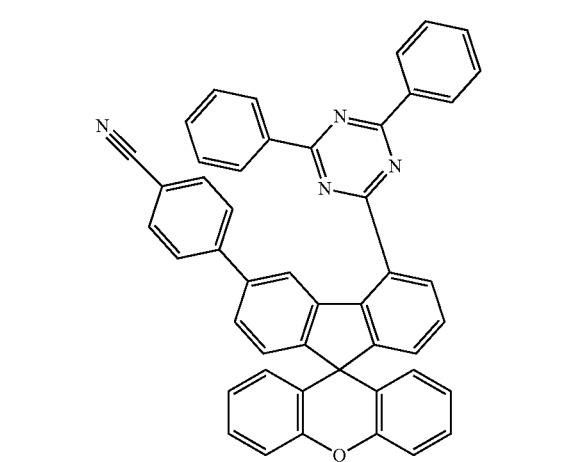
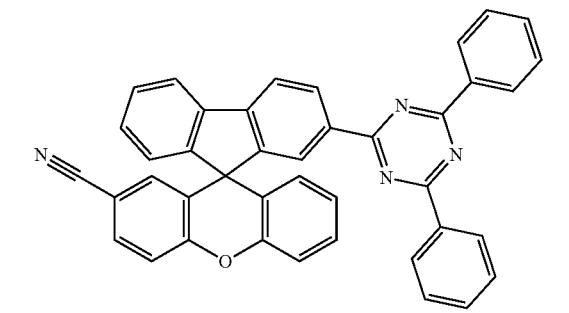
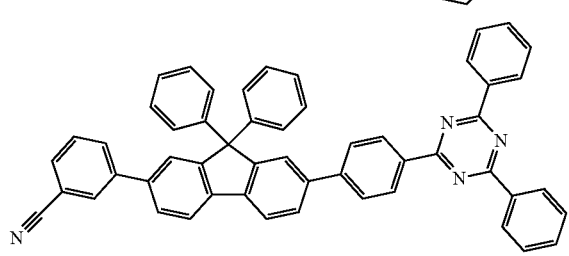
622
-continued
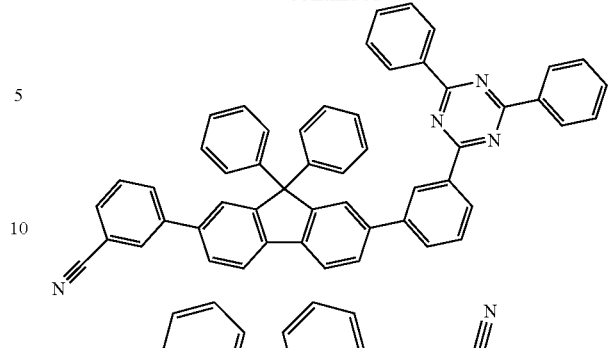
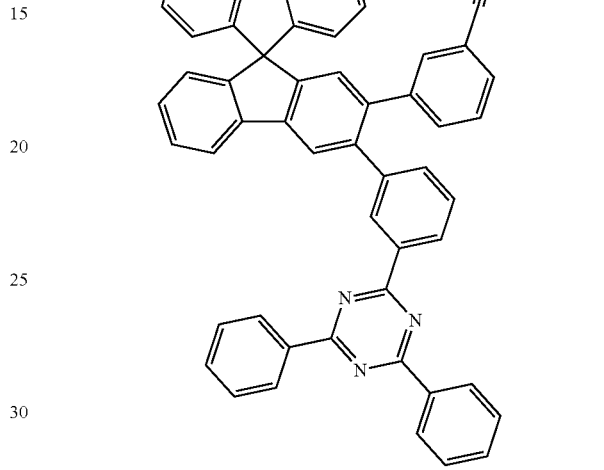
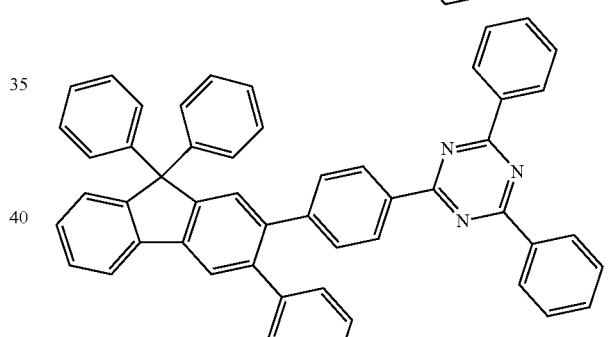
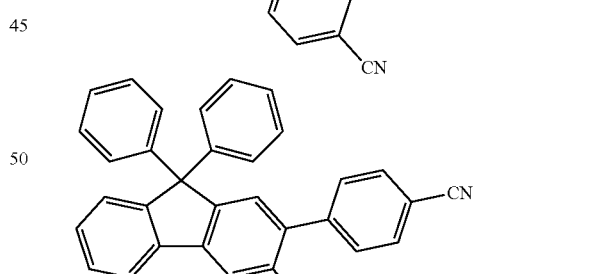
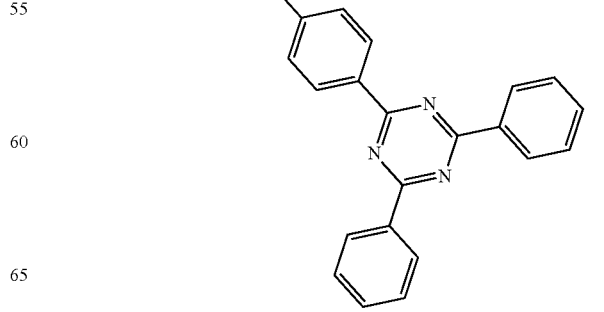

623
-continued
624
-continued
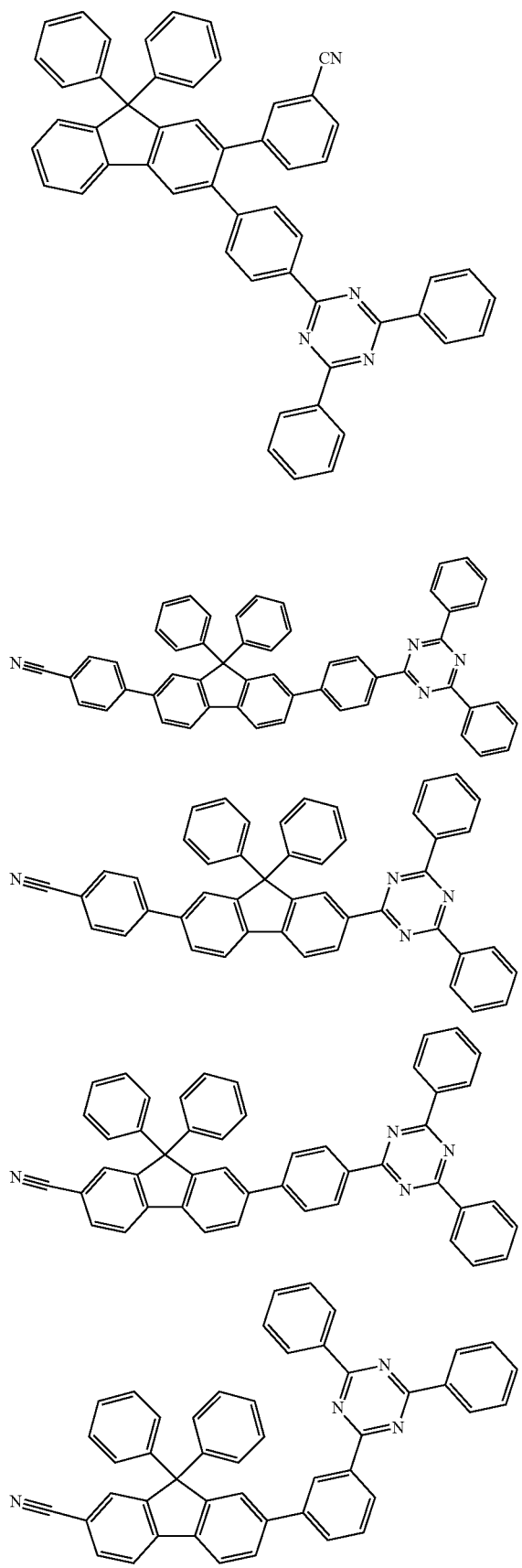
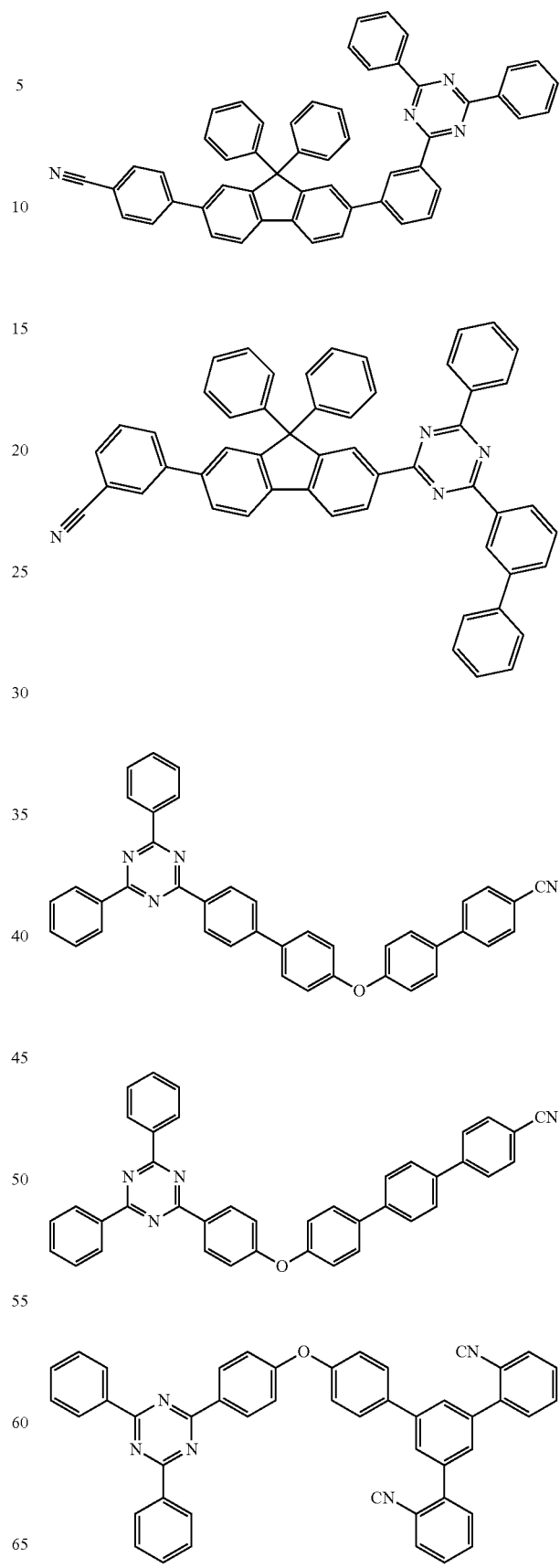

625
-continued
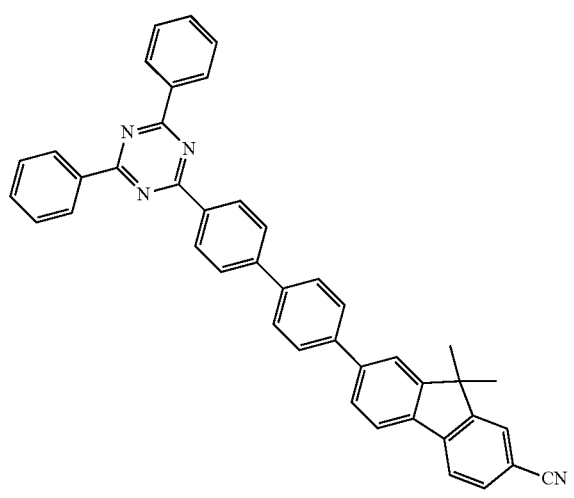
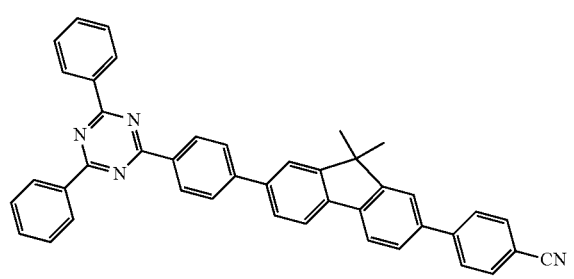
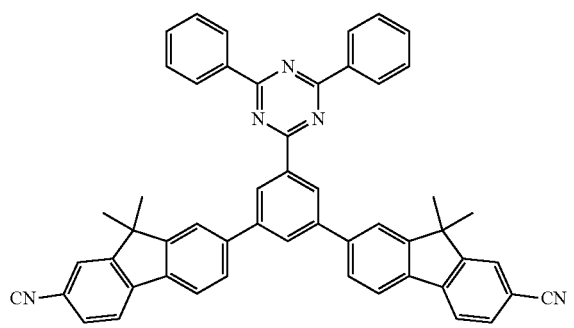
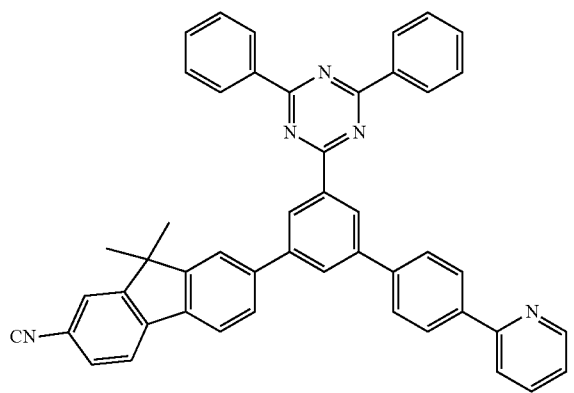
626
-continued
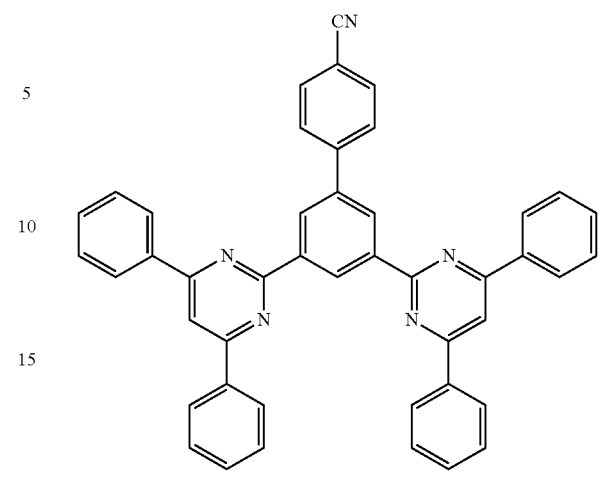
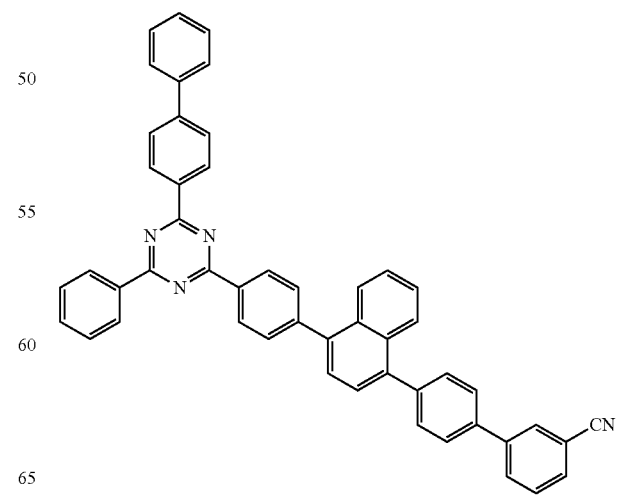

627
-continued

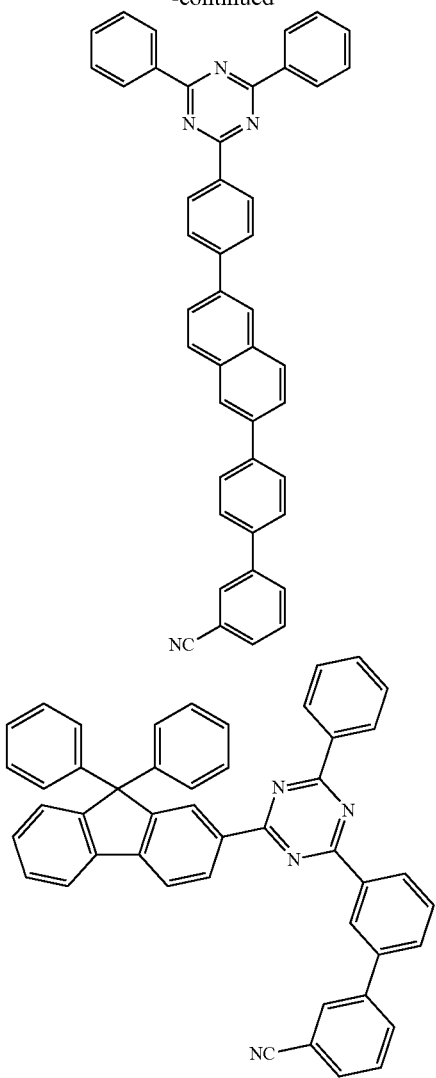

628
-continued

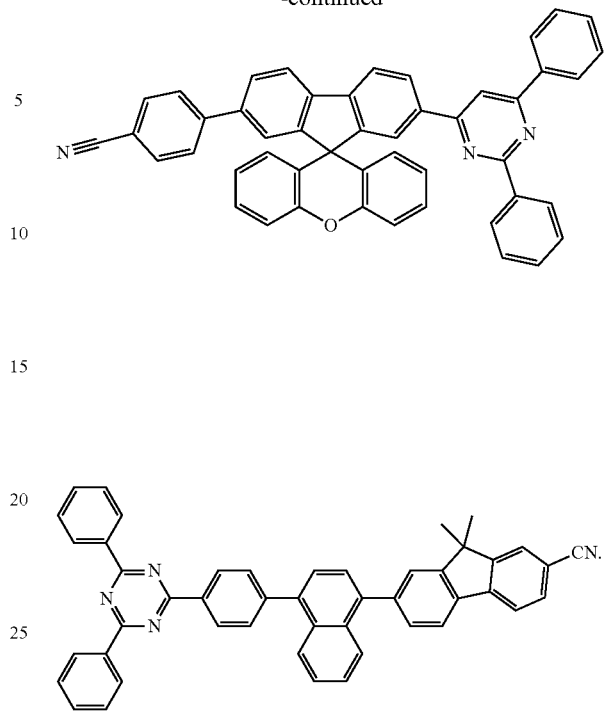

20. The organic light emitting device of claim 10, wherein the compound of Chemical Formula 1 and the compound of Chemical Formula 2 satisfy the following Equation 1:

$$|P_{El}| > |P_{Eb}| \qquad \text{<Equation 1>}$$

wherein in Equation 1:

$|P_{Eb}|$ means an absolute value of a dipole moment of the compound of Chemical Formula 1; and $|P_{El}|$ means an absolute value of a dipole moment of the compound of Chemical Formula 2.

* * * * *

UNITED STATES PATENT AND TRADEMARK OFFICE
CERTIFICATE OF CORRECTION

PATENT NO. : 12,029,115 B2
APPLICATION NO. : 17/251344
DATED : July 2, 2024
INVENTOR(S) : Heo et al.

Page 1 of 4

It is certified that error appears in the above-identified patent and that said Letters Patent is hereby corrected as shown below:

In the Claims

In Claim 7, Column 265, Lines 55-65, the structure should be:

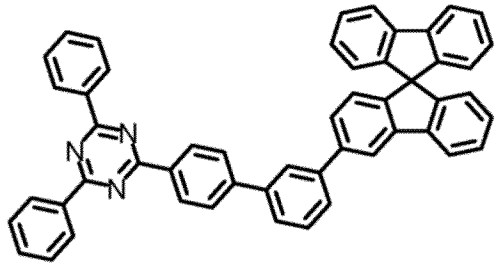

In Claim 7, Column 270, Lines 2-13, the structure should be:

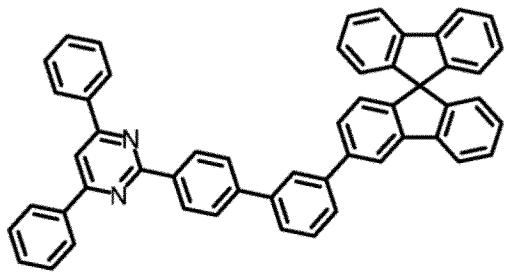

Signed and Sealed this
Twentieth Day of August, 2024

Katherine Kelly Vidal
*Director of the United States Patent and Trademark Office*

In Claim 7, Column 270, Lines 44-56, the structure should be:
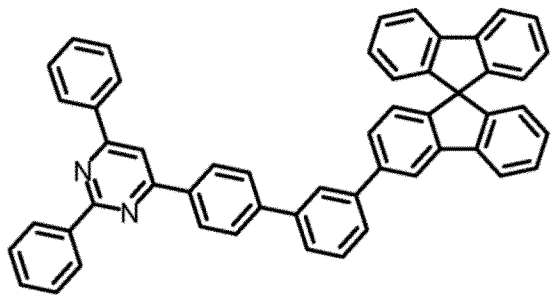
In Claim 7, Column 273, Lines 30-42, the structure should be:
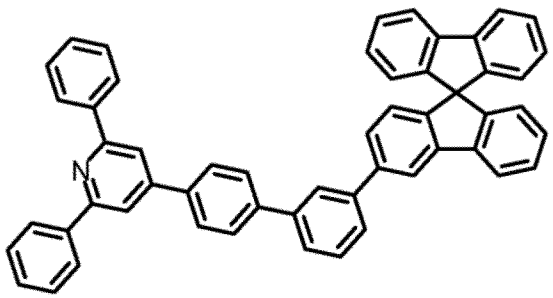
In Claim 8, Column 342, Lines 37-57, the structure should be:
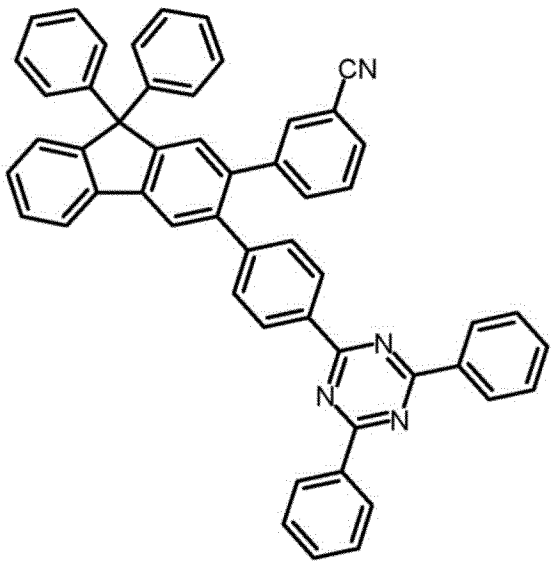
In Claim 8, Column 347, Lines 2-12, the structure should be:
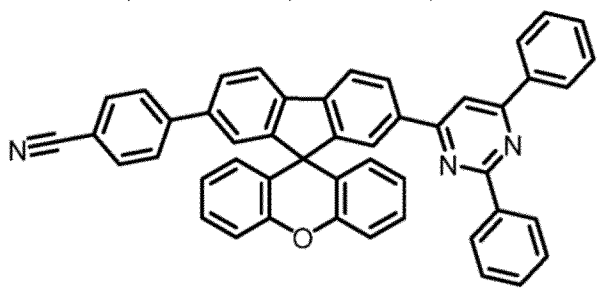

CERTIFICATE OF CORRECTION (continued)
U.S. Pat. No. 12,029,115 B2

Page 3 of 4

In Claim 15, Column 362, Lines 2-11, the structure should be:

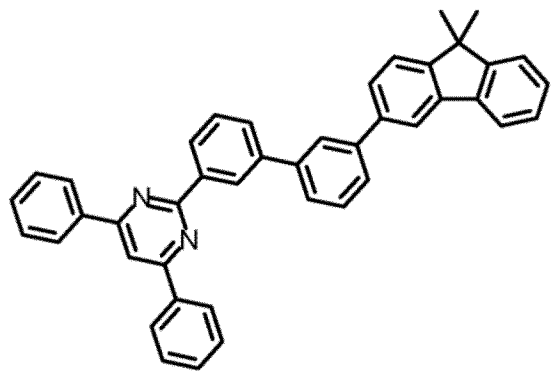

In Claim 15, Column 362, Lines 28-38, the structure should be:

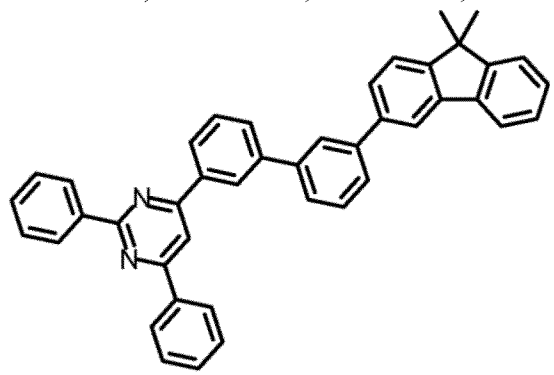

In Claim 18, Column 534, the structure of the second compound should be:

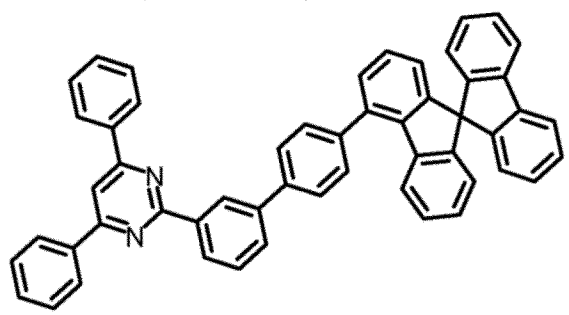

In Claim 18, Column 534, the structure of the third compound should be:

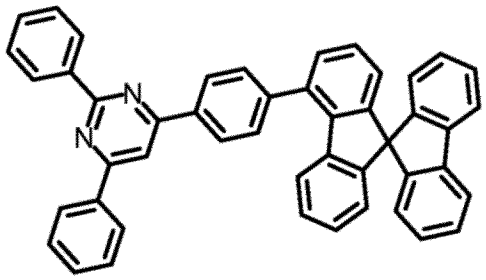

CERTIFICATE OF CORRECTION (continued)
U.S. Pat. No. 12,029,115 B2

In Claim 18, Column 557, Lines 27-37 the structure should be: